United States Patent
Atkinson et al.

(10) Patent No.: US 10,934,272 B2
(45) Date of Patent: Mar. 2, 2021

(54) PYRIDYL DERIVATIVES AS BROMODOMAIN INHIBITORS

(71) Applicant: GlaxoSmithKline Intellectual Property (No. 2) Limited, Middlesex (GB)

(72) Inventors: Stephen John Atkinson, Stevenage (GB); Emmanuel Hubert Demont, Stevenage (GB); Lee Andrew Harrison, Stevenage (GB); Etienne Levernier, Stevenage (GB); Alexander G. Preston, Stevenage (GB); Jonathan Thomas Seal, Stevenage (GB); Ian David Wall, Stevenage (GB); Robert J. Watson, Stevenage (GB); James Michael Woolven, Stevenage (GB)

(73) Assignee: GLAXOSMITHKLINE INTELLECTUAL PROPERTY (NO. 2) LIMITED, Middlesex (GB)

( * ) Notice: Subject to any disclaimer, the term of this patent is extended or adjusted under 35 U.S.C. 154(b) by 0 days.

(21) Appl. No.: 16/091,567

(22) PCT Filed: Apr. 5, 2017

(86) PCT No.: PCT/EP2017/058050
§ 371 (c)(1),
(2) Date: Oct. 5, 2018

(87) PCT Pub. No.: WO2017/174621
PCT Pub. Date: Oct. 12, 2017

(65) Prior Publication Data
US 2019/0119248 A1 Apr. 25, 2019

(30) Foreign Application Priority Data

Apr. 7, 2016 (GB) .................... 1605912
Mar. 1, 2017 (GB) .................... 1703273

(51) Int. Cl.
| | |
|---|---|
| C07D 401/12 | (2006.01) |
| C07D 401/14 | (2006.01) |
| C07D 405/12 | (2006.01) |
| C07D 413/12 | (2006.01) |
| C07D 471/04 | (2006.01) |
| C07D 413/14 | (2006.01) |
| A61K 45/06 | (2006.01) |
| A61K 31/4427 | (2006.01) |
| A61K 31/443 | (2006.01) |
| A61K 31/453 | (2006.01) |
| A61K 31/454 | (2006.01) |
| A61K 31/4545 | (2006.01) |
| A61K 31/496 | (2006.01) |
| A61K 31/5377 | (2006.01) |
| C07D 213/81 | (2006.01) |
| C07D 405/14 | (2006.01) |

(52) U.S. Cl.
CPC .......... *C07D 401/12* (2013.01); *A61K 31/443* (2013.01); *A61K 31/4427* (2013.01); *A61K 31/453* (2013.01); *A61K 31/454* (2013.01); *A61K 31/4545* (2013.01); *A61K 31/496* (2013.01); *A61K 31/5377* (2013.01); *A61K 45/06* (2013.01); *C07D 213/81* (2013.01); *C07D 401/14* (2013.01); *C07D 405/12* (2013.01); *C07D 405/14* (2013.01); *C07D 413/12* (2013.01); *C07D 413/14* (2013.01); *C07D 471/04* (2013.01)

(58) Field of Classification Search
CPC ................................................. C07D 401/12
USPC ........................................ 546/194; 514/318
See application file for complete search history.

(56) References Cited

U.S. PATENT DOCUMENTS

| | | |
|---|---|---|
| 2012/0208814 A1 | 8/2012 | Demont et al. |
| 2013/0012523 A1 | 1/2013 | Brough et al. |
| 2014/0179648 A1 | 6/2014 | Liu et al. |

FOREIGN PATENT DOCUMENTS

| | | |
|---|---|---|
| CN | 101889004 A | 11/2010 |
| EP | 1 357 111 B1 | 10/2003 |
| EP | 1 433 788 A1 | 6/2004 |
| EP | 1 477 186 A1 | 11/2004 |
| WO | WO 2004/033446 A1 | 4/2004 |
| WO | WO 2009/047359 A1 | 4/2009 |

(Continued)

OTHER PUBLICATIONS

Wells et al., "The dormancy, etc.," Cancer Res.,3811-3816. (Year: 2013).*
Chambers et al, "Dissemination and Growth, etc.," Nature Reviews, vol. 2, pp. 663-672, (Year: 2002).*
Klein, "Bronnodonnain protein, etc.," RMD Open, 4:e000744.doi:10. 1136/imopen. (Year: 2018).*
Klein et al., "Evaulating the bromdomain, etc.," Scientific Reports 8:11125, 1-7. (Year: 2018).*

(Continued)

*Primary Examiner* — Patricia L Morris
(74) *Attorney, Agent, or Firm* — Robert H. Brink; Duke M. Fitch; Edward R. Gimmi

(57) ABSTRACT

The present invention relates to compounds of formula (I) and salts thereof, pharmaceutical compositions containing such compounds and to their use in therapy.

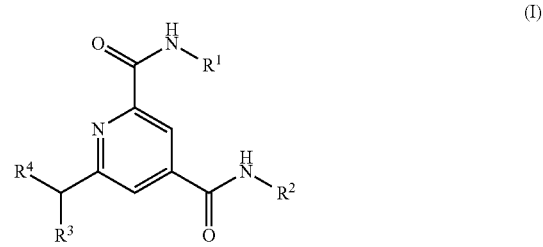

(I)

9 Claims, No Drawings

(56) References Cited

FOREIGN PATENT DOCUMENTS

| WO | WO 2014/074675 A1 | 5/2014 |
|---|---|---|
| WO | WO 2014/096965 A2 | 6/2014 |
| WO | WO 2015/015318 A2 | 2/2015 |
| WO | WO 2017/037116 A1 | 3/2017 |
| WO | WO 2017/060180 A1 | 4/2017 |
| WO | WO 2017/174621 A1 | 10/2017 |
| WO | WO 2017/202742 A1 | 11/2017 |

OTHER PUBLICATIONS

Zaware et al, "Bronnodonnain biology, etc," Nature Structural $ Molecular Biology,26, 870-879, (Year: 2019).*
White et al., "Emerging roles, etc.," Cellular Immunology 337, 48-53. (Year: 2019).*
Basheer et al., "BET bromodomain, etc.," Experimental Hematology, 43, 718-731. (Year: 2015).*
Stathis et al., "BET proteins, etc,.," Cancer Discovery, 24-36. (Year: 2018).*
Simone, Oncology: Introduction, Cecil Textbook of Medicine, ed Bennett et al. W.B. Saunders CO. 20th ed. vol. 1, pp. 1004-1010. (Year: 1996).*
Gura, Systems for Identifying New Drugs Are Often Faulty, Cancer Models, Science, vol. 278. No. 5340, pp. 1041-1042,. (Year: 1997).*
Johnson et al., Relationships between drug activity in NCI preclinical in vitro and in vivo and early clinical trials, British Journal of Cancer 64(10): 1424-1431. (Year: 2001).*
Golub et al., "Molecular Classification, etc.," Science, 286, 531-537. (Year: 1999).*
Pearce et al., "Failure modes in, etc.," Cancer Drug Design and Discovery, ed by Stephen Neidle, Chapter 18, pp. 424-435. (Year: 2008).*
Damasio, Alzheimer's Disease and related dementias, Cecil Textboo of Medicine, 20th Edition, vol. 2. pp. 1992-1996. (Year: 1996).*
Layzer, Degenerative diseases of the nervous system, Cecila Textbook of Medicine, 20th Edition, vol. 2, pp. 2050-2057. (Year: 1996).*
Dittmer et al., "Models for the Pyridine Nucleotide Coenzymes. Synthesis and Properties of Bridged Dinicotinamide Derivatives[1-3]", *J. Org. Chem.*, vol. 38, No. 16, pp. 2873-2882 (1973).
Gallenkamp et al., "Bromodomains and Their Pharmacological Inhibitors", *ChemMedChem*, vol. 9, No. 3, pp. 438-464 (2014).
Garnier et al., "BET bromodomain inhibitors: a patent review", Expert Opinion on Therapeutic Patents, vol. 24, No. 2, pp. 185-199 (2014).
International Search Report for International application No. PCT/EP2016/070519, dated Oct. 20, 2016, 4 pages.
International Search Report for International application No. PCT/EP2016/072216, International filing date: Sep. 20, 2016, 3 pages.
International Search Report for International application No. PCT/EP2016/073532, dated Nov. 30, 2016, 5 pages.
International Search Report for International application No. PCT/EP2017/058050, dated May 24, 2017, 5 pages.
International Search Report for International application No. PCT/EP2017/062208, dated Jul. 6, 2017, 5 pages.
International Search Report for International application No. PCT/EP2018/054730, dated May 4, 2018, 5 pages.
International Search Report for International application No. PCT/EP2018/054733, dated Jun. 11, 2018, 5 pages.
Non-Final Office Action for U.S. Appl. No. 15/766,222, USPTO, dated Oct. 4, 2018, 9 pages.
Notice of Allowance for U.S. Appl. No. 15/762,229, USPTO, dated Dec. 11, 2018, 9 pages.
Notice of Allowance for U.S. Appl. No. 15/766,222, USPTO, dated Jan. 17, 2019, 6 pages.
Notice of Allowance for U.S. Appl. No. 15/762,229, USPTO, dated Mar. 20, 2019, 9 pages.
Restriction Requirement for U.S. Appl. No. 15/757,199, USPTO, dated Feb. 11, 2019, 9 pages.

* cited by examiner

PYRIDYL DERIVATIVES AS BROMODOMAIN INHIBITORS

This application is a 371 of International Application No. PCT/EP2017/058050, filed Apr. 5, 2017, which claims the priority of GB Application No. 1605912.3, filed Apr. 7, 2016 and GB Application No. 1703273.1, filed Mar. 1, 2017, which are incorporated herein in their entireties.

FIELD OF THE INVENTION

The present invention is directed to pyridyl derivatives which are bromodomain inhibitors, processes for their preparation, pharmaceutical compositions comprising the compounds and the use of the compounds or the compositions in the treatment of various diseases or conditions, for example acute or chronic autoimmune and/or inflammatory conditions, viral infections and cancer.

BACKGROUND TO THE INVENTION

The genomes of eukaryotic organisms are highly organised within the nucleus of the cell. The long strands of duplex DNA are wrapped around an octomer of histone proteins (most usually comprising two copies of histones H2A, H2B, H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins recognise and bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRDT) which contain tandem bromodomains capable of binding to two acetylated lysine residues in close proximity, increasing the specificity of the interaction. Numbering from the N-terminal end of each BET protein the tandem bromodomains are typically labelled Binding Domain 1 (BD1) and Binding Domain 2 (BD2) (Chung et *J Med. Chem.*, 2011, 54, 3827-3838).

Chan et al. report that BET bromodomain inhibition suppresses transcriptional responses to cytokine-Jak-STAT signaling in a gene-specific manner in human monocytes, which suggests that BET inhibition reduces inflammation partially through suppression of cytokine activity. (Chan et al., *Eur. J. Immunol.*, 2015, 45: 287-297).

Klein et al. report that the bromodomain protein inhibitor I-BET151 suppresses expression of inflammatory genes and matrix degrading enzymes in rheumatoid arthritis synovial fibroblasts, which suggests a therapeutic potential in the targeting of epigenetic reader proteins in rheumatoid arthritis. (Klein et al., *Ann. Rheum. Dis.*, 2014, 0:1-8).

Park-Min et al. report that I-BET151 that targets bromo and extra-terminal (BET) proteins that 'read' chromatin states by binding to acetylated histones, strongly suppresses osteoclastogenesis. (Park-Min et al. *Nature Communications,* 2014, 5, 5418).

PCT patent applications PCT/EP2016/070519, PCT/EP2016/072216 and PCT/EP2016/073532 each describe a series of pyridone derivatives as bromodomain inhibitors.

SUMMARY OF THE INVENTION

The invention is directed to compounds of formula (I)

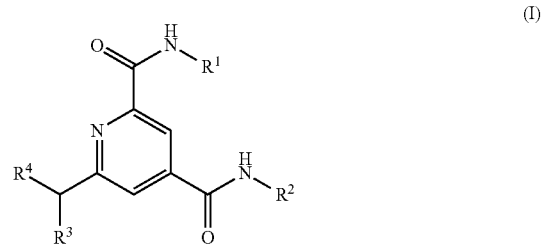

or a salt thereof
wherein:
$R^1$ is —$C_{1-3}$alkyl or cyclopropyl;
$R^2$ is —$C_{0-4}$alkyl-heterocyclyl, —$CH_2CH(OH)$-heterocyclyl or —$(CH_2)_pO$-heterocyclyl wherein each heterocyclyl is optionally substituted by one, two or three $R^5$ groups which may be the same or different;
$R^3$ is —H, —$C_{1-4}$alkyl, cyclopropyl, fluoro, chloro, —$CH_2F$, —$C_{0-3}$alkylOR$^{10}$ or $C_{0-3}$alkylCN;
$R^4$ is phenyl or a heteroaryl group wherein each are optionally substituted by one, two or three $R^6$ groups which may be the same or different;
each $R^5$ is independently halo, —$C_{1-4}$alkyl, $C_{3-4}$cycloalkyl, —$CH_2CF_3$, —$CH_2CHF_2$, —$CH_2CH_2F$, —$OCH_2CH_2OR^8$, —$C_{0-3}$alkylOR$^8$, —$C_{0-3}$alkylNR$^{11}R^{12}$, —$NHCH_2CH_2OR^8$, —$NHCO_2R^8$, oxo, —$CO_2R^8$, —$C(O)R^8$ or —$C(O)NR^{11}R^{12}$;
each $R^6$ is independently halo, —$C_{1-4}$alkyl, —$C_{0-3}$alkylOR$^7$, oxo, —$CO_2R^8$, —$C_{0-3}$alkylNR$^{16}R^{17}$, —$C_{0-3}$alkylCONR$^{16}R^{17}$, —CN, —$SO_2$—$C_{1-3}$alkyl or —$SO_2NR^{16}R^{17}$;
$R^7$ is —H, —$C_{1-3}$alkyl, —$C_{2-3}$alkylNR$^{16}R^{17}$ or —$C_{2-3}$alkylOH;
$R^8$ is —H or —$C_{1-4}$alkyl;
$R^{10}$ is —H, —$C_{1-3}$alkyl, —$C_{2-3}$alkylNR$^{14}R^{15}$ or —$C_{2-3}$alkylOH;
$R^{11}$ and $R^{12}$ are each independently selected from —H and —$C_{1-3}$alkyl; or $R^{11}$ and $R^{12}$ may join together with the nitrogen to which they are attached, to form a 4 to 7-membered heterocyclyl optionally substituted by one or two substituents independently selected from —$C_{1-3}$alkyl optionally substituted with up to 3 fluorine atoms, —$C_{2-4}$alkylOH, —OH and F;

$R^{14}$ and $R^{15}$ are each independently selected from —H and —$C_{1-3}$alkyl; or $R^{14}$ and $R^{15}$ may join together with the nitrogen to which they are attached, to form a 4 to 7-membered heterocyclyl optionally substituted by one or two substituents independently selected from —$C_{1-3}$alkyl optionally substituted with up to 3 fluorine atoms, —$C_{2-4}$alkylOH, —OH and F;

$R^{16}$ and $R^{17}$ are each independently selected from —H and —$C_{1-3}$alkyl; or $R^{16}$ and $R^{17}$ may join together with the nitrogen to which they are attached, to form a 4 to 7-membered heterocyclyl optionally substituted by one or two substituents independently selected from —$C_{1-3}$alkyl optionally substituted with up to 3 fluorine atoms, —$C_{2-4}$alkylOH, —OH and F; and p is an integer selected from 2, 3 or 4.

Compounds of the invention have been shown to be bromodomain inhibitors, in particular BD2 selective and may be useful in the treatment of various diseases or conditions, for example acute or chronic auto-immune and/or inflammatory conditions, for example rheumatoid arthritis and cancer. Accordingly, the invention is further directed to pharmaceutical compositions comprising a compound of formula (I), or a pharmaceutically acceptable salt thereof. The invention is still further directed to methods of treatment of diseases or conditions associated with bromodomains using a compound of formula (I) or a pharmaceutically acceptable salt thereof, or a pharmaceutical composition comprising a compound of formula (I) or a pharmaceutically acceptable salt thereof. The invention is yet further directed towards processes for the preparation of the compounds of formula (I).

DETAILED DESCRIPTION OF THE INVENTION

Compounds of formula (I) and salts thereof are referred to herein as "compounds of the invention".

"BD2" refers to Binding Domain 2 of any of the the BET family of proteins BRD2, BRD3, BRD4 or BRDT.

"Alkyl" refers to a saturated hydrocarbon chain having the specified number of carbon atoms. For example, the term "$C_{1-6}$alkyl" as used herein refers to a straight or branched alkyl group having from 1 to 6 carbon atoms. For example, the term "$C_{0-3}$alkyl" refers to a straight or branched alkyl group having from 0 (i.e. a bond) to 3 carbon atoms. Representative branched alkyl groups have one, two or three branches. An alkyl group may form part of a chain, for example, —$C_{0-4}$alkyl-heterocyclyl refers to a straight or branched alkyl chain having from 0 (i.e. a bond) to 4 carbon atoms linked to a heterocyclyl. "Alkyl" includes, but is not limited to, methyl, ethyl, n-propyl, iso-propyl, n-butyl, iso-butyl, t-butyl, pentyl and hexyl.

"Cycloalkyl" refers to a saturated hydrocarbon monocylic or bicyclic ring or a saturated spiro-linked bicyclic hydrocarbon ring, having the specified number of member atoms in the ring. For example, the term "$C_{3-7}$cycloalkyl" as used herein refers to a cycloakyl group having from 3 to 7 member atoms. Examples of $C_{3-7}$cycloalkyl groups include, but are not limited to, cyclopropyl, cyclobutyl, cyclopentyl, cyclohexyl, and spiro[3.3]heptane.

"Enantiomeric excess" (ee) is the excess of one enantiomer over the other expressed as a percentage. In a racemic modification, since both enantiomers are present in equal amounts, the enantiomeric excess is zero (0% ee). However, if one enantiomer were enriched such that it constitutes 95% of the product, then the enantiomeric excess would be 90% ee (the amount of the enriched enantiomer, 95%, minus the amount of the other enantiomer, 5%).

"Enantiomerically enriched" refers to products whose enantiomeric excess (ee) is greater than zero. For example, "enantiomerically enriched" refers to products whose enantiomeric excess is greater than 50% ee, greater than 75% ee, and greater than 90% ee.

"Enantiomerically pure" as used herein refers to products whose enantiomeric excess is 99% or greater.

"Half-life" (or "half-lives") refers to the time required for half of a quantity of a substance to be converted to another chemically distinct species in vitro or in vivo.

"Halo" refers to a halogen radical, for example, fluoro, chloro, bromo, or iodo.

"Heteroaryl" refers to a monocyclic or bicyclic group having 5, 6, 8, 9, 10 or 11 member atoms, including 1, 2 or 3 heteroatoms independently selected from nitrogen, sulphur and oxygen, wherein at least a portion of the group is aromatic. The point of attachment to the rest of the molecule may be by any suitable carbon or nitrogen atom. Examples of "heteroaryl" groups include, but are not limited to, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, triazinyl, benzofuranyl, isobenzofuryl, 2,3-dihydrobenzofuryl, 1,3-benzodioxolyl, dihydrobenzodioxinyl, benzothienyl, benzazepinyl, 2,3,4,5-tetrahydro-1H-benzo[d]azepinyl, indolizinyl, indolyl, indolinyl, isoindolyl, dihydroindolyl, benzimidazolyl, dihydrobenzimidazolyl, benzoxazolyl, dihydrobenzoxazolyl, benzthiazolyl, benzoisothiazolyl, dihydrobenzoisothiazolyl, indazolyl, imidazopyridinyl, pyrazolopyridinyl, pyrrolopyridinyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl.

"Heteroatom" refers to a nitrogen, sulfur, or oxygen atom.

"Heterocyclyl" refers to a non-aromatic heterocyclic monocyclic or bicyclic ring system containing 4, 5, 6, 7, 8, 9 or 10 ring member atoms, including one heteroatom and optionally containing a further heteroatom selected from nitrogen, oxygen or sulphur. Examples of "heterocyclyl" groups include, but are not limited to, azetidinyl, oxetanyl, thietanyl, pyrrolidinyl, pyrrolinyl, pyrazolidinyl, pyrazolinyl, imidazolidinyl, imidazolinyl, oxazolinyl, thiazolinyl, tetrahydrofuranyl, dihydrofuranyl, 1,3-dioxolanyl, piperidinyl, piperazinyl, homopiperazinyl, tetrahydropyranyl, dihydropyranyl, tetrahydrothiopyranyl, 1,3-dioxanyl, 1,4-dioxanyl, 1,3-oxathiolanyl, 1,3-oxathianyl, 1,3-dithianyl, 1,4-oxathiolanyl, 1,4-oxathianyl, 1,4-dithianyl, morpholinyl, thiomorpholinyl, hexahydro-1H-1,4-diazepinyl, azabicylo[3.2.1]octyl, azabicyclo[3.3.1]nonyl, azabicylo[4.3.0]nonyl, oxabicylo[2.2.1]heptyl, 1,1-dioxidotetrahydro-2H-thiopyranyl, 1,5,9-triazacyclododecyl, 3-oxabicyclo[3.1.0]hexanyl and 3-azabicyclo[3.1.0]hexanyl. "4 to 7-membered heterocyclyl" refers to a non-aromatic heterocyclic monocyclic or bicyclic ring system containing 4, 5, 6 or 7 ring member atoms, including one heteroatom and optionally containing a further heteroatom selected from nitrogen, oxygen or sulphur.

"Member atoms" refers to the atom or atoms that form a chain or ring. Where more than one member atom is present in a chain and within a ring, each member atom is covalently bound to an adjacent member atom in the chain or ring.

Atoms that make up a substituent group attached to a chain or ring are not member atoms in the chain or ring.

"Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as rearrangement, cyclisation, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

"Pharmaceutically acceptable excipient" refers to a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient are avoided. In addition, each excipient must of course be pharmaceutically acceptable e.g. of sufficiently high purity.

"rac" refers to the racemic mixture of the compounds of formula (I).

The compounds of the invention may exist in solid or liquid form. In the solid state, the compounds of the invention may exist in crystalline or non-crystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, iso-propyl alcohol, N,N-dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water. The invention includes all such solvates.

It will be further appreciated that certain compounds of the invention that exist in crystalline form, including the various solvates thereof, may exhibit polymorphism (i.e. the capacity to occur in different crystalline structures). These different crystalline forms are typically known as "polymorphs". The invention includes such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The compounds according to formula (I) contain may one or more asymmetric centres (also referred to as a chiral centres) and may, therefore, exist as individual enantiomers, diastereoisomers, or other stereoisomeric forms, or as mixtures thereof. Chiral centres, such as chiral carbon atoms, may also be present in a substituent such as an alkyl group. Where the stereochemistry of a chiral centre present in formula (I), or in any chemical structure illustrated herein, is not specified, the structure is intended to encompass any stereoisomer and all mixtures thereof. Thus, compounds according to formula (I) containing one or more chiral centres may be used as racemic mixtures, enantiomerically-enriched mixtures, or as enantiomerically-pure individual stereoisomers. Accordingly, the present invention encompasses all isomers of the compounds of formula (I) whether as individual isomers isolated such as to be substantially free of the other isomer (i.e. pure) or as mixtures (i.e. racemic mixtures). An individual isomer isolated such as to be substantially free of the other isomer (i.e. pure) may be isolated such that less than 10%, particularly less than about 1%, for example less than about 0.1% of the other isomer is present.

Racemic compounds with a single stereocentre are denoted with either no stereochemistry (single bond) or have the annotation (+/−) or rac. Racemic compounds with two or more stereocentres where relative stereochemistry is known are denoted cis or trans as drawn in the structure. Resolved single enantiomers with unknown absolute stereochemistry but known relative stereochemistry are referred to with (R* or S*) with the appropriate relative stereochemistry depicted.

Where diastereoisomers are represented and only the relative stereochemistry is referred to, the bold or hashed solid bond symbols (━/⋯) are used. Where the absolute stereochemistry is known and the compound is a single enantiomer, the bold or hashed wedges symbols (━/⋯) are used as appropriate.

Individual stereoisomers of a compound according to formula (I) which contain one or more asymmetric centres may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form. Alternatively, specific stereoisomers may be synthesised by asymmetric synthesis using optically active reagents, substrates, catalysts or solvents, or by converting one enantiomer to the other by asymmetric transformation.

It will be appreciated that, for compounds of formula (I) tautomers may be observed. Any comment relating to the biological activity of a tautomer should be taken to include both tautomers.

It is to be understood that the references herein to compounds of formula (I) and salts thereof covers the compounds of formula (I) as free bases, or as salts thereof, for example as pharmaceutically acceptable salts thereof. Thus, in one embodiment, the invention is directed to compounds of formula (I) as the free base. In another embodiment, the invention is directed to compounds of formula (I) and salts thereof. In a further embodiment, the invention is directed to compounds of formula (I) and pharmaceutically acceptable salts thereof.

Because of their potential use in medicine, salts of the compounds of formula (I) are desirably pharmaceutically acceptable. Suitable pharmaceutically acceptable salts can include acid addition salts or base addition salts. For a review of suitable pharmaceutically acceptable salts see Berge et al., *J. Pharm. Sci.*, 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable acid addition salt can be formed by reaction of a compound of formula (I) with a suitable inorganic or organic acid (such as hydrobromic, hydrochloric, sulphuric, nitric, phosphoric, succinic, maleic, acetic, propionic, fumaric, citric, tartaric, lactic, benzoic, salicylic, aspartic, p-toluenesulphonic, benzenesulphonic, methanesulphonic, ethanesulphonic, naphthalenesulphonic such as 2-naphthalenesulphonic, or hexanoic acid), optionally in a suitable solvent such as an organic solvent, to give the salt which is usually isolated for example by crystallisation and filtration or by evaporation followed by trituration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulphonate, benzenesulphonate, methanesulphonate, ethanesulphonate, naphthalenesulphonate (e.g. 2-naphthalenesulphonate) or hexanoate salt.

Other non-pharmaceutically acceptable salts, e.g. formates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated from the foregoing that included within the scope of the invention are solvates, isomers and polymorphic forms of the compounds of formula (I) and salts thereof.

Statement of the Invention

In a first aspect there are provided compounds of formula (I):

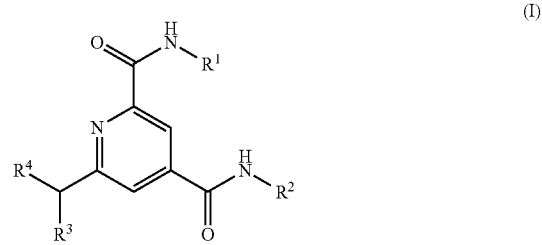

or a salt thereof $R^1$ is —$C_{1-3}$alkyl or cyclopropyl;

$R^2$ is —$C_{0-4}$alkyl-heterocyclyl, —$CH_2CH(OH)$-heterocyclyl or —$(CH_2)_pO$-heterocyclyl wherein each heterocyclyl is optionally substituted by one, two or three $R^5$ groups which may be the same or different;

$R^3$ is —H, —$C_{1-4}$alkyl, cyclopropyl, fluoro, chloro, —$CH_2F$, —$C_{0-3}$alkyl$OR^{10}$ or $C_{0-3}$alkylCN;

$R^4$ is phenyl or a heteroaryl group wherein each are optionally substituted by one, two or three $R^6$ groups which may be the same or different;

each $R^5$ is independently halo, —$C_{1-4}$alkyl, $C_{3-4}$cycloalkyl, —$CH_2CF_3$, —$CH_2CHF_2$, —$CH_2CH_2F$, —$OCH_2CH_2OR^8$, —$C_{0-3}$alkyl$OR^8$, —$C_{0-3}$alkyl$NR^{11}R^{12}$, —$NHCH_2CH_2OR^8$, —$NHCO_2R^8$, oxo, —$CO_2R^8$, —$C(O)R^8$ or —$C(O)NR^{11}R^{12}$;

each $R^6$ is independently halo, —$C_{1-4}$alkyl, —$C_{0-3}$alkyl$OR^7$, oxo, —$CO_2R^8$, —$C_{0-3}$alkyl$NR^{16}R^{17}$, —$C_{0-3}$alkyl-$CONR^{16}R^{17}$, —CN, —$SO_2$—$C_{1-3}$alkyl or —$SO_2NR^{16}R^{17}$;

$R^7$ is —H, —$C_{1-3}$alkyl, —$C_{2-3}$alkyl$NR^{16}R^{17}$ or —$C_{2-3}$alkylOH;

$R^8$ is —H or —$C_{1-4}$alkyl;

$R^{10}$ is —H, —$C_{1-3}$alkyl, —$C_{2-3}$alkyl$NR^{14}R^{15}$ or —$C_{2-3}$alkylOH;

$R^{11}$ and $R^{12}$ are each independently selected from —H and —$C_{1-3}$alkyl; or $R^{11}$ and $R^{12}$ may join together with the nitrogen to which they are attached, to form a 4 to 7-membered heterocyclyl optionally substituted by one or two substituents independently selected from —$C_{1-3}$alkyl optionally substituted with up to 3 fluorine atoms, —$C_{2-4}$alkylOH, —OH and F;

$R^{14}$ and $R^{15}$ are each independently selected from —H and —$C_{1-3}$alkyl; or $R^{14}$ and $R^{15}$ may join together with the nitrogen to which they are attached, to form a 4 to 7-membered heterocyclyl optionally substituted by one or two substituents independently selected from —$C_{1-3}$alkyl optionally substituted with up to 3 fluorine atoms, —$C_{2-4}$alkylOH, —OH and F;

$R^{16}$ and $R^{17}$ are each independently selected from —H and —$C_{1-3}$alkyl; or $R^{16}$ and $R^{17}$ may join together with the nitrogen to which they are attached, to form a 4 to 7-membered heterocyclyl optionally substituted by one or two substituents independently selected from —$C_{1-3}$alkyl optionally substituted with up to 3 fluorine atoms, —$C_{2-4}$alkylOH, —OH and F; and p is an integer selected from 2, 3 or 4.

In one embodiment there are provided compounds of formula (I) or a salt thereof wherein:

$R^1$ is —$C_{1-3}$alkyl or cyclopropyl;

$R^2$ is —$C_{0-4}$alkyl-heterocyclyl, —$CH_2CH(OH)$-heterocyclyl or —$(CH_2)_pO$-heterocyclyl wherein each heterocyclyl is optionally substituted by one, two or three $R^5$ groups which may be the same or different;

$R^3$ is —H, —$C_{1-4}$alkyl, cyclopropyl, fluoro or —$C_{0-3}$alkyl$OR^{10}$;

$R^4$ is phenyl or a heteroaryl group wherein each are optionally substituted by one, two or three $R^6$ groups which may be the same or different;

each $R^5$ is independently halo, —$C_{1-4}$alkyl, $C_{3-4}$cycloalkyl, —$CH_2CF_3$, —$CH_2CHF_2$, —$CH_2CH_2F$, —$OCH_2CH_2OR^8$, —$C_{0-3}$alkyl$OR^8$, —$C_{0-3}$alkyl$NR^{11}R^{12}$, —$NHCH_2CH_2OR^8$, —$NHCO_2R^8$, oxo, —$CO_2R^8$, —$C(O)R^8$ or —$C(O)NR^{11}R^{12}$;

each $R^6$ is independently halo, —$C_{1-4}$alkyl, —$C_{0-3}$alkyl$OR^7$, —$C_{0-3}$alkyl$NR^{16}R^{17}$, —$C_{0-3}$alkyl-$CONR^{16}R^{17}$, —CN, —$SO_2$—$C_{1-3}$alkyl or —$SO_2NR^{16}R^{17}$;

$R^7$ is —H, —$C_{1-3}$alkyl, —$C_{2-3}$alkyl$NR^{16}R^{17}$ or —$C_{2-3}$alkylOH;

$R^8$ is —H or —$C_{1-4}$alkyl;

$R^{10}$ is —H, —$C_{1-3}$alkyl, —$C_{2-3}$alkyl$NR^{14}R^{15}$ or —$C_{2-3}$alkylOH;

$R^{11}$ and $R^{12}$ are each independently selected from —H and —$C_{1-3}$alkyl; or $R^{11}$ and $R^{12}$ may join together with the nitrogen to which they are attached, to form a 4 to 7-membered heterocyclyl optionally substituted by one or two substituents independently selected from —$C_{1-3}$alkyl optionally substituted with up to 3 fluorine atoms, —$C_{2-4}$alkylOH, —OH and F;

$R^{14}$ and $R^{15}$ are each independently selected from —H and —$C_{1-3}$alkyl; or $R^{14}$ and $R^{15}$ may join together with the nitrogen to which they are attached, to form a 4 to 7-membered heterocyclyl optionally substituted by one or two substituents independently selected from —$C_{1-3}$alkyl optionally substituted with up to 3 fluorine atoms, —$C_{2-4}$alkylOH, —OH and F;

$R^{16}$ and $R^{17}$ are each independently selected from —H and —$C_{1-3}$alkyl; or $R^{16}$ and $R^{17}$ may join together with the nitrogen to which they are attached, to form a 4 to 7-membered heterocyclyl optionally substituted by one or two substituents independently selected from —$C_{1-3}$alkyl optionally substituted with up to 3 fluorine atoms, —$C_{2-4}$alkylOH, —OH and F; and p is an integer selected from 2, 3 or 4.

In one embodiment $R^1$ is methyl. In another embodiment $R^1$ is ethyl.

In one embodiment $R^2$ is —$C_{0-4}$alkyl-heterocyclyl wherein the heterocyclyl group is optionally substituted by one, two or three $R^5$ groups which may be the same or different. In another embodiment $R^2$ is —$C_{0-4}$alkyl-heterocyclyl wherein the heterocyclyl group is selected from oxetanyl, azetidinyl, tetrahydrofuranyl, piperidinyl, piperazinyl, morpholinyl, tetrahydro-2H-pyranyl, (1r,5s)-3-oxabicyclo[3.1.0]hexanyl and (1r,5s)-3-azabicyclo[3.1.0]hexanyl, optionally substituted by one or two $R^5$ groups which may be the same or different. In a further embodiment $R^2$ is —$C_{0-4}$alkyl-heterocyclyl wherein the heterocyclyl group is (1R,5S)-3-oxabicyclo[3.1.0]hexanyl, optionally substituted by one or two $R^5$ groups which may be the same or different. In a further embodiment $R^2$ is —$C_{0-4}$alkyl-heterocyclyl wherein the heterocyclyl group is 1,3-dioxan-2-yl, optionally substituted by one or two $R^5$ groups which may be the same or different.

In one embodiment $R^3$ is —H, —$C_{1-4}$alkyl, cyclopropyl, fluoro or —$C_{0-3}$alkyl$OR^{10}$. In one embodiment $R^3$ is —H, methyl, ethyl, fluoro, —$OCH_3$, —OH, —$CH_2F$, —$CH_2OMe$ or —$CH_2CN$. In one embodiment $R^3$ is —H, methyl, fluoro, —$OCH_3$ or —OH.

In one embodiment $R^4$ is phenyl optionally substituted by one, two or three $R^6$ groups which may be the same or different selected from —$C_{1-4}$alkyl, —$C_{0-3}$alkyl-$OR^7$ and CN. In one embodiment $R^4$ is phenyl optionally substituted by one, two or three $R^6$ groups which may be the same or different selected from halo, —$C_{1-4}$alkyl, —$C_{0-3}$alkyl-$OR^7$ and CN. In one embodiment $R^4$ is phenyl optionally substituted by one or two $R^6$ groups which may be the same or different selected from chloro, methyl, and —$OCH_3$.

In another embodiment $R^4$ is a heteroaryl group which is indolinyl optionally substituted by one, two or three $R^6$ groups which may be the same or different. In one embodiment $R^4$ is a heteroaryl group which is indolinyl optionally substituted by oxo.

In another embodiment $R^4$ is a heteroaryl group which is indolyl optionally substituted by one, two or three $R^6$ groups which may be the same or different. In another embodiment $R^4$ is a heteroaryl group which is indolyl optionally substituted by one or two $R^6$ groups which may be the same or different selected from fluoro, methyl, —CN, or —$CH_2CH_2OH$. In another embodiment $R^4$ is a heteroaryl group which is 1H-indol-4-yl.

In one embodiment each $R^6$ is independently halo, —$C_{1-4}$alkyl, —$C_{0-3}$alkyl$OR^7$, —$C_{0-3}$alkyl$NR^{16}R^{17}$, —$C_{0-3}$alkyl-$CONR^{16}R^{17}$, —CN, —502-$C_{1-3}$alkyl or —$SO_2NR^{16}R^{17}$. In one embodiment each $R^5$ is selected from halo, $C_{1-4}$alkyl, —$CH_2CHF_2$, oxo, —$C_{0-3}$alkyl$NR^{11}R^{12}$, —$CO_2C(CH_3)_3$ and —$C(O)R^8$. In one embodiment $R^5$ is selected from halo, $C_{1-4}$alkyl, —$CH_2CHF_2$, oxo, —$CO_2C(CH_3)_3$ and —$C(O)R^8$. In another embodiment $R^5$ is selected from fluoro, —$CO_2C(CH_3)_3$, —$CH_2CHF_2$, —$CH(CH_3)_2$, —$C(O)CH_3$, oxo and methyl. In another embodiment each $R^5$ is selected from fluoro, —$CO_2C(CH_3)_3$, —$CH_2CHF_2$, —$CH(CH_3)_2$, —$NH_2$, —$N(Me)_2$, —$C(O)CH_3$, oxo and methyl.

It is to be understood that the present invention covers all combinations of substituent groups described hereinabove.

Compounds of the invention include the compounds of Examples 1 to 172 and salts thereof.

Compounds of the invention include the compounds of Examples 1 to 87 and salts thereof.

In one embodiment the compound of formula (I) is selected from:

$N^4$-((1R,5S,6r)-3-Oxabicyclo[3.1.0]hexan-6-yl)-$N^2$-methyl-6-((S*)-1-phenylethyl)pyridine-2,4-dicarboxamide;

$N^2$-Methyl-$N^4$-(2-((S)-morpholin-2-yl)ethyl)-6-((S)-1-phenylethyl)pyridine-2,4-dicarboxamide;

6-((1H-Indol-4-yl)methyl)-$N^4$-((1R,5S,6r)-3-oxabicyclo[3.1.0]hexan-6-yl)-$N^2$-methylpyridine-2,4-dicarboxamide; and $N^4$-((1R,5S,6r)-3-Oxabicyclo[3.1.0]hexan-6-yl)-6-((S)-hydroxy(phenyl)methyl)-$N^2$-methylpyridine-2,4-dicarboxamide or a salt thereof In one embodiment the compound of formula (I) is selected from:

$N^4$-((1R,5S,6r)-3-oxabicyclo[3.1.0]hexan-6-yl)-6-((R*)-methoxy(phenyl)methyl)-$N^2$-methylpyridine-2,4-dicarboxamide;

$N^4$-(3-((2r,5r)-5-Amino-1,3-dioxan-2-yl)propyl)-6-benzyl-$N^2$-methylpyridine-2,4-dicarboxamide;

$N^4$-((1R,5S,6r)-3-Oxabicyclo[3.1.0]hexan-6-yl)-6-(indolin-4-ylmethyl)-$N^2$-methylpyridine-2,4-dicarboxamide; and $N^4$-(3-((2r,5S)-5-Amino-1,3-dioxan-2-yl)propyl)-6-((R*)-methoxy(phenyl)methyl)-$N^2$-methylpyridine-2,4-dicarboxamide or a salt thereof.

In one embodiment the compound of formula (I) is:

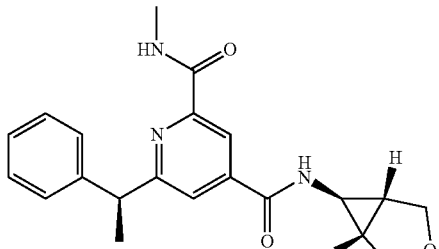

or a salt thereof.

In another embodiment, the compound of formula (I) is a salt of:

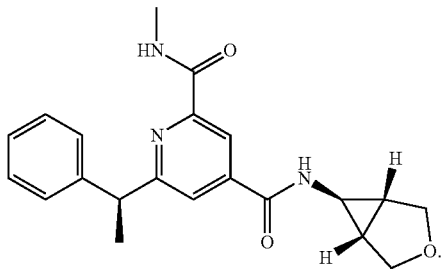 [SMILES: CNC(=O)c1cc(C(=O)N[C@H]2[C@@H]3COC[C@@H]32)cc([C@@H](C)c2ccccc2)n1]

In a further embodiment the compound of formula (I) is

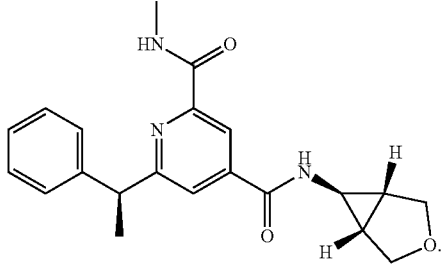 [SMILES: CNC(=O)c1cc(C(=O)N[C@H]2[C@@H]3COC[C@@H]32)cc([C@@H](C)c2ccccc2)n1]

In one embodiment the compound of formula (I) is:

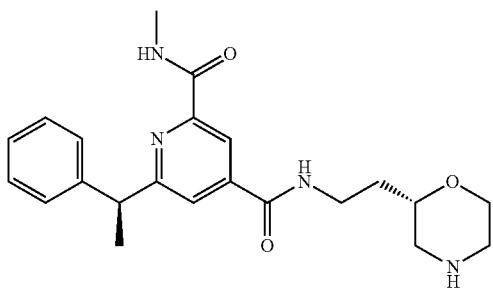 [SMILES: CNC(=O)c1cc(C(=O)NCC[C@H]2CNCCO2)cc([C@@H](C)c2ccccc2)n1]

or a salt thereof.

In another embodiment, the compound of formula (I) is a salt of:

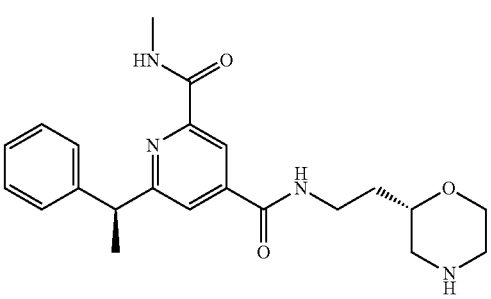

In a further embodiment the compound of formula (I) is

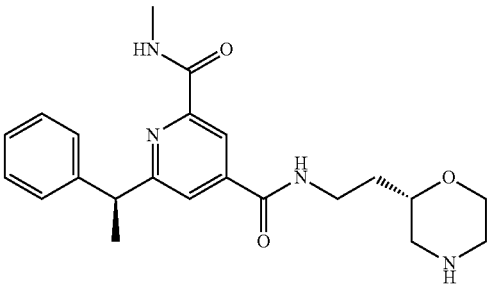

In one embodiment the compound of formula (I) is:

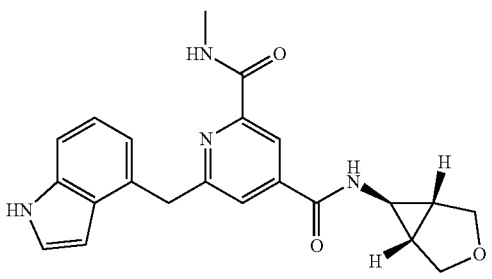 [SMILES: CNC(=O)c1cc(C(=O)N[C@H]2[C@@H]3COC[C@@H]32)cc(Cc2cccc3[nH]ccc23)n1]

or a salt thereof.

In another embodiment, the compound of formula (I) is a salt of:

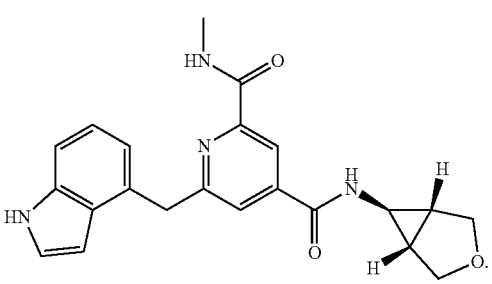 [SMILES: CNC(=O)c1cc(C(=O)N[C@H]2[C@@H]3COC[C@@H]32)cc(Cc2cccc3[nH]ccc23)n1]

In a further embodiment the compound of formula (I) is

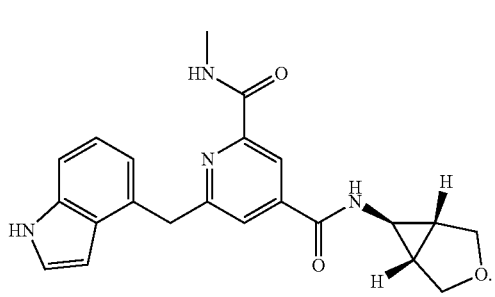 [SMILES: CNC(=O)c1cc(C(=O)N[C@H]2[C@@H]3COC[C@@H]32)cc(Cc2cccc3[nH]ccc23)n1]

In one embodiment the compound of formula (I) is:

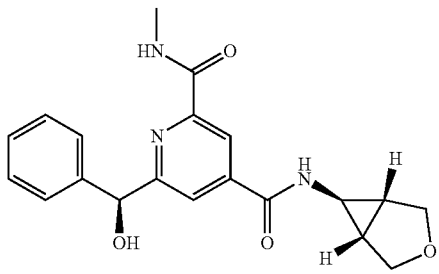 [SMILES: CNC(=O)c1cc(C(=O)N[C@H]2[C@@H]3COC[C@@H]32)cc([C@@H](O)c2ccccc2)n1]

or a salt thereof.

In another embodiment, the compound of formula (I) is a salt of:

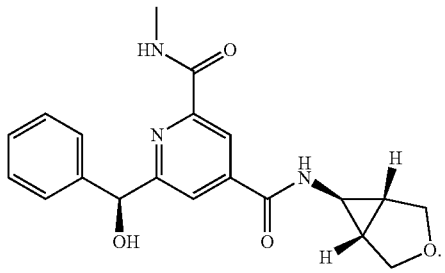 [SMILES: CNC(=O)c1cc(C(=O)N[C@H]2[C@@H]3COC[C@@H]32)cc([C@@H](O)c2ccccc2)n1]

In a further embodiment the compound of formula (I) is

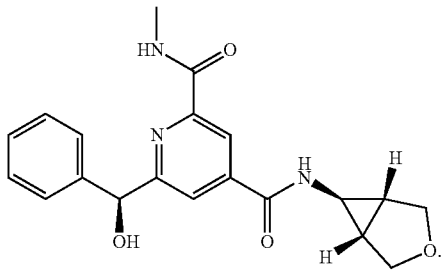 [SMILES: CNC(=O)c1cc(C(=O)N[C@H]2[C@@H]3COC[C@@H]32)cc([C@@H](O)c2ccccc2)n1]

In one embodiment the compound of formula (I) is:

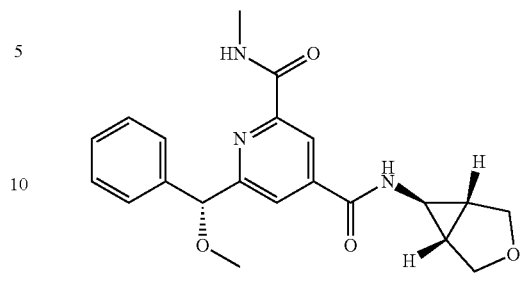

or a salt thereof.

In one embodiment the compound of formula (I) is:

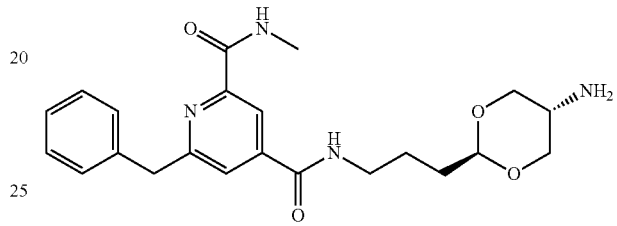

or a salt thereof.

In one embodiment the compound of formula (I) is:

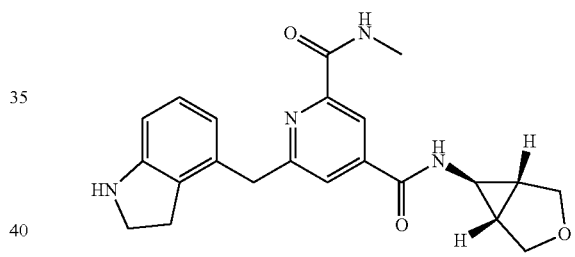

or a salt thereof.

In one embodiment the compound of formula (I) is:

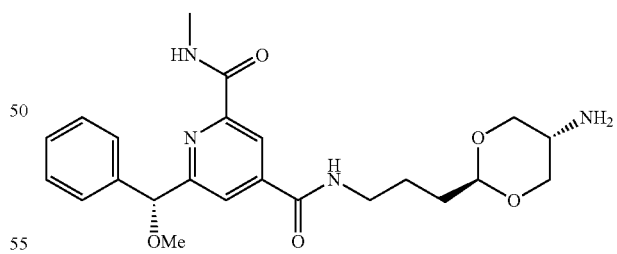

or a salt thereof.

In a second aspect of the present invention, there is provided a pharmaceutical composition comprising a compound of formula (I) or a pharmaceutically acceptable salt thereof and one or more pharmaceutically acceptable excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

Statement of Use

The compounds of formula (I) and salts thereof are bromodomain inhibitors, and thus are believed to have potential utility in the treatment of diseases or conditions for which a bromodomain inhibitor is indicated.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of acute or chronic autoimmune and/or inflammatory conditions such as rheumatoid arthritis, psoriatic arthritis, ankylosing spondylitis, osteoarthritis, acute gout, psoriasis, systemic lupus erythematosus, multiple sclerosis, inflammatory bowel disease (Crohn's disease and ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, hypercholesterolemia, atherosclerosis, Alzheimer's disease, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (keratoconjunctivitis Sicca), vernal keratoconjunctivitis, atopic keratoconjunctivitis, uveitis (such as anterior uveitis, pan uveitis, posterior uveitis, uveitis-associated macular edema), scleritis, diabetic retinopathy, diabetic macula edema, age-related macular dystrophy, hepatitis, pancreatitis, primary biliary cirrhosis, sclerosing cholangitis, Addison's disease, hypophysitis, thyroiditis, Type I diabetes, Type II diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement, acute rejection of transplanted organs and systemic sclerosis.

In one embodiment the acute or chronic autoimmune and/or inflammatory condition is a disorder of lipid metabolism mediated via the regulation of APO-A1 such as hypercholesterolemia, atherosclerosis or Alzheimer's disease.

In another embodiment the acute or chronic autoimmune and/or inflammatory condition is a respiratory disorder such as asthma or chronic obstructive airways disease.

In another embodiment the acute or chronic autoimmune and/or inflammatory condition is a systemic inflammatory disorder such as rheumatoid arthritis, osteoarthritis, acute gout, psoriasis, systemic lupus erythematosus, multiple sclerosis or inflammatory bowel disease (Crohn's disease or Ulcerative colitis).

In another embodiment, the acute or chronic autoimmune and/or inflammatory condition is multiple sclerosis.

In another embodiment, the acute or chronic autoimmune and/or inflammatory condition is Type I diabetes.

In another embodiment, the acute or chronic autoimmune and/or inflammatory condition is rheumatoid arthritis.

Bromodomain inhibitors may be useful in the treatment of depression.

Bromodomain inhibitors may be useful in the treatment of diseases or conditions which involve inflammatory responses to infections with bacteria, viruses, fungi, parasites or their toxins, such as sepsis, acute sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus. In one embodiment the disease or condition which involves an inflammatory response to an infection with bacteria, a virus, fungi, a parasite or their toxins is acute sepsis.

Bromodomain inhibitors may be useful in the treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of cardiovascular diseases such as coronary artery diseases (for example, angina or myocardial infarction), pulmonary arterial hypertension, cerebro-vascular ischaemia (stroke), hypertensive heart disease, rheumatic heart disease, cardiomyopathy, atrial fibrillation, congenital heart disease, endocarditis, aortic aneurysms or peripheral artery disease.

Bromodomain inhibitors may be useful in the treatment of fibrotic conditions such as idiopathic pulmonary fibrosis, pulmonary fibrosis, cystic fibrosis, progressive massive fibrosis, renal fibrosis, liver fibrosis, liver cirrhosis, non-alcoholic steatohepatitis (NASH), non-alcoholic fatty liver disease (NAFLD), post-operative stricture, keloid scar formation, scleroderma (including morphea and systemic sclerosis), cardiac fibrosis, atrial fibrosis, endomyocardial fibrosis, old myocardial infarction, arthrofibrosis, Dupuytren's contracture, mediastinal, myelofibrosis, Peyronie's disease, nephrogenic systemic fibrosis, retroperitoneal fibrosis and adhesive capsulitis.

Bromodomain inhibitors may be useful in the treatment of viral infections such as herpes simplex infections and reactivations, cold sores, herpes zoster infections and reactivations, chickenpox, shingles, human papilloma virus (HPV), human immunodeficiency virus (HIV), cervical neoplasia, adenovirus infections, including acute respiratory disease, poxvirus infections such as cowpox or smallpox, or African swine fever virus. In one embodiment the viral infection is a HPV infection of skin or cervical epithelia. In another embodiment the viral infection is a latent HIV infection.

Bromodomain inhibitors may be useful in the treatment of a wide variety of bone disorders such as osteoporosis, osteopenia, osteoarthritis and ankylosing spondylitis.

Bromodomain inhibitors may be useful in the treatment of cancer, including hematological cancers (such as leukaemia, lymphoma and multiple myeloma), epithelial cancers (including lung, breast or colon carcinomas), midline carcinomas, or mesenchymal, hepatic, renal or neurological tumours.

Bromodomain inhibitors may be useful in the treatment of one or more cancers selected from brain cancer (gliomas), glioblastomas, Bannayan-Zonana syndrome, Cowden disease, Lhermitte-Duclos disease, breast cancer, inflammatory breast cancer, colorectal cancer, Wilm's tumor, Ewing's sarcoma, rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukaemia, erythroleukemia, malignant lymphoma, Hodgkins lymphoma, non-Hodgkins lymphoma, lymphoblastic T-cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), NUT-midline carcinoma and testicular cancer.

In one embodiment the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is breast cancer. In another embodiment the cancer is colorectal cancer. In another embodiment the cancer is prostate cancer. In another embodiment the cancer is castration resistant prostate cancer.

Bromodomain inhibitors may be useful in the treatment of diseases associated with systemic inflammatory response syndrome, such as sepsis, burns, pancreatitis, major trauma, haemorrhage and ischaemia. In this embodiment, the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac or gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns.

The present invention thus provides a compound of formula (I) or a pharmaceutically acceptable salt thereof for use in therapy. The compound of formula (I) or a pharmaceutically acceptable salt thereof can be used in the treatment of diseases or conditions for which a bromodomain inhibitor is indicated.

The present invention thus provides a compound of formula (I) or a pharmaceutically acceptable salt thereof for use in the treatment of a disease or condition for which a bromodomain inhibitor is indicated. In one embodiment there is provided a compound of formula (I) or a pharmaceutically acceptable salt thereof for use in the treatment of acute or chronic auto-immune and/or inflammatory conditions. In one embodiment there is provided a compound of formula (I) or a pharmaceutically acceptable salt thereof for use in the treatment of rheumatoid arthritis. In another embodiment there is provided a compound of formula (I) or a pharmaceutically acceptable salt thereof for use in the treatment of diseases or conditions which involve inflammatory responses to infections with bacteria, viruses, fungi, parasites or their toxins. In another embodiment there is provided a compound of formula (I) or a pharmaceutically acceptable salt thereof for use in the treatment of conditions associated with ischaemia-reperfusion injury. In another embodiment there is provided a compound of formula (I) or a pharmaceutically acceptable salt thereof for use in the treatment of cardiovascular diseases. In another embodiment there is provided a compound of formula (I) or a pharmaceutically acceptable salt thereof for use in the treatment of fibrotic conditions. In another embodiment there is provided a compound of formula (I) or a pharmaceutically acceptable salt thereof for use in the treatment of viral infections. In another embodiment there is provided a compound of formula (I) or a pharmaceutically acceptable salt thereof for use in the treatment of bone disorders. In another embodiment there is provided a compound of formula (I) or a pharmaceutically acceptable salt thereof for use in the treatment of cancer. In a further embodiment there is provided a compound of formula (I) or a pharmaceutically acceptable salt thereof for use in the treatment of diseases associated with systemic inflammatory response syndrome.

Also provided is the use of a compound of formula (I) or a pharmaceutically acceptable salt thereof in the manufacture of a medicament for the treatment of diseases or conditions for which a bromodomain inhibitor is indicated. In one embodiment there is provided the use of a compound of formula (I) or a pharmaceutically acceptable salt thereof in the manufacture of a medicament for the treatment of acute or chronic auto-immune and/or inflammatory conditions. In one embodiment there is provided the use of a compound of formula (I) or a pharmaceutically acceptable salt thereof in the manufacture of a medicament for the treatment of rheumatoid arthritis. In another embodiment there is provided the use of a compound of formula (I) or a pharmaceutically acceptable salt thereof in the manufacture of a medicament for the treatment of diseases or conditions which involve inflammatory responses to infections with bacteria, viruses, fungi, parasites or their toxins. In another embodiment there is provided the use of a compound of formula (I) or a pharmaceutically acceptable salt thereof in the manufacture of a medicament for the treatment of conditions associated with ischaemia-reperfusion injury. In another embodiment there is provided the use of a compound of formula (I) or a pharmaceutically acceptable salt thereof in the manufacture of a medicament for the treatment of cardiovascular diseases. In another embodiment there is provided the use of a compound of formula (I) or a pharmaceutically acceptable salt thereof in the manufacture of a medicament for the treatment of fibrotic conditions. In another embodiment there is provided the use of a compound of formula (I) or a pharmaceutically acceptable salt thereof in the manufacture of a medicament for the treatment of viral infections. In another embodiment there is provided the use of a compound of formula (I) or a pharmaceutically acceptable salt thereof in the manufacture of a medicament for the treatment of cancer. In a further embodiment there is provided the use of a compound of formula (I) or a pharmaceutically acceptable salt thereof in the manufacture of a medicament for the treatment of diseases associated with systemic inflammatory response syndrome.

Also provided is a method of treating diseases or conditions for which a bromodomain inhibitor is indicated in a subject in need thereof which comprises administering a therapeutically effective amount of compound of formula (I) or a pharmaceutically acceptable salt thereof. In one embodiment there is provided a method of treating acute or chronic auto-immune and/or inflammatory conditions in a subject in need thereof which comprises administering a therapeutically effective amount of a compound of formula (I) or a pharmaceutically acceptable salt thereof. In one embodiment there is provided a method of treating rheumatoid arthritis in a subject in need thereof which comprises administering a therapeutically effective amount of a compound of formula (I) or a pharmaceutically acceptable salt thereof. In another embodiment there is provided a method of treating diseases or conditions which involve inflammatory responses to infections with bacteria, viruses, fungi, parasites or their toxins in a subject in need thereof which comprises administering a therapeutically effective amount of a compound of formula (I) or a pharmaceutically acceptable salt thereof. In another embodiment there is provided a method of treating conditions associated with ischaemia-reperfusion injury in a subject in need thereof which comprises administering a therapeutically effective amount of a compound of formula (I) or a pharmaceutically acceptable salt thereof. In another embodiment there is provided a method of treating cardiovascular diseases in a subject in need thereof which comprises administering a therapeutically effective amount of a compound of formula (I) or a pharmaceutically acceptable salt thereof. In another embodiment there is provided a method of treating fibrotic conditions in a subject in need thereof which comprises administering a therapeutically effective amount of a compound of formula (I) or a pharmaceutically acceptable salt thereof. In another embodiment there is provided a method of treating viral infections in a subject in need thereof which comprises administering a therapeutically effective amount of a compound of formula (I) or a pharmaceutically acceptable salt thereof. In another embodiment there is provided a method of treating cancer in a subject in need thereof which comprises administering a therapeutically effective amount of a compound of formula (I) or a pharmaceutically acceptable salt thereof. In a further embodiment there is provided a method of treating diseases associated with systemic inflammatory response syndrome in a subject in need thereof which comprises administering a therapeutically effective amount of a compound of formula (I) or a pharmaceutically acceptable salt thereof.

Suitably the subject in need thereof is a mammal, particularly a human.

The invention further provides for a method for inhibiting a bromodomain containing protein which comprises contacting the bromodomain containing protein with a compound of formula (I) or a pharmaceutically acceptable salt thereof.

As used herein the reference to the "treatment" of a particular disease or condition includes the prevention or prophylaxis of such a disease or condition.

Pharmaceutical Compositions/Routes of Administration/Dosages
Compositions

While it is possible that for use in therapy, a compound of formula (I) as well as pharmaceutically acceptable salts thereof may be administered as the raw chemical, it is common to present the active ingredient as a pharmaceutical composition. The compounds of formula (I) and pharmaceutically acceptable salts thereof will normally, but not necessarily, be formulated into pharmaceutical compositions prior to administration to a patient. Accordingly, in another aspect there is provided a pharmaceutical composition comprising a compound of formula (I), ora pharmaceutically acceptable salt thereof, and one or more pharmaceutically acceptable excipients. The compounds of formula (I) and pharmaceutically acceptable salts are as described above. The excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with one or more pharmaceutically acceptable excipients. A pharmaceutical composition comprising a compound of formula (I) or a pharmaceutically acceptable salt thereof may be prepared by, for example, admixture at ambient temperature and atmospheric pressure. The pharmaceutical composition can be used in the treatment of any of the conditions described herein.

In a further aspect the invention is directed to pharmaceutical compositions for the treatment of a disease or condition for which a bromodomain inhibitor is indicated comprising a compound of formula (I) or a pharmaceutically acceptable salt thereof.

Since the compounds of formula (I) are intended for use in pharmaceutical compositions it will be readily understood that they are each preferably provided in substantially pure form, for example, at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.25 mg to 1 g, or from 0.5 mg to 500 mg, or from 1 mg to 100 mg, of a compound of formula (I) or a pharmaceutically acceptable salt thereof.

The compound of formula (I) or a pharmaceutically acceptable salt thereof and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the subject from one organ, or portion of the body, to another organ, or portion of the body. Certain pharmaceutically acceptable excipients may be chosen for their ability to enhance subject compliance.

Suitable pharmaceutically-acceptable excipients include the following types of excipients: carriers, diluents, fillers, binders, disintegrants, lubricants, glidants, granulating agents, coating agents, wetting agents, solvents, co-solvents, suspending agents, emulsifiers, sweeteners, flavouring agents, flavour-masking agents, colouring agents, anti-caking agents, humectants, chelating agents, plasticisers, viscosity increasing agents, antioxidants, preservatives, stabilisers, surfactants, and buffering agents. The skilled artisan will appreciate that certain pharmaceutically-acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one embodiment the pharmaceutical composition is adapted for parenteral administration, particularly intravenous administration.

In one embodiment the pharmaceutical composition is adapted for oral administration.

In one embodiment the pharmaceutical composition is adapted for topical administration.

Pharmaceutical compositions adapted for parenteral administration include aqueous and non-aqueous sterile injection solutions (which may contain anti-oxidants, buffers, bacteriostats and solutes which render the composition isotonic with the blood of the intended recipient) and aqueous and non-aqueous sterile suspensions (which may include suspending agents and thickening agents). The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents (disintegrants) and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrants include starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Compositions for oral administration may be designed to provide a modified release profile so as to sustain or otherwise control the release of the therapeutically active agent.

Where appropriate, dosage unit compositions for oral administration can be microencapsulated. The composition may be prepared to prolong or sustain the release as for example by coating or embedding particulate material in polymers, wax or the like.

For compositions suitable and/or adapted for oral administration, the compound of formula (I) or a pharmaceutically acceptable salt thereof, may be in a particle-size-reduced form e.g. obtained by micronisation. The preferable particle size of the size-reduced (e.g. micronised) compound or salt is defined by a D50 value of about 0.5 to about 10 microns (for example as measured using laser diffraction).

The compounds of formula (I) and pharmaceutically acceptable salts thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of the compound of formula (I), or a pharmaceutically acceptable salt thereof, by weight of the composition.

For treatments of the eye or other external tissues, for example mouth and skin, the compositions are preferably applied as a topical ointment, cream, gel, spray or foam. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent. Compositions to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfate anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situgellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) *Adv. Drug Deliv.*

Rev. 3; 57:1595-639, herein incorporated by reference for purposes of its teachings of examples of polymers for use in ocular drug delivery.

Dosage forms for nasal or inhaled administration may conveniently be formulated as aerosols, solutions, suspensions, gels or dry powders.

For compositions suitable and/or adapted for inhaled administration, it is preferred that the compound of formula (I) or a pharmaceutically acceptable salt thereof, is in a particle-size-reduced form e.g. obtained by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metal salt of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in International Patent Application Publication No. WO 2005/044354 A1.

A therapeutically effective amount of a compound of formula (I) or a pharmaceutically acceptable salt thereof, will depend upon a number of factors including, for example, the age and weight of the patient, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 mg to 3000 mg, more preferably 0.5 mg to 1000 mg, of a compound of formula (I) or a pharmaceutically acceptable salt thereof, calculated as the free base. Each dosage unit for nasal or inhaled administration preferably contains from 0.001 mg to 50 mg, more preferably 0.01 mg to 5 mg, of a compound of the formula (I) or a pharmaceutically acceptable salt thereof, calculated as the free base.

The pharmaceutically acceptable compounds of formula (I) and pharmaceutically acceptable salts thereof, can be administered in a daily dose (for an adult patient) of, for example, an oral or parenteral dose of 0.01 mg to 3000 mg per day, 0.5 mg to 1000 mg per day or 100 mg to 2500 mg per day, or a nasal or inhaled dose of 0.001 mg to 50 mg per day or 0.01 mg to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof may be employed alone or in combination with other therapeutic agents. Combination therapies according to the present invention thus comprise the administration of at least one compound of formula (I) or a pharmaceutically acceptable salt thereof, and the use of at least one other therapeutically active agent. The compound(s) of formula (I) and pharmaceutically acceptable salts thereof, and the other therapeutically active agent(s) may be administered together in a single pharmaceutical composition or separately and, when administered separately this may occur simultaneously or sequentially in any order. The amounts of the compound(s) of formula (I) and pharmaceutically acceptable salts thereof, and the other therapeutically active agent(s) and the relative timings of administration will be selected in order to achieve the desired combined therapeutic effect. Thus in a further aspect, there is provided a combination comprising a compound of formula (I) or a pharmaceutically acceptable salt thereof, together with one or more other therapeutically active agents.

Thus in one aspect, the compound of formula (I) or a pharmaceutically acceptable salt thereof, and pharmaceutical compositions comprising a compound of formula (I) or a pharmaceutically acceptable salt thereof, according to the invention may be used in combination with or include one or more other therapeutic agents, for example selected from antibiotics, anti-virals, glucocorticosteroids, muscarinic antagonists, beta-2 agonists and Vitamin D3 analogues. In a further embodiment a compound of formula (I) or a pharmaceutically acceptable salt thereof may be used in combination with a further therapeutic agent which is suitable for the treatment of cancer. Examples of such further therapeutic agents are described in Cancer Principles and Practice of Oncology by V. T. Devita and S. Hellman (editors), 6$^{th}$ edition (2001), Lippincott Williams & Wilkins Publishers. A person of ordinary skill in the art would be able to discern which combinations of agents would be useful based on the particular characteristics of the drugs and the cancer involved. Further therapeutic agents to be used in combination with the compound of formula (I) or a pharmaceutically acceptable salt thereof include, but are not limited to, anti-microtubule agents (such as diterpenoids and vinca alkaloids); platinum coordination complexes; alkylating agents (such as nitrogen mustards, oxazaphosphorines, alkylsulphonates, nitrosoureas, and triazenes); antibiotic agents (such as anthracyclins, actinomycins and bleomycins); topoisomerase II inhibitors (such as epipodophyllotoxins); antimetabolites (such as purine and pyrimidine analogues and anti-folate compounds); topoisomerase I inhibitors (such as camptothecins; hormones and hormonal analogues); signal transduction pathway inhibitors (such as tyropsine receptor inhibitors); non-receptor tyrosine kinase angiogenesis inhibitors; immunotherapeutic agents (such as PD-1 inhibitors, including nivolumab and pembrolizumab, and CTLA-4 inhibitors, including ipilimumab); proapoptotic agents; epigenetic or transcriptional modulators (such as histone deacetylase inhibitors) and cell cycle signaling inhibitors.

It will be appreciated that when the compound of formula (I) or a pharmaceutically acceptable salt thereof, is administered in combination with other therapeutic agents normally administered by the inhaled, intravenous, oral or intranasal route, that the resultant pharmaceutical composition may be administered by the same routes. Alternatively the individual components of the composition may be administered by different routes.

It will be clear to a person skilled in the art that, where appropriate, the other therapeutic agent(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic agent. It will be clear also that, where appropriate, the therapeutic agents may be used in optically pure form.

The combinations referred to above may conveniently be presented for use in the form of a pharmaceutical composition and thus pharmaceutical compositions comprising a combination as defined above together with a pharmaceutically acceptable excipient represent a further aspect of the invention.

General Synthetic Routes

The compounds of the invention may be made by a variety of methods. Any previously defined variable will continue to have the previously defined meaning unless otherwise indicated. Illustrative general synthetic methods are set out in the following schemes, and can be readily adapted to prepare other compounds of the invention. Specific compounds of the invention are prepared in the Examples section.

Compounds of formula (I) may be prepared as described in any of the Schemes below:

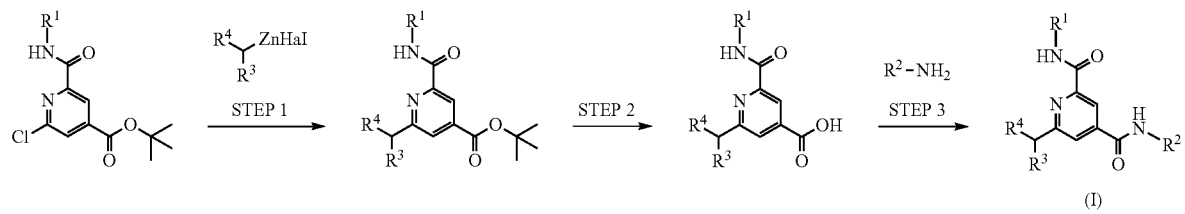

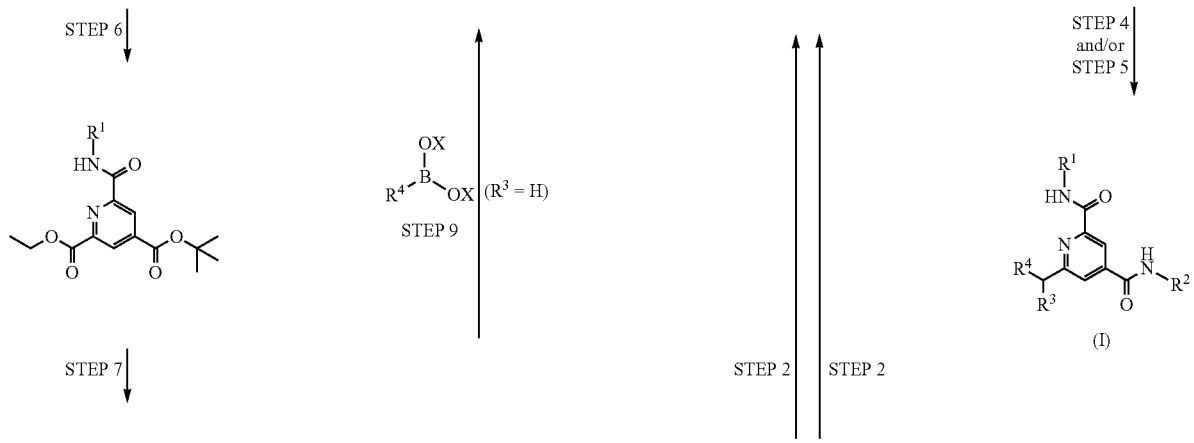

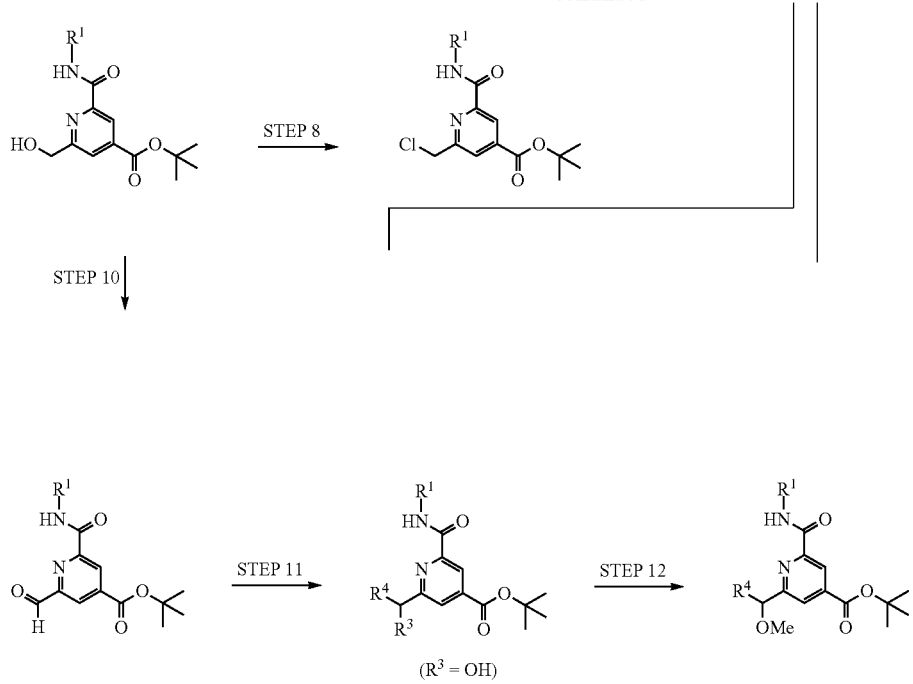

wherein R¹, R², R³ and R⁴ are as described above, Hal is chlorine or bromine and X is either H or joined together to form a cyclic boronate ester, such as —C(Me)₂C(Me)₂-.

In respect of the steps shown in Scheme 1 above the following reaction conditions may be utilised:

Step 1: is a Negishi cross coupling and may be carried out using a benzylzinc halide of formula R⁴CH(R³)ZnHal, in the presence of a palladium catalyst, such as PdCl₂(PPh₃)₂, optionally in the presence of an alternative phosphine ligand, in a suitable solvent, such as THF, at a suitable temperature, such as 70° C.

Step 2: is an acid or base-mediated ester cleavage and may be carried out using any suitable acid, such as TFA or any suitable base, such as NaOH, optionally in a suitable solvent, such as DCM or MeOH, at a suitable temperature, such as room temperature.

Step 3: is an amide coupling reaction and may be carried out using an amine reagent, R²—NH₂, in the presence of a suitable tertiary amine, such as triethylamine or DIPEA, in the presence of a suitable amide coupling reactant, such as HATU, in a suitable solvent, such as DCM or DMF, at a suitable temperature, such as room temperature.

Step 4: is an optional deprotection step to remove a protecting group, such as BOC and may be carried out using an acid such as TFA or HCl, in the presence of a suitable solvent, such as DCM or 1,4-dioxane, at a suitable temperature, such as room temperature.

Step 5: is an optional chiral separation, using a suitable chiral HPLC column and a suitable solvent system.

Step 6: is a carbonylation reaction and may be carried out using an alcohol reagent, such as EtOH, in the presence of a tertiary amine, such as triethylamine, in the presence of a palladium catalyst, such as [(R)-(+)-2,2'-bis(diphenylphosphino)-1,1'-binaphthyl]palladium(II) chloride, optionally in the presence of an alternative phosphine ligand, in the presence of carbon monoxide, in a suitable solvent, such as DMF, at a suitable temperature, such as 70° C.

Step 7: is a reduction and may be carried out using a reducing agent or combination of reagents, such as sodium borohydride and calcium chloride, in a suitable solvent or solvent mixture, such as ethanol and 2-MeTHF, at a suitable temperature, such as 0° C. to room temperature.

Step 8: is a chlorination reaction and may be carried out using a chlorinating reagent, such as thionyl chloride, in the presence of a suitable solvent, such as DCM, at a suitable temperature, such as room temperature.

Step 9: is a cross-coupling reaction, such as a Suzuki coupling and may be carried out using an arylmetal species, such as a arylboronic acid or arylboronate ester, R⁴—B(OX)₂ in the presence of a suitable palladium catalyst, such as PdCl₂(PPh₃)₂, optionally in the presence of an alternative phosphine ligand, in the presence of a suitable base, such as potassium carbonate, in the presence of a suitable solvent or solvent mixture, such as 1,4-dioxane and water, at a suitable temperature, such as 120° C.

Step 10: is an oxidation and may be carried out using a suitable oxidant, such as Dess-Martin periodinane in a suitable solvent, such as DCM, at a suitable temperature, such as room temperature.

Step 11: is a Grignard addition to an aldehyde, using a suitable Grignard reagent, such as phenylmagnesium bromide, in a suitable solvent, such as THF, at a suitable temperature, such as 0° C.

Step 12: is an alkylation reaction, such as a methylation, using a suitable alkylating reagent, such as Meerwein's salt, in the presence of a suitable base, such as Proton Sponge®, in a suitable solvent, such as dichloromethane, at a suitable temperature, such as room temperature.

Scheme 2

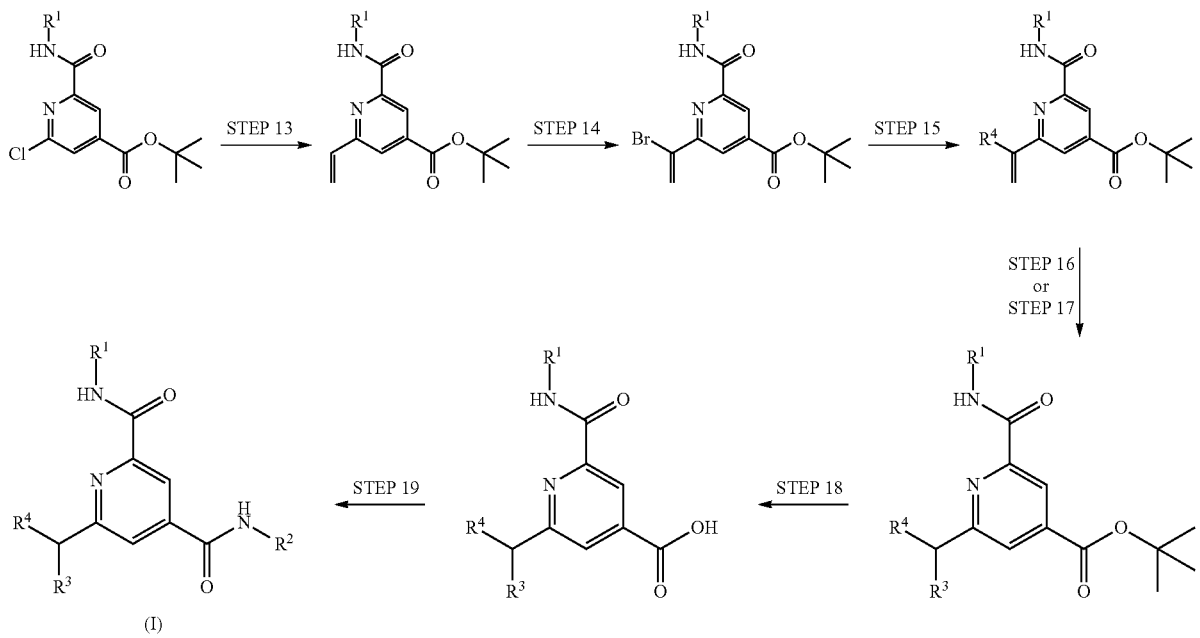

In respect of the steps shown in Scheme 2 above the following reaction conditions may be utilised:

Step 13: is a cross-coupling reaction, such as a Suzuki coupling and may be carried out using an arylmetal species, such as trivinylcyclotriboroxane pyridine complex in the presence of a suitable palladium catalyst, such as $PdCl_2(dppf)$, optionally in the presence of an alternative phosphine ligand, in the presence of a suitable base, such as potassium carbonate, in the presence of a suitable solvent or solvent mixture, such as ethanol and toluene, at a suitable temperature, such as 120° C., optionally using microwave irradiation.

Step 14: is a two step bromination/elimination reaction, the first step may be carried out using a suitable brominating reagent, such as bromine in the presence of a suitable solvent or solvent mixture, such as dichloromethane, at a suitable temperature, such as room temperature; the second step may be carried out using a suitable base, such as potassium hydroxide, in a suitable solvent, such as EtOH, at a suitable temperature, such as 50° C.

Step 15: is a cross-coupling reaction, such as a Suzuki coupling and may be carried out using an arylmetal species, such as an arylboronic acid or arylboronate ester, $R^4$—$B(OX)_2$ in the presence of a suitable palladium catalyst, such as PEPPSI-iPr, optionally in the presence of an alternative phosphine ligand, in the presence of a suitable base, such as tripotassium phosphate, in the presence of a suitable solvent or solvent mixture, such as 1,4-dioxane and water, at a suitable temperature, such as room temperature Step 16: is a hydrogenation reaction and may be carried out under a hydrogen atmosphere in the presence of a suitable metal catalyst, such as 10% Pd/C in the presence of a suitable solvent, such as EtOH, at a suitable temperature, such as room temperature.

Step 17: is a hydroboration reaction and may be carried out using a suitable hydroboration reagent, such as (2,3-dimethylbutan-2-yl)borane, in the presence of a suitable solvent, such as THF, at a suitable temperature, such as 0° C., with a suitable oxidative work up, such as the addition of water, hydrogen peroxide and sodium hydroxide, at a suitable temperature, such as 0° C. to room temperature.

Step 18: is an acid or base-mediated ester cleavage and may be carried out using any suitable acid, such as TFA or any suitable base, such as NaOH, optionally in a suitable solvent, such as DCM or MeOH, at a suitable temperature, such as room temperature.

Step 19: is an amide coupling reaction and may be carried out using an amine reagent, $R^2$—$NH_2$, in the presence of a suitable tertiary amine, such as triethylamine or DIPEA, in the presence of a suitable amide coupling reactant, such as HATU, in a suitable solvent, such as DCM or DMF, at a suitable temperature, such as room temperature.

It will be appreciated by those skilled in the art that it may be advantageous to protect one or more functional groups of the compounds described above. Examples of protecting groups and the means for their removal can be found in T. W. Greene 'Protective Groups in Organic Synthesis' (4th edition, J. Wiley and Sons, 2006), incorporated herein by reference as it relates to such procedures.

Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by acid mediated cleavage (e.g. using an acid such as hydrochloric acid in 1,4-dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—C(O)CF$_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain intermediate compounds described above form a yet further aspect of the invention.

General Methods

General Experimental Details

As used herein the symbols and conventions used in these processes, schemes and examples are consistent with those used in the contemporary scientific literature, for example, the Journal of the American Chemical Society. Unless otherwise noted, all starting materials were obtained from commercial suppliers and used without further purification. Specifically, the following abbreviations may be used in the examples and throughout the specification:

Abbreviations
AcOH acetic acid
BBr$_3$ boron tribromide
BH$_3$.THF borane tetrahydrofuran complex
BOC/Boc tert-butyloxycarbonyl
Boc$_2$O di-tert-butyl dicarbonate
BuLi butyllithium
Cs$_2$CO$_3$ cesium carbonate
CHCl$_3$ chloroform
Cobalt carbonyl dicobalt octacarbonyl
CV column volume
DCM dichloromethane
DIAD diisopropyl azodicarboxylate
DIBAL-H diisobutylaluminium hydride
DIPEA diisopropylethylamine
DMAP 4-dimethylaminopyridine
DMF dimethylformamide
DMSO dimethylsulfoxide
DMSO-d$_6$ deuterated dimethylsulfoxide
DPPA diphenylphosphoryl azide
dppb 1,4-bis(diphenylphosphino)butane
EDC 1-ethyl-3-(3-dimethylaminopropyl)carbodiimide
Et$_3$N triethylamine
EtOAc ethyl acetate
h hour(s)
HATU O-(7-azabenzotriazol-1-yl)-N,N,N',N'-tetramethyluronium hexafluorophosphate
HCl hydrochloric acid
HCO$_2$H formic acid
IPA isopropyl alcohol
Isolera Biotage® Flash purification system
KCN potassium cyanide
K$_2$CO$_3$ potassium carbonate
KI potassium iodide
KOH potassium hydroxide
LCMS liquid chromatography-mass spectrometry
LiBH$_4$ lithium borohydride
LiCl lithium chloride
LiHMDS lithium hexamethyldisilazide
LiOH lithium hydroxide
M molar (concentration)
MDAP mass directed autopreparative chromatography
MeCN acetonitrile
Meerwein's salt trimethyloxonium tetrafluoroborate
MeI methyl iodide
MeOH methanol
2-MeTHF 2-methyltetrahydrofuran
MgSO$_4$ magnesium sulphate
min minute(s)
Ms-Cl methanesulfonyl chloride
MTBE methyl tert-butyl ether
N normal (concentration)
N$_2$ nitrogen gas
NaBH$_4$ sodium borohydride
NaCN sodium cyanide
NaCNBH$_3$ sodium cyanoborohydride
Na$_2$CO$_3$ sodium carbonate
NaI sodium iodide
NaH sodium hydride
NaHCO$_3$ sodium bicarbonate
NaOH sodium hydroxide
Na(OAc)$_3$BH sodium triacetoxyborohydride
Na$_2$SO$_4$ sodium sulphate
NBS N-bromosuccinimide
NH$_3$ ammonia
NMP N-methyl-2-pyrrolidone
NUT nuclear protein in testis
obs obscured
Pd/C palladium on carbon
PdCl$_2$(dppf) (diphenylphosphino)ferrocene]palladium(II) dichloride
PdCl$_2$(PPh$_3$)$_2$ bis(triphenylphosphine)palladium(II) dichloride
PEPPSI iPr [1,3-bis(2,6-Diisopropylphenyl)imidazol-2-ylidene](3-chloropyridyl)palladium(II) dichloride
PPh$_3$ triphenylphosphine
Proton Sponge® N$^1$,N$^1$,N$^3$,N$^3$-tetramethylnaphthalene-1,8-diamine
RBF round bottomed flask
Rt retention time
rt room temperature
sat saturated
SCX Isolute strong cation exchange sorbent SPE
SiO$_2$ silicon dioxide
SNAP/SNAP Ultra Biotage® (silica) flash chromatography cartridge
SP4 Biotage® Flash purification system
SPE solid phase extraction
Tf$_2$O trifluoromethanesulfonic anhydride
TFA trifluoroacetic acid
THF tetrahydrofuran
TLC Thin layer chromatography
UPLC ultra performance liquid chromatography
XantPhos 1,1'-(9,9-dimethyl-9H-xanthene-4,5-diyl)bis[1,1-diphenylphosphine The names of the following compounds have been obtained using the compound naming programme "ACD Name Pro 6.02" or using the naming functionality of ChemDraw Ultra 12.0.

LCMS Methodology

Formic Method

LC conditions

The UPLC analysis was conducted on an Acquity UPLC CSH C18 column (50 mm×2.1 mm, i.d. 1.7 μm packing diameter) at 40° C.

The solvents employed were:
A=0.1% v/v solution of formic acid in water
B=0.1% v/v solution of formic acid in acetonitrile
The gradient employed was:

| Time (min) | Flow rate (mL/min) | % A | % B |
|---|---|---|---|
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.

MS Conditions
MS: Waters ZQ
Ionisation mode: Alternate-scan positive and negative electrospray
Scan range: 100 to 1000 AMU
Scan time: 0.27 sec
Inter scan delay: 0.10 sec
High pH Method
LC Conditions The UPLC analysis was conducted on an Acquity UPLC CSH C18 column (50 mm×2.1 mm, i.d. 1.7 µm packing diameter) at 40° C.

The solvents employed were:
A=10 mM ammonium hydrogen carbonate in water adjusted to pH10 with ammonia solution
B=acetonitrile
The gradient employed was:

| Time (min) | Flow rate (mL/min) | % A | % B |
|---|---|---|---|
| 0 | 1 | 97 | 3 |
| 0.05 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.

MS Conditions
MS: Waters ZQ
Ionisation mode: Alternate-scan positive and negative electrospray
Scan range: 100 to 1000 AMU
Scan time: 0.27 sec
Inter scan delay: 0.10 sec
TFA Method
LC Conditions The UPLC analysis was conducted on an Acquity UPLC CSH C18 column (50 mm×2.1 mm, i.d. 1.7 µm packing diameter) at 40° C.

The solvents employed were:
A=0.1% v/v solution of trifluoroacetic acid in water
B=0.1% v/v solution of trifluoroacetic acid in acetonitrile
The gradient employed was:

| Time (min) | Flow rate (mL/min) | % A | % B |
|---|---|---|---|
| 0 | 1 | 95 | 5 |
| 1.5 | 1 | 5 | 95 |
| 1.9 | 1 | 5 | 95 |
| 2.0 | 1 | 95 | 5 |

The UV detection was a summed signal from wavelength of 210 nm to 350 nm.

MS Conditions
MS: Waters ZQ
Ionisation mode: Alternate-scan positive and negative electrospray
Scan range: 100 to 1000 AMU
Scan time: 0.27 sec
Inter scan delay: 0.10 sec General MDAP Purification Methods Listed below are examples of mass-directed autopreparative chromatography (MDAP) methods that have been used or may be used in compound purification.

MDAP (High pH). The HPLC analysis was conducted on an Xselect CSH C18 column (150 mm×30 mm i.d. 5 µm packing diameter) at ambient temperature, eluting with 10 mM ammonium bicarbonate in water adjusted to pH 10 with ammonia solution (Solvent A) and acetonitrile (Solvent B) using an elution gradient of between 0 and 100% Solvent B over 15 or 25 min.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

MDAP (Formic). The HPLC analysis was conducted on an Xselect CSH C18 column (150 mm×30 mm i.d. 5 µm packing diameter) at ambient temperature, eluting with 0.1% formic acid in water (Solvent A) and 0.1% formic acid in acetonitrile (Solvent B) using an elution gradient of between 0 and 100% solvent B over 15 or 25 min.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

MDAP (TFA). The HPLC analysis was conducted on an Xselect CSH C18 column (150 mm×30 mm i.d. 5 µm packing diameter) at ambient temperature, eluting with 0.1% v/v solution of trifluoroacetic acid in water (Solvent A) and 0.1% v/v solution of trifluoroacetic acid in acetonitrile (Solvent B) using an elution gradient of between 0 and 100% solvent B over 15 or 25 min.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

NMR

Spectra were run on either a 400 MHz or 600 MHz NMR machine at 302 K.

Intermediates:

Intermediate 1: (1R,5S,6r)-3-Oxabicyclo[3.1.0]hexane-6-carboxylic acid

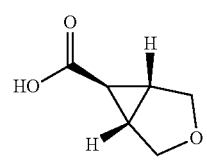

LiOH (751 mg, 31.4 mmol) was added to a solution of (1R,5S,6r)-ethyl 3-oxabicyclo[3.1.0]hexane-6-carboxylate (1000 mg, 6.27 mmol, commercially available from, for example, Pharmablock) in water (10 mL), THF (10 mL) and MeOH (10 mL) at rt. The resulting suspension was stirred for 3 h. For work-up, the mixture was evaporated, the remaining crude solid was dissolved in a minimum amount of water, and quenched with HCl (5 mL, 25% m/m), and extracted 4 times with MeOH/DCM solvent, the combined organic phases were dried over a hydrophobic frit, evaporated in vacuo, to yield the desired compound (1R,5S,6r)-3-oxabicyclo[3.1.0]hexane-6-carboxylic acid (750 mg, 5.85 mmol, 93% yield)

$^1$H NMR (400 MHz, DMSO-d$_6$) δ ppm 12.13 (s, 1H) 3.80 (d, J=8.6 Hz, 2H) 3.62 (d, J=8.6 Hz, 2H) 2.00-2.15 (m, 2H) 1.32 (t, J=3.1 Hz, 1H)

Intermediate 2: Benzyl (1R,5S,6r)-3-oxabicyclo[3.1.0]hexan-6-ylcarbamate

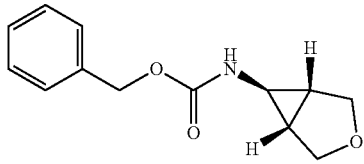 [SMILES: O=C(N[C@H]1[C@@H]2COC[C@@H]21)OCc1ccccc1]

(1R,5S,6r)-3-Oxabicyclo[3.1.0]hexane-6-carboxylic acid (340 mg, 2.65 mmol) was dissolved in toluene (12 mL), then Et$_3$N (1.110 mL, 7.96 mmol), diphenyl phosphorazidate (0.686 mL, 3.18 mmol) and benzyl alcohol (0.552 mL, 5.31 mmol) were added and the mixture was heated at reflux for 2 h. The solution was diluted with EtOAc (10 mL) and washed with water (10 mL) and NaHCO$_3$ solution (10 mL), the organic layer was dried and evaporated and the residue purified by chromatography on a 25 g silica column eluting with 0-50% EtOAc/cyclohexane and the product-containing fractions were evaporated in vacuo to give benzyl (1R,5S,6r)-3-oxabicyclo[3.1.0]hexan-6-ylcarbamate (460 mg, 1.972 mmol, 74.3% yield) as a white solid.

LCMS (2 min Formic): Rt=0.83 min, [MH]$^+$=234.3.

$^1$H NMR (400 MHz, CDCl$_3$) δ ppm 7.29-7.41 (m, 5H) 5.11 (br. s., 2H) 4.86 (br. s., 1H) 3.98 (d, J=8.3 Hz, 2H) 3.72 (d, J=8.6 Hz, 2H) 2.45-2.52 (m, 1H) 1.80 (br. s, 2H)

Intermediate 3: (1R,5S,6r)-3-Oxabicyclo[3.1.0]hexan-6-amine, hydrochloride

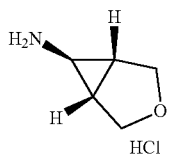

Benzyl (1R,5S,6r)-3-oxabicyclo[3.1.0]hexan-6-ylcarbamate (460 mg, 1.972 mmol) was dissolved in EtOH (20 mL) and the reaction was hydrogenated using an H-cube (settings: rt, 1 bar, 1 mL/min flow rate) and 10% Pd/C CatCart 30 as the catalyst. The reaction was cycled though the H-Cube for 1.5 h before acidifying the mixture with HCl (7M aqueous, 1.332 mL, 9.86 mmol) and evaporating in vacuo to yield an oily solid. The solid was dried in vacuo over 2 days to yield the desired product (1R,5S,6r)-3-oxabicyclo[3.1.0]hexan-6-amine, hydrochloride (262 mg, 1.836 mmol, 93% yield) as an off-white solid.

$^1$H NMR (400 MHz, DMSO-d$_6$) δ ppm 8.48 (br. s., 3H) 3.80 (d, J=8.8 Hz, 2H) 3.59 (d, J=8.6 Hz, 2H) 2.24 (t, J=2.3 Hz, 1H) 2.07 (t, J=2.6 Hz, 2H).

Intermediate 4: (+/−)-Ethyl 2-(4-benzylmorpholin-2-yl)acetate

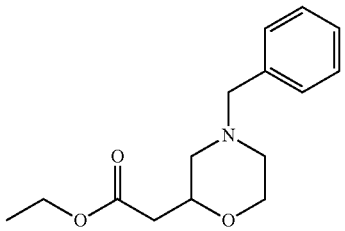 [SMILES: CCOC(=O)CC1CN(Cc2ccccc2)CCO1]

A mixture of 2-(benzylamino)ethanol (6.57 mL, 46.3 mmol, commercially available from, for example, Sigma-Aldrich) and Et$_3$N (6.45 mL, 46.3 mmol) in water (40 mL) was heated to reflux. (E)-Ethyl 4-bromobut-3-enoate (8.5 mL, 49.4 mmol, commercially available from, for example, Fluorochem) was added dropwise and the reaction mixture was heated at reflux for 2 h. The reaction mixture was cooled to rt and NaOH (2M solution, 10 mL, 20.00 mmol) was added. The reaction mixture was partitioned between EtOAc and water. The organic layer was separated and the aqueous layer further extracted with EtOAc (2×30 mL). The combined organic layers were dried (Na$_2$SO$_4$) and concentrated to give ~11 g of brown oil. This was purified by chromatography on SiO$_2$ (Biotage® SNAP 340 g cartridge, eluting with 5-50% EtOAc/cyclohexane) The appropriate fractions were combined and concentrated to give the desired product (4.17 g) as a pale yellow oil.

LCMS (2 min Formic): Rt=0.43 min, [MH]$^+$=264.2.

Intermediate 5: (+/−)-Ethyl 2-(morpholin-2-yl)

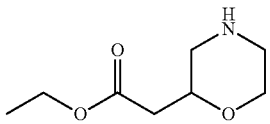

To a solution of ethyl 2-(4-benzylmorpholin-2-yl)acetate (3.15 g, 11.96 mmol) in EtOH (70 mL) was added ammonium formate (3.77 g, 59.8 mmol) and 10% Pd/C (3.82 g, 35.9 mmol). The reaction mixture was stirred at rt under N$_2$ overnight.

Separately, to a solution of ethyl 2-(4-benzylmorpholin-2-yl)acetate (375 mg, 1.424 mmol) in EtOH (10 mL) was added ammonium formate (449 mg, 7.12 mmol) and 10% Pd/C (555 mg, 5.21 mmol). The reaction mixture was stirred at rt under N$_2$ overnight.

The two reaction mixtures were combined and filtered though Celite®. The filtrate was concentrated in vacuo to give ethyl 2-(morpholin-2-yl)acetate (2.45 g, 12.02 mmol) as an off-white gummy solid which was used as is in subsequent reactions.

$^1$H NMR (400 MHz, DMSO-d$_6$) δ ppm 4.05 (q, J=7.1 Hz, 2H) 3.67-3.82 (m, 2H) 3.46 (td, J=11.3, 2.8 Hz, 1H) 2.87 (br. d, J=12.2 Hz, 1H) 2.75 (br. d, J=12.5 Hz, 1H) 2.60-2.70 (m, 1H) 2.40-2.48 (m, 2H) 2.34 (dd, J=15.7, 8.6 Hz, 1H) 1.17 (t, J=7.1 Hz, 3H)

Intermediate 6: (+/−)-tert-Butyl 2-(2-ethoxy-2-oxo-ethyl)morpholine-4-carboxylate

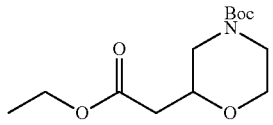 [SMILES: CCOC(=O)CC1CN(C(=O)OC(C)(C)C)CCO1]

To a solution of ethyl 2-(morpholin-2-yl)acetate (2.45 g, 14.14 mmol) in DCM (30 mL) was added Et$_3$N (3.94 mL, 28.3 mmol), Boc$_2$O (4.93 mL, 21.22 mmol) and DMAP (0.086 g, 0.707 mmol) and the reaction mixture stirred under N$_2$ at rt overnight. The reaction mixture was partitioned between DCM and 1M HCl. The organic layer was separated, washed with sat. NaHCO$_3$ solution, dried (Na$_2$SO$_4$) and then concentrated to give 3.03 g of an orange oil.

$^1$H NMR (400 MHz, MeOH-d$_4$) δ ppm 4.14 (q, J=7.1 Hz, 2H) 3.95 (dt, J=13.0, 1.9 Hz, 1H) 3.71-3.87 (m, 3H) 3.49 (td, J=11.7, 2.8 Hz, 1H) 2.86-3.00 (m, 1H) 2.60-2.77 (m, 1H) 2.49 (dd, J=6.6, 1.5 Hz, 2H) 1.47 (s, 9H) 1.25 (t, J=7.1 Hz, 3H)

Intermediate 7: (+/−)-tert-Butyl 2-(2-hydroxyethyl)morpholine-4-carboxylate

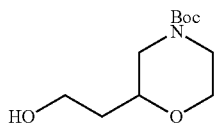 [SMILES: CC(C)(C)OC(=O)N1CCOC(CCO)C1]

tert-Butyl 2-(2-ethoxy-2-oxoethyl)morpholine-4-carboxylate (2.8 g, 10.24 mmol) was dissolved in THF (50 mL) and LiBH$_4$ (0.893 g, 41.0 mmol) was added, then the mixture was stirred over the weekend. The reaction mixture was cooled in an ice bath and quenched with saturated ammonium chloride solution (50 mL), then stirred for 1 h and extracted with EtOAc (2×100 mL). The combined organics were dried over Na$_2$SO$_4$ and evaporated in vacuo to give tert-butyl 2-(2-hydroxyethyl)morpholine-4-carboxylate (2.2 g, 9.51 mmol, 93% yield) as a colourless gum.

$^1$H NMR (400 MHz, CDCl$_3$) δ ppm 3.74-4.02 (m, 5H) 3.44-3.65 (m, 2H) 2.84-3.01 (m, 1H) 2.56-2.76 (m, 1H) 1.63-1.83 (m, 2H) 1.47 (s, 9H)

Intermediate 8: (+/−)-tert-Butyl 2-(2-((methylsulfonyl)oxy)ethyl)morpholine-4-carboxylate

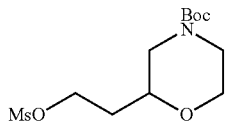 [SMILES: CC(C)(C)OC(=O)N1CCOC(CCOS(C)(=O)=O)C1]

Ms-Cl (0.815 mL, 10.46 mmol) was added to a solution of tert-butyl 2-(2-hydroxyethyl)morpholine-4-carboxylate (2.2 g, 9.51 mmol) and Et$_3$N (1.458 mL, 10.46 mmol) in DCM (50 mL) at 0° C. The resulting mixture was stirred at 0° C. for 1 h, then washed with water (50 mL). The organic layer was dried and evaporated in vacuo to give tert-butyl 2-(2-((methylsulfonyl)oxy)ethyl)morpholine-4-carboxylate (3.0 g, 9.70 mmol, 102% yield) as a pale yellow gum.

$^1$H NMR (400 MHz, CDCl$_3$) δ ppm 4.30-4.44 (m, 2H) 3.78-4.00 (m, 3H) 3.45-3.57 (m, 2H) 3.01 (s, 3H) 2.85-2.98 (m, 1H) 2.56-2.72 (m, 1H) 1.78-1.98 (m, 2H) 1.47 (s, 9H)

Intermediate 9: (+/−)-tert-Butyl 2-(2-cyanoethyl)morpholine-4-carboxylate

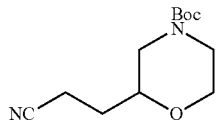

tert-Butyl 2-(2-((methylsulfonyl)oxy)ethyl)morpholine-4-carboxylate (3.0 g, 9.70 mmol) was dissolved in DMSO (30 mL), then KI (1.610 g, 9.70 mmol) and KCN (0.947 g, 14.55 mmol) were added and the mixture was heated at 80° C. for 1 h. The resulting brown suspension was diluted with water (100 mL) and extracted with EtOAc (2×50 mL). The combined organics were washed with water (2×100 mL), dried and evaporated in vacuo and the resulting oil was purified on a 50 g silica column eluting with 0-50% EtOAc/cyclohexane. The product-containing fractions (visualised by ninhydrin) were combined and evaporated in vacuo to give tert-butyl 2-(2-cyanoethyl)morpholine-4-carboxylate (1.42 g, 5.91 mmol, 60.9% yield) as a colourless oil.

$^1$H NMR (400 MHz, CDCl$_3$) δ ppm 3.80-4.00 (m, 3H) 3.39-3.58 (m, 2H) 2.83-3.01 (m, 1H) 2.56-2.71 (m, 1H) 2.50 (t, J=7.2 Hz, 2H) 1.69-1.87 (m, 2H) 1.47 (s, 9H

Intermediate 10: (+/−)-tert-Butyl 2-(3-aminopropyl)morpholine-4-carboxylate

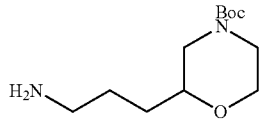 [SMILES: CC(C)(C)OC(=O)N1CCOC(CCCN)C1]

tert-Butyl 2-(2-cyanoethyl)morpholine-4-carboxylate (1.4 g, 5.83 mmol) was dissolved in THF (20 mL) and BH$_3$.THF (1M in THF, 23.30 mL, 23.30 mmol) was added, then the mixture was heated at 70° C. for 2 h. The solution was then cooled in an ice bath and quenched by the cautious addition of MeOH (20 mL) (effervescence) then evaporated in vacuo. The residue was dissolved in MeOH (20 mL), AcOH (2 mL) was added and the solution was stirred for 2 h, then evaporated in vacuo and the residue was purified by chromatography on a 25 g silica column eluting with 0-15% 2M NH$_3$ in MeOH/DCM to give two main ninhydrin-active components. The more polar component was collected to give tert-butyl 2-(3-aminopropyl)morpholine-4-carboxylate (180 mg, 0.737 mmol, 12.64% yield) as a colourless oil. The earlier running component was suspected to be a borane complex. This was collected and evaporated in vacuo to give a colourless oil (0.20 g). The material was dissolved in MeOH (10 mL) and 2M NaOH (10 mL) was added, then the mixture was stirred at reflux for 6 h, then evaporated in vacuo and the residue partitioned between water (10 mL) and DCM (10 mL). The organic layer was dried and evaporated in vacuo to give a colourless oil, which was purified by chromatography on a 10 g SNAP ultra cartridge, eluting with 0-20% 2M NH₃ in MeOHNH₃ in MeOH/DCM to give further desired product (100 mg)

¹H NMR (400 MHz, CDCl₃) δ ppm 3.70-3.97 (m, 3H) 3.44-3.55 (m, 1H) 3.26-3.40 (m, 1H) 2.92 (br. t, J=10.8, 10.8 Hz, 1H) 2.67-2.77 (m, 2H) 2.49-2.66 (m, 1H) 1.39-1.68 (m, 13H).

Intermediate 11: (S)-tert-Butyl 2-(3-ethoxy-3-oxo-prop-1-en-1-yl)morpholine-4-carboxylate, 77:23 mix of E/Z isomers

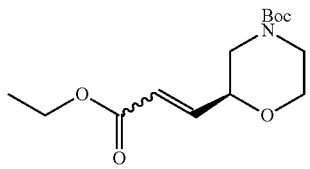 [SMILES: CCOC(=O)C=C[C@H]1CN(C(=O)OC(C)(C)C)CCO1]

(R)-tert-Butyl 2-(hydroxymethyl)morpholine-4-carboxylate (0.5 g, 2.301 mmol, commercially available from, for example, Activate Scientific) was dissolved in DCM (10 mL) and Dess-Martin periodinane (1.171 g, 2.76 mmol) was added, then the solution was stirred at rt for 2 h. The mixture was washed with NaHCO₃ solution (20 mL) and the organic layer dried and evaporated to give a colourless solid—NMR shows presence of desired aldehyde. The crude intermediate was dissolved in toluene (20 mL) and ethyl 2-(triphenylphosphoranylidene)acetate (1.042 g, 2.99 mmol) was added, then the mixture was heated at 90° C. overnight. The resulting suspension was filtered and the filtrate washed with water, then the organic layer was dried and evaporated in vacuo. The residue was purified by chromatography on a 25 g silica column eluting with 0-50% EtOAc/cyclohexane and the product-containing fractions were evaporated in vacuo to give (S)-tert-butyl 2-(3-ethoxy-3-oxoprop-1-en-1-yl)morpholine-4-carboxylate (0.45 g, 1.577 mmol, 68.5% yield) as a colourless gum and as a mixture of Z and E isomers which was used in the next step.

¹H NMR (400 MHz, CDCl₃) δ ppm 6.83 (dd, J=15.8, 4.3 Hz, 1H) 6.06-6.18 (m, 1.3H) 5.87 (dd, J=11.7, 1.5 Hz, 0.3H) 4.15-4.30 (m, 2.6H) 3.78-4.12 (m, 5.2H) 3.51-3.65 (m, 1.3H) 2.97 (br. t, J=10.6, 10.6 Hz, 1.3H) 2.56-2.77 (m, 1.3H) 1.48 (s, 11.7H) 1.22-1.36 (m, 3.9H)

Intermediate 12: (S)-tert-Butyl 2-(3-ethoxy-3-oxopropyl)morpholine-4-carboxylate

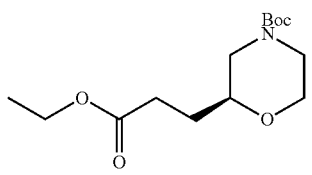 [SMILES: CCOC(=O)CC[C@H]1CN(C(=O)OC(C)(C)C)CCO1]

(S)-tert-butyl 2-(3-ethoxy-3-oxoprop-1-en-1-yl)morpholine-4-carboxylate (0.45 g, 1.577 mmol) was dissolved in EtOH (50 mL) and hydrogenated in an H-Cube on full mode using a Pd/C cat cart at 1 mL/min flow rate. The eluant was evaporated in vacuo to give (S)-tert-butyl 2-(3-ethoxy-3-oxopropyl)morpholine-4-carboxylate (0.40 g, 1.392 mmol, 88% yield) as a colourless gum.

¹H NMR (400 MHz, CDCl₃) δ ppm 4.14 (q, J=7.3 Hz, 2H) 3.74-3.98 (m, 3H) 3.48 (td, J=11.7, 2.8 Hz, 1H) 3.36 (dddd, J=10.4, 7.8, 4.8, 2.7 Hz, 1H) 2.92 (br. t, J=11.1, 11.1 Hz, 1H) 2.60 (br. t, J=9.5, 9.5 Hz, 1H) 2.35-2.53 (m, 2H) 1.70-1.86 (m, 2H) 1.47 (s, 9H) 1.26 (t, J=7.1 Hz, 3H)

Intermediate 13: (S)-tert-Butyl 2-(3-hydroxypropyl)morpholine-4-carboxylate

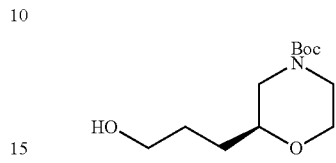

LiBH₄ (0.121 g, 5.57 mmol) was added to a solution of (S)-tert-butyl 2-(3-ethoxy-3-oxopropyl)morpholine-4-carboxylate (0.40 g, 1.392 mmol) in THF (10 mL) at 0° C., then the mixture was stirred overnight, allowing it to warm to rt. The reaction mixture was quenched by the very cautious addition of ammonium chloride solution (20 mL) and extracted with EtOAc (2×20 mL). The combined organics were dried and evaporated in vacuo to give (S)-tert-butyl 2-(3-hydroxypropyl)morpholine-4-carboxylate (0.30 g, 1.223 mmol, 88% yield).

¹H NMR (400 MHz, CDCl₃) δ ppm 3.73-3.99 (m, 3H) 3.58-3.69 (m, 2H) 3.49 (td, J=11.7, 2.8 Hz, 1H) 3.30-3.40 (m, 1H) 2.91 (br. t, J=10.8, 10.8 Hz, 1H) 2.49-2.68 (m, 1H) 2.16-2.40 (m, 1H) 1.62-1.76 (m, 2H) 1.48-1.60 (m, 2H) 1.45 (s, 9H)

Intermediate 14: (S)-tert-Butyl 2-(3-((methylsulfonyl)oxy)propyl)morpholine-4-carboxylate

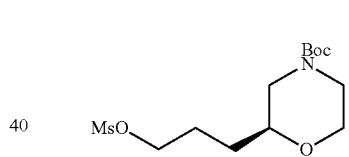

(S)-tert-Butyl 2-(3-hydroxypropyl)morpholine-4-carboxylate (0.30 g, 1.223 mmol) was dissolved in DCM (10 mL) and Et₃N (0.256 mL, 1.834 mmol) and Ms-Cl (0.124 mL, 1.590 mmol) were added. The solution was stirred for 2 h, then washed with water and the organic layer dried and evaporated in vacuo to give (S)-tert-butyl 2-(3-((methylsulfonyl)oxy)propyl)morpholine-4-carboxylate (0.39 g, 1.206 mmol, 99% yield) which was used in the next step immediately.

¹H NMR (400 MHz, CDCl₃) δ ppm 4.20-4.33 (m, 2H) 3.76-3.97 (m, 3H) 3.44-3.57 (m, 1H) 3.30-3.41 (m, 1H) 3.01 (s, 3H) 2.84-2.97 (m, 1H) 2.53-2.67 (m, 1H) 1.78-2.01 (m, 2H) 1.53-1.61 (m, 2H) 1.47 (s, 9H)

Intermediate 15: (S)-tert-Butyl 2-(3-azidopropyl)morpholine-4-carboxylate

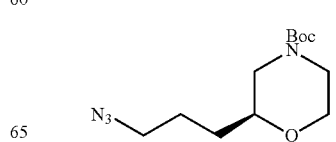

(S)-tert-Butyl 2-(3-((methylsulfonyl)oxy)propyl)morpholine-4-carboxylate (0.39 g, 1.206 mmol) was dissolved in DMF (5 mL) and sodium azide (0.235 g, 3.62 mmol) was added, then the mixture was heated at 80° C. for 2 h. The mixture was diluted with water (20 mL) and extracted with EtOAc (20 mL), the organic layer was washed with water (2×10 mL), dried and evaporated in vacuo to give (S)-tert-butyl 2-(3-azidopropyl)morpholine-4-carboxylate (300 mg, 1.110 mmol, 92% yield) as a colourless gum. The crude product was carried on to the next step without purification.

$^1$H NMR (400 MHz, CDCl$_3$) δ ppm 3.74-3.99 (m, 3H) 3.49 (td, J=11.7, 2.8 Hz, 1H) 3.24-3.40 (m, 3H) 2.85-3.00 (m, 1H) 2.49-2.68 (m, 1H) 1.61-1.85 (m, 2H) 1.45-1.58 (m, 11H)

Intermediate 16: (S)-tert-Butyl 2-(3-aminopropyl)morpholine-4-carboxylate

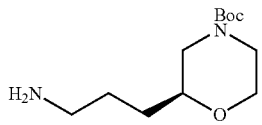 [SMILES: CC(C)(C)OC(=O)N1CCO[C@@H](CCCN)C1]

(S)-tert-Butyl 2-(3-azidopropyl)morpholine-4-carboxylate (300 mg, 1.110 mmol) was dissolved in EtOH (30 mL) and was hydrogenated in an H-Cube on full mode at 1 mL/min flow rate over a Pd/C cat cart. The eluant was evaporated in vacuo to give (S)-tert-butyl 2-(3-aminopropyl)morpholine-4-carboxylate (190 mg, 0.778 mmol, 70.1% yield) which was used in subsequent chemistry.

$^1$H NMR (400 MHz, CDCl$_3$) δ ppm 3.73-3.99 (m, 3H) 3.44-3.57 (m, 1H) 3.27-3.40 (m, 1H) 2.84-3.00 (m, 1H) 2.73 (t, J=6.7 Hz, 2H) 2.51-2.65 (m, 1H) 1.38-1.67 (m, 13H)

Intermediate 17: (R,E)-tert-Butyl 2-(3-ethoxy-3-oxoprop-1-en-1-yl)morpholine-4-carboxylate

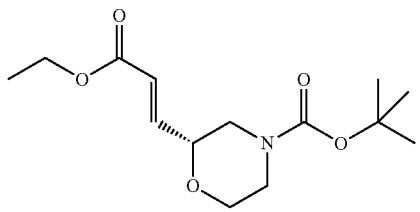 [SMILES: CCOC(=O)/C=C/[C@@H]1CN(C(=O)OC(C)(C)C)CCO1]

(S)-tert-Butyl 2-(hydroxymethyl)morpholine-4-carboxylate (5 g, 23.01 mmol, commercially available from, for example, AOK Chem) was dissolved in DCM (10 mL) and Dess-Martin periodinane (11.71 g, 27.6 mmol) was added, then the solution was stirred at rt for 2 h. The mixture was washed with NaHCO$_3$ solution (20 mL) and the organic layer dried and evaporated to give a colourless solid. NMR shows the presence of the desired aldehyde. The crude intermediate was dissolved in toluene (20 mL) and ethyl 2-(triphenylphosphoranylidene)acetate (10.42 g, 29.9 mmol) was added, then the mixture was heated at 90° C. overnight. The resulting suspension was filtered and the filtrate washed with water, then the organic layer was dried and evaporated in vacuo. The residue was purified by chromatography on a 25 g silica column eluting with 0-50% EtOAc/cyclohexane and the product-containing fractions were evaporated in vacuo to give (R,E)-tert-butyl 2-(3-ethoxy-3-oxoprop-1-en-1-yl)morpholine-4-carboxylate (1.9 g, 6.66 mmol, 28.9% yield) as a colourless gum.

$^1$H NMR (400 MHz, CDCl$_3$) δ ppm 6.84 (dd, J=15.9, 4.2 Hz, 1H) 6.02-6.24 (m, 1H) 4.15-4.34 (m, 2H) 4.02-4.12 (m, 1H) 3.80-3.99 (m, 2H) 3.49-3.67 (m, 1H) 2.98 (t, J=10.6 Hz, 1H) 2.70 (br. s., 1H) 1.49 (s, 9H) 1.26-1.36 (m, 4H)

Intermediate 18: (R)-tert-Butyl 2-(3-ethoxy-3-oxopropyl)morpholine-4-carboxylate

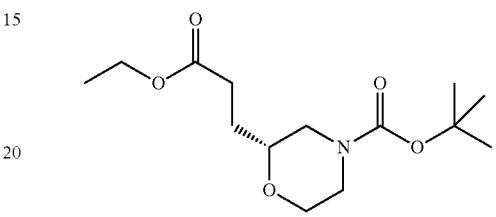

(R,E)-tert-Butyl 2-(3-ethoxy-3-oxoprop-1-en-1-yl)morpholine-4-carboxylate (1.8 g, 6.31 mmol) was dissolved in EtOH (60 mL) and hydrogenated in an H-Cube on full mode at 1 mL/min flow rate over a Pd/C cat cart. The eluant was evaporated in vacuo to give (R)-tert-butyl 2-(3-ethoxy-3-oxopropyl)morpholine-4-carboxylate (1.7 g, 5.92 mmol, 94% yield) as a colourless gum.

$^1$H NMR (400 MHz, CDCl$_3$) δ ppm 4.14 (q, J=7.1 Hz, 2H) 3.73-3.95 (m, 3H) 3.43-3.53 (m, 1H) 3.26-3.40 (m, 1H) 2.86-2.97 (m, 1H) 2.56-2.65 (m, 1H) 2.44 (spt, J=7.5 Hz, 2H) 1.72-1.82 (m, 2H) 1.44-1.48 (m, 9H) 1.26 (t, J=7.1 Hz, 3H)

Intermediate 19: (R)-tert-Butyl 2-(3-hydroxypropyl)morpholine-4-carboxylate

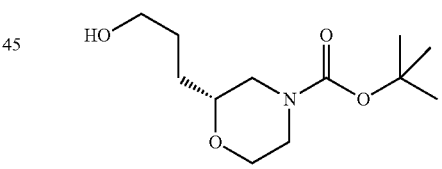

LiBH$_4$ (0.121 g, 5.57 mmol) was added to a solution of (S)-tert-butyl 2-(3-ethoxy-3-oxopropyl)morpholine-4-carboxylate (0.40 g, 1.392 mmol) in THF (10 mL) at 0° C., then the mixture was stirred overnight, allowing it to warm to rt. The reaction mixture was quenched by very cautious addition of ammonium chloride solution (20 mL) and extracted with EtOAc (2×20 mL). The combined organics were dried and evaporated in vacuo to give (S)-tert-butyl 2-(3-hydroxypropyl)morpholine-4-carboxylate (0.30 g, 1.223 mmol, 88% yield).

$^1$H NMR (400 MHz, CDCl$_3$) δ ppm 5.32 (s, 1H) 3.88 (br. s., 3H) 3.75-3.80 (m, 1H) 3.67 (br. d, J=2.2 Hz, 1H) 3.53 (td, J=11.0, 3.0 Hz, 1H) 3.34-3.43 (m, 1H) 2.88-2.99 (m, 1H) 2.57-2.68 (m, 1H) 1.71 (q, J=6.6 Hz, 2H) 1.53-1.62 (m, 2H) 1.48 (s, 9H)

Intermediate 20: (R)-tert-Butyl 2-(3-(methylsulfonyl)oxy)propyl)morpholine-4-carboxylate

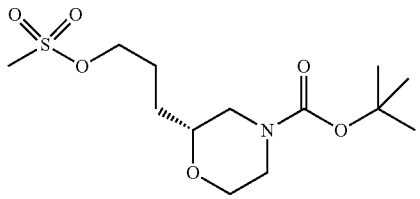 [SMILES: CC(C)(C)OC(=O)N1CCO[C@H](CCCOS(C)(=O)=O)C1]

(R)-tert-Butyl 2-(3-hydroxypropyl)morpholine-4-carboxylate (1.34 g, 5.46 mmol) was dissolved in DCM (10 mL) and Et₃N (1.142 mL, 8.19 mmol) and Ms-Cl (0.553 mL, 7.10 mmol) were added. The solution was stirred for 2 h, then washed with water and the organic layer dried and evaporated in vacuo to give a pale yellow oil. This was purified by chromatography on a 50 g silica column, eluting with 0-100% EtOAc/cyclohexane and the product-containing fractions were evaporated in vacuo to give (R)-tert-butyl 2-(3-((methylsulfonyl)oxy)propyl)morpholine-4-carboxylate (1.22 g, 3.77 mmol, 69.1% yield).

¹H NMR (400 MHz, CDCl₃) δ ppm 4.21-4.35 (m, 2H) 3.76-3.95 (m, 3H) 3.45-3.55 (m, 1H) 3.32-3.41 (m, 1H) 3.02 (s, 3H) 2.84-2.97 (m, 1H) 2.55-2.66 (m, 1H) 1.91-2.02 (m, 1H) 1.78-1.90 (m, 1H) 1.52-1.65 (m, 2H) 1.48 (s, 9H)

Intermediate 21: (R)-tert-Butyl 2-(3-azidopropyl)morpholine-4-carboxylate

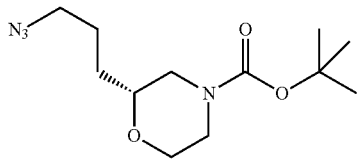 [SMILES: CC(C)(C)OC(=O)N1CCO[C@H](CCCN=[N+]=[N-])C1]

(R)-tert-Butyl 2-(3-((methylsulfonyl)oxy)propyl)morpholine-4-carboxylate (1.2 g, 3.71 mmol) was dissolved in DMF (5 mL) and sodium azide (0.724 g, 11.13 mmol) was added, then the mixture was heated at 80° C. for 2 h. The mixture was diluted with water (20 mL) and extracted with EtOAc (20 mL). The organic layer was washed with water (2×10 mL), dried and evaporated in vacuo to give (R)-tert-butyl 2-(3-azidopropyl)morpholine-4-carboxylate (0.96 g, 3.55 mmol, 96% yield) as a colourless gum.

¹H NMR (400 MHz, CDCl₃) δ ppm 4.12 (q, J=7.3 Hz, 1H) 3.74-3.97 (m, 3H) 3.49 (td, J=11.7, 2.8 Hz, 1H) 3.20-3.41 (m, 2H) 2.89-2.95 (m, 1H) 2.59 (br. s., 1H) 1.60-1.85 (m, 2H) 1.49-1.56 (m, 2H) 1.47 (s, 9H)

Intermediate 22: (R)-tert-Butyl 2-(3-aminopropyl)morpholine-4-carboxylate

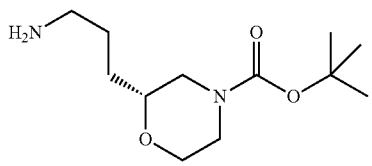 [SMILES: CC(C)(C)OC(=O)N1CCO[C@H](CCCN)C1]

(R)-tert-Butyl 2-(3-azidopropyl)morpholine-4-carboxylate (0.96 g, 3.55 mmol) was dissolved in EtOH (30 mL) and was hydrogenated in an H-Cube on full mode at 1 mL/min flow rate over a Pd/C cat cart. The eluant was evaporated in vacuo to give (R)-tert-butyl 2-(3-aminopropyl)morpholine-4-carboxylate (0.81 g, 3.32 mmol, 93% yield).

¹H NMR (400 MHz, CDCl₃-d) δ ppm 3.70-4.00 (m, 3H) 3.41-3.56 (m, 1H) 3.23-3.40 (m, 2H) 2.79-3.12 (m, 2H) 2.47-2.69 (m, 1H) 1.80-1.98 (m, 1H) 1.25-1.72 (m, 12H)

Intermediate 23: (S)-tert-Butyl 2-(((methylsulfonyl)oxy)methyl)morpholine-4-carboxylate

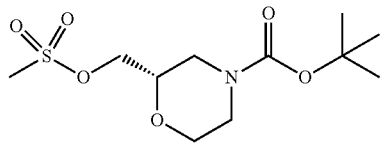 [SMILES: CC(C)(C)OC(=O)N1CCO[C@H](COS(C)(=O)=O)C1]

(S)-tert-Butyl 2-(hydroxymethyl)morpholine-4-carboxylate (commercially available from, for example, Activate Scientific) (3 g, 13.81 mmol) and Et₃N (3.85 mL, 27.6 mmol) were stirred in DCM (30 mL) at 0° C. Ms-Cl (1.614 mL, 20.71 mmol) was added portionwise over 5 min and the reaction stirred at rt for 4 h. The reaction was diluted with further DCM and was washed with 1N HCl (aq), NaHCO₃ (aq) and water, dried using a hydrophobic frit and concentrated to give (S)-tert-butyl 2-(((methylsulfonyl)oxy)methyl)morpholine-4-carboxylate (4.242 g, 14.36 mmol, 104% yield) as a yellow oil which was used crude in next step.

¹H NMR (400 MHz, DMSO-d₆) δ ppm 4.13-4.35 (m, 2H) 3.76-3.95 (m, 2H) 3.71 (br. d, J=13.2 Hz, 1H) 3.62 (br. ddt, J=10.6, 5.9, 3.1, 3.1 Hz, 1H) 3.43 (td, J=11.6, 2.7 Hz, 1H) 3.14-3.31 (m, 3H) 2.62-2.99 (m, 2H) 1.31-1.52 (m, 9H).

Intermediate 24: (R)-tert-Butyl 2-(cyanomethyl)morpholine-4-carboxylate

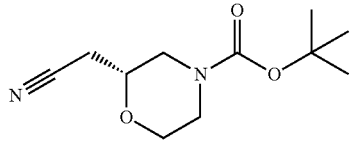 [SMILES: CC(C)(C)OC(=O)N1CCO[C@H](CC#N)C1]

(S)-tert-Butyl 2-(((methylsulfonyl)oxy)methyl)morpholine-4-carboxylate (4.2 g, 14.22 mmol), KCN (0.972 g, 14.93 mmol) and KI (3.54 g, 21.33 mmol) were stirred at 100° C. in DMSO (30 mL) for 4 h. The reaction was diluted with water and extracted with EtOAc, the organic layer was washed with water and brine, dried using a hydrophobic frit and concentrated to a yellow oil. This oil was purified using a SP4 flash chromatography, using a SNAP 50 g Si column and eluting with 0-50% EtOAc:cyclohexane to give (R)-tert-butyl 2-(cyanomethyl)morpholine-4-carboxylate (2.393 g, 10.58 mmol, 74.4% yield) as a white solid.

¹H NMR (400 MHz, DMSO-d₆) δ ppm 3.85 (br. dd, J=11.5, 2.2 Hz, 2H) 3.70 (br. d, J=13.2 Hz, 1H) 3.52-3.63 (m, 1H) 3.44 (td, J=11.6, 2.9 Hz, 1H) 2.79-2.93 (m, 2H) 2.67-2.79 (m, 1H) 2.57-2.67 (m, 1H) 1.41 (s, 9H).

Intermediate 25: (R)-tert-Butyl 2-(2-aminoethyl)morpholine-4-carboxylate

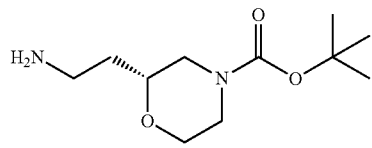 [SMILES: CC(C)(C)OC(=O)N1CCO[C@H](CCN)C1]

(R)-tert-Butyl 2-(cyanomethyl)morpholine-4-carboxylate (2.39 g, 10.56 mmol) was taken up in THF (20 mL) and stirred at rt, BH$_3$.THF (1M in THF, 15.84 mL, 15.84 mmol) was added over 10 min and the reaction stirred at rt for 2 h. The reaction was quenched by the careful addition of MeOH until all effervescence had stopped. The reaction was concentrated and diluted with MeOH and treated with 1M NaOH (50 mL) and stirred at rt for 2 h, a precipitate resulted. The reaction was concentrated to remove the MeOH and was diluted with water and extracted with EtOAc. The combined organics were washed with water, dried using a hydrophobic frit and concentrated to give the crude product as a colourless oil. This was further purified using SP4 flash chromatography, using a SNAP 50 g Si column and eluting with 0-8% 2M NH$_3$ in MeOH:DCM to give (R)-tert-butyl 2-(2-aminoethyl)morpholine-4-carboxylate (965 mg, 4.19 mmol, 39.7% yield) as a colourless oil.

$^1$H NMR (400 MHz, DMSO-d$_6$) δ ppm: 3.56-3.90 (m, 3H) 3.23-3.46 (m, 2H) 2.01-3.11 (obs m, 6H) 1.28-1.62 (m, 11H).

Intermediate 26: (S)-tert-Butyl 2-(cyanomethyl)morpholine-4-carboxylate

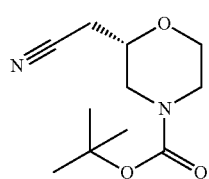 [SMILES: CC(C)(C)OC(=O)N1CCO[C@@H](CC#N)C1]

(R)-tert-Butyl 2-(((methylsulfonyl)oxy)methyl)morpholine-4-carboxylate (4 g, 13.54 mmol, commercially available from, for example, Matrix Scientific), KCN (0.926 g, 14.22 mmol) and KI (3.37 g, 20.31 mmol) were stirred at 80° C. in DMSO (30 mL) for 4 h and then at 100° C. for 3 h. The reaction was diluted with water and was extracted with EtOAc, the organic layer was washed with water and brine, dried using a hydrophobic frit and concentrated to a yellow oil. This oil was purified using a SP4 SNAP 50 g Si column, eluting with 0-50% EtOAc:Cyclohexane. The appropriate fractions were collected and concentrated in vacuo to give (S)-tert-butyl 2-(cyanomethyl)morpholine-4-carboxylate (2.693 g, 11.90 mmol, 88% yield) as a white solid.

$^1$H NMR (400 MHz, DMSO-d$_6$) δ ppm 3.78-3.92 (m, 2H) 3.70 (br. d, J=13.4 Hz, 1H) 3.53-3.63 (m, 1H) 3.45 (td, J=11.6, 2.9 Hz, 1H) 2.80-2.92 (m, 2H) 2.73 (dd, J=17.1, 7.1 Hz, 1H) 2.59-2.68 (m, 1H) 1.41 (s, 9H)

Intermediate 27: (S)-tert-Butyl 2-(2-aminoethyl)morpholine-4-carboxylate

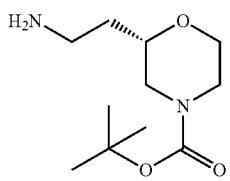 [SMILES: CC(C)(C)OC(=O)N1CCO[C@@H](CCN)C1]

(S)-tert-Butyl 2-(cyanomethyl)morpholine-4-carboxylate (2.6 g, 11.49 mmol) was taken up in THF (20 mL) and stirred at rt, borane tetrahydrofuran complex (1M in THF, 17.24 mL, 17.24 mmol) was added over 10 min and the reaction stirred at rt for 2 h. The reaction was quenched by careful addition of MeOH until all effervescence stopped. The reaction was concentrated and diluted with MeOH and treated with 1M NaOH (50 mL) and stirred at rt for 2 h, a precipitate resulted. The reaction was concentrated to remove the MeOH and was diluted with water and extracted with EtOAc, the combined organics were washed with water, dried using a hydrophobic frit and concentrated to a colourless oil. NMR suggests only recovered SM. The oil was again taken up in THF (20 mL), treated with borane tetrahydrofuran complex (1M in THF, 17.24 mL, 17.24 mmol) and stirred at 70° C. under reflux conditions for 4 h. The reaction was quenched by careful addition of MeOH until all effervescence stopped. The reaction was concentrated and diluted with MeOH and treated with 1M NaOH (50 mL) and stirred at rt for 1 h, a precipitate resulted. The reaction was concentrated to remove the MeOH and was diluted with water and extracted with EtOAc, the combined organics were washed with water, dried using a hydrophobic frit and concentrated to give the desired product (S)-tert-butyl 2-(2-aminoethyl)morpholine-4-carboxylate (763 mg, 3.31 mmol, 28.8% yield) as a colourless viscous oil.

$^1$H NMR (400 MHz, DMSO-d$_6$) δ ppm 3.64-3.81 (m, 3H) 3.24-3.42 (m, 3H) 2.76-2.89 (m, 1H) 2.53-2.63 (m, 2H) 1.38-1.54 (m, 11H)

Intermediate 28: (+/−)-1-tert-Butyl 3-ethyl 3-fluoropiperidine-1,3-dicarboxylate

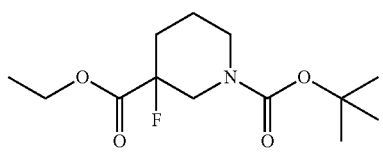 [SMILES: CCOC(=O)C1(F)CCCN(C(=O)OC(C)(C)C)C1]

1-tert-Butyl 3-ethyl piperidine-1,3-dicarboxylate (5 g, 19.43 mmol, commercially available form, for example, Sigma Aldrich) in THF (20 mL) was added dropwise to a solution of lithium bis(trimethylsilyl)amide (38.9 mL, 38.9 mmol) in THF (20 mL) at −78° C. under nitrogen, then the solution was allowed to warm to −20° C. over 1 h, then recooled to −78° C. A solution of N-fluoro-N-(phenylsulfonyl)benzenesulfonamide (12.25 g, 38.9 mmol) in THF (30 mL) was added dropwise, then the mixture was stirred for 2 h, allowing it to warm gradually to rt. The reaction mixture was quenched with saturated ammonium chloride solution (100 mL) and extracted with EtOAc (100 mL). The organic layer was washed with 1M NaOH solution (100 mL) and brine, then dried and evaporated to give a yellow oil. The crude product was dissolved in DCM and loaded onto a 50 g silica column, then eluted with 0-50% EtOAc/cyclohexane to give 1-tert-butyl 3-ethyl 3-fluoropiperidine-1,3-dicarboxylate (3.5 g, 12.71 mmol, 65.4% yield) as a colourless oil.

¹H NMR (400 MHz, CDCl₃-d) d ppm 4.27 (q, J=7.3 Hz, 2H) 3.17-3.44 (m, 1H) 2.70-2.92 (m, 1H) 1.98-2.21 (m, 2H) 1.78-1.96 (m, 2H) 1.60-1.72 (m, 2H) 1.45-1.51 (m, 9H) 1.33 (s, 3H)

Intermediate 29: (+/−)-tert-Butyl 3-fluoro-3-(hydroxymethyl)piperidine-1-carboxylate

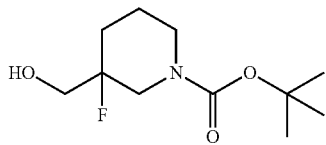 [SMILES: CC(C)(C)OC(=O)N1CCCC(F)(CO)C1]

1-tert-Butyl 3-ethyl 3-fluoropiperidine-1,3-dicarboxylate (3.5 g, 12.71 mmol) was dissolved in THF (50 mL) and LiBH₄ (0.831 g, 38.1 mmol) was added, then the mixture was stirred for 4 h at rt. Ammonium chloride (50 mL) was added, initially very cautiously, dropwise, then the mixture was stirred for 20 min before extraction with EtOAc (2×100 mL). The combined organics were dried over sodium sulphate and evaporated in vacuo to give tert-butyl 3-fluoro-3-(hydroxymethyl)piperidine-1-carboxylate (2.2 g, 9.43 mmol, 74.2% yield) as a colourless oil.

¹H NMR (400 MHz, CDCl₃) δ ppm 3.54-3.74 (m, 3H) 1.92 (br. s., 2H) 1.72-1.82 (m, 2H) 1.58-1.62 (m, 1H) 1.51-1.57 (m, 2H) 1.48 (s, 9H)

Intermediate 30: (+/−)-(E)-tert-Butyl 3-(3-ethoxy-3-oxoprop-1-en-1-yl)-3-fluoropiperidine-1-carboxylate

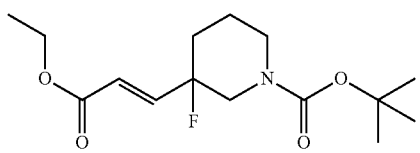 [SMILES: CCOC(=O)/C=C/C1(F)CCCN(C(=O)OC(C)(C)C)C1]

tert-Butyl 3-fluoro-3-(hydroxymethyl)piperidine-1-carboxylate (2.2 g, 9.43 mmol) was dissolved in DCM (60 mL) and Dess-Martin periodinane (4.80 g, 11.32 mmol) was added and the mixture was stirred at rt for 18 h, then washed with water and the organic layer dried over sodium sulphate and decanted into a clean, dry flask. Ethyl 2-(triphenylphosphoranylidene)acetate (4.93 g, 14.15 mmol) was added and the mixture was stirred overnight, then washed with water and the organic layer dried and evaporated in vacuo. The residue was purified on a 50 g silica column, eluting with 0-50% EtOAc/cyclohexane and the product-containing fractions were evaporated in vacuo to give (E)-tert-butyl 3-(3-ethoxy-3-oxoprop-1-en-1-yl)-3-fluoropiperidine-1-carboxylate (2.2 g, 7.30 mmol, 77% yield) as a colourless oil.

¹H NMR (400 MHz, CDCl₃) δ ppm 6.89 (dd, J=19.4, 15.8 Hz, 1H) 6.15 (d, J=15.9 Hz, 1H) 4.22 (q, J=7.1 Hz, 2H) 3.76-4.13 (m, 2H) 3.01-3.29 (m, 1H) 2.90-3.01 (m, 1H) 1.63-2.01 (m, 4H) 1.54-1.62 (m, 1H) 1.45-1.52 (m, 10H) 1.31 (t, J=7.1 Hz, 3H)

Intermediate 31: (+/−)-tert-Butyl 3-(3-ethoxy-3-oxopropyl)-3-fluoropiperidine-1-carboxylate

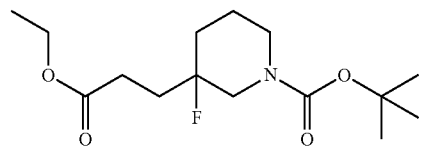 [SMILES: CCOC(=O)CCC1(F)CCCN(C(=O)OC(C)(C)C)C1]

(E)-tert-Butyl 3-(3-ethoxy-3-oxoprop-1-en-1-yl)-3-fluoropiperidine-1-carboxylate (2 g, 6.64 mmol) was dissolved in EtOH (50 mL) and hydrogenated over 5% Pd/C at atmospheric pressure overnight. The mixture was then filtered though Celite® under N₂ and the filtrate evaporated in vacuo to give tert-butyl 3-(3-ethoxy-3-oxopropyl)-3-fluoropiperidine-1-carboxylate (2.0 g, 6.59 mmol, 99% yield) as a colourless oil. NMR showed a significant amount of remaining starting material, therefore the crude product was dissolved in EtOH (50 mL) and hydrogenated in an H-Cube on full mode over a Pd/C cartridge. The eluant was evaporated in vacuo to give a colourless oil. NMR showed some remaining starting material and the solution was hydrogenated in the H-Cube again, then the eluant was evaporated in vacuo to give tert-butyl 3-(3-ethoxy-3-oxopropyl)-3-fluoropiperidine-1-carboxylate (2.0 g, 6.59 mmol, 99% yield).

¹H NMR (400 MHz, CDCl₃-d) δ ppm 4.14 (q, J=6.9 Hz, 2H) 3.70-3.99 (m, 2H) 2.91-3.24 (m, 2H) 2.47 (t, J=7.9 Hz, 2H) 1.71-2.04 (m, 4H) 1.42-1.66 (m, 11H) 1.26 (t, J=7.1 Hz, 3H)

Intermediate 32: (+/−)-tert-Butyl 3-fluoro-3-(3-hydroxypropyl)piperidine-1-carboxylate

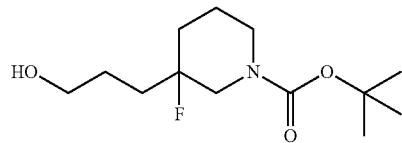 [SMILES: CC(C)(C)OC(=O)N1CCCC(F)(CCCO)C1]

LiBH₄ (0.431 g, 19.78 mmol) was added to a solution of tert-butyl 3-(3-ethoxy-3-oxopropyl)-3-fluoropiperidine-1-carboxylate (2 g, 6.59 mmol) in THF (30 mL) at rt under nitrogen and the mixture was stirred overnight, then quenched by very cautious, initially dropwise addition of ammonium chloride solution (50 mL). The mixture was stirred vigorously for 30 min, then extracted with EtOAc (2×50 mL) and the combined organics dried and evaporated in vacuo to give a colourless oil. This was dissolved in DCM and loaded onto a 50 g silica column, then eluted with 0-100% EtOAc/cyclohexane and the product-containing fractions were then evaporated in vacuo to give tert-butyl 3-fluoro-3-(3-hydroxypropyl)piperidine-1-carboxylate (1.6 g, 6.12 mmol, 93% yield) as a colourless oil.

¹H NMR (400 MHz, CDCl₃-d) δ ppm 3.59-3.93 (m, 4H) 2.93-3.17 (m, 2H) 1.86-2.01 (m, 1H) 1.48-1.85 (m, 9H) 1.43-1.48 (m, 9H)

Intermediate 33: (+/−)-tert-Butyl 3-fluoro-3-(3-((methylsulfonyl)oxy)propyl)piperidine-1-carboxylate

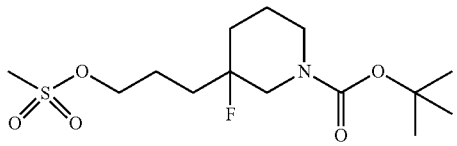 [SMILES: CC(C)(C)OC(=O)N1CCCC(F)(CCCOS(C)(=O)=O)C1]

tert-butyl 3-fluoro-3-(3-hydroxypropyl)piperidine-1-carboxylate (1.6 g, 6.12 mmol) was dissolved in DCM (50 mL) and Et₃N (1.280 mL, 9.18 mmol) was added, then the mixture was stirred at rt for 2 h. The solvent was washed with water (20 mL), dried and evaporated in vacuo to give a yellow oil (2.5 g) which was used directly.

$^1$H NMR (400 MHz, CDCl$_3$) δ ppm 4.20-4.32 (m, 2H) 3.70-3.97 (m, 2H) 3.07-3.19 (m, 1H) 2.97-3.06 (m, 4H) 1.86-2.00 (m, 3H) 1.58-1.85 (m, 4H) 1.49-1.57 (m, 1H) 1.46 (s, 9H)

Intermediate 34: (+/−)-tert-Butyl 3-(3-azidopropyl)-3-fluoropiperidine-1-carboxylate

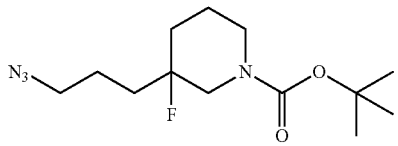 [SMILES: CC(C)(C)OC(=O)N1CCCC(F)(CCCN=[N+]=[N-])C1]

tert-Butyl 3-fluoro-3-(3-((methylsulfonyl)oxy)propyl)piperidine-1-carboxylate (2.5 g, 7.37 mmol) was dissolved in DMF (30 mL) then sodium azide (0.958 g, 14.73 mmol) was added and the mixture was heated at 80° C. for 2 h. The resulting suspension was diluted with water (100 mL) and extracted with EtOAc (2×50 mL). The combined organics were washed with water (2×50 mL), dried and evaporated in vacuo to give tert-butyl 3-(3-azidopropyl)-3-fluoropiperidine-1-carboxylate (2.8 g, 9.78 mmol) as a pale yellow oil, which was used in the next step without purification.

$^1$H NMR (400 MHz, CDCl$_3$) δ ppm 3.75 (dt, J=13.1, 4.1 Hz, 2H) 3.32 (t, J=6.5 Hz, 2H) 2.97-3.06 (m, 2H) 1.86-2.00 (m, 1H) 1.58-1.85 (m, 6H) 1.43-1.57 (m, 10H)

Intermediate 35: (+/−)-tert-Butyl 3-(3-aminopropyl)-3-fluoropiperidine-1-carboxylate

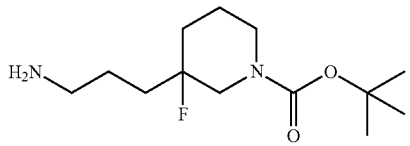 [SMILES: CC(C)(C)OC(=O)N1CCCC(F)(CCCN)C1]

tert-Butyl 3-(3-azidopropyl)-3-fluoropiperidine-1-carboxylate (2.8 g, 5.87 mmol) was dissolved in EtOH (60 mL) and hydrogenated in an H-Cube on full mode over a Pd/C cat. cart. The eluant was evaporated in vacuo to give a pale yellow oil. The crude material was dissolved in DCM and loaded onto a 25 g silica column, then eluted with 0-20% 2M NH$_3$ in MeOH/DCM and the appropriate fractions concentrated in vacuo to give tert-butyl 3-(3-aminopropyl)-3-fluoropiperidine-1-carboxylate (1.2 g, 4.61 mmol, 79% yield) as a colourless oil.

$^1$H NMR (400 MHz, CDCl$_3$) δ ppm 3.72-4.03 (m, 2H) 2.90-3.13 (m, 2H) 2.72 (t, J=6.5 Hz, 2H) 1.87-1.98 (m, 1H) 1.72-1.87 (m, 1H) 1.33-1.69 (m, 17H)

Intermediate 36: (R)-3-(1-(tert-Butoxycarbonyl)-3-fluoropiperidin-3-yl)propanoic acid

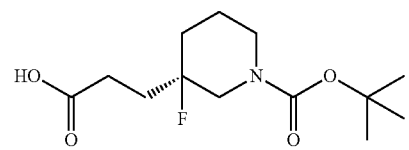 [SMILES: CC(C)(C)OC(=O)N1CCC[C@@](F)(CCC(=O)O)C1]

(R)-tert-Butyl 3-(3-ethoxy-3-oxopropyl)-3-fluoropiperidine-1-carboxylate (9.6 g, 31.6 mmol) was dissolved in EtOH (50 mL) and NaOH (2M aq, 47.5 mL, 95 mmol) was added, then the solution was stirred at rt for 4 h. The solvent was evaporated in vacuo and the residue was partitioned between water (100 mL) and ether (100 mL). The aqueous layer was acidified with 2M HCl to pH ~2 then extracted with EtOAc (2×100 mL). The organic layer was washed with water (100 mL), then dried and evaporated in vacuo to give (R)-3-(1-(tert-butoxycarbonyl)-3-fluoropiperidin-3-yl)propanoic acid (8.6 g, 31.2 mmol, 99% yield) as a colourless solid.

$^1$H NMR (400 MHz, CDCl$_3$) δ ppm 3.76 (dt, J=13.4, 4.2 Hz, 1H) 3.06 (d, J=8.6 Hz, 1H) 2.55 (t, J=7.8 Hz, 2H) 1.98-2.08 (m, 2H) 1.88-1.97 (m, 2H) 1.68-1.81 (m, 2H) 1.51-1.60 (m, 2H) 1.45-1.50 (m, 9H)

Intermediate 37: (R)-tert-Butyl 3-(2-(((benzyloxy)carbonyl)amino)ethyl)-3-fluoropiperidine-1-carboxylate

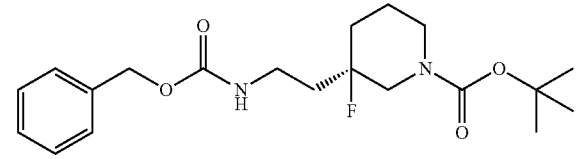 [SMILES: CC(C)(C)OC(=O)N1CCC[C@@](F)(CCNC(=O)OCc2ccccc2)C1]

Diphenyl phosphorazidate (8.08 mL, 37.5 mmol) was added to a mixture of (R)-3-(1-(tert-butoxycarbonyl)-3-fluoropiperidin-3-yl)propanoic acid (8.6 g, 31.2 mmol) and Et$_3$N (13.06 mL, 94 mmol) in toluene (50 mL), then the solution was stirred for 30 min at rt. Benzyl alcohol (6.50 mL, 62.5 mmol) was added and the mixture heated at reflux for 3 h. The reaction mixture was diluted with EtOAc (100 mL) and washed with water (100 mL), the organic layer dried and evaporated in vacuo and the residue purified by chromatography on a 340 g silica column eluting with 0-50% EtOAc/cyclohexane. The product-containing fractions were combined and evaporated in vacuo to give (R)-tert-butyl 3-(2-(((benzyloxy)carbonyl)amino)ethyl)-3-fluoropiperidine-1-carboxylate (8.9 g, 23.39 mmol, 74.9% yield) as a colourless gum.

$^1$H NMR (400 MHz, 393 K, DMSO-$d_6$) δ ppm 7.25-7.43 (m, 5H) 6.69 (br. s., 1H) 5.05 (s, 2H) 3.74-3.82 (m, 1H) 3.70 (dt, J=13.1, 4.2 Hz, 1H) 3.16-3.24 (m, 2H) 3.01-3.15 (m, 1H) 2.90-3.00 (m, 1H) 1.75-1.90 (m, 3H) 1.56-1.74 (m, 2H) 1.40-1.54 (m, 10H)

Intermediate 38: (R)-tert-Butyl 3-(2-aminoethyl)-3-fluoropiperidine-1-carboxylate

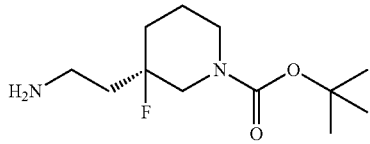 [SMILES: CC(C)(C)OC(=O)N1CCC[C@@](F)(CCN)C1]

(R)-tert-butyl 3-(2-(((benzyloxy)carbonyl)amino)ethyl)-3-fluoropiperidine-1-carboxylate (8.9 g, 23.39 mmol) was dissolved in EtOH (100 mL) and added to 5% Pd/C (2 g) under vacuum, then hydrogenated at atmospheric pressure over the weekend. The mixture was filtered though Celite® under $N_2$ and the filtrate evaporated in vacuo to give (R)-tert-butyl 3-(2-aminoethyl)-3-fluoropiperidine-1-carboxylate (6.0 g, 24.36 mmol, 104% yield) as a colourless oil.

$^1$H NMR (400 MHz, DMSO-$d_6$) δ ppm 3.80 (ddd, J=13.7, 9.8, 1.5 Hz, 1H) 3.69-3.75 (m, 1H) 3.01-3.13 (m, 1H) 2.90-2.99 (m, 1H) 2.74 (t, J=7.5 Hz, 2H) 1.80-1.87 (m, 1H) 1.66-1.76 (m, 3H) 1.56-1.64 (m, 1H) 1.46-1.53 (m, 1H) 1.43 (s, 9H)

Intermediate 39: (RE)-tert-Butyl 3-(3-ethoxy-3-oxoprop-1-en-1-yl)-3-fluoropiperidine-1-carboxylate

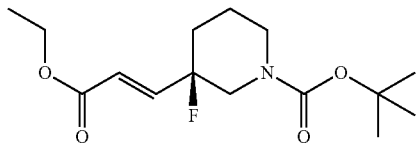 [SMILES: CCOC(=O)/C=C/[C@]1(F)CCCN(C(=O)OC(C)(C)C)C1]

(S)-tert-Butyl 3-fluoro-3-(hydroxymethyl)piperidine-1-carboxylate (10 g, 42.9 mmol, preparation described in the literature: *Org. Process Res. Dev.* 2015, 19, 7, 865-871)) was dissolved in DCM (60 mL) and Dess-Martin periodinane (23.64 g, 55.7 mmol) was added and the mixture was stirred at rt for 18 h, then washed with water and the organic layer dried over $Na_2SO_4$ and decanted into a clean, dry flask. Ethyl 2-(triphenylphosphoranylidene)acetate (19.41 g, 55.7 mmol) was added and the mixture was stirred overnight, then washed with water and the organic layer dried and evaporated in vacuo. The residue was purified on a 50 g silica column eluting with 0-50% EtOAc/cyclohexane and the product-containing fractions were evaporated in vacuo to give (R,E)-tert-butyl 3-(3-ethoxy-3-oxoprop-1-en-1-yl)-3-fluoropiperidine-1-carboxylate (10.5 g, 34.8 mmol, 81% yield) as a colourless oil.

$^1$H NMR (400 MHz, CDCl$_3$) δ ppm 6.89 (dd, J=19.6, 15.7 Hz, 1H) 6.15 (d, J=15.7 Hz, 1H) 4.13-4.28 (m, 2H) 3.80-4.10 (m, 2H) 2.86-3.25 (m, 2H) 1.52-2.04 (m, 4H) 1.46 (s, 9H) 1.30 (t, J=7.1 Hz, 3H)

Intermediate 40: (R)-tert-Butyl 3-(3-ethoxy-3-oxopropyl)-3-fluoropiperidine-1-carboxylate

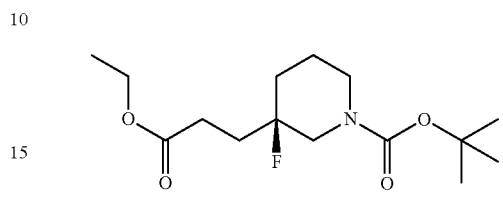

(R,E)-tert-Butyl 3-(3-ethoxy-3-oxoprop-1-en-1-yl)-3-fluoropiperidine-1-carboxylate (10 g, 33.2 mmol) was dissolved in EtOH (100 mL) and added to 5% Pd—C (2 g, 18.79 mmol) under $N_2$, then the mixture was hydrogenated at atmospheric pressure for 6 h, giving the expected uptake of hydrogen. The mixture was filtered though Celite® under $N_2$ and the filtrate evaporated in vacuo to give (R)-tert-butyl 3-(3-ethoxy-3-oxopropyl)-3-fluoropiperidine-1-carboxylate (9.5 g, 31.3 mmol, 94% yield) as a pale yellow oil.

$^1$H NMR (400 MHz, CDCl$_3$) δ ppm 4.05-4.22 (m, 2H) 3.66-4.01 (m, 2H) 2.88-3.23 (m, 2H) 2.47 (t, J=8.1 Hz, 2H) 1.84-2.12 (m, 3H) 1.71-1.84 (m, 1H) 1.47-1.71 (m, 2H) 1.45 (s, 9H) 1.21-1.32 (m, 3H)

Intermediate 41: (R)-tert-Butyl 3-fluoro-3-(3-hydroxypropyl)piperidine-1-carboxylate

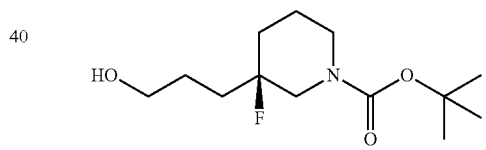

LiBH$_4$ (2.046 g, 94 mmol) was added to a solution of (R)-tert-butyl 3-(3-ethoxy-3-oxopropyl)-3-fluoropiperidine-1-carboxylate (9.5 g, 31.3 mmol) in THF (100 mL) and the mixture was stirred at rt under $N_2$ for 48 h, then cooled in an ice bath and quenched by very cautious, initially dropwise addition of ammonium chloride solution (100 mL) (strong effervescence on addition!), then the mixture was stirred for 20 min, diluted with EtOAc (100 mL) and the combined organics separated, dried over $Na_2SO_4$ and evaporated in vacuo to give a pale yellow oil. The crude material was dissolved in DCM and loaded onto a 100 g silica column, then eluted with 0-100% EtOAc/cyclohexane and the product-containing fractions were evaporated in vacuo to give (R)-tert-butyl 3-fluoro-3-(3-hydroxypropyl)piperidine-1-carboxylate (6.0 g, 22.96 mmol, 73.3% yield) which was carried though to the next step immediately.

$^1$H NMR (400 MHz, CDCl$_3$) δ ppm 3.61-3.93 (m, 4H) 2.94-3.14 (m, 2H) 1.87-1.99 (m, 1H) 1.48-1.86 (m, 7H) 1.45 (s, 9H)

Intermediate 42: (R)-tert-Butyl 3-fluoro-3-(3-((methylsulfonyl)oxy)propyl)piperidine-1-carboxylate

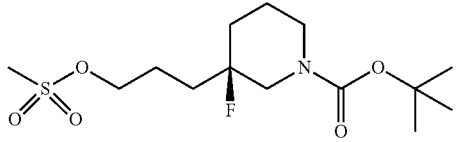 [SMILES: CC(C)(C)OC(=O)N1CCC[C@@](F)(CCCOS(C)(=O)=O)C1]

(R)-tert-Butyl 3-fluoro-3-(3-hydroxypropyl)piperidine-1-carboxylate (6 g, 22.96 mmol) was dissolved in DCM (100 mL), Et₃N (4.80 mL, 34.4 mmol) was added and the mixture was cooled in an ice bath, then Ms-Cl (2.326 mL, 29.8 mmol) was added dropwise (exotherm!) and the mixture was stirred for 2 h, allowing it to warm to rt. The solution was washed with water (100 mL) and brine (100 mL). The organic layer was dried and evaporated in vacuo to give (R)-tert-butyl 3-fluoro-3-(3-((methylsulfonyl)oxy)propyl)piperidine-1-carboxylate (7.2 g, 21.21 mmol, 92% yield) as a colourless oil which was used in the next step.

$^1$H NMR (400 MHz, CDCl₃) δ ppm 4.20-4.32 (m, 2H) 3.70-3.96 (m, 2H) 3.68 (s, 1H) 3.04-3.15 (m, 1H) 3.00-3.03 (m, 3H) 1.88-1.99 (m, 3H) 1.49-1.83 (m, 5H) 1.43-1.48 (m, 9H)

Intermediate 43: (R)-tert-Butyl 3-(3-azidopropyl)-3-fluoropiperidine-1-carboxylate

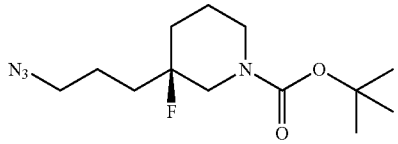 [SMILES: CC(C)(C)OC(=O)N1CCC[C@@](F)(CCCN=[N+]=[N-])C1]

Sodium azide (2.68 g, 41.2 mmol) was added to a solution of (R)-tert-butyl 3-fluoro-3-(3-((methylsulfonyl)oxy)propyl)piperidine-1-carboxylate (7 g, 20.62 mmol) in DMF (50 mL) and the mixture was heated at 70° C. for 2 h, then diluted with water (200 mL) and extracted with EtOAc (2×100 mL). The combined organics were washed with water (2×100 mL), dried and evaporated in vacuo to give the crude product as a colourless oil. The crude product was dissolved in DCM (10 mL) and loaded onto a 100 g silica column, then eluted with 0-50% EtOAc/cyclohexane and the product-containing fractions (visualised by ninhydrin) were evaporated in vacuo to give (R)-tert-butyl 3-(3-azidopropyl)-3-fluoropiperidine-1-carboxylate (5.2 g, 18.16 mmol, 88% yield) as a colourless oil which was carried though to the next step without further purification.

$^1$H NMR (400 MHz, CDCl₃) δ ppm 3.69-3.99 (m, 2H) 3.33 (t, J=6.5 Hz, 2H) 2.96-3.17 (m, 2H) 1.86-1.98 (m, 1H) 1.58-1.83 (m, 6H) 1.49-1.58 (m, 1H) 1.47 (s, 9H)

Intermediate 44: (S)-tert-Butyl 3-(3-aminopropyl)-3-fluoropiperidine-1-carboxylate

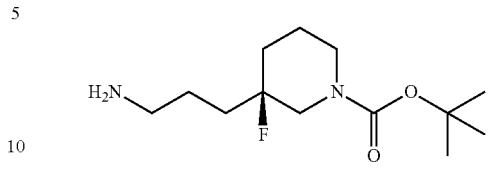

(R)-tert-Butyl 3-(3-azidopropyl)-3-fluoropiperidine-1-carboxylate (5.0 g, 17.46 mmol) was dissolved in THF (50 mL) and PPh₃ (5.50 g, 20.95 mmol) was added, then the mixture was stirred at rt over the weekend. Water (50 mL) was added and the mixture stirred vigorously for 2 h, then diluted with EtOAc (100 mL) and brine (50 mL) and the organic layer separated, dried and evaporated in vacuo to give a pale yellow oil. The crude product was dissolved in DCM (20 mL) and loaded onto a 100 g silica column, then eluted with 0-20% 2M methanoic ammonia/DCM and the product-containing fractions (visualised by ninhydrin) were evaporated in vacuo to give (S)-tert-butyl 3-(3-aminopropyl)-3-fluoropiperidine-1-carboxylate (4.0 g, 15.36 mmol, 88% yield) as a colourless oil.

$^1$H NMR (400 MHz, CDCl₃) δ ppm 3.72-4.02 (m, 2H) 2.89-3.12 (m, 2H) 2.72 (t, J=6.6 Hz, 2H) 1.86-1.98 (m, 1H) 1.72-1.85 (m, 1H) 1.48-1.70 (m, 6H) 1.46 (s, 9H)

Intermediate 45: (S)-tert-Butyl 2-((((trifluoromethyl)sulfonyl)oxy)methyl)morpholine-4-carboxylate

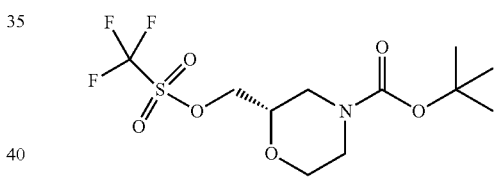

A stirred solution of (S)-tert-butyl 2-(hydroxymethyl)morpholine-4-carboxylate (200 g, 921 mmol) (commercially available from, for example, AOK chem) in DCM (1800 mL) under N₂ atmosphere was cooled to −20° C. Pyridine (82 mL, 1013 mmol) was added, followed by a solution of Tf₂O (171 mL, 1013 mmol), dissolved in DCM (200 mL) over 30 min. The reaction temperature was maintained at −25° C. for 1 h. The reaction mixture was warmed to 0° C. and diluted with 1N aqueous HCl (466 mL) and the organic layer was separated and washed with water (3×800 mL), brine solution (800 mL), dried over anhydrous Na₂SO₄, filtered and concentrated under vacuum to obtain the crude compound. The crude product was triturated with hexane (120 mL). The resulting solids were filtered though a Buchner funnel, washed with hexane (60 mL) dried under vacuum to afford (S)-tert-butyl 2-((((trifluoromethyl)sulfonyl)oxy)methyl)morpholine-4-carboxylate (203 g, 562 mmol, 61.0% yield) as a pale yellow solid.

LCMS (5 min formic): Rt=2.50 min, [MH]⁺=349.9.

LCMS 5 min formic method: Acq. Method Conditions: RND-FA-4.5-MIN; Column: Acquity BEH C18 (50 mm×2.1 mm, 1.7 µm); Mobile Phase: A: 0.1% Formic Acid in water; B: 0.1% Formic Acid in ACN; Time (min)/% B: 0/3, 0.4/3, 3.2/98, 3.8/98, 4.2/3, 4.5/3; Column Temp: 35° C., Flow Rate: 0.6 mL/min.

Intermediate 46: (S)-tert-Butyl 2-(cyano(hydroxy)methyl)morpholine-4-carboxylate, Mixture of Diastereomers at Undefined Stereocentre

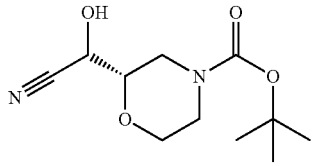 [SMILES: CC(C)(C)OC(=O)N1CCO[C@H](C(O)C#N)C1]

KCN (5.59 g, 86 mmol) was added to a solution of (S)-tert-butyl 2-((((trifluoromethyl)sulfonyl)oxy)methyl)morpholine-4-carboxylate (20 g, 57.3 mmol) in DMSO (50 mL), while cooling in an ice bath, then the mixture was stirred for 30 min, then allowed to warm to rt overnight. The mixture was diluted with water (500 mL) and extracted with EtOAc (2×200 mL). The combined organics were washed with water (2×200 mL), dried and evaporated in vacuo to give a dark brown oil. This was purified by chromatography on a 340 g silica column eluting with 0-60% EtOAc/cyclohexane and the product-containing fractions (visualised by ninhydrin) were collected by filtration to give a colourless oil —(S)-tert-butyl 2-(cyano(hydroxy)methyl)morpholine-4-carboxylate (10.2 g, 42.1 mmol, 73.5% yield).

$^1$H NMR (400 MHz, CDCl$_3$) δ ppm 4.48 (ddd, J=12.1, 8.2, 4.4 Hz, 1H) 4.04-4.10 (m, 1H) 4.00 (d, J=11.5 Hz, 1H) 3.91 (d, J=12.0 Hz, 1H) 3.66-3.75 (m, 1H) 3.56-3.65 (m, 1H) 2.76-3.12 (m, 2H) 1.45-1.53 (m, 9H)

Intermediate 47: (S)-tert-Butyl 2-(2-amino-1-hydroxyethyl)morpholine-4-carboxylate, Mixture of Diastereomers at Undefined Stereocentre

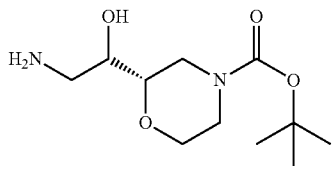 [SMILES: CC(C)(C)OC(=O)N1CCO[C@H](C(O)CN)C1]

(S)-tert-Butyl 2-(cyano(hydroxy)methyl)morpholine-4-carboxylate (8 g, 33.0 mmol) was dissolved in THF (10 mL) and BH$_3$.THF (1M in THF, 99 mL, 99 mmol) was added, then the mixture was heated under N$_2$ at 60° C. for 2 h. The mixture was cooled in an ice bath, then quenched by initially dropwise addition of MeOH (1000 mL). The resulting solution was heated at reflux for 1 h, then evaporated in vacuo and the residue purified by chromatography on a 100 g silica column, eluting with 0-20% NH$_3$ in MeOH/DCM to give the title compound (6.2 g) as a colourless oil.

$^1$H NMR (400 MHz, DMSO-d$_6$) δ ppm 4.00 (d, J=12.7 Hz, 1H) 3.75-3.85 (m, 2H) 3.70 (d, J=12.5 Hz, 2H) 3.27-3.40 (m, 4H) 3.19-3.25 (m, 1H) 3.18 (s, 9H)

Intermediate 48: (±)-tert-Butyl 3,3-difluoro-4-(2-hydroxyethyl)piperidine-1-carboxylate

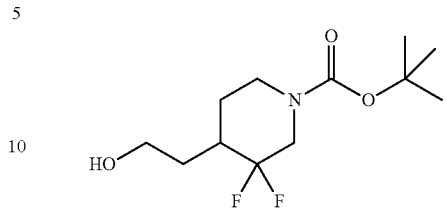

To a stirred solution of (±)-2-(1-(tert-butoxycarbonyl)-3,3-difluoropiperidin-4-yl)acetic acid (1.99 g, 7.13 mmol, commercially available from Activate Scientific) in THF (50 mL) at rt was added portionwise (5 mL aliquots) BH$_3$.THF (1.0 M in THF, 29.0 mL, 29.0 mmol). The mixture was stirred at rt under N$_2$ for 15.5 h before MeOH (50 mL) was carefully added. After stirring for a further 20 min the mixture was evaporated in vacuo and the residue partitioned between EtOAc (50 mL) and water (50 mL). Saturated aqueous brine solution (10 mL) was added to aid phase separation and the phases were separated. The aqueous phase was extracted with further EtOAc (3×40 mL), the combined organic extracts dried by passing through a cartridge fitted with a hydrophobic frit, the solvent evaporated under a stream of N$_2$ and the residue dried in vacuo to give a pale yellow viscous oil; (±)-tert-butyl 3,3-difluoro-4-(2-hydroxyethyl)piperidine-1-carboxylate (1.942 g, 7.32 mmol, 103% yield)

$^1$H NMR (400 MHz, DMSO-d$_6$) δ ppm 4.50 (t, J=5.5 Hz, 1H) 4.06 (br s, 1H) 3.89 (br d, 1H) 3.38-3.54 (m, 2H) 3.18 (br s, 1H) 2.87 (br s, 1H) 2.02-2.19 (m, 1H) 1.79-1.87 (m, 2H) 1.40 (s, 9H) 1.19-1.34 (m, 2H).

Intermediate 49: (±)-tert-Butyl 3,3-difluoro-4-(2-((methylsulfonyl)oxy)ethyl)piperidine-1-carboxylate

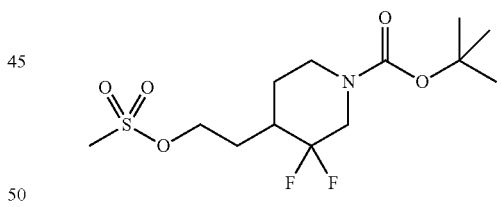

(±)-tert-Butyl 3,3-difluoro-4-(2-hydroxyethyl)piperidine-1-carboxylate (1.884 g, 7.10 mmol) was dissolved in DCM (60 mL) and Et$_3$N (1.48 mL, 10.62 mmol) and Ms-ClMs-Cl (0.719 mL, 9.23 mmol) were added. The solution was stirred at rt for 2.75 h, then washed with water (100 mL) and the aqueous phase extracted with DCM (2×100 mL). The combined organic phases were dried by passing them through a cartridge fitted with a hydrophobic frit and the solvent evaporated in vacuo to give a clear oil which crystallised to give a white solid; (±)-tert-butyl 3,3-difluoro-4-(2-((methylsulfonyl)oxy)ethyl)piperidine-1-carboxylate (2.467 g, 7.18 mmol, 101% yield)

$^1$H NMR (400 MHz, DMSO-d$_6$) δ ppm 4.23-4.33 (m, 2H) 4.09 (br s, 1H) 3.91 (br d, 1H) 3.21 (br s, 1H) 3.19 (s, 3H) 2.89 (br s, 1H) 2.02-2.23 (m, 2H) 1.85 (br dt, 1H) 1.56-1.66 (m, 1H) 1.40 (s, 9H) 1.24-1.38 (m, 2H).

Intermediate 50: (±)-tert-Butyl 4-(2-azidoethyl)-3,3-difluoropiperidine-1-carboxylate

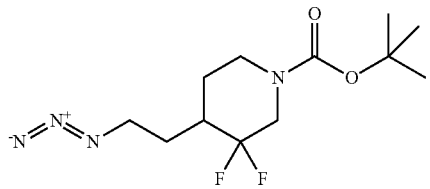

(±)-tert-Butyl 3,3-difluoro-4-(2-((methylsulfonyl)oxy)ethyl)piperidine-1-carboxylate (1.332 g, 3.88 mmol) was dissolved in DMF (10 mL) and sodium azide (301.5 mg, 4.64 mmol) was added. The mixture was stirred under $N_2$ at 80° C. for 4 h. After cooling, the mixture was diluted with 1M aqueous $Na_2CO_3$ solution (50 mL) and extracted with EtOAc (3×30 mL) [Note that 3 phases were observed in the separation, the EtOAc extracts being the least dense; on the 2nd and 3rd extractions some salting out of solid occurred in the lower phase and water (ca. ~10 mL) was added to help with this]. The combined organics were washed with water (2×40 mL) [Note that the 2nd water wash caused emulsification of the layers and saturated brine solution (ca. ~10 mL) was added to help the phases to separate], then dried and evaporated in vacuo to give a pale yellow oil; (±)-tert-butyl 4-(2-azidoethyl)-3,3-difluoropiperidine-1-carboxylate (1.23 g, 4.24 mmol, 109% yield) containing approximately 0.33 equivalents of DMF $^1$H NMR (400 MHz, DMSO-$d_6$) δ ppm 4.08 (br s, 1H) 3.89 (br d, 1H) 3.36-3.53 (m, 2H) 3.19 (br s, 1H) 2.88 (br s, 1H) 2.01-2.17 (m, 1H) 1.79-1.94 (m, 1H) 1.42-1.51 (m, 1H) 1.40 (s, 9H) 1.22-1.33 (m, 1H).

Intermediate 51: (±)-tert-Butyl 4-(2-aminoethyl)-3,3-difluoropiperidine-1-carboxylate

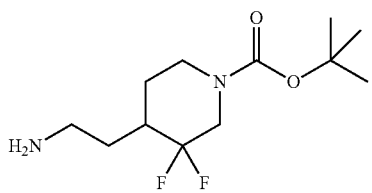 [SMILES: CC(C)(C)OC(=O)N1CCC(CCN)C(F)(F)C1]

A solution of (±)-tert-butyl 4-(2-azidoethyl)-3,3-difluoropiperidine-1-carboxylate (1.22 g, 4.20 mmol) in EtOAc (50 mL) was hydrogenated over a 10% Pd/C catalyst cartridge using a Thales 'H-Cube' flow apparatus in full hydrogen mode at 20° C. The solvent was evaporated from the collected solution in vacuo to give a colourless oil which by NMR analysis was determined to be a 6:5 mixture of starting azide to product amine. The residue was re-dissolved in EtOH (50 mL) and was again hydrogenated over a 10% Pd/C catalyst cartridge using a Thales 'H-Cube' flow apparatus in full hydrogen mode but this time at 40° C. The solvent was evaporated from the collected solution in vacuo to give a colourless oil (982.1 mg).

$^1$H NMR (400 MHz, DMSO-$d_6$) δ ppm 4.06 (br s, 1H) 3.88 (br d, 1H) 3.16 (br s, 1H) 2.86 (br s, 1H) 2.50-2.68 (m, 2H) 2.00-2.14 (m, 1H) 1.66-1.82 (m, 2H) 1.40 (s, 9H) 1.17-1.29 (m, 2H).

Intermediate 52: (±)-tert-Butyl 4,4-difluoro-3-(2-hydroxyethyl)piperidine-1-carboxylate

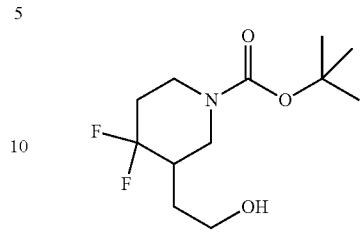

To a stirred solution of (±)-2-(1-(tert-butoxycarbonyl)-4,4-difluoropiperidin-3-yl)acetic acid (197.0 mg, 0.705 mmol, commercially available from Activate Scientific) in THF (5 mL) at rt was added $BH_3$.THF (1.0 M in THF, 2.8 mL, 2.80 mmol). The mixture was stirred at rt under $N_2$ for 2.5 h before MeOH (5 mL) was carefully added. After stirring for a further 10 min the mixture was evaporated in vacuo and the residue partitioned between EtOAc (5 mL) and water (5 mL). The aqueous phase was extracted with further EtOAc (3×4 mL), the combined organic extracts dried by passing through a cartridge fitted with a hydrophobic frit and the solvent evaporated under a stream of $N_2$ to give a colourless gum; (±)-tert-butyl 4,4-difluoro-3-(2-hydroxyethyl)piperidine-1-carboxylate (162.0 mg, 0.611 mmol, 87% yield)

$^1$H NMR (400 MHz, DMSO-$d_6$) δ ppm 4.56 (t, J=5.0 Hz, 1H) 3.69 (br s, 2H) 3.42-3.53 (m, 2H) 3.20 (br s, 1H) 2.97 (br s, 1H) 1.94-2.09 (m, 2H) 1.69-1.92 (m, 2H) 1.41 (s, 9H) 1.24-1.32 (m, 1H).

Intermediate 53: (±)-tert-Butyl 4,4-difluoro-3-(2-((methylsulfonyl)oxy)ethyl)piperidine-1-carboxylate

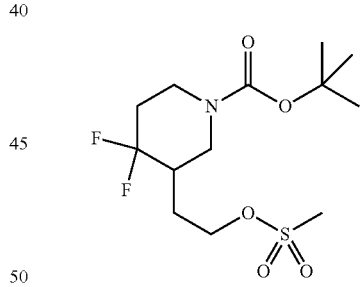

(±)-tert-Butyl 4,4-difluoro-3-(2-hydroxyethyl)piperidine-1-carboxylate (883 mg, 3.33 mmol) was dissolved in DCM (30 mL) and $Et_3N$ (0.70 mL, 5.02 mmol) and Ms-Cl (0.337 mL, 4.33 mmol) were added. The solution was stirred at rt for 2.75 h, then washed with water (50 mL) and the aqueous phase extracted with DCM (2×50 mL). The combined organic phases were dried by passing them through a cartridge fitted with a hydrophobic frit and the solvent evaporated in vacuo to give a white solid; (±)-tert-butyl 4,4-difluoro-3-(2-((methylsulfonyl)oxy)ethyl)piperidine-1-carboxylate (1.141 g, 3.32 mmol, 100% yield).

$^1$H NMR (400 MHz, DMSO-$d_6$) δ ppm 4.30 (dt, J=6.5 Hz, 2H) 3.81 (br s, 1H) 3.71 (br d, 1H) 3.20 (s, 3H) 3.15-3.22 (m, 1H) 2.99 (br s, 1H) 1.81-2.14 (m, 4H) 1.56-1.64 (m, 1H) 1.42 (s, 9H).

Intermediate 54: (±)-tert-Butyl 3-(2-cyanoethyl)-4,4-difluoropiperidine-1-carboxylate

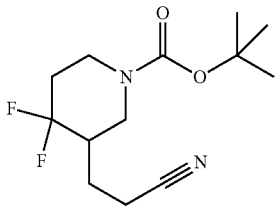 [SMILES: CC(C)(C)OC(=O)N1CCC(F)(F)C(CCC#N)C1]

(±)-tert-Butyl 4,4-difluoro-3-(2-((methylsulfonyl)oxy)ethyl)piperidine-1-carboxylate (207 mg, 0.602 mmol) was dissolved in DMSO (5 mL) and NaCN (31.5 mg, 0.643 mmol) was added. The mixture was stirred under $N_2$ at 55° C. for 17 h. The mixture was allowed to cool to rt and partitioned between water (10 mL) and diethyl ether (10 mL). The phases were separated and the aqueous phase extracted with further diethyl ether (3×10 mL). The combined organic phases were dried by filtering through a cartridge fitted with a hydrophobic frit and the solvent was evaporated in vacuo to give a yellow oil; crude (±)-tert-butyl 3-(2-cyanoethyl)-4,4-difluoropiperidine-1-carboxylate (150.6 mg, 0.549 mmol, 91% yield)

Intermediate 55: (±)-tert-Butyl 3-(3-aminopropyl)-4,4-difluoropiperidine-1-carboxylate

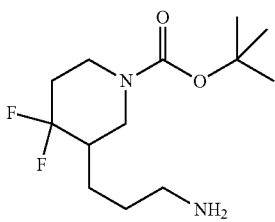 [SMILES: CC(C)(C)OC(=O)N1CCC(F)(F)C(CCCN)C1]

To a stirred solution of the crude (±)-tert-butyl 3-(2-cyanoethyl)-4,4-difluoropiperidine-1-carboxylate (71.7 mg, 0.261 mmol) in THF (2 mL) at rt was added $BH_3$.THF (1.0 M in THF, 1.0 mL, 1.000 mmol). The mixture was stirred at 70° C. under $N_2$ for 18.75 h. The mixture was allowed to cool to rt before MeOH (3 mL) was carefully added. After stirring for a further 70 min the mixture was evaporated in vacuo and the residue partitioned between EtOAc (5 mL) and water (5 mL). The aqueous phase was extracted with further EtOAc (3×4 mL), the combined organic extracts dried by passing through a cartridge fitted with a hydrophobic frit and the solvent evaporated under a stream of $N_2$ to give a colourless gum. The gum was redissolved in MeCN (ca. 2 mL) and applied to a 1 g SCX-2 ion-exchange cartridge which had been pre-wetted with MeCN. The cartridge was eluted with MeCN (2×5 mL) and MeOH (2×5 mL) followed by 2M ammonia in MeOH solution (3×5 mL). The first 10 mL of ammonia solution eluent fractions from the SCX-2 purification were evaporated under a stream of $N_2$ to give a colourless gum; crude (±)-tert-butyl 3-(3-aminopropyl)-4,4-difluoropiperidine-1-carboxylate (6.8 mg, 0.024 mmol, 9.35% yield)

Intermediate 56: (±)-tert-butyl 3-(2-azidoethyl)-4,4-difluoropiperidine-1-carboxylate

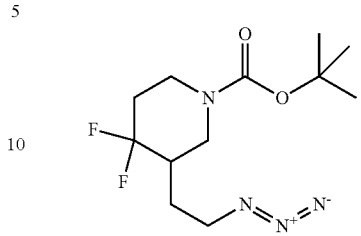

(±)-tert-Butyl 4,4-difluoro-3-(2-((methylsulfonyl)oxy)ethyl)piperidine-1-carboxylate (1.138 g, 3.31 mmol) was dissolved in DMF (20 mL) and sodium azide (263.3 mg, 4.05 mmol) was added. The mixture was stirred under $N_2$ at 80° C. for 4 h. After cooling, the mixture was diluted with 1M aqueous $Na_2CO_3$ solution (50 mL) and extracted with EtOAc (3×30 mL) [Note that 3 phases were observed in the separation, the EtOAc extracts being the least dense]. The combined organics were washed with water (2×40 mL), then dried and evaporated in vacuo to give a pale yellow oil; (±)-tert-butyl 3-(2-azidoethyl)-4,4-difluoropiperidine-1-carboxylate (0.980 g, 3.38 mmol, 102% yield) containing approximately 0.2 equivalents of DMF.

$^1$H NMR (400 MHz, DMSO-$d_6$) δ ppm 3.75 (br s, 1H) 3.68 (br d, 1H) 3.39-3.55 (m, 2H) 3.20 (br t, 1H) 2.99 (br s, 1H) 1.77-2.09 (m, 4H) 1.42 (s, 9H) 1.36-1.49 (m, 1H).

Intermediate 57: (±)-tert-Butyl 3-(2-aminoethyl)-4,4-difluoropiperidine-1-carboxylate

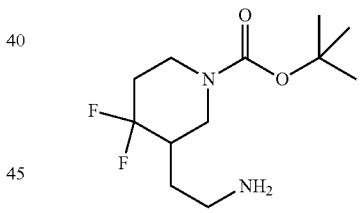

A solution of (±)-tert-butyl 3-(2-azidoethyl)-4,4-difluoropiperidine-1-carboxylate (978 mg, 3.37 mmol) in EtOAc (50 mL) was hydrogenated over a 10% Pd/C catalyst cartridge using a Thales 'H-Cube' flow apparatus in full hydrogen mode at 20° C. The solvent was evaporated from the collected solution in vacuo to give a colourless oil which by NMR analysis was determined to be a 5:4 mixture of starting azide to product amine. The residue was re-dissolved in EtOH (50 mL) and was again hydrogenated over a 10% Pd/C catalyst cartridge using a Thales 'H-Cube' flow apparatus in full hydrogen mode but this time at 40° C. The solvent was evaporated from the collected solution in vacuo to give a colourless oil, (±)-tert-butyl 3-(2-aminoethyl)-4,4-difluoropiperidine-1-carboxylate (796.3 mg, 3.01 mmol, 89% yield).

$^1$H NMR (400 MHz, DMSO-$d_6$) δ ppm 3.65 (br s, 2H) 3.23 (br s, 1H) 2.95 (br s, 1H) 2.63-2.69 (m, 1H) 2.52-2.59 (m, 1H) 1.93-2.08 (m, 2H) 1.76-1.91 (m, 1H) 1.56-1.65 (m, 1H) 1.47 (br s 1H) 1.41 (s, 9H) 1.15-1.27 (m, 1H).

Intermediate 58: tert-Butyl 4-(3-(1,3-dioxoisoindo-lin-2-yl)propyl)-3-oxopiperazine-1-carboxylate

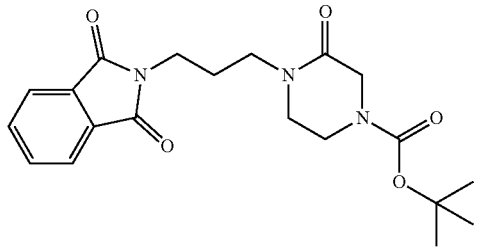 [SMILES: CC(C)(C)OC(=O)N1CCN(CCCN2C(=O)c3ccccc3C2=O)C(=O)C1]

To a mixture of sodium hydride (60% dispersion in mineral oils, 0.1209 g, 3.02 mmol) in THF (5 mL) was added a suspension of tert-butyl 3-oxopiperazine-1-carboxylate (0.5019 g, 2.507 mmol, commercially available from Alfa Aesar) in THF (10 mL). The mixture was stirred at rt for 45 min, after which 2-(3-bromopropyl)isoindoline-1,3-dione (0.6855 g, 2.56 mmol, commercially available from Sigma-Aldrich) was added. The mixture was stirred at rt for a further 65 h. The reaction mixture was quenched with saturated ammonium chloride (approx. 8 mL) and water (approx. 8 mL) and the layers separated. The aqueous layer was extracted with EtOAc (2×15 mL) and the organic layers combined and filtered through a cartridge fitted with a hydrophobic frit. The filtrate was evaporated in vacuo to give a yellow oily solid which was redissolved in approx. 3:1 DMSO:MeCN (9 mL) and directly purified by MDAP (3×3 mL injection, high pH). The required fractions were evaporated under a stream of N$_2$, redissolved in MeOH (approx. 2 mL each) and combined. This solution was evaporated under a stream of N$_2$ and the residue dried in vacuo to give a colourless glassy solid. This was redissolved in MeOH (approx. 5 mL) and directly applied to the top of a 10 g Isolute aminopropyl ion exchange column. The column was eluted with 4 column volumes of MeOH. The first fraction was evaporated in vacuo to give a colourless gum. tert-butyl 4-(3-(1,3-dioxoisoindolin-2-yl)propyl)-3-oxopiperazine-1-carboxylate (237.4 mg, 0.613 mmol, 24.45% yield).

LCMS (2 min high pH); Rt=1.00 min, m/z=388 for [MH]$^+$

Intermediate 59: tert-Butyl 4-(3-aminopropyl)-3-oxopiperazine-1-carboxylate

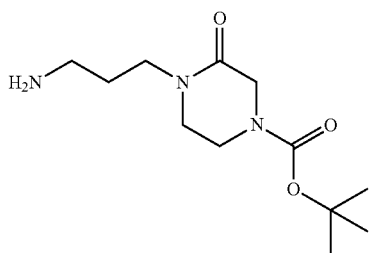 [SMILES: CC(C)(C)OC(=O)N1CCN(CCCN)C(=O)C1]

To a solution of tert-butyl 4-(3-(1,3-dioxoisoindolin-2-yl)propyl)-3-oxopiperazine-1-carboxylate (225.6 mg, 0.582 mmol) in EtOH (5 mL) was added hydrazine hydrate (0.055 mL, 1.771 mmol). The reaction mixture was warmed to 40° C. and stirred for 20 h and 30 min. The reaction mixture was cooled to rt and filtered and the filtrate evaporated under a stream of N$_2$ to give a white solid. This was redissolved in MeOH (2 mL) and directly purified by MDAP (2×1 mL injection, high pH). The required fractions were evaporated under a stream of N$_2$, redissolved in MeOH (approx. 2 mL each) and combined. This solution was evaporated under a stream of N$_2$ to give a colourless viscous oil. tert-butyl 4-(3-aminopropyl)-3-oxopiperazine-1-carboxylate (47.3 mg, 0.184 mmol, 31.6% yield).

LCMS (2 min high pH); Rt=0.67 min, m/z=258 for [MH]$^+$

Intermediate 60: 2-(3-(3-Oxopiperazin-1-yl)propyl)isoindoline-1,3-dione

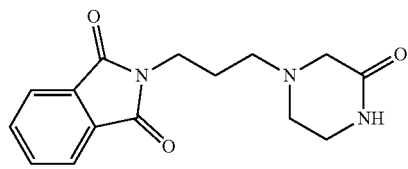 [SMILES: O=C1CN(CCCN2C(=O)c3ccccc3C2=O)CCN1]

A mixture of 3-(1,3-dioxoisoindolin-2-yl)propanal (499.4 mg, 2.458 mmol, commercially available from Fluorochem), piperazin-2-one (376.1 mg, 3.76 mmol, commercially available from Sigma Aldrich) and Na(OAc)$_3$BH (779.9 mg, 3.68 mmol) in 2-MeTHF (20 mL) was stirred at rt for 21 h 40 min. Further Na(OAc)$_3$BH (516.6 mg, 2.437 mmol) was added after 3 h. AcOH (0.014 mL, 0.246 mmol) was added after 4 h 45 min. After 20 h 40 min further 2-MeTHF (5 mL) was added and the reaction mixture was heated to 60° C. Further Na(OAc)$_3$BH (279.9 mg, 1.321 mmol) was added after 3 h 20 min at 60° C. Further Na(OAc)$_3$BH (496.8 mg, 2.344 mmol) was added after 25 h 45 min at 60° C. The mixture was removed from heating and stirring after a total of 31 h at 60° C. and cooled to rt. To this mixture was added sat. NaHCO$_3$ (2 mL) and water (8 mL). The mixture was stirred at rt for 20 min and extracted with EtOAc (3×10 mL). The organic layer was filtered through a cartridge fitted with a hydrophobic frit and the volatiles evaporated in vacuo to give an oil which was redissolved in MeOH (approx. 5 mL) and applied to the top of a 20 g Isolute aminopropyl ion exchange column. The column was eluted with 4 column volumes of MeOH and 4 column volumes of aqueous 2M HCl. The second MeOH fraction was evaporated in vacuo to give a pale yellow solid; 2-(3-(3-oxopiperazin-1-yl)propyl)isoindoline-1,3-dione (595.1 mg, 2.071 mmol, 84% yield).

LCMS (2 min high pH); Rt=0.71 min, m/z=288 for [MH]$^+$

Intermediate 61: 4-(3-Aminopropyl)piperazin-2-one

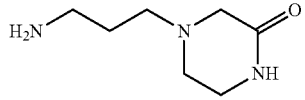 [SMILES: NCCCN1CCNC(=O)C1]

To a mixture of 2-(3-(3-oxopiperazin-1-yl)propyl)isoindoline-1,3-dione (590.1 mg, 2.054 mmol) in EtOH (12 mL) was added hydrazine hydrate (0.191 mL, 6.16 mmol). The mixture was stirred at rt for 24.5 h. The mixture was then applied to the top of a 20 g Isolute SCX-2 ion exchange cartridge. The cartridge was eluted with 4 column volumes of MeOH and 4 column volumes of 2M NH₃ in MeOH. The basic fractions were evaporated in vacuo and the residue was dissolved in 10 mM aqueous ammonium bicarbonate buffer solution (pH 10, 6 mL) and directly purified by MDAP (2×3 mL injection, high pH). The required fractions were combined and evaporated in vacuo to give a pale yellow viscous oil; 4-(3-aminopropyl)piperazin-2-one (273.6 mg, 1.740 mmol, 85% yield).

LCMS (2 min high pH); Rt=0.21 min, m/z=158 for [MH]⁺

Intermediate 62: 2-(3-(4-Methyl-3-oxopiperazin-1-yl)propyl)isoindoline-1,3-dione

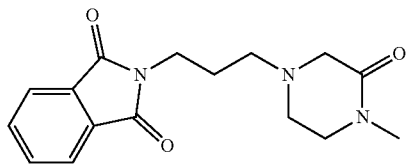 [SMILES: CN1CCN(CCCN2C(=O)c3ccccc3C2=O)CC1=O]

To a mixture of 3-(1,3-dioxoisoindolin-2-yl)propanal (515 mg, 2.53 mmol, commercially available from Fluorochem) and Na(OAc)₃BH (815.9 mg, 3.85 mmol) in 2-MeTHF (20 mL) was added 1-methylpiperazin-2-one (0.420 mL, 3.82 mmol, commercially available from Fluorochem). The mixture was stirred at rt for 4 h 45 min. To the reaction mixture was added aqueous 2M Na₂CO₃ (10 mL) and this mixture stirred at rt for 10 min giving an aqueous phase at approximately pH 10. The layers were separated and the aqueous layer washed with EtOAc (2×10 mL). The organic layers were filtered through a cartridge fitted with a hydrophobic frit and the filtrate evaporated in vacuo to give a pale yellow crystalline solid. 2-(3-(4-methyl-3-oxopiperazin-1-yl)propyl)isoindoline-1,3-dione (660.5 mg, 2.192 mmol, 86% yield).

LCMS (2 min high pH); Rt=0.74 min, m/z=302 for [MH]⁺

Intermediate 63: 4-(3-Aminopropyl)-1-methylpiperazin-2-one

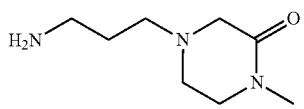

To a mixture of 2-(3-(4-methyl-3-oxopiperazin-1-yl)propyl)isoindoline-1,3-dione (656.7 mg, 2.179 mmol) in EtOH (15 mL) was added hydrazine hydrate (0.200 mL, 6.44 mmol) and the mixture stirred at rt for 41.5 h. The mixture was heated to 40° C. and stirred for a further 7 h 25 min. The mixture was removed from heat and stirring and cooled to rt. The mixture was then filtered and the filtrate applied to the top of a 20 g Isolute SCX-2 ion exchange column. The column was eluted with 4 column volumes of MeOH and 4 column volumes of 2M NH₃ in MeOH. The basic fractions were evaporated in vacuo to give a yellow oil. This was redissolved in MeOH (6 mL) and purified by MDAP (2×3 mL injection, high pH). The required fractions were evaporated in vacuo, redissolved in DCM (approx. 10 mL) and evaporated in vacuo to give a pale yellow viscous oil; 4-(3-aminopropyl)-1-methylpiperazin-2-one (260.9 mg, 1.524 mmol, 69.9% yield).

LCMS (2 min high pH); Rt=0.35 min, m/z=172 for [MH]⁺

Intermediate 64: tert-Butyl 2-chloro-6-(methylcarbamoyl)isonicotinate

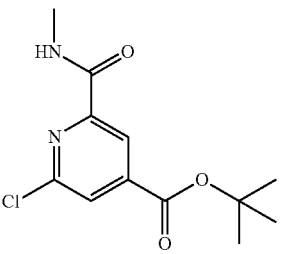 [SMILES: CNC(=O)c1cc(C(=O)OC(C)(C)C)cc(Cl)n1]

2,4,6-Tripropyl-1,3,5,2,4,6-trioxatriphosphinane 2,4,6-trioxide (40.7 g, 64.0 mmol) was added to a solution of 4-(tert-butoxycarbonyl)-6-chloropicolinic acid (15 g, 58.2 mmol, commercially available from, for example, Anichem) and Et₃N (16.23 mL, 116 mmol) in DCM (100 mL) at rt, then the mixture was stirred for 20 min before addition of methanamine (2M in THF, 38.8 mL, 78 mmol). The mixture was stirred for 2 h, then washed with water (100 mL) and saturated NaHCO₃ solution, then dried and evaporated in vacuo to give a pale yellow gum. This was dissolved in DCM and loaded onto a 340 g silica column, then eluted with 0-40% EtOAc/cyclohexane and the product-containing fractions were evaporated in vacuo to give tert-butyl 2-chloro-6-(methylcarbamoyl)isonicotinate (6.9 g, 25.5 mmol, 43.8% yield) as a pale yellow gum which crystallised on standing.

LCMS (2 min High pH): Rt=1.16 min, [MH]⁺=271.2.
¹H NMR (400 MHz, CDCl₃) δ ppm 8.55 (d, J=1.2 Hz, 1H) 7.95 (d, J=1.2 Hz, 1H) 7.79 (br. s, 1H) 3.05 (d, J=4.9 Hz, 3H) 1.61 (s, 9H)

Intermediate 65: 4-tert-Butyl 2-ethyl 6-(methylcarbamoyl)pyridine-2,4-dicarboxylate

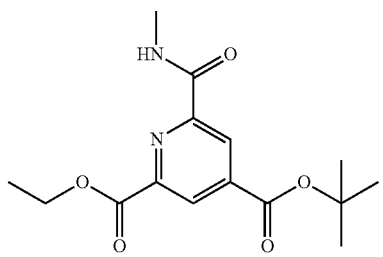 [SMILES: CCOC(=O)c1cc(C(=O)OC(C)(C)C)cc(C(=O)NC)n1]

tert-Butyl 2-chloro-6-(methylcarbamoyl)isonicotinate (4.2 g, 15.51 mmol) was dissolved in a mixture of DMF (50 mL) and EtOH (50 mL), then Et₃N (4.71 g, 46.5 mmol) and [(R)-(+)-2,2'-bis(diphenylphosphino)-1,1'-binaphthyl]palladium(II) chloride (0.621 g, 0.776 mmol) were added and the mixture was purged with carbon monoxide, then sealed and a balloon full of carbon monoxide fitted. The mixture was heated at 70° C. over the weekend, then evaporated in vacuo and the residue was partitioned between water (100 mL) and EtOAc (100 mL). The organic layer was washed with water (100 mL), dried and evaporated in vacuo. The dark brown residue was purified by chromatography on a 100 g silica column eluting with 0-50% EtOAc/cyclohexane to give 4-tert-butyl 2-ethyl 6-(methylcarbamoyl)pyridine-2,4-dicarboxylate (4.2 g, 13.62 mmol, 88% yield) as a pale yellow gum.

LCMS (2 min High pH): Rt=1.11 min, [MH]+=309.2.

$^1$H NMR (400 MHz, CDCl$_3$) δ ppm 8.80 (d, J=1.5 Hz, 1H) 8.67 (d, J=1.7 Hz, 1H) 8.08 (br. d, J=3.4 Hz, 1H) 4.50 (q, J=7.1 Hz, 2H) 3.08 (d, J=5.1 Hz, 3H) 1.63 (s, 9H) 1.46 (t, J=7.1 Hz, 3H)

Intermediate 66: tert-Butyl 2-(hydroxymethyl)-6-(methylcarbamoyl)isonicotinate

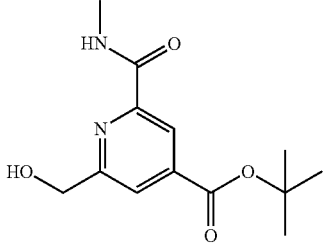 [SMILES: CNC(=O)c1cc(C(=O)OC(C)(C)C)cc(CO)n1]

Calcium chloride (4.54 g, 40.9 mmol) was added to a solution of 4-tert-butyl 2-ethyl 6-(methylcarbamoyl)pyridine-2,4-dicarboxylate (4.2 g, 13.62 mmol) in a mixture of EtOH (50 mL) and 2-MeTHF (50.0 mL) at 0° C., then NaBH$_4$ (0.773 g, 20.43 mmol) was added and the resulting red mixture was stirred for 2 h allowing the mixture to warm to rt. The mixture was allowed to stand overnight, then cooled in an ice bath and ammonium chloride solution (100 mL) added slowly over 20 min. The mixture was extracted with EtOAc (2×150 mL), then the organics were dried and evaporated in vacuo and the residue purified by chromatography on a 50 g silica column to give tert-butyl 2-(hydroxymethyl)-6-(methylcarbamoyl)isonicotinate (2.2 g, 8.26 mmol, 60.6% yield) as a beige solid.

LCMS (2 min High pH): Rt=0.84 min, [MH]+=267.3.

$^1$H NMR (400 MHz, CDCl$_3$) δ ppm 8.49-8.58 (m, 1H) 7.90-8.02 (m, 2H) 4.87 (s, 2H) 3.05 (d, J=5.1 Hz, 3H) 1.61 (s, 9H)

Intermediate 67: tert-Butyl 2-(chloromethyl)-6-(methylcarbamoyl)isonicotinate

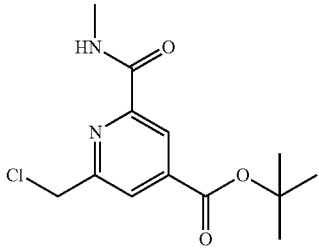 [SMILES: CNC(=O)c1cc(C(=O)OC(C)(C)C)cc(CCl)n1]

tert-butyl 2-(hydroxymethyl)-6-(methylcarbamoyl)isonicotinate (1.5 g, 5.63 mmol) was dissolved in DCM (5 mL), thionyl chloride (1.257 mL, 16.90 mmol) was added and the reaction stirred at rt for 4 h, then the mixture was quenched by the addition of saturated NaHCO$_3$ solution and the mixture was stirred for 20 min, then the organic layer was separated, dried and evaporated in vacuo to give tert-butyl 2-(chloromethyl)-6-(methylcarbamoyl)isonicotinate (1.35 g, 4.74 mmol, 84% yield) as a colourless solid.

LCMS (2 min High pH): Rt=1.13 min, [MH]+=285.2.

$^1$H NMR (400 MHz, CDCl$_3$) δ ppm 8.59 (d, J=1.2 Hz, 1H) 8.11 (d, J=1.2 Hz, 1H) 7.95 (br. s., 1H) 4.72 (s, 2H) 3.07 (d, J=5.1 Hz, 3H) 1.62 (s, 9H)

Intermediate 68: tert-Butyl 2-formyl-6-(methylcarbamoyl)isonicotinate

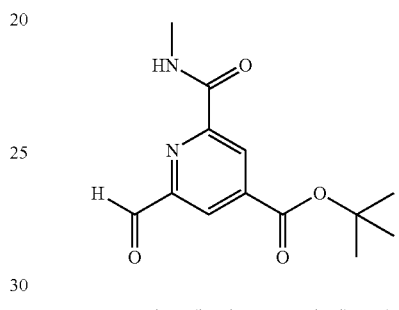

tert-Butyl 2-(hydroxymethyl)-6-(methylcarbamoyl)isonicotinate (543 mg, 2.039 mmol) was dissolved in DCM (5 mL). Dess-Martin periodinane (1009 mg, 2.380 mmol) was added and the mixture stirred at rt for 3 h. Sodium thiosulfate was added to the reaction mixture then NaHCO$_3$ was also added. The resultant mixture was stirred for 15 min. The aqueous phase was extracted with DCM three times and the combined organic layers were dried over MgSO$_4$ and evaporated. The crude product was purified by chromatography on SiO$_2$ (Biotage® SNAP 10 g, eluting with 0-50% EtOAc/cyclohexane). The desired fractions were concentrated to give tert-butyl 2-formyl-6-(methylcarbamoyl)isonicotinate (501 mg, 1.706 mmol, 84% yield) as a colourless oil.

LCMS (2 min Formic): Rt=0.97 min, [MH]$^+$=265.3.

$^1$H NMR (400 MHz, CDCl$_3$) δ ppm 10.14 (s, 1H) 8.88 (d, J=1.5 Hz, 1H) 8.55 (d, J=1.5 Hz, 1H) 8.00 (br. s., 1H) 3.12 (d, J=4.9 Hz, 3H) 1.62-1.66 (m, 9H)

Intermediate 69: tert-Butyl 2-benzyl-6-(methylcarbamoyl)isonicotinate

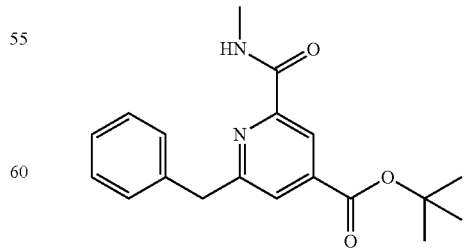

tert-Butyl 2-chloro-6-(methylcarbamoyl)isonicotinate (5 g, 18.47 mmol, commercially available from, for example, Anichem) and PdCl$_2$(PPh$_3$)$_2$ (1.296 g, 1.847 mmol) were dissolved in THF (50 mL) and benzylzinc(II) bromide (0.5M in THF, 55.4 mL, 27.7 mmol) was added, then the mixture was heated at 70° C. for 2 h. The solvent was evaporated in vacuo and the residue purified by chromatography on a 100 g silica column eluting with 0-50% EtOAc/cyclohexane to give tert-butyl 2-benzyl-6-(methylcarbamoyl)isonicotinate (5.7 g, 17.46 mmol, 95% yield) as a dark brown oil which was used in the next step without further purification.

LCMS (2 min High pH): Rt=1.30 min, [MH]$^+$=327.3.

$^1$H NMR (400 MHz, CDCl$_3$) δ ppm 8.48 (d, J=1.2 Hz, 1H) 7.97-8.07 (m, 1H) 7.81 (d, J=1.2 Hz, 1H) 7.30-7.37 (m, 2H) 7.21-7.29 (m, 3H) 4.24 (s, 2H) 3.07 (d, J=5.1 Hz, 3H) 1.55-1.64 (m, 9H)

Intermediate 70:
2-Benzyl-6-(methylcarbamoyl)isonicotinic acid

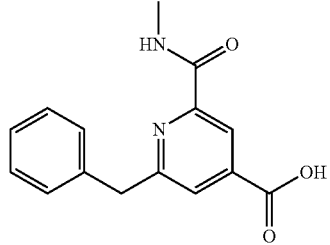 [SMILES: CNC(=O)c1cc(C(=O)O)cc(Cc2ccccc2)n1]

tert-Butyl 2-benzyl-6-(methylcarbamoyl)isonicotinate (2.5 g, 7.66 mmol) was dissolved in DCM (30 mL), then TFA (10 mL, 130 mmol) was added and the mixture was stirred for 3 h at rt. The solvent was evaporated in vacuo to give a pale yellow gum. The crude material was dissolved in DCM (100 mL) and washed with water (100 mL), the organic layer was dried and evaporated in vacuo to give 2-benzyl-6-(methylcarbamoyl)isonicotinic acid (2.0 g, 7.40 mmol, 97% yield) as a pale yellow solid LCMS (2 min High pH): Rt=0.63 min, [MH]$^+$=271.3.

$^1$H NMR (400 MHz, DMSO-d$_6$) δ ppm 8.77 (s, 1H) 8.22 (d, J=1.2 Hz, 1H) 7.83 (d, J=1.5 Hz, 1H) 7.35-7.39 (m, 2H) 7.31 (t, J=7.6 Hz, 2H) 7.19-7.25 (m, 1H) 4.26 (s, 2H) 2.86 (d, J=4.9 Hz, 3H). One exchangeable proton not observed.

Intermediate 71: tert-Butyl 2-(3-methoxybenzyl)-6-(methylcarbamoyl)isonicotinate

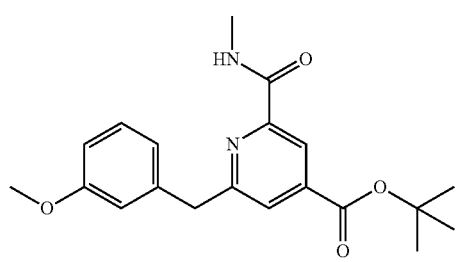 [SMILES: CNC(=O)c1cc(C(=O)OC(C)(C)C)cc(Cc2cccc(OC)c2)n1]

tert-Butyl 2-chloro-6-(methylcarbamoyl)isonicotinate (1.5 g, 5.54 mmol) was dissolved in THF (20 mL) and PdCl$_2$(PPh$_3$)$_2$ (0.389 g, 0.554 mmol) was added. The solution was sparged with N$_2$ for 5 min, then (3-methoxybenzyl)zinc(II) bromide (0.5M in THF, 20 mL, 10.00 mmol) was added and the mixture heated at 70° C. for 2 h. The solution was diluted with EtOAc (100 mL) and washed with water (100 mL), dried and evaporated in vacuo. The residue was purified by chromatography on a 50 g silica column eluting with 0-50% EtOAc/cyclohexane and the product-containing fractions evaporated in vacuo to give tert-butyl 2-(3-methoxybenzyl)-6-(methylcarbamoyl)isonicotinate (1.65 g, 4.63 mmol, 84% yield) as a dark yellow oil.

LCMS (2 min High pH): Rt=1.29 min, [MH]$^+$=357.3.

Intermediate 72: 2-(3-Methoxybenzyl)-6-(methylcarbamoyl)isonicotinic acid

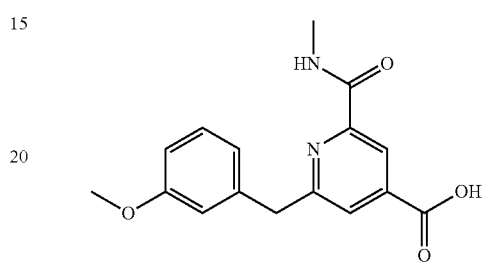

tert-Butyl 2-(3-methoxybenzyl)-6-(methylcarbamoyl)isonicotinate (2.5 g, 7.01 mmol) was dissolved in DCM (30 mL), then TFA (10 mL, 130 mmol) was added and the mixture was stirred for 18 h at rt. The solvent was evaporated in vacuo to give a pale yellow gum. This was dissolved in DCM (50 mL) and washed with water (50 mL). The organic layer was dried and evaporated in vacuo to give 2-(3-methoxybenzyl)-6-(methylcarbamoyl)isonicotinic acid (1.8 g, 5.99 mmol, 85% yield) as a pale yellow solid.

LCMS (2 min High pH): Rt=0.64 min, [MH]$^+$=301.2.

Intermediate 73: (+/−)-tert-Butyl 2-(methylcarbamoyl)-6-(1-phenylethyl)isonicotinate

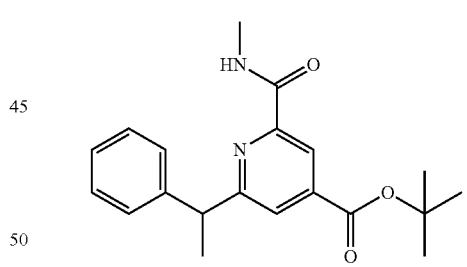

tert-Butyl 2-chloro-6-(methylcarbamoyl)isonicotinate (0.5 g, 1.847 mmol) was dissolved in THF (20 mL) and PdCl$_2$(PPh$_3$)$_2$ (0.130 g, 0.185 mmol) was added. The solution was sparged with N$_2$ for 5 min, then (1-phenylethyl)zinc(II) bromide (0.5M in THF, 7.39 mL, 3.69 mmol, commercially available from, for example, Sigma Aldrich) was added and the mixture heated at 70° C. for 2 h.

The solution was diluted with EtOAc (100 mL) and washed with water (100 mL), dried and evaporated in vacuo. The residue was purified by chromatography on a 25 g silica column eluting with 0-50% EtOAc/cyclohexane and the product-containing fractions evaporated in vacuoto give tert-butyl 2-(methylcarbamoyl)-6-(1-phenylethyl)isonicotinate (0.41 g, 1.204 mmol, 65.2% yield) as a dark yellow oil.

LCMS (2 min High pH): Rt=1.37 min, [MH]$^+$=341.3.

$^1$H NMR (400 MHz, CDCl$_3$) δ ppm 8.45 (d, J=1.5 Hz, 1H) 8.02 (br. s., 1H) 7.81 (d, J=1.2 Hz, 1H) 7.18-7.36 (obs. m, 5H) 4.38 (q, J=7.3 Hz, 1H) 3.07 (d, J=5.1 Hz, 3H) 1.74 (d, J=7.3 Hz, 3H) 1.59 (s, 9H)

Intermediate 74: (+/−)-2-(Methylcarbamoyl)-6-(1-phenylethyl)isonicotinic acid

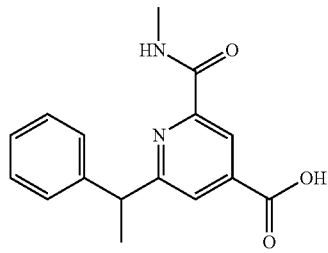

tert-Butyl 2-(methylcarbamoyl)-6-(1-phenylethyl)isonicotinate (0.41 g, 1.204 mmol) was dissolved in TFA (6 mL) and stirred for 3 h at rt, then the mixture was evaporated in vacuo and the residue partitioned between water (20 mL) and DCM (20 mL). The organic layer was dried and evaporated in vacuo to give 2-(methylcarbamoyl)-6-(1-phenylethyl)isonicotinic acid (305 mg, 1.073 mmol, 89% yield) as a grey foam.

LCMS (2 min High pH): Rt=0.69 min, [MH]$^+$=285.2.

$^1$H NMR (400 MHz, DMSO-d$_6$) δ ppm 13.74 (br. s., 1H) 8.75 (m, J=4.9 Hz, 1H) 8.21 (d, J=1.5 Hz, 1H) 7.82 (d, J=1.5 Hz, 1H) 7.42 (br. d, J=7.1 Hz, 1H) 7.30 (t, J=7.5 Hz, 2H) 7.16-7.23 (m, 1H) 4.47 (q, J=7.1 Hz, 1H) 2.89 (d, J=4.9 Hz, 3H) 1.72 (d, J=7.3 Hz, 3H)

Intermediate 75: (R*)-tert-Butyl 2-(methylcarbamoyl)-6-(1-phenylethyl)isonicotinate Intermediate 76: (S*)-tert-Butyl 2-(methylcarbamoyl)-6-(1-phenylethyl)isonicotinate

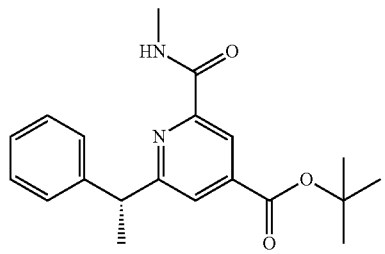 [SMILES: CNC(=O)c1cc(C(=O)OC(C)(C)C)cc(C(C)c2ccccc2)n1]

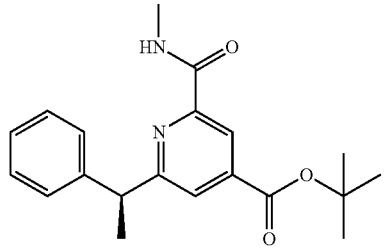

tert-Butyl 2-(methylcarbamoyl)-6-(1-phenylethyl)isonicotinate (1500 mg) was submitted for chiral purification. The racemate was dissolved in EtOH (60 mL) with sonication and gentle heating. 1250 µL automatic injections via preparative autosampler were made onto the column which was eluted with heptane:EtOH:isopropylamine (2000:40:4, premixed), flow rate=42.5 mL/min, detection: UV Diode Array at 280 nm (Band width 140 nm, reference 400 nm bandwidth 100 nm), column: Chiralcel OD-H (250×30 mm). Collection was triggered via funnel bed fraction collector, Using a UV threshold with collection starting after 9 min. Fractions from 10-12 min were bulked and labelled peak 1, fractions from 13.5-17 min were bulked and labelled peak 2. The bulked fractions were concentrated in vacuo and then taken up in EtOH (3×4 mL) and transferred to tared glass vials and these blown down to dryness under a stream of N$_2$.

Peak 1 provided Intermediate 75 (497 mg).

LCMS (2 min High pH): Rt=1.35 min, [MH]$^+$=341.3.

Peak 2 provided Intermediate 76 (517 mg).

LCMS (2 min High pH): Rt=1.35 min, [MH]$^+$=341.3.

Intermediate 77: (R*)-2-(Methylcarbamoyl)-6-(1-phenylethyl)isonicotinic acid

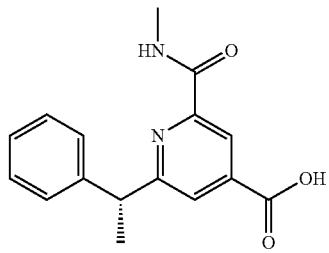 [SMILES: CNC(=O)c1cc(C(=O)O)cc([C@H](C)c2ccccc2)n1]

(R*)-tert-Butyl 2-(methylcarbamoyl)-6-(1-phenylethyl) isonicotinate (497 mg, 1.460 mmol, Intermediate 75) was taken up in DCM (5 mL), TFA (0.5 mL, 6.49 mmol) was added and the reaction left to stir at rt overnight. TFA (0.5 mL, 6.49 mmol) was added again and the reaction was refluxed at 50° C. for 3 h. More TFA (1 mL) was added to the reaction, which was then left to stir for a further 2 h. The reaction was concentrated in vacuo. The sample was loaded in MeOH and purified by SPE on sulphonic acid (SCX) 2 g and eluted through with MeOH. The appropriate fractions were combined and evaporated in vacuo to give the required product (350 mg) as a pink solid.

LCMS (2 min High pH): Rt=0.68 min, [MH]$^+$=285.2.

Intermediate 78: 2-(3-Cyanobenzyl)-6-(methylcarbamoyl)isonicotinic acid

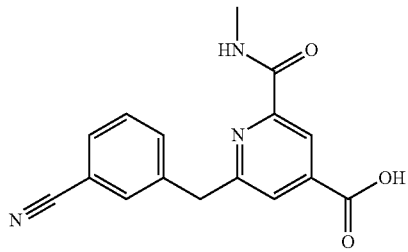 [SMILES: CNC(=O)c1cc(C(=O)O)cc(Cc2cccc(C#N)c2)n1]

tert-Butyl 2-(chloromethyl)-6-(methylcarbamoyl)isonicotinate (100 mg, 0.351 mmol) was combined with (3-cyanophenyl)boronic acid (103 mg, 0.702 mmol), $K_2CO_3$ (291 mg, 2.107 mmol) and $PdCl_2(dppf)$ (55 mg, 0.075 mmol) in 1,4-dioxane (2 mL) and water (1 mL) in a 2 mL microwave vial. This was heated at 120° C. for 40 min. The solution was filtered though Celite®, partitioned between EtOAc (10 mL) and water (10 mL). extracted with EtOAc (2×10 mL), dried through a hydrophobic frit and concentrated. The carboxylic acid was found to reside in the aqueous layer so the organic residue was discarded. The aqueous layer was adjusted to pH 6 with 2M HCl and further extracted with EtOAc (2×30 mL). The organic layers were dried ($Na_2SO_4$) and concentrated to give the desired product (47 mg) as a pale orange solid.

LCMS (2 min Formic): Rt=0.87 min, [MH]+=296.3.

Intermediate 79: tert-Butyl 2-(2-methoxybenzyl)-6-(methylcarbamoyl)isonicotinate

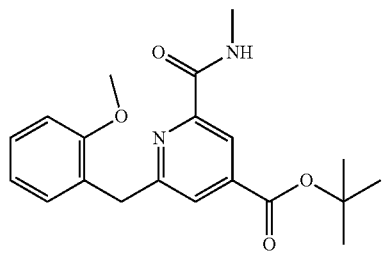 [SMILES: CNC(=O)c1cc(C(=O)OC(C)(C)C)cc(Cc2ccccc2OC)n1]

A mixture of tert-butyl 2-chloro-6-(methylcarbamoyl)isonicotinate (206.9 mg, 0.764 mmol) and $PdCl_2(PPh_3)_2$ (84.0 mg, 0.120 mmol) in THF (2.0 mL) was stirred in a microwave vial at rt for 5 min under a stream of $N_2$ to purge the vial. To this was added (2-methoxybenzyl)zinc(II) chloride (0.5M in THF, 2.2 mL, 1.100 mmol, commercially available from Sigma Aldrich), the vial was resealed and the mixture heated in a microwave reactor at 110° C. for 30 min. The reaction mixture was then filtered through a 2.5 g Celite® cartridge and washed with EtOAc (approx. 20 mL). To the filtrate was added 2M aqueous $Na_2CO_3$ (20 mL) and water (5 mL) and the layers separated. The aqueous layer was extracted with further EtOAc (2×20 mL) and the organic layers combined and filtered through a cartridge fitted with a hydrophobic frit. The filtrate was evaporated in vacuo to give a viscous black oil which was redissolved in DCM (approx. 5 mL), directly applied to the top of a 25 g SNAP silica column and purified by Biotage® SP4 flash column chromatography. The column was eluted with a gradient of 10%-50% EtOAc in cyclohexane. The required fractions were evaporated in vacuo to give a light yellow gum; tert-butyl 2-(2-methoxybenzyl)-6-(methylcarbamoyl)isonicotinate (232.3 mg, 0.652 mmol, 85% yield).

LCMS (2 min high pH); Rt=1.31 min, m/z=357 for [MH]+

Intermediate 80: 2-(2-Methoxybenzyl)-6-(methylcarbamoyl)isonicotinic acid

To a solution of tert-butyl 2-(2-methoxybenzyl)-6-(methylcarbamoyl)isonicotinate (228.0 mg, 0.640 mmol) in DCM (10 mL) was added TFA (2.0 mL, 26.0 mmol) dropwise. The resulting yellow solution was stirred at rt for 53 h, after which it was evaporated in vacuo to give a yellow gum. This was triturated with MeCN (approx. 10 mL), the supernatant was removed and the remaining white solid dried in vacuo. The supernatant was evaporated under a stream of $N_2$ and the residue triturated with diethyl ether (approx. 2 mL). The ether supernatant was removed and the residue was added to the previous white solid. The combined solid was dried in vacuo to give a white solid; 2-(2-methoxybenzyl)-6-(methylcarbamoyl)isonicotinic acid (157.7 mg, 0.525 mmol, 82% yield).

LCMS (2 min high pH); Rt=0.65 min, m/z=301 for [MH]+

Intermediate 81: tert-Butyl 2-(3-hydroxybenzyl)-6-(methylcarbamoyl)isonicotinate tert-Butyl 2-(chloromethyl)-6-(methylcarbamoyl)isonicotinate (130 mg, 0.457 mmol), 3-(4,4,5,5-tetramethyl-1,3,2-dioxaborolan-2-yl)phenol (151 mg, 0.685 mmol), $K_2CO_3$ (189 mg, 1.370 mmol) and $PdCl_2(dppf)$ (33.4 mg, 0.046 mmol) were added to a microwave vial, 2-MeTHF (2 mL) and water (1 mL) were added and the mixture was heated at 100° C. for 1 h. The mixture was diluted with EtOAc (10 mL) and washed with saturated ammonium chloride solution, the organic layer was dried and evaporated in vacuo and the residue purified by chromatography on a 10 g silica column, eluting with 0-50% EtOAc/cyclohexane to give tert-butyl 2-(3-hydroxybenzyl)-6-(methylcarbamoyl)isonicotinate (95 mg, 0.277 mmol, 60.8% yield) as a pale yellow foam.

LCMS (2 min High pH): Rt=1.11 min, [MH]+=343.2.

Intermediate 82: tert-Butyl 2-(3-(2-hydroxyethoxy)benzyl)-6-(methylcarbamoyl)isonicotinate

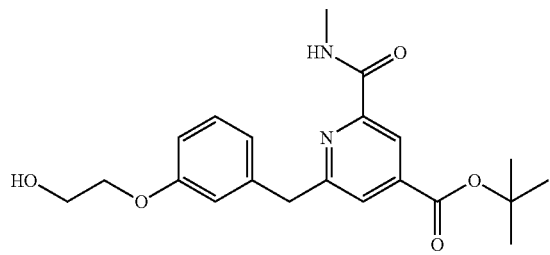 [SMILES: CNC(=O)c1cc(C(=O)OC(C)(C)C)cc(Cc2cccc(OCCO)c2)n1]

tert-Butyl 2-(3-hydroxybenzyl)-6-(methylcarbamoyl)isonicotinate (90 mg, 0.263 mmol) was dissolved in DMF (2 mL) and K$_2$CO$_3$ (109 mg, 0.789 mmol) and 1,3-dioxolan-2-one (69.4 mg, 0.789 mmol) were added, then the mixture was heated at 100° C. for 3 h. The mixture was diluted with water (10 mL) and extracted with EtOAc, the organic layer was washed with water (10 mL), dried and evaporated in vacuo and the residue purified by chromatography on a 10 g silica column eluting with 0-100% EtOAc/cyclohexane to give tert-butyl 2-(3-(2-hydroxyethoxy)benzyl)-6-(methylcarbamoyl)isonicotinate (55 mg, 0.142 mmol, 54.1% yield) as a colourless gum.

LCMS (2 min High pH): Rt=1.10 min, [MH]+=387.4.

Intermediate 83: 2-(3-(2-Hydroxyethoxy)benzyl)-6-(methylcarbamoyl)isonicotinic acid

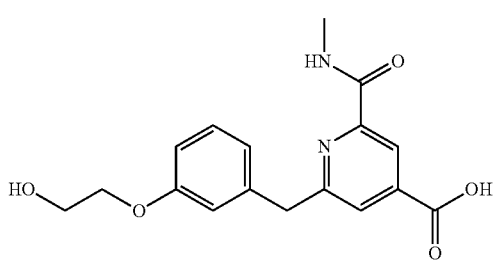 [SMILES: CNC(=O)c1cc(C(=O)O)cc(Cc2cccc(OCCO)c2)n1]

HCl (4M in 1,4-dioxane, 2 mL, 8.00 mmol) was added to tert-butyl 2-(3-(2-hydroxyethoxy)benzyl)-6-(methylcarbamoyl)isonicotinate (166 mg, 0.430 mmol) and the resultant mixture stirred over the weekend. The solvent was removed, then TFA (1 mL, 12.98 mmol) was added and the resultant mixture stirred for 6 h. The solvent was removed, then dimethylamine (2M in THF, 3 mL, 6.00 mmol) was added and the resultant mixture stirred for 15 min. The reaction mixture was then concentrated to give the desired product (296 mg) with a purity of 45%, this was used without further purification.

LCMS (2 min Formic): Rt=0.76 min, [MH]+=331.1.

Intermediate 84: tert-Butyl 2-(4-cyanobenzyl)-6-(methylcarbamoyl)isonicotinate

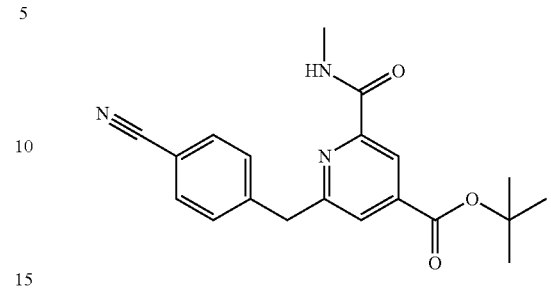

tert-Butyl 2-(chloromethyl)-6-(methylcarbamoyl)isonicotinate (75 mg, 0.263 mmol) was combined with (4-cyanophenyl)boronic acid (77 mg, 0.527 mmol), K$_2$CO$_3$ (218 mg, 1.580 mmol) and PdCl$_2$(dppf) (40 mg, 0.055 mmol) in 1,4-dioxane (2 mL) and water (1 mL) in a 2 mL microwave vial. This was heated at 120° C. for 40 min. The solution was filtered though Celite®, partitioned between EtOAc (10 mL) and water (10 mL), extracted with EtOAc (2×10 mL), dried over a hydrophobic frit and concentrated to give 217 mg of crude brown residue. This was purified by chromatography on SiO$_2$ (Biotage® SNAP 25 g cartridge, eluting with 0-50% EtOAc/cyclohexane). The desired fractions were concentrated to give the desired product (66 mg) as a brown oil.

LCMS (2 min Formic): Rt=1.19 min, [MH]+=352.1.

Intermediate 85: 2-(4-Cyanobenzyl)-6-(methylcarbamoyl)isonicotinic acid

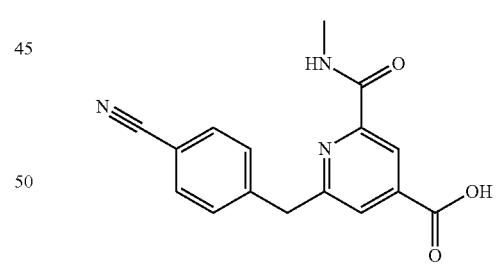

To a solution of tert-butyl 2-(4-cyanobenzyl)-6-(methylcarbamoyl)isonicotinate (66 mg, 0.188 mmol) in DCM (2 mL) was added TFA (0.5 mL, 6.49 mmol) and reaction mixture stirred under N$_2$ at rt for 2 days. The reaction mixture was concentrated in vacuo and the residue partitioned between EtOAc and water. The organic layer was separated, dried with a hydrophobic frit and concentrated to give the desired product (62 mg) as an orange solid.

LCMS (2 min Formic): Rt=0.86 min, [MH]+=296.1.

Intermediate 86: tert-Butyl 2-((1H-indol-4-yl)methyl)-6-(methylcarbamoyl)isonicotinate

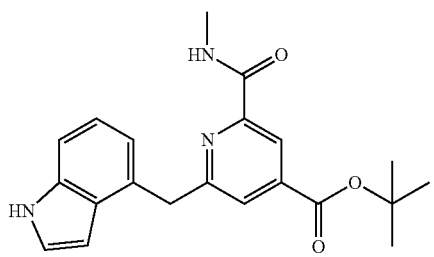 [SMILES: CNC(=O)c1cc(C(=O)OC(C)(C)C)cc(Cc2cccc3[nH]ccc23)n1]

tert-Butyl 2-(chloromethyl)-6-(methylcarbamoyl)isonicotinate (100 mg, 0.351 mmol) was combined with (1H-indol-4-yl)boronic acid (113 mg, 0.702 mmol), $K_2CO_3$ (291 mg, 2.107 mmol) and $PdCl_2$(dppf) (51.4 mg, 0.070 mmol) in 1,4-dioxane (1 mL) and water (0.5 mL) in a 2 mL microwave vial. This was heated at 120° C. for 40 min. The solution was filtered though Celite® eluting with EtOAc (10 mL) dried and concentrated. This was purified by chromatography on $SiO_2$ (Biotage® SNAP 10 g, eluting with 0-60% EtOAc/cyclohexane). The desired fractions were concentrated to give tert-butyl 2-((1H-indol-4-yl)methyl)-6-(methylcarbamoyl)isonicotinate (75.4 mg, 0.165 mmol, 47.0% yield) as a white solid.

LCMS (2 min Formic): Rt=1.20 min, [MH]+=366.2.

$^1$H NMR (400 MHz, MeOH-$d_4$) δ ppm 8.30 (d, J=1.2 Hz, 1H) 7.76 (d, J=1.2 Hz, 1H) 7.31 (d, J=8.3 Hz, 1H) 7.21 (d, J=3.2 Hz, 1H) 7.03-7.11 (m, 1H) 6.91 (br. d, J=7.1 Hz, 1H) 4.52 (s, 2H) 2.99 (s, 3H) 1.54 (s, 9H)

Intermediate 87: 2-((1H-Indol-4-yl)methyl)-6-(methylcarbamoyl)isonicotinic acid

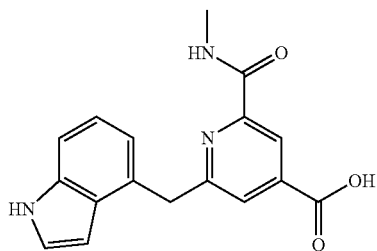 [SMILES: CNC(=O)c1cc(C(=O)O)cc(Cc2cccc3[nH]ccc23)n1]

To a solution of tert-butyl 2-((1H-indol-4-yl)methyl)-6-(methylcarbamoyl)isonicotinate (75.4 mg, 0.165 mmol) in DCM (3 mL) was added TFA (0.60 mL, 7.79 mmol) and reaction mixture was stirred at rt overnight. Further TFA (0.3 mL, 0.165 mmol) was added and the resultant mixture stirred for 3 h. The reaction mixture was concentrated in vacuo to give 2-((1H-indol-4-yl)methyl)-6-(methylcarbamoyl)isonicotinic acid (184 mg, 0.149 mmol, 90% yield).

LCMS (2 min Formic): Rt=0.88 min, [MH]+=310.1.

$^1$H NMR (400 MHz, DMSO-$d_6$) δ ppm 11.59-12.89 (m, 1H) 11.11 (br. s., 1H) 8.76 (d, J=4.9 Hz, 1H) 8.19 (d, J=1.2 Hz, 1H) 7.71 (d, J=1.5 Hz, 1H) 7.21-7.39 (m, 2H) 7.05 (t, J=7.6 Hz, 1H) 6.95 (d, J=6.8 Hz, 1H) 6.46-6.56 (m, 1H) 4.48 (s, 2H) 2.88 (d, J=4.9 Hz, 3H).

Intermediate 88: tert-Butyl 2-(4-methylbenzyl)-6-(methylcarbamoyl)isonicotinate

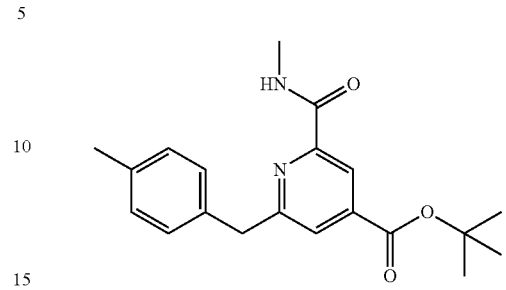

tert-Butyl 2-chloro-6-(methylcarbamoyl)isonicotinate (500 mg, 1.847 mmol) and $PdCl_2(PPh_3)_2$ (194 mg, 0.277 mmol) were added to a microwave vial before being sealed. The vessel was purged with $N_2$ before THF (1 mL) and (4-methylbenzyl)zinc(II) chloride (0.5M in THF, 5.54 mL, 2.77 mmol) were added. The reaction was heated in a Biotage® initiator microwave for 30 min at 110° C. Further (4-methylbenzyl)zinc(III) chloride (0.5M in THF, 3 mL) was added and the reaction heated to 110° C. in the Biotage® Initiator microwave for a further 30 min. The reaction was then filtered though Celite®. The crude product was applied to a 25 g SNAP ULTRA silica cartridge in the minimum of DCM and purified by flash chromatography, eluting with 0%-50% (10% 2M $NH_3$ in MeOH in DCM) in DCM. The appropriate fractions were combined and concentrated in vacuo. to afford the title compound (834 mg).

LCMS (2 min Formic): Rt=1.35 min, [MH]+=341.2.

Intermediate 89: 2-(4-Methylbenzyl)-6-(methylcarbamoyl)isonicotinic acid

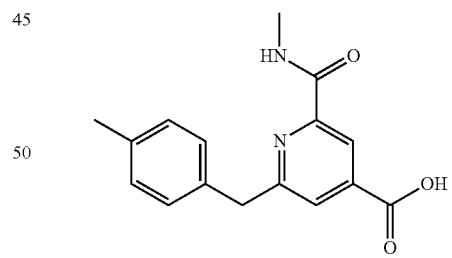

tert-Butyl 2-(4-methylbenzyl)-6-(methylcarbamoyl)isonicotinate (834 mg, 2.450 mmol) was taken up in DCM (10 mL). TFA (1 mL, 12.98 mmol) was added and the reaction left to stir at rt overnight. Further TFA (1 mL, 12.98 mmol) was added again and the reaction left to stir for a further 3 h. The reaction had still not gone to completion. The reaction was heated to 50° C. and left for a further 2 h. The reaction was concentrated in vacuo. to afford the title compound (662 mg) which was used directly in the next step.

LCMS (2 min Formic): Rt=1.01 min, [MH]+=285.1

Intermediate 90: (+/−)-tert-Butyl 2-(hydroxy(phenyl)methyl)-6-(methylcarbamoyl)isonicotinate

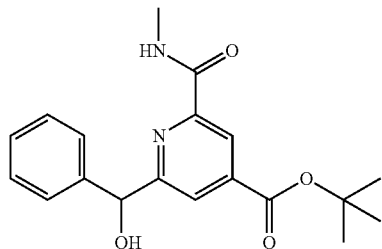 [SMILES: CNC(=O)c1cc(C(=O)OC(C)(C)C)cc(C(O)c2ccccc2)n1]

To a solution of tert-butyl 2-formyl-6-(methylcarbamoyl)isonicotinate (118 mg, 0.447 mmol) in THF (1.5 mL) at 0° C., was added dropwise phenylmagnesium bromide (2 mL, 2.000 mmol). The reaction mixture was stirred for 2 h. The reaction mixture was poured onto ammonium chloride aqueous solution and extracted with EtOAc (20 mL×3). The organic layer was dried over MgSO$_4$ and concentrated in vacuo. The crude product was purified by chromatography on SiO$_2$ (Biotage® SNAP 10 g, eluting with 0-60% EtOAc/cyclohexane). The desired fractions were concentrated to give tert-butyl 2-(hydroxy(phenyl)methyl)-6-(methylcarbamoyl)isonicotinate (43 mg, 0.107 mmol, 23.91% yield).

LCMS (2 min Formic): Rt=1.09 min, [MH]$^+$=343.3

$^1$H NMR (400 MHz, MeOH-d$_4$) δ ppm 8.38 (d, J=1.2 Hz, 1H) 8.05 (d, J=1.2 Hz, 1H) 7.42-7.47 (m, 2H) 7.22-7.36 (m, 3H) 5.95 (s, 1H) 2.99 (s, 3H) 1.60 (s, 9H)

Intermediate 91: (+/−)-2-(Hydroxy(phenyl)methyl)-6-(methylcarbamoyl)isonicotinic acid

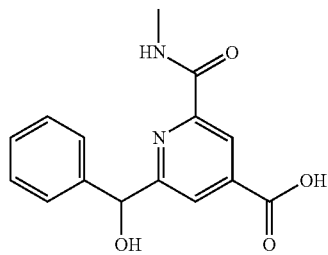 [SMILES: CNC(=O)c1cc(C(=O)O)cc(C(O)c2ccccc2)n1]

To a solution of tert-butyl 2-(hydroxy(phenyl)methyl)-6-(methylcarbamoyl)isonicotinate (43 mg, 0.126 mmol) in DCM (0.5 mL) was added TFA (0.4 mL, 5.19 mmol) and the reaction mixture was stirred for 2 h and then overnight. Further TFA (0.4 mL, 0.126 mmol) was added and the reaction mixture was stirred for 5 h, then the solvent was removed to give 2-(hydroxy(phenyl)methyl)-6-(methylcarbamoyl)isonicotinic acid (47.9 mg, 0.117 mmol, 93% yield, 70% purity) which was used directly in the next step.

LCMS (2 min Formic): Rt=0.74 min, [MH]$^+$=287.1

$^1$H NMR (400 MHz, MeOH-d$_4$) δ ppm 8.45 (d, J=1.2 Hz, 1H) 8.10 (d, J=1.5 Hz, 1H) 7.41-7.48 (m, 2H) 7.21-7.38 (m, 3H) 5.97 (s, 1H) 2.99 (s, 3H).

Intermediate 92: tert-Butyl 2-(3-methylbenzyl)-6-(methylcarbamoyl)isonicotinate

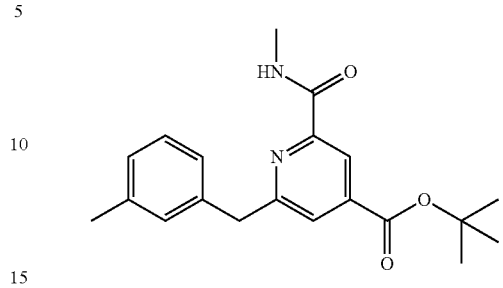

tert-Butyl 2-chloro-6-(methylcarbamoyl)isonicotinate (500 mg, 1.847 mmol) and PdCl$_2$(PPh$_3$)$_2$ (194 mg, 0.277 mmol) were added to a microwave vial before being sealed. The system was purged with N$_2$ before (3-methylbenzyl)zinc(II) chloride (0.5M in THF, 5.54 mL, 2.77 mmol) and THF (1 mL) were added. The reaction vessel was sealed and heated in Biotage® Initiator microwave to 110° C. for 30 min. The reaction was then concentrated in vacuo. The crude product was applied to a 25 g SNAP ULTRA silica cartridge in the minimum of DCM and purified by flash chromatography, eluting with 0-75% (10% 2M NH$_3$ in MeOH in DCM). The appropriate fractions were combined and concentrated in vacuo.

LCMS (2 min Formic): Rt=1.35 min, [MH]$^+$=341.1

Intermediate 93: 2-(3-Methylbenzyl)-6-(methylcarbamoyl)isonicotinic acid

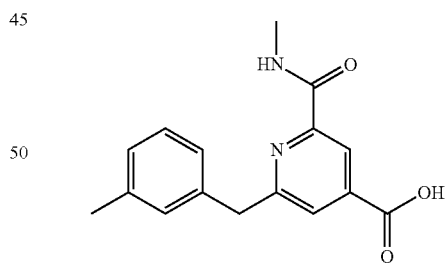

tert-Butyl 2-(3-methylbenzyl)-6-(methylcarbamoyl)isonicotinate (592 mg, 1.739 mmol) was taken up in DCM (5 mL). TFA (1 mL, 12.98 mmol) was added and the reaction was left to stir at rt for 2 h. The reaction was stirred at 50° C. overnight. The reaction was concentrated in vacuo to afford the title compound (472 mg) which was used directly in the next step.

LCMS (2 min Formic): Rt=1.00 min, [MH]$^+$=285.1

Intermediate 94: tert-butyl 4-(2-(2-benzyl-6-(methylcarbamoyl)isonicotinamido)ethyl)piperidine-1-carboxylate

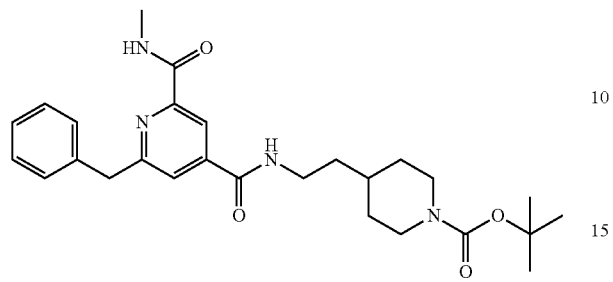

2-Benzyl-6-(methylcarbamoyl)isonicotinic acid (70 mg, 0.259 mmol), HATU (156 mg, 0.410 mmol), DIPEA (0.14 mL, 0.802 mmol) and DMF (3 mL) were stirred at rt under N$_2$ then tert-butyl 4-(2-aminoethyl)piperidine-1-carboxylate (120 mg, 0.526 mmol) was added and the reaction stirred at rt under N$_2$ for 3 h. Further tert-butyl 4-(2-aminoethyl)piperidine-1-carboxylate (120 mg, 0.526 mmol) was added and the reaction stirred under N$_2$ at rt for 1 h. Further HATU (147 mg, 0.387 mmol), DIPEA (0.14 mL, 0.802 mmol), tert-butyl 4-(2-aminoethyl)piperidine-1-carboxylate (118 mg, 0.518 mmol) and DMF (3 mL) were added and the reaction stirred for 18 h. The solution was concentrated to give 1.2 g of an orange oil. This was purified by chromatography on SiO$_2$ (Biotage® SNAP 25 g cartridge, eluting with 0-100% EtOAc/cyclohexane). The appropriate fractions were concentrated to give 44 mg of a yellow oil. This was further purified by MDAP (Formic). The fractions containing the desired product were concentrated to give tert-butyl 4-(2-(2-benzyl-6-(methylcarbamoyl)isonicotinamido)ethyl)piperidine-1-carboxylate (15 mg, 0.028 mmol, 10.85% yield) as a white solid LCMS (2 min Formic): Rt=1.23 min, [MH]+=481.5.

Intermediate 95: (S)-tert-Butyl 2-(3-(2-((1H-indol-4-yl)methyl)-6-(methylcarbamoyl)isonicotinamido)propyl)morpholine-4-carboxylate

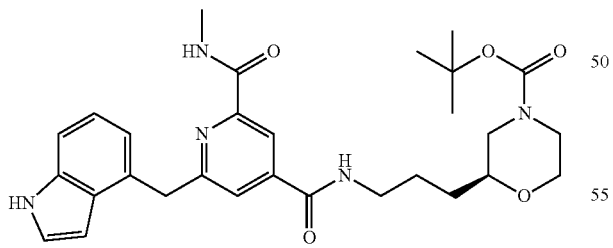

To a solution of 2-((1H-indol-4-yl)methyl)-6-(methylcarbamoyl)isonicotinic acid (184 mg, 0.149 mmol) in DMF (0.85 mL) was added HATU (91 mg, 0.239 mmol) followed by (S)-tert-butyl 2-(3-aminopropyl)morpholine-4-carboxylate (72.7 mg, 0.297 mmol) and DIPEA (0.130 mL, 0.744 mmol). The resulting reaction mixture was stirred at rt overnight. The reaction mixture was purified directly by MDAP (Formic). The fractions containing desired product were partitioned between sat. NaHCO$_3$ solution and DCM. The organic layer was extracted with DCM (2×20 mL) then dried and concentrated in vacuo to give (S)-tert-butyl 2-(3-(2-((1H-indol-4-yl)methyl)-6-(methylcarbamoyl)isonicotinamido)propyl)morpholine-4-carboxylate (28.7 mg, 0.048 mmol, 32.4% yield) as a colourless oil.

LCMS (2 min Formic): Rt=1.10 min, [MH]+=536.4.

Intermediate 96: (S)-tert-Butyl 2-(3-(2-benzyl-6-(methylcarbamoyl)isonicotinamido)propyl)morpholine-4-carboxylate

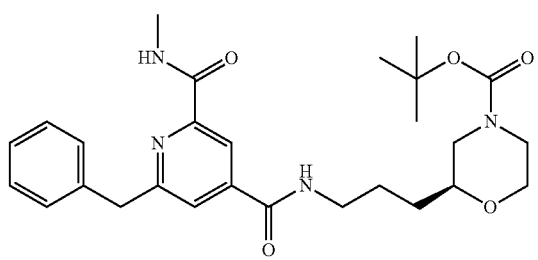 [SMILES: CNC(=O)c1cc(C(=O)NCCC[C@H]2CN(C(=O)OC(C)(C)C)CCO2)cc(Cc2ccccc2)n1]

To a solution of 2-benzyl-6-(methylcarbamoyl)isonicotinic acid (40 mg, 0.148 mmol) in DMF (0.7 mL) was added HATU (91 mg, 0.239 mmol) followed by (S)-tert-butyl 2-(3-aminopropyl)morpholine-4-carboxylate (68 mg, 0.278 mmol) and DIPEA (0.10 mL, 0.573 mmol). The resulting reaction mixture was stirred at rt overnight. The reaction mixture was purified directly by MDAP (Formic). The fractions containing the desired product were partitioned between saturated Na$_2$CO$_3$ solution and DCM. The organic layer was extracted with DCM (2×20 mL) then dried and concentrated in vacuo to give (S)-tert-butyl 2-(3-(2-benzyl-6-(methylcarbamoyl)isonicotinamido)propyl)morpholine-4-carboxylate (56 mg, 0.101 mmol, 68.6% yield) as a colourless oil.

LCMS (2 min Formic): Rt=1.16 min, [MH]+=497.2.

Intermediate 97: (S)-tert-Butyl 2-(2-(2-benzyl-6-(methylcarbamoyl)isonicotinamido)ethyl)morpholine-4-carboxylate

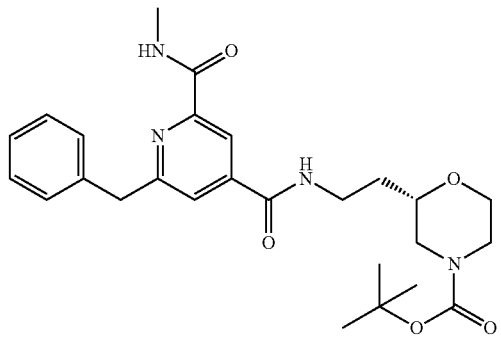 [SMILES: CNC(=O)c1cc(C(=O)NCC[C@H]2CN(C(=O)OC(C)(C)C)CCO2)cc(Cc2ccccc2)n1]

To a solution of (S)-tert-butyl 2-(2-aminoethyl)morpholine-4-carboxylate (320 mg, 1.387 mmol) in DMF (2 mL) was added 2-benzyl-6-(methylcarbamoyl)isonicotinic acid (250 mg, 0.925 mmol) followed by HATU (528 mg, 1.387 mmol) and DIPEA (0.65 mL, 3.72 mmol). The resulting reaction mixture was stirred at rt overnight. The reaction was extracted with LiCl and EtOAc three times then with 2M HCl. The combined organic phases were dried, then concentrated in vacuo. The crude product was purified by chromatography on SiO$_2$ (Biotage® SNAP 10 g, eluting with 0-60% EtOAc/cyclohexane). The desired fractions were concentrated to give the crude product. This was base washed 2 times and extracted with DCM. The combined organic phases were dried then concentrated in vacuo to give (S)-tert-butyl 2-(2-(2-benzyl-6-(methylcarbamoyl)isonicotinamido)ethyl)morpholine-4-carboxylate (92 mg, 0.172 mmol, 18.55% yield).

The same column was flashed with 25% EtOH in EtOAc. The fractions containing additional product were concentrated in vacuo, then the yellow oil obtained was base washed and extracted with DCM 3 times. The combined organic layer was dried then concentrated in vacuo to give further product—(S)-tert-butyl 2-(2-(2-benzyl-6-(methylcarbamoyl)isonicotinamido)ethyl)morpholine-4-carboxylate (77 mg, 0.144 mmol, 15.53% yield) as a colourless oil.

LCMS (2 min Formic): Rt=1.13 min, [MH]+=483.3.

Intermediate 98: (R)-tert-Butyl 2-(2-(2-benzyl-6-(methylcarbamoyl)isonicotinamido)ethyl)morpholine-4-carboxylate

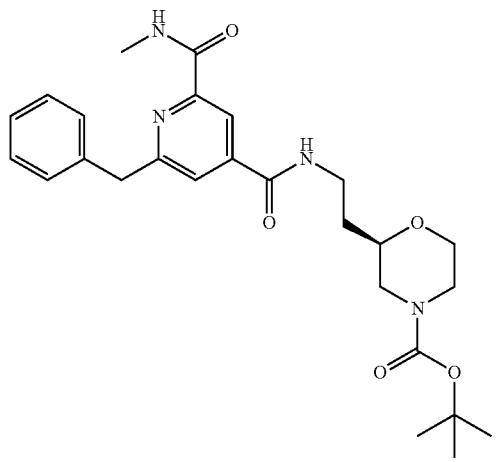 [SMILES: CNC(=O)c1cc(C(=O)NCC[C@@H]2CN(C(=O)OC(C)(C)C)CCO2)cc(Cc2ccccc2)n1]

(R)-tert-Butyl 2-(2-aminoethyl)morpholine-4-carboxylate (205 mg, 0.888 mmol) and 2-benzyl-6-(methylcarbamoyl)isonicotinic acid (200 mg, 0.740 mmol) were combined in DCM (5 mL) and HATU (366 mg, 0.962 mmol) and Et$_3$N (0.134 mL, 0.962 mmol) were added, then the mixture was stirred overnight at rt, then washed with water (10 mL) and the organic layer dried and evaporated in vacuo. The residue was purified by chromatography on a 25 g silica column eluting with 0-100% EtOAc/cyclohexane and the product-containing fractions were evaporated in vacuo to give (R)-tert-butyl 2-(2-(2-benzyl-6-(methylcarbamoyl)isonicotinamido)ethyl)morpholine-4-carboxylate (280 mg, 0.580 mmol, 78% yield)

LCMS (2 min high pH): Rt=1.16 min, [MH]$^+$=483.

Intermediate 99: (R)-tert-Butyl 3-(2-(2-benzyl-6-(methylcarbamoyl)isonicotinamido)ethyl)-3-fluoropiperidine-1-carboxylate

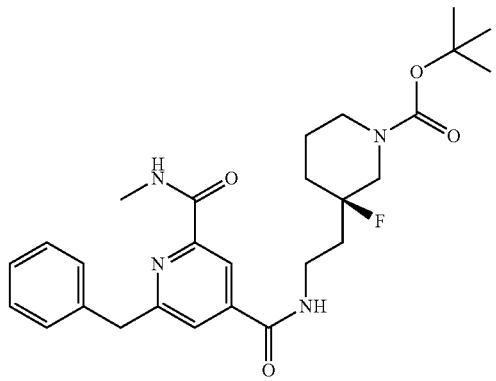 [SMILES: CNC(=O)c1cc(C(=O)NCC[C@]2(F)CCCN(C(=O)OC(C)(C)C)C2)cc(Cc2ccccc2)n1]

(R)-tert-Butyl 3-(2-aminoethyl)-3-fluoropiperidine-1-carboxylate (182 mg, 0.740 mmol) and 2-benzyl-6-(methylcarbamoyl)isonicotinic acid (200 mg, 0.740 mmol) were combined in DCM (5 mL), then HATU (366 mg, 0.962 mmol) and Et$_3$N (0.206 mL, 1.480 mmol) were added and the mixture was stirred for 2 h at rt, then washed with water, 0.5M HCl and NaHCO$_3$ solution, dried and evaporated in vacuo to give a grey gum. This was purified by chromatography on a 10 g silica column, eluting with 0-100% EtOAc/cyclohexane. The product-containing fractions were combined and evaporated in vacuo to give (R)-tert-butyl 3-(2-(2-benzyl-6-(methylcarbamoyl)isonicotinamido)ethyl)-3-fluoropiperidine-1-carboxylate (220 mg, 0.441 mmol, 59.6% yield) as a colourless gum.

LCMS (2 min high pH): Rt=1.20 min, [MH]$^+$=499.

Intermediate 100: (S)-tert-Butyl 3-(3-(2-benzyl-6-(methylcarbamoyl)isonicotinamido)propyl)-3-fluoropiperidine-1-carboxylate

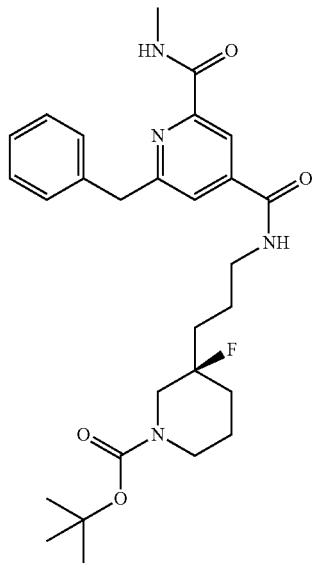 [SMILES: CNC(=O)c1cc(C(=O)NCCC[C@]2(F)CCCN(C(=O)OC(C)(C)C)C2)cc(Cc2ccccc2)n1]

To a solution of 2-benzyl-6-(methylcarbamoyl)isonicotinic acid (212 mg, 0.784 mmol) in DMF (2 mL) was added HATU (449 mg, 1.182 mmol) followed by (S)-tert-butyl 3-(3-aminopropyl)-3-fluoropiperidine-1-carboxylate (204 mg, 0.784 mmol) and DIPEA (0.6 mL, 3.44 mmol). The resulting reaction mixture was stirred at rt overnight. This was extracted with sat. LiCl solution and EtOAc three times then with 2M HCl. The combined organic phases were dried then concentrated in vacuo. The crude product was purified by chromatography on SiO$_2$ (Biotage® SNAP 10 g, eluting with 0-40% EtOAc/cyclohexane). The desired fractions were concentrated to give the product which was still impure. The reaction mixture was purified by MDAP (High pH). The desired fractions were combined and concentrated in vacuo to give (S)-tert-butyl 3-(3-(2-benzyl-6-(methylcarbamoyl)isonicotinamido)propyl)-3-fluoropiperidine-1-carboxylate (190.5 mg, 0.353 mmol, 45.0% yield) as a colourless oil.

LCMS (2 min Formic): Rt=1.22 min, [MH]$^+$=513.2

Intermediate 101: (3S)-tert-Butyl 3-fluoro-3-(3-(2-(methylcarbamoyl)-6-(1-phenylethyl)isonicotinamido)propyl)piperidine-1-carboxylate, 1:1 Mixture of Diastereomers at the Undefined Stereocentre

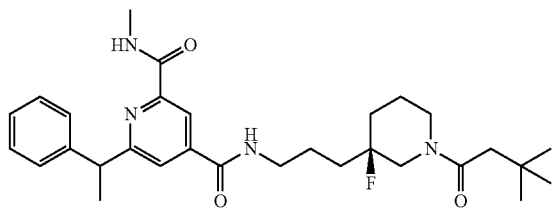 [SMILES: CNC(=O)c1cc(C(=O)NCCC[C@]2(F)CCCN(C(=O)CC(C)(C)C)C2)cc(C(C)c2ccccc2)n1]

2-(Methylcarbamoyl)-6-(1-phenylethyl)isonicotinic acid (80 mg, 0.281 mmol) was taken up in DMF (5 mL). DIPEA (0.147 mL, 0.844 mmol) and HATU (160 mg, 0.422 mmol) were added and the reaction left to stir at rt for 10 min. (S)-tert-Butyl 3-(3-aminopropyl)-3-fluoropiperidine-1-carboxylate (110 mg, 0.422 mmol) was added and the reaction left to stir overnight. The reaction was concentrated in vacuo. The residue was taken up in ethyl acetate (10 mL) and washed with NaHCO$_3$ (10 mL). The organic phase was washed with brine before being dried over Na$_2$SO$_4$, filtered though a hydrophobic frit and concentrated in vacuo. The sample was dissolved in 1:1 DMSO:MeCN (3 mL) and purified by MDAP (High pH). The solvent was evaporated in vacuo to give the required product (147 mg).

LCMS (2 min High pH): Rt=1.28 min, [MH]$^+$=527.4

Intermediate 102: (1R,5S,6s)-tert-Butyl 6-(2-benzyl-6-(methylcarbamoyl)isonicotinamido)-3-azabicyclo[3.1.0]hexane-3-carboxylate

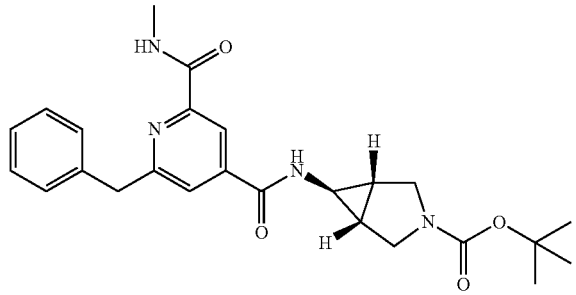 [SMILES: CNC(=O)c1cc(C(=O)N[C@H]2[C@@H]3CN(C(=O)OC(C)(C)C)C[C@@H]32)cc(Cc2ccccc2)n1]

2-Benzyl-6-(methylcarbamoyl)isonicotinic acid (50 mg, 0.185 mmol) was taken up in DMF (5 mL). DIPEA (0.097 mL, 0.555 mmol), HATU (106 mg, 0.277 mmol) and (1R,5S,6s)-tert-butyl 6-amino-3-azabicyclo[3.1.0]hexane-3-carboxylate (50 mg, 0.252 mmol, commercially available from, for example, Fluorochem) were added and the reaction was left to stir at rt for 2 h. The reaction was concentrated in vacuo. The residue was taken up in EtOAc (10 mL) and extracted using NaHCO$_3$ (10 mL). The organic phase was washed with brine (10 mL) before being dried over Na$_2$SO$_4$, filtered though a hydrophobic frit and concentrated in vacuo.

LCMS (2 min High pH): Rt=1.13 min, [MH]$^+$=451.4

Intermediate 103: 6-Benzyl-N$^4$-((1R,5S,6s)-3-azabicyclo[3.1.0]hexan-6-yl)-N$^2$-methylpyridine-2,4-dicarboxamide

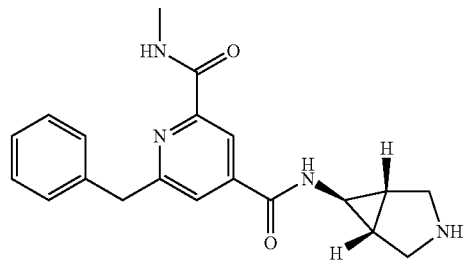 [SMILES: CNC(=O)c1cc(C(=O)N[C@H]2[C@@H]3CNC[C@@H]32)cc(Cc2ccccc2)n1]

(1R,5S,6s)-tert-Butyl 6-(2-benzyl-6-(methylcarbamoyl)isonicotinamido)-3-azabicyclo[3.1.0]hexane-3-carboxylate (111 mg, 0.246 mmol) was taken up in DCM (5 mL). TFA (0.5 mL, 6.49 mmol) was added and the reaction left to stir at rt overnight. The reaction was concentrated in vacuo. The sample was loaded in MeOH and purified by SPE on sulphonic acid (SCX) 1 g using MeOH followed by 2M ammonia/MeOH. The appropriate fractions were combined and evaporated in vacuo. The crude product was applied to a 10 g SNAP ULTRA silica cartridge in the minimum of DCM and purified by flash chromatography, eluting with 0-100% (10% 2M NH$_3$ in MeOH in DCM). The appropriate fractions were combined and concentrated in vacuo. Cross contamination of another product occurred. The sample was dissolved in 1:1 DMSO:MeCN (3 mL) and purified by MDAP (High pH). The solvent was evaporated in vacuo to give the required product (27 mg) as a yellow oil.

LCMS (2 min High pH): Rt=0.82 min, [MH]$^+$=351.3

Intermediate 104: (S)-tert-Butyl 2-(3-(2-(methylcarbamoyl)-6-((R*)-1-phenylethyl)isonicotinamido)propyl)morpholine-4-carboxylate

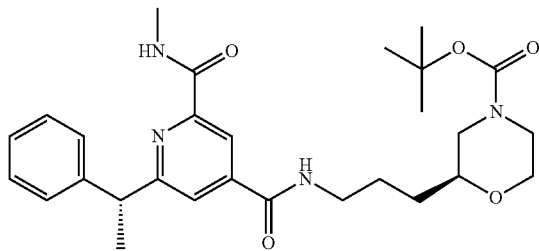 [SMILES: CNC(=O)c1cc(C(=O)NCCC[C@H]2CN(C(=O)OC(C)(C)C)CCO2)cc([C@H](C)c2ccccc2)n1]

(R*)-2-(Methylcarbamoyl)-6-(1-phenylethyl)isonicotinic acid (100 mg, 0.352 mmol) was taken up in DMF. DIPEA (184 μL, 1.055 mmol) and HATU (201 mg, 0.528 mmol) were added and the reaction left to stir at rt for 10 min. (S)-tert-Butyl 2-(3-aminopropyl)morpholine-4-carboxylate (129 mg, 0.528 mmol) was added and the reaction left to stir for a further 1 h. The reaction was concentrated in vacuo. The residue was taken up in EtOAc (10 mL) and extracted using NaHCO$_3$ solution (10 mL). The organic phase was washed with brine (10 mL) before being dried over Na$_2$SO$_4$, filtered through a hydrophobic frit and concentrated in vacuo. The crude product was applied to a 10 g SNAP ULTRA silica cartridge in the minimum of DCM and purified by flash chromatography, eluting with 0-75% (3:1 EtOAc:EtOH). The appropriate fractions were combined and concentrated in vacuo. to afford the desired product (151 mg).

LCMS (2 min High pH): Rt=1.22 min, [MH]$^+$=511.4

Intermediate 105: (R)-tert-Butyl 2-(2-(2-(3-methylbenzyl)-6-(methylcarbamoyl)isonicotinamido)ethyl)morpholine-4-carboxylate

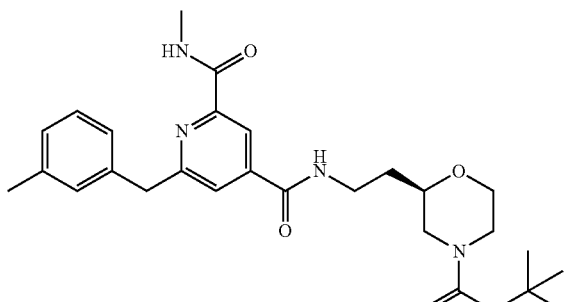

2-(3-Methylbenzyl)-6-(methylcarbamoyl)isonicotinic acid (52 mg, 0.183 mmol) was taken up in DMF (5 mL). DIPEA (0.096 mL, 0.549 mmol), HATU (104 mg, 0.274 mmol) and (R)-tert-butyl 2-(2-aminoethyl)morpholine-4-carboxylate (42.1 mg, 0.183 mmol) were added and the reaction left to stir at rt overnight. The reaction was then concentrated in vacuo. The residue was taken up in EtOAc (10 mL) and extracted using NaHCO$_3$ (10 mL). The organic phase was washed with brine (10 mL) before being dried over Na$_2$SO$_4$, filtered though a hydrophobic frit and concentrated in vacuo. The crude product was applied to a 10 g SNAP ULTRA silica cartridge in the minimum of DCM and purified by flash chromatography, eluting with 0-100% (3:1 EtOAc:EtOH). The appropriate fractions were combined and concentrated in vacuo to afford the desired product (50 mg).

LCMS (2 min Formic): Rt=1.19 min, [MH]$^+$=497.5

Intermediate 106: (1R,5S,6s)-tert-Butyl 6-(2-((1H-indol-4-yl)methyl)-6-(methylcarbamoyl)isonicotinamido)-3-azabicyclo[3.1.0]hexane-3-carboxylate

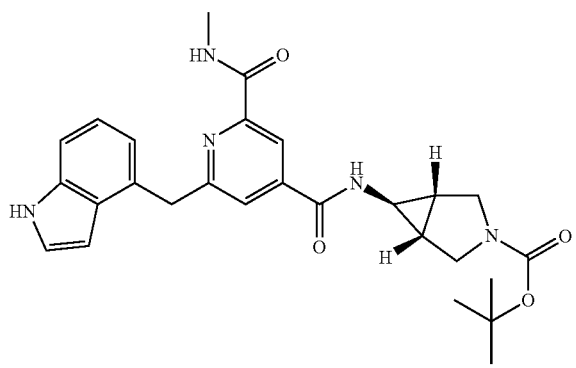 [SMILES: CNC(=O)c1cc(C(=O)N[C@H]2[C@@H]3CN(C(=O)OC(C)(C)C)C[C@@H]32)cc(Cc2cccc3[nH]ccc23)n1]

2-((1H-Indol-4-yl)methyl)-6-(methylcarbamoyl)isonicotinic acid (168 mg, 0.543 mmol) was taken up in DMF (5 mL). DIPEA (0.285 mL, 1.629 mmol) and HATU (310 mg, 0.815 mmol) were added and the reaction left to stir at rt for 10 min. tert-Butyl 6-amino-3-azabicyclo[3.1.0]hexane-3-carboxylate (108 mg, 0.543 mmol) was added and the reaction was left to stir for a further 1 h. The reaction was concentrated in vacuo. The residue was taken up in EtOAc (10 mL) and extracted with NaHCO$_3$ solution (10 mL). The organic phase was washed with brine (10 mL) before being dried over Na$_2$SO$_4$, filtered through a hydrophobic frit and concentrated in vacuo. to afford the desired product (350 mg) as a brown solid.

LCMS (2 min High pH): Rt=1.08 min, [MH]$^+$=490.4.

Intermediate 107: (R)-tert-Butyl 3-(3-(2-((1H-indol-4-yl)methyl)-6-(methylcarbamoyl)isonicotinamido)propyl)-3-fluoropiperidine-1-carboxylate

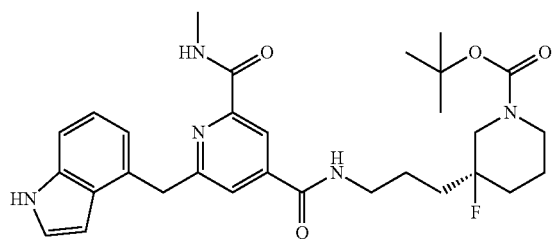 [SMILES: CNC(=O)c1cc(C(=O)NCCC[C@@]2(F)CCCN(C(=O)OC(C)(C)C)C2)cc(Cc2cccc3[nH]ccc23)n1]

2-((1H-Indol-4-yl)methyl)-6-(methylcarbamoyl)isonicotinic acid (150 mg, 0.485 mmol) was taken up in DMF (5 mL). DIPEA (0.254 mL, 1.455 mmol) and HATU (277 mg, 0.727 mmol) were added and the reaction was left to stir at rt for 10 min. (1R,5S,6s)-tert-Butyl 3-(3-aminopropyl)-3-fluoropiperidine-1-carboxylate (126 mg, 0.485 mmol, commercially available from, for example, FluoroChem) was added and the reaction left to stir for a further 2 h. The reaction was concentrated in vacuo. The residue was taken up in EtOAc (10 mL) and washed with NaHCO$_3$ solution (10 mL). The organic phase was washed with brine (10 mL) before being dried over Na$_2$SO$_4$, filtered through a hydrophobic frit and concentrated in vacuo to afford the desired product (340 mg) as a brown solid.

LCMS (2 min High pH): Rt=1.17 min, [MH]$^+$=552.4.

Intermediate 108: (2R)-tert-Butyl 2-(2-(2-(methylcarbamoyl)-6-(1-phenylethyl)isonicotinamido)ethyl)morpholine-4-carboxylate, 1:1 Mixture of Diastereomers at Undefined Stereocentre

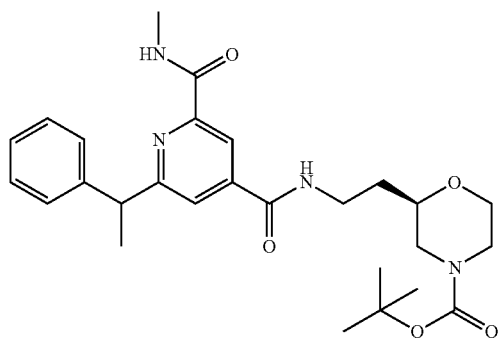 [SMILES: CNC(=O)c1cc(C(=O)NCC[C@@H]2CN(C(=O)OC(C)(C)C)CCO2)cc(C(C)c2ccccc2)n1]

2-(Methylcarbamoyl)-6-(1-phenylethyl)isonicotinic acid (100 mg, 0.352 mmol) was taken up in DMF (4 mL), DIPEA (0.184 mL, 1.055 mmol) was added, shortly followed by HATU (201 mg, 0.528 mmol) and the reaction left to stir at rt for 10 min. (R)-tert-Butyl 2-(2-aminoethyl)morpholine-4-carboxylate (122 mg, 0.528 mmol) was added and the reaction left to stir for a further 3 h. The reaction was concentrated in vacuo. The residue was dissolved in ethyl acetate (20 mL) and washed with NaHCO$_3$ (20 mL). The organic phase was washed with brine (20 mL) before being dried over Na$_2$SO$_4$ and concentrated in vacuo. The crude product was applied to a 10 g SNAP ULTRA silica cartridge in the minimum of DCM and purified by flash chromatography, eluting with 5-100% EtOAc/cyclohexane. The appropriate fractions were combined and concentrated in vacuo to afford the desired product as a yellow oil (133 mg).

LCMS (2 min High pH): Rt=1.21 min, [MH]$^+$=497.4.

Intermediate 109: (2S)-tert-Butyl 2-(2-(2-(methylcarbamoyl)-6-(1-phenylethyl)isonicotinamido)ethyl)morpholine-4-carboxylate, 1:1 Mixture of Diastereomers at Undefined Stereocentre

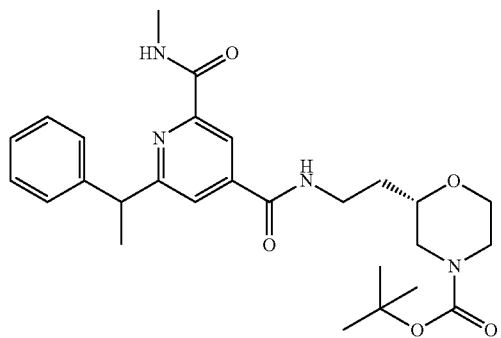 [SMILES: CNC(=O)c1cc(C(=O)NCC[C@H]2CN(C(=O)OC(C)(C)C)CCO2)cc(C(C)c2ccccc2)n1]

2-(Methylcarbamoyl)-6-(1-phenylethyl)isonicotinic acid (100 mg, 0.352 mmol) was taken up in DMF (4 mL). DIPEA (0.184 mL, 1.055 mmol) was added, shortly followed by HATU (201 mg, 0.528 mmol) and the reaction left to stir at rt for 10 min. (S)-tert-Butyl 2-(2-aminoethyl)morpholine-4-carboxylate (122 mg, 0.528 mmol) was added and the reaction left to stir for 5 h. The reaction was concentrated in vacuo. The residue was taken up in EtOAc (20 mL) and extracted with NaHCO$_3$ (20 mL). The organic phase was washed with brine (20 mL) before being filtered through a hydrophobic frit and concentrated in vacuo. The crude product was applied to a 25 g SNAP ULTRA silica cartridge in the minimum of DCM and purified by flash chromatography, eluting with 5-50% (3:1 EtOAc:EtOH). The appropriate fractions were combined and concentrated in vacuo to afford the desired product (87.1 mg).

LCMS (2 min High pH): Rt=1.21 min, [MH]$^+$=497.4.

$^1$H NMR (400 MHz, MeOH-d$_4$) δ ppm 8.25 (s, 1H) 7.73 (s, 1H) 7.20-7.36 (m, 4H) 7.10-7.18 (m, 1H) 4.38 (q, J=6.8 Hz, 1H) 3.73-3.90 (m, 3H) 3.36-3.54 (m, 4H) 2.99 (s, 3H) 2.89 (br. s., 1H) 2.50-2.75 (m, 1H) 1.66-1.79 (m, 5H) 1.42 (s, 9H)

Intermediate 110: (±)-tert-Butyl 3-(3-(2-benzyl-6-(methylcarbamoyl)isonicotinamido)propyl)-4,4-difluoropiperidine-1-carboxylate

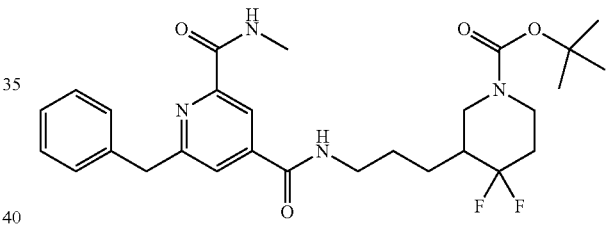

To a solution of HATU (15.3 mg, 0.040 mmol), (±)-tert-butyl 3-(3-aminopropyl)-4,4-difluoropiperidine-1-carboxylate (6.8 mg, 0.024 mmol) and 2-benzyl-6-(methylcarbamoyl)isonicotinic acid (7.6 mg, 0.028 mmol) in DMF (0.5 mL), was added DIPEA (12.0 µL, 0.069 mmol). The mixture was stirred at rt for 90 min. The mixture was partitioned between EtOAc (2 mL) and 1M aqueous Na$_2$CO$_3$ solution (2 mL). The aqueous phase was extracted with further EtOAc (3×2 mL), the combined organic extracts dried by passing through a cartridge fitted with a hydrophobic frit and the solvent evaporated under a stream of N$_2$ to give an orange gum. The gum was redissolved in DCM (ca. 2 mL) and applied to a 2 g SPE silica cartridge which had been pre-wetted with cyclohexane. The cartridge was eluted with an elutropic gradient of solvents; cyclohexane (2×7 mL), DCM (2×7 mL), chloroform (7 mL), diethyl ether (7 mL) and EtOAc (3×7 mL). Each 7 mL fraction was evaporated under a stream of N$_2$; Fraction 7 (1st EtOAc fraction) was re-dissolved in a 1:1 mixture of DCM and EtOAc (~2 mL) and was evaporated under a stream of N$_2$ to give a yellow glass; (±)-tert-butyl 3-(3-(2-benzyl-6-(methylcarbamoyl)isonicotinamido)propyl)-4,4-difluoropiperidine-1-carboxylate (7.1 mg, 0.013 mmol, 54.8% yield).

LCMS (2 min formic); Rt=1.27 min, m/z=531 for [MH]$^+$

Intermediate 111: tert-Butyl 4-(3-(2-benzyl-6-(methylcarbamoyl)isonicotinamido)propyl)-3-oxopiperazine-1-carboxylate

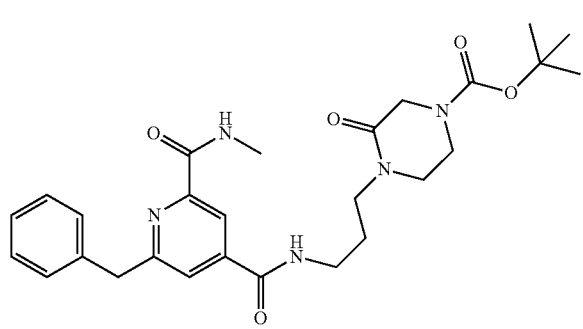 [SMILES: CNC(=O)c1cc(C(=O)NCCCN2CCN(C(=O)OC(C)(C)C)CC2=O)cc(Cc2ccccc2)n1]

To a mixture of tert-butyl 4-(3-aminopropyl)-3-oxopiperazine-1-carboxylate (47.3 mg, 0.184 mmol), 2-benzyl-6-(methylcarbamoyl)isonicotinic acid (44.1 mg, 0.163 mmol) and HATU (73.3 mg, 0.193 mmol) in DMF (1 mL) was added DIPEA (0.085 mL, 0.489 mmol). The mixture was stirred at rt for 4 h. The reaction mixture was diluted with DMSO (approx. 1 mL) and directly purified by MDAP (2×1 mL injection, high pH). The required fractions were evaporated under a stream of $N_2$, redissolved in MeOH (approx. 2 mL each) and combined. This solution was evaporated under a stream of $N_2$ and dried in vacuo to give the a pale pink glassy solid; tert-butyl 4-(3-(2-benzyl-6-(methylcarbamoyl)isonicotinamido)propyl)-3-oxopiperazine-1-carboxylate (50.2 mg, 0.099 mmol, 60.4% yield).

LCMS (2 min high pH); Rt=1.06 min, m/z=510 for [MH]+

Intermediate 112: 3-Fluoro-4-(4,4,5,5-tetramethyl-1,3,2-dioxaborolan-2-yl)-1H-indole

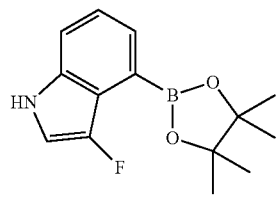

4,4,4',4',5,5,5',5'-Octamethyl-2,2'-bi(1,3,2-dioxaborolane) (1008 mg, 3.97 mmol), 4-bromo-3-fluoro-1H-indole (500 mg, 2.34 mmol, commercially available from, for example, Fluorochem), PdCl$_2$(dppf) (171 mg, 0.23 mmol) and potassium acetate (688 mg, 7.01 mmol) were added to a microwave vial and the system purged. 1,4-Dioxane (15 mL) was added and the reaction vessel was sealed and heated in Biotage Initiator microwave to 100° C. for 30 min. After cooling the reaction was filtered through celite and washed with ethyl acetate. The reaction was concentrated in vacuo. The residue was then extracted using ethyl acetate (20 mL) and water (20 mL) and brine (20 mL). The organic phase was dried over sodium sulphate, filtered through a hydrophobic frit and concentrated in vacuo, to afford 3-fluoro-4-(4,4,5,5-tetramethyl-1,3,2-dioxaborolan-2-yl)-1H-indole (490 mg, 1.877 mmol, 80% yield) as a brown solid which used without purification in the next step.

LCMS (2 min High pH): Rt=1.17 min, [MH]+=262.3.

Intermediate 113: 2-(4-(4,4,5,5-Tetramethyl-1,3,2-dioxaborolan-2-yl)-1H-indol-1-yl)ethanol

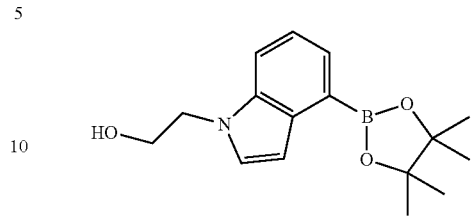

4,4,4',4',5,5,5',5'-Octamethyl-2,2'-bi(1,3,2-dioxaborolane) (1100 mg, 4.33 mmol), 2-(4-bromo-1H-indol-1-yl)ethanol (612 mg, 2.55 mmol, commercially available from, for example, Fluorochem), potassium acetate (750 mg, 7.65 mmol) and PdCl$_2$(dppf) (187 mg, 0.26 mmol) were added to a microwave vial. 1,4-Dioxane (10 mL) was added and the reaction vessel sealed and heated in Biotage Initiator microwave to 110° C. for 30 min. After cooling the reaction was filtered through celite and washed with ethyl acetate (20 mL). The filtrate was extracted using water (20 mL) and brine (20 mL). The organic phase was dried over sodium sulphate, filtered through a hydrophobic frit and concentrated in vacuo. to afford the product, 2-(4-(4,4,5,5-tetramethyl-1,3,2-dioxaborolan-2-yl)-1H-indol-1-yl) ethanol (915 mg, 2.55 mmol, 100% yield) as a brown oil, which was of sufficient purity to carry forward to the next step.

LCMS (2 min Formic): Rt=1.11 min, [MH]+=288.1.

Intermediate 114: 4-(4,4,5,5-Tetramethyl-1,3,2-dioxaborolan-2-yl)indolin-2-one

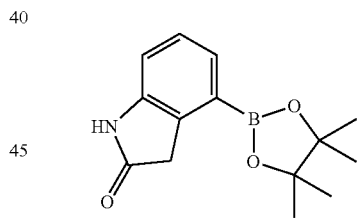

A mixture of 4,4,4',4',5,5,5',5'-octamethyl-2,2'-bi(1,3,2-dioxaborolane) (1.903 g, 7.49 mmol, commercially available from, for example, Fluorochem), 4-bromoindolin-2-one (1.038 g, 4.90 mmol, commercially available from, for example, Fluorochem), [1,1'-bis(diphenylphosphino)ferrocene]dichloropalladium(II), complex with dichloromethane [Pd(dppf)Cl$_2$.DCM] (0.601 g, 0.73 mmol) and potassium acetate (1.480 g, 15.08 mmol) in 1,4-dioxane (30 mL) was stirred at 110° C. for 2 h. The mixture was allowed to cool to rt before being filtered through a 10 g celite cartridge. The cartridge was washed through with ethyl acetate (3×30 mL) and the combined filtrates were evaporated in vacuo to give a brown liquid which was re-dissolved in DCM (ca. 10 mL), loaded onto a 100 g SNAP silica cartridge and purified by Biotage SP4 semi-automated flash column chromatography eluting with a gradient of 20 to 50% ethyl acetate in cyclohexane. The required fractions were combined and evaporated in vacuo, this was re-dissolved in DCM (ca. 10 mL), transferred to a tarred vial and the solvent evaporated under a stream of nitrogen. The residue was triturated with ether (5×5 mL), decanting away the mother liquor each time, and the residue dried under a stream of nitrogen and in vacuo to give the desired product 4-(4,4,5,5-tetramethyl-1,3,2-dioxaborolan-2-yl)indolin-2-one (941.8 mg, 3.63 mmol, 74% yield) as a cream solid.

LCMS (2 min Formic): Rt=0.93 min, [MH]+=260.3.

Intermediate 115:
4-Bromo-1H-indole-2-carboxamide

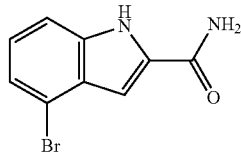 [SMILES: NC(=O)c1cc2c(Br)cccc2[nH]1]

To a suspension of 4-bromo-1H-indole-2-carboxylic acid (0.276 mL, 2.12 mmol, commercially available from, for example, Ark Pharm) in dichloromethane (15 mL) was added oxalyl chloride (0.220 mL, 2.51 mmol). The suspension was stirred at rt for approx. 3 days in total. During this time, DMF (0.020 mL, 0.26 mmol) was added after 5.5 h. Further oxalyl chloride (0.100 mL, 1.14 mmol) was added after 23.75 h. Further oxalyl chloride (0.100 mL, 1.142 mmol) was added after 27.15 h. The reaction mixture was left to stir over the weekend, during which time the solvent had evaporated to give a sticky light brown solid. This was redissolved in dichloromethane (15 mL) and to this solution was added oxalyl chloride (0.100 mL, 1.14 mmol) and DMF (0.020 mL, 0.26 mmol). The resulting solution was stirred for a further 2 h 45 min to afford a brown solution. This solution was added dropwise to a stirring solution of ammonia (35% in water) (10 mL, 162 mmol) and ice (approx. 10 g) and the resulting mixture left to stand for approx. 3 h. To this was added ethyl acetate (10 mL) and water (10 mL) and the layers separated. To the aqueous layer was added brine (approx. 5 mL) and this was extracted with further ethyl acetate (3×30 mL). The organic layers, which contained a brown precipitate, were combined and evaporated in vacuo to give a brown solid. This was transferred in methanol (approx. 10 mL) and this emulsion evaporated in vacuo to give a brown solid. This solid was triturated with dichloromethane (approx. 3×20 mL) and the supernatant filtered. The filtrate was concentrated to approx. 10 mL, directly applied to the top of a 50 g SNAP cartridge and purified by flash column chromatography. The column was eluted with a gradient of 20%-70% ethyl acetate in cyclohexane. The required fractions were evaporated in vacuo to give 4-bromo-1H-indole-2-carboxamide (95.0 mg, 0.40 mmol, 19% yield) as an off-white solid.

LCMS (2 min High pH): Rt=0.87 min, [M-H]-=237.1.

Intermediate 116: 4-Bromo-1H-indole-2-carbonitrile

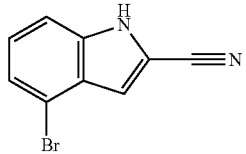 [SMILES: N#Cc1cc2c(Br)cccc2[nH]1]

To a solution of 4-bromo-1H-indole-2-carboxamide (207.3 mg, 0.87 mmol) in ethyl acetate (8 mL) in a microwave vial was added 2,4,6-tripropyl-1,3,5,2,4,6-trioxatriphosphinane 2,4,6-trioxide (50% in ethyl acetate, 0.630 mL, 1.06 mmol). The vial was sealed and the mixture stirred in a microwave reactor at 100° C. for 1.5 h. The vial was resealed and the mixture stirred in a microwave reactor at 100° C. for a further total of 2 h. Further 2,4,6-tripropyl-1,3,5,2,4,6-trioxatriphosphinane 2,4,6-trioxide (50% in ethyl acetate, 0.250 mL, 0.42 mmol) was added, the vial resealed and the mixture stirred in a microwave reactor at 100° C. for a further 3.5 h. To the reaction mixture was added water (10 mL) and the layers separated. The aqueous layer was extracted with further ethyl acetate (2×10 mL) and the organic layers combined and filtered through a cartridge fitted with a hydrophobic frit. The filtrate was evaporated in vacuo to give a light yellow crystalline solid. This was redissolved in DMSO (2 mL) and directly purified by MDAP (high pH). The required fractions were evaporated under a stream of nitrogen, redissolved in methanol (approx. 2 mL each) and combined. This solution was evaporated under a stream of nitrogen and the residue dried in vacuo to give the desired product 4-bromo-1H-indole-2-carbonitrile (145.0 mg, 0.66 mmol, 76% yield) as a glassy white solid.

LCMS (2 min High pH): Rt=1.14 min, [M-H]-=219.0.

Intermediate 117: 4-(4,4,5,5-Tetramethyl-1,3,2-dioxaborolan-2-yl)-1H-indole-2-carbonitrile

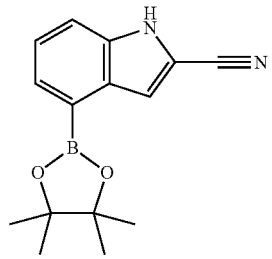 [SMILES: CC1(C)OB(c2cccc3[nH]c(C#N)cc23)OC1(C)C]

A mixture of 4-bromo-1H-indole-2-carbonitrile (141.3 mg, 0.64 mmol), 4,4,4',4',5,5,5',5'-octamethyl-2,2'-bi(1,3,2-dioxaborolane) (263.8 mg, 1.04 mmol), [1,1'-bis(diphenylphosphino)ferrocene]dichloropalladium(II) (44.3 mg, 0.06 mmol) and potassium acetate (182.7 mg, 1.86 mmol) in 1,4-dioxane (5 mL) was stirred at reflux for 5.75 h, after which it was removed from heat and left to cool to rt while stirring. The mixture was left to stand overnight under nitrogen. The mixture was filtered through a 2.5 g Celite cartridge and the cartridge washed with ethyl acetate (approx. 20 mL). To the filtrate was added brine (25 mL) and the layers separated. The aqueous layer was extracted with further ethyl acetate (2×25 mL). The organic phases were combined, filtered through a cartridge fitted with a hydrophobic frit and the filtrate evaporated in vacuo. The residue was redissolved in dichloromethane (approx. 5 mL) and directly applied to the top of a 25 g SNAP cartridge and purified by flash column chromatography. The column was eluted with a gradient of 0%-40% ethyl acetate in cyclohexane. The appropriate fractions were combined and evaporated in vacuo to give 4-(4,4,5,5-tetramethyl-1,3,2-dioxaborolan-2-yl)-1H-indole-2-carbonitrile (72.4 mg, 0.27 mmol, 42% yield) as a colourless gum which slowly formed colourless crystals on standing.

LCMS (2 min High pH): Rt=1.29 min, [M-H]-=267.2.

Intermediate 118: 4-(4,4,5,5-Tetramethyl-1,3,2-di-oxaborolan-2-yl)-1H-indole-3-carbonitrile

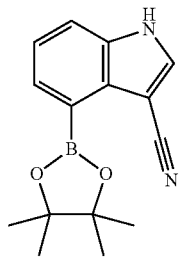 [SMILES: CC1(C)OB(c2cccc3[nH]cc(C#N)c23)OC1(C)C]

A mixture of 4-bromo-1H-indole-3-carbonitrile (500.3 mg, 2.26 mmol), 4,4,4',4',5,5,5',5'-octamethyl-2,2'-bi(1,3,2-dioxaborolane) (694.3 mg, 2.73 mmol), [1,1'-bis(diphenylphosphino)ferrocene]dichloropalladium(II) (169.6 mg, 0.23 mmol) and potassium acetate (668.8 mg, 6.81 mmol) in 1,4-dioxane (12 mL) was stirred at reflux for 21.5 h. Further 4,4,4',4',5,5,5',5'-octamethyl-2,2'-bi(1,3,2-dioxaborolane) (288.4 mg, 1.14 mmol) was added after 5.5 h. The mixture was removed from heating and left to cool to rt, after which it was filtered through a 10 g Celite cartridge. This was washed with ethyl acetate (approx. 3×10 mL). To the filtrate was added water (10 mL) and brine (30 mL) and the layers separated. The aqueous layer was extracted with further ethyl acetate (2×30 mL) and the organic layers combined and filtered through a cartridge fitted with a hydrophobic frit. The filtrate was evaporated in vacuo, redissolved in dichloromethane (approx. 10 mL) and directly applied to the top of a 100 g SNAP cartridge and purified by flash column chromatography. The column was eluted with a gradient of 0%-40% ethyl acetate in cyclohexane. The required fractions were combined and evaporated in vacuo to give 4-(4,4,5,5-tetramethyl-1,3,2-dioxaborolan-2-yl)-1H-indole-3-carbonitrile (80 wt % purity, 481.8 mg, 1.44 mmol, 64% yield) as a viscous yellow oil which formed light yellow crystals upon standing.

LCMS (2 min High pH): Rt=1.08 min, [M−H]−=269.3.

Intermediate 119: Benzyl 4-bromoindoline-1-carboxylate

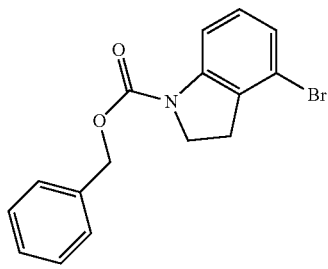 [SMILES: O=C(OCc1ccccc1)N1CCc2c(Br)cccc21]

To a stirred mixture of 4-bromoindoline (991.8 mg, 5.01 mmol, commercially available from Fluorochem) and sodium bicarbonate (1.100 g, 13.09 mmol) in water (30 mL) and tetrahydrofuran (12 mL) was added dropwise benzyl chloroformate (0.85 mL, 5.98 mmol). The mixture was stirred at rt for 24 h before leaving to stand for 20 h. The mixture was extracted with ethyl acetate (3×80 mL) and the combined organic phases were washed with saturated aqueous brine solution (30 mL) and dried by filtration through a cartridge fitted with a hydrophobic frit. The solvent was evaporated from the organic phase in vacuo to give a light brown crystalline solid which was redissolved in dichloromethane (ca. 12 mL) and was purified by SP4 flash column chromatography (100 g silica cartridge) eluting with a gradient of 0-30% ethyl acetate in cyclohexane. The required fractions were combined and the solvent evaporated in vacuo. The residue was redissolved in dichloromethane (ca. 12 mL), transferred to a tarred vial, the solvent evaporated under a stream of nitrogen and the residue dried in vacuo to give benzyl 4-bromoindoline-1-carboxylate (1.602 g, 4.82 mmol, 96% yield) as a pale pink solid.

LCMS (2 mins formic) Peak $R_f$=1.44 min, m/z=332, 334 for [MH]+

Intermediate 120: Benzyl 4-(4,4,5,5-tetra methyl-1,3,2-dioxaborolan-2-yl)indoline-1-carboxylate

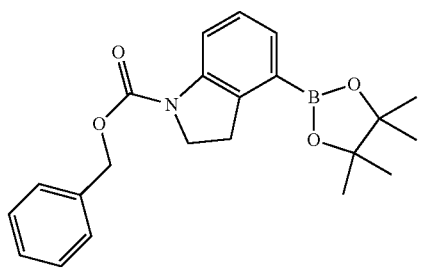 [SMILES: CC1(C)OB(c2cccc3c2CCN3C(=O)OCc2ccccc2)OC1(C)C]

To a stirred mixture of benzyl 4-bromoindoline-1-carboxylate (1.108 g, 3.34 mmol), potassium acetate (0.965 g, 9.83 mmol) and bis(pinacolato)diboron (1.014 g, 3.99 mmol) in 1,4-dioxane (15 mL) was added [1,1'-bis(diphenylphosphino)ferrocene]dichloropalladium(II), complex with dichloromethane (259.6 mg, 0.36 mmol). The mixture was stirred at 100° C. for 140 min before being diluted with ethyl acetate (10 mL) and filtered through a 10 g Celite cartridge. The cartridge was washed through with further ethyl acetate (3×20 mL). The solvent was evaporated in vacuo and the residue was re-dissolved in ethyl acetate (100 mL) and washed with water (50 mL) and saturated brine solution (~30 mL added to aid phase separation). The organic phase was washed with a further portion of water (50 mL) and saturated brine solution (30 mL), the phases were separated and the organic phase dried by filtration through a cartridge fitted with a hydrophobic frit. The solvent was evaporated from the organic phase in vacuo to give a dark brown oil which was redissolved in dichloromethane (ca. 10 mL) and the solution applied to a 50 g SNAP silica cartridge. The sample was purified by Biotage SP4 flash column chromatography eluting with a gradient of 0-25% ethyl acetate in cyclohexane. The required fractions were combined and the solvent evaporated in vacuo. The residue was dried in vacuo to give benzyl 4-(4,4,5,5-tetramethyl-1,3,2-dioxaborolan-2-yl)indoline-1-carboxylate (1.148 g, 3.03 mmol, 91% yield) with approx. 85% purity as a pale yellow viscous oil, which crystallised upon standing to a pale yellow solid.

LCMS (2 mins formic) Peak $R_f$=1.55 min, m/z=380 for [MH]+

Intermediate 121: (±)-tert-Butyl 4-(2-cyanoethyl)-3,3-difluoropiperidine-1-carboxylate

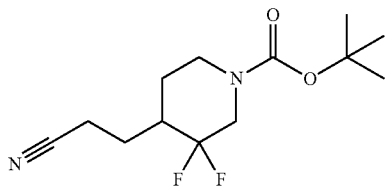 [SMILES: CC(C)(C)OC(=O)N1CCC(CCC#N)C(F)(F)C1]

(±)-tert-Butyl 3,3-difluoro-4-(2-((methylsulfonyl)oxy)ethyl)piperidine-1-carboxylate (1.095 g, 3.19 mmol) was dissolved in dimethyl sulfoxide (23 mL) and sodium cyanide (165.5 mg, 3.38 mmol) was added. The mixture was stirred at rt for 3.5 h before heating at 55° C. for 25 h. The mixture was allowed to cool and after standing at rt for 48 h was partitioned between water (50 mL) and ether (50 mL). The phases were separated and the aqueous phase extracted with further ether (3×50 mL). The combined organic phases were dried by filtering through a cartridge fitted with a hydrophobic frit and the solvent was evaporated in vacuo to give a pale yellow oil. The oil was re-dissolved in dichloromethane (~8 mL) and was purified by Biotage SP4 flash column chromatography (sample applied to a SNAP 25 g silica cartridge which had been pre-wetted with cyclohexane). The column was eluted with a gradient of 0 to 40% ethyl acetate in cyclohexane. The required fractions were combined and the solvent evaporated in vacuo, the residual colourless oil re-dissolved in dichloromethane (~10 mL) and transferred to a tarred vial and the solvent evaporated under a stream of nitrogen to give (±)-tert-butyl 4-(2-cyanoethyl)-3,3-difluoropiperidine-1-carboxylate (752.9 mg, 2.74 mmol, 86% yield) as a mobile colourless oil which over the course of a week crystallised to give a white solid.

TLC (silica plate; 1:1 ethyl acetate/cyclohexane) $R_f$=0.63, visualised with KMnO$_4$ (develops faintly at first then strengthens to a yellow spot over a number of h)

$^1$H NMR (400 MHz, CDCl$_3$) δ ppm 4.33 (br s, 1H) 4.19 (br s, 1H) 2.97 (br d, 1H) 2.78 (br s, 1H) 2.43-2.59 (m, 2H) 2.11-2.20 (m, 1H) 1.96-2.10 (m, 1H) 1.76-1.83 (m, 1H) 1.62-1.71 (m, 1H) 1.49-1.57 (m, 1H) 1.48 (s, 9H).

Intermediate 122: (±)-tert-Butyl 4-(3-aminopropyl)-3,3-difluoropiperidine-1-carboxylate

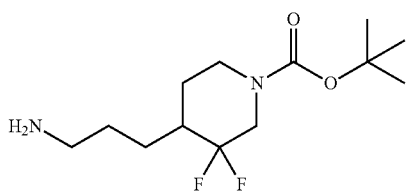 [SMILES: CC(C)(C)OC(=O)N1CCC(CCCN)C(F)(F)C1]

A mixture of (±)-tert-butyl 4-(2-cyanoethyl)-3,3-difluoropiperidine-1-carboxylate (108.6 mg, 0.40 mmol) and sodium borohydride (34.7 mg, 0.92 mmol) in THF (3 mL) was stirred under nitrogen and cooled to 0° C. (ice bath) before a solution of iodine (100 mg, 0.40 mmol) in THF (2 mL) was added dropwise over 50 min. The mixture was heated at reflux under nitrogen for 3.75 h before methanol (1 mL) was added (vigorous reaction—care!) and the mixture heated at reflux for a further 30 min. After cooling to rt, the mixture was applied directly to a 5 g Isolute SCX-2 ion exchange cartridge which had been pre-wetted with methanol. The cartridge was eluted with methanol (2×10 mL) followed by 2M ammonia in methanol solution (3×10 mL). The basic fractions were combined and the solvent evaporated in vacuo to give a colourless oily residue which was redissolved in 2:1 dichloromethane/methanol (ca. 8 mL), transferred to a tarred vial and and the solvent evaporated under a stream of nitrogen to give (±)-tert-butyl 4-(3-aminopropyl)-3,3-difluoropiperidine-1-carboxylate (51.6 mg, 0.19 mmol, 47% yield) as a colourless viscous oil.

$^1$H NMR (400 MHz, DMSO-d$_6$) δ ppm 4.05 (br s, 1H) 3.88 (br d, 1H) 3.16 (br s, 2H) 2.87 (br s, 1H) 2.51-2.56 (m, 2H) 1.62-1.99 (m, 4H) 1.14-1.50 (m, 4H) 1.40 (s, 9H).

Intermediate 123: (+/−)-4-tert-Butyl 2-ethyl 2-methylmorpholine-2,4-dicarboxylate

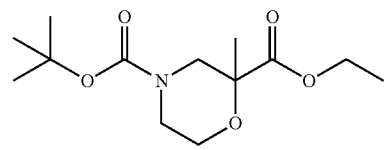 [SMILES: CCOC(=O)C1(C)CN(C(=O)OC(C)(C)C)CCO1]

4-tert-Butyl 2-ethyl morpholine-2,4-dicarboxylate (3 g, 11.57 mmol, commercially available from, for example, Fluorochem) in THF (10 mL) was added to a solution of LiHMDS (1M in THF, 11.57 ml, 11.57 mmol) in THF (20 mL) at −78° C. and the solution was stirred for 20 min, then MeI (1.447 mL, 23.14 mmol) was added and the mixture stirred at −78° C. for 1 h, then allowed to warm to rt. The mixture was diluted with water (100 mL) and extracted with EtOAc (2×100 mL). The combined organics were dried and evaporated in vacuo. The crude product was purified by chromatography on a 50 g silica column eluting with 0-50% EtOAc/cyclohexane and product-containing fractions were evaporated in vacuo to give (+/−)-4-tert-butyl 2-ethyl 2-methylmorpholine-2,4-dicarboxylate (1.8 g, 6.59 mmol, 56.9% yield) as a colourless oil.

$^1$H NMR (400 MHz, CDCl$_3$-d) δ ppm 4.37 (dd, J=13.2, 1.0 Hz, 1H) 4.32-4.14 (m, 2H) 3.92-3.65 (m, 3H) 3.03 (br. s., 1H) 2.87 (d, J=13.2 Hz, 1H) 1.50-1.42 (m, 9H) 1.40-1.36 (m, 3H) 1.34-1.24 (m, 3H).

Intermediate 124: (+/−)-tert-Butyl 2-(hydroxymethyl)-2-methylmorpholine-4-carboxylate

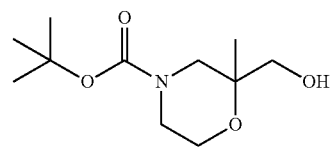 [SMILES: CC(C)(C)OC(=O)N1CCOC(C)(CO)C1]

(+/−)-4-tert-Butyl 2-ethyl 2-methylmorpholine-2,4-dicarboxylate (1.8 g, 6.59 mmol) was dissolved in 2-methyl THF (30 mL) and cooled in an ice bath, then LiBH$_4$ (0.574 g, 26.3 mmol) was added and the mixture stirred overnight under nitrogen. The mixture was quenched with methanol (20 mL) added very cautiously dropwise, then evaporated in vacuo and the residue partitioned between 0.5M HCl (50 mL) and EtOAc (50 mL), the organic layer dried and evaporated in vacuo to give (+/−)-tert-butyl 2-(hydroxymethyl)-2-methylmorpholine-4-carboxylate (1.6 g, 6.92 mmol, 105% yield) as a colourless oil.

$^1$H NMR (400 MHz, DMSO-$d_6$) δ ppm 3.67-3.56 (m, 2H) 3.49-3.41 (m, 1H) 3.38-3.28 (m, 3H) 3.21-3.12 (m, 2H) 1.47-1.40 (m, 9H) 1.10 (s, 3H). 1 exchangeable proton not observed.

Intermediate 125: (+/−)-tert-Butyl 2-formyl-2-methylmorpholine-4-carboxylate

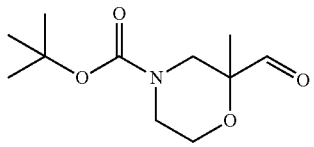 [SMILES: CC(C)(C)OC(=O)N1CCOC(C)(C=O)C1]

(+/−)-tert-Butyl 2-(hydroxymethyl)-2-methylmorpholine-4-carboxylate (0.8 g, 3.46 mmol) was taken up in dichloromethane (30 mL) under nitrogen and cooled in an ice bath. DMP (1.614 g, 3.80 mmol) was added and the reaction left to stir and warm up overnight. The reaction was quenched with sat. NaHCO$_3$ (25 mL) and stirred for 30 min. The mixture was partitioned and the aqueous layer re-extracted with 20% MeOH in DCM (25 mL). The combined organics were washed with brine (50 mL) and filtered through a hydrophobic frit then concentrated in vacuo to give (+/−)-tert-butyl 2-formyl-2-methylmorpholine-4-carboxylate (90 wt % purity, 0.7 g, 2.75 mmol, 79% yield) as a cream solid.

$^1$H NMR (400 MHz, CDCl$_3$-d) δ ppm 9.61 (s, 1H) 4.14 (dd, J=14.2, 7.1 Hz, 1H) 3.96-3.58 (m, 3H) 3.15-3.01 (m, 1H) 2.93 (d, J=13.4 Hz, 1H) 1.57-1.35 (m, 9H) 1.31-1.11 (m, 3H).

Intermediate 126: (+/−)-(E)-tert-Butyl 2-(3-ethoxy-3-oxoprop-1-en-1-yl)-2-methylmorpholine-4-carboxylate

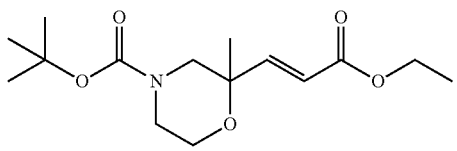 [SMILES: CCOC(=O)/C=C/C1(C)CN(C(=O)OC(C)(C)C)CCO1]

(+/−)-tert-Butyl 2-formyl-2-methylmorpholine-4-carboxylate (90 wt %, 0.7 g, 3.05 mmol) was suspended in toluene (25 mL). (Carbethoxymethylene)triphenylphosphorane (1.276 g, 3.66 mmol) was added and the reaction stirred at rt overnight. The reaction mixture was filtered and the filter cake washed with toluene (25 mL) and water (50 mL). The filtrate was separated and the organic layer eluted through a hydrophobic frit then concentrated in vacuo. The crude product was applied to a 25 g SNAP cartridge in the minimum of DCM and eluted with 0-50% ethyl acetate in cyclohexane. The appropriate fractions were concentrated in vacuo to give (+/−)-(E)-tert-butyl 2-(3-ethoxy-3-oxoprop-1-en-1-yl)-2-methylmorpholine-4-carboxylate (495 mg, 1.57 mmol, 57% yield) as a yellow oil.

$^1$H NMR (400 MHz, CDCl$_3$-d) δ ppm 6.84 (d, J=16.1 Hz, 1H) 6.09 (d, J=16.1 Hz, 1H) 4.30-4.12 (m, 2H) 3.81 (d, J=13.4 Hz, 1H) 3.70 (d, J=3.2 Hz, 3H) 3.26-3.04 (m, 2H) 1.55-1.40 (m, 9H) 1.36-1.20 (m, 6H).

Intermediate 127: (+/−)-tert-Butyl 2-(3-ethoxy-3-oxopropyl)-2-methylmorpholine-4-carboxylate

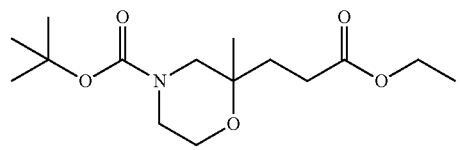 [SMILES: CCOC(=O)CCC1(C)CN(C(=O)OC(C)(C)C)CCO1]

(+/−)-(E)-tert-Butyl 2-(3-ethoxy-3-oxoprop-1-en-1-yl)-2-methylmorpholine-4-carboxylate (495 mg, 1.65 mmol) was taken up in ethanol (10 mL). Ammonium formate (521 mg, 8.27 mmol) and 5% Pd/C paste (50 mg, 0.47 mmol) were added and the reaction heated to 85° C. for 2 h. The reaction was cooled and filtered through Celite. The filter cake was washed with ethanol (10 mL) and the filtrate concentrated in vacuo. The residue was taken up in ethanol (10 mL). Ammonium formate (521 mg, 8.27 mmol) and 5% Pd/C paste (50 mg, 0.47 mmol) were added and the reaction heated to 85° C. for 4 h. The reaction was cooled and filtered through Celite. The filter cake was washed with ethanol (10 mL) and the filtrate concentrated in vacuo to give (+/−)-tert-butyl 2-(3-ethoxy-3-oxopropyl)-2-methylmorpholine-4-carboxylate (556 mg, 1.66 mmol, 100% yield) as a white solid.

$^1$H NMR (400 MHz, CDCl$_3$-d) δ ppm 4.12 (q, J=7.2 Hz, 2H) 3.62 (t, J=4.8 Hz, 2H) 3.44-3.30 (m, 2H) 3.29-3.10 (m, 2H) 2.35 (t, J=8.2 Hz, 2H) 2.08-1.97 (m, 1H) 1.68 (dt, J=14.4, 8.1 Hz, 1H) 1.49-1.38 (m, 9H) 1.24 (t, J=7.1 Hz, 3H) 1.12 (s, 3H).

Intermediate 128: (+/−)-tert-Butyl 2-(3-hydroxypropyl)-2-methylmorpholine-4-carboxylate

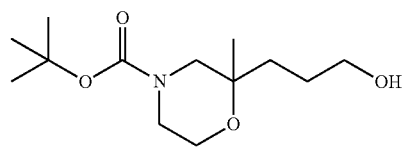 [SMILES: CC(C)(C)OC(=O)N1CCOC(C)(CCCO)C1]

(+/−)-tert-Butyl 2-(3-ethoxy-3-oxopropyl)-2-methylmorpholine-4-carboxylate (556 mg, 1.85 mmol) was taken up in tetrahydrofuran (10 mL) under nitrogen and cooled in an ice bath. LiBH$_4$ (2 M in THF, 2.77 mL, 5.53 mmol) was added slowly and the reaction left to stir and warm up overnight. The reaction was cooled in an ice bath and carefully quenched with NH$_4$Cl solution (20 mL). The reaction mixture was partitioned between EtOAc (25 mL) and water (25 mL) and the aqueous layer re-extracted with EtOAc (25 mL). The combined organics were eluted through a hydrophobic frit and concentrated in vacuo. The residue was taken up in tetrahydrofuran (10 mL) under nitrogen and cooled in an ice bath. LiBH$_4$ (2M in THF, 2.77 mL, 5.53 mmol) was added slowly and the reaction left to stir and warm up overnight. The reaction mixture was cooled and carefully quenched with sat. NH$_4$Cl solution (50 mL). The mixture was partitioned between EtOAc (50 mL) and water (50 mL) and the aqueous layer re-extracted with EtOAc (50 mL). The combined organics were eluted through a hydrophobic frit then concentrated in vacuo to give (+/−)-tert-butyl 2-(3-hydroxypropyl)-2-methylmorpholine-4-carboxylate (90 wt % purity, 400 mg, 1.39 mmol, 75% yield) as a clear oil.

$^1$H NMR (400 MHz, CDCl$_3$-d) δ ppm 3.83-3.71 (m, 1H) 3.70-3.56 (m, 3H) 3.50-3.14 (m, 4H) 2.13 (br. s., 1H) 1.77-1.40 (m, 13H) 1.18-1.09 (m, 3H).

Intermediate 129: (+/−)-tert-Butyl 2-(3-azidopropyl)-2-methylmorpholine-4-carboxylate

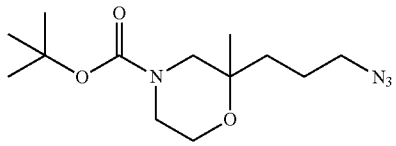 [SMILES: CC(C)(C)OC(=O)N1CCOC(C)(CCCN=[N+]=[N-])C1]

(+/−)-tert-Butyl 2-(3-hydroxypropyl)-2-methylmorpholine-4-carboxylate (90 wt %, 400 mg, 1.39 mmol) was taken up in dichloromethane (10 mL) and cooled in an ice bath. Et$_3$N (0.645 mL, 4.63 mmol) was added followed by methanesulfonyl chloride (0.180 mL, 2.31 mmol). The reaction was left to stir and warm up to rt. After 5 h, the reaction was diluted with DCM (10 mL) and washed with water (20 mL). The organic layer was eluted through a hydrophobic frit and concentrated in vacuo. The residue was taken up in DMF (5 mL). Sodium azide (175 mg, 2.68 mmol) was added and the reaction heated to 70° C. for 4 h. The reaction was cooled and partitioned between EtOAc (25 mL) and sat. NaHCO$_3$ solution (25 mL). The aqueous layer was re-extracted with EtOAc (2×25 mL) and the combined organics eluted through a hydrophobic frit then concentrated in vacuo to give (+/−)-tert-butyl 2-(3-azidopropyl)-2-methylmorpholine-4-carboxylate (90 wt % purity, 326 mg, 1.03 mmol, 85% yield) as a clear oil.

$^1$H NMR (400 MHz, CDCl$_3$-d) δ ppm 3.80-3.15 (m, 8H) 1.81-1.38 (m, 13H) 1.11-1.23 (m, 3H).

Intermediate 130: (+/−)-tert-Butyl 2-(3-aminopropyl)-2-methylmorpholine-4-carboxylate

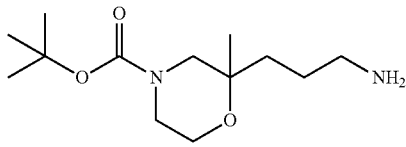 [SMILES: CC(C)(C)OC(=O)N1CCOC(C)(CCCN)C1]

(+/−)-tert-Butyl 2-(3-azidopropyl)-2-methylmorpholine-4-carboxylate (90 wt %, 353 mg, 1.12 mmol) was taken up in tetrahydrofuran (5 mL) and water (5 mL). Ph$_3$P (391 mg, 1.49 mmol) was added and the reaction stirred at rt overnight then left to stand for three days. The reaction was partitioned between EtOAc (25 mL) and brine (25 mL). The organic layer was eluted through a hydrophobic frit then concentrated in vacuo to give a yellow oil. The crude product was applied to a 10 g SNAP Ultra cartridge in the minimum of DCM and eluted with 1-10% 2M NH$_3$ in methanol in DCM. The appropriate fractions were concentrated in vacuo to give (+/−)-tert-butyl 2-(3-aminopropyl)-2-methylmorpholine-4-carboxylate (90 wt % purity, 180.9 mg, 0.63 mmol, 56% yield) as a clear oil.

$^1$H NMR (400 MHz, CDCl$_3$-d) δ ppm 3.63-3.42 (m, 2H) 3.37-3.01 (m, 4H) 2.67-2.49 (m, 2H) 1.64-1.20 (m, 15H) 1.10-0.97 (m, 3H).

Intermediate 131: 2-(1,3-Dihydroxypropan-2-yl)isoindoline-1,3-dione

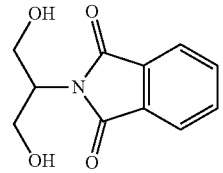 [SMILES: O=C1c2ccccc2C(=O)N1C(CO)CO]

To a stirring solution of 2-aminopropane-1,3-diol (327.2 mg, 3.59 mmol, commercially available from, for example, Sigma-Aldrich) in DMF (15 mL) was added phthalic anhydride (533.6 mg, 3.60 mmol) portionwise. The resulting colourless solution was stirred at 90° C. under nitrogen for 5 h, after which the reaction mixture was cooled to rt and the volatiles evaporated in vacuo. This was partitioned between ethyl acetate (25 mL) and water (25 mL) and the layers separated. The aqueous phase was extracted with further ethyl acetate (4×25 mL) and the organic layers combined and filtered through a cartridge fitted with a hydrophobic frit. The filtrate was evaporated in vacuo. This was redissolved in ethyl acetate (approx. 4 mL) and 3:1 ethyl acetate:ethanol (approx. 4 mL) and directly applied to the top of a 25 g SNAP cartridge and purified by flash column chromatography. The column was eluted with a gradient of 0%-40% (3:1 ethyl acetate:ethanol) in cyclohexane. The appropriate fractions were combined and evaporated in vacuo to give 2-(1,3-dihydroxypropan-2-yl)isoindoline-1,3-dione (380.0 mg, 1.72 mmol, 48% yield) as a white solid.

LCMS (2 min High pH): Rt=0.55 min, [MH]+=222.3.

Intermediate 132: 2-Chloro-6-(methylcarbamoyl)isonicotinic acid

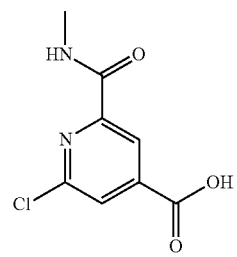

To a solution of tert-butyl 2-chloro-6-(methylcarbamoyl)isonicotinate (5.06 g, 18.69 mmol, commercially available from, for example, Anichem) in DCM (20 mL) was added TFA (10 mL, 130 mmol) and the reaction mixture was stirred under N$_2$ at rt for 4 h. The reaction mixture was concentrated in vacuo for an extended period to remove as much TFA residue as possible, to give 2-chloro-6-(methylcarbamoyl)isonicotinic acid (4.21 g, 18.64 mmol, 100% yield) as a white solid.

LCMS (2 min Formic): Rt=0.71 min, [MH]+=215.1.

Intermediate 133: 4-tert-Butyl 2-methyl 6-(methylcarbamoyl)pyridine-2,4-dicarboxlate

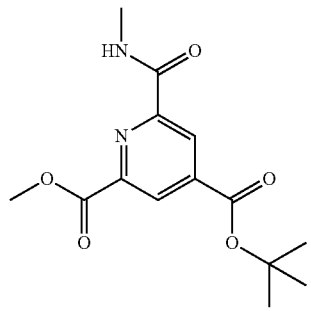 [SMILES: CNC(=O)c1cc(C(=O)OC(C)(C)C)cc(C(=O)OC)n1]

tert-Butyl 2-chloro-6-(methylcarbamoyl)isonicotinate (10 g, 36.9 mmol, commercially available from, for example, Anichem), palladium(II) acetate (0.829 g, 3.69 mmol), Xantphos (2.137 g, 3.69 mmol), triethylamine (15.45 ml, 111 mmol), DMF (100 mL) and methanol (100 mL) were combined. The mixture was purged with nitrogen, then with carbon monoxide and then the mixture was heated for 48 h under a balloon of carbon monoxide. The mixture was evaporated in vacuo and the residue was partitioned between water (500 mL) and EtOAc (500 mL). The organic layer was washed with water (500 mL), dried and evaporated in vacuo and the residue purified by chromatography on a 100 g silica column eluting with 0-100% EtOAc/cyclohexane to give 4-tert-butyl 2-methyl 6-(methylcarbamoyl)pyridine-2,4-dicarboxylate (5.8 g, 19.71 mmol, 53% yield) as a pale yellow solid.

$^1$H NMR (400 MHz, CDCl$_3$-d) δ ppm 8.81 (d, J=1.5 Hz, 1H) 8.68 (d, J=1.5 Hz, 1H) 8.06 (br. s., 1H) 4.04 (s, 3H) 3.08 (d, J=5.1 Hz, 3H) 1.63 (s, 9H).

Intermediate 134: 2-(Methoxycarbonyl)-6-(methylcarbamoyl)isonicotinic acid

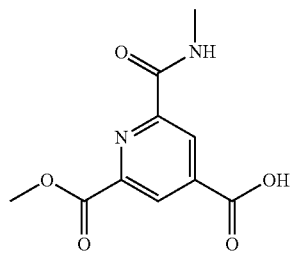 [SMILES: CNC(=O)c1cc(C(=O)O)cc(C(=O)OC)n1]

4-tert-Butyl 2-methyl 6-(methylcarbamoyl)pyridine-2,4-dicarboxylate (3 g, 10.19 mmol) was dissolved in DCM (20 mL) and 2,2,2-trifluoroacetic acid (11.62 g, 102 mmol) was added, then the solution was stirred at rt for 4 h. The solvent was evaporated in vacuo to give 2-(methoxycarbonyl)-6-(methylcarbamoyl)isonicotinic acid (2.55 g, 10.71 mmol, 105% yield) as a pale yellow solid, which was used in the next step without purification.

$^1$H NMR (400 MHz, DMSO-d$_6$) δ ppm 8.61 (d, J=4.9 Hz, 1H) 8.55 (d, J=1.5 Hz, 1H) 8.50 (d, J=1.5 Hz, 1H) 3.96 (s, 3H) 2.88 (d, J=4.9 Hz, 3H)

Intermediate 135: 2-(Ethoxycarbonyl)-6-(methylcarbamoyl)isonicotinic acid

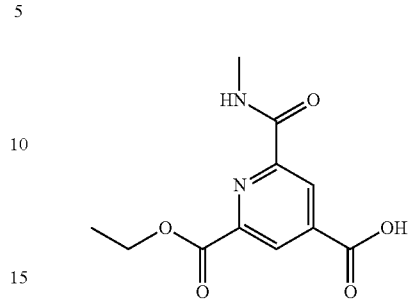

To a solution of 4-tert-butyl 2-ethyl 6-(methylcarbamoyl)pyridine-2,4-dicarboxylate (55.6 mg, 0.18 mmol) in dichloromethane (1 mL) was added trifluoroacetic acid (0.550 mL, 7.14 mmol). The resulting orange solution was stirred at rt for 1 h 10 min. The volatiles were evaporated under a stream of nitrogen. The crude product was triturated with diethyl ether (2×1 mL) and the resulting white solid residue dried under a stream of nitrogen to give 2-(ethoxycarbonyl)-6-(methylcarbamoyl)isonicotinic acid (34.5 mg, 0.14 mmol, 76% yield) as a white solid.

LCMS (2 min High pH): Rt=0.45 min, [MH]$^+$=253.3.

Intermediate 136: Ethyl 4-((1R,5S,6r)-3-oxabicyclo[3.1.0]hexan-6-ylcarbamoyl)-6-(methylcarbamoyl)picolinate

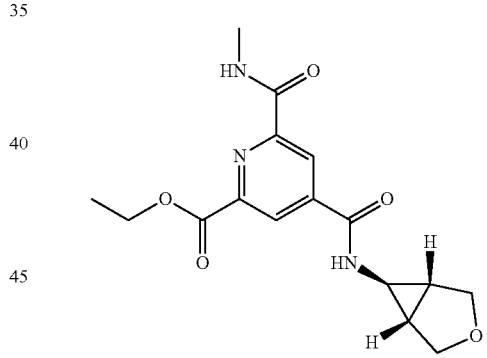

To a solution of 2-(ethoxycarbonyl)-6-(methylcarbamoyl)isonicotinic acid (0.621 g, 2.46 mmol), (1R,5S,6r)-3-oxabicyclo[3.1.0]hexan-6-amine hydrochloride (0.410 g, 3.02 mmol) and HATU (1.167 g, 3.07 mmol) in DMF (20 mL) was added DIPEA (1.70 mL, 9.73 mmol). The solution was stirred at rt for 5 h. Further (1R,5S,6r)-3-oxabicyclo[3.1.0]hexan-6-amine hydrochloride (0.130 g, 0.96 mmol) was added after 2.5 h. Further HATU (0.283 g, 0.74 mmol) and DIPEA (0.250 mL, 1.43 mmol) were added after 3 h 40 min. The solution was removed from stirring and the volatiles evaporated in vacuo. To this was added ethyl acetate (20 mL), 2M aqueous Na$_2$CO$_3$ (10 mL) and water (20 mL) and the layers separated. The aqueous layer was extracted with further ethyl acetate (2×20 mL) and the organic layers combined and filtered through a cartridge fitted with a hydrophobic frit. The filtrate was evaporated in vacuo, redissolved in dichloromethane (approx. 10 mL) and directly applied to the top of a 50 g SNAP cartridge and purified by flash column chromatography. The column was eluted with a gradient of 10%-50% ethyl acetate:ethanol (3:1) in cyclohexane. The required fractions were evaporated in vacuo to give ethyl 4-((1R,5S,6r)-3-oxabicyclo[3.1.0]hexan-6-ylcarbannoyl)-6-(methylcarbamoyl)picolinate (704.9 mg, 2.12 mmol, 86% yield) as a yellow solid.

LCMS (2 min High pH): Rt=0.70 min, [MH]+=334.2.

Intermediate 137: Methyl 4-((1R,5S,6r)-3-oxabicyclo[3.1.0]hexan-6-ylcarbamoyl)-6-(methylcarbamoyl)picolinate

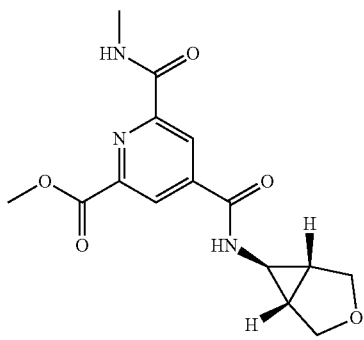 [SMILES: CNC(=O)c1cc(C(=O)N[C@H]2[C@@H]3COC[C@@H]32)cc(C(=O)OC)n1]

2-(Methoxycarbonyl)-6-(methylcarbamoyl)isonicotinic acid (2.4 g, 10.08 mmol) was suspended in DCM (50 mL) and Et$_3$N (4.21 mL, 30.2 mmol) and HATU (5.75 g, 15.11 mmol) were added, then the mixture was stirred for 20 min before the addition of (1R,5S,6r)-3-oxabicyclo[3.1.0]hexan-6-amine hydrochloride (2.049 g, 15.11 mmol). The solution was stirred for 2 h, then washed with water (2×100 mL) and the organic layer dried and evaporated in vacuo. This was suspended in EtOAc (20 mL) and sonicated for 10 min, then the solid was collected by filtration and washed with ether (20 mL) to give methyl 4-((1R,5S,6r)-3-oxabicyclo[3.1.0]hexan-6-ylcarbamoyl)-6-(methylcarbamoyl)picolinate (1.20 g, 3.76 mmol, 37% yield).

LCMS (2 min Formic): Rt=0.59 min, [MH]+=320.1.

Intermediate 138: N$^4$-((1R,5S,6r)-3-Oxabicyclo[3.1.0]hexan-6-yl)-6-(hydroxymethyl)-N$^2$-methylpyridine-2,4-dicarboxamide

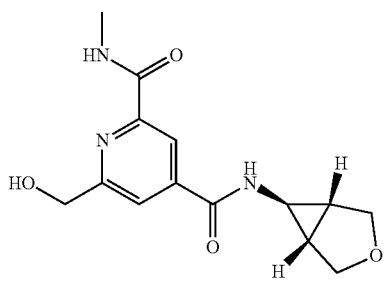 [SMILES: CNC(=O)c1cc(C(=O)N[C@H]2[C@@H]3COC[C@@H]32)cc(CO)n1]

A suspension of ethyl 4-((1R,5S,6r)-3-oxabicyclo[3.1.0]hexan-6-ylcarbamoyl)-6-(methylcarbamoyl)picolinate (615.8 mg, 1.85 mmol) and calcium chloride (411.8 mg, 3.71 mmol) in ethanol (12 mL) and 2-methyltetrahydrofuran (12 mL) was cooled to approx. 0° C. in an ice bath. To this was added sodium borohydride (116.8 mg, 3.09 mmol) portionwise. The resulting light pink solution was allowed to warm to rt and stirred for 16 h, after which sat. aqueous NH$_4$Cl (5 mL) was added and the solution stirred at rt for a further 10 min. To this mixture was added water (15 mL) and the resulting cloudy white mixture concentrated in vacuo to remove the organic solvents. The resulting solution was extracted with ethyl acetate (3×20 mL) and the organic layers combined and filtered through a cartridge fitted with a hydrophobic frit. The aqueous phase was concentrated to 5 mL and to this was added brine (15 mL). This was extracted with further ethyl acetate (2×20 mL). The organic phase was filtered through a cartridge fitted with a hydrophobic frit and combined with the filtered organic phase from the first extraction. The aqueous phase was evaporated in vacuo and redissolved in the minimum volume of water (approx. 15 mL). It was then extracted with further ethyl acetate (4×15 mL). These organic phases were combined, filtered through a cartridge fitted with a hydrophobic frit and combined with the previous combined organic phases. This solution was evaporated in vacuo to give N$^4$-((1R,5S,6r)-3-oxabicyclo[3.1.0]hexan-6-yl)-6-(hydroxymethyl)-N$^2$-methylpyridine-2,4-dicarboxamide (85 wt % purity, 530.6 mg, 1.55 mmol, 84% yield) as a sticky light brown solid.

LCMS (2 min High pH): Rt=0.52 min, [MH]+=292.3.

Alternative Procedure:

Methyl 4-((1R,5S,6r)-3-oxabicyclo[3.1.0]hexan-6-ylcarbamoyl)-6-(methylcarbamoyl)picolinate (1.94 g, 6.08 mmol) was dissolved in a mixture of 2-methyl THF (70 mL) and ethanol (70 mL) and then calcium chloride (2.023 g, 18.23 mmol) was added and the mixture stirred vigorously for 10 min. The mixture was then cooled in an ice bath under nitrogen and sodium tetrahydroborate (0.345 g, 9.11 mmol) was added in small portions over 20 min. The resulting mixture was stirred rapidly overnight, allowing it to warm to rt, then quenched by dropwise addition of ammonium chloride solution (100 mL). The mixture was extracted with EtOAc (3×100 mL) and the combined organics washed with brine, dried and evaporated in vacuo to give a colourless solid. The crude was mostly dissolved in a mixture of DCM (20 mL) and methanol (3 mL) and loaded onto a 100 g silica column. The column was eluted with 0-100% (25% EtOH/EtOAc)/cyclohexane and the product-containing fractions were evaporated in vacuo to give N$^4$-((1R,5S,6r)-3-oxabicyclo[3.1.0]hexan-6-yl)-6-(hydroxymethyl)-N$^2$-methylpyridine-2,4-dicarboxamide (0.80 g, 2.75 mmol, 45.2% yield) as a colourless solid.

LCMS (2 min Formic): Rt=0.47 min, [MH]+=292.3.

Intermediate 139: N$^4$-((1R,5S,6r)-3-Oxabicyclo[3.1.0]hexan-6-yl)-6-(chloromethyl)-N$^2$-methylpyridine-2,4-dicarboxamide

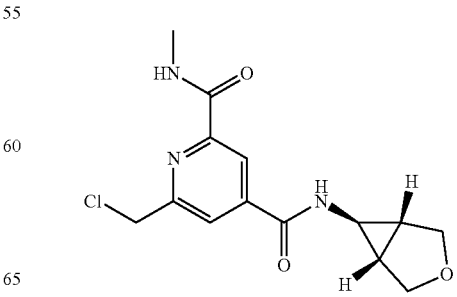

To a suspension of N⁴-((1R,5S,6r)-3-oxabicyclo[3.1.0]hexan-6-yl)-6-(hydroxymethyl)-N²-methylpyridine-2,4-dicarboxamide (85 wt %, 502.3 mg, 1.47 mmol) in dichloromethane (15 mL) was added thionyl chloride (0.400 mL, 5.48 mmol) dropwise. The suspension was stirred at 40° C. for 2.75 h, after which it was cooled to rt and the volatiles were evaporated in vacuo. The residue was redissolved in dichloromethane (approx. 5 mL) and ethyl acetate (approx. 5 mL) and directly applied to the top of a 25 g SNAP cartridge and purified by flash column chromatography. The column was eluted with a gradient of 0%-40% ethyl acetate: ethanol (3:1) in cyclohexane. The required fractions were evaporated in vacuo to give N⁴-((1R,5S,6r)-3-oxabicyclo[3.1.0]hexan-6-yl)-6-(chloromethyl)-N²-methylpyridine-2,4-dicarboxamide (249.5 mg, 0.81 mmol, 55% yield) as a white solid.

LCMS (2 min High pH): Rt=0.70 min, [MH]+=310.2.

Intermediate 140: N⁴-((1R,5S,6r)-3-Oxabicyclo[3.1.0]hexan-6-yl)-6-formyl-N²-methylpyridine-2,4-dicarboxamide

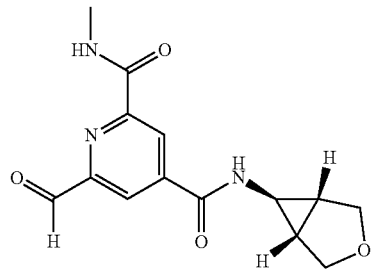 [SMILES: CNC(=O)c1cc(C(=O)N[C@H]2[C@@H]3COC[C@@H]32)cc(C=O)n1]

N⁴-((1R,5S,6r)-3-Oxabicyclo[3.1.0]hexan-6-yl)-6-(hydroxymethyl)-N²-methylpyridine-2,4-dicarboxamide (1.072 g, 3.68 mmol) was taken up in dichloromethane (50 mL). Dess-Martin periodinane (1.717 g, 4.05 mmol) was added and the reaction left to stir for 2 h. Sodium thiosulphate solution (50 mL) was added and the reaction left to stir for a further 15 min. The organic and aqueous phases were separated. The aqueous phase was washed with DCM (2×50 mL). The combined organic phase was dried over sodium sulphate and filtered through a hydrophobic frit before being concentrated in vacuo. The aqueous phase was re-extracted using DCM (2×20 mL) followed by further extraction using EtOAc (2×20 mL). The combined organics were combined with the previous residue and concentrated in vacuo to afford N⁴-((1R,5S,6r)-3-oxabicyclo[3.1.0]hexan-6-yl)-6-formyl-N²-methylpyridine-2,4-dicarboxamide (674 mg, 2.33 mmol, 63% yield).

LCMS (2 min High pH): Rt=0.54. min, [MH]+=290.2.

Intermediate 141: tert-Butyl 2-chloro-6-(ethylcarbamoyl)isonicotinate

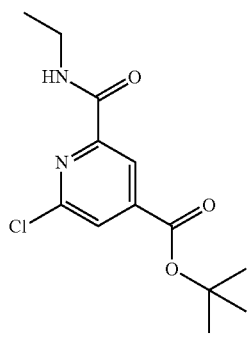 [SMILES: CCNC(=O)c1cc(C(=O)OC(C)(C)C)cc(Cl)n1]

A mixture of 4-(tert-butoxycarbonyl)-6-chloropicolinic acid (4.085 g, 15.85 mmol, commercially available from, for example, Anichem), ethylamine hydrochloride (4.528 g, 55.5 mmol) and HATU (7.093 g, 18.65 mmol) in DMF (41 mL) was stirred at rt under nitrogen. Triethylamine (10 mL, 71.7 mmol) was added and the mixture stirred for 2 h. The majority of the volatiles were evaporated in vacuo to give an orange/brown slurry which was partitioned between ethyl acetate (100 mL) and 2M aqueous sodium carbonate solution (100 mL). The phases were separated and the aqueous phase was extracted with further ethyl acetate (2×50 mL). The combined organic extracts were washed with water (50 mL) and saturated brine solution (50 mL) before being filtered through a cartridge fitted with a hydrophobic frit. The solvent was evaporated in vacuo to give a viscous orange/brown oil, which was redissolved in dichloromethane (ca. 10 mL), loaded onto a 100 g SNAP silica cartridge and purified by flash column chromatography eluting with a gradient of 0 to 30% ethyl acetate in cyclohexane. The required fractions were combined and evaporated in vacuo, the residue re-dissolved in dichloromethane (ca. 15 mL), the solvent evaporated in vacuo and the residue dried in vacuo to give tert-butyl 2-chloro-6-(ethylcarbamoyl)isonicotinate (2.607 g, 9.15 mmol, 58% yield) as a pale yellow oil which crystallised upon standing to a pale yellow crystalline solid.

LCMS (2 min Formic): Rt=1.21 min, [MH]+=285.2.

¹H NMR (400 MHz, CDCl₃-d) δ ppm 8.56 (s, 1H) 7.96 (s, 1H) 7.80 (br. s., 1H) 3.53 (quin, J=6.8 Hz, 2H) 1.61 (s, 9H) 1.29 (t, J=7.2 Hz, 3H).

Intermediate 142: 4-tert-Butyl 2-methyl 6-(ethylcarbamoyl)pyridine-2,4-dicarboxylate

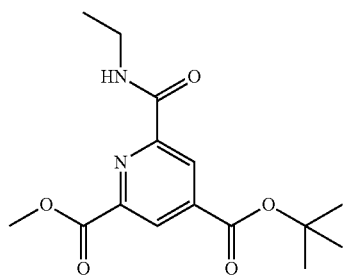 [SMILES: CCNC(=O)c1cc(C(=O)OC(C)(C)C)cc(C(=O)OC)n1]

To a solution of tert-butyl 2-chloro-6-(ethylcarbamoyl)isonicotinate (1005 mg, 3.53 mmol), XantPhos (211.1 mg, 0.37 mmol) and palladium(II) acetate (85.6 mg, 0.38 mmol) in methanol (15 mL) and DMF (15 mL) was added triethylamine (1.48 mL, 10.62 mmol). Carbon monoxide gas was bubbled through the solution at rt for approx. 5 min, after which a balloon of carbon monoxide was fitted and the solution stirred at 70° C. for 2.5 h. The reaction mixture was allowed to cool to rt and left to stand under a carbon monoxide atmosphere overnight, after which the flask was purged with nitrogen and the volatiles were evaporated in vacuo. The residue was partitioned between ethyl acetate (40 mL) and 1:1 sat. aqueous lithium chloride:water (40 mL) and the layers separated. The aqueous phase was extracted with further ethyl acetate (2×40 mL) and the organic layers combined and filtered through a cartridge fitted with a hydrophobic frit. The filtrate was evaporated in vacuo, redissolved in dichloromethane (5 mL) and ethyl acetate (3 mL) and directly applied to the top of a 100 g SNAP silica cartridge and purified by flash column chromatography. The column was eluted with a gradient of 0%-40% ethyl acetate in cyclohexane. The appropriate fractions were combined, evaporated in vacuo, transferred in dichloromethane (approx. 10 mL) and this solution evaporated in vacuo to give 4-tert-butyl 2-methyl 6-(ethylcarbamoyl)pyridine-2,4-dicarboxylate (899.9 mg, 2.92 mmol, 83% yield) as a sticky yellow solid.

LCMS (2 min High pH): Rt=1.04 min, [MH]+=309.3.

$^1$H NMR (400 MHz, CDCl$_3$-d) δ ppm 8.82 (s, 1H) 8.68 (s, 1H) 8.11 (br. s., 1H) 4.05 (s, 3H) 3.56 (quin, J=6.8 Hz, 2H) 1.63 (s, 9H) 1.30 (t, J=7.2 Hz, 3H)

Intermediate 143: tert-Butyl 2-(ethylcarbamoyl)-6-(hydroxymethyl)isonicotinate

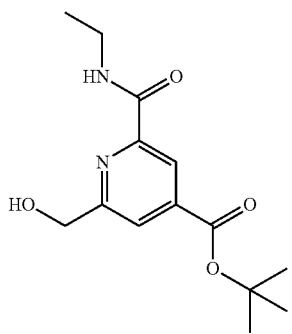 [SMILES: CCNC(=O)c1cc(C(=O)OC(C)(C)C)cc(CO)n1]

To a stirring suspension of 4-tert-butyl 2-methyl 6-(ethylcarbamoyl)pyridine-2,4-dicarboxylate (900 mg, 2.92 mmol) and calcium chloride (656.3 mg, 5.91 mmol) in ethanol (10 mL) and 2-methyltetrahydrofuran (10 mL) at 0° C. under nitrogen was added sodium borohydride (163.2 mg, 4.31 mmol) portionwise. The reaction mixture was allowed to warm to rt and stirred under nitrogen for a further 43 h. Further sodium borohydride (81.8 mg, 2.16 mmol) was added after 19.5 h. The reaction mixture was quenched with sat. aqueous NH$_4$Cl (5 mL) and the resulting mixture stirred at rt for a further 1 h and left to stand for a further 4 h. To this was added water (10 mL) and the organic solvents removed in vacuo. To the resulting mixture was added further water (20 mL) and ethyl acetate (30 mL) and the layers separated. The aqueous phase was extracted with further ethyl acetate (2×30 mL) and the organic layers combined and filtered through a cartridge fitted with a hydrophobic frit. The filtrate was evaporated in vacuo, then redissolved in dichloromethane (2 mL) and directly applied to the top of a 25 g SNAP silica cartridge and purified by flash column chromatography. The column was eluted with a gradient of 20%-70% ethyl acetate in cyclohexane. The appropriate fractions were combined and evaporated in vacuo to give tert-butyl 2-(ethylcarbamoyl)-6-(hydroxymethyl)isonicotinate (371.1 mg, 1.32 mmol, 45% yield) as a sticky light yellow solid.

LCMS (2 min High pH): Rt=0.90 min, [MH]+=281.2.

Intermediate 144: tert-Butyl 2-(chloromethyl)-6-(ethylcarbamoyl)isonicotinate

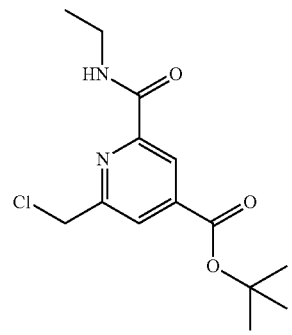 [SMILES: CCNC(=O)c1cc(C(=O)OC(C)(C)C)cc(CCl)n1]

To a stirring solution of tert-butyl 2-(ethylcarbamoyl)-6-(hydroxymethyl)isonicotinate (340 mg, 1.213 mmol) in dichloromethane (10 mL) was added thionyl chloride (0.450 mL, 6.17 mmol) dropwise. The resulting mixture was stirred at rt under nitrogen for a total of 45.5 h, during which further thionyl chloride (0.400 mL, 5.48 mmol) was added after 21.75 h. The volatiles were evaporated under a stream of nitrogen and then the crude product was azeotroped with acetonitrile (3×10 mL), evaporating in vacuo to give tert-butyl 2-(chloromethyl)-6-(ethylcarbamoyl)isonicotinate (348.1 mg, 1.165 mmol, 96% yield) as a sticky brown oil.

LCMS (2 min High pH): Rt=1.17 min, [MH]+=299.3.

$^1$H NMR (400 MHz, CDCl$_3$-d) δ ppm 8.59 (d, J=1.0 Hz, 1H) 8.11 (d, J=1.2 Hz, 1H) 7.96 (br. s., 1H) 4.73 (s, 2H) 3.62-3.50 (m, 2H) 1.71-1.53 (m, 9H) 1.30 (t, J=7.2 Hz, 3H)

Intermediate 145: 6-Chloro-N$^4$-(4,4-diethoxybutyl)-N$^2$-methylpyridine-2,4-dicarboxamide

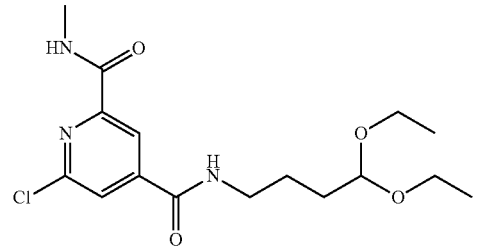 [SMILES: CCOC(CCCNC(=O)c1cc(Cl)nc(C(=O)NC)c1)OCC]

To a solution of 2-chloro-6-(methylcarbamoyl)isonicotinic acid (2 g, 8.85 mmol) and HATU (3.70 g, 9.74 mmol) in DMF (20 mL) was added DIPEA (3.09 mL, 17.71 mmol) followed by 4,4-diethoxybutan-1-amine (1.68 mL, 9.74 mmol). The resulting solution was stirred at rt for 16 h. Water (60 mL) and EtOAc (60 mL) were added and the layers separated. The aqueous layer was further extracted with ethyl acetate (2×30 mL). The combined organics were back-extracted with water (2×30 mL) and sat. aqueous LiCl (30 mL) and then dried (Na$_2$SO$_4$), filtered and concentrated in vacuo to give a dark oil. This was re-dissolved in DCM and directly applied to the top of a 100 g SNAP silica cartridge and purified by SP4 flash column chromatography. The column was eluted with a gradient of 30-70% ethyl acetate in cyclohexane. The appropriate fractions were collected and concentrated in vacuo to afford the product, 6-chloro-N$^4$-(4,4-diethoxybutyl)-N$^2$-methylpyridine-2,4-dicarboxamide (2.39 g, 6.68 mmol, 75% yield) as a yellow oil.

LCMS (2 min High pH): Rt=0.92 min, [MH]−=356.2.

Intermediate 146: 6-Chloro-N$^4$-(3-((2r,5r)-5-(1,3-dioxoisoindolin-2-yl)-1,3-dioxan-2-yl)propyl)-N$^2$-methylpyridine-2,4-dicarboxamide

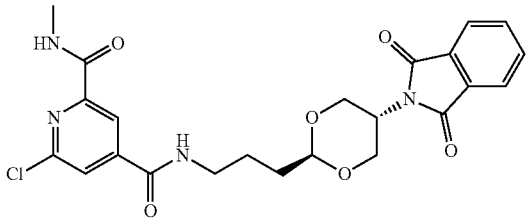 [SMILES: CNC(=O)c1cc(C(=O)NCCC[C@H]2OC[C@H](N3C(=O)c4ccccc4C3=O)CO2)cc(Cl)n1]

To a solution of 6-chloro-N$^4$-(4,4-diethoxybutyl)-N$^2$-methylpyridine-2,4-dicarboxamide (2.39 g, 6.68 mmol) in toluene (30 mL) was added 2-(1,3-dihydroxypropan-2-yl)isoindoline-1,3-dione (1.477 g, 6.68 mmol) and p-toluenesulfonic acid monohydrate (0.254 g, 1.34 mmol). The resulting suspension was stirred at 90° C. under nitrogen for 2 h, after which the reaction mixture was allowed to cool to rt and partitioned between ethyl acetate (100 mL), and sat. aq. sodium bicarbonate (100 mL) and the layers separated. A large amount of precipitate remained in the aqueous layer. The aqueous phase was extracted with further ethyl acetate (2×100 mL) which gradually dissolved the precipitate, and the organic phases were combined with the suspension and directly evaporated in vacuo to give a yellow solid, which was still impure. The poorly soluble product was triturated with Et$_2$O and filtered. The residue was collected and dried in vacuo to afford the desired, 6-chloro-N$^4$-(3-((2r,5r)-5-(1,3-dioxoisoindolin-2-yl)-1,3-dioxan-2-yl)propyl)-N$^2$-methylpyridine-2,4-dicarboxamide (1.666 g, 3.42 mmol, 51% yield).

LCMS (2 min Formic): Rt=1.01 min, [MH]+=487.3.

Intermediate 147: tert-Butyl 2-(methylcarbamoyl)-6-vinylisonicotinate

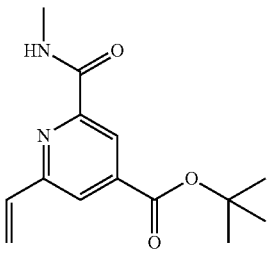 [SMILES: C=Cc1cc(C(=O)OC(C)(C)C)cc(C(=O)NC)n1]

A suspension of tert-butyl 2-chloro-6-(methylcarbamoyl)isonicotinate (0.801 g, 2.96 mmol), 2,4,6-trivinylcyclotriboroxane pyridine complex (1.063 g, 4.42 mmol), PdCl$_2$(dppf) (0.1040 g, 0.142 mmol) and potassium carbonate (1.2526 g, 9.06 mmol) in ethanol (5 mL) and toluene (5 mL) in a sealed microwave vial was heated in a microwave reactor at 120° C. for 40 min. The vial was resealed and the mixture heated in a microwave reactor for a further 20 min. The reaction mixture was filtered through a 10 g celite cartridge and the cartridge washed with ethyl acetate (approx. 30 mL). The filtrate was evaporated in vacuo to give a viscous dark red oil (1.30 g). This was redissolved in DCM (approx. 3 mL) and directly applied to the top of a 50 g SNAP silica cartridge and purified by SP4 flash column chromatography. The column was eluted with a gradient of 0%-40% EtOAc in cyclohexane.

The appropriate fractions were combined and evaporated in vacuo to give a viscous dark brown oil (816 mg). This was redissolved in DCM (approx. 3 mL) and directly applied to the top of a 50 g SNAP silica cartridge and further purified by SP4 flash column chromatography. The column was eluted with a gradient of 15%-40% ethyl acetate in cyclohexane. The appropriate fractions were combined and evaporated in vacuo to give the desired product as a viscous light yellow oil (738.1 mg)—tert-butyl 2-(methylcarbamoyl)-6-vinylisonicotinate (738.1 mg, 2.81 mmol, 95% yield).

LCMS (2 min High pH): Rt=1.14 min, [MH]+=263.3.

Intermediate 148: tert-Butyl 2-(1-bromovinyl)-6-(methylcarbamoyl)isonicotinate

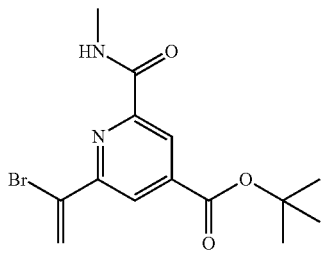 [SMILES: C=C(Br)c1cc(C(=O)OC(C)(C)C)cc(C(=O)NC)n1]

Bromine (0.34 mL, 6.64 mmol) was added to tert-butyl 2-(methylcarbamoyl)-6-vinylisonicotinate (910 mg, 3.47 mmol) in DCM (6 mL). The resulting solution was stirred at rt for 30 min. The solvent was removed in vacuo then of EtOH (8 mL) with KOH (389 mg, 6.94 mmol) at 50° C. was added and the reaction mixture was stirred for 15 min. The reaction mixture was partitioned between water (10 mL) and brine (2 mL) and EtOAc (10 mL). The organic layer was separated and the aqueous layer was extracted with further portions of EtOAc (3×10 mL). The combined organic phase was dried over a hydrophobic frit then concentrated in vacuo to give tert-butyl 2-(1-bromovinyl)-6-(methylcarbamoyl)isonicotinate (1.31 g, 3.30 mmol, 95% yield).

LCMS (2 min Formic): Rt=1.26 min, [MH]+=341.1, 343.1.

Intermediate 149: tert-Butyl 2-(1-(1H-indol-4-yl)vinyl)-6-(methylcarbamoyl)isonicotinate

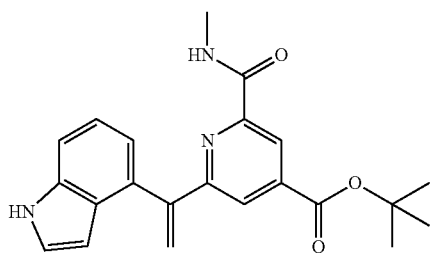 [SMILES: C=C(c1cc(C(=O)OC(C)(C)C)cc(C(=O)NC)n1)c1cccc2[nH]ccc12]

tert-Butyl 2-(1-bromovinyl)-6-(methylcarbamoyl)isonicotinate (1.31 g, 3.84 mmol), (1H-indol-4-yl)boronic acid (0.742 g, 4.61 mmol), tripotassium phosphate (2.445 g, 11.52 mmol) and PEPPSI iPr (0.262 g, 0.384 mmol) were purged under nitrogen for 10 min. 1,4-Dioxane (20 mL) and water (10 mL) were added and the reaction left to stir at rt for 3 h. PEPPSI iPr (0.262 g, 0.384 mmol) was added again and the reaction left to stir overnight. The reaction was concentrated in vacuo. The residue was taken up in DCM (40 mL) and washed with water (2×40 mL) and brine (40 mL). The organic phase was dried over sodium sulphate, filtered through a hydrophobic frit and concentrated in vacuo to afford tert-butyl 2-(1-(1H-indol-4-yl)vinyl)-6-(methylcarbamoyl)isonicotinate (1.5 g, 3.18 mmol, 83% yield).

LCMS (2 min High pH): Rt=1.25 min, [MH]+=378.4.

Intermediate 150: tert-Butyl 2-(1-(1H-indol-4-yl)vinyl)-6-(methylcarbamoyl)isonicotinate

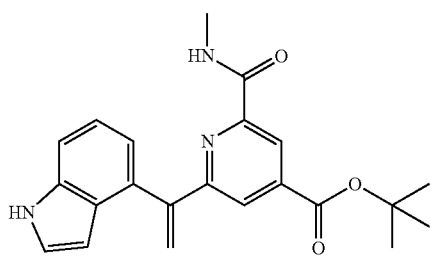 [SMILES: C=C(c1cc(C(=O)OC(C)(C)C)cc(C(=O)NC)n1)c1cccc2[nH]ccc12]

tert-Butyl 2-(1-bromovinyl)-6-(methylcarbamoyl)isonicotinate (1.31 g, 3.84 mmol), (1H-indol-4-yl)boronic acid (0.742 g, 4.61 mmol), tripotassium phosphate (2.445 g, 11.52 mmol) and PEPPSI iPr (0.262 g, 0.384 mmol) were purged under nitrogen for 10 min. 1,4-Dioxane (20 mL) and water (10 mL) were added and the reaction left to stir at rt for 3 h. Further PEPPSI iPr (0.262 g, 0.384 mmol) was added and the reaction left to stir overnight. The reaction was concentrated in vacuo. The residue was taken up in DCM (40 mL) and washed with water (2×40 mL) and brine (40 mL). The organic phase was dried over sodium sulphate, filtered through a hydrophobic frit and concentrated in vacuo to afford tert-butyl 2-(1-(1H-indol-4-yl)vinyl)-6-(methylcarbamoyl)isonicotinate (1.5 g, 3.18 mmol, 83% yield).

LCMS (2 min High pH): Rt=1.25 min, [MH]+=378.4.

Intermediate 151: (+/−)-tert-Butyl 2-(1-(1H-indol-4-yl)ethyl)-6-(methylcarbamoyl)isonicotinate

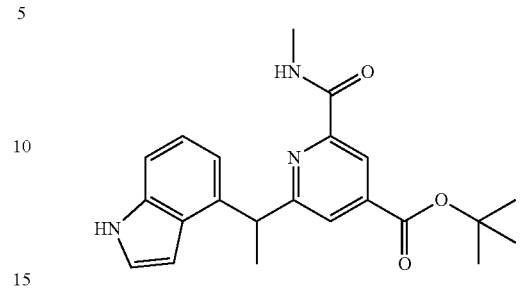

tert-Butyl 2-(1-(1H-indol-4-yl)vinyl)-6-(methylcarbamoyl)isonicotinate (1.5 g, 3.18 mmol) was hydrogenated using a Pd—C (0.068 g, 0.636 mmol) catalyst in ethanol (20 mL). The reaction was left to stir at rt overnight. The reaction was filtered through celite before being concentrated in vacuo. The crude product was applied to a SNAP ULTRA silica cartridge (100 g) in the minimum of DCM and purified by flash chromatography, eluting with 5-50% EtOAc in cyclohexane. The appropriate fractions were combined and concentrated in vacuo to afford tert-butyl 2-(1-(1H-indol-4-yl)ethyl)-6-(methylcarbamoyl)isonicotinate (512 mg, 1.35 mmol, 42% yield).

LCMS (2 min Formic): Rt=1.24 min, [MH]+=380.4.

Intermediate 152: (+/−)-2-(1-(1H-Indol-4-yl)ethyl)-6-(methylcarbamoyl)isonicotinic acid

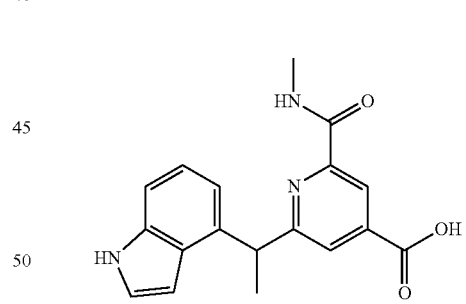

tert-Butyl 2-(1-(1H-indol-4-yl)ethyl)-6-(methylcarbamoyl)isonicotinate (512 mg, 1.35 mmol) was taken up in methanol (7.5 mL) and THF (7.5 mL). NaOH (6.75 mL, 13.49 mmol, 2M) was added and the reaction left to stir at rt for 2 h. The reaction was concentrated in vacuo. The residue was taken up in water and acidified to pH2 using 2M HCl. The precipitate was filtered off to give the desired product, 2-(1-(1H-indol-4-yl)ethyl)-6-(methylcarbamoyl)isonicotinic acid (450 mg, 1.39 mmol).

LCMS (2 min High pH): Rt=0.63 min, [MH]+=324.3.

Intermediate 153: (R)-tert-Butyl 2-(methylcarbamoyl)-6-(1-phenylethyl)isonicotinate

Intermediate 154: (S)-tert-Butyl 2-(methylcarbamoyl)-6-(1-phenylethyl)isonicotinate

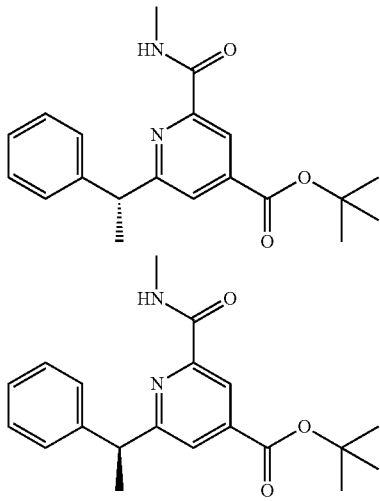

Intermediate 73 (7.78 g) was purified by chiral HPLC. The racemate was dissolved in EtOH (150 mL). Injection: 1.1 mL of the solution was injected via preparative autosampler, onto the column (20% EtOH/heptane+0.2% isopropylamine, flow rate=42.5 mL/min, detection wavelength=280 nm, band width 140 nm, reference 400 nm bandwidth 100 nm, Column 30 mm×25 cm Chiralcel OJ-H). Fractions from 11.2-13.7 min were bulked and labelled peak 1. Fractions from 15.7-19 min were bulked and labelled peak 2. The bulked fractions were concentrated in vacuo and then transferred to weighed flasks.

The fractions corresponding to peak 1 were collected to afford intermediate 153 (2.84 g)

LCMS (2 min High pH): Rt=1.35 min, [MH]$^+$=341.3

The fractions corresponding to peak 2 were collected to afford intermediate 154 (2.80 g)

LCMS (2 min High pH): Rt=1.35 min, [MH]$^+$=341.3

$^1$H NMR (400 MHz, CDCl$_3$) δ ppm 8.46 (d, J=1.2 Hz, 1H) 8.03 (br. s., 1H) 7.82 (d, J=1.5 Hz, 1H) 7.20-7.36 (m, 5H) 4.39 (q, J=7.2 Hz, 1H) 3.08 (d, J=5.1 Hz, 3H) 1.76 (d, J=7.1 Hz, 3H) 1.60 (s, 9H)

Intermediate 155: (S)-2-(Methylcarbamoyl)-6-(1-phenylethyl)isonicotinic acid

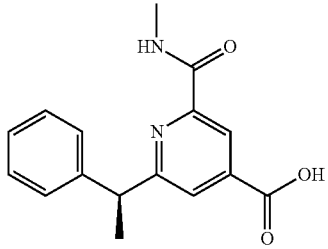 [SMILES: CNC(=O)c1cc(C(=O)O)cc([C@@H](C)c2ccccc2)n1]

A mixture of (S)-tert-butyl 2-(methylcarbamoyl)-6-(1-phenylethyl)isonicotinate (2.19 g, 6.43 mmol, intermediate 154) and trifluoroacetic acid (10 mL, 130 mmol) in DCM (15 mL) was stirred at rt for 19 h. The volatiles were evaporated from the mixture in vacuo and the oily residue redissolved in acetonitrile (ca. 10 mL) and the solvent evaporated in vacuo. The orange oily residue had ether (ca. 10 mL) added and a white solid precipitated. The solid was filtered, washed with ether (2×5 mL) and dried in vacuo to give the desired product as a white solid; (S)-2-(methylcarbamoyl)-6-(1-phenylethyl)isonicotinic acid (1.18 g, 4.14 mmol, 64% yield)

The solvent from the mother liquor of the second ether wash was evaporated under a stream of nitrogen to give a second batch of the desired product as a white solid; (S)-2-(methylcarbamoyl)-6-(1-phenylethyl)isonicotinic acid (95.6 mg, 0.336 mmol, 5.23% yield)

The solvent from the combined mother liquors of the initial trituration and first ether wash were evaporated under a stream of nitrogen and the orange viscous oil which resulted was triturated with ether (5 mL). The mother liquor was decanted away and the solid triturated with further ether (3×5 mL), each time decanting the mother liquor. The solid was dried in vacuo to give a third batch of the desired product as a cream solid, yield; (S)-2-(methylcarbamoyl)-6-(1-phenylethyl)isonicotinic acid (310.8 mg, 1.09 mmol, 17% yield)

The combined mother liquors from the isolation of the above batch were evaporated under a stream of nitrogen and the resultant orange semi-crystalline solid was washed with ether (3 mL). The mother liquor was decanted away and the solid triturated with further ether (3×3 mL), each time decanting the mother liquor. The solid was dried in vacuo to give a fourth batch of the desired product as a cream solid (100.4 mg)

Total product isolated summed over the four batches=1.68 g, 92%.

LCMS (2 min Formic): Rt=1.00 min, [MH]$^+$=285.3

1H NMR (400 MHz, DMSO-d6) δ ppm 13.81 (br. s., 1H) 8.80 (q, J=4.5 Hz, 1H) 8.22 (s, 1H) 7.83 (d, J=1.5 Hz, 1H) 7.43 (d, J=7.1 Hz, 2H) 7.27-7.34 (m, 2H) 7.16-7.24 (m, 1H) 4.48 (q, J=7.3 Hz, 1H) 2.90 (d, J=4.9 Hz, 3H) 1.73 (d, J=7.3 Hz, 3H)

Intermediate 156: (R)-2-(Methylcarbamoyl)-6-(1-phenylethyl)isonicotinic acid

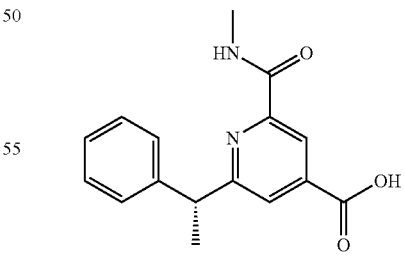

(R)-tert-Butyl 2-(methylcarbamoyl)-6-(1-phenylethyl) isonicotinate (497 mg, 1.46 mmol, intermediate 10) was taken up in DCM (5 mL), TFA (0.5 mL, 6.49 mmol) was added and the reaction left to stir at rt overnight. TFA (0.5 mL, 6.49 mmol) was added again and the reaction was refluxed at 50° C. for 3 h. More TFA (1 mL) was added to the reaction, which was then left to stir for a further 2 h. The reaction was concentrated in vacuo. The sample was loaded in methanol and purified by SPE on sulphonic acid (SCX, 2 g) and eluted through with methanol. The appropriate fractions were combined and evaporated in vacuo to give the required product (350 mg) as a pink solid.

LCMS (2 min High pH): Rt=0.68 min, [MH]+=285.2.

Intermediate 157: tert-Butyl 2-benzyl-6-(ethylcarbamoyl)isonicotinate

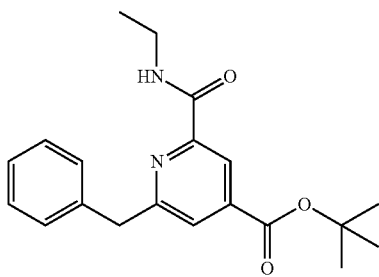 [SMILES: CCNC(=O)c1cc(C(=O)OC(C)(C)C)cc(Cc2ccccc2)n1]

A solution of tert-butyl 2-chloro-6-(ethylcarbamoyl)isonicotinate (228 mg, 0.80 mmol) and bis(triphenylphosphine) palladium(II) chloride (55.6 mg, 0.08 mmol) in tetrahydrofuran (6 mL) in a sealed microwave vial was stirred under nitrogen at rt for 10 min, after which benzylzinc(II) bromide (0.5 M in THF, 2.40 mL, 1.20 mmol) was added dropwise. The vial was resealed and the mixture heated in a microwave reactor at 110° C. for 30 min. The reaction mixture was filtered through a 2.5 g Celite cartridge and the cartridge washed with ethyl acetate (20 mL). To the filtrate was added water (20 mL) and brine (5 mL) and the layers separated. The aqueous layer was extracted with further ethyl acetate (2×25 mL) and the combined organic layers washed with brine (2×20 mL) and filtered through a 10 g Celite cartridge. The cartridge was washed with ethyl acetate (30 mL) and the filtrate filtered through a cartridge fitted with a hydrophobic frit. This filtrate was evaporated in vacuo, then redissolved in dichloromethane (3 mL) and directly applied to the top of a 25 g SNAP silica cartridge and purified by flash column chromatography. The column was eluted with a gradient of 0%-30% ethyl acetate in cyclohexane. The appropriate fractions were combined, evaporated in vacuo, the residue transferred in dichloromethane (approx. 5 mL) and this solution evaporated in vacuo to give tert-butyl 2-benzyl-6-(ethylcarbamoyl)isonicotinate (212.7 mg, 0.63 mmol, 78% yield) as a viscous dark yellow oil.

LCMS (2 min High pH): Rt=1.35 min, [MH]+=341.3.

Intermediate 158: 2-Benzyl-6-(ethylcarbamoyl)isonicotinic acid

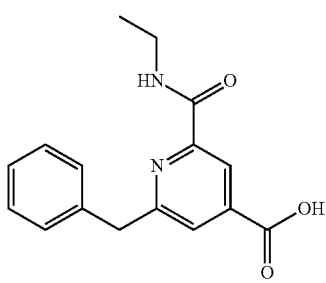 [SMILES: CCNC(=O)c1cc(C(=O)O)cc(Cc2ccccc2)n1]

To a stirring solution of tert-butyl 2-benzyl-6-(ethylcarbamoyl)isonicotinate (212 mg, 0.62 mmol) in dichloromethane (6 mL) was added trifluoroacetic acid (1.5 mL, 19.47 mmol) dropwise. The resulting solution was stirred at rt under nitrogen for 17.5 h, after which the volatiles were evaporated in vacuo, azeotroping with acetonitrile (2×5 mL) and diethyl ether (5 mL) to give 2-benzyl-6-(ethylcarbamoyl)isonicotinic acid (170.1 mg, 0.60 mmol, 96% yield) as a yellow solid.

LCMS (2 min High pH): Rt=0.68 min, [MH]+=285.3.

Intermediate 159: tert-Butyl 2-((1H-indol-4-yl)methyl)-6-(ethylcarbamoyl)isonicotinate

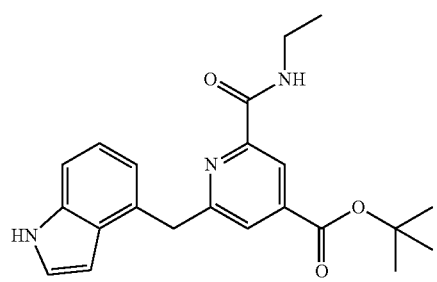 [SMILES: CCNC(=O)c1cc(C(=O)OC(C)(C)C)cc(Cc2cccc3[nH]ccc23)n1]

A suspension of tert-butyl 2-(chloromethyl)-6-(ethylcarbamoyl)isonicotinate (345 mg, 1.16 mmol), (1H-indol-4-yl) boronic acid (273.7 mg, 1.70 mmol, commercially available from, for example, Fluorochem), [1,1'-bis(diphenylphosphino)ferrocene]dichloropalladium(II) (166.2 mg, 0.23 mmol) and potassium carbonate (475.1 mg, 3.44 mmol) in 1,4-dioxane (8 mL) and water (4 mL) was stirred at rt under nitrogen for 3.5 h. To the reaction mixture was added ethyl acetate (10 mL) and water (10 mL) and the layers separated. The aqueous phase was extracted with further ethyl acetate (2×10 mL) and organic layers combined and filtered through a 10 g Celite cartridge. The cartridge was washed with ethyl acetate (2×10 mL) and the filtrate filtered through a cartridge fitted with a hydrophobic frit. This filtrate was evaporated in vacuo, redissolved in dichloromethane (approx. 3 mL) and directly applied to the top of a 25 g SNAP silica cartridge and purified by flash column chromatography. The column was eluted with a gradient of 0%-30% ethyl acetate in cyclohexane. The appropriate fraction was evaporated in vacuo to give tert-butyl 2-((1H-indol-4-yl)methyl)-6-(ethylcarbamoyl)isonicotinate (256.5 mg, 0.68 mmol, 59% yield) as a fluffy cream solid.

LCMS (2 min High pH): Rt=1.26 min, [MH]+=380.2.

Intermediate 160: 2-((1H-Indol-4-yl)methyl)-6-(ethylcarbamoyl)isonicotinic acid

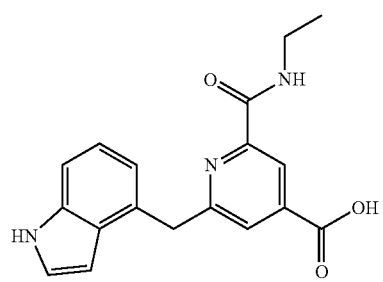 [SMILES: CCNC(=O)c1cc(C(=O)O)cc(Cc2cccc3[nH]ccc23)n1]

To a solution of tert-butyl 2-((1H-indol-4-yl)methyl)-6-(ethylcarbamoyl)isonicotinate (114.7 mg, 0.30 mmol) in methanol (1.5 mL) and THF (1.5 mL) was added sodium hydroxide (94.3 mg, 2.36 mmol). The resulting colourless solution was stirred at rt for 100 min, after which the volatiles were evaporated under a stream of nitrogen. The gummy residue was redissolved in water (1 mL) to give a pale pink solution and again the volatiles were evaporated under a stream of nitrogen to give a yellow solid. The residue was redissolved in water (5 mL), giving a peach coloured clear solution whose pH was ascertained to be 14, and to this solution was added 2M hydrochloric acid (2 mL) to afford a yellow precipitate (the supernatant pH was ascertained to be 1). The precipitate was filtered and the filtered solid was washed with further 2M hydrochloric acid (4 mL) before ether (ca. 10 mL) was used in an attempt to wash the solid, but which resulted in the solid dissolving in the ether. The ether phase was evaporated under a stream of nitrogen and the residue dried in vacuo to give the desired product as an orange solid, 2-((1H-indol-4-yl)methyl)-6-(ethylcarbamoyl)isonicotinic acid (91.7 mg, 0.28 mmol, 94% yield).

LCMS (2 min High pH): Rt=0.65 min, [MH]+=324.4.

Intermediate 161: tert-Butyl 2-((1H-pyrrolo[2,3-c]pyridin-4-yl)methyl)-6-(methylcarbamoyl)isonicotinate

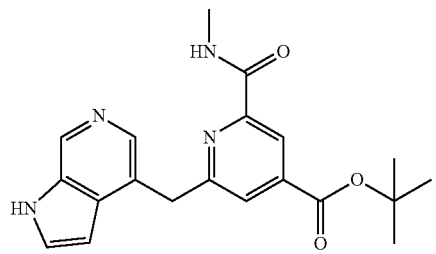 [SMILES: CNC(=O)c1cc(C(=O)OC(C)(C)C)cc(Cc2cncc3[nH]ccc23)n1]

tert-Butyl 2-(chloromethyl)-6-(methylcarbamoyl)isonicotinate (30 mg, 0.105 mmol) was combined with 4-(4,4,5,5-tetramethyl-1,3,2-dioxaborolan-2-yl)-1H-pyrrolo[2,3-c]pyridine (50 mg, 0.21 mmol), potassium carbonate (50 mg, 0.36 mmol) and PdCl$_2$(dppf) (15.42 mg, 0.02 mmol) in 1,4-dioxane (1 mL) and water (0.5 mL) in a 2 mL microwave vial. This was heated at 110° C. for 40 min. The solution was filtered through celite, eluent EtOAc (10 mL), then washed with water. The aqueous phase was extracted 3 times with EtOAc. Then the combined organic phase was dried and concentrated in vacuo. This was purified by chromatography on SiO$_2$ (Biotage SNAP 10 g cartridge, eluting with 0 to 50% ethyl acetate in cyclohexane, then 30 to 100% (25% EtOH/EtOAc) in cyclohexane. The desired fractions were concentrated in vacuo to give tert-butyl 2-((1H-pyrrolo[2,3-c]pyridin-4-yl)methyl)-6-(methylcarbamoyl)isonicotinate (40 mg, 0.10 mmol, 93% yield) as yellow oil.

LCMS (2 min High pH): Rt=0.63 min, [MH]+=367.3.

Intermediate 162: 2-((1H-Pyrrolo[2,3-c]pyridin-4-yl)methyl)-6-(methylcarbamoyl)isonicotinic acid

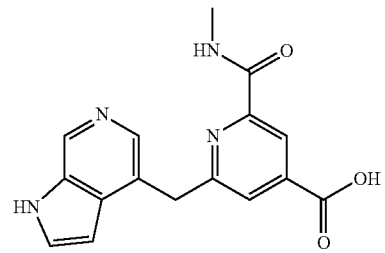 [SMILES: CNC(=O)c1cc(C(=O)O)cc(Cc2cncc3[nH]ccc23)n1]

To a solution of tert-butyl 2-((1H-pyrrolo[2,3-c]pyridin-4-yl)methyl)-6-(methylcarbamoyl)isonicotinate (40 mg, 0.11 mmol) in DCM (0.5 mL) was added 2,2,2-trifluoroacetic acid (0.3 mL, 3.89 mmol) and reaction mixture was stirred overnight. The solvent was removed in vacuo then MeOH (5 mL) and DCM (5 mL) were added and the solvent was removed in vacuo then ether (10 mL) was added and the solvent was removed in vacuo to give 2-((1H-pyrrolo[2,3-c]pyridin-4-yl)methyl)-6-(methylcarbamoyl)isonicotinic acid (67 mg, 0.11 mmol, 99% yield, 50% purity)

LCMS (2 min High pH): Rt=0.41 min, [MH]+=311.2.

Intermediate 163: Benzyl 4-((4-(tert-butoxycarbonyl)-6-(methylcarbamoyl)pyridin-2-yl)methyl)indoline-1-carboxylate

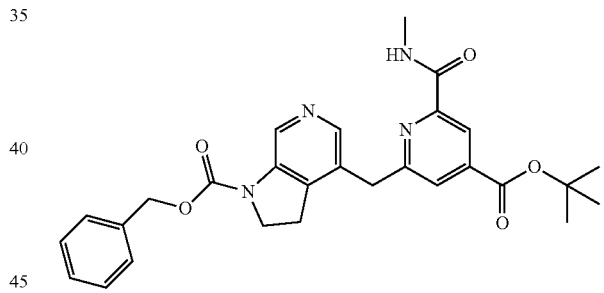

tert-Butyl 2-(chloromethyl)-6-(methylcarbamoyl)isonicotinate (110 mg, 0.386 mmol) was combined with benzyl 4-(4,4,5,5-tetramethyl-1,3,2-dioxaborolan-2-yl)indoline-1-carboxylate (285.5 mg, 0.602 mmol), potassium carbonate (183 mg, 1.321 mmol) and PdCl$_2$(dppf) (56.5 mg, 0.077 mmol) in 1,4-dioxane (1 mL) and water (0.5 mL) in a 2 mL microwave vial. This was heated at 120° C. for 40 min. The solution was then filtered through Celite® (eluent EtOAc), dried and then concentrated. This was purified by chromatography on SiO$_2$ (Biotage® SNAP 10 g, eluting with 0-30% ethyl acetate/cyclohexane). The desired fractions were concentrated to give benzyl 4-((4-(tert-butoxycarbonyl)-6-(methylcarbamoyl)pyridin-2-yl)methyl)indoline-1-carboxylate (138.7 mg, 0.249 mmol, 64% yield) as a colourless oil.

LCMS (2 min Formic): Rt=1.44 min, [MH]+502.2.

$^1$H NMR (400 MHz, MeOH-d$_4$) δ ppm 8.33 (d, J=1.5 Hz, 1H) 7.55-7.77 (m, 2H) 7.25-7.45 (m, 5H) 7.11 (t, J=7.2 Hz, 1H) 6.84 (d, J=7.6 Hz, 1H) 5.21 (br. s., 2H) 4.18 (s, 2H) 3.97 (t, J=8.7 Hz, 2H) 2.92-3.05 (m, 5H) 1.56 (s, 9H) exchangeable protons not observed Intermediate 164: 2-((1-((Benzyloxy)carbonyl)indolin-4-yl)methyl)-6-(methylcarbamoyl)isonicotinic acid

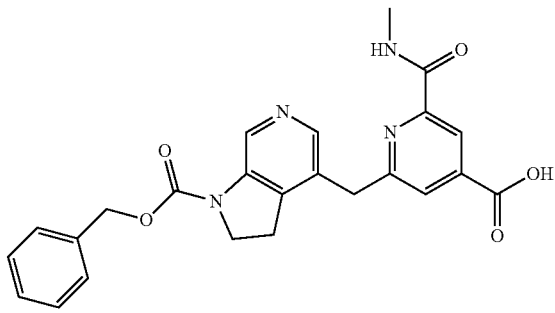 [SMILES: CNC(=O)c1cc(C(=O)O)cc(Cc2cncc3c2CCN3C(=O)OCc2ccccc2)n1]

To a solution of benzyl 4-((4-(tert-butoxycarbonyl)-6-(methylcarbamoyl)pyridin-2-yl)methyl)indoline-1-carboxylate (138.7 mg, 0.221 mmol) in DCM (4 mL) was added 2,2,2-trifluoroacetic acid (0.7 mL, 9.09 mmol) and the reaction mixture was stirred for 4 h. Further 2,2,2-trifluoroacetic acid (1 mL, 12.98 mmol) was added and the resultant mixture was stirred overnight. The reaction mixture was concentrated to give a brown solid. EtOAc (10 mL) was added to the brown solid, then the resulting mixture was base washed 5 times with sodium bicarbonate solution, then the aqueous phase was neutralised with a solution of 2M HCl (10 mL), then it was extracted with EtOAc. The combined organic phases were dried (a solid appeared so the solution was filtered) and then concentrated in vacuo to give a brown oil—2-((1-((benzyloxy)carbonyl)indolin-4-yl)methyl)-6-(methylcarbamoyl)isonicotinic acid (109 mg, 0.196 mmol, 88% yield).

LCMS (2 min Formic): Rt=1.18 min, [MH]+446.2.

$^1$H NMR (400 MHz, MeOH-$d_4$) δ ppm 8.40 (d, J=1.0 Hz, 1H) 7.78 (d, J=1.2 Hz, 1H) 7.68 (br. s., 1H) 7.25-7.44 (m, 5H) 7.12 (br. t, J=7.0, 7.0 Hz, 1H) 6.86 (d, J=7.8 Hz, 1H) 5.22 (br. s., 2H) 4.20 (s, 2H) 3.99 (t, J=8.7 Hz, 2H) 2.93-3.06 (m, 5H), exchangeable protons not observed Intermediate 165: Benzyl 4-(1-(4-(tert-butoxycarbonyl)-6-(methylcarbamoyl)pyridin-2-yl)vinyl)indoline-1-carboxylate

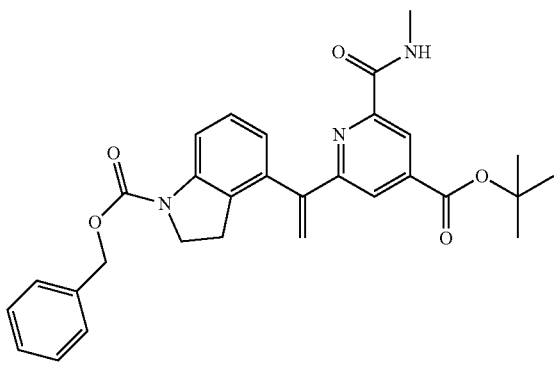 [SMILES: C=C(c1cc(C(=O)OC(C)(C)C)cc(C(=O)NC)n1)c1cccc2c1CCN2C(=O)OCc1ccccc1]

A mixture of benzyl 4-(4,4,5,5-tetramethyl-1,3,2-dioxaborolan-2-yl)indoline-1-carboxylate (453.8 mg, 1.197 mmol), tert-butyl 2-(1-bromovinyl)-6-(methylcarbamoyl) isonicotinate (393 mg, 0.979 mmol), [1,3-bis(2,6-diisopropylphenyl)imidazol-2-ylidene](3-chloropyridyl)palladium (II) dichloride (PEPPSI-iPr) (69.0 mg, 0.10 mmol) and tripotassium phosphate (640.9 mg, 3.02 mmol) in 1,4-dioxane (6 mL) and water (3 mL) was degassed with nitrogen for 5 min, after which it was stirred at rt with exclusion of light (flask wrapped in foil) under nitrogen for 23 h. After allowing to cool to rt and leaving to stand for 46 h, the mixture was filtered through a 2.5 g Celite cartridge, which was washed subsequently with ethyl acetate (3×10 mL). The combined filtrate was washed with a mixture of water (20 mL) and saturated brine solution (10 mL) and the aqueous phase back-extracted with ethyl acetate (15 mL). The combined organic phases were washed with a further mixture of water (10 mL) and saturated brine solution (50 mL) and the organic phase was dried by filtering through a cartridge fitted with a hydrophobic frit. The solvent was evaporated in vacuo and the residue was redissolved in dichloromethane (ca. 6 mL) and the solution applied to a 25 g SNAP Ultra Silica cartridge. The sample was purified by Biotage SP4 flash column chromatography eluting with a gradient of 0-30% ethyl acetate in cyclohexane. The required fractions were combined and the solvent evaporated in vacuo. The residue was dried in vacuo to give benzyl 4-(1-(4-(tert-butoxycarbonyl)-6-(methylcarbamoyl)pyridin-2-yl)vinyl)indoline-1-carboxylate (230.0 mg, 0.45 mmol, 46% yield) as a pale yellow crunchy foam.

LCMS (2 mins formic) Peak $R_t$=1.49 min, m/z=514 for [MH]$^+$

Intermediate 166: (±)-tert-Butyl 2-(1-(indolin-4-yl)ethyl)-6-(methylcarbamoyl)isonicotinate

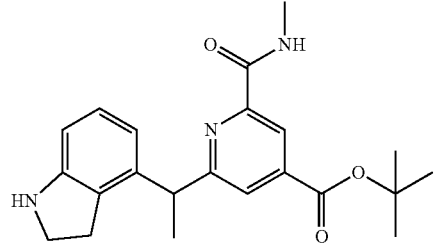 [SMILES: CNC(=O)c1cc(C(=O)OC(C)(C)C)cc(C(C)c2cccc3c2CCN3)n1]

A solution of (±)-benzyl 4-(1-(4-(tert-butoxycarbonyl)-6-(methylcarbamoyl)pyridin-2-yl)vinyl)indoline-1-carboxylate (227.5 mg, 0.44 mmol) in ethanol (10 mL) was hydrogenated over a 10% Pd/C catalyst cartridge using a Thales 'H-Cube' flow apparatus in full hydrogen mode at 20° C. The mixture was passed through the H-Cube a second time under the same conditions and the solvent evaporated in vacuo to give a pale yellow crunchy foam. This product was redissolved in dichloromethane (ca. 3 mL) and was applied to the top of a 10 g SNAP Ultra silica cartridge which had been pre-wetted with cyclohexane. The cartridge was eluted using Biotage SP4 flash chromatography with a gradient of 0-100% ethyl acetate in cyclohexane. The required fractions were combined and the solvent evaporated in vacuo to give a residue which was redissolved in dichloromethane (~4 mL) and transferred to a tarred vial, the solvent evaporated under a stream of nitrogen and the residue dried in vacuo to give (±)-tert-butyl 2-(1-(indolin-4-yl)ethyl)-6-(methylcarbamoyl)isonicotinate (145.8 mg, 0.38 mmol, 86% yield) as a pale yellow crystalline solid.

LCMS (2 mins formic) Peak $R_t$=0.81 min, m/z=382 for [MH]$^+$

Intermediate 167: (±)-2-(1-(1-Formylindolin-4-yl)ethyl)-6-(methylcarbamoyl)isonicotinic acid

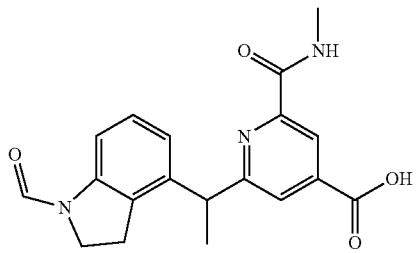 [SMILES: CNC(=O)c1cc(C(=O)O)cc(C(C)c2cccc3c2CCN3C=O)n1]

A solution of (±)-tert-butyl 2-(1-(indolin-4-yl)ethyl)-6-(methylcarbamoyl)isonicotinate (145.8 mg, 0.38 mmol) in water (2 mL) and tetrahydrofuran (2 mL) had sodium hydroxide (196.3 mg, 4.91 mmol) added and was stirred at rt for 105 min. Methanol (2 mL) was added and stirring at rt was continued for a further 90 min. The mixture was concentrated under a stream of nitrogen and the residue partitioned between 2M aqueous hydrochloric acid (5 mL) and ethyl acetate (5 mL). The phases were separated (aqueous phase pH checked and found to be 1) and the aqueous phase was extracted with further ethyl acetate (3×5 mL). The aqueous phase was evaporated under a stream of nitrogen, the residue was re-dissolved in methanol (4 mL) and water (2 mL), and the solution applied to an 'Isolute' aminopropyl ion-exchange cartridge which had been pre-wetted with methanol. The cartridge was eluted with methanol (3×20 mL) followed by water (2×20 mL) and then 2M hydrochloric acid (2×20 mL). The neutral fractions had the solvent evaporated under a stream of nitrogen before the residue was suspended in a 3:1 mixture of methanol/water (3 mL), the supernatant removed and purified by MDAP (3×1 mL injection; formic). The required fractions were combined and the solvent evaporated in vacuo. The residue was redissolved in methanol (~6 mL) and transferred to a tarred vial, the solvent evaporated under a stream of nitrogen and the residue dried in vacuo to give (±)-2-(1-(1-formylindolin-4-yl)ethyl)-6-(methylcarbamoyl)isonicotinic acid (110.8 mg, 0.31 mmol, 82% yield) as a colourless sticky solid.

LCMS (2 mins formic) Peak $R_t$=0.84 min, m/z=354 for [MH]$^+$

Intermediate 168: tert-Butyl 2-(1-(3-methoxyphenyl)ethyl)-6-(methylcarbamoyl)isonicotinate

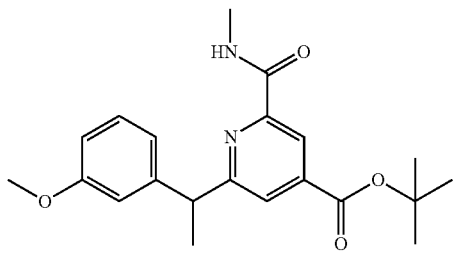 [SMILES: CNC(=O)c1cc(C(=O)OC(C)(C)C)cc(C(C)c2cccc(OC)c2)n1]

tert-Butyl 2-(3-methoxybenzyl)-6-(methylcarbamoyl)isonicotinate (110 mg, 0.31 mmol) and palladium(II) acetate (62.4 mg, 0.28 mmol) were dissolved in THF (1 mL) and cooled to −78° C. in a cardice/acetone bath under N$_2$. LiHMDS (1M in THF, 0.95 mL, 0.950 mmol) was added dropwise and the reaction mixture left to stir for 45 min. MeI (0.03 mL, 0.480 mmol) was added and the resultant mixture was stirred for 2 h. Further MeI (0.01 mL, 0.160 mmol) was added and the resultant mixture was stirred for 1 h. MeI (0.02 mL, 0.320 mmol) was added to the reaction mixture and the resultant mixture was stirred for 1.5 h. Then the solution was allowed to warm up and water (2 mL) was added to give a first batch of reaction mixture.

In a separate flask, tert-butyl 2-(3-methoxybenzyl)-6-(methylcarbamoyl)isonicotinate (39 mg, 0.11 mmol) was dissolved in THF (0.35 mL) and cooled to −78° C. in a cardice/acetone bath under N$_2$. LiHMDS (1M in THF, 0.33 mL, 0.330 mmol) was added dropwise and the reaction mixture left to stir for 45 min (colour change: colourless to yellow to dark green). MeI (0.06 mL, 0.320 mmol, from a stock solution of 0.03 mL MeI in 0.06 mL THF) was added (colour change: dark green to yellow solution) and the resultant mixture was stirred for 1 h to give a second batch of reaction mixture.

The reaction mixtures were combined and extracted with water (10 mL) and EtOAc (3×10 mL). The combined organic phases were dried over a hydrophobic filter then the solvent was removed in vacuo. The crude product was purified by chromatography on SiO$_2$ (Biotage SNAP column (10 g), eluent 0 to 40% ethyl acetate/cyclohexane). The combined desired fractions were concentrated in vacuo to give tert-butyl 2-(1-(3-methoxyphenyl)ethyl)-6-(methylcarbamoyl)isonicotinate (57.3 mg, 0.15 mmol, 32% yield) as an orange oil.

LCMS (2 min Formic): Rt=1.31 min, [MH]$^+$=371.3.

Intermediate 169: 2-(1-(3-Methoxyphenyl)ethyl)-6-(methylcarbamoyl)isonicotinic acid

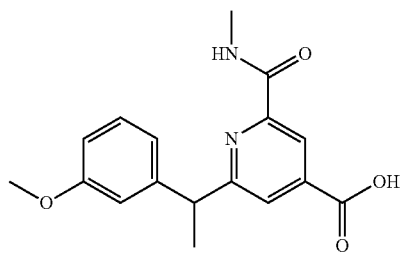

To a solution of tert-butyl 2-(1-(3-methoxyphenyl)ethyl)-6-(methylcarbamoyl)isonicotinate (57.3 mg, 0.16 mmol) in DCM (0.5 mL) was added 2,2,2-trifluoroacetic acid (0.5 mL, 6.49 mmol) and the reaction mixture was stirred over the weekend. A further portion of 2,2,2-trifluoroacetic acid (0.5 mL, 6.49 mmol) was added and the reaction mixture was stirred for 2 h. The solvent was removed in vacuo to give 2-(1-(3-methoxyphenyl)ethyl)-6-(methylcarbamoyl)isonicotinic acid (81 mg, 0.14 mmol, 92%, 55% purity) as a black oil.

LCMS (2 min Formic): Rt=1.00 min, [MH]$^+$=315.2.

Intermediate 170: tert-Butyl 2-(methylcarbamoyl)-6-(1 phenylpropyl)isonicotinate

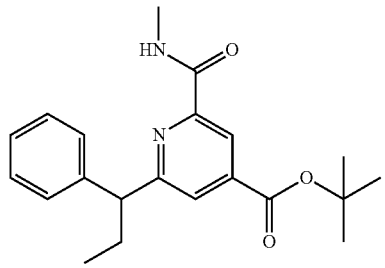 [SMILES: CCC(c1ccccc1)c1cc(C(=O)OC(C)(C)C)cc(C(=O)NC)n1]

tert-Butyl 2-benzyl-6-(methylcarbamoyl)isonicotinate (100 mg, 0.29 mmol) was dissolved in THF (0.5 mL) and cooled to −78° C. in a cardice/acetone bath under $N_2$. LiHMDS (0.7 mL, 0.700 mmol, 1M in THF) was added dropwise and the reaction mixture left to stir for 35 min. Iodoethane (0.04 mL, 0.50 mmol) was added and the resultant mixture was stirred for 1 h then allowed to warm up. The reaction mixture was stirred at rt for 1.5 h. Water (0.1 mL) was added. The reaction was washed with water (10 mL) and extracted three times with EtOAc (3×15 mL) then the combined organic phases were dried over a hydrophobic frit then concentrated in vacuo. This was purified by flash chromatography on a silica column (10 g), eluting with 0 to 30% ethyl acetate in cyclohexane. The combined desired fractions were concentrated in vacuo to afford tert-butyl 2-(methylcarbamoyl)-6-(1-phenylpropyl)isonicotinate (75.3 mg, 0.20 mmol, 69% yield) as a colourless oil.

LCMS (2 min Formic): Rt=1.39 min, $[MH]^+$=355.3.

Intermediate 171: 2-(methylcarbamoyl)-6-(1-phenylpropyl)isonicotinic acid

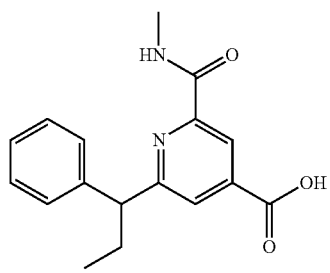 [SMILES: CCC(c1ccccc1)c1cc(C(=O)O)cc(C(=O)NC)n1]

tert-Butyl 2-(methylcarbamoyl)-6-(1-phenylpropyl)isonicotinate (75 mg, 0.212 mmol) was dissolved in THF (2 mL) and hydrochloric acid (2M, 1.1 mL, 2.20 mmol) was added. The mixture was stirred under reflux overnight. A further 1 mL of HCl (5M) was added and the resultant mixture was stirred for 22 h under reflux. The solvent was evaporated under vacuum to give a white solid, 2-(methylcarbamoyl)-6-(1-phenylpropyl)isonicotinic acid (80 mg, 0.20 mmol, 95% yield)

LCMS (2 min Formic): Rt=1.08 min, $[MH]^+$=299.2.

Intermediate 172: tert-Butyl 2-(methylcarbamoyl)-6-(1-phenylvinyl)isonicotinate

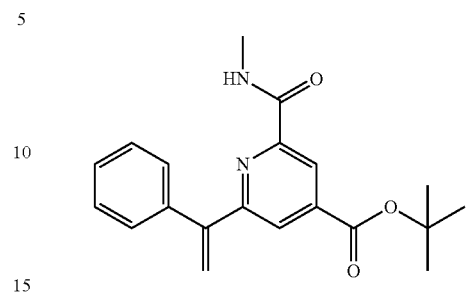

(1-Phenylvinyl)boronic acid (2.62 g, 17.73 mmol, commercially available from, for example, Sigma-Aldrich), tert-butyl 2-chloro-6-(methylcarbamoyl)isonicotinate (4 g, 14.78 mmol, commercially available from, for example, Anichem), tripotassium phosphate (9.41 g, 44.3 mmol) and PEPPSI iPr (1.004 g, 1.478 mmol) were dissolved in 1,4-dioxane (24 mL) and water (12 mL) at rt and degassed under nitrogen. The resulting solution was stirred at 70° C. for 2 h. The reaction was cooled to rt, diluted with water (20 mL), extracting with DCM (3×25 mL). The combined organics were passed through a hydrophobic frit and concentrated in vacuo to give a yellow foam. This was purified by flash chromatography on $SiO_2$ (Biotage SNAP 100 g cartridge, eluting with 0-60% ethyl acetate/cyclohexane) to give tert-butyl 2-(methylcarbamoyl)-6-(1-phenylvinyl)isonicotinate (4.06 g, 11.40 mmol, 77% yield, 95% purity) as a pale yellow foam.

LCMS (2 min Formic): Rt=1.35 min, [MH]+=339.2.

Intermediate 173: tert-Butyl 2-(2-hydroxy-1-phenylethyl)-6-(methylcarbamoyl)isonicotinate

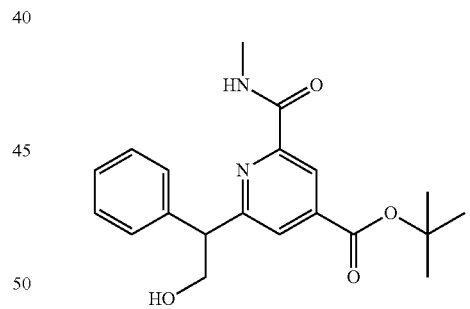

(2,3-Dimethylbutan-2-yl)borane (0.66 M in THF, 30.0 mL, 19.80 mmol, preparation of which is described in the literature: For example H. C. Brown and E. Negishi, *J. Am. Chem. Soc.*, 94, 3567 (1972) was added to tert-butyl 2-(methylcarbamoyl)-6-(1-phenylvinyl)isonicotinate (3.94 g, 9.90 mmol) under nitrogen at 0° C. in a round bottomed flask. The reaction mixture was stirred for 1.5 h at rt then water (30 mL) was added. Hydrogen peroxide (35% w/w in water, 24.26 mL, 277 mmol) and sodium hydroxide (2M, 24.74 mL, 49.5 mmol) were added at 0° C. The reaction mixture was stirred at 0° C. for 25 min then allowed to warm up. The reaction mixture was then stirred for 2 h. Citric acid (10%, 30 mL) and EtOAc (30 mL) were added. The organic layer was separated and the aqueous layer was extracted with further portions of EtOAc (3×50 mL). The combined organic phases were dried over a hydrophobic frit then concentrated in vacuo. This was purified by chromatography on SiO$_2$ (Biotage SNAP 50 g, eluent 0 to 100% EtOAc/cyclohexane). The combined desired fractions were concentrated in vacuo to give tert-butyl 2-(2-hydroxy-1-phenylethyl)-6-(methylcarbamoyl)isonicotinate (1.15 g, 3.07 mmol, 31% yield, 95% purity).

LCMS (2 min Formic): Rt=1.08 min, [MH]+=357.3.

Intermediate 174: tert-Butyl 2-(2-methoxy-1-phenylethyl)-6-(methylcarbamoyl)isonicotinate

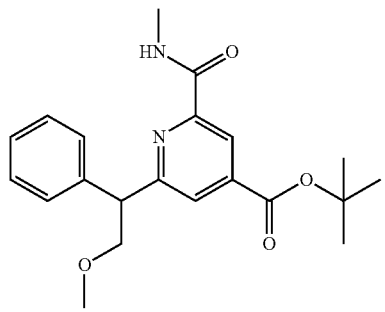 [SMILES: CNC(=O)c1cc(C(=O)OC(C)(C)C)cc(C(COC)c2ccccc2)n1]

tert-Butyl 2-(2-hydroxy-1-phenylethyl)-6-(methylcarbamoyl)isonicotinate (80 mg, 0.22 mmol) and N$^1$,N$^1$,N$^8$,N$^8$-tetramethylnaphthalene-1,8-diamine (144 mg, 0.67 mmol) were dissolved in DCM (1 mL). Trimethyloxonium tetrafluoroborate (100 mg, 0.67 mmol) was added slowly and the reaction mixture was stirred under nitrogen for 30 h. N$^1$,N$^1$,N$^8$,N$^8$-Tetramethylnaphthalene-1,8-diamine (144 mg, 0.67 mmol) and trimethyloxonium tetrafluoroborate (100 mg, 0.67 mmol) were added and the reaction mixture was stirred under nitrogen for 20 h. Sodium bicarbonate solution (10 mL) was added together with DCM (10 mL). The layers were separated and the aqueous phase was extracted with further portions of DCM (2×10 mL). The combined organic phase was dried over a hydrophobic frit then concentrated in vacuo. This was purified by chromatography on SiO$_2$ (Biotage SNAP 10 g, eluent 0 to 30% EtOAc/cyclohexane). The combined desired fractions were concentrated in vacuo to give the crude title product. A solution of 2M HCl (10 mL) was added together with DCM (10 mL). The layers were separated and the aqueous phase was extracted with further portions of DCM (2×10 mL). The combined organic phase was dried over a hydrophobic frit then concentrated in vacuo to give tert-butyl 2-(2-methoxy-1-phenylethyl)-6-(methylcarbamoyl)isonicotinate (42 mg, 0.10 mmol, 45% yield, 89% purity) as a pink oil.

LCMS (2 min Formic): Rt=1.24 min, [MH]+=371.4.

Intermediate 175: 2-(2-Methoxy-1-phenylethyl)-6-(methylcarbamoyl)isonicotinic acid

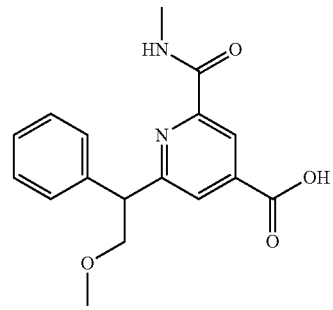 [SMILES: CNC(=O)c1cc(C(=O)O)cc(C(COC)c2ccccc2)n1]

To a solution of tert-butyl 2-(2-methoxy-1-phenylethyl)-6-(methylcarbamoyl)isonicotinate (38 mg, 0.09 mmol, 89% wt.) in DCM (1 mL) was added TFA (0.5 mL, 6.49 mmol) and the reaction mixture was stirred for 3 h. The reaction mixture was concentrated in vacuo then DCM (5 mL) was added and the reaction mixture was concentrated in vacuo. Ether (5 mL) was added and the reaction mixture was concentrated in vacuo (4 times) to give 2-(2-methoxy-1-phenylethyl)-6-(methylcarbamoyl)isonicotinic acid (73 mg, 0.08 mmol, 89% yield, 35% purity) as a yellow oil.

LCMS (2 min Formic): Rt=0.91 min, [MH]+=315.2.

Intermediate 176: tert-Butyl 2-(methylcarbamoyl)-6-(1-(2-oxoindolin-4-yl)vinyl)isonicotinate

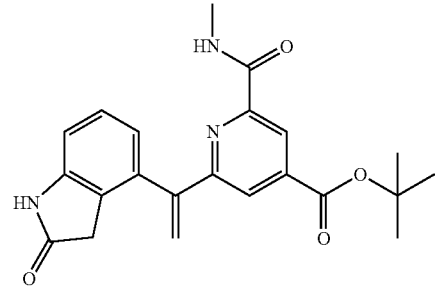 [SMILES: C=C(c1cc(C(=O)OC(C)(C)C)cc(C(=O)NC)n1)c1cccc2c1CC(=O)N2]

A solution of tert-butyl 2-(1-bromovinyl)-6-(methylcarbamoyl)isonicotinate (350 mg, 0.72 mmol), 4-(4,4,5,5-tetramethyl-1,3,2-dioxaborolan-2-yl)indolin-2-one (276.9 mg, 1.07 mmol), [1,3-bis(2,6-diisopropylphenyl)imidazol-2-ylidene](3-chloropyridyl)palladium(II) dichloride (PEPPSI-iPr) (71.0 mg, 0.10 mmol) and tripotassium phosphate (566.8 mg, 2.67 mmol) in 1,4-dioxane (6 mL) and water (3 mL) was stirred under nitrogen at rt in the dark for 19 h. The reaction mixture was filtered through a 2.5 g celite cartridge and the cartridge washed with ethyl acetate (approx. 10 mL). To the filtrate was added water (5 mL) and brine (5 mL) and the layers separated. The aqueous layer was extracted with further ethyl acetate (2×10 mL) and the organic phases were combined and filtered through a cartridge fitted with a hydrophobic frit. The filtrate was evaporated in vacuo to give a sticky brown solid (556.7 mg). This was redissolved in DMSO (6 mL) and directly purified by MDAP (high pH). The required fractions were combined and evaporated in vacuo to give tert-butyl 2-(methylcarbamoyl)-6-(1-(2-oxoindolin-4-yl)vinyl)isonicotinate (157.7 mg, 0.40 mmol, 56% yield) as a light yellow solid.

LCMS (2 min High pH): Rt=1.05 min, [MH]+=394.4

Intermediate 177: (+/−)-tert-Butyl 2-(methylcarbamoyl)-6-(1-(2-oxoindolin-4-yl)ethyl)isonicotinate

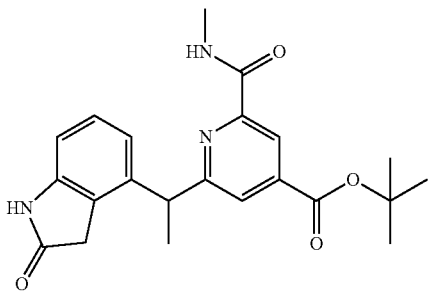 [SMILES: CNC(=O)c1cc(C(=O)OC(C)(C)C)cc(C(C)c2cccc3c2CC(=O)N3)n1]

A solution of tert-butyl 2-(methylcarbamoyl)-6-(1-(2-oxoindolin-4-yl)vinyl)isonicotinate (260 mg, 0.66 mmol) in ethyl acetate (20 mL) and ethanol (20 mL) was hydrogenated using a Thales H-Cube apparatus at 20° C. in full $H_2$ mode over a 10% palladium on carbon catalyst cartridge for 1 pass. The solution was evaporated in vacuo to give (±)-tert-butyl 2-(methylcarbamoyl)-6-(1-(2-oxoindolin-4-yl)ethyl)isonicotinate (257.1 mg, 0.65 mmol, 98% yield) as a yellow gum.

LCMS (2 min High pH): Rt=1.05 min, [MH]+=396.4.

Intermediate 178: (+/−)-2-(Methylcarbamoyl)-6-(1-(2-oxoindolin-4-yl)ethyl)isonicotinic acid

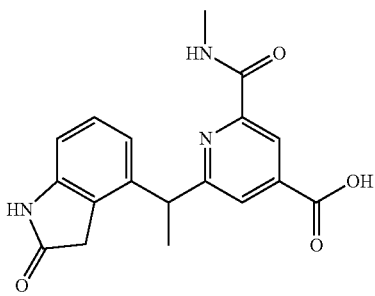 [SMILES: CNC(=O)c1cc(C(=O)O)cc(C(C)c2cccc3c2CC(=O)N3)n1]

(±)-tert-Butyl 2-(methylcarbamoyl)-6-(1-(2-oxoindolin-4-yl)ethyl)isonicotinate (257 mg, 0.65 mmol) was combined with a second crude batch of (±)-tert-butyl 2-(methylcarbamoyl)-6-(1-(2-oxoindolin-4-yl)ethyl)isonicotinate (approx. 10 mg) in DCM (8 mL). Trifluoroacetic acid (1.0 mL, 12.98 mmol) was added dropwise. The resulting orange solution was stirred at rt under nitrogen for a total of 2 days, during which further DCM (4.0 mL, after 7.5 h) and trifluoroacetic acid (0.5 mL, 6.49 mmol, after 23.75 h) were added. The volatiles were evaporated in vacuo to give a dark red gum, which was azeotroped with acetonitrile (3×5 mL) and the volatiles evaporated in vacuo to give a sticky pink solid. To this was added water (5 mL) and DCM (5 mL) and the layers separated using a cartridge fitted with a hydrophobic frit. The aqueous layer was washed with further DCM (2×5 mL) and evaporated in vacuo to give a brown gum. This was azeotroped with diethyl ether (5 mL) and the volatiles evaporated in vacuo to give (±)-2-(methylcarbamoyl)-6-(1-(2-oxoindolin-4-yl)ethyl)isonicotinic acid (158.9 mg, 0.40 mmol, 61% yield) as a brown solid.

LCMS (2 min High pH): Rt=0.54 min, [MH]+=340.2.

Intermediate 179: (+/−)-tert-Butyl 2-(hydroxy(phenyl)methyl)-6-(methylcarbamoyl)isonicotinate

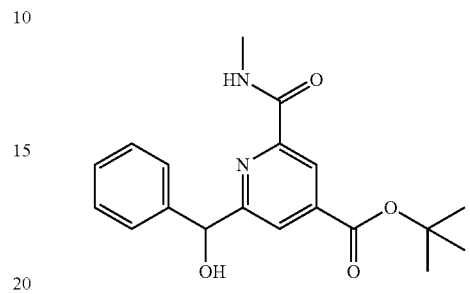

To a solution of tert-butyl 2-formyl-6-(methylcarbamoyl) isonicotinate (118 mg, 0.447 mmol) in THF (1.5 mL) at 0° C., was added dropwise phenylmagnesium bromide (1M in THF, 2 mL, 2 mmol). The reaction mixture was stirred for 2 h. The reaction mixture was poured onto a saturated ammonium chloride aqueous solution and extracted with EtOAc (20 mL×3). The organic layer was dried over $MgSO_4$ and concentrated in vacuo. The crude product was purified by chromatography on $SiO_2$ (Biotage® SNAP 10 g, eluting with 0-60% ethyl acetate/cyclohexane). The desired fractions were concentrated to give tert-butyl 2-(hydroxy(phenyl)methyl)-6-(methylcarbamoyl)isonicotinate (43 mg, 0.107 mmol, 24% yield).

LCMS (2 min Formic): Rt=1.09 min, [MH]+=343.3.

$^1$H NMR (400 MHz, MeOH-$d_4$) δ ppm 8.38 (d, J=1.2 Hz, 1H) 8.05 (d, J=1.2 Hz, 1H) 7.42-7.47 (m, 2H) 7.22-7.36 (m, 3H) 5.95 (s, 1H) 2.99 (s, 3H) 1.60 (s, 9H). Exchangeables not observed.

Intermediate 180: tert-Butyl 2-((3-fluoro-1H-indol-4-yl)methyl)-6-(methylcarbamoyl)isonicotinate

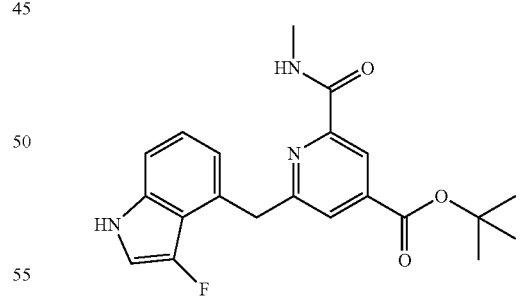

3-Fluoro-4-(4,4,5,5-tetramethyl-1,3,2-dioxaborolan-2-yl)-1H-indole (330 mg, 1.26 mmol), tert-butyl 2-(chloromethyl)-6-(methylcarbamoyl)isonicotinate (300 mg, 1.054 mmol), $PdCl_2(dppf)$ (77 mg, 0.11 mmol) and potassium carbonate (437 mg, 3.16 mmol) were degassed with nitrogen for 10 min. 1,4-Dioxane (4 mL) and water (2 mL) were added and the reaction left to stir at rt for 2 h. Further $PdCl_2(dppf)$ (77 mg, 0.11 mmol) was added again and the reaction left to stir for a further 1 h. The reaction was concentrated in vacuo. The residue was taken up in DCM (15 mL) and washed with water (15 mL) and brine (15 mL). The organic phase was dried over sodium sulphate, filtered through a hydrophobic frit and concentrated in vacuo. The crude product was applied to a SNAP ULTRA silica cartridge (25 g) in the minimum of DCM and purified by flash chromatography, eluting with 0-30% EtOAc in cyclohexane. The appropriate fractions were combined and concentrated in vacuo to afford the desired product, tert-butyl 2-((3-fluoro-1H-indol-4-yl)methyl)-6-(methylcarbamoyl)isonicotinate (134 mg, 0.35 mmol, 33% yield) as a cream solid.

LCMS (2 min High pH): Rt=1.23 min, [MH]+=384.4.

Intermediate 181: 2-((3-Fluoro-1H-indol-4-yl)methyl)-6-(methylcarbamoyl)isonicotinic acid

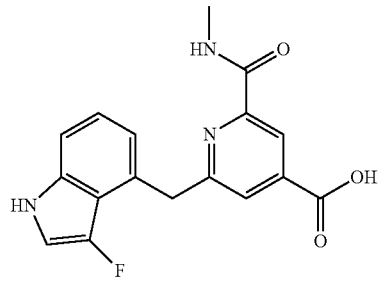 [SMILES: CNC(=O)c1cc(C(=O)O)cc(Cc2cccc3[nH]cc(F)c23)n1]

tert-Butyl 2-((3-fluoro-1H-indol-4-yl)methyl)-6-(methylcarbamoyl)isonicotinate (203 mg, 0.53 mmol) was taken up in methanol (2 mL) and THF (2 mL). NaOH (2.65 mL, 5.29 mmol, 2M) was added and the reaction left to stir at rt for 2 h. The reaction was concentrated in vacuo. The residue was dissolved in water and acidified to pH 2 using HCl. The precipitate was filtered off. to afford 2-((3-fluoro-1H-indol-4-yl)methyl)-6-(methylcarbamoyl)isonicotinic acid (154 mg, 0.47 mmol, 89% yield).

LCMS (2 min High pH): Rt=0.62 min, [MH]+=328.2.

Intermediate 182: tert-Butyl 2-((1-(2-hydroxyethyl)-1H-indol-4-yl)methyl)-6-(methylcarbamoyl)isonicotinate

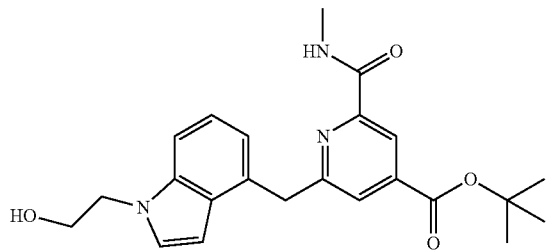 [SMILES: CNC(=O)c1cc(C(=O)OC(C)(C)C)cc(Cc2cccc3c2ccn3CCO)n1]

2-(4-(4,4,5,5-Tetramethyl-1,3,2-dioxaborolan-2-yl)-1H-indol-1-yl)ethanol (732 mg, 2.55 mmol), tert-butyl 2-(chloromethyl)-6-(methylcarbamoyl)isonicotinate (653 mg, 2.29 mmol), PdCl$_2$(dppf) (187 mg, 0.26 mmol) and potassium carbonate (1057 mg, 7.65 mmol) were added to a microwave vial. 1,4-Dioxane (10 mL) and water (5 mL) were added and the reaction vessel sealed and heated in Biotage Initiator microwave to 110° C. for 30 min. After cooling the reaction was filtered through celite and washed with ethyl acetate (15 mL). The filtrate was concentrated in vacuo. The residue was taken up in ethyl acetate (20 mL) and washed with water (20 mL) and brine (20 mL). The organic phase was filtered through celite before being further filtered through a hydrophobic frit and concentrated in vacuo. The sample was dissolved in 1:1 MeCN:DMSO (3 mL) and purified by MDAP (High pH). The solvent was evaporated in vacuo to give the required product, tert-butyl 2-((1-(2-hydroxyethyl)-1H-indol-4-yl)methyl)-6-(methylcarbamoyl)isonicotinate (149 mg, 0.36 mmol, 14% yield) as a brown oil.

LCMS (2 min High pH): Rt=1.13 min, [MH]+=410.4.

Intermediate 183: 2-((1-(2-Hydroxyethyl)-1H-indol-4-yl)methyl)-6-(methylcarbamoyl)isonicotinic acid

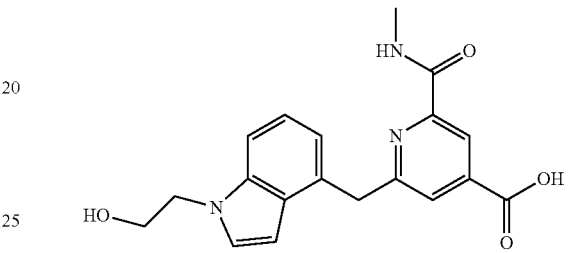

tert-Butyl 2-((1-(2-hydroxyethyl)-1H-indol-4-yl)methyl)-6-(methylcarbamoyl)isonicotinate (149 mg, 0.36 mmol) was taken up in DCM (2 mL). TFA (0.5 mL, 6.49 mmol) was added and the reaction left to stir at rt for 3 h. The reaction was concentrated in vacuo and the product, 2-((1-(2-hydroxyethyl)-1H-indol-4-yl)methyl)-6-(methylcarbamoyl)isonicotinic acid (129 mg, 0.364 mmol, 100% yield) was used directly in the next step.

LCMS (2 min High pH): Rt=0.60 min, [MH]+=354.3.

Intermediate 184: 2-(Methylcarbamoyl)-6-((3-(2,2,2-trifluoroacetyl)-1H-indol-4-yl)methyl)isonicotinic acid

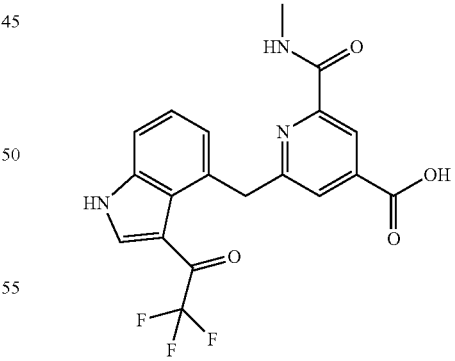

TFA (5 mL, 64.9 mmol) was added to a solution of tert-butyl 2-((1H-indol-4-yl)methyl)-6-(methylcarbamoyl)isonicotinate (1.32 g, 3.61 mmol) in DCM (10 mL) and the solution was allowed to stir overnight, then evaporated in vacuo to give a dark red gum. The crude product was dissolved in methanol (20 mL) and allowed to stand, giving a dense beige solid precipitate, which was dried to give 2-(methylcarbamoyl)-6-((3-(2,2,2-trifluoroacetyl)-1H-indol-4-yl)methyl)isonicotinic acid (550 mg, 1.36 mmol, 38% yield). The compound was carried through to the next step.
LCMS (2 min Formic): Rt=0.97 min, [MH]+=406.2.

Intermediate 185: (+/−)-tert-Butyl 2-(methoxy(phenyl)methyl)-6-(methylcarbamoyl)isonicotinate

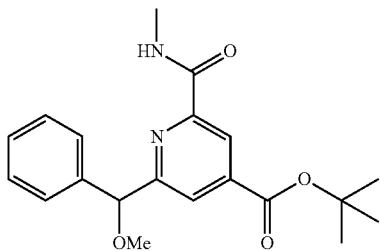 [SMILES: CNC(=O)c1cc(C(=O)OC(C)(C)C)cc(C(OC)c2ccccc2)n1]

Trimethyloxonium tetrafluoroborate (1.426 g, 9.64 mmol) was added to a mixture of tert-butyl 2-(hydroxy(phenyl)methyl)-6-(methylcarbamoyl)isonicotinate (1.1 g, 3.21 mmol) and $N^1,N^1,N^8,N^8$-tetramethylnaphthalene-1,8-diamine (2.066 g, 9.64 mmol) in DCM (10 mL) at rt and the mixture was stirred for 4 h, then diluted with EtOAc (50 mL) and washed with saturated sodium bicarbonate solution (50 mL) and 0.5M HCl (50 mL). The organic layer was dried and evaporated in vacuo and the residue purified by chromatography on a silica column (25 g) eluting with 0-60% EtOAc/cyclohexane. The product-containing fractions were evaporated in vacuo to give (+/−)-tert-butyl 2-(methoxy(phenyl)methyl)-6-(methylcarbamoyl)isonicotinate (440 mg, 1.23 mmol, 38% yield) as a colourless gum.
LCMS (2 min High pH): Rt=1.25 min, [MH]+=357.3.
$^1$H NMR (400 MHz, CDCl$_3$) δ ppm 8.51 (s, 1H) 8.18 (s, 1H) 7.91 (br. s., 1H) 7.40-7.45 (m, 2H) 7.36 (t, J=7.3 Hz, 2H) 7.26-7.32 (m, 1H) 5.42 (s, 1H) 3.46 (s, 3H) 3.05 (d, J=5.1 Hz, 3H) 1.62 (s, 9H)

Intermediate 186: (+/−)-2-(Methoxy(phenyl)methyl)-6-(methylcarbamoyl)isonicotinic acid

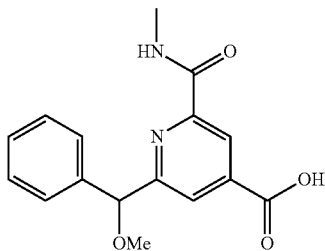

tert-Butyl 2-(methoxy(phenyl)methyl)-6-(methylcarbamoyl)isonicotinate (400 mg, 1.12 mmol) was dissolved in methanol, then NaOH (2 mL, 4.00 mmol, 2M) was added and the mixture was stirred for 3 h at rt. The solvent was evaporated in vacuo and the residue dissolved in water (10 mL) and acidified with 2M HCl to pH4, then extracted with DCM (2×20 mL). The solvent was dried and evaporated in vacuo to give 2-(methoxy(phenyl)methyl)-6-(methylcarbamoyl)isonicotinic acid (325 mg, 1.08 mmol, 96% yield) as a colourless gum.
LCMS (2 min High pH): Rt=0.60 min, [MH]+=301.2.

$^1$H NMR (400 MHz, CDCl$_3$) δ ppm 8.71 (s, 1H) 8.30 (s, 1H) 7.90-7.99 (m, 1H) 7.41-7.47 (m, 2H) 7.37 (t, J=7.5 Hz, 2H) 7.28-7.33 (m, 1H) 5.45 (s, 1H) 3.48 (s, 3H) 3.08 (d, J=4.9 Hz, 3H). One exchangeable proton not observed.

Intermediate 187: tert-Butyl 2-(1-(2-methoxyphenyl)vinyl)-6-(methylcarbamoyl)isonicotinate

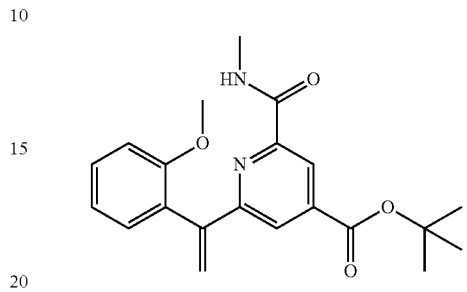

A mixture of tert-butyl 2-(1-bromovinyl)-6-(methylcarbamoyl)isonicotinate (207.9 mg, 0.24 mmol), 2-(2-methoxyphenyl)-4,4,5,5-tetramethyl-1,3,2-dioxaborolane (97.4 mg, 0.42 mmol), [1,3-bis(2,6-diisopropylphenyl)imidazol-2-ylidene](3-chloropyridyl)palladium(II) dichloride (20.2 mg, 0.03 mmol) and tripotassium phosphate (189.5 mg, 0.89 mmol) in 1,4-dioxane (3 mL) and water (1.5 mL) was degassed with nitrogen for 5 min. The mixture was stirred at rt in the dark under nitrogen for 21 h. The reaction mixture was filtered through a 10 g Celite cartridge and the cartridge washed with ethyl acetate (approx. 20 mL). To the filtrate was added water (20 mL) and the layers separated. The aqueous layer was extracted with further ethyl acetate (2×20 mL) and the organic phases were combined and filtered through a cartridge fitted with a hydrophobic frit. The filtrate was evaporated in vacuo, redissolved in DMSO (2 mL) and directly purified by MDAP (high pH). The required fractions were combined and evaporated in vacuo to give tert-butyl 2-(1-(2-methoxyphenyl)vinyl)-6-(methylcarbamoyl)isonicotinate (36.7 mg, 0.10 mmol, 41% yield) as a brown gum.
LCMS (2 min High pH): Rt=1.34 min, [MH]+=369.3.

Intermediate 188: (+/−)-tert-Butyl 2-(1-(2-methoxyphenyl)ethyl)-6-(methylcarbamoyl)isonicotinate

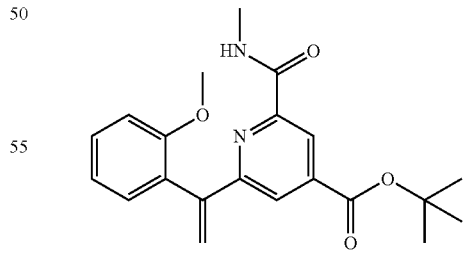

A solution of tert-butyl 2-(1-(2-methoxyphenyl)vinyl)-6-(methylcarbamoyl)isonicotinate (73 mg, 0.20 mmol) in ethyl acetate (5 mL) was hydrogenated using a Thales H-Cube apparatus at 20° C. in full H$_2$ mode over a 10% palladium on carbon catalyst cartridge with recirculation through the apparatus for 45 min after the first pass. The reaction mixture was evaporated in vacuo to give (+/−)-tertbutyl 2-(1-(2-methoxyphenyl)ethyl)-6-(methylcarbamoyl) isonicotinate (74.5 mg, 0.20 mmol) as a yellow gum.
LCMS (2 min Formic): Rt=1.36 min, [MH]+=371.3.

Intermediate 189: (+/−)-2-(1-(2-Methoxyphenyl) ethyl)-6-(methylcarbamoyl)isonicotinic acid

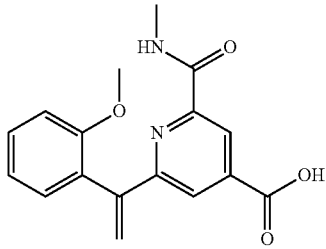 [SMILES: C=C(c1cc(C(=O)O)cc(C(=O)NC)n1)c1ccccc1OC]

A mixture of (+/−)-tert-butyl 2-(1-(2-methoxyphenyl) ethyl)-6-(methylcarbamoyl)isonicotinate (74.5 mg, 0.20 mmol) and sodium hydroxide (70.1 mg, 1.75 mmol) in methanol (1 mL) and tetrahydrofuran (1 mL) was stirred at rt for 1.25 h. The volatiles were evaporated under a stream of nitrogen. To this was added water (5 mL) and 2M aqueous HCl (approx. 1 mL), which afforded a light yellow precipitate. The suspension was filtered and the filtrate extracted with ethyl acetate (5 mL). The solid precipitate was combined with the organic extract; this solution was evaporated under a stream of nitrogen and the residue dried in vacuo to give (+/−)-2-(1-(2-methoxyphenyl)ethyl)-6-(methylcarbamoyl)isonicotinic acid (56.1 mg, 0.18 mmol, 89% yield) as a sticky orange solid.
LCMS (2 min High pH): Rt=0.69 min, [MH]+=315.2.

Intermediate 190: (S*)-2-((3-Fluorophenyl)(hydroxy)methyl)-6-(methylcarbamoyl)isonicotinic acid

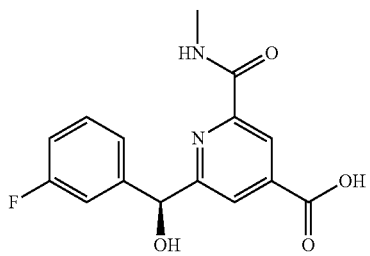 [SMILES: CNC(=O)c1cc(C(=O)O)cc([C@@H](O)c2cccc(F)c2)n1]

(3-Fluorophenyl)magnesium bromide (10.41 mL, 10.41 mmol, 1M in THF) was added dropwise to a solution of tert-butyl 2-formyl-6-(methylcarbamoyl)isonicotinate (1.1 g, 4.16 mmol) in THF at −78° C. and the mixture was stirred for 30 min, then allowed to warm to −20° C. and the mixture was then quenched with saturated ammonium chloride solution (10 mL) and extracted with EtOAc (20 mL). The organic layer was dried and evaporated in vacuo to give an orange gum, which was purified by flash chromatography on a silica column (50 g) eluting with 0-100% EtOAc/cyclohexane. The product-containing fractions were evaporated in vacuo to give tert-butyl 2-((3-fluorophenyl)(hydroxy) methyl)-6-(methylcarbamoyl)isonicotinate (1.25 g, 3.47 mmol, 83% yield) as a colourless gum. The impure product was dissolved in methanol and NaOH (6 mL, 12.00 mmol, 2M aq.) was added, then the mixture was allowed to stand at rt over the weekend. The solvent was evaporated to half its original volume and the resulting solution was acidified to pH 3 with 2M HCl, then allowed to stand for 2 h, giving a dense precipitate. This was collected by filtration and washed with water, the solid then dried in the vacuum oven to give 2-((3-fluorophenyl)(hydroxy)methyl)-6-(methylcarbamoyl)isonicotinic acid (0.71 g, 2.33 mmol, 56% yield) as a colourless solid.
LCMS (2 min High pH): Rt=0.52 min, [MH]+=305.4.

Intermediate 191: (+/−)-tert-Butyl 2-(hydroxy(o-tolyl)methyl)-6-(methylcarbamoyl)isonicotinate

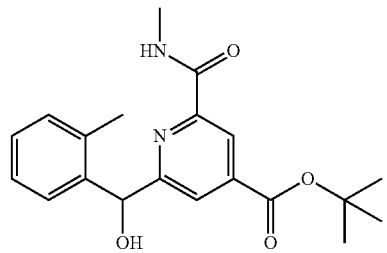 [SMILES: CNC(=O)c1cc(C(=O)OC(C)(C)C)cc(C(O)c2ccccc2C)n1]

o-Tolylmagnesium bromide (2M in ether, 4.73 mL, 9.46 mmol) was added to a solution of tert-butyl 2-formyl-6-(methylcarbamoyl)isonicotinate (1000 mg, 3.78 mmol) in THF at −78° C. and the mixture was stirred for 30 min at −78° C., then allowed to warm to rt. Ammonium chloride solution (5 mL) was added dropwise, then the mixture was diluted with water (20 mL) and extracted with EtOAc (2×20 mL). The combined organics were washed with brine, dried and evaporated in vacuo. The crude product was purified by chromatography on a 50 g silica column eluting with 0-100% EtOAc/cyclohexane and the product-containing fractions were evaporated in vacuo to give (+/−)-tert-butyl 2-(hydroxy(o-tolyl)methyl)-6-(methylcarbamoyl)isonicotinate (80 wt % purity, 0.74 g, 1.66 mmol, 44% yield) as a colourless gum.
LCMS (2 min High pH): Rt=1.14. min, [MH]+=357.3.

Intermediate 192: (+/−)-2-(Hydroxy(o-tolyl) methyl)-6-(methylcarbamoyl)isonicotinic acid

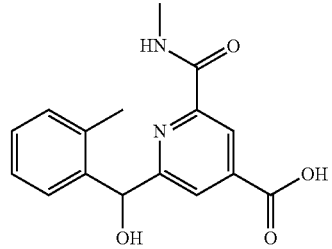 [SMILES: CNC(=O)c1cc(C(=O)O)cc(C(O)c2ccccc2C)n1]

NaOH (2M, 2.491 mL, 4.98 mmol) was added to a solution of (+/−)-tert-butyl 2-(hydroxy(o-tolyl)methyl)-6-(methylcarbamoyl)isonicotinate (80 wt %, 0.74 g, 1.66 mmol) in methanol (10 mL) at rt and the solution was stirred for 2 h, then evaporated in vacuo and the residue partitioned between water (20 mL) and ether (20 mL). The aqueous layer was acidified with 2M HCl to pH 4, then extracted with EtOAc (2×20 mL). The mixture included solid at the interface, which was collected by filtration, washed with EtOAc and dried in the vacuum oven to give (+/−)-2-(hydroxy(o-tolyl)methyl)-6-(methylcarbamoyl)isonicotinic acid (220 mg, 0.73 mmol, 44% yield) as a colourless solid. The filtrate was transferred to a separating funnel, the organic layer separated and combined with the first EtOAc extract (20 mL, above), then the combined organics were, dried and evaporated in vacuo to give further 2-(hydroxy(o-tolyl)methyl)-6-(methylcarbamoyl)isonicotinic acid (170 mg, 0.566 mmol, 34% yield) as a colourless foam.

LCMS (2 min High pH): Rt=0.54 min, [MH]+=301.2.

Intermediate 193: tert-Butyl 2-(4-fluorobenzyl)-6-(methylcarbamoyl)isonicotinate

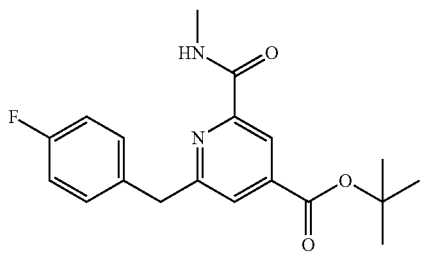 [SMILES: CNC(=O)c1cc(C(=O)OC(C)(C)C)cc(Cc2ccc(F)cc2)n1]

tert-Butyl 2-chloro-6-(methylcarbamoyl)isonicotinate (276 mg, 1.02 mmol), (4-fluorobenzyl)zinc(II) chloride (2100 μL, 1.05 mmol, 0.5M in THF) and PdCl$_2$(PPh$_3$)$_2$ (185 mg, 0.26 mmol) were dissolved in THF (600 μL) and heated at 100° C. for 30 min in the microwave. Further (4-fluorobenzyl)zinc(II) chloride (1600 μL, 0.80 mmol, 0.5M in THF) was added before further heating at 100° C. in the microwave. The reaction mixture was filtered through celite (eluent EtOAc). The solvent was removed in vacuo to give 1.422 g of crude black oil. This was dissolved in DCM with a few drops of methanol and purified by chromatography on SiO$_2$ (Biotage SNAP 50 g, eluting with 0-40% ethyl acetate/cyclohexane). The desired fractions were concentrated in vacuo to give tert-butyl 2-(4-fluorobenzyl)-6-(methylcarbamoyl)isonicotinate (325 mg, 0.85 mmol, 83% yield) as a white solid.

LCMS (2 min Formic): Rt=1.27 min, [MH]+=345.1.

Intermediate 194: 2-(4-Fluorobenzyl)-6-(methylcarbamoyl)isonicotinic acid

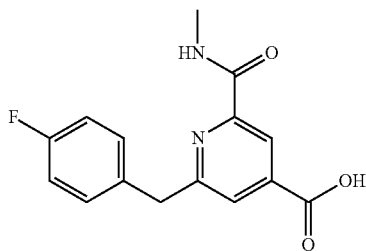 [SMILES: CNC(=O)c1cc(C(=O)O)cc(Cc2ccc(F)cc2)n1]

To a solution of tert-butyl 2-(4-fluorobenzyl)-6-(methylcarbamoyl)isonicotinate (325 mg, 0.94 mmol) in 1,4-dioxane (2.4 mL) was added LiOH (49 mg, 2.05 mmol) followed by water (2.4 mL). The reaction mixture was stirred at rt for 1 h. The reaction mixture was concentrated in vacuo before being dissolved in water. Acetic acid was added to the solution until a pH of 4 had been achieved. The solution was then partitioned between water and EtOAc. The layers were separated followed by two further aqueous extractions using two portions of EtOAc (2×15 mL). The organic layers were combined, dried (hydrophobic frit) and concentrated in vacuo to give 2-(4-fluorobenzyl)-6-(methylcarbamoyl)isonicotinic acid (262 mg, 0.82 mmol, 87% yield) as a white solid.

LCMS (2 min Formic): Rt=0.94 min, [MH]+=289.1.

Intermediate 195: N$^4$-((1R,5S,6r)-3-Oxabicyclo[3.1.0]hexan-6-yl)-6-(chloro(phenyl)methyl)-N$^2$-methylpyridine-2,4-dicarboxamide

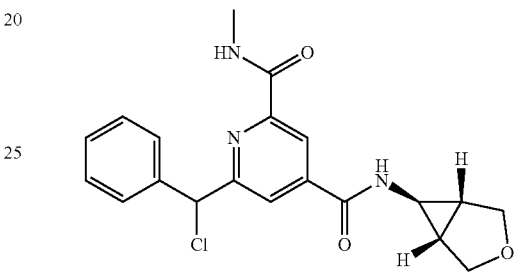

To a solution of N$^4$-((1R,5S,6r)-3-oxabicyclo[3.1.0]hexan-6-yl)-6-(hydroxy(phenyl)methyl)-N$^2$-methylpyridine-2,4-dicarboxamide (191 mg, 0.468 mmol, 90% wt.) in DCM (8 mL) at 0° C., was added dropwise thionyl chloride (0.25 mL, 3.43 mmol). The reaction mixture was then stirred at rt overnight. SOCl$_2$ (0.1 mL) was added and the resultant mixture was stirred for 1 h, then concentrated in vacuo to give N$^4$-((1R,5S,6r)-3-oxabicyclo[3.1.0]hexan-6-yl)-6-(chloro(phenyl)methyl)-N$^2$-methylpyridine-2,4-dicarboxamide (300 mg, 0.43 mmol, yield 91%, 55% purity).

LCMS (2 min Formic): Rt=0.94 min, [MH]+=386.2.

Intermediate 196: N$^4$-((1R,5S,6r)-3-Oxabicyclo[3.1.0]hexan-6-yl)-6-(hydroxy(pyridin-2-yl)methyl)-N$^2$-methylpyridine-2,4-dicarboxamide

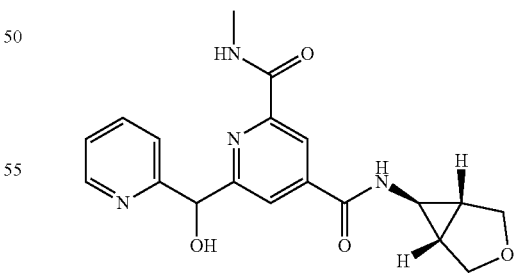

In a round bottom flask dried and under N$_2$ with lithium chloride (101 mg, 2.38 mmol) was added 2-bromopyridine (0.289 mL, 2.97 mmol, commercially available from, for example, Sigma-Aldrich) and THF (0.5 mL) at rt. The reaction mixture was then stirred at rt for 30 min then isopropylmagnesium chloride solution (2M in THF, 1.48 mL, 2.96 mmol, commercially available from, for example, Sigma-Aldrich) was added and the resultant mixture was stirred for 45 min to give pyridin-2-ylmagnesium chloride (yield is assumed to be 100% and the reaction mixture was used crude directly in the next step). To a solution of pyridin-2-ylmagnesium chloride (410 mg, 2.249 mmol) in THF (0.5 mL) at 0° C. under nitrogen, was added dropwise N$^4$-((1R,5S,6r)-3-oxabicyclo[3.1.0]hexan-6-yl)-6-formyl-N$^2$-methylpyridine-2,4-dicarboxamide (180 mg, 0.56 mmol, 90% wt.) in THF (2 mL). The reaction mixture was allowed to warm up to rt and was stirred for 2 h. Ammonium chloride aqueous solution (0.5 mL) was added. The reaction mixture was concentrated in vacuo. MeOH (2 mL) was added and this was purified by MDAP (high pH). The desired fractions were concentrated to give N$^4$-((1R,5S,6r)-3-oxabicyclo[3.1.0]hexan-6-yl)-6-(hydroxy(pyridin-2-yl)methyl)-N$^2$-methylpyridine-2,4-dicarboxamide (62 mg, 0.16 mmol, 29% yield).

LCMS (2 min Formic): Rt=0.46 min, [MH]+=369.3.

Intermediate 197: (±)-tert-Butyl 4-(3-(2-benzyl-6-(methylcarbamoyl)isonicotinamido)propyl)-3,3-difluoropiperidine-1-carboxylate

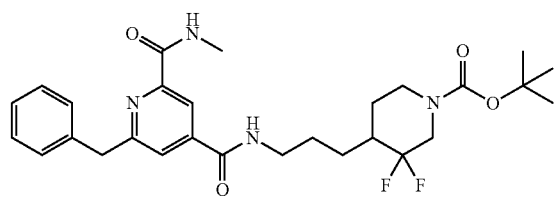 [SMILES: CNC(=O)c1cc(C(=O)NCCCC2CCN(C(=O)OC(C)(C)C)CC2(F)F)cc(Cc2ccccc2)n1]

To a solution of 2-benzyl-6-(methylcarbamoyl)isonicotinic acid (41.4 mg, 0.15 mmol), (±)-tert-butyl 4-(3-aminopropyl)-3,3-difluoropiperidine-1-carboxylate (45.4 mg, 0.16 mmol) and HATU (95.8 mg, 0.25 mmol) in DMF (1.5 mL) was added DIPEA (0.080 mL, 0.46 mmol). The mixture was stirred at rt for 50 min. The reaction mixture was concentrated under a stream of nitrogen, diluted with acetonitrile to a total volume of 2 mL and directly purified by MDAP (2×1 mL injection; formic) and the required fractions combined and evaporated in vacuo. The residue was suspended in dichloromethane, transferred to a tarred vial and the solvent evaporated under a stream of nitrogen to give (±)-tert-butyl 4-(3-(2-benzyl-6-(methylcarbamoyl)isonicotinamido)propyl)-3,3-difluoropiperidine-1-carboxylate (52.3 mg, 0.10 mmol, 64% yield) as a colourless glass.

LCMS (2 mins formic) Peak R$_f$=1.26 min, m/z=531 for [MH]$^+$

Intermediate 198: (S)-tert-Butyl 2-(3-(2-(methylcarbamoyl)-6-((S*)-1-phenylethyl)isonicotinamido)propyl)morpholine-4-carboxylate

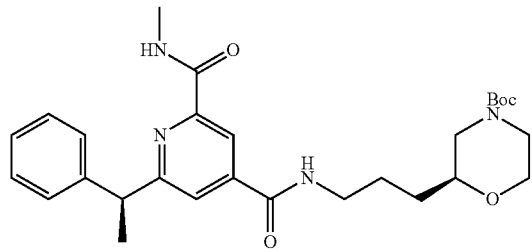 [SMILES: CNC(=O)c1cc(C(=O)NCCC[C@H]2CN(C(=O)OC(C)(C)C)CCO2)cc([C@@H](C)c2ccccc2)n1]

2-(Methylcarbamoyl)-6-(1-phenylethyl)isonicotinic acid (100 mg, 0.35 mmol) was taken up in DMF (5 mL). DIPEA (0.184 mL, 1.06 mmol) and HATU (201 mg, 0.53 mmol) were added and the reaction was left to stir at rt for 10 min. (S)-tert-Butyl 2-(3-aminopropyl)morpholine-4-carboxylate (129 mg, 0.528 mmol) was added and the reaction left to stir overnight. The reaction was concentrated in vacuo. The residue was taken up in ethyl acetate (10 mL) and extracted using sodium bicarbonate solution (10 mL). The organic phase was washed with brine (10 mL), before being dried over sodium sulphate, filtered through a hydrophobic frit and concentrated in vacuo. The crude product was applied to a 10 g SNAP ULTRA silica cartridge in the minimum of DCM and purified by flash chromatography, eluting with 0-75% (3:1 EtOAc:EtOH) in cyclohexane. The appropriate fractions were combined and concentrated in vacuo to afford the title compound (108 mg).

LCMS (2 min High pH): Rt=1.22 min, [MH]+=511.4.

Intermediate 199: (1R,5S,6s)-tert-Butyl 6-(2-(3-methylbenzyl)-6-(methylcarbamoyl)isonicotinamido)-3-azabicyclo[3.1.0]hexane-3-carboxylate

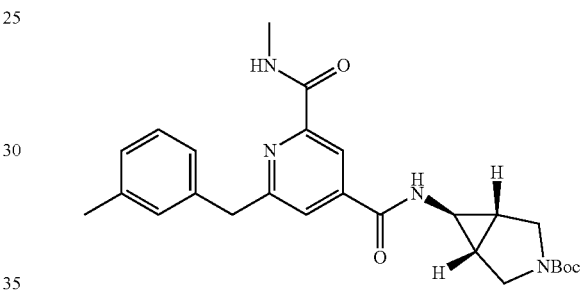

2-(3-Methylbenzyl)-6-(methylcarbamoyl)isonicotinic acid (160 mg, 0.56 mmol) was taken up in DMF (5 mL). DIPEA (0.295 mL, 1.69 mmol), HATU (321 mg, 0.84 mmol) and (1R,5S,6s)-tert-butyl 6-amino-3-azabicyclo[3.1.0]hexane-3-carboxylate (167 mg, 0.84 mmol) were added and the reaction left to stir at rt overnight. The reaction was concentrated in vacuo. The residue was taken up in ethyl acetate (10 mL) and extracted using aq. sodium bicarbonate solution (10 mL). The organic phase was washed with brine before being dried over sodium sulphate, filtered through a hydrophobic frit and concentrated in vacuo to afford the title compound (295 mg) which was used without purification in the next step.

LCMS (2 min High pH): Rt=1.19 min, [MH]+=465.4.

Intermediate 200: Benzyl 4-((4-((1R,5S,6r)-3-oxabicyclo[3.1.0]hexan-6-ylcarbamoyl)-6-(methylcarbamoyl)pyridin-2-yl)methyl)indoline-1-carboxylate

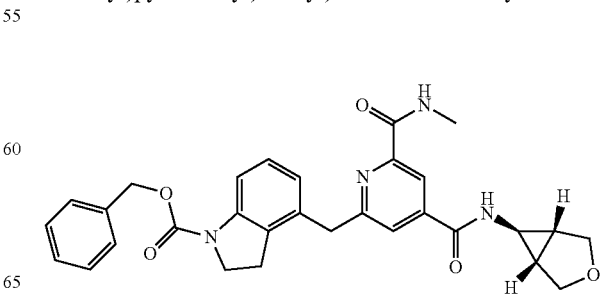

To a mixture of 2-((1-((benzyloxy)carbonyl)indolin-4-yl)methyl)-6-(methylcarbamoyl)isonicotinic acid (122.1 mg, 0.27 mmol), (1R,5S,6r)-3-oxabicyclo[3.1.0]hexan-6-amine, hydrochloride (55.4 mg, 0.41 mmol) and HATU (161.3 mg, 0.42 mmol) was added DIPEA (0.168 mL, 0.96 mmol) and DMF (2 mL) and the mixture was stirred at rt for 70 min. The mixture was concentrated under a stream of nitrogen and made up to 3 mL with acetonitrile before being directly purified by MDAP (1×3 mL injection; high pH). The required fractions were evaporated under a stream of nitrogen, the residues were redissolved in dichloromethane (approx. 4 mL) combined and transferred to a tarred vial. The solvent was evaporated under a stream of nitrogen and dried in vacuo to give benzyl 4-((4-(((1R,5S,6r)-3-oxabicyclo[3.1.0]hexan-6-yl)carbamoyl)-6-(methylcarbamoyl)pyridin-2-yl)methyl)indoline-1-carboxylate (101.3 mg, 0.19 mmol, 70% yield) as a yellow crunchy foam.

LCMS (2 mins formic) Peak $R_t$=1.12 mins, m/z=527 for [MH]$^+$ $^1$H NMR (400 MHz, CDCl$_3$) δ ppm 8.17 (s, 1H) 7.93-8.02 (m, 1H) 7.76-7.92 (m, 1H) 7.72 (d, J=1.2 Hz, 1H) 7.31-7.48 (m, 5H) 7.09-7.22 (m, 1H) 6.82 (d, J=7.6 Hz, 1H) 6.63 (br. s., 1H) 5.28 (br. s., 2H) 4.14 (s, 2H) 4.00-4.09 (m, 4H) 3.76 (d, J=8.3 Hz, 2H) 2.94-3.08 (m, 5H) 2.75 (br. d, J=2.2 Hz, 1H) 1.89 (s, 2H)

Intermediate 201: (S*)-tert-Butyl 3,3-difluoro-4-(3-(2-(methylcarbamoyl)-6-((S)-1-phenylethyl)isonicotinamido)propyl)piperidine-1-carboxylate Diastereomer 1

Intermediate 202: (R*)-tert-Butyl 3,3-difluoro-4-(3-(2-(methylcarbamoyl)-6-((S)-1-phenylethyl)isonicotinamido)propyl)piperidine-1-carboxylate Diastereomer 2

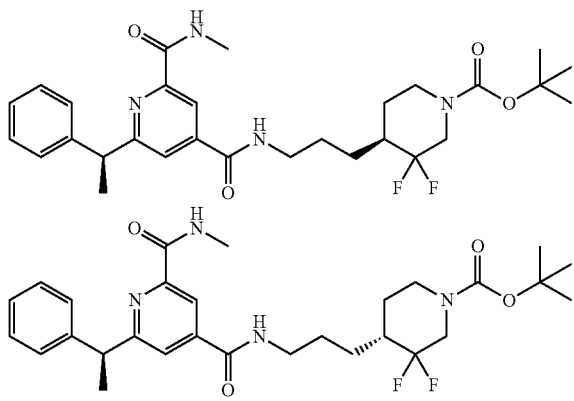

Example 117 (84.4 mg) was purified by chiral HPLC. The racemate was dissolved in EtOH (2 mL). Injection: 2×1 mL of the solution was injected onto the column [20% EtOH (+0.2% isopropylamine)/heptane (+0.2% isopropylamine), flow rate=30 mL/min, detection wavelength=215 nm, 4. Ref 550, 100, Column 30 mm×25 cm Chiralpak IC (5 μm), lot no. IC10028-01]. Total number of injections=2. Fractions from 23.5-27 mins were bulked and labelled peak 1. Fractions from 29-35 mins were bulked and labelled peak 2. Each set of the bulked pure fractions were concentrated in vacuo and then transferred to tarred vials and dried in vacuo.

The fractions corresponding to peak 1 were collected to afford (S*)-tert-butyl 3,3-difluoro-4-(3-(2-(methylcarbamoyl)-6-((S)-1-phenylethyl)isonicotinamido)propyl)piperidine-1-carboxylate, diastereomer 1 (35.0 mg, 0.06 mmol) as a colourless glass.

LCMS (2 min Formic): $R_t$=1.30 min, m/z=545 for [MH]$^+$

The fractions corresponding to peak 2 were collected to afford (R*)-tert-butyl 3,3-difluoro-4-(3-(2-(methylcarbamoyl)-6-((S)-1-phenylethyl)isonicotinamido)propyl)piperidine-1-carboxylate, diastereomer 2 (39.4 mg, 0.07 mmol) as a colourless glass.

LCMS (2 min Formic): $R_t$=1.30 min, m/z=545 for [MH]$^+$

Intermediate 203: (R*)-tert-Butyl 3,3-difluoro-4-(2-(2-(methylcarbamoyl)-6-((S)-1-phenylethyl)isonicotinamido)ethyl)piperidine-1-carboxylate, diastereomer 1

Intermediate 204: (S*)-tert-Butyl 3,3-difluoro-4-(2-(2-(methylcarbamoyl)-6-((S)-1-phenylethyl)isonicotinamido)ethyl)piperidine-1-carboxylate, diastereomer 2

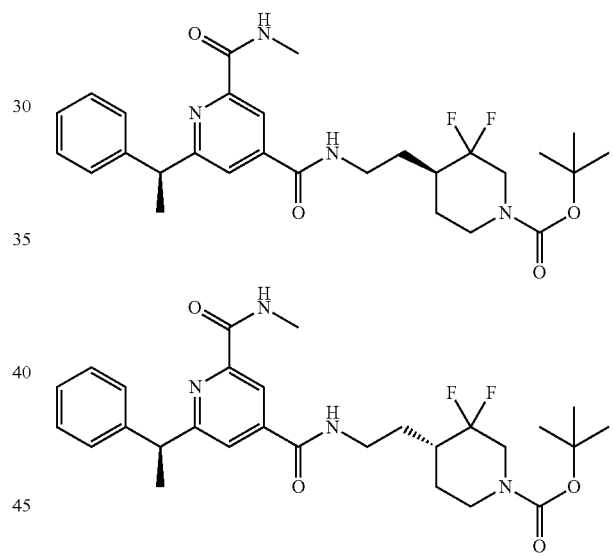

Example 118 (74.6 mg) was purified by chiral HPLC. The racemate was dissolved in EtOH (2 mL). Injection: 2 mL of the solution was injected onto the column [40% EtOH (+0.2% isopropylamine)/heptane (+0.2% isopropylamine), flow rate=30 mL/min, detection wavelength=215 nm, 4. Ref 550, 100, Column 30 mm×25 cm Chiralpak IC (5 μm), lot no. IC10028-01]. Total number of injections=1. Fractions from 12.5-14.5 mins were bulked and labelled peak 1. Fractions from 18-23 mins were bulked and labelled peak 2. Each set of the bulked pure fractions were concentrated in vacuo and then transferred to tarred vials and dried in vacuo.

The fractions corresponding to peak 1 were collected to afford (R*)-tert-butyl 3,3-difluoro-4-(2-(2-(methylcarbamoyl)-6-((S)-1-phenylethyl)isonicotinamido)ethyl)piperidine-1-carboxylate Diastereomer 1 (31.8 mg, 0.06 mmol) as a colourless glass.

LCMS (2 min Formic): $R_t$=1.27 min, m/z=531 for [MH]$^+$

The fractions corresponding to peak 2 were collected to afford (S*)-tert-butyl 3,3-difluoro-4-(2-(2-(methylcarbamoyl)-6-((S)-1-phenylethyl)isonicotinamido)ethyl)piperidine-1-carboxylate Diastereomer 2 (32.8 mg, 0.06 mmol) as a colourless glass.

LCMS (2 min Formic): R$_t$=1.27 min, m/z=531 for [MH]$^+$

Intermediate 205: (S*)-tert-Butyl 4,4-difluoro-3-(2-(2-(methylcarbamoyl)-6-((S)-1-phenylethyl)isonicotinamido)ethyl)piperidine-1-carboxylate, diastereomer 1

Intermediate 206: (R*)-tert-Butyl 4,4-difluoro-3-(2-(2-(methylcarbamoyl)-6-((S)-1-phenylethyl)isonicotinamido)ethyl)piperidine-1-carboxylate, diastereomer 2

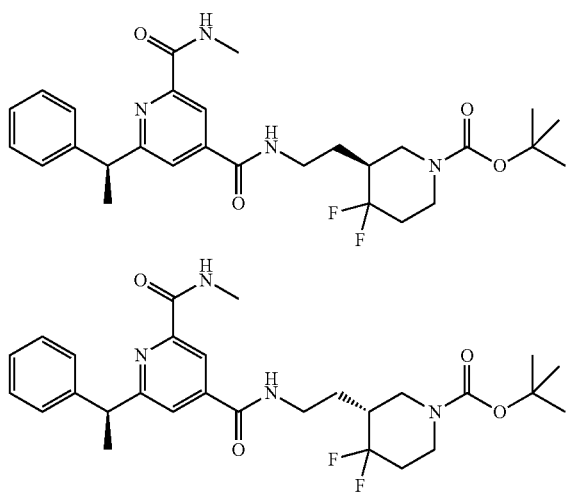

Example 119 (59.2 mg) was purified by chiral HPLC. The racemate was dissolved in EtOH (2 mL). Injection: 2×1 mL of the solution was injected onto the column [20% EtOH (+0.2% isopropylamine)/heptane (+0.2% isopropylamine), flow rate=30 mL/min, detection wavelength=215 nm, 4. Ref 550, 100, Column 30 mm×25 cm Chiralpak IC (5 µm), lot no. IC10028-01]. Total number of injections=2. Fractions from 23-26 mins were bulked and labelled peak 1. Fractions from 28.5-33 mins were bulked and labelled peak 2. Each set of the bulked pure fractions were concentrated in vacuo and then transferred to tarred vials and dried in vacuo.

The fractions corresponding to peak 1 were collected to afford (S*)-tert-butyl 4,4-difluoro-3-(2-(2-(methylcarbamoyl)-6-((S)-1-phenylethyl)isonicotinamido)ethyl)piperidine-1-carboxylate, diastereomer 1 (24.9 mg, 0.05 mmol) as a colourless glass.

LCMS (2 min Formic): R$_t$=1.28 min, m/z=531 for [MH]$^+$

The fractions corresponding to peak 2 were collected to afford (R*)-tert-butyl 4,4-difluoro-3-(2-(2-(methylcarbamoyl)-6-((S)-1-phenylethyl)isonicotinamido)ethyl)piperidine-1-carboxylate, diastereomer 2 (25.7 mg, 0.05 mmol) as a colourless glass.

LCMS (2 min Formic): R$_t$=1.28 min, m/z=531 for [MH]$^+$

Intermediate 207: (+/−)-tert-Butyl 2-(3-(2-benzyl-6-(methylcarbamoyl)isonicotinamido)propyl)-2-methylmorpholine-4-carboxylate

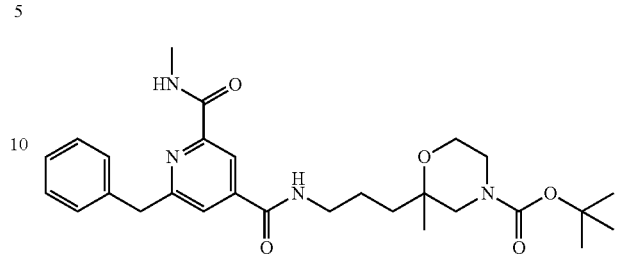

2-Benzyl-6-(methylcarbamoyl)isonicotinic acid (55 mg, 0.20 mmol) was taken up in DMF (2 mL). DIPEA (0.071 mL, 0.41 mmol) then HATU (116 mg, 0.31 mmol) was added and the reaction stirred at rt for 5 min. (+/−)-tert-Butyl 2-(3-aminopropyl)-2-methylmorpholine-4-carboxylate (90 wt %, 60 mg, 0.21 mmol) in dichloromethane (2 mL) was added and the reaction stirred for 45 min at rt. The reaction was left to stand overnight and then concentrated in vacuo. The residue was partitioned between EtOAc (25 mL) and sat. NaHCO$_3$ (25 mL). The organic layer was dried with Na$_2$SO$_4$, filtered through a hydrophobic frit and concentrated in vacuo. The crude product was applied to a 10 g SNAP Ultra cartridge in the minimum of DCM and eluted with 5-40% (3:1 EtOAc:EtOH) in cyclohexane. The appropriate fractions were concentrated in vacuo to give tert-butyl 2-(3-(2-benzyl-6-(methylcarbamoyl)isonicotinamido)propyl)-2-methylmorpholine-4-carboxylate (70 wt % purity, 91.6 mg, 0.13 mmol, 62% yield) as a yellow solid.

LCMS (2 min High pH): Rt=1.17 min, [MH]+=511.4.

Intermediate 208: 6-Benzyl-N$^4$-(4,4-diethoxybutyl)-N$^2$-methylpyridine-2,4-dicarboxamide

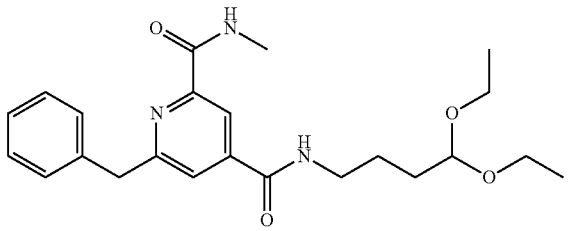 [SMILES: CCOC(CCCNC(=O)c1cc(Cc2ccccc2)nc(C(=O)NC)c1)OCC]

To a mixture of 2-benzyl-6-(methylcarbamoyl)isonicotinic acid (522.1 mg, 1.93 mmol) and HATU (1.071 g, 2.82 mmol) in DMF (7 mL) was added 4,4-diethoxybutan-1-amine (0.467 mL, 2.70 mmol, commercially available from, for example, Fluorochem) followed by DIPEA (1.0 mL, 5.73 mmol). The mixture was stirred at rt under nitrogen for 17.25 h before being concentrated in vacuo. The mixture was diluted with acetonitrile (7 mL) and was directly purified by MDAP (3×3 mL injection; high pH). The required fractions were combined and the solvent evaporated in vacuo. The residue was redissolved in dichloromethane (approx. 10 mL) and was transferred to a tarred vial before the solvent was evaporated under a stream of nitrogen and dried in vacuo to give 6-benzyl-N$^4$-(4,4-diethoxybutyl)-N$^2$-methylpyridine-2,4-dicarboxamide (0.651 g, 1.58 mmol, 82% yield) as a pale yellow gum.

LCMS (2 mins formic) Peak R$_t$=1.08 mins, m/z=414 for [MH]$^+$

¹H NMR (400 MHz, CDCl₃) δ ppm 8.23 (d, J=1.5 Hz, 1H) 7.98-8.10 (m, 1H) 7.80 (d, J=1.5 Hz, 1H) 7.30-7.36 (m, 2H) 7.22-7.29 (m, 3H) 6.73-6.82 (m, 1H) 4.51-4.56 (m, 1H) 4.23 (s, 2H) 3.69 (dq, J=9.3, 7.1 Hz, 2H) 3.46-3.57 (m, 4H) 3.07 (d, J=5.1 Hz, 3H) 1.70-1.76 (m, 4H) 1.21 (t, J=7.1 Hz, 6H)

Intermediate 209: 6-Benzyl-N⁴-(3-((2r,5r)-5-(1,3-dioxoisoindolin-2-yl)-1,3-dioxan-2-yl)propyl)-N²-methylpyridine-2,4-dicarboxamide

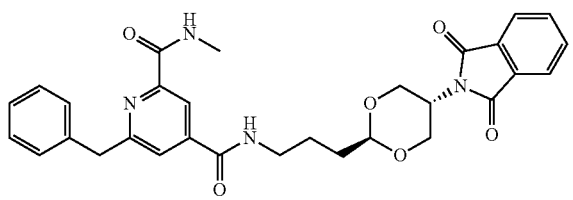 [SMILES: CNC(=O)c1cc(C(=O)NCCC[C@H]2OC[C@H](N3C(=O)c4ccccc4C3=O)CO2)cc(Cc2ccccc2)n1]

A mixture of 6-benzyl-N⁴-(4,4-diethoxybutyl)-N²-methylpyridine-2,4-dicarboxamide (0.648 g, 1.57 mmol), 2-(1,3-dihydroxypropan-2-yl)isoindoline-1,3-dione (0.362 g, 1.64 mmol) and p-toluenesulfonic acid monohydrate (62.7 mg, 0.33 mmol) in toluene (13.5 mL) was stirred at 70° C. under nitrogen for 125 min before being allowed to cool to rt. The mixture was partitioned between ethyl acetate (30 mL) and 1M sodium carbonate solution (30 mL). The phases were separated and the aqueous phase was extracted with further ethyl acetate (2×20 mL) and the combined organic phases were back washed with saturated brine solution (20 mL). The organic phase was dried by passing through a cartridge fitted with a hydrophobic frit and the solvent evaporated in vacuo. The residue was dissolved in DCM (approx. 5 mL), loaded onto a 50 g silica cartridge and purified by Biotage SP4 flash column chromatography eluting with a gradient of 20-60% ethyl acetate in cyclohexane. The required fractions were combined and the solvent evaporated in vacuo. The residue was redissolved in dichloromethane (approx. 15 mL) and was transferred to a tarred vial before the solvent was evaporated under a stream of nitrogen and then dried in vacuo to give 6-benzyl-N⁴-(3-((2r,5r)-5-(1,3-dioxoisoindolin-2-yl)-1,3-dioxan-2-yl)propyl)-N²-methylpyridine-2,4-dicarboxamide (0.510 g, 0.94 mmol, 60% yield) as a white solid.

LCMS (2 mins formic) Peak R$_f$=1.13 mins, m/z=543 for [MH]⁺

¹H NMR (400 MHz, CDCl₃) δ ppm 8.21 (d, J=1.2 Hz, 1H) 7.99-8.07 (m, 1H) 7.81-7.90 (m, 3H) 7.72-7.79 (m, 2H) 7.20-7.36 (m, 5H) 4.74-4.79 (m, 1H) 4.55-4.65 (m, 1H) 4.41-4.50 (m, 2H) 4.24 (s, 2H) 4.04-4.14 (m, 3H) 3.47-3.56 (m, 2H) 3.02 (d, J=5.1 Hz, 3H) 1.78-1.85 (m, 4H)

Intermediate 210: 6-Benzyl-N⁴-(3,3-diethoxypropyl)-N²-methylpyridine-2,4-dicarboxamide

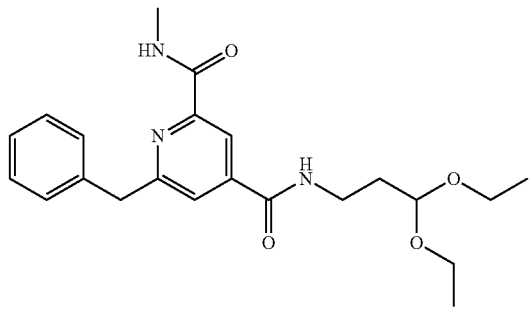 [SMILES: CCOC(CCNC(=O)c1cc(Cc2ccccc2)nc(C(=O)NC)c1)OCC]

To a mixture of 2-benzyl-6-(methylcarbamoyl)isonicotinic acid (77.8 mg, 0.29 mmol) and HATU (142.9 mg, 0.38 mmol) in DMF (1.5 mL) was added 3,3-diethoxypropan-1-amine (0.061 mL, 0.37 mmol) and DIPEA (0.151 mL, 0.86 mmol). The mixture was stirred at rt for 4.5 h, after which the volatiles were evaporated under a stream of nitrogen. This was redissolved in DMSO (3 mL) and directly purified by MDAP (high pH). The required fractions were combined and evaporated in vacuo to give 6-benzyl-N⁴-(3,3-diethoxypropyl)-N²-methylpyridine-2,4-dicarboxamide (91.3 mg, 0.23 mmol, 79% yield) a light brown gum.

LCMS (2 min High pH): Rt=1.08 min, [MH]+=400.4.

Intermediate 211: 6-Benzyl-N⁴-(2-((2r,5r)-5-(1,3-dioxoisoindolin-2-yl)-1,3-dioxan-2-yl)ethyl)-N²-methylpyridine-2,4-dicarboxamide

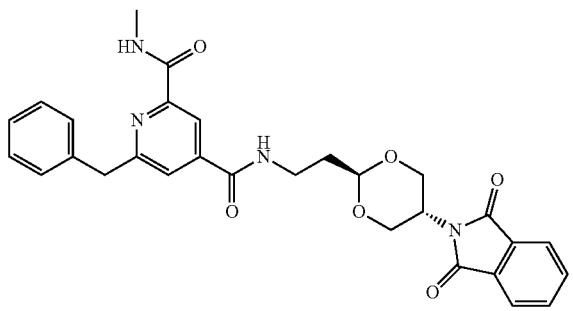 [SMILES: CNC(=O)c1cc(C(=O)NCC[C@H]2OC[C@H](N3C(=O)c4ccccc4C3=O)CO2)cc(Cc2ccccc2)n1]

A mixture of 6-benzyl-N⁴-(3,3-diethoxypropyl)-N²-methylpyridine-2,4-dicarboxamide (87.6 mg, 0.22 mmol), 2-(1,3-dihydroxypropan-2-yl)isoindoline-1,3-dione (48.8 mg, 0.22 mmol) and p-toluenesulfonic acid monohydrate (8.5 mg, 0.05 mmol) in toluene (3 mL) was stirred at 110° C. under nitrogen for 2 h. The reaction mixture was then cooled to rt and the volatiles evaporated in vacuo to give a yellow solid. This was partitioned between ethyl acetate (5 mL), water (3 mL) and sat. aqueous Na₂CO₃ (2 mL) and the layers separated. The aqueous phase was extracted with dichloromethane (3×5 mL) and ethyl acetate (5 mL) and the organic layers were combined and filtered through a cartridge fitted with a hydrophobic frit. The filtrate was evaporated under a stream of nitrogen. This was redissolved in DMSO (1 mL) and directly purified by MDAP (high pH). The required fractions were combined and evaporated in vacuo to give 6-benzyl-N⁴-(2-((2r,5r)-5-(1,3-dioxoisoindolin-2-yl)-1,3-dioxan-2-yl)ethyl)-N²-methylpyridine-2,4-dicarboxamide (71.0 mg, 0.13 mmol, 61% yield) as a white solid.

LCMS (2 min High pH): Rt=1.12 min, [MH]+=529.4.

Intermediate 212: 6-(3-Chlorobenzyl)-N⁴-(3-((2r,5r)-5-(1,3-dioxoisoindolin-2-yl)-1,3-dioxan-2-yl)propyl)-N²-methylpyridine-2,4-dicarboxamide

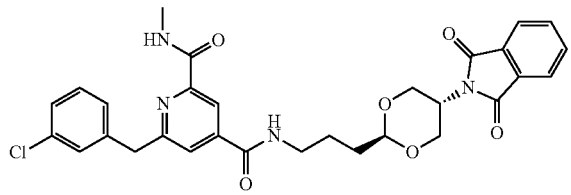 [SMILES: CNC(=O)c1cc(C(=O)NCCC[C@H]2OC[C@H](N3C(=O)c4ccccc4C3=O)CO2)cc(Cc2cccc(Cl)c2)n1]

6-Chloro-N⁴-(3-((2s,5s)-5-(1,3-dioxoisoindolin-2-yl)-1,3-dioxan-2-yl)propyl)-N²-methylpyridine-2,4-dicarboxamide (152 mg, 0.312 mmol), (3-chlorobenzyl)zinc(II) chloride (1300 µL, 0.650 mmol, 0.5M in THF) and PdCl₂(PPh₃)₂ (36 mg, 0.05 mmol) were dissolved in THF (210 µL) and heated at 100° C. for 30 min in the microwave. Further (3-chlorobenzyl)zinc(II) chloride (620 µL, 0.310 mmol, 0.5M in THF) and PdCl₂(PPh₃)₂ (32.9 mg, 0.05 mmol) were added to the reaction mixture before heating at 100° C. for 30 min. The reaction mixture was filtered through celite (eluent EtOAc). The solvent was removed in vacuo to give 637 mg of crude brown solid. This was dissolved in DCM with a few drops of methanol and purified by chromatography on SiO₂ (Biotage SNAP 10 g, eluting with 0-50% ethyl acetate/cyclohexane). The desired fractions were concentrated in vacuo to give 6-(3-chlorobenzyl)-N⁴-(3-((2s,5s)-5-(1,3-dioxoisoindolin-2-yl)-1,3-dioxan-2-yl)propyl)-N²-methylpyridine-2,4-dicarboxamide (50 mg, 0.07 mmol, 24% yield, 85% purity) as a very pale brown (almost white) solid.

LCMS (2 min Formic): Rt=1.20 min, [MH]+=577.0.

Intermediate 213: 6-(2-Chlorobenzyl)-N⁴-(3-((2r,5r)-5-(1,3-dioxoisoindolin-2-yl)-1,3-dioxan-2-yl)propyl)-N²-methylpyridine-2,4-dicarboxamide

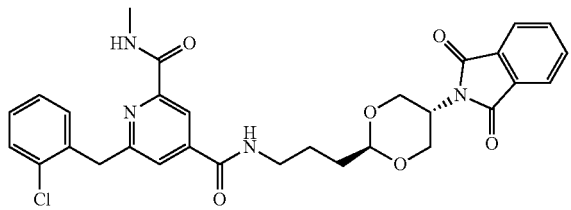 [SMILES: CNC(=O)c1cc(C(=O)NCCC[C@H]2OC[C@H](N3C(=O)c4ccccc4C3=O)CO2)cc(Cc2ccccc2Cl)n1]

6-Chloro-N⁴-(3-((2s,5s)-5-(1,3-dioxoisoindolin-2-yl)-1,3-dioxan-2-yl)propyl)-N²-methylpyridine-2,4-dicarboxamide (155 mg, 0.32 mmol), (2-chlorobenzyl)zinc(II) chloride (1300 µL, 0.650 mmol, 0.5M in THF) and PdCl₂(PPh₃)₂ (35 mg, 0.05 mmol) were dissolved in THF (210 µL) and heated at 100° C. for 30 min in the microwave. A further amount of (2-chlorobenzyl)zinc(II) chloride (640 µL, 0.320 mmol, 0.5M in THF) and PdCl₂(PPh₃)₂ (15.64 mg, 0.02 mmol) were added before heating the reaction mixture in a microwave for 30 min at 100° C. The reaction mixture was filtered through celite (eluent EtOAc). The solvent was removed in vacuo to give 587 mg of crude brown/black solid. This was purified by chromatography on SiO₂ (Biotage SNAP 10 g, eluting with 0-40% (25% ethanol:ethyl acetate)/cyclohexane). The desired fractions were concentrated in vacuo to give 6-(2-chlorobenzyl)-N⁴-(3-((2s,5s)-5-(1,3-dioxoisoindolin-2-yl)-1,3-dioxan-2-yl)propyl)-N²-methylpyridine-2,4-dicarboxamide (117 mg, 0.18 mmol, 57% yield) as a white solid.

LCMS (2 min Formic): Rt=1.19 min, [MH]+=577.3.

Intermediate 214: N⁴-(3-((2r,5r)-5-(1,3-Dioxoisoindolin-2-yl)-1,3-dioxan-2-yl)propyl)-N²-methyl-6-(3-methylbenzyl)pyridine-2,4-dicarboxamide

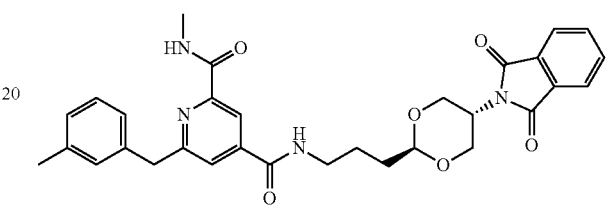

6-Chloro-N⁴-(3-((2r,5r)-5-(1,3-dioxoisoindolin-2-yl)-1,3-dioxan-2-yl)propyl)-N²-methylpyridine-2,4-dicarboxamide (154 mg, 0.32 mmol), (3-methylbenzyl)zinc(II) chloride (1300 µL, 0.650 mmol, 0.5M in THF), and PdCl₂(PPh₃)₂ (42 mg, 0.060 mmol) were dissolved in THF (211 µL) and heated at 100° C. for 30 min in the microwave. More (3-methylbenzyl)zinc(II) chloride (630 µL, 0.315 mmol, 0.5M in THF) and PdCl₂(PPh₃)₂ (19 mg, 0.03 mmol) were added before heating at 100° C. in the microwave for 30 min. The reaction mixture was filtered through celite (eluent EtOAc). The solvent was removed in vacuo to give 602 mg of crude brown solid. This was purified by chromatography on SiO₂ (Biotage SNAP 10 g, eluting with 0-50% ethyl acetate/cyclohexane). The desired fractions were concentrated in vacuo to give N⁴-(3-((2r,5r)-5-(1,3-dioxoisoindolin-2-yl)-1,3-dioxan-2-yl)propyl)-N²-methyl-6-(3-methylbenzyl)pyridine-2,4-dicarboxamide (67 mg, 0.12 mmol, 38% yield) as a colourless oil.

LCMS (2 min Formic): Rt=1.18 min, [MH]+=557.4.

Intermediate 215: N⁴-(3-((2r,5r)-5-(1,3-Dioxoisoindolin-2-yl)-1,3-dioxan-2-yl)propyl)-6-(2-methoxybenzyl)-N²-methylpyridine-2,4-dicarboxamide

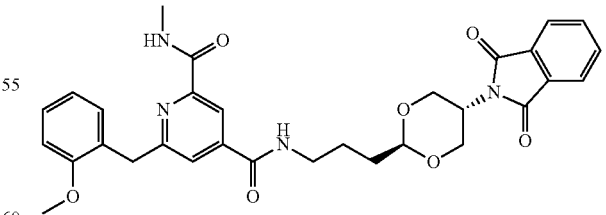

6-Chloro-N⁴-(3-((2s,5s)-5-(1,3-dioxoisoindolin-2-yl)-1,3-dioxan-2-yl)propyl)-N²-methylpyridine-2,4-dicarboxamide (153 mg, 0.314 mmol), (2-methoxybenzyl)zinc(II) chloride (1300 µL, 0.65 mmol, 0.5M in THF) and PdCl₂(PPh₃)₂ (47 mg, 0.07 mmol) were dissolved in THF (210 µL) and heated at 100° C. for 30 min in the microwave. Further PdCl$_2$(PPh$_3$)$_2$ (37 mg, 0.05 mmol) and (2-methoxybenzyl)zinc(II) chloride (628 µL, 0.31 mmol, 0.5M in THF) were added before heating in the microwave for a further 30 min at 100° C. The reaction mixture was filtered through celite (eluent EtOAc). The solvent was removed in vacuo to give 589 mg of crude brown solid. This was dissolved in DCM with a few drops of methanol and purified by chromatography on SiO$_2$ (Biotage SNAP 10 g, eluting with 0-60% ethyl acetate/cyclohexane). The desired fractions were concentrated in vacuo to give the title compound as a, still impure, yellow oil with black solid. The 134 mg of still impure product were redissolved in DCM and a few drops of methanol and purified by chromatography on SiO$_2$ (Biotage SNAP 10 g, eluting with 0-60% ethyl acetate/cyclohexane). The desired fractions were concentrated in vacuo to give N$^4$-(3-((2s,5s)-5-(1,3-dioxoisoindolin-2-yl)-1,3-dioxan-2-yl)propyl)-6-(2-methoxybenzyl)-N$^2$-methylpyridine-2,4-dicarboxamide (51 mg, 0.08 mmol, 24% yield).

LCMS (2 min Formic): Rt=1.14 min, [MH]+=573.1.

Intermediate 216: (S)—N$^4$-(4,4-Diethoxybutyl)-M$^2$-methyl-6-(1-phenylethyl)pyridine-2,4-dicarboxamide

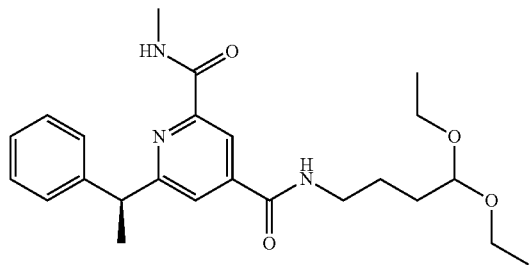 [SMILES: CCOC(CCCNC(=O)c1cc(C(=O)NC)nc([C@@H](C)c2ccccc2)c1)OCC]

To a solution of (S)-2-(methylcarbamoyl)-6-(1-phenylethyl)isonicotinic acid (120.1 mg, 0.42 mmol) and HATU (243.8 mg, 0.64 mmol) in DMF (2 mL) was added 4,4-diethoxybutan-1-amine (0.110 mL, 0.63 mmol) and DIPEA (0.221 mL, 1.27 mmol). The resulting solution was stirred at rt for 1.5 h, after which it was diluted with DMSO (4 mL) and directly purified by MDAP (high pH). The required fractions were evaporated under a stream of nitrogen, redissolved in methanol and combined. This solution was evaporated under a stream of nitrogen and the residue dried in vacuo to give (S)—N$^4$-(4,4-diethoxybutyl)-N$^2$-methyl-6-(1-phenylethyl)pyridine-2,4-dicarboxamide (152.2 mg, 0.36 mmol, 84% yield) as a yellow gum.

LCMS (2 min High pH): Rt=1.14 min, [MH]+=428.5.

Intermediate 217: N$^4$-(3-((2r,5S)-5-(1,3-Dioxoisoindolin-2-yl)-1,3-dioxan-2-yl)propyl)-N$^2$-methyl-6-((S)-1-phenylethyl)pyridine-2,4-dicarboxamide

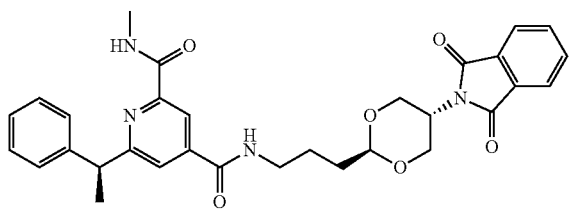 [SMILES: CNC(=O)c1cc(C(=O)NCCC[C@H]2OC[C@H](N3C(=O)c4ccccc4C3=O)CO2)cc([C@@H](C)c2ccccc2)n1]

To a solution of (S)—N$^4$-(4,4-diethoxybutyl)-N$^2$-methyl-6-(1-phenylethyl)pyridine-2,4-dicarboxamide (150 mg, 0.35 mmol) in toluene (3 mL) was added 2-(1,3-dihydroxypropan-2-yl)isoindoline-1,3-dione (79.3 mg, 0.36 mmol) and p-toluenesulfonic acid monohydrate (14.2 mg, 0.08 mmol). The resulting suspension was stirred at 70° C. under nitrogen for 2 h, after which the reaction mixture was allowed to cool to rt and the volatiles evaporated in vacuo. This was partitioned between ethyl acetate (5 mL) and 1M aqueous sodium carbonate (5 mL) and the layers separated. The aqueous phase was extracted with further ethyl acetate (2×5 mL) and the organic phases were combined and filtered through a cartridge fitted with a hydrophobic frit. The filtrate was evaporated under a stream of nitrogen. This was redissolved in DMSO (1 mL) and acetonitrile (1 mL) and directly purified by MDAP (high pH). The required fractions were combined and evaporated in vacuo to afford N$^4$-(3-((2r,5S)-5-(1,3-dioxoisoindolin-2-yl)-1,3-dioxan-2-yl)propyl)-N$^2$-methyl-6-((S)-1-phenylethyl)pyridine-2,4-dicarboxamide (113.0 mg, 0.20 mmol, 58% yield) as a white solid.

LCMS (2 min High pH): Rt=1.18 min, [MH]+=557.4.

Intermediate 218: (+/−)-N$^4$-(4,4-Diethoxybutyl)-6-(methoxy(phenyl)methyl)-N2-methylpyridine-2,4-dicarboxamide

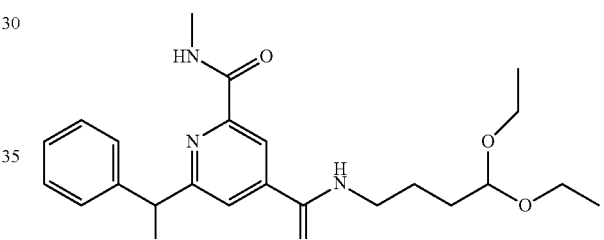

To a solution of 2-(methoxy(phenyl)methyl)-6-(methylcarbamoyl)isonicotinic acid (150 mg, 0.50 mmol) and HATU (209 mg, 0.55 mmol) in DMF (1.5 mL) was added DIPEA (0.174 mL, 1.00 mmol) followed by 4,4-diethoxybutan-1-amine (0.095 mL, 0.55 mmol). The resulting solution was stirred at rt for 2 h. Further HATU (50 mg), DIPEA (43 µL) and 4,4-diethoxybutan-1-amine (24 µL) were added sequentially and the reaction stirred for a further 2 h and then quenched. Water (20 mL) and EtOAc (20 mL) was added and the layers separated. The aqueous layer was further extracted with ethyl acetate (2×10 mL). The combined organics were back-extracted with water (2×10 mL) and sat. aqueous LiCl (10 mL) and then dried (Na$_2$SO$_4$), filtered and concentrated in vacuo to give a dark oil. This was redissolved in DCM and directly applied to the top of a SNAP silica cartridge (10 g) and purified by SP4 flash column chromatography. The column was eluted with a gradient of 30-100% ethyl acetate in cyclohexane. The appropriate fractions were collected and concentrated in vacuo to afford the product as a yellow oil —N$^4$-(4,4-diethoxybutyl)-6-(methoxy(phenyl)methyl)-N$^2$-methylpyridine-2,4-dicarboxamide (183 mg, 0.41 mmol, 83% yield)

LCMS (2 min Formic): Rt=1.07 min, [MH]+=444.4.

$^1$H NMR (400 MHz, DMSO-d$_6$) δ ppm 8.98 (t, J=5.5 Hz, 1H) 8.63 (q, J=4.6 Hz, 1H) 8.30 (d, J=1.7 Hz, 1H) 8.04 (d, J=1.7 Hz, 1H) 7.45-7.52 (m, 2H) 7.31-7.38 (m, 2H) 7.23-7.30 (m, 1H) 5.49 (s, 1H) 4.45-4.50 (m, 1H) 3.55 (dq, J=9.5, 7.1 Hz, 2H) 3.42 (dq, J=9.5, 7.0 Hz, 2H) 3.37 (s, 3H) 3.23-3.30 (obs. m, 2H) 2.86 (d, J=4.9 Hz, 3H) 1.51-1.59 (m, 4H) 1.10 (t, J=7.0 Hz, 6H)

Intermediate 219: (+/−)-N⁴-(3-((2r,5r)-5-(1,3-Dioxoisoindolin-2-yl)-1,3-dioxan-2-yl)propyl)-6-(methoxy(phenyl)methyl)-N²-methylpyridine-2,4-dicarboxamide

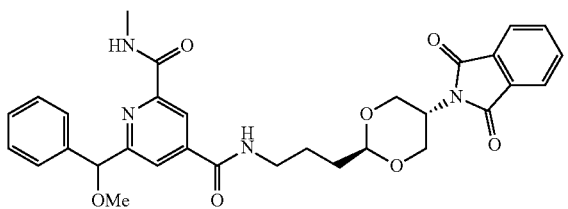 [SMILES: CNC(=O)c1cc(C(=O)NCCC[C@H]2OC[C@H](N3C(=O)c4ccccc4C3=O)CO2)cc(C(OC)c2ccccc2)n1]

To a solution of N⁴-(4,4-diethoxybutyl)-6-(methoxy(phenyl)methyl)-N²-methylpyridine-2,4-dicarboxamide (183 mg, 0.41 mmol) in toluene (2 mL) was added 2-(1,3-dihydroxypropan-2-yl)isoindoline-1,3-dione (91 mg, 0.41 mmol) and p-toluenesulfonic acid monohydrate (15.7 mg, 0.08 mmol). The resulting suspension was stirred at 90° C. under nitrogen for 2 h, after which the reaction mixture was allowed to cool to rt and partitioned between ethyl acetate (20 mL), and sat. aq. sodium bicarbonate (20 mL) and the layers separated. The aqueous phase was extracted with further ethyl acetate (2×20 mL), and the organic phases were combined, dried (MgSO₄), filtered and the filtrate concentrated in vacuo to a yellow oil. The residue was taken up in DCM and added to a SNAP silica (10 g) cartridge and was purified by flash SP4 chromatography eluting with 30→100% EtOAc/cyclohexane. The appropriate fractions were collected and dried in vacuo to afford the desired product —N⁴-(3-((2r,5r)-5-(1,3-dioxoisoindolin-2-yl)-1,3-dioxan-2-yl)propyl)-6-(methoxy(phenyl)methyl)-N²-methylpyridine-2,4-dicarboxamide (162 mg, 0.283 mmol, 69% yield).

LCMS (2 min Formic): Rt=1.12 min, [MH]+=573.3.

¹H NMR (400 MHz, DMSO-d₆) δ ppm 9.00 (t, J=5.5 Hz, 1H) 8.63 (q, J=4.3 Hz, 1H) 8.31 (d, J=1.5 Hz, 1H) 8.06 (d, J=1.5 Hz, 1H) 7.80-7.90 (m, 4H) 7.49 (d, J=7.1 Hz, 2H) 7.35 (t, J=7.5 Hz, 2H) 7.22-7.30 (m, 1H) 5.49 (s, 1H) 4.67 (t, J=4.4 Hz, 1H) 4.19-4.29 (m, 3H) 4.00-4.07 (obs. m, 2H) 3.37 (s, 3H) 3.25-3.33 (obs. m, 2H) 2.87 (d, J=4.9 Hz, 3H) 1.56-1.71 (m, 4H)

Intermediate 220: (+/−)-tert-Butyl 2-(methylcarbamoyl)-6-(2-((methylsulfonyl)oxy)-1-phenylethyl)isonicotinate

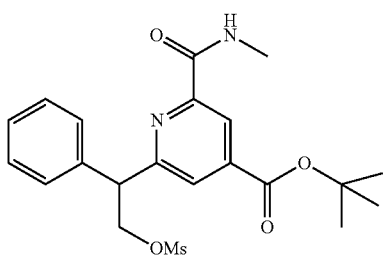 [SMILES: CNC(=O)c1cc(C(=O)OC(C)(C)C)cc(C(COS(C)(=O)=O)c2ccccc2)n1]

(+/−)-tert-Butyl 2-(2-hydroxy-1-phenylethyl)-6-(methylcarbamoyl)isonicotinate (200 mg, 0.561 mmol) was taken up in DCM (5 mL) under nitrogen. Et₃N (0.235 mL, 1.683 mmol) was added followed by Ms-Cl (0.066 mL, 0.842 mmol) and the reaction stirred at rt for 1 h. The reaction was partitioned between DCM and water (10 mL) and the aqueous layer was re-extracted with DCM (2×10 mL). The combined organics were eluted through a hydrophobic frit then concentrated in vacuo to give (+/−)-tert-butyl 2-(methylcarbamoyl)-6-(2-((methylsulfonyl)oxy)-1-phenylethyl)isonicotinate (313 mg, 0.540 mmol, 96% yield, 75% wt.) as a yellow oil.

LCMS (2 min High pH) R_t=1.20 min, m/z=435.6 for [MH]+

Intermediate 221: (+/−)-2-(2-Cyano-1-phenylethyl)-6-(methylcarbamoyl)isonicotinic acid

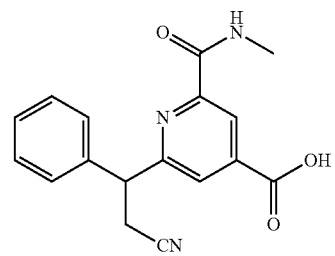 [SMILES: CNC(=O)c1cc(C(=O)O)cc(C(CC#N)c2ccccc2)n1]

(+/−)-tert-Butyl 2-(methylcarbamoyl)-6-(2-((methylsulfonyl)oxy)-1-phenylethyl)isonicotinate (313 mg, 0.54 mmol, 75% wt.), Et₃N (0.226 mL, 1.621 mmol) and NaCN (61 mg, 1.245 mmol) were combined in DMSO (5 mL) in a microwave vial and heated to 160° C. for 30 min in a Biotage initiator microwave. The reaction mixture was partitioned between EtOAc and water (15 mL each). The aqueous layer was re-extracted with EtOAc (2×15 mL) and the combined organics were dried (Na₂SO₄), filtered through a hydrophobic frit and concentrated in vacuo to yield an orange oil. The crude product was applied to a 25 g ULTRA silica SNAP cartridge in the minimum of DCM and eluted with 5-40% EtOAc in cyclohexane. The appropriate fractions were concentrated in vacuo to give (+/−)-tert-butyl 2-(2-cyano-1-phenylethyl)-6-(methylcarbamoyl) isonicotinate (78 mg, 0.203 mmol, 38% yield) as a yellow solid. LCMS of the aqueous layer showed the presence of the acid so it was carefully acidified with 2N HCl and extracted with EtOAc (2×15 mL). The combined organics were dried (Na₂SO₄), filtered through a hydrophobic frit and concentrated in vacuo to give (+/−)-2-(2-cyano-1-phenylethyl)-6-(methylcarbamoyl)isonicotinic acid (182 mg, 0.294 mmol, 55% yield) as a brown oil.

LCMS (2 min High pH) R_t=0.62 min, m/z=310.4 for [MH]+

EXAMPLES

Example 1 tert-Butyl 4-(3-(2-benzyl-6-(methylcarbamoyl)isonicotinamido)propyl)piperidine-1-carboxylate

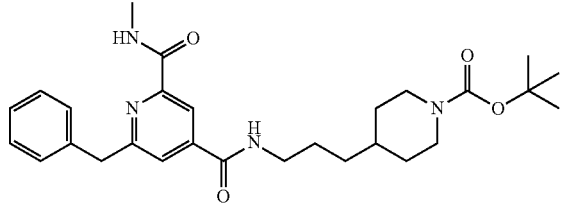 [SMILES: CNC(=O)c1cc(C(=O)NCCCC2CCN(C(=O)OC(C)(C)C)CC2)cc(Cc2ccccc2)n1]

2-Benzyl-6-(methylcarbamoyl)isonicotinic acid (50 mg, 0.185 mmol), HATU (112 mg, 0.295 mmol), DIPEA (0.097 mL, 0.555 mmol) and DMF (3 mL) were stirred at rt under $N_2$ then tert-butyl 4-(3-aminopropyl)piperidine-1-carboxylate (100 mg, 0.413 mmol) was added and the reaction stirred at rt under $N_2$ for 2 h. The solution was concentrated to give 300 mg of an orange oil. This was purified by chromatography on $SiO_2$ (Biotage® SNAP 25 g cartridge, eluting with 0-100% ethylacetate/cyclohexane). The appropriate fractions were concentrated to give 25 mg of a yellow oil. The reaction was purified by MDAP (Formic). The fractions containing the desired product were concentrated to give tert-butyl 4-(3-(2-benzyl-6-(methylcarbamoyl)isonicotinamido)propyl)piperidine-1-carboxylate (18 mg, 0.033 mmol, 17.70% yield) as an off white solid.

LCMS (2 min Formic): Rt=1.28 min, [MH]+=495.5.

Example 2

6-Benzyl-$N^2$-methyl-$N^4$-(2-(piperidin-4-yl)ethyl)pyridine-2,4-dicarboxamide

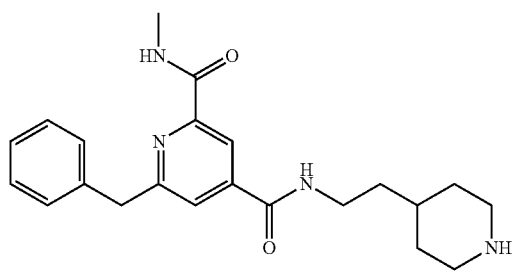 [SMILES: CNC(=O)c1cc(C(=O)NCCC2CCNCC2)cc(Cc2ccccc2)n1]

tert-Butyl 4-(2-(2-benzyl-6-(methylcarbamoyl)isonicotinamido)ethyl)piperidine-1-carboxylate (10 mg, 0.021 mmol) and TFA (0.5 mL, 6.49 mmol) were stirred at rt in DCM (2 mL) for 1 h. The reaction mixture was concentrated and loaded onto a 1 g SCX cartridge (pre-conditioned with MeOH) and eluted with MeOH (20 mL) followed by 2M $NH_3$ in MeOH (20 mL). The ammonia fractions containing product were combined and concentrated to give 6-benzyl-$N^2$-methyl-$N^4$-(2-(piperidin-4-yl)ethyl)pyridine-2,4-dicarboxamide (7 mg, 0.017 mmol, 80% yield) as a colourless oil.

LCMS (2 min Formic): Rt=0.59 min, [MH]+=381.3.

Example 3

6-Benzyl-$N^2$-methyl-$N^4$-(3-(piperidin-4-yl)propyl)pyridine-2,4-dicarboxamide

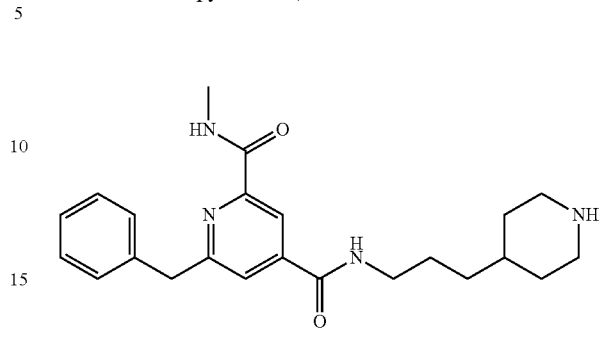

tert-Butyl 4-(3-(2-benzyl-6-(methylcarbamoyl)isonicotinamido)propyl)piperidine-1-carboxylate (15 mg, 0.030 mmol) and TFA (0.5 mL, 6.49 mmol) were stirred at rt in DCM (2 mL) for 1 h. The reaction mixture was concentrated and loaded onto a 1 g SCX cartridge (pre-conditioned with MeOH) and eluted with MeOH (20 mL) followed by 2M $NH_3$ in MeOH (20 mL). The ammonia fractions containing product were combined and concentrated to give 19 mg of an off white solid. This was purified by MDAP (Formic). The fractions containing the desired product were concentrated to give 6-benzyl-$N^2$-methyl-$N^4$-(3-(piperidin-4-yl)propyl)pyridine-2,4-dicarboxamide (5 mg, 0.011 mmol, 37.6% yield) as a colourless oil.

LCMS (2 min Formic): Rt=0.61 min, [MH]+=395.3.

Example 4

6-Benzyl-$N^4$-((1R,5S,6r)-3-oxabicyclo[3.1.0]hexan-6-yl)-$N^2$-methylpyridine-2,4-dicarboxamide

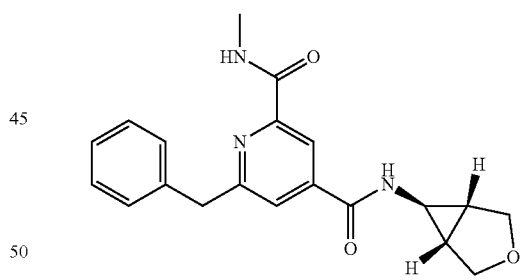

To a solution of 2-benzyl-6-(methylcarbamoyl)isonicotinic acid, trifluoroacetic acid salt (100 mg, 0.260 mmol) and HATU (198 mg, 0.520 mmol) in DMF (2400 µL) was added DIPEA (227 µL, 1.301 mmol) and (1R,5S,6r)-3-oxabicyclo[3.1.0]hexan-6-amine hydrochloride (53 mg, 0.391 mmol). The reaction mixture was poured onto water:saturated $NaHCO_3$ (1:1) and extracted with EtOAc (3×10 mL). The combined organics were washed with brine (2×5 mL), dried though a hydrophobic frit and evaporated in vacuo. The residue (102 mg) was loaded in DCM onto a 10 g SNAP cartridge and purified via Biotage® SP4 flash chromatography, eluting from 12-62% (3:1 EtOAc:EtOH)/cyclohexane. The relevant fractions were combined and evaporated in vacuo to yield the desired product as a colourless glass. The glass was sonicated with diethyl ether and evapo-

Example 5

6-Benzyl-$N^2$-methyl-$N^4$-(oxetan-3-yl)pyridine-2,4-dicarboxamide

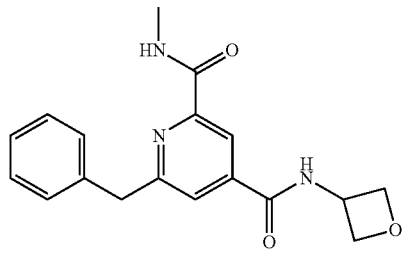 [SMILES: CNC(=O)c1cc(C(=O)NC2COC2)cc(Cc2ccccc2)n1]

2-benzyl-6-(methylcarbamoyl)isonicotinic acid (58 mg, 0.215 mmol) was suspended in DCM (10 mL) in a scintillation vial and Et$_3$N (0.060 mL, 0.429 mmol) and HATU (106 mg, 0.279 mmol) were added, then the mixture was stirred for 20 min before the addition of oxetan-3-amine (31.4 mg, 0.429 mmol). The resulting yellow solution was stirred for 2 h, then washed with water (10 mL), dried and evaporated in vacuo and the residue purified by chromatography on a 10 g silica column to give 6-benzyl-$N^2$-methyl-$N^4$-(oxetan-3-yl)pyridine-2,4-dicarboxamide (15 mg, 0.046 mmol, 21.48% yield) as a colourless solid.

LCMS (2 min High pH): Rt=0.87 min, [MH]$^+$=326.2.

Example 6

(+/−)-6-(3-Methoxybenzyl)-$N^2$-methyl-$N^4$-(2-(morpholin-2-yl)ethyl)pyridine-2,4-dicarboxamide

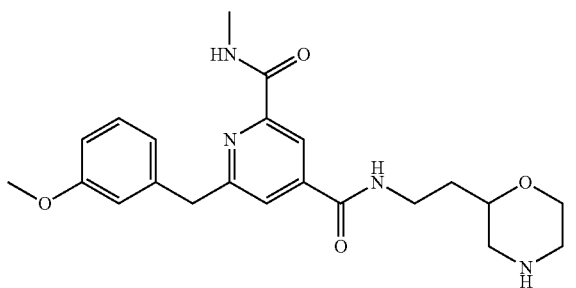 [SMILES: CNC(=O)c1cc(C(=O)NCCC2CNCCO2)cc(Cc2cccc(OC)c2)n1]

2-(3-Methoxybenzyl)-6-(methylcarbamoyl)isonicotinic acid (40 mg, 0.133 mmol) was suspended in DCM (10 mL) in a scintiallation vial, and Et$_3$N (0.037 mL, 0.266 mmol) and HATU (65.8 mg, 0.173 mmol) were added, then the mixture was stirred for 20 min before the addition of tert-butyl 2-(2-aminoethyl)morpholine-4-carboxylate (40 mg, 0.174 mmol, the preparation of which has been reported in International Patent Application Publication No. WO 2003/097618). The resulting yellow solution was stirred for 2 h, then washed with water (10 mL), dried and evaporated in vacuo to give a pale yellow gum. The impure material was dissolved in DCM (2 mL) and treated with TFA (1 mL). The solution was stirred for 1 h at rt, then evaporated in vacuo and the residue dissolved in MeOH and loaded onto a 5 g SCX cartridge. This was washed with MeOH (20 mL), then eluted with 2M NH$_3$ in MeOH and the eluant evaporated in vacuo to give 6-(3-methoxybenzyl)-$N^2$-methyl-$N^4$-(2-(morpholin-2-yl)ethyl)pyridine-2,4-dicarboxamide (20 mg, 0.048 mmol, 36.4% yield).

LCMS (2 min High pH): Rt=0.83 min, [MH]$^+$=413.4.

Example 7

(+/−)-6-(3-Methoxybenzyl)-$N^2$-methyl-$N^4$-(2-(4-methylmorpholin-2-yl)ethyl)pyridine-2,4-dicarboxamide

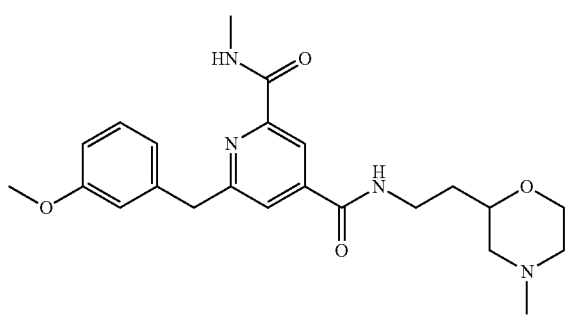 [SMILES: CNC(=O)c1cc(C(=O)NCCC2CN(C)CCO2)cc(Cc2cccc(OC)c2)n1]

To a solution of 2-(3-methoxybenzyl)-6-(methylcarbamoyl)isonicotinic acid (70 mg, 0.233 mmol) in DMF (1 mL) was added HATU (133 mg, 0.350 mmol), followed by 2-(4-methylmorpholin-2-yl)ethanamine, big-hydrochloride (76 mg, 0.350 mmol, commercially available from, for example, Azepine product list) and DIPEA (0.204 mL, 1.165 mmol). The resulting reaction mixture was stirred at rt during 4 h (formed yellow solution). The reaction mixture was purified directly by MDAP (Formic). The fractions containing desired product were partitioned between sat. NaHCO$_3$ solution and DCM. The organic layer was extracted with DCM (2×20 mL), dried (Na$_2$SO$_4$) and concentrated in vacuo to give 6-(3-methoxybenzyl)-$N^2$-methyl-$N^4$-(2-(4-methylmorpholin-2-yl)ethyl)pyridine-2,4-dicarboxamide (35 mg, 0.074 mmol, 31.7% yield) as a yellow oil.

LCMS (2 min Formic): Rt=0.62 min, [MH]+=427.3.

Example 8

(+/−)-tert-Butyl 2-(2-(2-(methylcarbamoyl)-6-(1-phenylethyl)isonicotinamido)ethyl)morpholine-4-carboxylate

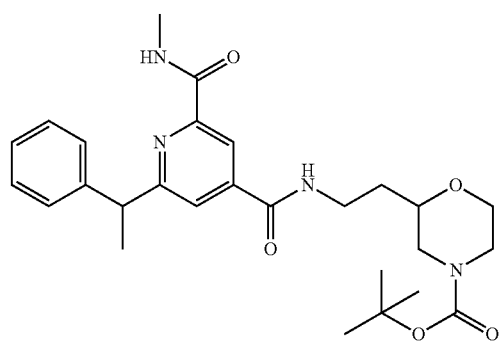 [SMILES: CNC(=O)c1cc(C(=O)NCCC2CN(C(=O)OC(C)(C)C)CCO2)cc(C(C)c2ccccc2)n1]

2-(Methylcarbamoyl)-6-(1-phenylethyl)isonicotinic acid (50 mg, 0.176 mmol) was taken up in DMF (2 mL), HATU (100 mg, 0.264 mmol) was added, immediately followed by DIPEA (0.092 mL, 0.528 mmol) and the reaction left to stir at rt for 10 min. tert-Butyl 2-(2-aminoethyl)morpholine-4-carboxylate (60.8 mg, 0.264 mmol, the preparation of which has been reported in patent: WO2003097618) dissolved in DMF (1 mL), was added and the reaction left to stir for 1 h. The reaction was concentrated in vacuo. The residue was dissolved in ethyl acetate (10 mL) and washed with NaHCO$_3$ (10 mL). The aqueous layer was washed with EtOAc (10 mL). The combined organic layers were washed with brine (10 mL) before being dried over sodium sulfate and filtered though a hydrophobic frit. The mixture was concentrated in vacuo. The crude product was purified by MDAP (high pH). The appropriate fractions were concentrated in vacuo to afford—tert-butyl 2-(2-(2-(methylcarbamoyl)-6-(1-phenylethyl)isonicotinamido)ethyl)morpholine-4-carboxylate (11.9 mg, 0.024 mmol, 13.63% yield).

LCMS (2 min High pH): Rt=1.22 min, [MH]$^+$=497.4.

Examples 9-11 and 15

Amide array of
2-benzyl-6-(methylcarbamoyl)isonicotinic acid
Monomers

| Ex No. | Reagent Name | Structure | MW | Reagent Mass (g) | mmol |
|---|---|---|---|---|---|
| 9 | 3-Morpholinopropan-1-amine | 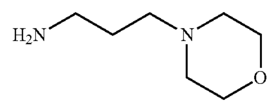 | 144.2 | 0.017 | 0.120 |
| 10 | (+/−)-Tetrahydrofuran-3-amine | 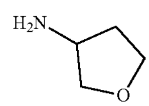 | 87.1 | 0.010 | 0.120 |
| 11 | tert-Butyl 4-(3-aminopropyl)piperazine-1-carboxylate | 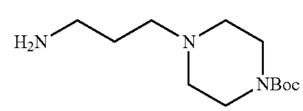 [SMILES: CC(C)(C)OC(=O)N1CCN(CCCN)CC1] | 243.4 | 0.029 | 0.120 |
| 15 | (+/−)-2-(4-Methylmorpholin-2-yl)ethanamine | 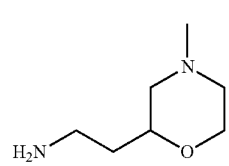 | 144.2 | 0.017 | 0.120 |

A stock solution was prepared containing 2-benzyl-6-(methylcarbamoyl)isonicotinic acid (162 mg) plus HATU (228 mg) dissolved together in DMF (3 mL). DIPEA (330 μL) was added and the vials capped and shaken to aid dissolution. An aliquot of this reaction mixture (0.5 mL, 0.1 mmol) was added to a set of preweighed amines with the structures shown above (0.12 mmol) in matrix vials (1.2 mL). The vials were capped and shaken to disperse the contents and stood at rt for 18 h. The samples were injected (0.6 mL) as is and purified by MDAP (High pH). The solvent was dried under a stream of $N_2$ to give the required product.

BOC deprotection of example 11: the Boc-protected intermediate was redissolved in 4 N HCl/1,4-dioxane (0.5 mL) and DCM (0.5 mL) was added. The vial was capped and stood at rt for 1 h. The solvent was removed to dryness to afford Example 11 as its HCl salt.

EXAMPLES

| Ex No. | Name | Structure | Mass (mg) | Yield (%) | [MH]+ | Rt (min) * |
|---|---|---|---|---|---|---|
| 9 | 6-Benzyl-$N^2$-methyl-$N^4$-(3-morpholinopropyl)pyridine-2,4-dicarboxamide | 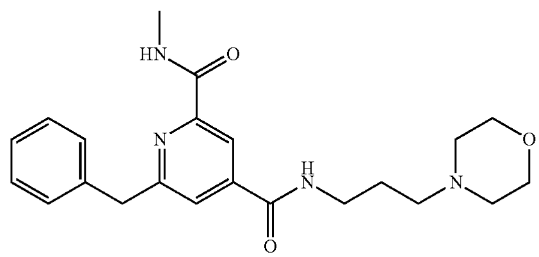 [SMILES: CNC(=O)c1cc(C(=O)NCCCN2CCOCC2)cc(Cc2ccccc2)n1] | 15.2 | 35 | 397 | 0.55 |
| 10 | (+/−)-6-Benzyl-$N^2$-methyl-$N^4$-(tetrahydrofuran-3-yl)pyridine-2,4-dicarboxamide | 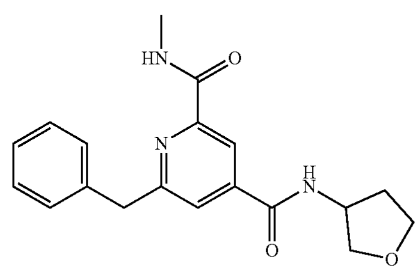 [SMILES: CNC(=O)c1cc(C(=O)NC2CCOC2)cc(Cc2ccccc2)n1] | 15.1 | 40 | 340 | 0.86 |
| 11 | 6-Benzyl-$N^2$-methyl-$N^4$-(3-(piperazin-1-yl)propyl)pyridine-2,4-dicarboxamide | 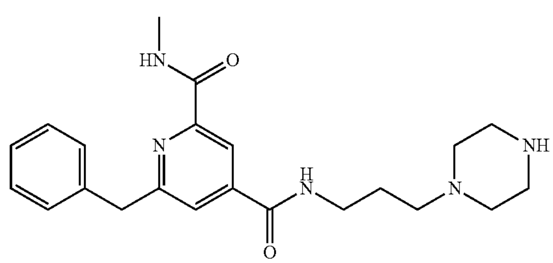 | 8.2 | 17 | 396 | 0.45 |
| 15 | (+/−)-6-Benzyl-$N^2$-methyl-$N^4$-(2-(4-methylmorpholin-2-yl)ethyl)pyridine-2,4-dicarboxamide | 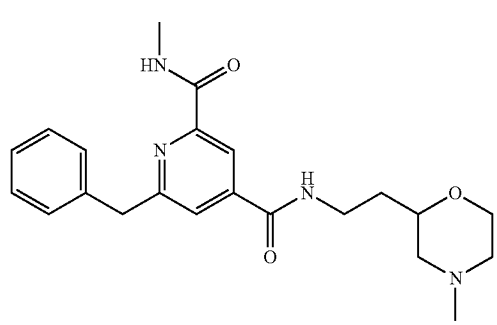 [SMILES: CNC(=O)c1cc(C(=O)NCCC2CN(C)CCO2)cc(Cc2ccccc2)n1] | 19.5 | 44 | 397 | 0.58 |

* All LCMS were conducted using 2 min Formic.

Example 12

(+/−)-N²-Methyl-N⁴-(2-(morpholin-2-yl)ethyl)-6-(1-phenylethyl)pyridine-2,4-dicarboxamide

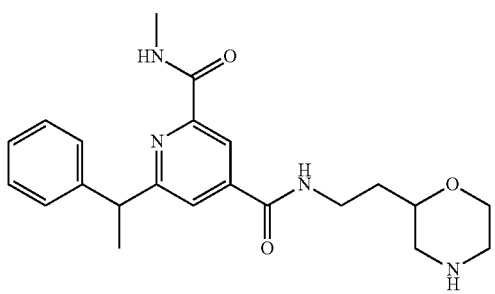 [SMILES: CNC(=O)c1cc(C(=O)NCCC2CNCCO2)cc(C(C)c2ccccc2)n1]

tert-Butyl 2-(2-(methylcarbamoyl)-6-(1-phenylethyl) isonicotinamido)morpholine-4-carboxylate (8.1 mg, 0.017 mmol) was dissolved in DCM (2 mL), TFA (0.5 mL, 6.49 mmol) was added and the reaction left to stir at rt for 30 min. The mixture was concentrated in vacuo. The sample was loaded in MeOH and purified by SPE on sulphonic acid (SCX) 500 mg eluting with MeOH followed by 2M ammonia/MeOH. The appropriate fractions were combined and evaporated in vacuo to afford the desired product (4.3 mg).

LCMS (2 min High pH): Rt=0.89 min, [MH]⁺=397.4.

Example 13

N⁴-((1R,5S,6r)-3-Oxabicyclo[3.1.0]hexan-6-yl)-6-(3-methoxybenzyl)-N²-methylpyridine-2,4-dicarboxamide

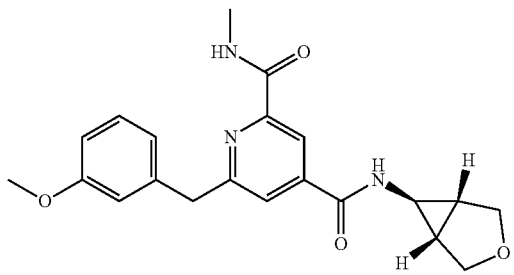 [SMILES: CNC(=O)c1cc(C(=O)N[C@H]2[C@@H]3COC[C@@H]32)cc(Cc2cccc(OC)c2)n1]

To a solution of 2-(3-methoxybenzyl)-6-(methylcarbamoyl)isonicotinic acid (48 mg, 0.160 mmol) in DMF (1 mL) was added HATU (91 mg, 0.240 mmol) followed by (1R,5S,6r)-3-oxabicyclo[3.1.0]hexan-6-amine, hydrochloride (31.7 mg, 0.234 mmol) and DIPEA (0.140 mL, 0.799 mmol). The resulting reaction mixture was stirred at rt for 1 h (formed a yellow solution). The reaction mixture was stirred at rt for a further 2 h. A further portion of HATU (70 mg, 0.184 mmol) and (1R,5S,6r)-3-oxabicyclo[3.1.0]hexan-6-amine, hydrochloride (30 mg, 0.221 mmol) were added and reaction stirred at rt for a further 1 h. The reaction mixture was purified directly by MDAP (Formic). The fractions containing desired product were partitioned between sat. NaHCO₃ solution and DCM. The organic layer was extracted with DCM (2×20 mL), dried (Na₂SO₄) and concentrated in vacuo to give N⁴-(3-oxabicyclo[3.1.0] hexan-6-yl)-6-(3-methoxybenzyl)-N²-methylpyridine-2,4-dicarboxamide (44 mg, 0.115 mmol, 72.2% yield) as a white oil.

LCMS (2 min Formic): Rt=0.88 min, [MH]⁺=382.2.

Example 14

(+/−)-tert-Butyl 4-(2-(2-(methylcarbamoyl)-6-(1-phenylethyl)isonicotinamido)ethyl)piperidine-1-carboxylate

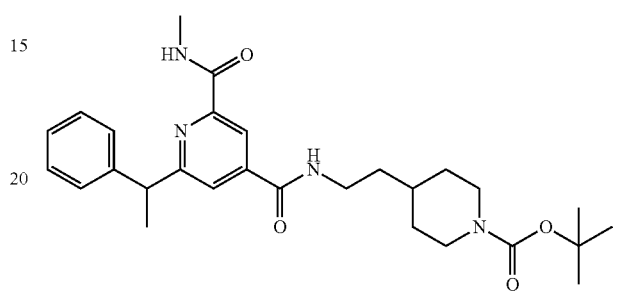

2-(Methylcarbamoyl)-6-(1-phenylethyl)isonicotinic acid (50 mg, 0.176 mmol) was taken up in DMF (2 mL). DIPEA (0.092 mL, 0.528 mmol) was added, shortly followed by HATU (100 mg, 0.264 mmol) and the reaction left to stir at rt for 10 min. tert-Butyl 4-(2-aminoethyl)piperidine-1-carboxylate (0.01061 mL, 0.176 mmol), dissolved in DMF (1 mL), was added to the reaction and it was left to stir for a further 1 h. The reaction was concentrated in vacuo. The residue was dissolved in EtOAc (10 mL) and then washed with NaHCO₃ (10 mL). The aqueous layer was washed with EtOAc (10 mL) to remove any residual organic compounds. The combined organic layers were washed with brine (10 mL) before being dried over Na₂SO₄ and filtered through a hydrophobic frit. The sample was dissolved in 1:1 MeOH:DMSO (0.8 mL) and purified by MDAP (High pH). The solvent was evaporated in vacuo to give the required product (42.7 mg).

LCMS (2 min High pH): Rt=1.30 min, [MH]⁺=495.4.

Example 16

(+/−)-N²-Methyl-6-(1-phenylethyl)-N⁴-(2-(piperidin-4-yl)ethyl)pyridine-2,4-dicarboxamide

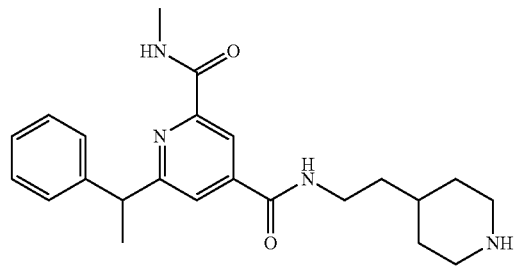 [SMILES: CNC(=O)c1cc(C(=O)NCCC2CCNCC2)cc(C(C)c2ccccc2)n1]

tert-Butyl 4-(2-(2-(methylcarbamoyl)-6-(1-phenylethyl) isonicotinamido)ethyl)piperidine-1-carboxylate (39.7 mg, 0.080 mmol) was taken up in DCM (2 mL). TFA (0.5 mL, 6.49 mmol) was added and the reaction left to stir at rt for 30 min. The reaction was left to stir for another 1.5 h. The reaction was then left to stir overnight. The reaction was concentrated in vacuo. The sample was loaded in MeOH and purified by SPE on sulphonic acid (SCX, 500 mg). The appropriate fractions were combined and evaporated in vacuo to give the required product (3.7 mg) as a yellow solid.

LCMS (2 min High pH): Rt=0.94 min, [MH]+=395.4.

Example 17

$N^4$-((1R,5S,6s)-3-Azabicyclo[3.1.0]hexan-6-yl)-6-(3-methoxybenzyl)-$N^2$-methylpyridine-2,4-dicarboxamide

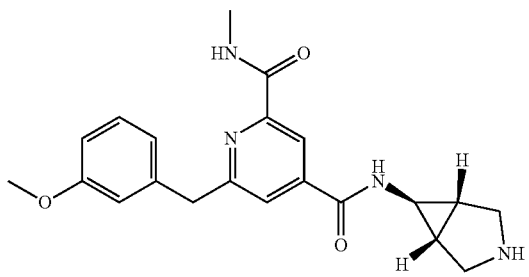 [SMILES: CNC(=O)c1cc(C(=O)N[C@H]2[C@@H]3CNC[C@@H]32)cc(Cc2cccc(OC)c2)n1]

To a solution of (1R,5S,6s)-tert-butyl 6-(2-(3-methoxybenzyl)-6-(methylcarbamoyl)isonicotinamido)-3-azabicyclo[3.1.0]hexane-3-carboxylate (342 mg, 0.712 mmol) in DCM (5 mL) was added TFA (1 mL, 12.98 mmol) and the reaction mixture was stirred under $N_2$ at rt for 2 h. The reaction mixture was concentrated to give 983 mg of a yellow oil and loaded onto a 5 g SCX cartridge (pre-conditioned with MeOH) and eluted with MeOH (30 mL) followed by 2M $NH_3$ in MeOH (30 mL). The ammonia fractions containing product were combined and concentrated to give $N^4$-((1R,5S,6s)-3-azabicyclo[3.1.0]hexan-6-yl)-6-(3-methoxybenzyl)-$N^2$-methylpyridine-2,4-dicarboxamide (229 mg, 0.602 mmol, 84.6% yield) as a white solid.

LCMS (2 min Formic): Rt=0.56 min, [MH]+=381.3.

Example 18

(1R,5S,6s)-tert-Butyl 6-(2-(3-methoxybenzyl)-6-(methylcarbamoyl)isonicotinamido)-3-azabicyclo[3.1.0]hexane-3-carboxylate

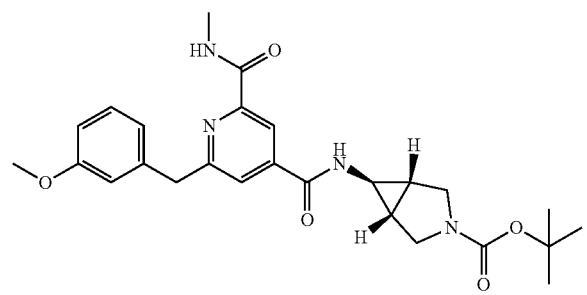 [SMILES: CNC(=O)c1cc(C(=O)N[C@H]2[C@@H]3CN(C(=O)OC(C)(C)C)C[C@@H]32)cc(Cc2cccc(OC)c2)n1]

To a solution of 2-(3-methoxybenzyl)-6-(methylcarbamoyl)isonicotinic acid (250 mg, 0.832 mmol) in DMF (3 mL) was added HATU (475 mg, 1.249 mmol) followed by (1R,5S,6r)-tert-butyl 6-amino-3-azabicyclo[3.1.0]hexane-3-carboxylate (248 mg, 1.249 mmol, commercially available from, for example, Fluorochem) and DIPEA (0.582 mL, 3.33 mmol). The resulting reaction mixture was stirred at rt for 1 h (formed yellow solution). This was then washed with LiCl (20 mL), partitioned between EtOAc (40 mL) and water (40 mL), the aqueous phase was extracted with EtOAc (2×40 mL), dried over a hydrophobic frit and concentrated to give 930 mg of an orange oil. This was loaded onto a KP-Sil 50 g SNAP Biotage® cartridge and purified by flash chromatography (gradient 10%-80% ethyl actetate/cyclohexane). The fractions containing product were combined and concentrated to give the title compound (350 mg) as a white solid.

LCMS (2 min Formic): Rt=1.11 min, [MH]+=481.2.

Example 19

6-(3-Methoxybenzyl)-$N^2$-methyl-$N^4$-((1R,5S,6s)-3-methyl-3-azabicyclo[3.1.0]hexan-6-yl)pyridine-2,4-dicarboxamide

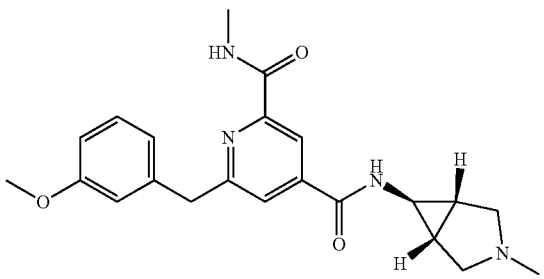

$N^4$-((1R,5S,6s)-3-Azabicyclo[3.1.0]hexan-6-yl)-6-(3-methoxybenzyl)-$N^2$-methylpyridine-2,4-dicarboxamide (56 mg, 0.147 mmol), formic acid (0.011 mL, 0.294 mmol), 37% formaldehyde in water (0.022 mL, 0.294 mmol) and MeOH (2 mL) were heated at 45° C. under $N_2$ for 2 h. $NaHCO_3$ solution (10 mL) was added. The reaction mixture was extracted with DCM (3×30 mL), dried over a hydrophobic frit and concentrated to give 190 mg of crude pale yellow residue. This was purified by chromatography on $SiO_2$ (Biotage® SNAP 10 g cartridge, eluting with 10-60% 2M $NH_3$ in MeOH/DCM). The fractions containing the desired product were concentrated in vacuo to give 6-(3-methoxybenzyl)-$N^2$-methyl-$N^4$-((1R,5S,6s)-3-methyl-3-azabicyclo[3.1.0]hexan-6-yl)pyridine-2,4-dicarboxamide (60 mg, 0.137 mmol, 93% yield) as a white solid.

LCMS (2 min Formic): Rt=0.58 min, [MH]+=395.3.

Example 20

N⁴-((1R,5S,6s)-3-Acetyl-3-azabicyclo[3.1.0]hexan-6-yl)-6-(3-methoxybenzyl)-N²-methylpyridine-2,4-dicarboxamide

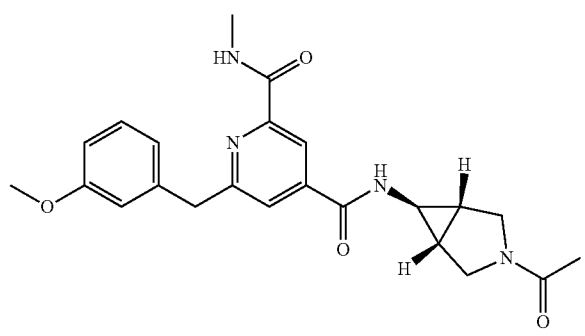 [SMILES: CNC(=O)c1cc(C(=O)N[C@H]2[C@@H]3CN(C(C)=O)C[C@@H]32)cc(Cc2cccc(OC)c2)n1]

N⁴-((1R,5S,6s)-3-azabicyclo[3.1.0]hexan-6-yl)-6-(3-methoxybenzyl)-N²-methylpyridine-2,4-dicarboxamide (57.8 mg, 0.152 mmol) was dissolved in DMF (1 mL), then Et₃N (0.025 mL, 0.182 mmol) and acetyl chloride (0.013 mL, 0.182 mmol) were added and the mixture was stirred for 1.5 h at rt. Further portions of Et₃N (0.025 mL, 0.182 mmol) and acetyl chloride (0.013 mL, 0.182 mmol) were added to the reaction mixture and the reaction stirred for 2 h. Further portions of Et₃N (0.025 mL, 0.182 mmol) and acetyl chloride (0.013 mL, 0.182 mmol) were added to the reaction mixture and the reaction mixture stirred overnight. Further portions of Et₃N (0.025 mL, 0.182 mmol) and acetyl chloride (0.013 mL, 0.182 mmol) were added to the reaction mixture (with some droplets of DCM in 1 mL of DMF to help to dissolve the insoluble compound) and the reaction mixture stirred overnight. The solution was purified by MDAP (formic) to give as a colourless solid N⁴-((1R,5S,6s)-3-acetyl-3-azabicyclo[3.1.0]hexan-6-yl)-6-(3-methoxybenzyl)-N²-methylpyridine-2,4-dicarboxamide (27.1 mg, 0.058 mmol, 38.0% yield).

LCMS (2 min Formic): Rt=0.83 min, [MH]+=423.2.

Examples 21-22

Amide array of 2-benzyl-6-(methylcarbamoyl)isonicotinic acid

Monomers

| Ex No. | Reagent Name | Structure | MW | Reagent Mass (g) | mmol |
|---|---|---|---|---|---|
| 21 | Tetrahydro-2H-pyran-4-amine | 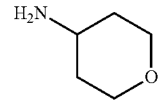 | 101.15 | 0.012 | 0.120 |
| 22 | (1R,5S,6s)-tert-Butyl 6-amino-3-azabicyclo[3.1.0]hexane-3-carboxylate | 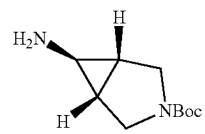 [SMILES: CC(C)(C)OC(=O)N1C[C@@H]2[C@@H](N)[C@@H]2C1] | 198.26 | 0.024 | 0.120 |

A stock solution was prepared of 2-benzyl-6-(methylcarbamoyl)isonicotinic acid (0.243 g) plus HATU (0.342 g) dissolved together in DMF (4.5 mL). DIPEA was added (480 µL), and the vial capped and shaken to aid dissolution. An aliquot of this reaction mixture (0.75 mL, 0.15 mmol) was added to a set of preweighed amines (0.180 mmol), shown in the table above, in matrix vials (1.2 mL). These vials were capped and shaken to disperse contents and stood at rt for 2 h. The samples were injected as is and purified by MDAP (High pH). The solvent was dried under a stream of N₂ to give the required product amides.

BOC deprotection for compounds for example 22: the Boc-protected intermediate was redissolved in 4 M HCl/1,4-dioxane (0.75 mL) and DCM (0.75 mL) was added. The vial was capped and stood at rt for 1 h. The solvent was removed to dryness to afford the desired product as its HCl salt.

EXAMPLES

| Ex No. | Name | Structure | Mass (mg) | Yield (%) | [MH]+ | Rt (min) * |
|---|---|---|---|---|---|---|
| 21 | 6-Benzyl-N²-methyl-N⁴-(tetrahydro-2H-pyran-4-yl)pyridine-2,4-dicarboxamide | 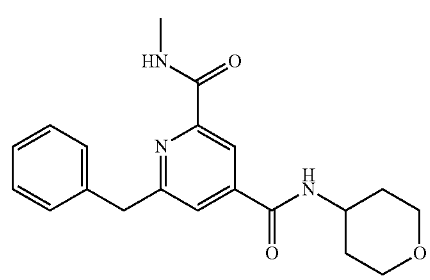 [SMILES: CNC(=O)c1cc(C(=O)NC2CCOCC2)cc(Cc2ccccc2)n1] | 15.7 | 27 | 354 | 0.89 |

| Ex No. | Name | Structure | Mass (mg) | Yield (%) | [MH]+ | Rt (min) * |
|---|---|---|---|---|---|---|
| 22 | 6-Benzyl-N⁴-((1R,5S,6s)-3-azabicyclo[3.1.0]hexan-6-yl)-N²-methylpyridine-2,4-dicarboxamide hydrochloride | 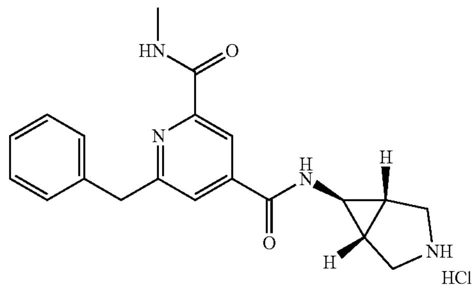 [SMILES: CNC(=O)c1cc(C(=O)N[C@H]2[C@@H]3CNC[C@@H]32)cc(Cc2ccccc2)n1 ; Cl] | 38 | 59 | 351 | 0.56 |

* All LCMS were conducted using 2 min Formic.

Example 23

N⁴-((1R,5S,6r)-3-Oxabicyclo[3.1.0]hexan-6-yl)-6-(3-(2-hydroxyethoxy)benzyl)-N²-methylpyridine-2,4-dicarboxamide

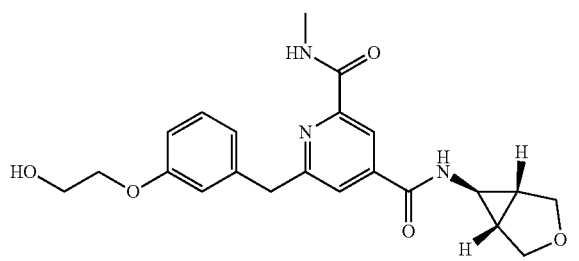 [SMILES: CNC(=O)c1cc(C(=O)N[C@H]2[C@@H]3COC[C@@H]32)cc(Cc2cccc(OCCO)c2)n1]

To a solution of 2-(3-(2-hydroxyethoxy)benzyl)-6-(methylcarbamoyl)isonicotinic acid (98 mg, 0.297 mmol) in DMF (1 mL) was added HATU (169 mg, 0.445 mmol) followed by (1R,5S,6r)-3-oxabicyclo[3.1.0]hexan-6-amine (58.8 mg, 0.593 mmol) and DIPEA (0.259 mL, 1.483 mmol). The resulting reaction mixture was stirred at rt overnight. The reaction mixture was purified directly by MDAP (TFA). The fractions containing the desired product were partitioned between sat. NaHCO₃ solution and DCM. The organic layer was extracted with DCM (2×20 mL) then dried and concentrated in vacuo to give N⁴-((1R,5S,6r)-3-oxabicyclo[3.1.0]hexan-6-yl)-6-(3-(2-hydroxyethoxy)benzyl)-N²-methylpyridine-2,4-dicarboxamide (7 mg, 0.015 mmol, 5.16% yield) as a colourless oil.

LCMS (2 min Formic): Rt=0.74 min, [MH]+=412.1

Examples 24-25

Amide array of 2-benzyl-6-(methylcarbamoyl)isonicotinic acid Monomers

| Ex No. | Reagent Name | Structure | MW | Reagent Mass (g) | mmol |
|---|---|---|---|---|---|
| 24 | (+/−)-tert-Butyl 3-(2-aminoethyl)piperidine-1-carboxylate | 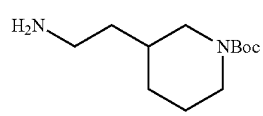 [SMILES: CC(C)(C)OC(=O)N1CCCC(CCN)C1] | 228.33 | 0.023 | 0.100 |
| 25 | 2-(Tetrahydro-2H-pyran-4-yl)ethanamine | 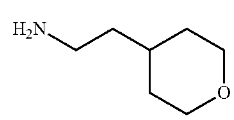 | 129.20 | 0.013 | 0.100 |

2-Benzyl-6-(methylcarbamoyl)isonicotinic acid was added to HATU (0.038 g, 0.100 mmol) and DIPEA (0.052 mL, 0.300 mmol) and dissolved in DMF (0.5 mL) and left for 5 min. This solution was dispensed to the amine monomers (0.100 mmol) shown in the table and left for 24 h at 22° C. The samples were purified directly by MDAP (high pH). The solvent was dried under a stream of $N_2$ to give the required products. For example 24, the Boc-protected intermediate was dissolved in DCM (300 µL), to this solution was added 4M HCl in 1,4-dioxane (500 µL). The solution was left for 2 h at 20° C. The solvent was removed in the blowdown unit to provide example 25 as its HCl salt.

EXAMPLES

| Ex No. | Name | Structure | Mass (mg) | Yield (%) | [MH]+ | Rt (min) * |
|---|---|---|---|---|---|---|
| 24 | (+/−)-6-Benzyl-$N^2$-methyl-$N^4$-(2-(piperidin-3-yl)ethyl)pyridine-2,4-dicarboxamide hydrochloride | 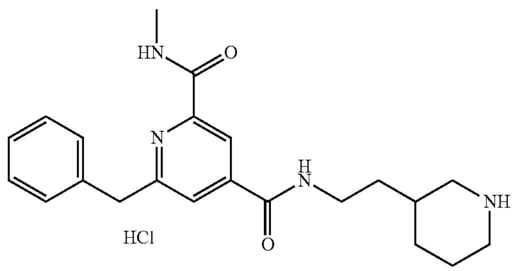 [SMILES: CNC(=O)c1cc(C(=O)NCCC2CCCNC2)cc(Cc2ccccc2)n1 ; Cl] | 10.9 | 24 | 381 | 0.61 |
| 25 | 6-Benzyl-$N^2$-methyl-$N^4$-(2-(tetrahydro-2H-pyran-4-yl)ethyl)pyridine-2,4-dicarboxamide | 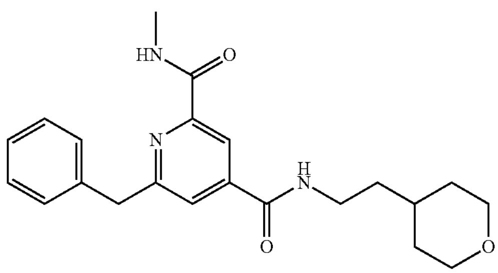 [SMILES: CNC(=O)c1cc(C(=O)NCCC2CCOCC2)cc(Cc2ccccc2)n1] | 8 | 17 | 382 | 0.96 |

* All LCMS were conducted using 2 min Formic.

Example 26

(+/−)-6-(3-Methoxybenzyl)-$N^2$-methyl-$N^4$-(3-(morpholin-2-yl)propyl)pyridine-2,4-dicarboxamide

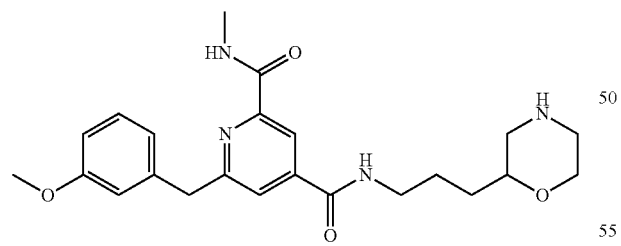

tert-Butyl 2-(3-(2-(3-methoxybenzyl)-6-(methylcarbamoyl)isonicotinamido)propyl)morpholine-4-carboxylate (60 mg, 0.114 mmol) was dissolved in a mixture of DCM (2 mL) and TFA (1 mL) and the solution was stirred for 2 h at rt, then evaporated in vacuo and the residue dissolved in MeOH and loaded onto a 5 g SCX cartridge. This was washed with MeOH (20 mL), then eluted with 2M $NH_3$ in MeOH (20 mL) and the eluant evaporated in vacuo to give 6-(3-methoxybenzyl)-$N^2$-methyl-$N^4$-(3-(morpholin-2-yl)propyl) pyridine-2,4-dicarboxamide (40 mg, 0.094 mmol, 82% yield)

LCMS (2 min High pH): Rt=0.86 min, [MH]+=427.4.

Example 27

$N^2$-Methyl-$N^4$-(3-((S)-morpholin-2-yl)propyl)-6-(1-phenylethyl)pyridine-2,4-dicarboxamide, 1:1 Mixture of Diastereomers at Undefined Stereocentre

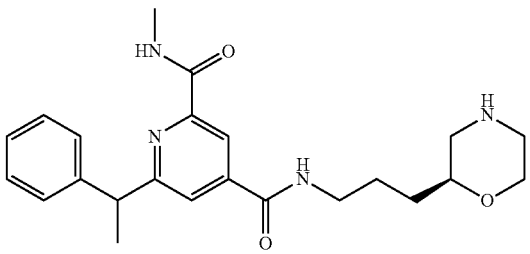

2-(Methylcarbamoyl)-6-(1-phenylethyl)isonicotinic acid (40 mg, 0.141 mmol), HATU (80 mg, 0.211 mmol), $Et_3N$ (39.2 µl, 0.281 mmol) and (S)-tert-butyl 2-(3-aminopropyl) morpholine-4-carboxylate (44.7 mg, 0.183 mmol) were dissolved in DMF (1 mL) and stirred for 1 h, then the mixture was stirred for 1 h at rt. The mixture was purified by MDAP (high pH) to give the intermediate Boc-protected compound (2S)-tert-butyl 2-(3-(2-(methylcarbamoyl)-6-(1-phenylethyl)isonicotinamido)propyl)morpholine-4-carboxylate (35 mg, 0.069 mmol, 48.7% yield)

The Boc-protected compound was dissolved in DCM (1 mL) and treated with TFA (0.5 mL) and the mixture was stirred for 1 h at rt, then evaporated in vacuo and the residue was dissolved in MeOH and loaded onto a 5 g SCX cartridge. This was washed with MeOH (10 mL), then eluted with 2M NH$_3$ in MeOH and the eluant evaporated in vacuo to give N$^2$-methyl-N$^4$-(3-((S)-morpholin-2-yl)propyl)-6-(1-phenylethyl)pyridine-2,4-dicarboxamide (18 mg, 0.044 mmol, 31.2% yield) as a pale yellow gum.

LCMS (2 min High pH): Rt=0.92 min, [MH]$^+$=411.4.

Example 28

(R)-6-(3-Methoxybenzyl)-N$^2$-methyl-N$^4$-(3-(morpholin-2-yl)propyl)pyridine-2,4-dicarboxamide

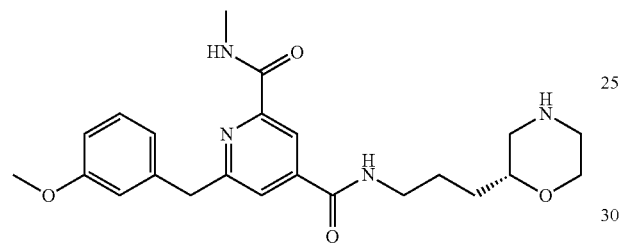

To a 20 mL vial, 2-(3-methoxybenzyl)-6-(methylcarbamoyl)isonicotinic acid (80 mg, 0.266 mmol) was dissolved in DMF (2 mL), then HATU (152 mg, 0.400 mmol) and Et$_3$N (0.074 mL, 0.533 mmol) were added and the mixture was stirred for 20 min at rt, then (R)-tert-butyl 2-(3-aminopropyl)morpholine-4-carboxylate (85 mg, 0.346 mmol) was added and the solution was stirred for 2 h. The resulting mixture was diluted with water (10 mL) and extracted with EtOAc (10 mL). The solvent was evaporated in vacuo, then the residue was dissolved in DCM and treated with TFA (1 mL). The solution was allowed to stand for 1 h, then evaporated in vacuo and the residue purified by MDAP (High pH) to give (R)-6-(3-methoxybenzyl)-N$^2$-methyl-N$^4$-(3-(morpholin-2-yl)propyl)pyridine-2,4-dicarboxamide (40 mg, 0.094 mmol, 35.2% yield) as a pale yellow glass.

LCMS (2 min high pH): Rt=0.86 min, [MH]$^+$=427.

Example 29

(S)-6-(3-Methoxybenzyl)-N$^2$-methyl-N$^4$-(3-(morpholin-2-yl)propyl)pyridine-2,4-dicarboxamide

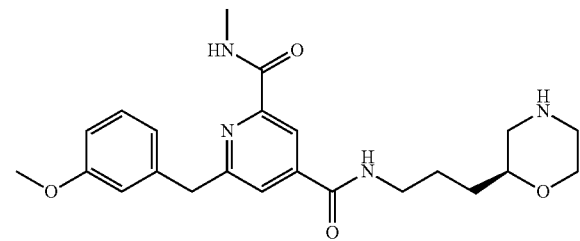 [SMILES: CNC(=O)c1cc(C(=O)NCCC[C@H]2CNCCO2)cc(Cc2cccc(OC)c2)n1]

To a 20 mL vial, 2-(3-methoxybenzyl)-6-(methylcarbamoyl)isonicotinic acid (80 mg, 0.266 mmol) was dissolved in DMF (2 mL), then HATU (152 mg, 0.400 mmol) and Et$_3$N (0.074 mL, 0.533 mmol) were added and the mixture was stirred for 20 min at rt, then (S)-tert-butyl 2-(3-aminopropyl)morpholine-4-carboxylate (85 mg, 0.346 mmol) was added and the solution was stirred for 2 h. The resulting mixture was diluted with water (10 mL) and extracted with EtOAc (10 mL). The solvent was evaporated in vacuo, then the residue was dissolved in DCM and treated with TFA (1 mL). The solution was allowed to stand for 1 h, then evaporated in vacuo and the residue purified by MDAP (High pH) to give (S)-6-(3-methoxybenzyl)-N$^2$-methyl-N$^4$-(3-(morpholin-2-yl)propyl)pyridine-2,4-dicarboxamide (40 mg, 0.094 mmol, 35.2% yield).

LCMS (2 min high pH): Rt=0.86 min, [MH]$^+$=427.

Example 30

N$^2$-Methyl-N$^4$-(2-((S)-morpholin-2-yl)ethyl)-6-(1-phenylethyl)pyridine-2,4-dicarboxamide, 1:1 Mixture of Diastereomers at Undefined Stereocentre

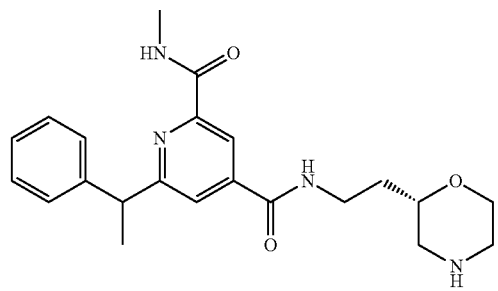 [SMILES: CNC(=O)c1cc(C(=O)NCC[C@H]2CNCCO2)cc(C(C)c2ccccc2)n1]

(2S)-tert-Butyl 2-(2-(2-(methylcarbamoyl)-6-(1-phenylethyl)isonicotinamido)ethyl)morpholine-4-carboxylate (87.1 mg, 0.175 mmol) was taken up in DCM (2 mL), TFA (0.5 mL, 6.49 mmol) was added and the reaction left to stir at rt for 2 h. The reaction was concentrated in vacuo. The sample was loaded in MeOH and purified by SPE on sulphonic acid (SCX, 1 g), the column was eluted with MeOH, followed by 2M NH$_3$ in MeOH. The appropriate fractions were combined and evaporated in vacuo to give the crude product. This was dissolved in 1:1 MeOH:DMSO (1 mL) and purified by MDAP (High pH). The solvent was evaporated in vacuo to afford the desired product (25.1 mg).

LCMS (2 min High pH): Rt=0.90 min, [MH]$^+$=397.4.

$^1$H NMR (400 MHz, MeOH-d$_4$) δ ppm 8.24 (d, J=1.2 Hz, 1H) 7.73 (d, J=1.0 Hz, 1H) 7.22-7.38 (m, 4H) 7.11-7.21 (m, 1H) 4.41 (q, J=7.3 Hz, 1H) 3.82 (d, J=11.5 Hz, 1H) 3.38-3.66 (m, 5H) 3.00 (s, 3H) 2.86 (br. d, J=12.2 Hz, 1H) 2.78 (m, J=5.4 Hz, 2H) 2.52 (dd, J=12.2, 10.8 Hz, 1H) 1.64-1.80 (m, 5H)

Example 31

N²-Methyl-N⁴-(2-((R)-morpholin-2-yl)ethyl)-6-(1-phenylethyl)pyridine-2,4-dicarboxamide, 1:1 Mixture of Diastereomers at Undefined Stereocentre

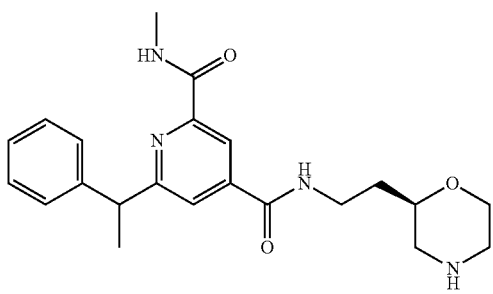 [SMILES: CNC(=O)c1cc(C(=O)NCC[C@@H]2CNCCO2)cc(C(C)c2ccccc2)n1]

(2R)-tert-Butyl 2-(2-(2-(methylcarbamoyl)-6-(1-phenylethyl)isonicotinamido)ethyl)morpholine-4-carboxylate (133 mg, 0.268 mmol) was taken up in DCM (2 mL), TFA (0.5 mL, 6.49 mmol) was added and the reaction left to stir overnight at rt. The reaction was concentrated in vacuo. The sample was loaded in MeOH and purified by SPE on sulphonic acid (SCX, 1 g), the column was eluted with MeOH, followed by 2M NH₃ in MeOH. The appropriate fractions were combined and evaporated in vacuo to give the crude product. This was dissolved in 1:1 MeOH:DMSO (1 mL) and purified by MDAP (High pH). The solvent was evaporated in vacuo to give the required product (32.3 mg) as a yellow oil.

LCMS (2 min High pH): Rt=0.90 min, [MH]⁺=397.4.

Example 32

(+/−)-N⁴-((1R,5S,6r)-3-Oxabicyclo[3.1.0]hexan-6-yl)-N²-methyl-6-(1-phenylethyl)pyridine-2,4-dicarboxamide

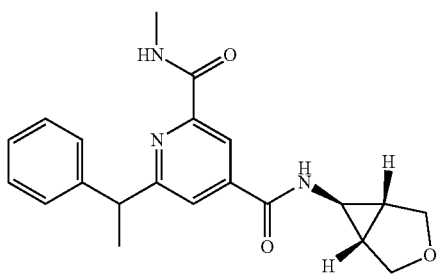 [SMILES: CNC(=O)c1cc(C(=O)N[C@H]2[C@@H]3COC[C@@H]32)cc(C(C)c2ccccc2)n1]

2-(Methylcarbamoyl)-6-(1-phenylethyl)isonicotinic acid (140 mg, 0.492 mmol) was taken up in DMF (4 mL), DIPEA (0.258 mL, 1.477 mmol), HATU (281 mg, 0.739 mmol) and 3-oxabicyclo[3.1.0]hexan-6-amine, hydrochloride (100 mg, 0.739 mmol) were added and the reaction left to stir at rt for 2 h. The reaction was concentrated in vacuo. The residue was taken up in EtOAc (20 mL) and washed with NaHCO₃ solution (20 mL), the organic phase was washed with brine (20 mL) before being dried over Na₂SO₄, filtered through a hydrophobic frit and concentrated in vacuo. The crude product was applied to a 10 g SNAP ULTRA silica cartridge in the minimum of DCM and purified by flash chromatography, eluting with 0-50% (3:1 EtOAc:EtOH). The appropriate fractions were combined and concentrated in vacuo. A 20 mg sample was dissolved in DCM (1 mL) and purified by MDAP (High pH). The solvent was evaporated in vacuo to give the required product (14 mg) as a white solid. The remaining product which was not applied to an MDAP was submitted for chiral separation (see examples 38 and 39).

LCMS (2 min High pH): Rt=0.98 min, [MH]⁺=366.3.

¹H NMR (400 MHz, MeOH-d₄) δ ppm 8.22 (d, J=1.5 Hz, 1H) 7.73 (d, J=1.5 Hz, 1H) 7.23-7.38 (m, 4H) 7.18 (t, J=7.6 Hz, 1H) 4.42 (q, J=7.3 Hz, 1H) 3.99 (d, J=8.6 Hz, 2H) 3.73 (d, J=8.3 Hz, 2H) 3.01 (s, 3H) 2.63 (t, J=2.3 Hz, 1H) 1.94 (br. s, 2H) 1.76 (d, J=7.3 Hz, 3H).

Example 33

(+/−)-6-Benzyl-N⁴-(3-(3-fluoropiperidin-3-yl)propyl)-N²-methylpyridine-2,4-dicarboxamide

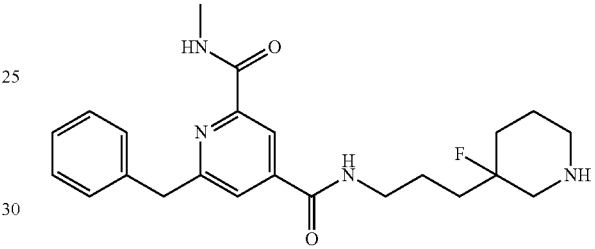

tert-Butyl 3-(3-(2-benzyl-6-(methylcarbamoyl)isonicotinamido)propyl)-3-fluoropiperidine-1-carboxylate (140 mg, 0.273 mmol) was dissolved in DCM (3 mL) and TFA (1 mL) was added, then the mixture was stirred for 2 h at rt. The solvent was evaporated in vacuo and the residue was dissolved in MeOH and loaded onto a 5 g SCX cartridge. This was washed with MeOH (20 mL) and then eluted with 2M NH₃ in MeOH (20 mL). The eluant was evaporated in vacuo to give 6-benzyl-N⁴-(3-(3-fluoropiperidin-3-yl)propyl)-N²-methylpyridine-2,4-dicarboxamide (90 mg, 0.218 mmol, 80% yield) as a colourless gum.

LCMS (2 min high pH): Rt=0.96 min, [MH]⁺=413.

Example 34

(+/−)-tert-Butyl 3-(3-(2-benzyl-6-(methylcarbamoyl)isonicotinamido)propyl)-3-fluoropiperidine-1-carboxylate

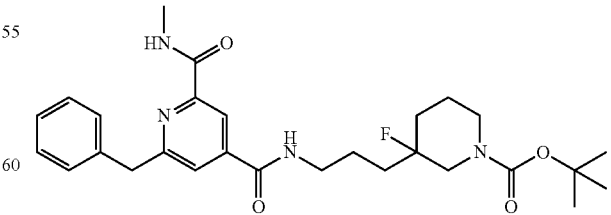

tert-Butyl 3-(3-aminopropyl)-3-fluoropiperidine-1-carboxylate (173 mg, 0.666 mmol) and 2-benzyl-6-(methylcarbamoyl)isonicotinic acid (150 mg, 0.555 mmol) were combined in DCM (5 mL) and HATU (274 mg, 0.721 mmol) and Et₃N (0.101 mL, 0.721 mmol) were added, then the mixture was stirred overnight at rt. The solvent was evaporated in vacuo and the residue purified by MDAP (High pH) in two injections to give tert-butyl 3-(3-(2-benzyl-6-(methylcarbamoyl)isonicotinamido)propyl)-3-fluoropiperidine-1-carboxylate (160 mg, 0.312 mmol, 56.2% yield) as a colourless solid.

LCMS (2 min high pH): Rt=1.23 min, [MH]⁺=513.

Example 35

(S)-6-((1H-Indol-4-yl)methyl)-N²-methyl-N⁴-(3-(morpholin-2-yl)propyl)pyridine-2,4-dicarboxamide

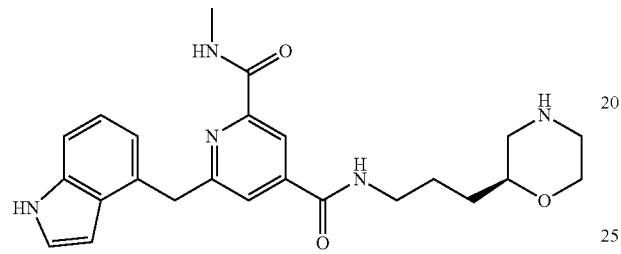

To a solution of (S)-tert-butyl 2-(3-(2-((1H-indol-4-yl)methyl)-6-(methylcarbamoyl)isonicotinamido)propyl)morpholine-4-carboxylate (28.7 mg, 0.048 mmol) in DCM (1 mL) was added TFA (0.05 mL, 0.649 mmol) and reaction mixture was stirred overnight. Further TFA (0.05 mL, 0.048 mmol) was added and the solution stirred for 1 h. The reaction mixture was concentrated in vacuo. The reaction mixture was taken up in MeOH and added to an SCX cartridge (1 g). The cartridge was first eluted with MeOH and the product then eluted with 2M NH₃ in MeOH. The desired fractions were combined and concentrated to give (S)-6-((1H-indol-4-yl)methyl)-N²-methyl-N⁴-(3-(morpholin-2-yl)propyl)pyridine-2,4-dicarboxamide (23.0 mg, 0.048 mmol, 99% yield).

LCMS (2 min Formic): Rt=0.58 min, [MH]+=436.3.

Example 36

(R)-6-Benzyl-N²-methyl-N⁴-(2-(morpholin-2-yl)ethyl)pyridine-2,4-dicarboxamide

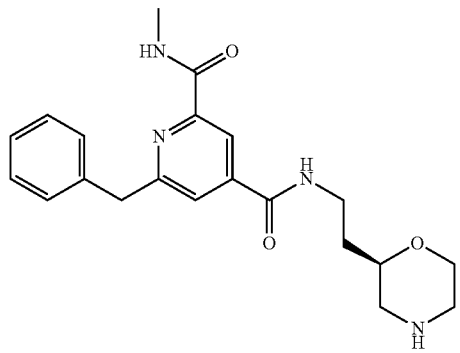 [SMILES: CNC(=O)c1cc(C(=O)NCC[C@@H]2CNCCO2)cc(Cc2ccccc2)n1]

(R)-tert-Butyl 2-(2-(2-benzyl-6-(methylcarbamoyl)isonicotinamido)ethyl)morpholine-4-carboxylate (280 mg, 0.580 mmol) was dissolved in DCM (5 mL) and then TFA (2 mL, 26.0 mmol) was added and the mixture was stirred for 2 h at rt. The solvent was evaporated in vacuo and the residue dissolved in MeOH and loaded onto a 5 g SCX2 cartridge. This was washed with MeOH (20 mL), then eluted with 2M NH₃ in MeOH (20 mL) and the eluant evaporated in vacuo to give (R)-6-benzyl-N²-methyl-N⁴-(2-(morpholin-2-yl)ethyl)pyridine-2,4-dicarboxamide (180 mg, 0.471 mmol, 81% yield) as a colourless foam.

LCMS (2 min high pH): Rt=0.84 min, [MH]⁺=383.

Example 37

(S)-6-Benzyl-N²-methyl-N⁴-(3-(morpholin-2-yl)propyl)pyridine-2,4-dicarboxamide

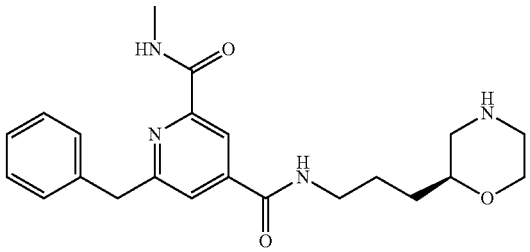 [SMILES: CNC(=O)c1cc(C(=O)NCCC[C@H]2CNCCO2)cc(Cc2ccccc2)n1]

To a solution of (S)-tert-butyl 2-(3-(2-benzyl-6-(methylcarbamoyl)isonicotinamido)propyl)morpholine-4-carboxylate (56 mg, 0.113 mmol) in DCM (1 mL) was added TFA (0.17 mL, 2.207 mmol) and the reaction mixture was stirred overnight. The reaction mixture was concentrated in vacuo. The reaction mixture was taken up in MeOH and added to an SCX cartridge (1 g). The cartridge was first eluted with MeOH and the product then eluted with 2M NH₃ in MeOH. The desired fractions were combined and concentrated in vacuo to give (S)-6-benzyl-N²-methyl-N⁴-(3-(morpholin-2-yl)propyl)pyridine-2,4-dicarboxamide (40.1 mg, 0.096 mmol, 85% yield)

LCMS (2 min Formic): Rt=0.59 min, [MH]+=397.3.

Example 38

N⁴-((1R,5S,6r)-3-Oxabicyclo[3.1.0]hexan-6-yl)-N²-methyl-6-((S*)-1-phenylethyl)pyridine-2,4-dicarboxamide Example 39

N⁴-((1R,5S,6r)-3-oxabicyclo[3.1.0]hexan-6-yl)-N²-methyl-6-((R*)-1-phenylethyl)pyridine-2,4-dicarboxamide

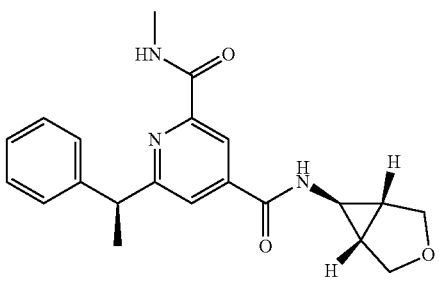

-continued

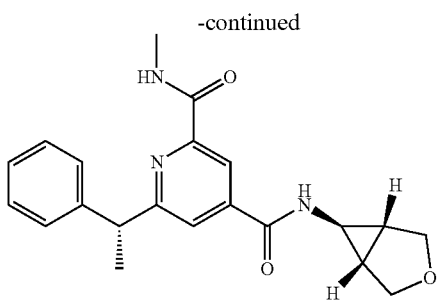

(+/−)-N[4]-((1R,5S,6r)-3-Oxabicyclo[3.1.0]hexan-6-yl)-N[2]-methyl-6-(1-phenylethyl)pyridine-2,4-dicarboxamide (75 mg) was submitted for chiral purification. The racemate (75 mg) was dissolved in EtOH (3 mL). Injection: 1 mL of the solution was injected onto the column (25% EtOH/Heptane, flow rate=30 mL/min, wavelength=215 nm, column: 30 mm×25 cm Chiralpak AD-H (5 μm), total number of injections=3). Fractions from 14.5-16.5 min were bulked and labelled peak 1, fractions from 18-21 min were bulked and labelled peak 2 (a further prep of peak 2 was required in order to improve the purity, this took 1 injection using the method above). The bulked fractions were concentrated in vacuo and then transferred to weighed flasks—the final compounds were recovered from DCM and heptane in order to obtain a solid.

Peak 1 provided Example 39 (11.2 mg).

LCMS (2 min High pH): Rt=0.98 min, [MH]$^+$=366.3.

Peak 2 provided Example 38 (24 mg).

LCMS (2 min High pH): Rt=0.98 min, [MH]$^+$=366.3.

$^1$H NMR (400 MHz, MeOH-d$_4$) δ ppm 8.22 (d, J=1.5 Hz, 1H) 7.73 (d, J=1.5 Hz, 1H) 7.23-7.38 (m, 4H) 7.18 (t, J=7.6 Hz, 1H) 4.42 (q, J=7.3 Hz, 1H) 3.99 (d, J=8.6 Hz, 2H) 3.73 (d, J=8.3 Hz, 2H) 3.01 (s, 3H) 2.63 (t, J=2.3 Hz, 1H) 1.94 (br. s, 2H) 1.76 (d, J=7.3 Hz, 3H).

Example 40

N$^2$-Methyl-N$^4$-(2-((S)-morpholin-2-yl)ethyl)-6-((R*)-1-phenylethyl)pyridine-2,4-dicarboxamide Example 41

N$^2$-Methyl-N$^4$-(2-((S)-morpholin-2-yl)ethyl)-6-((S*)-1-phenylethyl)pyridine-2,4-dicarboxamide

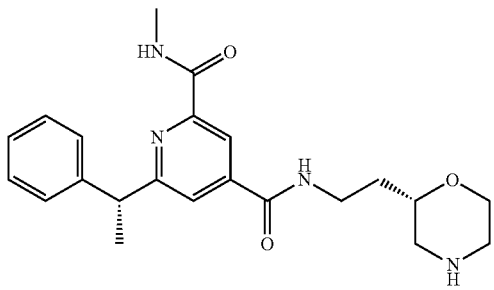

-continued

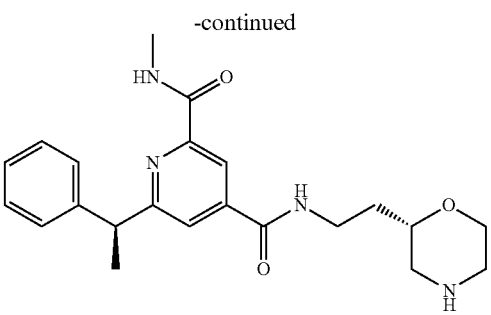

(+/−)-(N$^2$-Methyl-N$^4$-(2-((S)-morpholin-2-yl)ethyl)-6-(1-phenylethyl)pyridine-2,4-dicarboxamide) (23 mg) was submitted for chiral purification. The racemate (23 mg) was dissolved in EtOH (1 mL). Injection: 1 mL of the solution was injected onto the column (30% EtOH (+0.2% isopropylamine)/heptane (+0.2% isopropylamine), flow rate=30 mL/min, wavelength=215 nm, column: 30 mm×25 cm Chiralpak AD-H (5 μm), total number of injections=1). Fractions from 30-40 min were bulked and labelled peak 1, fractions from 46-66 min were bulked and labelled peak 2. The bulked fractions were concentrated in vacuo and then transferred to weighed flasks—the final compounds were recovered from DCM and heptane in order to obtain a solid.

Peak 1 provided Example 41 (6.9 mg).

LCMS (2 min High pH): Rt=0.91 min, [MH]$^+$=397.4.

$^1$H NMR (400 MHz, MeOH-d$_4$) δ ppm 8.24 (d, J=1.5 Hz, 1H) 7.73 (d, J=1.5 Hz, 1H) 7.23-7.38 (m, 4H) 7.13-7.22 (m, 1H) 4.43 (q, J=7.1 Hz, 1H) 3.82 (br. d, J=11.2 Hz, 1H) 3.43-3.61 (m, 4H) 3.01 (s, 3H) 2.83 (dd, J=12.5, 2.2 Hz, 1H) 2.72-2.78 (m, 2H) 2.50 (dd, J=12.5, 10.3 Hz, 1H) 1.76 (d, J=7.3 Hz, 3H) 1.63-1.73 (m, 2H)

Peak 2 provided Example 40 (6.3 mg).

LCMS (2 min High pH): Rt=0.91 min, [MH]$^+$=397.4.

Example 41b

N$^2$-Methyl-N$^4$-(2-((S)-morpholin-2-yl)ethyl)-6-((S*)-1-phenylethyl)pyridine-2,4-dicarboxamide hydrochloride

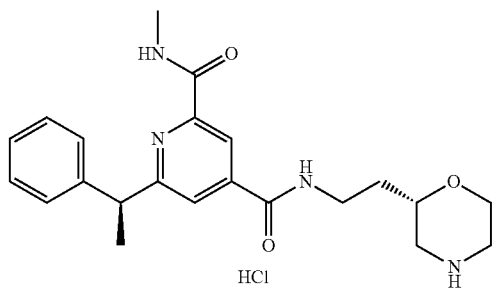 [SMILES: CNC(=O)c1cc(C(=O)NCC[C@H]2CNCCO2)cc([C@@H](C)c2ccccc2)n1 ; Cl]

N$^2$-Methyl-N$^4$-(2-((S)-morpholin-2-yl)ethyl)-6-((S*)-1-phenylethyl)pyridine-2,4-dicarboxamide (122 mg, 0.308 mmol), a gum in a haystack vial, was taken up in DCM (1 mL) with the aid of sonication. HCl (1M in Et$_2$O, 0.308 mL, 0.308 mmol) was added and the vial sonicated for 5 min and then blown down under N$_2$. The resultant brown gum was triturated with Et$_2$O (1 mL) and blown down again under N$_2$ to afford the product as a cream solid —N$^2$-methyl-N$^4$-(2-

((S)-morpholin-2-yl)ethyl)-6-((S*)-1-phenylethyl)pyridine-2,4-dicarboxamide, hydrochloride (102 mg, 0.236 mmol, 77% yield)

LCMS (2 min Formic): Rt=0.63 min, [MH]+=397.3.

Example 42

(S)-6-Benzyl-$N^2$-methyl-$N^4$-(2-(morpholin-2-yl)ethyl)pyridine-2,4-dicarboxamide

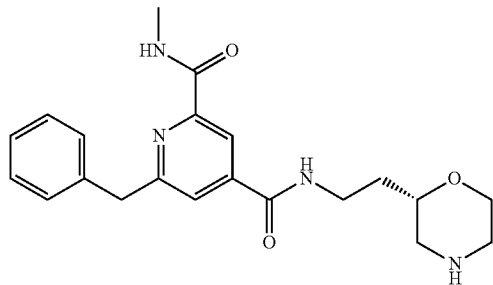 [SMILES: CNC(=O)c1cc(C(=O)NCC[C@H]2CNCCO2)cc(Cc2ccccc2)n1]

To a solution of (S)-tert-butyl 2-(2-(2-benzyl-6-(methylcarbamoyl)isonicotinamido)ethyl)morpholine-4-carboxylate (92 mg, 0.191 mmol) in DCM (2 mL) was added TFA (0.8 mL, 10.38 mmol) and the reaction mixture was stirred overnight. The reaction mixture was concentrated in vacuo. The reaction mixture was taken up in MeOH and added to an SCX cartridge (1 g). The cartridge was first eluted with MeOH and the product then eluted with 2M $NH_3$ in MeOH. The desired fractions were combined and concentrated in vacuo to give (S)-6-benzyl-$N^2$-methyl-$N^4$-(2-(morpholin-2-yl)ethyl)pyridine-2,4-dicarboxamide (65.6 mg, 0.154 mmol, 81% yield)

LCMS (2 min Formic): Rt=0.58 min, [MH]+=383.3.

Example 43

(S)-6-Benzyl-$N^4$-(3-(4-isopropylmorpholin-2-yl)propyl)-$N^2$-methylpyridine-2,4-dicarboxamide

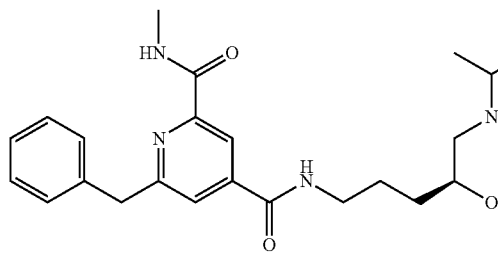

To a solution of (S)-6-benzyl-$N^2$-methyl-$N^4$-(3-(morpholin-2-yl)propyl)pyridine-2,4-dicarboxamide (47 mg, 0.119 mmol) in MeOH (0.5 mL) was added $NaCNBH_3$ (15 mg, 0.239 mmol), propan-2-one (35 μL, 0.476 mmol) and AcOH (2.71 μL, 0.047 mmol). The resultant mixture was stirred at rt for 2 h. AcOH (2.71 μL, 0.119 mmol), $NaCNBH_3$ (7.45 mg, 0.119 mmol) and propan-2-one (20 μL, 0.119 mmol) were added and the resultant mixture was stirred at rt for 45 min. The reaction mixture was purified by MDAP (High pH). The desired fractions were combined and concentrated in vacuo to give the desired product as a colourless oil (S)-6-benzyl-$N^4$-(3-(4-isopropylmorpholin-2-yl)propyl)-$N^2$-methylpyridine-2,4-dicarboxamide (21.7 mg, 0.047 mmol, 39.7% yield).

LCMS (2 min Formic): Rt=1.05 min, [MH]+=439.5.

Example 44

6-Benzyl-$N^4$-((R*)-2-hydroxy-2-((S)-morpholin-2-yl)ethyl)-$N^2$-methylpyridine-2,4-dicarboxamide Example 45

6-Benzyl-$N^4$-((S*)-2-hydroxy-2-((S)-morpholin-2-yl)ethyl)-$N^2$-methylpyridine-2,4-dicarboxamide

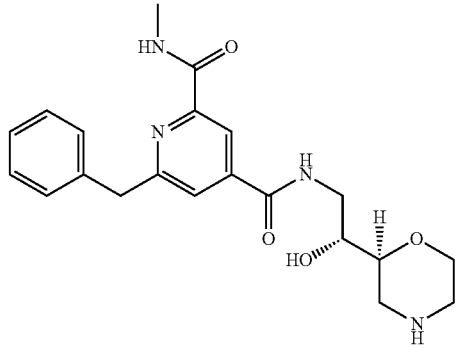

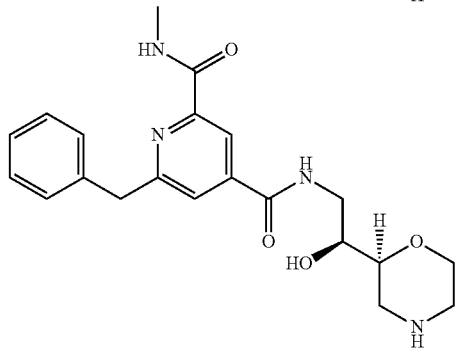

(S)-tert-Butyl 2-(2-amino-1-hydroxyethyl)morpholine-4-carboxylate (416 mg, 1.687 mmol) and 2-benzyl-6-(methylcarbamoyl)isonicotinic acid (380 mg, 1.406 mmol) were combined in DCM (5 mL) and HATU (695 mg, 1.828 mmol) and $Et_3N$ (0.255 mL, 1.828 mmol) were added, then the mixture was stirred overnight at rt. 1 mL of the reaction mixture was purified by MDAP (high pH) to give two separate fractions, which were evaporated in vacuo. Both were dissolved in DCM (5 mL each) and TFA (1 mL) was added, then the solutions were allowed to stand for 3 h, then evaporated in vacuo and the residues dissolved in MeOH and loaded onto 5 g SCX cartridges, which were washed with MeOH (10 mL), then eluted with 2M $NH_3$ in MeOH and the eluant evaporated in vacuo to give:

Example 44

6-Benzyl-$N^4$-((R*)-2-hydroxy-2-((S)-morpholin-2-yl)ethyl)-$N^2$-methylpyridine-2,4-dicarboxamide (20 mg, 0.050 mmol, 3.57% yield)

LCMS (2 min high pH): Rt=0.78 min, $[MH]^+$=399.

Example 45

6-Benzyl-$N^4$-((S*)-2-hydroxy-2-((S)-morpholin-2-yl)ethyl)-$N^2$-methylpyridine-2,4-dicarboxamide (18 mg, 0.045 mmol, 3.21% yield)

LCMS (2 min high pH): Rt=0.79 min, $[MH]^+$=399.

Example 46

(S)-6-((1H-Indol-4-yl)methyl)-$N^4$-(3-(4-isopropylmorpholin-2-yl)propyl)-$N^2$-methylpyridine-2,4-dicarboxamide

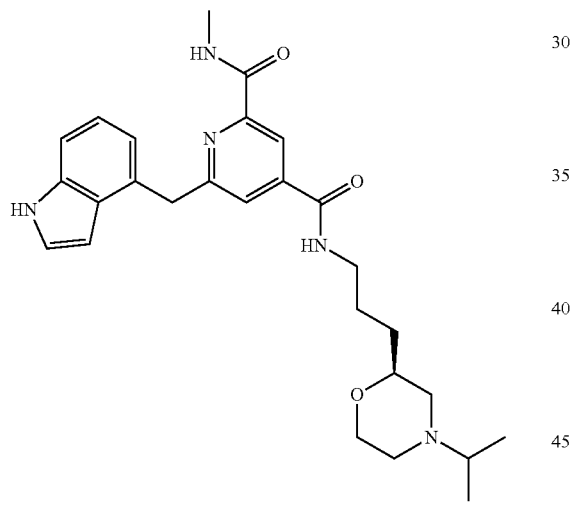

To a solution of ((S)-6-((1H-indol-4-yl)methyl)-$N^2$-methyl-$N^4$-(3-(morpholin-2-yl)propyl)pyridine-2,4-dicarboxamide (19 mg, 0.044 mmol) in MeOH (0.5 mL) was added NaCNBH$_3$ (10.97 mg, 0.175 mmol), propan-2-one (0.01 mL, 0.136 mmol) and AcOH (1.048 mg, 0.017 mmol). The resultant mixture was stirred at rt for 5 h. Further propan-2-one (7.60 mg, 0.131 mmol), AcOH (1.048 mg, 0.017 mmol) and NaCNBH$_3$ (10.97 mg, 0.175 mmol) were added and the resultant mixture was stirred at rt for 1 h. The reaction mixture was purified by MDAP (High pH). The desired fractions were combined and concentrated in vacuo to give (S)-6-((1H-indol-4-yl)methyl)-$N^4$-(3-(4-isopropylmorpholin-2-yl)propyl)-$N^2$-methylpyridine-2,4-dicarboxamide (16.2 mg, 0.031 mmol, 70.0% yield) as a colourless oil.

LCMS (2 min Formic): Rt=0.61 min, $[MH]^+$=478.3

Example 47

(R)-6-Benzyl-$N^4$-(3-(3-fluoropiperidin-3-yl)propyl)-$N^2$-methylpyridine-2,4-dicarboxamide

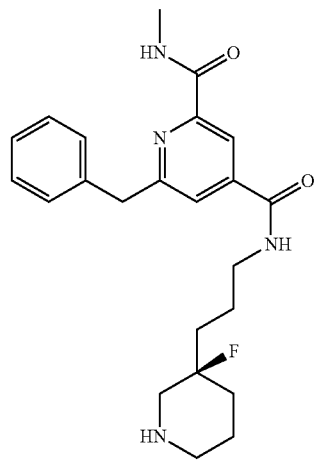 [SMILES: CNC(=O)c1cc(C(=O)NCCC[C@]2(F)CCCNC2)cc(Cc2ccccc2)n1]

To a solution of (S)-tert-butyl 3-(3-(2-benzyl-6-(methylcarbamoyl)isonicotinamido)propyl)-3-fluoropiperidine-1-carboxylate (190.5 mg, 0.372 mmol) in DCM (2 mL) was added 2,2,2-TFA (0.40 mL, 5.19 mmol) and the reaction mixture was stirred overnight. The reaction mixture was concentrated in vacuo. The reaction mixture was taken up in MeOH and added to an SCX cartridge (5 g). The cartridge was first eluted with MeOH and the product then eluted with 2M NH$_3$ in MeOH. The desired fractions were combined and concentrated in vacuo to give (R)-6-benzyl-$N^4$-(3-(3-fluoropiperidin-3-yl)propyl)-$N^2$-methylpyridine-2,4-dicarboxamide (153.6 mg, 0.354 mmol, 95% yield)

LCMS (2 min Formic): Rt=0.61 min, $[MH]^+$=413.3

Example 48

(S)-6-Benzyl-$N^4$-(3-(3-fluoro-1-isopropylpiperidin-3-yl)propyl)-$N^2$-methylpyridine-2,4-dicarboxamide

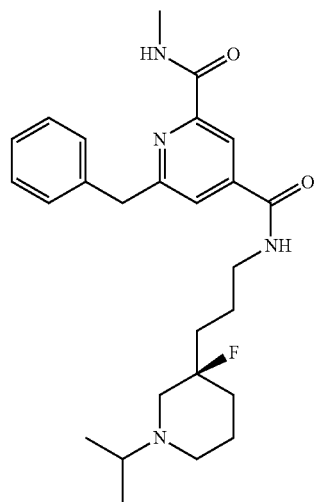 [SMILES: CNC(=O)c1cc(C(=O)NCCC[C@]2(F)CCCN(C(C)C)C2)cc(Cc2ccccc2)n1]

To a solution of ((R)-6-benzyl-$N^4$-(3-(3-fluoropiperidin-3-yl)propyl)-$N^2$-methylpyridine-2,4-dicarboxamide (30 mg, 0.073 mmol) in MeOH (0.5 mL) was added NaCNBH$_3$ (22.85 mg, 0.364 mmol), propan-2-one (0.02 mL, 0.273 mmol) and AcOH (4.37 mg, 0.073 mmol). The resultant mixture was stirred at rt for 2 h. Further propan-2-one (0.02 mL, 0.273 mmol), AcOH (4.37 mg, 0.073 mmol) and NaCNBH$_3$ (22.85 mg, 0.364 mmol) were added and the resultant mixture was stirred at rt for 3 h. The reaction mixture was purified by MDAP (High pH). The desired fractions were combined and concentrated in vacuo to give (S)-6-benzyl-$N^4$-(3-(3-fluoro-1-isopropylpiperidin-3-yl)propyl)-$N^2$-methylpyridine-2,4-dicarboxamide (22 mg, 0.044 mmol, 59.9% yield) as a colourless oil.

LCMS (2 min Formic): Rt=0.64 min, [MH]$^+$=455.3

Example 49

(R)-6-Benzyl-$N^4$-(2-(4-isopropylmorpholin-2-yl)ethyl)-$N^2$-methylpyridine-2,4-dicarboxamide

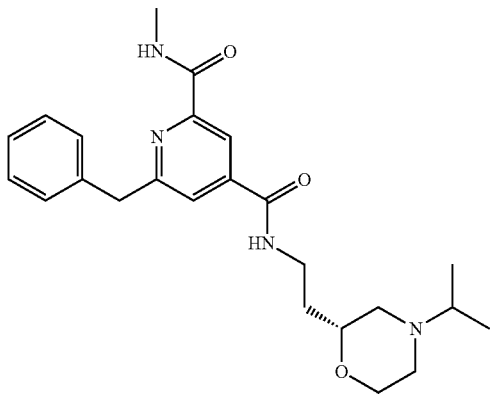 [SMILES: CNC(=O)c1cc(C(=O)NCC[C@@H]2CN(C(C)C)CCO2)cc(Cc2ccccc2)n1]

(R)-6-Benzyl-$N^2$-methyl-$N^4$-(2-(morpholin-2-yl)ethyl)pyridine-2,4-dicarboxamide (180 mg, 0.471 mmol) was dissolved in DCM (10 mL) and acetone (0.173 mL, 2.353 mmol) and Na(OAc)$_3$BH (499 mg, 2.353 mmol) were added, then the mixture was stirred at rt over the weekend. The mixture was quenched with NaHCO$_3$ solution (50 mL) and extracted with DCM (30 mL), the organic layer was dried and evaporated in vacuo to give a colourless gum. The crude product was purified by chromatography on a 25 g SNAP cartridge eluting with 0-10% 2M NH$_3$ in MeOH/DCM. The product-containing fractions were evaporated in vacuo to give (R)-6-benzyl-$N^4$-(2-(4-isopropylmorpholin-2-yl)ethyl)-$N^2$-methylpyridine-2,4-dicarboxamide (110 mg, 0.259 mmol, 55.1% yield) as a colourless foam.

LCMS (2 min Formic): Rt=0.61 min, [MH]$^+$=425.

Example 50

(±)-6-Benzyl-$N^4$-(3-(4,4-difluoropiperidin-3-yl)propyl)-$N^2$-methylpyridine-2,4-dicarboxamide

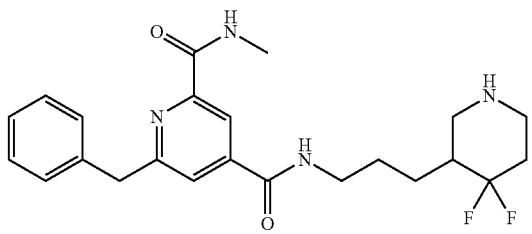 [SMILES: CNC(=O)c1cc(C(=O)NCCCC2CNCCC2(F)F)cc(Cc2ccccc2)n1]

A solution of (±)-tert-butyl 3-(3-(2-benzyl-6-(methylcarbamoyl)isonicotinamido)propyl)-4,4-difluoropiperidine-1-carboxylate (7.1 mg, 0.013 mmol) in 1,4-dioxane (0.1 mL) had HCl (4.0M solution in 1,4-dioxane, 200 µL, 0.800 mmol) added to it. The mixture was stirred at rt for 3.5 h. The mixture was evaporated to dryness under a stream of N$_2$ and the residue was redissolved in MeOH (ca. 0.5 mL) and applied to a 1 g SCX2 ion-exchange cartridge which had been pre-wetted with MeOH. The cartridge was eluted with MeOH (2×5 mL) followed by 2M ammonia in MeOH solution (3×5 mL). The basic fractions from the SCX purification were combined and evaporated under a stream of N$_2$ to give a yellow glass; (±)-6-benzyl-$N^4$-(3-(4,4-difluoropiperidin-3-yl)propyl)-$N^2$-methylpyridine-2,4-dicarboxamide (4.0 mg, 9.29 µmol, 69.4% yield)

LCMS (2 min formic); Rt=0.64 min, m/z=431 for [MH]+

Example 51

6-((1H-Indol-4-yl)methyl)-$N^4$-((1R,5S,6r)-3-oxabicyclo[3.1.0]hexan-6-yl)-$N^2$-methylpyridine-2,4-dicarboxamide

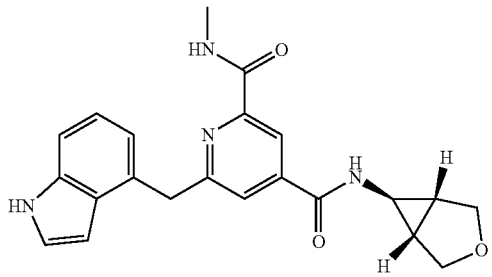 [SMILES: CNC(=O)c1cc(C(=O)N[C@H]2[C@@H]3COC[C@@H]32)cc(Cc2cccc3[nH]ccc23)n1]

2-((1H-Indol-4-yl)methyl)-6-(methylcarbamoyl)isonicotinic acid (150 mg, 0.485 mmol) was taken up in DMF (5 mL). DIPEA (0.254 mL, 1.455 mmol) and HATU (277 mg, 0.727 mmol) were added and the reaction left to stir at rt 10 min. (1R,5S,6s)-3-Oxabicyclo[3.1.0]hexan-6-amine, hydrochloride (132 mg, 0.970 mmol) was added and the reaction was left to stir for a further 3 h. The reaction was concentrated in vacuo. The residue was taken up in EtOAc (10 mL) and extracted with NaHCO$_3$ solution (10 mL). The organic phase was washed with brine (10 mL) before being dried over Na$_2$SO$_4$, filtered through a hydrophobic frit and concentrated in vacuo. The samples were dissolved in 1:1 DMSO:MeCN (1 mL) and purified by MDAP (High pH).

The solvent was evaporated in vacuo to give the required product (28.5 mg) as a brown oil.

LCMS (2 min High pH): Rt=0.86 min, [MH]⁺=391.4.

¹H NMR (400 MHz, CDCl₃) δ ppm 8.58 (br. s., 1H) 8.25 (d, J=1.2 Hz, 1H) 8.03-8.16 (m, 1H) 7.78 (d, J=1.5 Hz, 1H) 7.32 (br. d, J=2.4 Hz, 1H) 7.27 (d, J=8.1 Hz, 1H) 7.07-7.16 (m, 2H) 6.93 (d, J=7.1 Hz, 1H) 6.51 (t, J=2.1 Hz, 1H) 4.46 (s, 2H) 3.99 (d, J=8.6 Hz, 2H) 3.70 (d, J=8.6 Hz, 2H) 2.96 (d, J=5.1 Hz, 3H) 2.68 (d, J=2.4 Hz, 1H) 1.83 (br. s, 2H)

Example 52

(S)-6-((1H-Indol-4-yl)methyl)-N⁴-(3-(3-fluoropiperidin-3-yl)propyl)-N²-methylpyridine-2,4-dicarboxamide

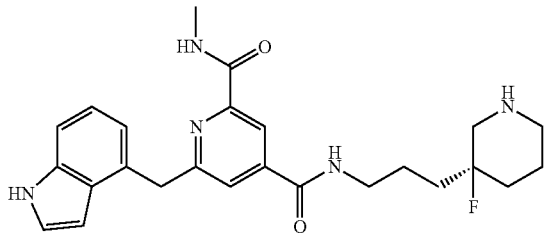 [SMILES: CNC(=O)c1cc(C(=O)NCCC[C@@]2(F)CCCNC2)cc(Cc2cccc3[nH]ccc23)n1]

(R)-tert-Butyl 3-(3-(2-((1H-indol-4-yl)methyl)-6-(methylcarbamoyl)isonicotinamido)propyl)-3-fluoropiperidine-1-carboxylate (340 mg, 0.616 mmol) was taken up in DCM (5 mL), TFA (0.5 mL, 6.49 mmol) was added and the reaction left to stir for at rt for 2 h. The reaction was concentrated in vacuo. The sample was loaded in MeOH and purified by SPE on sulphonic acid (SCX, 2 g) eluting with MeOH followed by 2M ammonia/MeOH. The appropriate fractions were combined and evaporated in vacuo. The crude product was dissolved in 1:1 DMSO:MeCN (1 mL) and purified by MDAP (High pH). The solvent was evaporated in vacuo to give the required product (112 mg) as a brown oil.

LCMS (2 min High pH): Rt=0.88 min, [MH]⁺=452.5.

Example 53

N²-Methyl-N⁴-(2-((R)-morpholin-2-yl)ethyl)-6-((S*)-1-phenylethyl)pyridine-2,4-dicarboxamide Example 54

N²-Methyl-N⁴-(2-((R)-morpholin-2-yl)ethyl)-6-((R*)-1-phenylethyl)pyridine-2,4-dicarboxamide

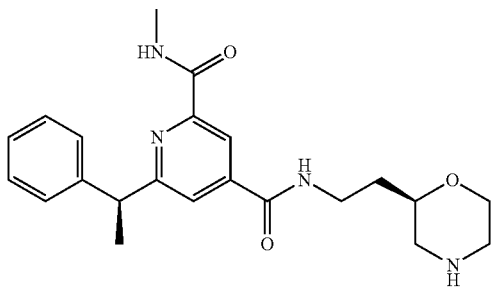

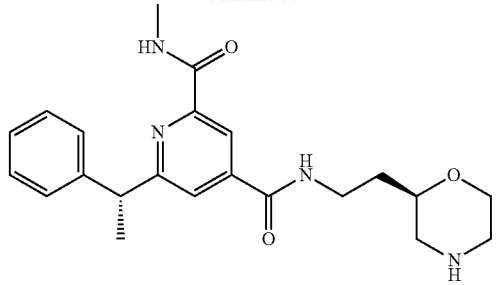

N²-Methyl-N⁴-(2-((R)-morpholin-2-yl)ethyl)-6-(1-phenylethyl)pyridine-2,4-dicarboxamide (30 mg) was submitted for chiral separation. 0.5 mL injections were made onto the column which was eluted with 10% EtOH (+0.2% isopropylamine)/heptane (+0.2% isopropylamine), flow rate=42.5 mL/min, detection: UV Diode Array at 280 nm (Band width 140 nm, reference 400 nm bandwidth 100 nm), column: Chiralcel OD-H (250×30 mm). Fractions from 18-20.5 min were bulked and labelled peak 1, fractions from 22-25 min were bulked and labelled peak 2. The bulked fractions were concentrated in vacuo and then taken up in EtOH (3×4 mL) and transferred to tared glass vials and these blown down to dryness under a stream of N₂.

Peak 1 provided Example 53 (8.7 mg).
LCMS (2 min High pH): Rt=0.88 min, [MH]⁺=397.4.
Peak 2 provided Example 54 (9.9 mg).
LCMS (2 min High pH): Rt=0.88 min, [MH]⁺=397.4.

Example 55

6-((1H-Indol-4-yl)methyl)-N⁴-((1r,5S,6s)-3-azabicyclo[3.1.0]hexan-6-yl)-N²-methylpyridine-2,4-dicarboxamide

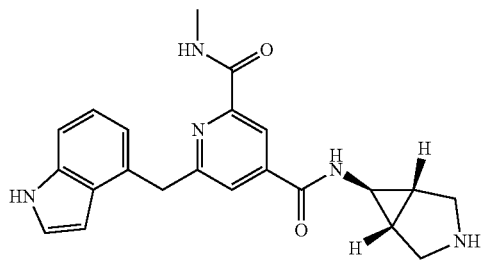 [SMILES: CNC(=O)c1cc(C(=O)N[C@H]2[C@@H]3CNC[C@@H]32)cc(Cc2cccc3[nH]ccc23)n1]

(1R,5S,6s)-tert-Butyl 6-(2-((1H-indol-4-yl)methyl)-6-(methylcarbamoyl)isonicotinamido)-3-azabicyclo[3.1.0]hexane-3-carboxylate (340 mg, 0.694 mmol) was taken up in DCM (5 mL), TFA (0.5 mL, 6.49 mmol) was added and the reaction left to stir at rt for 2 h. TFA (0.5 mL, 6.49 mmol) was added again and the reaction left to stir for a further 1 h. The reaction was concentrated in vacuo. The sample was loaded in MeOH and purified by SPE on sulphonic acid (SCX, 2 g) eluting with MeOH followed by 2M ammonia/MeOH. The appropriate fractions were combined and evaporated in vacuo to give the crude product. The crude product was dissolved in 1:1 MeCN:DMSO (1 mL) and purified by MDAP (High pH). The solvent was evaporated in vacuo, but was still impure. The crude product was dissolved in 1:1 MeCN:DMSO (1 mL) and purified by MDAP (High pH). The solvent was evaporated in vacuo to give the required product (24 mg) as a yellow solid.

LCMS (2 min High pH): Rt=0.77 min, [MH]⁺=390.4.

Example 56

(R)-6-Benzyl-N⁴-(2-(3-fluoropiperidin-3-yl)ethyl)-N²-methylpyridine-2,4-dicarboxamide

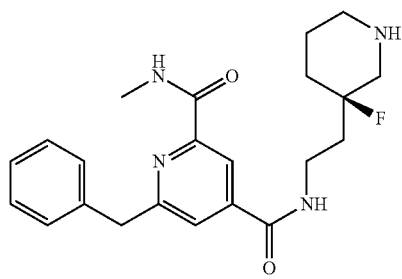 [SMILES: CNC(=O)c1cc(C(=O)NCC[C@]2(F)CCCNC2)cc(Cc2ccccc2)n1]

(R)-tert-Butyl 3-(2-(2-benzyl-6-(methylcarbamoyl)isonicotinamido)ethyl)-3-fluoropiperidine-1-carboxylate (200 mg, 0.401 mmol) was dissolved in DCM (3 mL) and TFA (1 mL) was added, then the mixture was stirred at rt for 2 h. The solvent was evaporated in vacuo and the residue was dissolved in MeOH and loaded onto a 5 g SCX cartridge, which was washed with MeOH (20 mL), then eluted with 2M NH₃ in MeOH and the eluant evaporated in vacuo to give (R)-6-benzyl-N⁴-(2-(3-fluoropiperidin-3-yl)ethyl)-N²-methylpyridine-2,4-dicarboxamide (135 mg, 0.339 mmol, 84% yield) as a colourless foam.

LCMS (2 min Formic): Rt=0.61 min, [MH]⁺=399.

Example 57

N²-Methyl-N⁴-(3-((S)-morpholin-2-yl)propyl)-6-((R*)-1-phenylethyl)pyridine-2,4-dicarboxamide

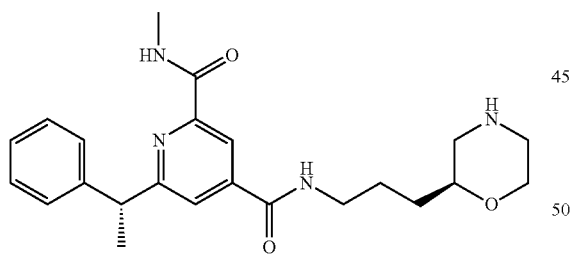

(S)-tert-Butyl 2-(3-(2-(methylcarbamoyl)-6-((R*)-1-phenylethyl)isonicotinamido)propyl)morpholine-4-carboxylate (151 mg, 0.296 mmol) was taken up in DCM (5 mL). TFA (0.5 mL, 6.49 mmol) was added and the reaction was left to stir at rt overnight. The reaction was concentrated in vacuo, The sample was loaded in MeOH and purified by SPE on sulphonic acid (SCX) 1 g eluting with MeOH, followed by 2M ammonia/MeOH. The appropriate fractions were combined and evaporated in vacuo. The samples were dissolved in 1:1 MeCN:DMSO (1 mL) and purified by MDAP (High pH). The solvent was evaporated in vacuo to give the required product, (36.6 mg) as a yellow gel.

LCMS (2 min High pH): Rt=0.91 min, [MH]⁺=411.4.

Example 58

N⁴-((1R,5S,6s)-3-Acetyl-3-azabicyclo[3.1.0]hexan-6-yl)-6-benzyl-N²-methylpyridine-2,4-dicarboxamide

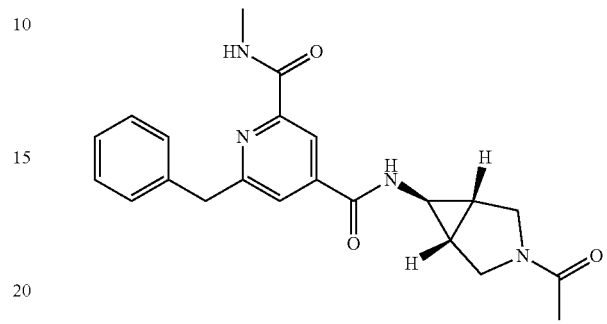

6-Benzyl-N⁴-((1R,5S)-3-azabicyclo[3.1.0]hexan-6-yl)-N²-methylpyridine-2,4-dicarboxamide (120 mg, 0.342 mmol) was taken up in DMF (5 mL). Acetyl chloride (0.146 mL, 2.055 mmol) and Et₃N (0.095 mL, 0.685 mmol) were added and the reaction left to stir at rt for 2 h. The reaction was concentrated in vacuo. The residue was taken up in EtOAc (10 mL) and washed with water (10 mL). The organic phase was dried over Na₂SO₄ and filtered though a hydrophobic frit. The residue was taken up in EtOAc (10 mL) and washed with NaHCO₃ (10 mL). The organic phase was concentrated in vacuo to afford the desired product. (53 mg) as a brown oil.

LCMS (2 min High pH): Rt=0.84 min, [MH]⁺=393.4

Example 59

(R)-6-Benzyl-N⁴-(2-(4-(2,2-difluoroethyl)morpholin-2-yl)ethyl)-N²-methylpyridine-2,4-dicarboxamide

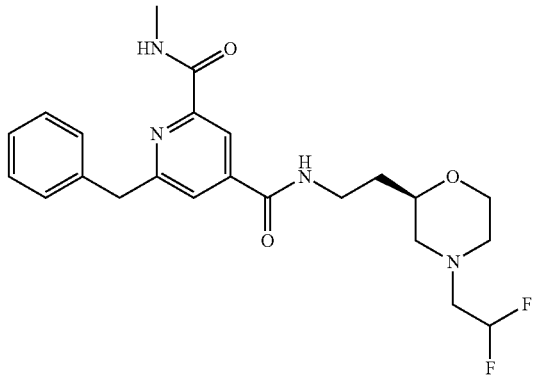 [SMILES: CNC(=O)c1cc(C(=O)NCC[C@@H]2CN(CC(F)F)CCO2)cc(Cc2ccccc2)n1]

(R)-6-Benzyl-N²-methyl-N⁴-(2-(morpholin-2-yl)ethyl)pyridine-2,4-dicarboxamide (22 mg, 0.058 mmol), 2-bromo-1,1-difluoroethane (25.01 mg, 0.173 mmol), K₂CO₃ (15.90 mg, 0.115 mmol) in MeCN (1 mL) was sealed in a microwave vial and heated in a Biotage® Initiator microwave to 140° C. for 2 h. Further 2-bromo-1,1-difluoroethane (25.01 mg, 0.173 mmol) was added and the reaction was sealed and heated in the microwave to 140° C. for a further 1 h. The reaction was concentrated in vacuo and the residue was taken up in EtOAc (10 mL) and extracted with NaHCO₃ (10 mL). The organic phase was washed with brine (10 mL) before being dried over Na₂SO₄, filtered though a hydrophobic frit and concentrated in vacuo. The sample was dissolved in 1:1 MeCN:DMSO (1 mL) and purified by MDAP (High pH). The solvent was evaporated in vacuo to give the required product (9.3 mg) as a brown oil.

LCMS (2 min High pH): Rt=1.02 min, [MH]⁺=447.4

Example 60

6-Benzyl-N²-methyl-N⁴-(3-(4-methyl-3-oxopiperazin-1-yl)propyl)pyridine-2,4-dicarboxamide

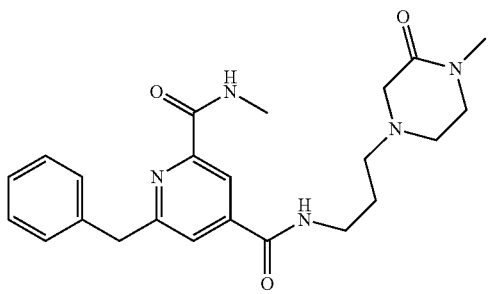 [SMILES: CNC(=O)c1cc(C(=O)NCCCN2CCN(C)C(=O)C2)cc(Cc2ccccc2)n1]

To a mixture of 2-benzyl-6-(methylcarbamoyl)isonicotinic acid (51.9 mg, 0.192 mmol), 4-(3-aminopropyl)-1-methylpiperazin-2-one (35.0 mg, 0.204 mmol) and HATU (96 mg, 0.252 mmol) in DMF (1 mL) was added DIPEA (0.100 mL, 0.573 mmol). The mixture was stirred at rt for 3 h 20 min. Further 4-(3-aminopropyl)-1-methylpiperazin-2-one (11.5 mg, 0.067 mmol) in DMF (0.20 mL) was added and the mixture stirred for a further 1 h. Further HATU (28.0 mg, 0.074 mmol) was added. Stirring continued for a further 30 min. The mixture was left to stand for approx 65 h, after which it was stirred at rt for a further 2.5 h. The solution was diluted with DMSO (1 mL) and directly purified by MDAP (2×1 mL injection, high pH). The required fractions were evaporated under a stream of N₂, redissolved in MeOH (approx. 2 mL each) and combined. This solution was evaporated under a stream of N₂ and the residue dried in vacuo to give a yellow gum; 6-benzyl-N²-methyl-N⁴-(3-(4-methyl-3-oxopiperazin-1-yl)propyl)pyridine-2,4-dicarboxamide (53.2 mg, 0.126 mmol, 65.4% yield).

LCMS (2 min high pH); Rt=0.84 min, m/z=424 for [MH]⁺

Example 61

6-Benzyl-N²-methyl-N⁴-(3-(3-oxopiperazin-1-yl)propyl)pyridine-2,4-dicarboxamide

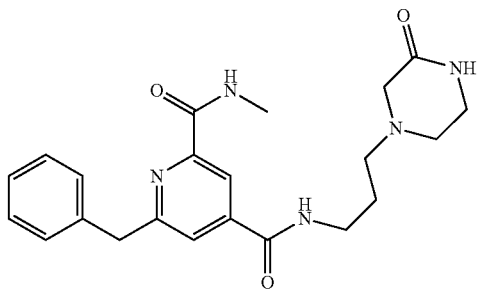 [SMILES: CNC(=O)c1cc(C(=O)NCCCN2CCNC(=O)C2)cc(Cc2ccccc2)n1]

To a mixture of 2-benzyl-6-(methylcarbamoyl)isonicotinic acid (53.2 mg, 0.197 mmol), 4-(3-aminopropyl)piperazin-2-one (35.3 mg, 0.225 mmol) and HATU (89 mg, 0.234 mmol) in DMF (1 mL) was added DIPEA (0.100 mL, 0.573 mmol). The mixture was stirred at rt for 9 h. Further 4-(3-aminopropyl)piperazin-2-one (8.9 mg, 0.057 mmol) in DMF (0.20 mL) was added after 3 h 10 min.

Further HATU (26.7 mg, 0.070 mmol) was added after 4 h 20 min. The solution was diluted with DMSO (up to a total of 2 mL) and directly purified by MDAP (2×1 mL injection, high pH). The required fractions were evaporated under a stream of N₂, redissolved in MeOH (approx. 2 mL each) and combined. This solution was evaporated under a stream of N₂ and the residue dried in vacuo to give a light yellow glassy solid; 6-benzyl-N²-methyl-N⁴-(3-(3-oxopiperazin-1-yl)propyl)pyridine-2,4-dicarboxamide (57.9 mg, 0.141 mmol, 71.8% yield).

LCMS (2 min high pH); Rt=0.80 min, m/z=410 for [MH]⁺

Example 62

(±)-tert-Butyl 4-(2-(2-benzyl-6-(methylcarbamoyl)isonicotinamido)ethyl)-3,3-difluoropiperidine-1-carboxylate

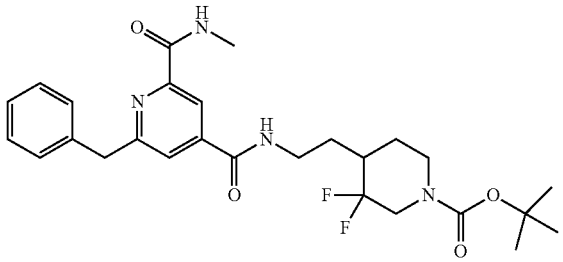 [SMILES: CNC(=O)c1cc(C(=O)NCCC2CCN(C(=O)OC(C)(C)C)CC2(F)F)cc(Cc2ccccc2)n1]

To a solution of 2-benzyl-6-(methylcarbamoyl)isonicotinic acid (97.4 mg, 0.360 mmol), (±)-tert-butyl 4-(2-aminoethyl)-3,3-difluoropiperidine-1-carboxylate (99.6 mg, 0.377 mmol) and HATU (203.6 mg, 0.535 mmol) in DMF (1.8 mL) was added DIPEA (0.189 mL, 1.081 mmol). The mixture was stirred at rt for 45 min. The reaction mixture was diluted with MeCN to a total volume of 3 mL and directly purified by MDAP (3×1 mL injection; formic) and the required fractions were combined and evaporated in vacuo. The residue was suspended in DCM, transferred to a tarred vial and the solvent evaporated under a stream of $N_2$ to give a white crunchy foam; (±)-tert-butyl 4-(2-(2-benzyl-6-(methylcarbamoyl)isonicotinamido)ethyl)-3,3-difluoropiperidine-1-carboxylate (114.3 mg, 0.221 mmol, 61.4% yield)

LCMS (2 min formic); Rt=1.23 min, m/z=517 for [MH]⁺

Example 63

N⁴-(3-((R)-3-Fluoropiperidin-3-yl)propyl)-N²-methyl-6-(1-phenylethyl)pyridine-2,4-dicarboxamide, 1:1 Mixture of Diastereomers at Undefined Stereocentre

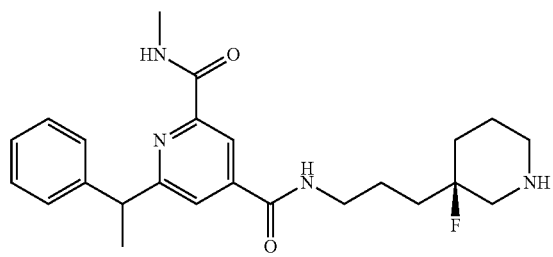 [SMILES: CNC(=O)c1cc(C(=O)NCCC[C@]2(F)CCCNC2)cc(C(C)c2ccccc2)n1]

(3S)-tert-Butyl 3-fluoro-3-(3-(2-(methylcarbamoyl)-6-(1-phenylethyl)isonicotinamido)propyl)piperidine-1-carboxylate (147 mg, 0.28 mmol) was taken up in DCM (5 mL), TFA (0.5 mL, 6.49 mmol) was added and the reaction left to stir at rt for 2 h. The reaction was concentrated in vacuo to afford the desired product (83 mg) as a brown oil. LCMS (2 min High pH): Rt=1.00 min, [MH]⁺=427.

Example 64

6-Benzyl-N²-methyl-N⁴-(3-(2-oxopiperazin-1-yl)propyl)pyridine-2,4-dicarboxamide, hydrochloride

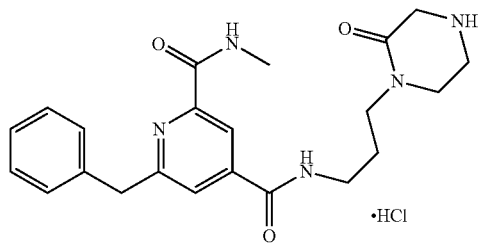 [SMILES: CNC(=O)c1cc(C(=O)NCCCN2CCNCC2=O)cc(Cc2ccccc2)n1 ; Cl]

To a solution of tert-butyl 4-(3-(2-benzyl-6-(methylcarbamoyl)isonicotinamido)propyl)-3-oxopiperazine-1-carboxylate (50.2 mg, 0.099 mmol) in 1,4-dioxane (1 mL) was added HCl (4.0M in 1,4-dioxane, 1.0 mL, 4.00 mmol) dropwise. The mixture was stirred at rt for 5 h 10 min. Further HCl (4.0M in 1,4-dioxane, 0.2 mL, 0.800 mmol) was added after 3 h 20 min. The mixture was evaporated under a stream of $N_2$ and the residue dried in vacuo to give a yellow solid (48.6 mg). This was triturated with diethyl ether (2×1 mL) and the residue left to dry in air and then dried in vacuo to give a yellow solid; 6-benzyl-N²-methyl-N⁴-(3-(2-oxopiperazin-1-yl)propyl)pyridine-2,4-dicarboxamide, hydrochloride (39.3 mg, 0.088 mmol, 89% yield).

LCMS (2 min high pH); Rt=0.79 min, m/z=410 for [MH]⁺

Example 65

6-Benzyl-N⁴-((1R,5S,6s)-3-(2,2-difluoroethyl)-3-azabicyclo[3.1.0]hexan-6-yl)-N²-methylpyridine-2,4-dicarboxamide

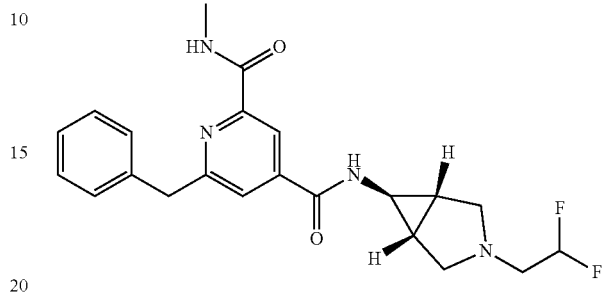

6-Benzyl-N⁴-((1R,5S,6s)-3-azabicyclo[3.1.0]hexan-6-yl)-N²-methylpyridine-2,4-dicarboxamide (27 mg, 0.077 mmol), $K_2CO_3$ (21.30 mg, 0.154 mmol), DMF (1 mL) and 2-bromo-1,1-difluoroethane (33.5 mg, 0.231 mmol) were added to a microwave vial. The reaction vessel was sealed and heated in Biotage® Initiator microwave to 140° C. for 1 h. The reaction was concentrated in vacuo. The residue was taken up in ethyl acetate (10 mL) and extracted using $NaHCO_3$ (10 mL). The organic phase was washed with brine (10 mL) before being dried over $Na_2SO_4$, filtered though a hydrophobic frit and concentrated in vacuo. The sample was dissolved in 1:1 MeCN:DMSO (1 mL) and purified by MDAP (High pH). The solvent was evaporated in vacuo to give the required product (12 mg) as a brown oil.

LCMS (2 min Formic): Rt=0.63 min, [MH]⁺=415.2

Example 66

(±)-6-Benzyl-N⁴-(2-(4,4-difluoropiperidin-3-yl)ethyl)-N²-methylpyridine-2,4-dicarboxamide, hydrochloride

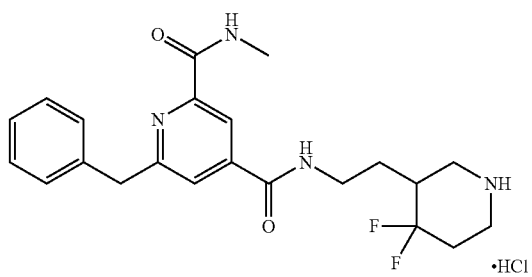 [SMILES: CNC(=O)c1cc(C(=O)NCCC2CNCCC2(F)F)cc(Cc2ccccc2)n1 ; Cl]

A solution of (±)-tert-butyl 3-(2-(2-benzyl-6-(methylcarbamoyl)isonicotinamido)ethyl)-4,4-difluoropiperidine-1-carboxylate (119.6 mg, 0.232 mmol) in 1,4-dioxane (2 mL) had HCl (4.0 M solution in 1,4-dioxane, 2.3 mL, 9.20 mmol) added to it. The mixture was stirred at rt for 2.25 h. The mixture was evaporated to dryness under a stream of $N_2$ and the residue triturated with diethyl ether (2×4 mL). The solid material was dried in vacuo to give a cream solid; (±)-6- benzyl-N⁴-(2-(4,4-difluoropiperidin-3-yl)ethyl)-N²-methylpyridine-2,4-dicarboxamide, hydrochloride (110.6 mg, 0.244 mmol)

LCMS (2 min formic); Rt=0.62 min, m/z=417 for [MH]⁺

Example 67

(±)-6-Benzyl-N⁴-(2-(3,3-difluoropiperidin-4-yl)ethyl)-N²-methylpyridine-2,4-dicarboxamide, hydrochloride

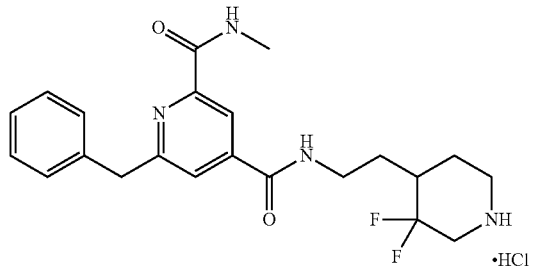 [SMILES: CNC(=O)c1cc(C(=O)NCCC2CCNCC2(F)F)cc(Cc2ccccc2)n1 ; Cl]

A solution of (±)-tert-butyl 4-(2-(2-benzyl-6-(methylcarbamoyl)isonicotinamido)ethyl)-3,3-difluoropiperidine-1-carboxylate (103.5 mg, 0.200 mmol) in 1,4-dioxane (2 mL) had HCl (4.0 M solution in 1,4-dioxane, 2.0 mL, 8.00 mmol) added to it. The mixture was stirred at rt for 2.25 h. The mixture was evaporated to dryness under a stream of N₂ and the residue triturated with diethyl ether (2×4 mL). The solid material was dried in vacuo to give a cream solid; (±)-6-benzyl-N⁴-(2-(3,3-difluoropiperidin-4-yl)ethyl)-N²-methylpyridine-2,4-dicarboxamide, hydrochloride (93.4 mg, 0.206 mmol)

LCMS (2 min formic); Rt=0.60 min, m/z=417 for [MH]⁺

Example 68

N⁴-((1R,5S,6r)-3-Oxabicyclo[3.1.0]hexan-6-yl)-6-(4-cyanobenzyl)-N²-methylpyridine-2,4-dicarboxamide

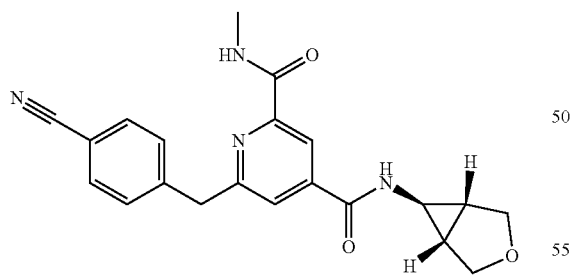

To a solution of 2-(4-cyanobenzyl)-6-(methylcarbamoyl)isonicotinic acid (57 mg, 0.193 mmol) in DMF (0.8 mL) was added HATU (110 mg, 0.290 mmol) followed by (1R,5S,6r)-3-oxabicyclo[3.1.0]hexan-6-amine, hydrochloride (40 mg, 0.295 mmol) and DIPEA (0.169 mL, 0.965 mmol). The resulting reaction mixture was stirred at rt in air for 1 h. The reaction mixture was purified by MDAP (Formic) and the fractions containing desired product were partitioned between sat. NaHCO₃ solution and DCM. The organic layer was extracted with DCM (2×20 mL), dried (Na₂SO₄) and concentrated in vacuo to give N⁴-((1R,5S,6r)-3-oxabicyclo[3.1.0]hexan-6-yl)-6-(4-cyanobenzyl)-N²-methylpyridine-2,4-dicarboxamide (33 mg, 0.079 mmol, 40.9% yield) as a pale pink solid.

LCMS (2 min Formic): Rt=0.82 min, [MH]+=377.2.

Example 69

N⁴-((1R,5S,6r)-3-Oxabicyclo[3.1.0]hexan-6-yl)-N²-methyl-6-(4-methylbenzyl)pyridine-2,4-dicarboxamide

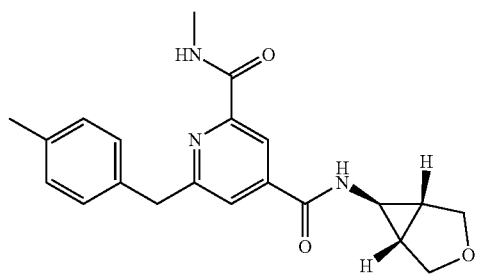 [SMILES: CNC(=O)c1cc(C(=O)N[C@H]2[C@@H]3COC[C@@H]32)cc(Cc2ccc(C)cc2)n1]

2-(4-Methylbenzyl)-6-(methylcarbamoyl)isonicotinic acid (50 mg, 0.176 mmol) was taken up in DMF (5 mL). DIPEA (0.092 mL, 0.528 mmol) and HATU (100 mg, 0.264 mmol) were added and the reaction left to stir at rt for 10 min. (1R,5S,6r)-3-Oxabicyclo[3.1.0]hexan-6-amine, hydrochloride (35.8 mg, 0.264 mmol) was added and the reaction left to stir for a further 2 h. The reaction was concentrated in vacuo. The residue was taken up in EtOAc (10 mL) and extracted using NaHCO₃ (10 mL). The organic phase was washed with brine (10 mL) before being dried over Na₂SO₄, filtered though a hydrophobic frit and concentrated in vacuo. The samples were dissolved in 1:1 MeCN:DMSO (1 mL) and purified by MDAP (High pH). The solvent was evaporated in vacuo to give the required product (9.8 mg) as a brown glass.

LCMS (2 min High pH): Rt=0.99 min, [MH]⁺=366.3

Example 70

N⁴-((1R,5S,6r)-3-Oxabicyclo[3.1.0]hexan-6-yl)-6-((S)-hydroxy(phenyl)methyl)-N²-methylpyridine-2,4-dicarboxamide

Example 71

N⁴-((1R,5S,6r)-3-Oxabicyclo[3.1.0]hexan-6-yl)-6-((R)-hydroxy(phenyl)methyl)-N²-methylpyridine-2,4-dicarboxamide

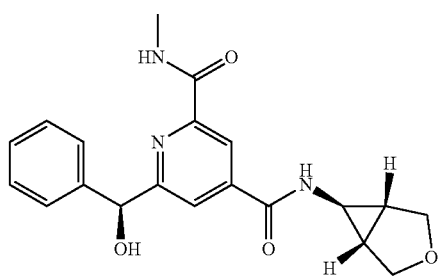

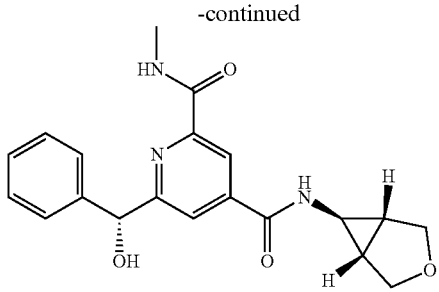

(+/−)-N⁴-((1R,5S,6r)-3-Oxabicyclo[3.1.0]hexan-6-yl)-6-(hydroxy(phenyl)methyl)-N²-methylpyridine-2,4-dicarboxamide (15 mg) was purified by chiral HPLC. The racemate was dissolved in EtOH (1.5 mL). Injection: 1.5 mL of the solution was injected onto the column (30% EtOH/Heptane, flow rate=20 mL/min, detection wavelength=215 nm, Column 2 cm×25 cm (R:R) Whelk-O1,Serial No. 49788). Fractions from 17-19.5 min were bulked and labelled peak 1. Fractions from 20.5-24 min were bulked and labelled peak 2. The bulked fractions were concentrated in vacuo and then transferred to weighed flasks.

The fractions corresponding to peak 1 were collected to afford Example 70 (7 mg)

LCMS (2 min Formic): Rt=0.72 min, [MH]⁺=368.3

The fractions corresponding to peak 2 were collected to afford Example 71 (7 mg)

LCMS (2 min Formic): Rt=0.72 min, [MH]⁺=368.3

Example 72

N⁴-((1R,5S,6r)-3-Oxabicyclo[3.1.0]hexan-6-yl)-N²-methyl-6-(3-methylbenzyl)pyridine-2,4-dicarboxamide

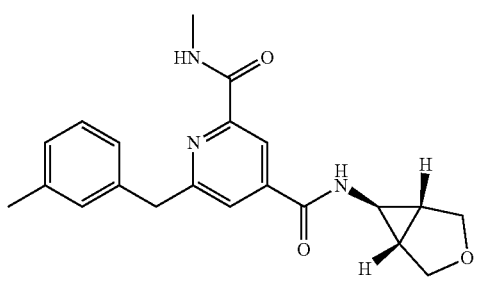 [SMILES: CNC(=O)c1cc(C(=O)N[C@H]2[C@@H]3COC[C@@H]32)cc(Cc2cccc(C)c2)n1]

2-(3-Methylbenzyl)-6-(methylcarbamoyl)isonicotinic acid (50 mg, 0.176 mmol) was taken up in DMF (5 mL). DIPEA (0.092 mL, 0.528 mmol), HATU (100 mg, 0.264 mmol) and (1R,5S,6r)-3-oxabicyclo[3.1.0]hexan-6-amine, hydrochloride (35.8 mg, 0.264 mmol) were added and the reaction left to stir at rt for 1 h. The reaction was concentrated in vacuo. The residue was taken up in EtOAc (10 mL) and extracted using NaHCO₃ (10 mL). The organic phase was washed with brine (10 mL) before being dried over Na₂SO₄, filtered though a hydrophobic frit and concentrated in vacuo. The samples were dissolved in 1:1 MeCN:DMSO (1 mL) and purified by MDAP (High pH). The solvent was evaporated in vacuo to give the required product (23 mg) as a white powder.

LCMS (2 min Formic): Rt=0.96 min, [MH]⁺=366.4

Example 73

N⁴-((1R,5S,6r)-3-Oxabicyclo[3.1.0]hexan-6-yl)-6-(3-cyanobenzyl)-N²-methylpyridine-2,4-dicarboxamide

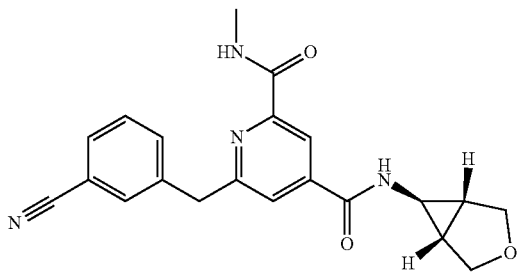 [SMILES: CNC(=O)c1cc(C(=O)N[C@H]2[C@@H]3COC[C@@H]32)cc(Cc2cccc(C#N)c2)n1]

To a solution of 2-(3-cyanobenzyl)-6-(methylcarbamoyl)isonicotinic acid (47 mg, 0.159 mmol) in DMF (0.8 mL) was added HATU (91 mg, 0.239 mmol) followed by (1R,5S,6r)-3-oxabicyclo[3.1.0]hexan-6-amine, hydrochloride (40 mg, 0.295 mmol) and DIPEA (0.139 mL, 0.796 mmol). The resulting reaction mixture was stirred at rt in air for 1 h. The reaction mixture was purified by MDAP (Formic) acid. The fractions containing the desired product were partitioned between sat. NaHCO₃ solution and DCM. The organic layer was extracted (2×20 mL), dried (Na₂SO₄) and concentrated in vacuo to give N⁴-((1R,5S,6r)-3-oxabicyclo[3.1.0]hexan-6-yl)-6-(3-cyanobenzyl)-N²-methylpyridine-2,4-dicarboxamide (37 mg, 0.088 mmol, 55.6% yield) as a white solid.

LCMS (2 min Formic): Rt=0.83 min, [MH]+=377.3.

Example 74

(R)—N²-Methyl-6-(3-methylbenzyl)-N⁴-(2-(morpholin-2-yl)ethyl)pyridine-2,4-dicarboxamide

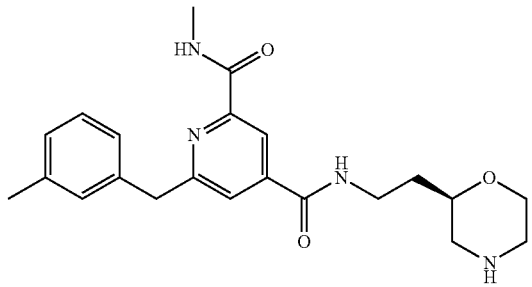 [SMILES: CNC(=O)c1cc(C(=O)NCC[C@@H]2CNCCO2)cc(Cc2cccc(C)c2)n1]

(R)-tert-Butyl 2-(2-(2-(3-methylbenzyl)-6-(methylcarbamoyl)isonicotinamido)ethyl)morpholine-4-carboxylate (50 mg, 0.101 mmol) was taken up in DCM (5 mL). TFA (0.5 mL, 6.49 mmol) was added and the reaction left to stir at rt for 2 h. The reaction was then concentrated in vacuo. The crude product was loaded in MeOH and purified by SPE on sulphonic acid (SCX) 1 g using MeOH, followed by 2M ammonia/MeOH. The appropriate fractions were combined and evaporated in vacuo. The crude product was applied to a 10 g SNAP silica cartridge in the minimum of DCM and purified by flash chromatography, eluting with 0-100% (3:1

EtOAc:EtOH). The column was extended using 0-100% (10% 2M NH₃ in MeOH) in DCM. The appropriate fractions were combined and concentrated in vacuo. The sample was dissolved in 1:1 MeCN:DMSO (1 mL) and purified by MDAP (High pH). The solvent was evaporated in vacuo to give the required product (15 mg) as a yellow glass.

LCMS (2 min Formic): Rt=0.90 min, [MH]⁺=397.4

Example 75

N⁴-((1R,5S,6r)-3-Oxabicyclo[3.1.0]hexan-6-yl)-6-(2-methoxybenzyl)-N²-methylpyridine-2,4-dicarboxamide

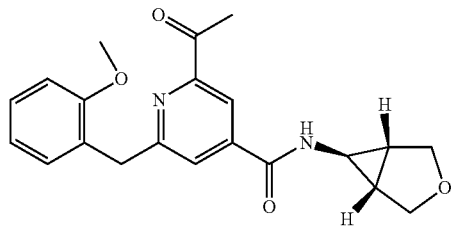 [SMILES: COc1ccccc1Cc1cc(C(=O)N[C@H]2[C@@H]3COC[C@@H]32)cc(C(C)=O)n1]

To a solution of 2-(2-methoxybenzyl)-6-(methylcarbamoyl)isonicotinic acid (47.8 mg, 0.159 mmol), (1R,5S,6r)-3-oxabicyclo[3.1.0]hexan-6-amine, hydrochloride (23.40 mg, 0.173 mmol, commercially available from Manchester Organics) and HATU (75 mg, 0.197 mmol) in DMF (1 mL) was added N, N-diisopropylethylamine (0.111 mL, 0.637 mmol). The solution was stirred at rt for 30 min, after which the volatiles were evaporated under a stream of N₂ to give a sticky dark orange solid. This was redissolved in approx 1:1 DMSO:DMF (2 mL) and directly purified by MDAP (2×1 mL injection, high pH). The required fractions were evaporated under a stream of N₂, redissolved in MeOH (approx. 2 mL each) and combined. This solution was evaporated under a stream of N₂ and the residue dried in vacuo to give a white solid; N⁴-((1R,5S,6r)-3-oxabicyclo [3.1.0]hexan-6-yl)-6-(2-methoxybenzyl)-N²-methylpyridine-2,4-dicarboxamide (49.1 mg, 0.129 mmol, 81% yield).

LCMS (2 min high pH); Rt=0.93 min, m/z=382 for [MH]+

Example 76

(+/−)-N⁴-((1R,5S,6r)-3-Oxabicyclo[3.1.0]hexan-6-yl)-6-(hydroxy(phenyl)methyl)-N²-methylpyridine-2,4-dicarboxamide

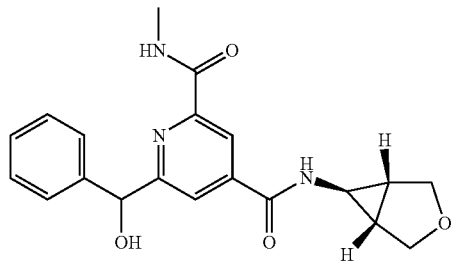 [SMILES: CNC(=O)c1cc(C(=O)N[C@H]2[C@@H]3COC[C@@H]32)cc(C(O)c2ccccc2)n1]

To a solution of 2-(hydroxy(phenyl)methyl)-6-(methylcarbamoyl)isonicotinic acid (47.9 mg, 0.167 mmol) in DMF (0.7 mL) was added HATU (95 mg, 0.251 mmol) followed by (1R,5S,6r)-3-oxabicyclo[3.1.0]hexan-6-amine (25 mg, 0.252 mmol) and DIPEA (0.10 mL, 0.573 mmol). The resulting reaction mixture was stirred at rt overnight. The reaction mixture was purified directly by MDAP (high pH). The fractions containing the desired product were concentrated in vacuo to give N⁴-((1R,5S,6r)-3-oxabicyclo[3.1.0] hexan-6-yl)-6-(hydroxy(phenyl)methyl)-N²-methylpyridine-2,4-dicarboxamide (18.4 mg, 0.048 mmol, 28.4% yield) as a colourless oil.

LCMS (2 min Formic): Rt=0.73 min, [MH]⁺=368.3
¹H NMR (400 MHz, CDCl₃) δ ppm 8.28 (d, J=1.5 Hz, 1H) 7.85-8.00 (m, 2H) 7.21-7.45 (obs. m, 5H) 6.85 (br. s., 1H) 5.90 (s, 1H) 4.05 (dd, J=8.6, 1.7 Hz, 2H) 3.87-3.99 (m, 1H) 3.75 (d, J=9.0 Hz, 2H) 3.04 (d, J=5.1 Hz, 3H) 2.70-2.79 (m, 1H) 1.83-1.95 (m, 2H).

Example 77

(+/−)-tert-Butyl 2-(3-(2-(3-methoxybenzyl)-6-(methylcarbamoyl)isonicotinamido)propyl)morpholine-4-carboxylate

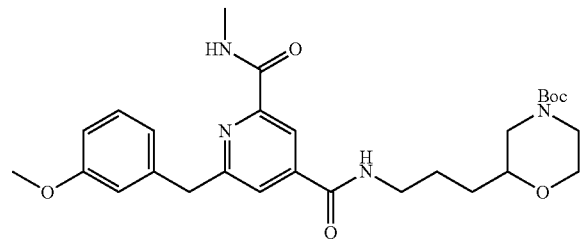 [SMILES: CNC(=O)c1cc(C(=O)NCCCC2CN(C(=O)OC(C)(C)C)CCO2)cc(Cc2cccc(OC)c2)n1]

2-(3-Methoxybenzyl)-6-(methylcarbamoyl)isonicotinic acid (80 mg, 0.266 mmol) was dissolved in DMF (2 mL), then HATU (152 mg, 0.400 mmol) and Et₃N (0.074 mL, 0.533 mmol) were added and the mixture was stirred for 20 min at rt, then tert-butyl 2-(3-aminopropyl)morpholine-4-carboxylate (65.1 mg, 0.266 mmol) was added and the solution was stirred for 2 h. The resulting mixture was purified directly by MDAP (High pH) to give tert-butyl 2-(3-(2-(3-methoxybenzyl)-6-(methylcarbamoyl)isonicotinamido)propyl)morpholine-4-carboxylate (85 mg, 0.161 mmol, 60.6% yield) as a pale yellow glass.

LCMS (2 min High pH): Rt=1.17 min, [MH]⁺=527.4.

Example 78

(±)-tert-Butyl 3-(2-(2-benzyl-6-(methylcarbamoyl) isonicotinamido)ethyl)-4,4-difluoropiperidine-1-carboxylate

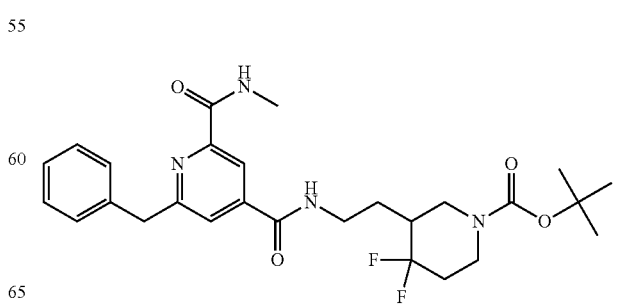

To a solution of 2-benzyl-6-(methylcarbamoyl)isonicotinic acid (99.0 mg, 0.366 mmol), (±)-tert-butyl 3-(2-aminoethyl)-4,4-difluoropiperidine-1-carboxylate (99.7 mg, 0.377 mmol) and HATU (202.9 mg, 0.534 mmol) in DMF (1.8 mL) was added DIPEA (0.192 mL, 1.099 mmol). The mixture was stirred at rt for 45 min. The reaction mixture was diluted with MeCN to a total volume of 3 mL and directly purified by MDAP (3×1 mL injection; formic) and the required fractions were combined and evaporated in vacuo. The residue was suspended in DCM, transferred to a tarred vial and the solvent evaporated under a stream of $N_2$ to give a white crunchy foam; (±)-tert-butyl 3-(2-(2-benzyl-6-(methylcarbamoyl)isonicotinamido)ethyl)-4,4-difluoropiperidine-1-carboxylate (131.5 mg, 0.255 mmol, 69.5% yield)

LCMS (2 min formic); Rt=1.23 min, m/z=517 for [MH]

Examples 79-87

Examples 79-87 were prepared in an analogous manner to the previous examples

| Ex No. | Name | Structure | [MH]+ | Rt (min)* |
|---|---|---|---|---|
| 79 | 6-(3-Methoxybenzyl)-$N^2$-methyl-$N^4$-(tetrahydro-2H-pyran-4-yl)pyridine-2,4-dicarboxamide | 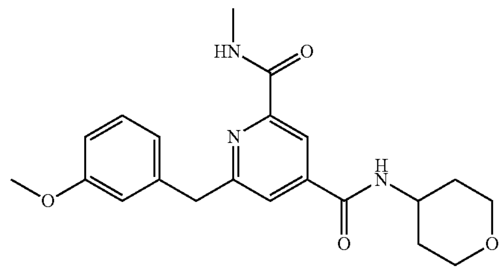 [SMILES: CNC(=O)c1cc(C(=O)NC2CCOCC2)cc(Cc2cccc(OC)c2)n1] | 384.3 (high pH) | 0.93 |
| 80 | (+/−)-$N^4$-(2-(4-Acetylmorpholin-2-yl)ethyl)-6-(3-methoxybenzyl)-$N^2$-methylpyridine-2,4-dicarboxamide | 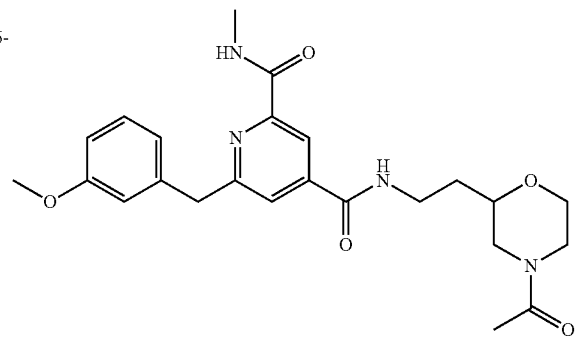 | 455.3 (TFA) | 0.81 |
| 81 | (+/−)-6-Benzyl-$N^2$-methyl-$N^4$-(tetrahydro-2H-pyran-3-yl)pyridine-2,4-dicarboxamide | 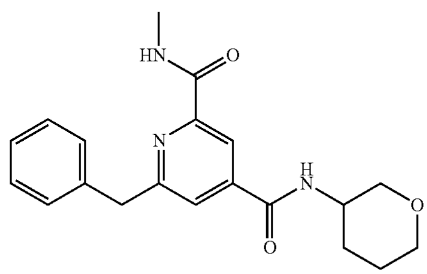 [SMILES: CNC(=O)c1cc(C(=O)NC2CCCOC2)cc(Cc2ccccc2)n1] | 354.3 (formic) | 0.91 |
| 82 | (+/−)-6-Benzyl-$N^2$-methyl-$N^4$-((tetrahydrofuran-3-yl)methyl)pyridine-2,4-dicarboxamide | 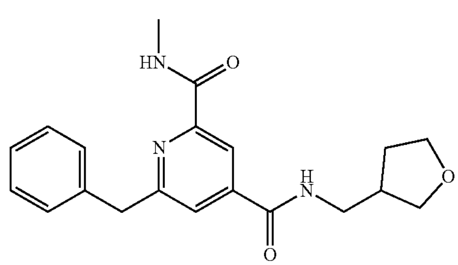 [SMILES: CNC(=O)c1cc(C(=O)NCC2CCOC2)cc(Cc2ccccc2)n1] | 354.2 (formic) | 0.88 |

-continued

| Ex No. | Name | Structure | [MH]⁺ | Rt (min)* |
|---|---|---|---|---|
| 83 | (+/−)-N⁴-(2-(4-Acetylmorpholin-2-yl)ethyl)-6-benzyl-N²-methylpyridine-2,4-dicarboxamide | 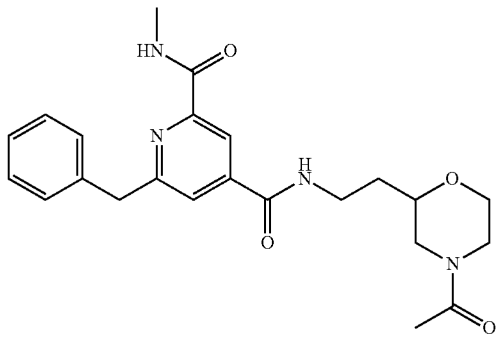 [SMILES: CNC(=O)c1cc(C(=O)NCCC2CN(C(C)=O)CCO2)cc(Cc2ccccc2)n1] | 425.2 (formic) | 0.83 |
| 84 | (+/−)-6-Benzyl-N²-methyl-N⁴-((tetrahydrofuran-2-yl)methyl)pyridine-2,4-dicarboxamide | 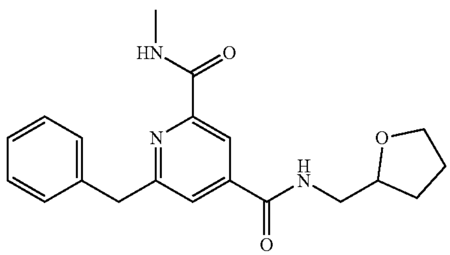 [SMILES: CNC(=O)c1cc(C(=O)NCC2CCCO2)cc(Cc2ccccc2)n1] | 354.2 (formic) | 0.92 |
| 85 | (+/−)-6-Benzyl-N²-methyl-N⁴-((tetrahydro-2H-pyran-2-yl)methyl)pyridine-2,4-dicarboxamide | 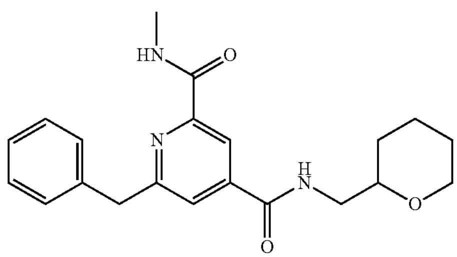 [SMILES: CNC(=O)c1cc(C(=O)NCC2CCCCO2)cc(Cc2ccccc2)n1] | 367.8 (formic) | 1.00 |
| 86 | N⁴-(Azetidin-3-yl)-6-benzyl-N²-methylpyridine-2,4-dicarboxamide | 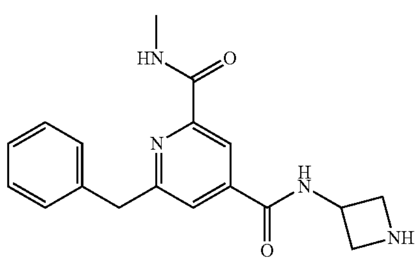 [SMILES: CNC(=O)c1cc(C(=O)NC2CNC2)cc(Cc2ccccc2)n1] | 325.1 (formic) | 0.54 |
| 87 | 6-Benzyl-N²-methyl-N⁴-((tetrahydro-2H-pyran-4-yl)methyl)pyridine-2,4-dicarboxamide | 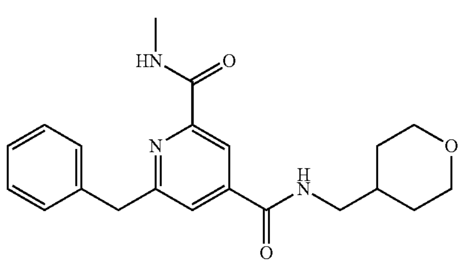 [SMILES: CNC(=O)c1cc(C(=O)NCC2CCOCC2)cc(Cc2ccccc2)n1] | 368.3 (formic) | 0.91 |

Example 88

N²-Methyl-N⁴-(3-((S)-morpholin-2-yl)propyl)-6-((S*)-1-phenylethyl)pyridine-2,4-dicarboxamide

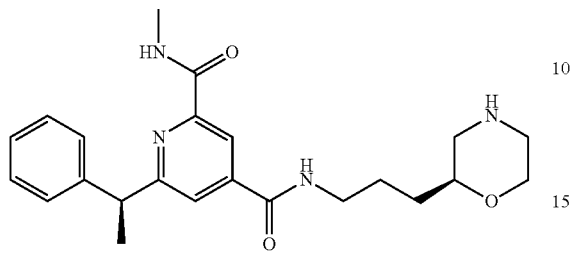

(2S)-tert-Butyl 2-(3-(2-(methylcarbamoyl)-6-(1-phenylethyl)isonicotinamido)propyl)morpholine-4-carboxylate (108 mg, 0.21 mmol) was taken up in DCM (5 mL). TFA (0.5 mL, 6.49 mmol) was added and the reaction was left to stir at rt for 2 h. The reaction was concentrated in vacuo. The sample was loaded in methanol and purified by SPE on sulphonic acid (SCX, 1 g) eluting with methanol, followed by 2M ammonia/methanol. The appropriate fractions were combined and evaporated in vacuo. The samples were dissolved in 1:1 MeCN:DMSO (1 mL) and purified by MDAP (High pH). The solvent was evaporated in vacuo to give the required product (32 mg) as a clear oil.

LCMS (2 min High pH): Rt=0.90 min, [MH]+=411.2.

Example 89

6-((1H-Pyrrolo[2,3-c]pyridin-4-yl)methyl)-N⁴-((1R,5S,6r)-3-oxabicyclo[3.1.0]hexan-6-yl)-N²-methylpyridine-2,4-dicarboxamide

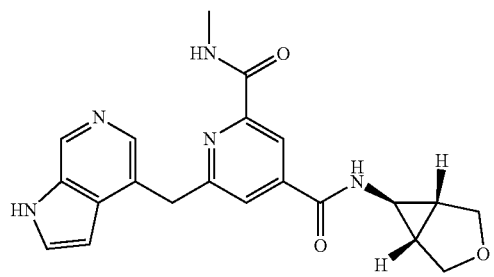 [SMILES: CNC(=O)c1cc(C(=O)N[C@H]2[C@@H]3COC[C@@H]32)cc(Cc2cncc3[nH]ccc23)n1]

To a solution of 2-((1H-pyrrolo[2,3-c]pyridin-4-yl)methyl)-6-(methylcarbamoyl)isonicotinic acid (67 mg, 0.11 mmol, 50% wt.) in DMF (0.8 mL) was added DIPEA (0.06 mL, 0.344 mmol) followed by HATU (61.6 mg, 0.16 mmol) and (1R,5S,6r)-3-oxabicyclo[3.1.0]hexan-6-amine, hydrochloride (21.96 mg, 0.162 mmol). The resulting reaction mixture was stirred at rt for 2 h. The reaction mixture was purified directly by MDAP (high pH). Fractions containing the desired product were concentrated in vacuo to give 6-((1H-pyrrolo[2,3-c]pyridin-4-yl)methyl)-N⁴-((1R,5S,6r)-3-oxabicyclo[3.1.0]hexan-6-yl)-N²-methylpyridine-2,4-dicarboxamide (15 mg, 0.036 mmol, 34% yield) as a colourless oil.

LCMS (2 min Formic): Rt=0.43 min, [MH]+=392.3

Example 90

N⁴-((1r,5S,6s)-3-Azabicyclo[3.1.0]hexan-6-yl)-N²-methyl-6-(3-methylbenzyl)pyridine-2,4-dicarboxamide

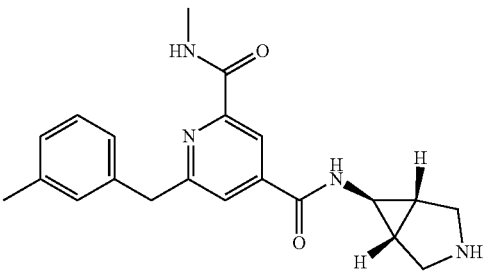 [SMILES: CNC(=O)c1cc(C(=O)N[C@H]2[C@@H]3CNC[C@@H]32)cc(Cc2cccc(C)c2)n1]

(1R,5S,6s)-tert-Butyl 6-(2-(3-methylbenzyl)-6-(methylcarbamoyl)isonicotinamido)-3-azabicyclo[3.1.0]hexane-3-carboxylate (295 mg, 0.635 mmol) was taken up in DCM (5 mL). TFA (0.5 mL, 6.49 mmol) was added and the reaction left to stir at rt for 3 h. The reaction was concentrated in vacuo. The sample was loaded in methanol and purified by SPE on sulphonic acid (SCX, 1 g) eluting with methanol, followed by 2M ammonia/methanol. The appropriate fractions were combined and evaporated in vacuo. The samples were dissolved in 1:1 MeCN:DMSO (3 mL) and purified by MDAP (High pH). The solvent was evaporated in vacuo to give the required product (68 mg) as a white solid.

LCMS (2 min Formic): Rt=0.62 min, [MH]+=365.3.

Example 91

N⁴-((1R,5S,6r)-3-Oxabicyclo[3.1.0]hexan-6-yl)-6-((3-fluoro-1H-indol-4-yl)methyl)-N2-methylpyridine-2,4-dicarboxamide

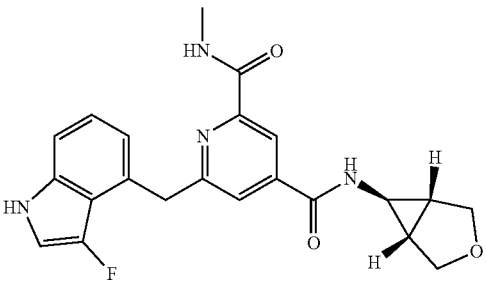 [SMILES: CNC(=O)c1cc(C(=O)N[C@H]2[C@@H]3COC[C@@H]32)cc(Cc2cccc3[nH]cc(F)c23)n1]

2-((3-Fluoro-1H-indol-4-yl)methyl)-6-(methylcarbamoyl)isonicotinic acid (154 mg, 0.471 mmol) was taken up in DMF (5 mL). DIPEA (0.247 mL, 1.41 mmol), HATU (268 mg, 0.71 mmol) and (1R,5S,6r)-3-oxabicyclo[3.1.0]hexan-6-amine, hydrochloride (96 mg, 0.706 mmol) were added and the reaction left to stir for 2 h. The reaction was concentrated in vacuo. The residue was taken up in ethyl acetate (15 mL) and extracted using aq. sodium bicarbonate solution (15 mL) and brine (2×15 mL). The organic phase was dried over sodium sulphate, filtered through a hydrophobic frit and concentrated in vacuo. The crude product was applied to a SNAP ULTRA silica cartridge (25 g) in the minimum of DCM and purified by flash chromatography, eluting with 5-50% (3:1 EtOAc:EtOH) in cyclohexane. The appropriate fractions were combined and concentrated in vacuo to afford N⁴-((1R,5S,6r)-3-oxabicyclo[3.1.0]hexan-6-yl)-6-((3-fluoro-1H-indol-4-yl)methyl)-N²-methylpyridine-2,4-dicarboxamide (96 mg, 0.235 mmol, 50% yield).

LCMS (2 min High pH): Rt=0.89 min, [MH]+=409.4.

Example 92

N⁴-((1R,5S,6r)-3-Oxabicyclo[3.1.0]hexan-6-yl)-6-(1-(3-methoxyphenyl)ethyl)-N²-methylpyridine-2,4-dicarboxamide

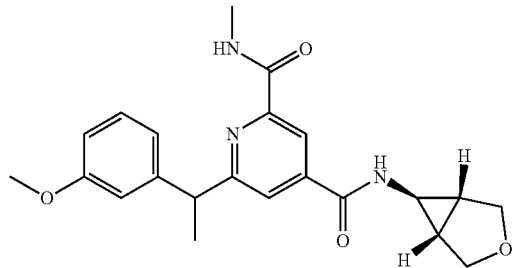 [SMILES: CNC(=O)c1cc(C(=O)N[C@H]2[C@@H]3COC[C@@H]32)cc(C(C)c2cccc(OC)c2)n1]

To a solution of 2-(1-(3-methoxyphenyl)ethyl)-6-(methylcarbamoyl)isonicotinic acid (81 mg, 0.142 mmol, 55% wt.) in DMF (0.7 mL) was added DIPEA (0.06 mL, 0.344 mmol) followed by HATU (85 mg, 0.224 mmol) and (1R,5S,6r)-3-oxabicyclo[3.1.0]hexan-6-amine, hydrochloride (30 mg, 0.22 mmol). The resulting reaction mixture was stirred at rt for 2 h. The reaction mixture was purified directly by MDAP (high pH). Fractions containing desired product were concentrated in vacuo to give N⁴-((1R,5S,6r)-3-oxabicyclo[3.1.0]hexan-6-yl)-6-(1-(3-methoxyphenyl)ethyl)-N²-methylpyridine-2,4-dicarboxamide (34 mg, 0.08 mmol, 58% yield) as a colourless oil.

LCMS (2 min Formic): Rt=0.95 min, [MH]+=396.3.

Example 93

N⁴-((1R,5S,6r)-3-Oxabicyclo[3.1.0]hexan-6-yl)-6-((2-cyano-1H-indol-4-yl)methyl)-N²-methylpyridine-2,4-dicarboxamide

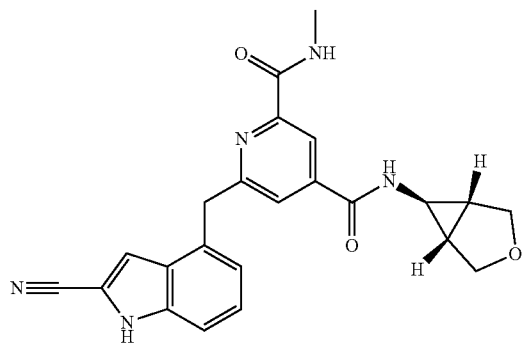 [SMILES: CNC(=O)c1cc(C(=O)N[C@H]2[C@@H]3COC[C@@H]32)cc(Cc2cccc3[nH]c(C#N)cc23)n1]

A mixture of 4-(4,4,5,5-tetramethyl-1,3,2-dioxaborolan-2-yl)-1H-indole-2-carbonitrile (27.0 mg, 0.10 mmol), N⁴-((1R,5S,6r)-3-oxabicyclo[3.1.0]hexan-6-yl)-6-(chloromethyl)-N²-methylpyridine-2,4-dicarboxamide (30.9 mg, 0.10 mmol), [1,1'-bis(diphenylphosphino)ferrocene]dichloropalladium(II) (11.0 mg, 0.02 mmol) and potassium carbonate (29.0 mg, 0.21 mmol) in 1,4-dioxane (0.80 mL) and water (0.40 mL) in a sealed microwave vial was heated in a microwave reactor at 80° C. for 30 min. The reaction mixture was filtered though a 2.5 g Celite cartridge and the cartridge washed with ethyl acetate (approx. 10 mL). To the filtrate was added water (10 mL) and the layers separated. The aqueous layer was extracted with further ethyl acetate (2×10 mL). The organic phase was filtered through a cartridge fitted with a hydrophobic frit and the filtrate evaporated in vacuo to give a brown gum. This was redissolved in DMSO (1 mL) and directly purified by MDAP (high pH). The appropriate fraction was evaporated under a stream of nitrogen and redissolved in methanol (approx. 2 mL) and dichloromethane (approx. 2 mL). This solution was evaporated under a stream of nitrogen and the residue dried in vacuo to give N⁴-((1R,5S,6r)-3-oxabicyclo[3.1.0]hexan-6-yl)-6-((2-cyano-1H-indol-4-yl)methyl)-N²-methylpyridine-2,4-dicarboxamide (8.7 mg, 0.02 mmol, 21% yield) as a white solid.

LCMS (2 min Formic): Rt=0.88 min, [MH]+=416.4.

Example 94

N⁴-((1R,5S,6r)-3-Oxabicyclo[3.1.0]hexan-6-yl)-6-((3-cyano-1H-indol-4-yl)methyl)-N²-methylpyridine-2,4-dicarboxamide

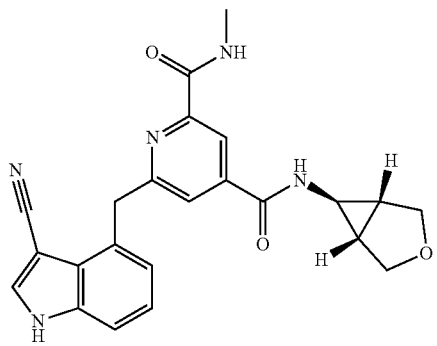 [SMILES: CNC(=O)c1cc(C(=O)N[C@H]2[C@@H]3COC[C@@H]32)cc(Cc2cccc3[nH]cc(C#N)c23)n1]

A mixture of 4-(4,4,5,5-tetramethyl-1,3,2-dioxaborolan-2-yl)-1H-indole-3-carbonitrile (80 wt %, 23.8 mg, 0.07 mmol), N⁴-((1R,5S,6r)-3-oxabicyclo[3.1.0]hexan-6-yl)-6-(chloromethyl)-N²-methylpyridine-2,4-dicarboxamide (20.6 mg, 0.07 mmol), [1,1'-bis(diphenylphosphino)ferrocene]dichloropalladium(II) (8.9 mg, 0.01 mmol) and potassium carbonate (18.2 mg, 0.13 mmol) in 1,4-dioxane (0.50 mL) and water (0.25 mL) in a sealed microwave vial was heated in a microwave reactor at 80° C. for 30 min. The reaction mixture was filtered though a 2.5 g Celite cartridge and the cartridge washed with ethyl acetate (approx. 10 mL). To the filtrate was added brine (10 mL) and the layers separated. The aqueous layer was extracted with further ethyl acetate (2×10 mL). The organic layers were combined and washed with water (2×10 mL). The organic phase was filtered through a cartridge fitted with a hydrophobic frit and the filtrate evaporated in vacuo to give a brown solid. This was redissolved in DMSO (1 mL) and directly purified by MDAP (high pH). The required fraction was evaporated under a stream of nitrogen and redissolved in methanol (approx. 2 mL) and dichloromethane (approx. 2 mL). This solution was evaporated under a stream of nitrogen and the residue dried in vacuo to give N⁴-((1R,5S,6r)-3-oxabicyclo[3.1.0]hexan-6-yl)-6-((3-cyano-1H-indol-4-yl)methyl)-N²-methylpyridine-2,4-dicarboxamide (14.0 mg, 0.03 mmol, 51% yield) as a white solid.

LCMS (2 min High pH): Rt=0.82 min, [MH]+=416.4.

Example 95

N⁴-((1R,5S,6r)-3-Oxabicyclo[3.1.0]hexan-6-yl)-N²-methyl-6-(1-phenylpropyl)pyridine-2,4-dicarboxamide

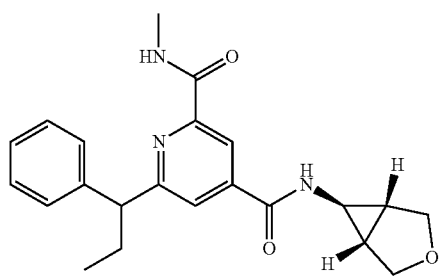

To a solution of 2-(methylcarbamoyl)-6-(1-phenylpropyl)isonicotinic acid (80 mg, 0.20 mmol) in DMF (0.7 mL) was added DIPEA (0.10 mL, 0.573 mmol) followed by HATU (115 mg, 0.302 mmol) and (1R,5S,6r)-3-oxabicyclo[3.1.0]hexan-6-amine, hydrochloride (40.9 mg, 0.30 mmol). The resulting reaction mixture was stirred at rt for 2 h. The reaction mixture was purified directly by MDAP (high pH). The fractions containing the desired product were concentrated in vacuo to give N⁴-((1R,5S,6r)-3-oxabicyclo[3.1.0]hexan-6-yl)-N²-methyl-6-(1-phenylpropyl)pyridine-2,4-dicarboxamide (26 mg, 0.07 mmol, 32% yield) as a colourless oil.

LCMS (2 min Formic): Rt=1.02 min, [MH]+=380.3

Example 96

N⁴-((1R,5S,6r)-3-Oxabicyclo[3.1.0]hexan-6-yl)-N²-methyl-6-((R*)-1-phenylpropyl)pyridine-2,4-dicarboxamide Example 97

N⁴-((1R,5S,6r)-3-Oxabicyclo[3.1.0]hexan-6-yl)-N²-methyl-6-((S*)-1-phenylpropyl)pyridine-2,4-dicarboxamide

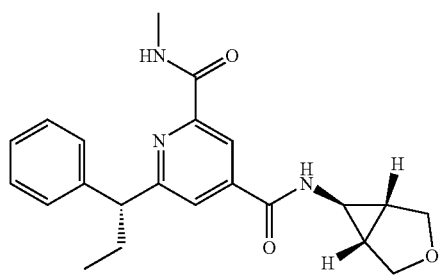

-continued

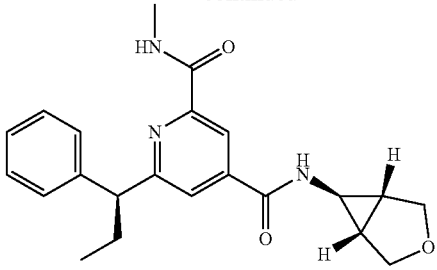

Example 95 (24 mg) was purified by chiral HPLC. The racemate was dissolved in EtOH (1 mL). Injection: 1 mL of the solution was injected onto the column (10% EtOH (+0.2% isopropylamine)/heptane (+0.2% isopropylamine), flow rate=30 mL/min, detection wavelength=215 nm, 4. Ref 550, 100, Column 30 mm×25 cm Chiralpak AD-H (5 μm), lot no. #ADH13231). Total number of injections=1. Fractions from 25-28.5 min were bulked and labelled peak 1. Fractions from 31-36 min were bulked and labelled peak 2. Fractions from peak 2 needed a further purification as above to increase the purity. The bulked pure fractions were concentrated in vacuo and then transferred to weighed flasks.

The fractions corresponding to peak 1 were collected to afford example 96 (10 mg)

LCMS (2 min Formic): Rt=1.02 min, [MH]+=380.3.

The fractions corresponding to peak 2 were collected to afford example 97 (11 mg)

LCMS (2 min Formic): Rt=1.02 min, [MH]+=380.3.

Example 98

N⁴-((1R,5S,6r)-3-Oxabicyclo[3.1.0]hexan-6-yl)-6-((1-(2-hydroxyethyl)-1H-indol-4-yl)methyl)-N²-methylpyridine-2,4-dicarboxamide

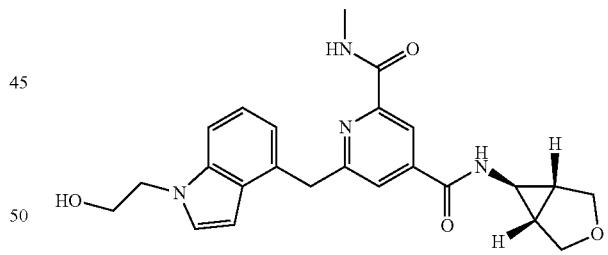

2-((1-(2-Hydroxyethyl)-1H-indol-4-yl)methyl)-6-(methylcarbamoyl)isonicotinic acid (129 mg, 0.37 mmol) was taken up in DMF (5 mL). (1R,5S,6r)-3-Oxabicyclo[3.1.0]hexan-6-amine, hydrochloride (74.2 mg, 0.548 mmol), HATU (208 mg, 0.548 mmol) and DIPEA (0.191 mL, 1.10 mmol) were added and the reaction left to stir at rt for 1 h. The reaction was concentrated in vacuo. The samples were dissolved in 1:1 MeCN:DMSO (3 mL) and purified by MDAP (High pH). The solvent was evaporated in vacuo to give the required product, N⁴-((1R,5S,6r)-3-oxabicyclo[3.1.0]hexan-6-yl)-6-((1-(2-hydroxyethyl)-1H-indol-4-yl)methyl)-N²-methylpyridine-2,4-dicarboxamide (43 mg, 0.099 mmol, 27% yield).

LCMS (2 min High pH): Rt=0.82 min, [MH]+=435.4.

209

Example 99

N⁴-((1R,5S,6r)-3-Oxabicyclo[3.1.0]hexan-6-yl)-N²-methyl-6-((3-(2,2,2-trifluoroacetyl)-1H-indol-4-yl)methyl)pyridine-2,4-dicarboxamide

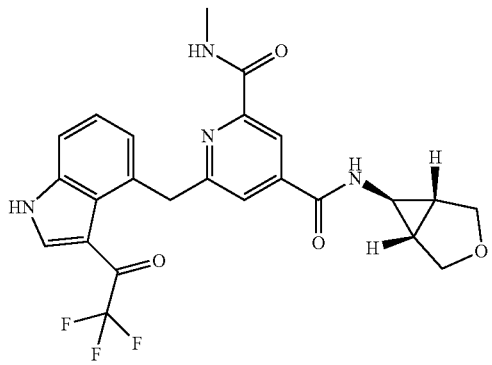 [SMILES: CNC(=O)c1cc(C(=O)N[C@H]2[C@@H]3COC[C@@H]32)cc(Cc2cccc3[nH]cc(C(=O)C(F)(F)F)c23)n1]

2-(Methylcarbamoyl)-6-((3-(2,2,2-trifluoroacetyl)-1H-indol-4-yl)methyl)isonicotinic acid (550 mg, 1.36 mmol) was suspended in DCM (20 mL) and Et₃N (0.473 mL, 3.39 mmol) was added, giving a clear solution. HATU (1032 mg, 2.71 mmol) was added and the resulting suspension was stirred for 20 min, then (1R,5S,6r)-3-oxabicyclo[3.1.0] hexan-6-amine, hydrochloride (368 mg, 2.71 mmol) was added and the mixture stirred for 3 h, giving a dense suspension. This was evaporated in vacuo and the residue was stirred with water (20 mL) for 2 h, then the resulting suspension was filtered and washed with water (10 mL) and ether (10 mL), to give a pale yellow impure solid. 100 mg of the solid was purified by MDAP (Formic) to give N⁴-((1R,5S,6r)-3-oxabicyclo[3.1.0]hexan-6-yl)-N²-methyl-6-((3-(2,2,2-trifluoroacetyl)-1H-indol-4-yl)methyl)pyridine-2,4-dicarboxamide (45 mg, 0.093 mmol, 7% yield) as a colourless solid.

LCMS (2 min High pH): Rt=0.95 min, [MH]+=487.3.

Example 100

(±)-6-Benzyl-N⁴-(3-(3,3-difluoropiperidin-4-yl)propyl)-N²-methylpyridine-2,4-dicarboxamide hydrochloride

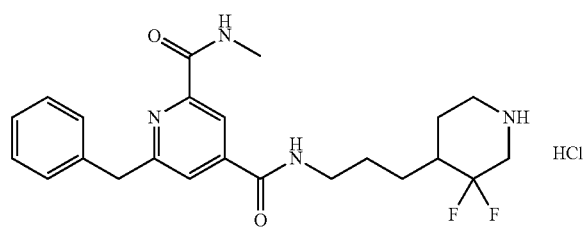 [SMILES: CNC(=O)c1cc(C(=O)NCCCC2CCNCC2(F)F)cc(Cc2ccccc2)n1 ; Cl]

210

A solution of (±)-tert-butyl 4-(3-(2-benzyl-6-(methylcarbamoyl)isonicotinamido)propyl)-3,3-difluoropiperidine-1-carboxylate (46.5 mg, 0.09 mmol) in 1,4-dioxane (15 mL) had hydrochloric acid (4.0 M solution in 1,4-dioxane, 0.90 mL, 3.60 mmol) added to it. The mixture was stirred at rt for 5.75 h. After 5 h further hydrochloric acid (4.0 M solution in 1,4-dioxane, 1.0 mL, 4.00 mmol) was added and stirring continued for a further 50 min. The mixture was evaporated to dryness under a stream of nitrogen and the sticky yellow residue was triturated in ether (3×5 mL), decanting the supernatant away each time. The solid residue was transferred to a tarred vial as a suspension in ether (3 mL), the solvent evaporated under a stream of nitrogen and the residue dried in vacuo to give (±)-6-benzyl-N⁴-(3-(3,3-difluoropiperidin-4-yl)propyl)-N²-methylpyridine-2,4-dicarboxamide hydrochloride (39.4 mg, 0.08 mmol, 96% yield) as a pale yellow solid.

LCMS (2 mins formic) Peak Rt=0.62 min, m/z=431 for [MH]+

Example 101

N⁴-((1R,5S,6r)-3-Oxabicyclo[3.1.0]hexan-6-yl)-6-(methoxy(phenyl)methyl)-N²-methylpyridine-2,4-dicarboxamide

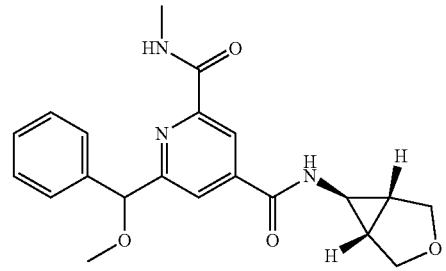 [SMILES: CNC(=O)c1cc(C(=O)N[C@H]2[C@@H]3COC[C@@H]32)cc(C(OC)c2ccccc2)n1]

N⁴-((1R,5S,6r)-3-Oxabicyclo[3.1.0]hexan-6-yl)-6-(chloro(phenyl)methyl)-N²-methylpyridine-2,4-dicarboxamide (300 mg, 0.43 mmol, 55% wt) in methanol (3 mL) was added to a microwave vial. This was heated at 60° C. for 45 min. The reaction mixture was resubmitted to the microwave at 75° C. for 40 min. The reaction mixture was resubmitted to the microwave at 85° C. for 3 h 45 min. The reaction mixture was concentrated in vacuo. Purification was carried out by flash chromatography on SiO₂ (Biotage SNAP 10 g, eluting with 40 to 100% ethyl acetate/cyclohexane. The desired fractions were combined and concentrated in vacuo to give N⁴-((1R,5S,6r)-3-oxabicyclo[3.1.0] hexan-6-yl)-6-(methoxy(phenyl)methyl)-N²-methylpyridine-2,4-dicarboxamide (52 mg, 0.12 mmol, 29% yield) as a colourless oil.

LCMS (2 min Formic): Rt=0.86 min, [MH]+=382.3

Example 102

N⁴-((1R,5S,6r)-3-Oxabicyclo[3.1.0]hexan-6-yl)-6-((S*)-1-(3-methoxyphenyl)ethyl)-N²-methylpyridine-2,4-dicarboxamide

Example 103

N⁴-((1R,5S,6r)-3-Oxabicyclo[3.1.0]hexan-6-yl)-6-((R*)-1-(3-methoxyphenyl)ethyl)-N²-methylpyridine-2,4-dicarboxamide

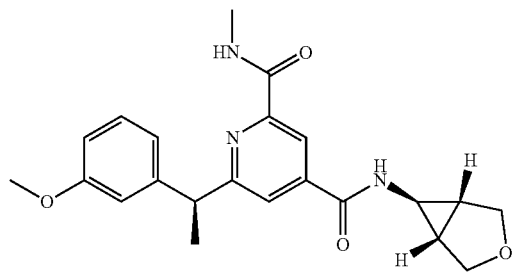

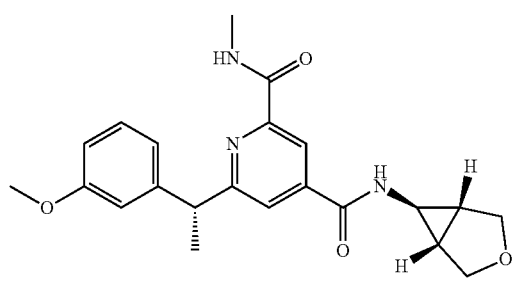

Example 92 (30 mg) was purified by chiral HPLC. The racemate was dissolved in EtOH (2 mL) then diluted with one volume of mobile phase. Injection: 0.4 mL manual injections via rheodyne valve. Column: Chiralcel OJ-H (250×30 mm). Flow rate: 42.5 mL/min (54 bar). Detection: UV Diode Array at 280 nm (Band width 140 nm, reference 400 nm bandwidth 100 nm). Mobile phase A: Heptane containing 0.2% v/v isopropylamine. Mobile phase B: Ethanol containing 0.2% v/v isopropylamine. Isocratic method 95:5 mobile phase A: mobile phase B. Runtime 55 min. Fractions from 39-43 min were bulked and labelled peak 1. Fractions from 45-51 min were bulked and labelled peak 2. The bulked pure fractions were concentrated in vacuo and then transferred to weighed flasks.

The fractions corresponding to peak 1 were collected to afford example 102 (10 mg)

LCMS (2 min Formic): Rt=0.95 min, [MH]+=396.3.

The fractions corresponding to peak 2 were collected to afford example 103 (20 mg)

LCMS (2 min Formic): Rt=0.95 min, [MH]+=396.3.

Example 104

N⁴-((1R,5S,6r)-3-Oxabicyclo[3.1.0]hexan-6-yl)-6-((S*)-methoxy(phenyl)methyl)-N²-methylpyridine-2,4-dicarboxamide

Example 105

N⁴-((1R,5S,6r)-3-oxabicyclo[3.1.0]hexan-6-yl)-6-((R*)-methoxy(phenyl)methyl)-N²-methylpyridine-2,4-dicarboxamide

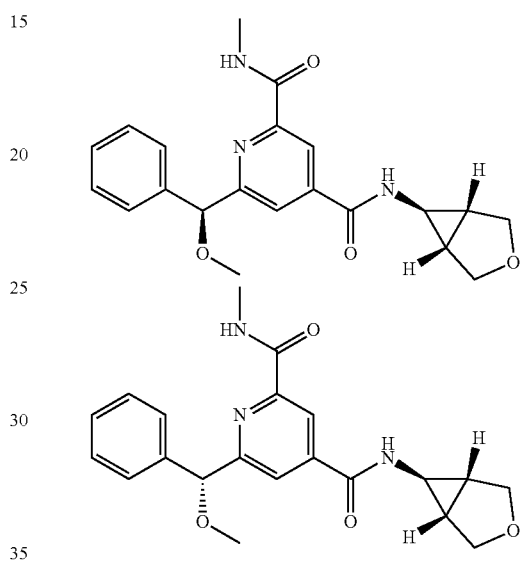

tert-Butyl 2-(hydroxy(phenyl)methyl)-6-(methylcarbamoyl)isonicotinate (0.42 g, 1.23 mmol) was dissolved in dichloromethane (10 mL) and N¹,N¹,N³,N³-tetramethylnaphthalene-1,8-diamine (0.789 g, 3.68 mmol) was added, followed by trimethyloxonium tetrafluoroborate (0.544 g, 3.68 mmol) and the mixture was stirred at rt overnight. Further trimethyloxonium tetrafluoroborate (0.544 g, 3.68 mmol) was added, then the mixture stirred for 24 h at rt. The solution was partitioned between 0.5M HCl (50 mL) and EtOAc (50 mL). The organic layer was dried and evaporated in vacuo. The residue was then partitioned between EtOAc (20 mL) and 0.5M NaOH solution, the organic layer discarded and the aqueous acidified with 2M HCl. This was then extracted with EtOAc (2×20 mL) and the combined organics dried and evaporated in vacuo to give a beige solid. The crude material was suspended in DCM (10 mL) and Et₃N (0.513 mL, 3.68 mmol), HATU (0.700 g, 1.84 mmol) and (1R,5S,6r)-3-oxabicyclo[3.1.0]hexan-6-amine hydrochloride (0.249 g, 1.84 mmol) were added, then the mixture was stirred for 1 h at rt. The solution was washed with water (2×10 mL), dried and evaporated in vacuo and the residue purified by chromatography on a 25 g silica column eluting with 0-25% EtOH/EtOAc. The product-containing fractions were evaporated in vacuo to give a pale yellow gum (70 mg).

This was purified by chiral HPLC. The material was dissolved in EtOH (2 mL). Injection: 1 mL of the solution was injected onto the column (50% EtOH (+0.2% isopropylamine)/heptane (+0.2% isopropylamine), flow rate=30 mL/min, detection wavelength=215 nm, 4. Ref 550, 100, Column 30 mm×25 cm Chiralpak IC (5 μm), lot no. IC10028-01). Total number of injections=2. Fractions from 10.5-12 min were bulked and labelled peak 1. Fractions from 13-15 min were bulked and labelled peak 2. The bulked pure fractions were concentrated in vacuo and then transferred to weighed flasks.

The fractions corresponding to peak 1 were collected to afford example 104 (18 mg)

LCMS (2 min High pH): Rt=0.87 min, [MH]+=382.3.

The fractions corresponding to peak 2 were collected to afford example 105 (22 mg)

LCMS (2 min High pH): Rt=0.87 min, [MH]+=382.3.

$^1$H NMR (400 MHz, CDCl$_3$) δ ppm 8.29 (d, J=1.5 Hz, 1H) 8.16 (d, J=1.5 Hz, 1H) 7.89-7.98 (m, 1H) 7.39-7.44 (m, 2H) 7.33-7.38 (m, 2H) 7.26-7.32 (m, 1H) 6.87 (br. s., 1H) 5.41 (s, 1H) 4.08 (d, J=8.6 Hz, 2H) 3.78 (d, J=8.3 Hz, 2H) 3.45 (s, 3H) 3.03 (d, J=5.1 Hz, 3H) 2.79 (q, J=2.3 Hz, 1H) 1.92 (s, 2H)

Example 106

(+/−)-6-(1-(1H-Indol-4-yl)ethyl)-N$^4$-((1R,5S,6r)-3-oxabicyclo[3.1.0]hexan-6-yl)-N$^2$-methylpyridine-2,4-dicarboxamide

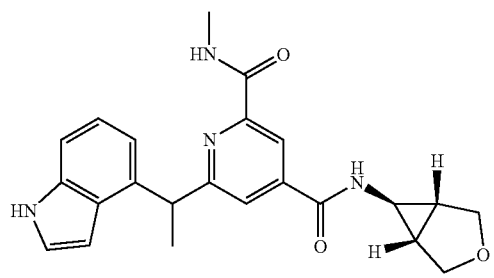 [SMILES: CNC(=O)c1cc(C(=O)N[C@H]2[C@@H]3COC[C@@H]32)cc(C(C)c2cccc3[nH]ccc23)n1]

2-(1-(1H-Indol-4-yl)ethyl)-6-(methylcarbamoyl)isonicotinic acid (450 mg, 1.39 mmol) was taken up in DMF (15 mL). DIPEA (0.73 mL, 4.18 mmol), HATU (794 mg, 2.09 mmol) and (1R,5S,6r)-3-oxabicyclo[3.1.0]hexan-6-amine, hydrochloride (283 mg, 2.09 mmol) were added and the reaction left to stir at rt for 1 h. The reaction was concentrated in vacuo. The residue was taken up in ethyl acetate (20 mL) and was extracted using aq. sodium bicarbonate solution (2×20 mL) and brine (20 mL). The organic phase was dried over sodium sulphate, filtered through a hydrophobic frit and concentrated in vacuo. The crude product was applied to a SNAP ULTRA silica cartridge (25 g) in the minimum of DCM and purified by flash chromatography, eluting with 5-40% (3:1 EtOAc:EtOH) in cyclohexane. The appropriate fractions were combined and concentrated in vacuo to afford 6-(1-(1H-indol-4-yl)ethyl)-N$^4$-((1R,5S,6r)-3-oxabicyclo[3.1.0]hexan-6-yl)-N2-methylpyridine-2,4-dicarboxamide (530 mg, 1.310 mmol, 94% yield).

LCMS (2 min Formic): Rt=0.89 min, [MH]+=405.4.

Example 107

(+/−)-6-Benzyl-N$^2$-methyl-N$^4$-(3-(2-methylmorpholin-2-yl)propyl)pyridine-2,4-dicarboxamide

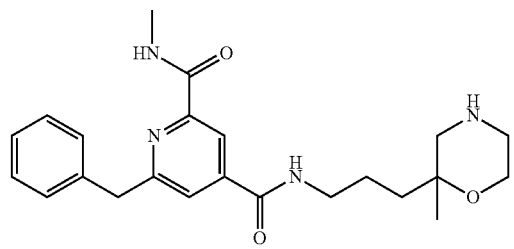 [SMILES: CNC(=O)c1cc(C(=O)NCCCC2(C)CNCCO2)cc(Cc2ccccc2)n1]

(+/−)-tert-Butyl 2-(3-(2-benzyl-6-(methylcarbamoyl)isonicotinamido)propyl)-2-methylmorpholine-4-carboxylate (70 wt %, 91.6 mg, 0.13 mmol) was taken up in dichloromethane (4 mL) and TFA (0.5 mL, 6.49 mmol) added. The reaction was stirred at rt for 1 h. The reaction was concentrated in vacuo. The residue was taken up in dichloromethane (4 mL) and TFA (0.5 mL, 6.49 mmol) added and the reaction stirred at rt for 90 min. The reaction was concentrated in vacuo and purified by MDAP (high pH). The appropriate fractions were concentrated in vacuo to give (+/−)-6-benzyl-N$^2$-methyl-N$^4$-(3-(2-methylmorpholin-2-yl)propyl)pyridine-2,4-dicarboxamide (37.3 mg, 0.09 mmol, 48% yield) as a cream solid.

LCMS (2 min High pH): Rt=0.87 min, [MH]+=411.5

Example 108

N$^4$-((1R,5S,6r)-3-Oxabicyclo[3.1.0]hexan-6-yl)-6-(chloro(pyridin-2-yl)methyl)-N$^2$-methylpyridine-2,4-dicarboxamide

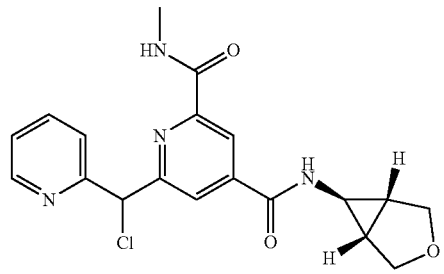 [SMILES: CNC(=O)c1cc(C(=O)N[C@H]2[C@@H]3COC[C@@H]32)cc(C(Cl)c2ccccn2)n1]

To a solution of N$^4$-((1R,5S,6r)-3-oxabicyclo[3.1.0]hexan-6-yl)-6-(hydroxy(pyridin-2-yl)methyl)-N$^2$-methylpyridine-2,4-dicarboxamide (68 mg, 0.18 mmol) in DCM (1 mL), was added dropwise thionyl chloride (0.05 mL, 0.69 mmol). The reaction mixture was then stirred at rt overnight.

Thionyl chloride (0.4 mL) was added and the resultant mixture was stirred for 1 h then concentrated in vacuo to give crude N$^4$-((1R,5S,6r)-3-oxabicyclo[3.1.0]hexan-6-yl)-6-(chloro(pyridin-2-yl)methyl)-N$^2$-methylpyridine-2,4-dicarboxamide (97 mg, 0.13 mmol, 76% yield, 53% purity) which was taken on crude.

$N^4$-((1R,5S,6r)-3-Oxabicyclo[3.1.0]hexan-6-yl)-6-(chloro(pyridin-2-yl)methyl)-$N^2$-methylpyridine-2,4-dicarboxamide (97 mg, 0.14 mmol, 55% wt.) in methanol (1.5 mL) was put in a microwave vial. This was heated at 90° C. for 1 h. The reaction mixture was resubmitted to the microwave at 100° C. for 30 min. The reaction mixture was resubmitted to the microwave at 110° C. for 20 min. DMAP (3.4 mg, 0.03 mmol) was added and the reaction mixture was resubmitted to the microwave at 110° C. for 20 min. The reaction mixture was resubmitted to the microwave at 110° C. for 20 min. Purification was carried out by MDAP (high pH) to recover unreacted chloride. The desired fractions were combined and concentrated in vacuo to give $N^4$-((1R,5S,6r)-3-oxabicyclo[3.1.0]hexan-6-yl)-6-(chloro(pyridin-2-yl)methyl)-$N^2$-methylpyridine-2,4-dicarboxamide (15 mg, 0.04 mmol, 25% yield, 90% purity) as a colourless oil.

LCMS (2 min Formic): Rt=0.79 min, [MH]+=387.3.

Example 109

$N^4$-(2-((2r,5r)-5-Amino-1,3-dioxan-2-yl)ethyl)-6-benzyl-$N^2$-methylpyridine-2,4-dicarboxamide

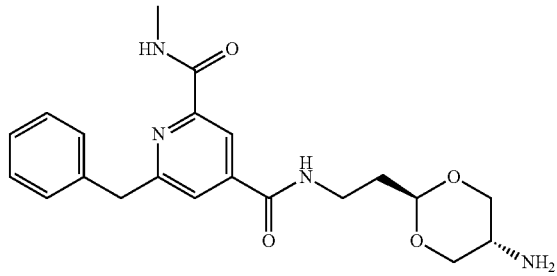 [SMILES: CNC(=O)c1cc(C(=O)NCC[C@H]2OC[C@H](N)CO2)cc(Cc2ccccc2)n1]

To a suspension of 6-benzyl-$N^4$-(2-((2r,5r)-5-(1,3-dioxoisoindolin-2-yl)-1,3-dioxan-2-yl)ethyl)-$N^2$-methylpyridine-2,4-dicarboxamide (65 mg, 0.12 mmol) in ethanol (3 mL) was added hydrazine hydrate (20.0 µL, 0.41 mmol). The suspension was stirred at rt for 22.5 h and at 40° C. for a further 26 h. Further hydrazine hydrate (20.0 µL, 0.41 mmol) was added after a total of 41 h. Further ethanol (3 mL) was added after 48.5 h and the mixture was stirred at rt for a further two days. The reaction mixture was filtered and the cartridge washed with ethanol (approx. 20 mL). The filtrate was evaporated in vacuo. This was redissolved in DMSO (1 mL) and directly purified by MDAP (high pH). The required fraction was evaporated under a stream of nitrogen and the residue dried in vacuo to give $N^4$-(2-((2r,5r)-5-amino-1,3-dioxan-2-yl)ethyl)-6-benzyl-$N^2$-methylpyridine-2,4-dicarboxamide (24.0 mg, 0.06 mmol, 49% yield) as a colourless gum.

LCMS (2 min High pH): Rt=0.82 min, [MH]+=399.4.

Example 110

6-((S*)-1-(1H-Indol-4-yl)ethyl)-$N^4$-((1R,5S,6r)-3-oxabicyclo[3.1.0]hexan-6-yl)-$N^2$-methylpyridine-2,4-dicarboxamide Example 111

6-((R*)-1-(1H-Indol-4-yl)ethyl)-$N^4$-((1R,5S,6r)-3-oxabicyclo[3.1.0]hexan-6-yl)-$N^2$-methylpyridine-2,4-dicarboxamide

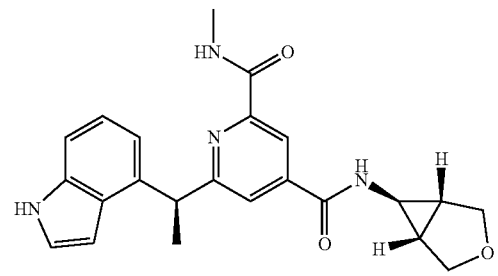

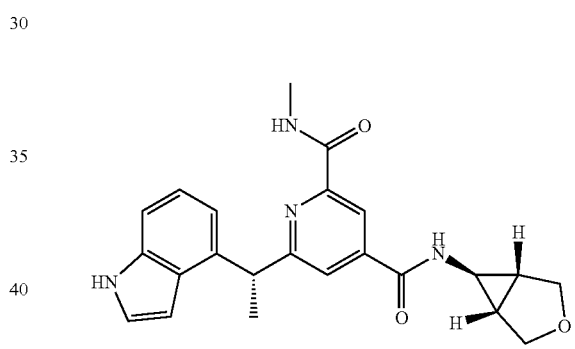

Example 106 (486 mg) was purified by chiral HPLC. The racemate was dissolved in EtOH (50 mL). Injection: 1.5 mL of the solution was injected onto the column via an autosampler (35% EtOH/heptane, flow rate=20 mL/min, detection: UV Diode Array at 280 nm (Band width 140 nm, reference 400 nm bandwidth 100 nm), Column 20 mm×25 cm Regis Whelk O1 [R,R] (5 µm)). Fractions from 22-26 min were bulked and labelled peak 1. Fractions from 28-33 min were bulked and labelled peak 2. The bulked pure fractions were concentrated in vacuo and then transferred to weighed flasks using EtOH and the sample blown down to dryness under a stream of nitrogen gas.

The fractions corresponding to peak 1 were collected to afford example 110 (158 mg)

LCMS (2 min Formic): Rt=0.90 min, [MH]+=405.3.

The fractions corresponding to peak 2 were collected to afford example 111 (173 mg)

LCMS (2 min Formic): Rt=0.90 min, [MH]+=405.3.

Example 112

(+/−)-N⁴-((1R,5S,6r)-3-Oxabicyclo[3.1.0]hexan-6-yl)-6-(1-(2-methoxyphenyl)ethyl)-N²-methylpyridine-2,4-dicarboxamide

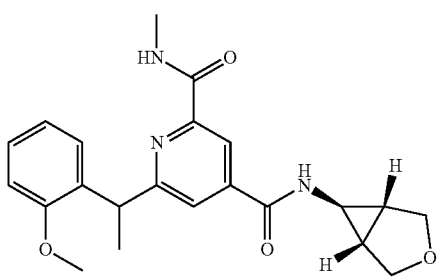 [SMILES: CNC(=O)c1cc(C(=O)N[C@H]2[C@@H]3COC[C@@H]32)cc(C(C)c2ccccc2OC)n1]

To a mixture of (+/−)-2-(1-(2-methoxyphenyl)ethyl)-6-(methylcarbamoyl)isonicotinic acid (52.3 mg, 0.17 mmol), (1R,5S,6r)-3-oxabicyclo[3.1.0]hexan-6-amine hydrochloride (29.5 mg, 0.22 mmol) and HATU (82.2 mg, 0.22 mmol) in DMF (1.5 mL) was added DIPEA (0.120 mL, 0.69 mmol). The mixture was stirred at rt for 2.5 h, after which it was diluted with DMSO and directly purified by MDAP (formic). The required fractions were combined and evaporated in vacuo to give (+/−)-N⁴-((1R,5S,6r)-3-oxabicyclo[3.1.0]hexan-6-yl)-6-(1-(2-methoxyphenyl)ethyl)-N²-methylpyridine-2,4-dicarboxamide (53.5 mg, 0.14 mmol, 81% yield) as a light yellow gum.

LCMS (2 min Formic): Rt=0.98 min, [MH]+=396.3.

Example 113

N⁴-(3-((2r,5r)-5-Amino-1,3-dioxan-2-yl)propyl)-6-benzyl-N²-methylpyridine-2,4-dicarboxamide

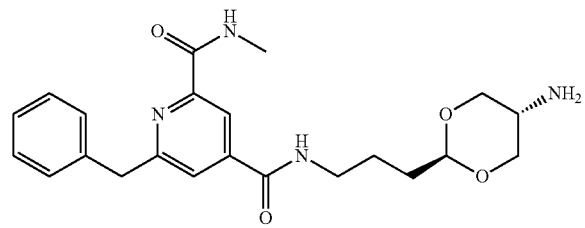 [SMILES: CNC(=O)c1cc(C(=O)NCCC[C@H]2OC[C@H](N)CO2)cc(Cc2ccccc2)n1]

To 6-benzyl-N⁴-(3-((2r,5r)-5-(1,3-dioxoisoindolin-2-yl)-1,3-dioxan-2-yl)propyl)-N²-methylpyridine-2,4-dicarboxamide (0.508 g, 0.94 mmol) in ethanol (6 mL) was added hydrazine hydrate (0.184 mL, 3.75 mmol). The mixture was stirred at rt for 21.5 h before being diluted with further ethanol (20 mL) and stirred at rt for a further 67.5 h. The mixture was heated at 55° C. for 4.5 h before being allowed to cool, then filtered. The solvent was evaporated in vacuo and the residue was diluted with methanol (approx. 20 mL) before being evaporated under a stream of nitrogen. The residue was dissolved in DMSO (approx. 6 mL) and directly purified by MDAP (2×3 mL injection; high pH). The required fractions had their solvent evaporated under a stream of nitrogen. The residues were dissolved in methanol and combined before the solvent was evaporated under a stream of nitrogen to give a yellow oil which was dried in vacuo. The residue was triturated with ether (2×5 mL), each time decanting away the mother liquor. The solid was dried under a stream of nitrogen and in vacuo to give N⁴-(3-((2r,5r)-5-amino-1,3-dioxan-2-yl)propyl)-6-benzyl-N²-methylpyridine-2,4-dicarboxamide (0.244 g, 0.59 mmol, 63% yield) as a cream solid.

LCMS (2 mins formic) Peak Rt=0.58 min, m/z=413 for [MH]+

¹H NMR (400 MHz, DMSO-d₆) δ ppm 8.87 (t, J=5.5 Hz, 1H) 8.65-8.74 (m, 1H) 8.24 (d, J=1.5 Hz, 1H) 7.79 (d, J=1.5 Hz, 1H) 7.27-7.40 (m, 4H) 7.18-7.25 (m, 1H) 4.39 (t, J=4.8 Hz, 1H) 4.22 (s, 2H) 3.92 (dd, J=11.0, 4.9 Hz, 2H) 3.20-3.28 (obs. m, 2H) 3.15 (t, J=10.8 Hz, 2H) 2.87 (d, J=4.6 Hz, 3H) 2.71-2.82 (m, 1H) 1.47-1.63 (m, 4H). Two exchangeable protons not observed

Example 114

N⁴-((1R,5S,6r)-3-Oxabicyclo[3.1.0]hexan-6-yl)-6-(2-methoxy-1-phenylethyl)-N²-methylpyridine-2,4-dicarboxamide

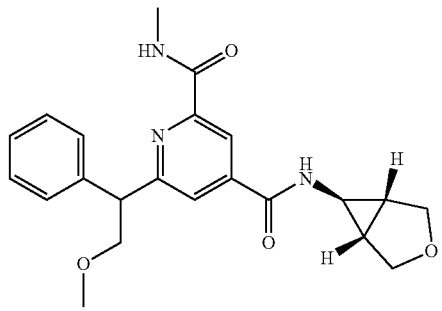 [SMILES: CNC(=O)c1cc(C(=O)N[C@H]2[C@@H]3COC[C@@H]32)cc(C(COC)c2ccccc2)n1]

To a solution of 2-(2-methoxy-1-phenylethyl)-6-(methylcarbamoyl)isonicotinic acid (73 mg, 0.12 mmol) in DMF (0.8 mL) was added HATU (66.2 mg, 0.174 mmol) followed by DIPEA (0.05 mL, 0.29 mmol) and (1R,5S,6r)-3-oxabicyclo[3.1.0]hexan-6-amine, hydrochloride (23.6 mg, 0.17 mmol). The resulting reaction mixture was stirred over the weekend. The reaction mixture was partitioned between sat. LiCl solution (10 mL) and EtOAc (10 mL). The organic layer was separated and the aqueous layer was extracted with further portions of EtOAc (3×10 mL) The combined organic phases were dried over a hydrophobic frit then concentrated in vacuo. This was purified by flash chromatography on SiO₂ (Biotage SNAP 10 g cartridge, eluent 1 to 100% EtOAc/cyclohexane, 0 to 100% (25% EtOH in EtOAc)/cyclohexane). The combined desired fractions were concentrated in vacuo to give N⁴-((1R,5S,6r)-3-oxa bicyclo[3.1.0]hexan-6-yl)-6-(2-methoxy-1-phenylethyl)-N²-methylpyridine-2,4-dicarboxamide (40.9 mg, 0.10 mmol, 85% yield).

LCMS (2 min Formic): Rt=0.88 min, [MH]+=396.4.

Example 115

(+/−)-N⁴-((1R,5S,6r)-3-Oxabicyclo[3.1.0]hexan-6-yl)-N²-methyl-6-(1-(2-oxoindolin-4-yl)ethyl)pyridine-2,4-dicarboxamide

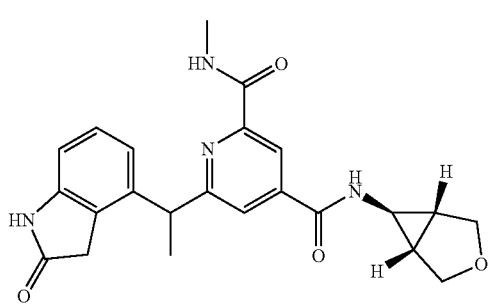 [SMILES: CNC(=O)c1cc(C(=O)N[C@H]2[C@@H]3COC[C@@H]32)cc(C(C)c2cccc3c2CC(=O)N3)n1]

2-(Methylcarbamoyl)-6-(1-(2-oxoindolin-4-yl)ethyl)isonicotinic acid (74 mg, 0.22 mmol) was dissolved in DMF (0.8 mL). DIPEA (0.190 mL, 1.09 mmol) was added, followed by HATU (120 mg, 0.32 mmol) and (1R,5S,6r)-3-oxabicyclo[3.1.0]hexan-6-amine, hydrochloride (48 mg, 0.35 mmol) and the reaction mixture was stirred under nitrogen for 2.5 h. The reaction mixture was purified by MDAP (high pH). Fractions containing the desired product were concentrated in vacuo to give N⁴-((1R,5S,6r)-3-oxabicyclo[3.1.0]hexan-6-yl)-N²-methyl-6-(1-(2-oxoindolin-4-yl)ethyl)pyridine-2,4-dicarboxamide (48 mg, 0.10 mmol, 47% yield).

LCMS (2 min Formic): Rt=0.75 min, [MH]+=421.4.

Example 116

(+/−)-N⁴-((1R,5S,6r)-3-Oxabicyclo[3.1.0]hexan-6-yl)-6-(hydroxy(2-methoxyphenyl)methyl)-N²-methylpyridine-2,4-dicarboxamide

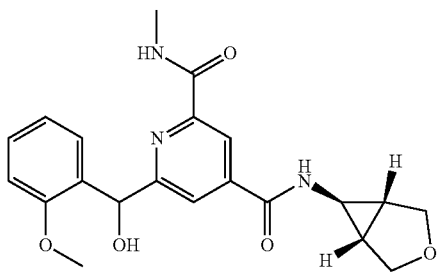 [SMILES: CNC(=O)c1cc(C(=O)N[C@H]2[C@@H]3COC[C@@H]32)cc(C(O)c2ccccc2OC)n1]

To a stirring solution of (2-methoxyphenyl)magnesium bromide (1.0 M in THF, 1.4 mL, 1.40 mmol) at approx. 0° C. under nitrogen was added a suspension of N⁴-((1R,5S,6r)-3-oxabicyclo[3.1.0]hexan-6-yl)-6-formyl-N²-methylpyridine-2,4-dicarboxamide (99.3 mg, 0.34 mmol) in anhydrous tetrahydrofuran (3 mL) dropwise. The resulting brown suspension was stirred at 0° C. under nitrogen for 3.5 h. Further (2-methoxyphenyl)magnesium bromide (1.0 M in THF, 0.50 mL, 0.50 mmol) was added dropwise after 2.5 h. To the reaction mixture was added a solution of sat. aqueous ammonium chloride (2 mL) and water (2 mL) dropwise and the mixture stirred at 0° C. for a further 5 min. The layers were separated and the aqueous phase extracted with ethyl acetate (3×5 mL). The organic layers were combined and filtered through a cartridge fitted with a hydrophobic frit. The filtrate was evaporated under a stream of nitrogen. This was redissolved in DMSO (2 mL) and directly purified by MDAP (high pH). The required fractions were combined and evaporated in vacuo, then transferred in methanol (approx. 5 mL) and this solution evaporated under a stream of nitrogen and the residue dried in vacuo to give (+/−)-N⁴-((1R,5S,6r)-3-oxabicyclo[3.1.0]hexan-6-yl)-6-(hydroxy(2-methoxyphenyl)methyl)-N²-methylpyridine-2,4-dicarboxamide (56.4 mg, 0.14 mmol, 41% yield) as an orange solid.

LCMS (2 min High pH): Rt=0.77 min, [MH]+=398.4.

Example 117 tert-Butyl 3,3-difluoro-4-(3-(2-(methylcarbamoyl)-6-((S)-1-phenylethyl)isonicotinamido)propyl)piperidine-1-carboxylate, Mixture of Diastereomers

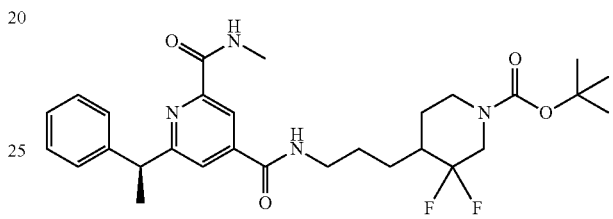

A mixture of (S)-2-(methylcarbamoyl)-6-(1-phenylethyl)isonicotinic acid (64.5 mg, 0.23 mmol) and HATU (104.4 mg, 0.28 mmol) had a solution of (±)-tert-butyl 4-(3-aminopropyl)-3,3-difluoropiperidine-1-carboxylate (67.8 mg, 0.24 mmol) in DMF (1.8 mL) added to it. DIPEA (0.119 mL, 0.68 mmol) was added and the mixture was stirred at rt for 2.5 h. The mixture was concentrated under a stream of nitrogen and diluted with acetonitrile to a total volume of 2 mL and directly purified by MDAP (2×1 mL injection; formic) and the required fractions were combined and evaporated in vacuo. The residue was redissolved in a 2:1 mixture of dichloromethane/methanol (~10 mL), transferred to a tarred vial, the solvent evaporated under a stream of nitrogen and the residue dried in vacuo to give tert-butyl 3,3-difluoro-4-(3-(2-(methylcarbamoyl)-6-((S)-1-phenylethyl)isonicotinamido)propyl)piperidine-1-carboxylate (88.7 mg, 0.16 mmol, 72% yield) as a colourless glass.

LCMS (2 mins formic) Peak R$_t$=1.30 min, m/z=545 for [MH]+

Example 118 tert-Butyl 3,3-difluoro-4-(2-(2-(methylcarbamoyl)-6-((S)-1-phenylethyl)isonicotinamido)ethyl)piperidine-1-carboxylate, Mixture of Diastereomers

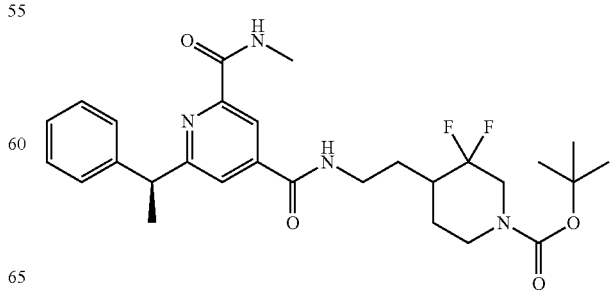

A mixture of (S)-2-(methylcarbamoyl)-6-(1-phenylethyl) isonicotinic acid (66.0 mg, 0.23 mmol) and HATU (105.0 mg, 0.28 mmol) had a solution of (±)-tert-butyl 4-(2-aminoethyl)-3,3-difluoropiperidine-1-carboxylate (74.7 mg, 0.28 mmol) in DMF (1.8 mL) added to it. DIPEA (0.122 mL, 0.70 mmol) was added and the mixture was stirred at rt for 2.5 h. The mixture was concentrated under a stream of nitrogen and diluted with acetonitrile to a total volume of 2 mL and directly purified by MDAP (2×1 mL injection; formic) and the required fractions were combined and evaporated in vacuo. The residue was redissolved in a 2:1 mixture of dichloromethane/methanol (~10 mL), transferred to a tarred vial, the solvent evaporated under a stream of nitrogen and the residue dried in vacuo to give tert-butyl 3,3-difluoro-4-(2-(2-(methylcarbamoyl)-6-((S)-1-phenylethyl)isonicotinamido)ethyl)piperidine-1-carboxylate (79.6 mg, 0.15 mmol, 65% yield) as a colourless glass.

LCMS (2 mins formic) Peak $R_t$=1.28 min, m/z=531 for [MH]$^+$

Example 119 tert-Butyl 4,4-difluoro-3-(2-(2-(methylcarbamoyl)-6-((S)-1-phenylethyl)isonicotinamido)ethyl)piperidine-1-carboxylate, Mixture of Diastereomers

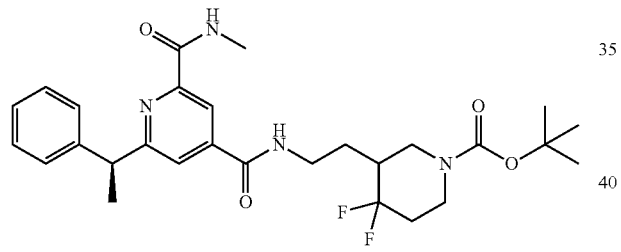

A mixture of (S)-2-(methylcarbamoyl)-6-(1-phenylethyl) isonicotinic acid (66.4 mg, 0.234 mmol) and HATurl (108.0 mg, 0.28 mmol) had a solution of (±)-tert-butyl 3-(2-aminoethyl)-4,4-difluoropiperidine-1-carboxylate (52.4 mg, 0.20 mmol) in DMF (1.8 mL) added to it. DIPEA (0.122 mL, 0.70 mmol) was added and the mixture was stirred at rt for 2.5 h. The mixture was concentrated under a stream of nitrogen and diluted with acetonitrile to a total volume of 2 mL and directly purified by MDAP (2×1 mL injection; formic) and the required fractions were combined and evaporated in vacuo. The residue was redissolved in a 2:1 mixture of dichloromethane/methanol (~10 mL), transferred to a tarred vial, the solvent evaporated under a stream of nitrogen and the residue dried in vacuo to give tert-butyl 4,4-difluoro-3-(2-(2-(methylcarbamoyl)-6-((S)-1-phenylethyl)isonicotinamido)ethyl)piperidine-1-carboxylate (63.7 mg, 0.12 mmol, 51% yield) as a colourless glass.

LCMS (2 mins formic) Peak $R_t$=1.28 min, m/z=531 for [MH]$^+$

Example 167

N$^4$-((1R,5S,6r)-3-Oxabicyclo[3.1.0]hexan-6-yl)-6-((S*)-2-methoxy-1-phenylethyl)-N$^2$-methylpyridine-2,4-dicarboxamide

Example 120

N$^4$-((1R,5S,6r)-3-Oxabicyclo[3.1.0]hexan-6-yl)-6-((R*)-2-methoxy-1-phenylethyl)-N$^2$-methylpyridine-2,4-dicarboxamide

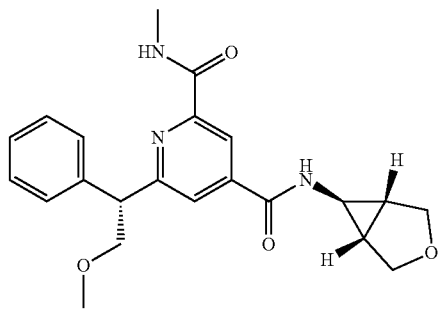

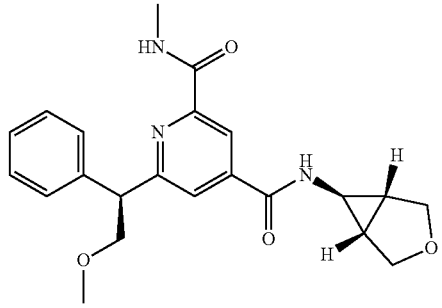

Example 114 (35 mg) was purified by chiral HPLC. The racemate was dissolved in EtOH (2 mL) and heptane (1 mL). Injection: 1 mL of the solution was injected onto the column (10% EtOH/heptane, flow rate=30 mL/min, detection wavelength=215 nm, 4. Ref 550, 100, Column 30 mm×25 cm Chiralcel OD-H (5 µm), lot no. #ODH11158-01). Total number of injections=4. Fractions from 18-20.6 min were bulked and labelled peak 1. Fractions from 20.6-21.2 min were bulked and labelled mix, Fractions from 21.2-24.6 min were bulked and labelled peak 2. The bulked mixed fractions were concentrated in vacuo and reprocessed using the above method. The bulked pure fractions were concentrated in vacuo and then transferred to weighed flasks.

The fractions corresponding to peak 1 were collected to afford example 167 (10 mg)

LCMS (2 min Formic): Rt=0.88 min, [MH]+=396.4.

The fractions corresponding to peak 2 were collected to afford example 120 (8 mg)

LCMS (2 min Formic): Rt=0.88 min, [MH]+=396.4.

Example 121

N⁴-((1R,5S,6r)-3-Oxabicyclo[3.1.0]hexan-6-yl)-6-((S*)-hydroxy(2-methoxyphenyl)methyl)-N²-methylpyridine-2,4-dicarboxamide

Example 122

N⁴-((1R,5S,6r)-3-Oxabicyclo[3.1.0]hexan-6-yl)-6-((R*)-hydroxy(2-methoxyphenyl)methyl)-N²-methylpyridine-2,4-dicarboxamide

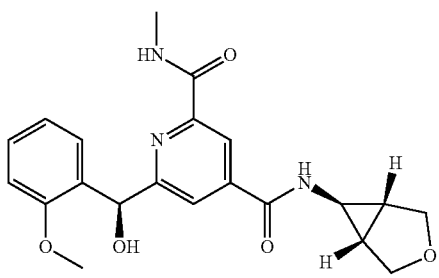

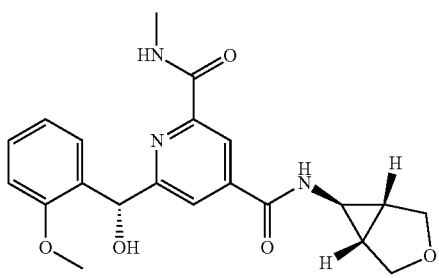

Example 116 (48 mg) was purified by chiral HPLC. The racemate was dissolved in EtOH (1 mL). Injection: 1 mL of the solution was injected onto the column (20% EtOH/heptane, flow rate=30 mL/min, detection wavelength=215 nm, 4. Ref 550, 100, Column 30 mm×25 cm Chiralcel OD-H (5 µm), lot no. ODH11158-01). Total number of injections=1. Fractions from 10.5-13 min were bulked and labelled peak 1. Fractions from 15.5-20 min were bulked and labelled peak 2. The bulked pure fractions were concentrated in vacuo and then transferred to weighed flasks.

The fractions corresponding to peak 1 were collected to afford example 121 (17.1 mg)

LCMS (2 min High pH): Rt=0.77 min, [MH]+=398.4.

The fractions corresponding to peak 2 were collected to afford example 122 (14.4 mg)

LCMS (2 min High pH): Rt=0.77 min, [MH]+=398.4.

Example 123

N⁴-(2-((S*)-3,3-Difluoropiperidin-4-yl)ethyl)-N²-methyl-6-((S)-1-phenylethyl)pyridine-2,4-dicarboxamide, hydrochloride, diastereomer 1

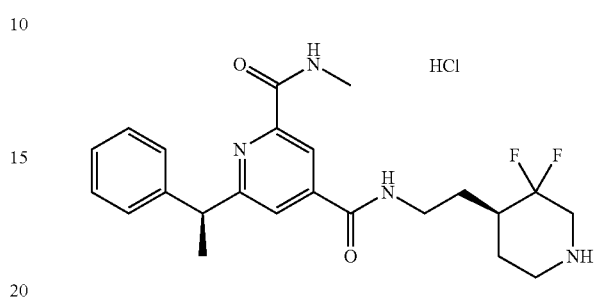

A solution of (S*)-tert-butyl 3,3-difluoro-4-(2-(2-(methylcarbamoyl)-6-((S)-1-phenylethyl)isonicotinamido)ethyl)piperidine-1-carboxylate, diastereomer 1 (31.8 mg, 0.06 mmol, intermediate 203) in 1,4-dioxane (0.5 mL) had hydrogen chloride (4.0 M solution in 1,4-dioxane) (1.0 mL, 4.00 mmol) added to it. The mixture was stirred at rt for 5 h. The mixture was evaporated to dryness under a stream of nitrogen and the residue was triturated with ether (2×3 mL), decanting the supernatant away each time. The solid residue was dried under a stream of nitrogen and then in vacuo to give N⁴-(2-((S)-3,3-difluoropiperidin-4-yl)ethyl)-N²-methyl-6-((S)-1-phenylethyl)pyridine-2,4-dicarboxamide hydrochloride, diastereomer 1 (27.8 mg, 0.06 mmol, 99% yield) as a cream solid.

LCMS (2 mins formic) Peak $R_t$=0.64 min, m/z=431 for [MH]⁺

Example 124

N⁴-(2-((R*)-3,3-Difluoropiperidin-4-yl)ethyl)-N²-methyl-6-((S)-1-phenylethyl)pyridine-2,4-dicarboxamide, hydrochloride, diastereomer 2

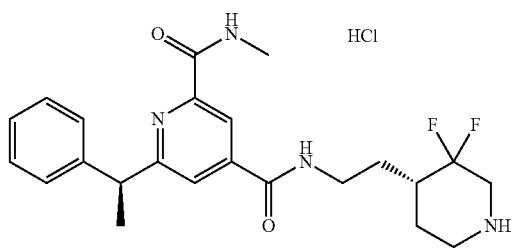 [SMILES: CNC(=O)c1cc(C(=O)NCC[C@H]2CCNCC2(F)F)cc([C@@H](C)c2ccccc2)n1 ; Cl]

A solution of (R*)-tert-butyl 3,3-difluoro-4-(2-(2-(methylcarbamoyl)-6-((S)-1-phenylethyl)isonicotinamido)ethyl)piperidine-1-carboxylate, diastereomer 2 (32.8 mg, 0.06 mmol, intermediate 204) in 1,4-dioxane (0.5 mL) had hydrogen chloride (4.0 M solution in 1,4-dioxane, 1.0 mL, 4.00 mmol) added to it. The mixture was stirred at rt for 5 h. The mixture was evaporated to dryness under a stream of nitrogen and the residue was triturated with ether (2×3 mL), decanting the supernatant away each time. The solid residue was dried under a stream of nitrogen and then in vacuo to give N$^4$-(2-((R*)-3,3-difluoropiperidin-4-yl)ethyl)-N$^2$-methyl-6-((S)-1-phenylethyl)pyridine-2,4-dicarboxamide hydrochloride, diastereomer 2 (29.1 mg, 0.06 mmol) as a cream solid.

LCMS (2 mins formic) Peak R$_f$=0.64 min, m/z=431 for [MH]$^+$

Example 125

(±)-N$^4$-((1R,5S,6r)-3-Oxabicyclo[3.1.0]hexan-6-yl)-6-(1-(1-formylindolin-4-yl)ethyl)-N$^2$-methylpyridine-2,4-dicarboxamide

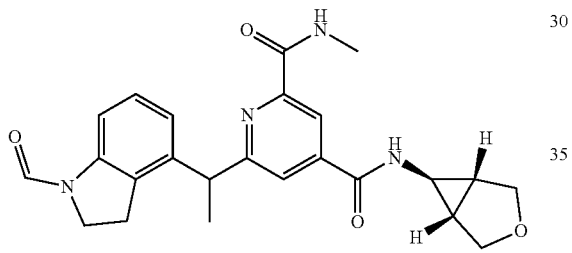

To a mixture of (±)-2-(1-(1-formylindolin-4-yl)ethyl)-6-(methylcarbamoyl)isonicotinic acid (59.4 mg, 0.168 mmol) and HATU (99.8 mg, 0.26 mmol) was added (1R,5S,6r)-3-oxabicyclo[3.1.0]hexan-6-amine, hydrochloride (26.2 mg, 0.19 mmol) and DMF (0.8 mL). DIPEA (0.088 mL, 0.50 mmol) was added and the mixture was stirred at rt for 90 min. Further (1R,5S,6r)-3-oxabicyclo[3.1.0]hexan-6-amine hydrochloride (17.2 mg, 0.13 mmol) was added and stirring was continued for 30 min before further HATU (69.5 mg, 0.18 mmol) and DIPEA (0.060 mL, 0.34 mmol) were added and stirring continued for a further 45 min. After leaving to stand for 15 h the mixture was concentrated under a stream of nitrogen, diluted with acetonitrile to a total volume of 2 mL and directly purified by MDAP (2×1 mL injection; formic). The required fractions were evaporated under a stream of nitrogen, the residues were each redissolved in 1:1 methanol/dichloromethane (~6 mL), combined and transferred to a tarred vial, the solvent evaporated under a stream of nitrogen and the residue dried in vacuo to give (±)-N$^4$-((1R,5S,6r)-3-oxabicyclo[3.1.0]hexan-6-yl)-6-(1-(1-formylindolin-4-yl)ethyl)-N$^2$-methylpyridine-2,4-dicarboxamide (64.0 mg, 0.15 mmol, 88% yield) as a cream solid.

LCMS (2 min Formic): Rt=0.79 min, m/z=435 for [MH]$^+$

Example 126

N$^4$-((1R,5S,6r)-3-Oxabicyclo[3.1.0]hexan-6-yl)-6-((S*)-1-(2-methoxyphenyl)ethyl)-N$^2$-methylpyridine-2,4-dicarboxamide Example 127

N$^4$-((1R,5S,6r)-3-Oxabicyclo[3.1.0]hexan-6-yl)-6-((R*)-1-(2-methoxyphenyl)ethyl)-N$^2$-methylpyridine-2,4-dicarboxamide

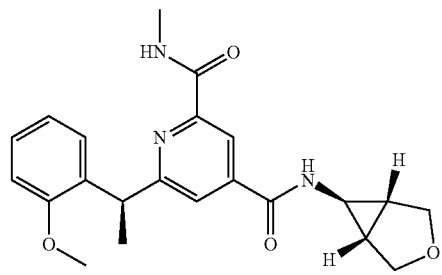

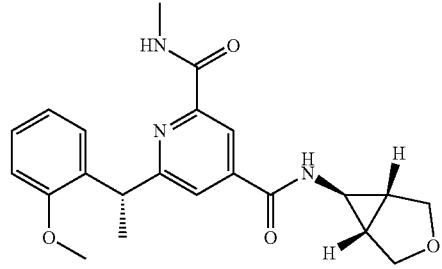

Example 112 (43 mg) was purified by chiral HPLC. The racemate was dissolved in EtOH (5 mL). Injection: 0.25 mL of the solution was injected onto the column (25% EtOH/heptane, flow rate=20 mL/min, detection wavelength=280 nm, 4. Ref 400, 100, Column 21.1 mm×25 cm (R-R) Whelk O-1 (5 µm)). Total number of injections=20. Fractions from 24-27 min were bulked and labelled peak 1. Fractions from 29-34 min were bulked and labelled peak 2. The bulked pure fractions were concentrated in vacuo and then transferred to weighed flasks.

The fractions corresponding to peak 1 were collected to afford example 126 (16.9 mg)

LCMS (2 min High pH): Rt=0.97 min, [MH]+=396.4.

The fractions corresponding to peak 2 were collected to afford example 127 (18.0 mg)

LCMS (2 min High pH): Rt=0.97 min, [MH]+=396.4.

Example 128

(±)-N⁴-((1R,5S,6r)-3-Oxabicyclo[3.1.0]hexan-6-yl)-6-(1-(indolin-4-yl)ethyl)-N²-methylpyridine-2,4-dicarboxamide

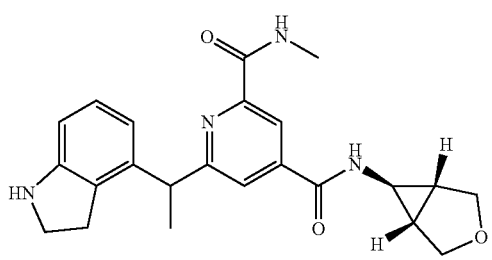 [SMILES: CNC(=O)c1cc(C(=O)N[C@H]2[C@@H]3COC[C@@H]32)cc(C(C)c2cccc3c2CCN3)n1]

A solution of (±)-N⁴-((1R,5S,6r)-3-oxabicyclo[3.1.0]hexan-6-yl)-6-(1-(1-formylindolin-4-yl)ethyl)-N²-methylpyridine-2,4-dicarboxamide (52.7 mg, 0.12 mmol) in water (1 mL) and methanol (2 mL) had sodium hydroxide (106.8 mg, 2.67 mmol) added and was stirred at rt for 30 h. The methanol was evaporated from the mixture under a stream of nitrogen, water (3 mL) was added and the aqueous mixture extracted with ethyl acetate (4×5 mL). The combined organic extracts were dried by passing through a cartridge fitted with a hydrophobic frit and the solvent evaporated under a stream of nitrogen. The residue was redissolved in methanol (1 mL) and was purified by MDAP (1 mL injection; high pH). The required fraction was evaporated under a stream of nitrogen and the residue was redissolved in dichloromethane (~6 mL), transferred to a tarred vial, the solvent evaporated under a stream of nitrogen and the residue dried in vacuo to give (±)-N⁴-((1R,5S,6r)-3-oxabicyclo[3.1.0]hexan-6-yl)-6-(1-(indolin-4-yl)ethyl)-N²-methylpyridine-2,4-dicarboxamide (27.0 mg, 0.07 mmol, 55% yield) as a pale yellow solid.

LCMS (2 min formic) Peak $R_f$=0.51 min, m/z=407 for [MH]⁺

Example 129

(+/−)-N⁴-((1R,5S,6r)-3-Oxabicyclo[3.1.0]hexan-6-yl)-6-(hydroxy(m-tolyl)methyl)-N²-methylpyridine-2,4-dicarboxamide

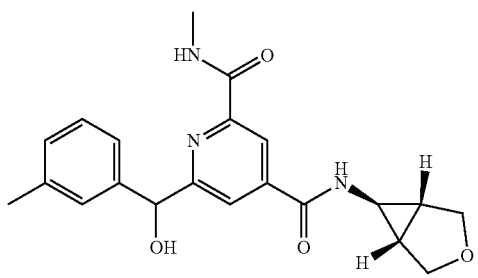 [SMILES: CNC(=O)c1cc(C(=O)N[C@H]2[C@@H]3COC[C@@H]32)cc(C(O)c2cccc(C)c2)n1]

N⁴-((1R,5S,6r)-3-Oxabicyclo[3.1.0]hexan-6-yl)-6-formyl-N²-methylpyridine-2,4-dicarboxamide (90 mg, 0.31 mmol) was suspended in THF (10 mL) and cooled in an ice bath under nitrogen, then m-tolylmagnesium bromide (0.5M in THF, 2.178 mL, 1.09 mmol) was added dropwise and the mixture was stirred for 2 h. Sat. aq. ammonium chloride solution (5 mL) was added, then the mixture was diluted with water (10 mL) and extracted with EtOAc (2×10 mL). The organics were dried and evaporated in vacuo and the residue purified by chromatography on a 10 g silica column to give (+/−)-N⁴-((1R,5S,6r)-3-oxabicyclo[3.1.0]hexan-6-yl)-6-(hydroxy(m-tolyl)methyl)-N²-methylpyridine-2,4-dicarboxamide (92 mg, 0.24 mmol, 78% yield) as a colourless solid.

LCMS (2 min High pH): Rt=0.79 min, [MH]+=382.4.

Example 130

N⁴-((1R,5S,6r)-3-Oxabicyclo[3.1.0]hexan-6-yl)-6-(indolin-4-ylmethyl)-N²-methylpyridine-2,4-dicarboxamide

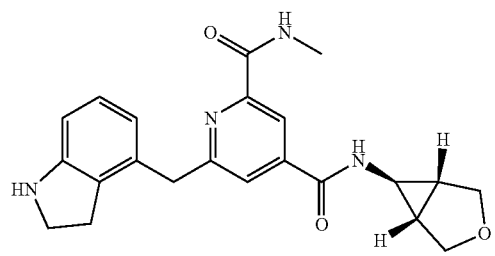 [SMILES: CNC(=O)c1cc(C(=O)N[C@H]2[C@@H]3COC[C@@H]32)cc(Cc2cccc3c2CCN3)n1]

A solution of benzyl 4-((4-(((1R,5S,6r)-3-oxabicyclo[3.1.0]hexan-6-yl)carbamoyl)-6-(methylcarbamoyl)pyridin-2-yl)methyl)indoline-1-carboxylate (99.3 mg, 0.19 mmol) in ethanol (10 mL) was hydrogenated using a 10% palladium on carbon cartridge on a Thales H-Cube apparatus using ethanol as the carrier solvent. The solvent was evaporated in vacuo to give a yellow oil which was dissolved in methanol and concentrated under a stream of nitrogen. The residue was redissolved in DMSO (~2 mL) and directly purified by MDAP (2×1 mL injection; high pH). The desired product was not collected and so the combined wastes were evaporated in vacuo and the light brown oil remaining was dissolved in DMSO and transferred to a vial before being concentrated under a stream of nitrogen. The residue was dissolved in warm ethanol and upon cooling a solid precipitated out. The solid was filtered and washed with ether before being dried in vacuo to give N⁴-((1R,5S,6r)-3-oxabicyclo[3.1.0]hexan-6-yl)-6-(indolin-4-ylmethyl)-N²-methylpyridine-2,4-dicarboxamide (36.5 mg, 0.09 mmol, 49% yield) as a light brown solid.

LCMS (2 min High pH) Peak $R_f$=0.79 mins, m/z=393 for [MH]⁺

¹H NMR (400 MHz, DMSO-d₆) δ ppm 8.94 (br. d, J=3.2 Hz, 1H) 8.65 (br. d, J=4.4 Hz, 1H) 8.25 (s, 1H) 7.67 (s, 1H) 6.87 (t, J=7.6 Hz, 1H) 6.33-6.46 (m, 2H) 5.47 (br. s., 1H) 4.11 (s, 2H) 3.86 (d, J=8.3 Hz, 2H) 3.64 (d, J=8.1 Hz, 2H) 3.40 (t, J=8.3 Hz, 2H) 2.78-2.95 (m, 5H) 2.61 (br. s., 1H) 1.93 (br. s., 2H)

Example 131

(+/−)-N$^4$-((1R,5S,6r)-3-Oxabicyclo[3.1.0]hexan-6-yl)-6-(hydroxy(o-tolyl)methyl)-N$^2$-methylpyridine-2,4-dicarboxamide

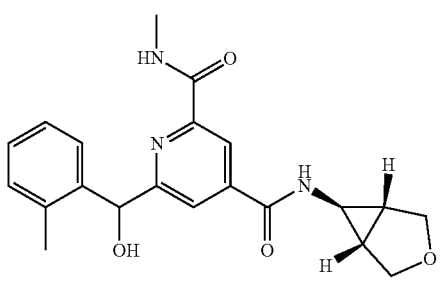 [SMILES: CNC(=O)c1cc(C(=O)N[C@H]2[C@@H]3COC[C@@H]32)cc(C(O)c2ccccc2C)n1]

(+/−)-2-(Hydroxy(o-tolyl)methyl)-6-(methylcarbamoyl)isonicotinic acid (200 mg, 0.67 mmol) was dissolved in DMF (3 mL) and HATU (329 mg, 0.87 mmol), Et$_3$N (0.278 mL, 2.00 mmol) and (1R,5S,6r)-3-oxabicyclo[3.1.0]hexan-6-amine hydrochloride (135 mg, 1.00 mmol) were added, then the mixture was stirred for 2 h at rt. The solution was allowed to stand overnight, then purified directly by MDAP (high pH) to give (+/−)-N$^4$-((1R,5S,6r)-3-oxabicyclo[3.1.0]hexan-6-yl)-6-(hydroxy(o-tolyl)methyl)-N$^2$-methylpyridine-2,4-dicarboxamide (12 mg, 0.03 mmol, 5% yield) as a colourless gum.

LCMS (2 min High pH): Rt=0.79 min, [MH]+=382.3.

Example 132

N$^4$-(3-((2r,5S)-5-Amino-1,3-dioxan-2-yl)propyl)-N$^2$-methyl-6-((S)-1-phenylethyl)pyridine-2,4-dicarboxamide

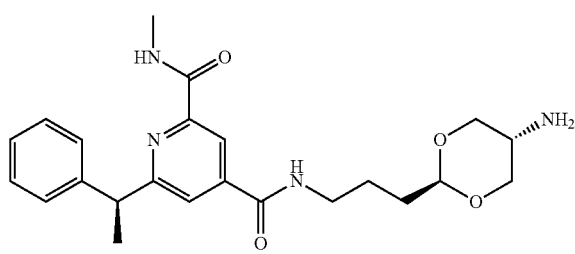 [SMILES: CNC(=O)c1cc(C(=O)NCCC[C@H]2OC[C@H](N)CO2)cc([C@@H](C)c2ccccc2)n1]

To a suspension of N$^4$-(3-((2r,5S)-5-(1,3-dioxoisoindolin-2-yl)-1,3-dioxan-2-yl)propyl)-N$^2$-methyl-6-((S)-1-phenylethyl)pyridine-2,4-dicarboxamide (113 mg, 0.20 mmol) in ethanol (3 mL) was added hydrazine hydrate (0.030 mL, 0.61 mmol). This suspension was stirred under nitrogen at rt for 28 h, after which the reaction mixture was filtered and the solid washed with ethanol (3×5 mL). The filtrate was evaporated in vacuo, then redissolved in DMSO (1 mL) and directly purified by MDAP (high pH). The required fraction was evaporated in vacuo to give N$^4$-(3-((2r,5S)-5-amino-1,3-dioxan-2-yl)propyl)-N$^2$-methyl-6-((S)-1-phenylethyl)pyridine-2,4-dicarboxamide (44.4 mg, 0.10 mmol, 51% yield) as a colourless gum.

LCMS (2 min Formic): Rt=0.62 min, [MH]+=427.5.

Example 133

N$^4$-(3-((S*)-3,3-Difluoropiperidin-4-yl)propyl)-N$^2$-methyl-6-((S)-1-phenylethyl)pyridine-2,4-dicarboxamide hydrochloride, diastereomer 1

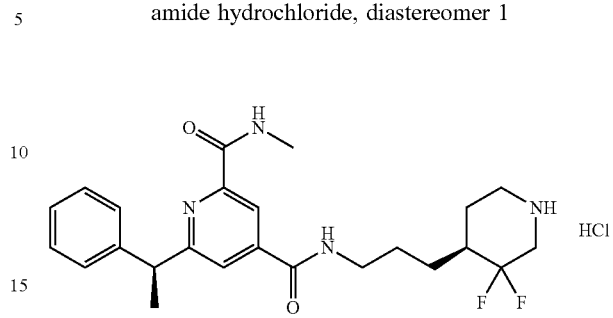

A solution of (S*)-tert-butyl 3,3-difluoro-4-(3-(2-(methylcarbamoyl)-6-((S)-1-phenylethyl)isonicotinamido)propyl)piperidine-1-carboxylate, diastereomer 1 (35.0 mg, 0.06 mmol, intermediate 201) in 1,4-dioxane (0.5 mL) had hydrogen chloride (4.0 M solution in 1,4-dioxane, 0.80 mL, 3.20 mmol) added to it. The mixture was stirred at rt for 4.75 h. The mixture was evaporated to dryness under a stream of nitrogen and the residue was triturated with ether (2×3 mL), decanting the supernatant away each time. The solid residue was dried under a stream of nitrogen and then in vacuo to give N$^4$-(3-((S*)-3,3-difluoropiperidin-4-yl)propyl)-N$^2$-methyl-6-((S)-1-phenylethyl)pyridine-2,4-dicarboxamide, hydrochloride, diastereomer 2 (29.3 mg, 0.06 mmol, 95% yield) as a pale yellow solid.

LCMS (2 min formic) Peak R$_t$=0.67 min, m/z=445 for [MH]$^+$

Example 134

N$^4$-(3-((R*)-3,3-Difluoropiperidin-4-yl)propyl)-N$^2$-methyl-6-((S)-1-phenylethyl)pyridine-2,4-dicarboxamide hydrochloride, diastereomer 2

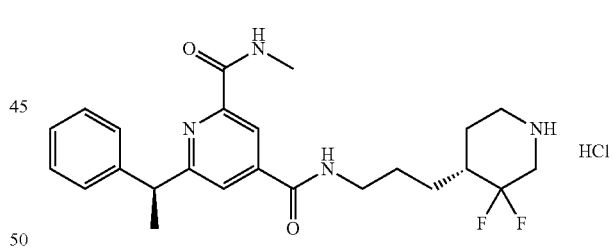

A solution of (R*)-tert-butyl 3,3-difluoro-4-(3-(2-(methylcarbamoyl)-6-((S)-1-phenylethyl)isonicotinamido)propyl)piperidine-1-carboxylate, diastereomer 2 (39.4 mg, 0.07 mmol, intermediate 202) in 1,4-dioxane (0.5 mL) had hydrogen chloride (4.0 M solution in 1,4-dioxane, 0.80 mL 3.20 mmol) added to it. The mixture was stirred at rt for 4.75 h. The mixture was evaporated to dryness under a stream of nitrogen and the residue was triturated with ether (2×3 mL), decanting the supernatant away each time. The solid residue was dried under a stream of nitrogen and then in vacuo to give N$^4$-(3-((R*)-3,3-difluoropiperidin-4-yl)propyl)-N$^2$-methyl-6-((S)-1-phenylethyl)pyridine-2,4-dicarboxamide hydrochloride, diastereomer 2 (34.5 mg, 0.072 mmol, 99% yield) as a pale yellow solid.

LCMS (2 min formic) Peak R$_t$=0.66 min, m/z=445 for [MH]$^+$

Example 135

N[4]-(2-((S*)-4,4-Difluoropiperidin-3-yl)ethyl)-N[2]-methyl-6-((S)-1-phenylethyl)pyridine-2,4-dicarboxamide hydrochloride, diastereomer 1

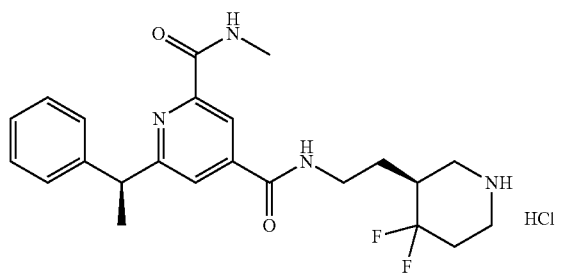 [SMILES: CNC(=O)c1cc(C(=O)NCC[C@H]2CNCCC2(F)F)cc([C@@H](C)c2ccccc2)n1 ; Cl]

A solution of (S*)-tert-butyl 4,4-difluoro-3-(2-(2-(methylcarbamoyl)-6-((S)-1-phenylethyl)isonicotinamido)ethyl)piperidine-1-carboxylate, diastereomer 1 (24.9 mg, 0.05 mmol, intermediate 205) in 1,4-dioxane (0.5 mL) had hydrogen chloride (4.0 M solution in 1,4-dioxane, 0.60 mL, 2.40 mmol) added to it. The mixture was stirred at rt for 4.75 h. The mixture was evaporated to dryness under a stream of nitrogen and the residue was triturated with ether (2×3 mL), decanting the supernatant away each time. The solid residue was dried under a stream of nitrogen and then in vacuo to give N[4]-(2-((S)-4,4-difluoropiperidin-3-yl)ethyl)-N[2]-methyl-6-((S)-1-phenylethyl)pyridine-2,4-dicarboxamide hydrochloride, diastereomer 1 (20.1 mg, 0.04 mmol, 92% yield) as a pale yellow solid.

LCMS (2 min formic) Peak $R_t$=0.67 min, m/z=431 for [MH]$^+$

Example 136

N[4]-(2-((R*)-4,4-Difluoropiperidin-3-yl)ethyl)-N[2]-methyl-6-((S)-1-phenylethyl)pyridine-2,4-dicarboxamide hydrochloride, diastereomer 2

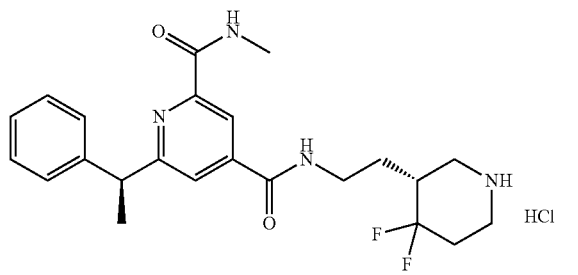 [SMILES: CNC(=O)c1cc(C(=O)NCC[C@@H]2CNCCC2(F)F)cc([C@@H](C)c2ccccc2)n1 ; Cl]

A solution of (R*)-tert-butyl 4,4-difluoro-3-(2-(2-(methylcarbamoyl)-6-((S)-1-phenylethyl)isonicotinamido)ethyl)piperidine-1-carboxylate, diastereomer 2 (25.7 mg, 0.05 mmol, intermediate 206) in 1,4-dioxane (0.5 mL) had hydrogen chloride (4.0 M solution in 1,4-dioxane, 0.60 mL, 2.40 mmol) added to it. The mixture was stirred at rt for 4.75 h. The mixture was evaporated to dryness under a stream of nitrogen and the residue was triturated with ether (2×3 mL), decanting the supernatant away each time. The solid residue was dried under a stream of nitrogen and then in vacuo to give N[4]-(2-((R*)-4,4-difluoropiperidin-3-yl)ethyl)-N[2]-methyl-6-((S)-1-phenylethyl)pyridine-2,4-dicarboxamide hydrochloride, diastereomer 2 (19.8 mg, 0.04 mmol, 88% yield) as a pale yellow solid.

LCMS (2 min formic) Peak $R_t$=0.66 min, m/z=431 for [MH]$^+$

Example 137

(+/−)-N[4]-((1R,5S,6r)-3-Oxabicyclo[3.1.0]hexan-6-yl)-6-(hydroxy(p-tolyl)methyl)-N[2]-methylpyridine-2,4-dicarboxamide

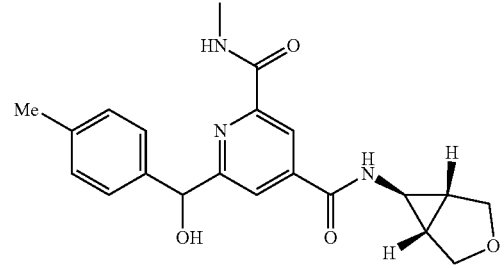 [SMILES: CNC(=O)c1cc(C(=O)N[C@H]2[C@@H]3COC[C@@H]32)cc(C(O)c2ccc(C)cc2)n1]

N[4]-((1R,5S,6r)-3-Oxabicyclo[3.1.0]hexan-6-yl)-6-formyl-N[2]-methylpyridine-2,4-dicarboxamide (200 mg, 0.691 mmol) was suspended in THF (10 mL) and cooled in an ice bath under nitrogen, then p-tolylmagnesium bromide (2.074 mL, 2.074 mmol, 1M in THF, commercially available from, for example, Sigma-Aldrich) was added dropwise and the mixture was stirred for 2 h. Ammonium chloride solution (sat. aq., 5 mL) was added, then the mixture was diluted with water (10 mL) and extracted with EtOAc (2×10 mL). The organics were dried and evaporated in vacuo and the residue purified by chromatography on a silica column (10 g) eluting with 0-100% (25% EtOH/EtOAc)/cyclohexane to give N[4]-((1R,5S,6r)-3-oxabicyclo[3.1.0]hexan-6-yl)-6-(hydroxy(p-tolypmethyl)-N[2]-methylpyridine-2,4-dicarboxamide (23 mg, 0.060 mmol, 9% yield) as a colourless solid.

LCMS (2 min High pH): Rt=0.81 min, [MH]+=382.4.

Example 138

(+/−)-N[4]-((1R,5S,6r)-3-Oxabicyclo[3.1.0]hexan-6-yl)-6-((2-chlorophenyl)(hydroxy)methyl)-N[2]-methylpyridine-2,4-dicarboxamide

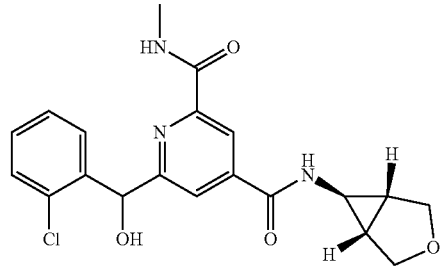 [SMILES: CNC(=O)c1cc(C(=O)N[C@H]2[C@@H]3COC[C@@H]32)cc(C(O)c2ccccc2Cl)n1]

1-Bromo-2-chlorobenzene (1.221 mL, 10.45 mmol, commercially available from, for example, Sigma-Aldrich) was added dropwise over 20 min to a flask containing magnesium (0.279 g, 11.49 mmol) and THF (20 mL). Iodine (20 mg, 0.079 mmol) was added and the mixture was stirred under nitrogen for 2 h at rt, resulting in complete consumption of the magnesium turnings. The solution was used directly without characterisation.

$N^4$-((1R,5S,6r)-3-oxabicyclo[3.1.0]hexan-6-yl)-6-formyl-$N^2$-methylpyridine-2,4-dicarboxamide (200 mg, 0.691 mmol) was suspended in THF (10 mL) and cooled in an ice bath under nitrogen, then (2-chlorophenyl)magnesium bromide (4.15 mL, 2.074 mmol, 0.5M in THF) was added dropwise and the mixture was stirred for 2 h, giving an orange suspension. Ammonium chloride solution (sat. aq., 5 mL) was added, then the mixture was diluted with water (10 mL) and extracted with EtOAc (2×10 mL). The organics were dried and evaporated in vacuo and the residue purified by chromatography on a silica column (10 g) eluting with 0-100% (25% EtOH/EtOAc)/cyclohexane to give a pale yellow gum. The crude product was dissolved in DCM and loaded onto a silica column (25 g), then eluted with 0-100% (25% EtOH/EtOAc)/cyclohexane and the product-containing fractions were evaporated in vacuo to give a colourless foam (85 mg). This was purified by MDAP (high pH) to give $N^4$-((1R,5S,6r)-3-oxabicyclo[3.1.0]hexan-6-yl)-6-((2-chlorophenyl)(hydroxy)methyl)-$N^2$-methylpyridine-2,4-dicarboxamide (58 mg, 0.144 mmol, 21% yield) as a colourless solid LCMS (2 min High pH): Rt=0.81 min, [MH]+=402.3.

Example 139

(R*)-6-Benzyl-$N^2$-methyl-$N^4$-(3-(2-methylmorpholin-2-yl)propyl)pyridine-2,4-dicarboxamide Example 140

(S*)-6-Benzyl-$N^2$-methyl-$N^4$-(3-(2-methylmorpholin-2-yl)propyl)pyridine-2,4-dicarboxamide

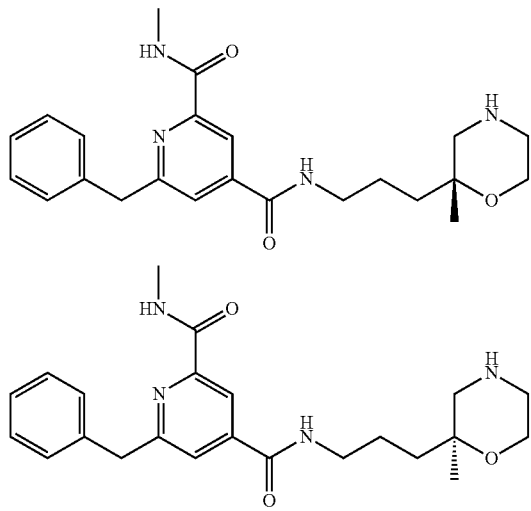

Example 107 (35 mg) was purified by chiral HPLC. The racemate was dissolved in EtOH (1 mL). Injection: 1 mL of the solution was injected onto the column (20% EtOH (+0.2% isopropylamine)/heptane (+0.2% isopropylamine), flow rate=30 mL/min, detection: wavelength, 215 nm, 4. Ref. 550, 100; Column 30 mm×25 cm Chiralpak IC (5 μm), Lot No. IC10028-01). Fractions from 30-32.5 min were bulked and labelled peak 1. Fractions from 35-39 min were bulked and labelled peak 2. The bulked pure fractions were concentrated in vacuo and then transferred to weighed flasks.

The fractions corresponding to peak 1 were collected to afford example 139 (6 mg)

LCMS (2 min High pH): Rt=0.86 min, [MH]+=411.4.

The fractions corresponding to peak 2 were collected to afford example 140 (6 mg)

LCMS (2 min High pH): Rt=0.85 min, [MH]+=411.5.

Example 141

6-Benzyl-$N^4$-((1R,5S,6r)-3-oxabicyclo[3.1.0]hexan-6-yl)-$N^2$-ethylpyridine-2,4-dicarboxamide

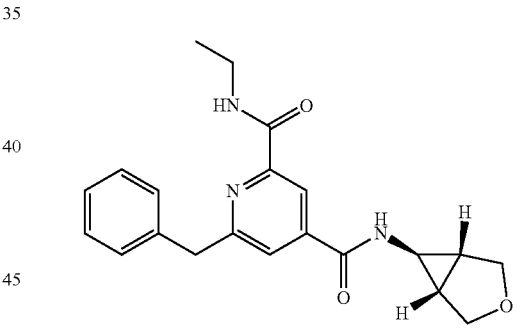

To a solution of 2-benzyl-6-(ethylcarbamoyl)isonicotinic acid (52.2 mg, 0.18 mmol), (1R,5S,6r)-3-oxabicyclo[3.1.0]hexan-6-amine hydrochloride (36.3 mg, 0.27 mmol) and HATU (100.0 mg, 0.26 mmol) in DMF (1 mL) was added DIPEA (0.128 mL, 0.73 mmol). The reaction mixture was stirred at rt for 2.5 h, after which it was diluted with DMSO (2 mL) and directly purified by MDAP (high pH). The required fraction was evaporated under a stream of nitrogen, transferred in acetonitrile (approx. 2 mL), the volatiles were evaporated under a stream of nitrogen and the residue dried in vacuo to give 6-benzyl-$N^4$-((1R,5S,6r)-3-oxabicyclo[3.1.0]hexan-6-yl)-$N^2$-ethylpyridine-2,4-dicarboxamide (56.7 mg, 0.16 mmol, 85% yield) as a glassy white solid.

LCMS (2 min High pH): Rt=0.96 min, [MH]+=366.4.

Example 168

N⁴-((1R,5S,6r)-3-Oxabicyclo[3.1.0]hexan-6-yl)-6-((R*)-hydroxy(p-tolyl)methyl)-N²-methylpyridine-2,4-dicarboxamide

Example 142

N⁴-((1R,5S,6r)-3-Oxabicyclo[3.1.0]hexan-6-yl)-6-((S*)-hydroxy(p-tolyl)methyl)-N²-methylpyridine-2,4-dicarboxamide

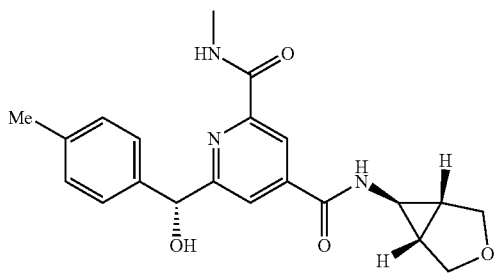

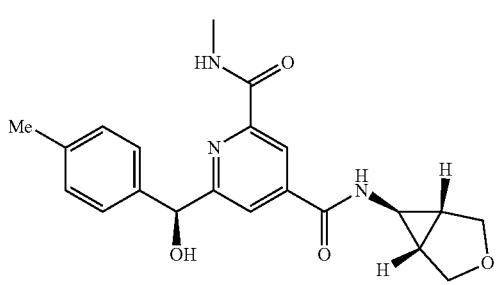

Example 137 (24 mg) was purified by chiral HPLC. The racemate was dissolved in EtOH (1 mL). Injection: 1 mL of the solution was injected onto the column (20% EtOH (+0.2% isopropylamine)/heptane (+0.2% isopropylamine), flow rate=30 mL/min, detection: wavelength, 215 nm, 4. Ref. 550, 100; Column 30 mm×25 cm Chiralpak IC (5 μm), Lot No. IC10028-01). Fractions from 27-29 min were bulked and labelled peak 1. Fractions from 31-34 min were bulked and labelled peak 2. The bulked pure fractions were concentrated in vacuo and then transferred to weighed flasks.

The fractions corresponding to peak 2 were collected to afford example 168 (9 mg)

LCMS (2 min Formic): Rt=0.78 min, [MH]+=382.4.

The fractions corresponding to peak 2 were collected to afford example 142 (10 mg)

LCMS (2 min Formic): Rt=0.78 min, [MH]+=382.4.

Example 169

N⁴-((1R,5S,6r)-3-Oxabicyclo[3.1.0]hexan-6-yl)-6-((R*)-hydroxy(o-tolyl)methyl)-N²-methylpyridine-2,4-dicarboxamide

Example 143

N⁴-((1R,5S,6r)-3-Oxabicyclo[3.1.0]hexan-6-yl)-6-((S*)-hydroxy(o-tolyl)methyl)-N²-methylpyridine-2,4-dicarboxamide

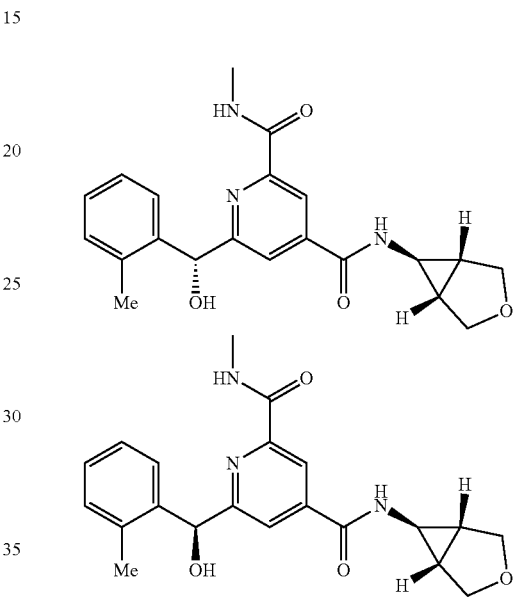

2-(Hydroxy(o-tolyl)methyl)-6-(methylcarbamoyl)isonicotinic acid (220 mg, 0.73 mmol) was dissolved in DCM (10 mL) and HATU (362 mg, 0.952 mmol), Et₃N (0.306 mL, 2.20 mmol) and (1R,5S,6r)-3-oxabicyclo[3.1.0]hexan-6-amine, hydrochloride (149 mg, 1.099 mmol) were added, then the mixture was stirred for 2 h at rt. The solution was washed with water (2×20 mL) and saturated sodium bicarbonate solution (20 mL), dried and evaporated in vacuo to give N⁴-((1R,5S,6r)-3-oxabicyclo[3.1.0]hexan-6-yl)-6-(hydroxy(o-tolyl)methyl)-N²-methylpyridine-2,4-dicarboxamide (275 mg, 0.721 mmol, 98% yield) as a colourless gum.

The racemate (200 mg) was purified by chiral HPLC. The racemate was dissolved in EtOH (5 mL). Injection: 1 mL of the solution was injected onto the column (20% EtOH (+0.2% isopropylamine)/heptane (+0.2% isopropylamine), flow rate=30 mL/min, detection: wavelength, 215 nm, 4. Ref. 550, 100; Column 30 mm×25 cm Chiralpak IC (5 μm), Lot No. IC10028-01). Total number of injections=7. Fractions from 29.5-31 min were bulked and labelled peak 1. Fractions from 31-34 min were bulked and labelled mix. Fractions from 34-39 min were bulked and labelled peak 2. The bulked mix fractions were vac'ed down and reprocessed using the prep method above. The bulked pure fractions were concentrated in vacuo and then transferred to weighed flasks. NOTE: Isomer 2 needed further purification in order to improve the purity. This required 2 injections.

The fractions corresponding to peak 2 were collected to afford example 169 (104 mg) (103 mg)

LCMS (2 min Formic): Rt=0.79 min, [MH]+=382.3.

The fractions corresponding to peak 2 were collected to afford example 143 (104 mg)

LCMS (2 min High pH): Rt=0.79 min, [MH]+=382.3.

Example 144

$N^4$-((1R,5S,6r)-3-Oxabicyclo[3.1.0]hexan-6-yl)-6-((S*)-1-(indolin-4-yl)ethyl)-N2-methylpyridine-2,4-dicarboxamide Example 145

$N^4$-((1R,5S,6r)-3-Oxabicyclo[3.1.0]hexan-6-yl)-6-((R*)-1-(indolin-4-yl)ethyl)-$N^2$-methylpyridine-2,4-dicarboxamide

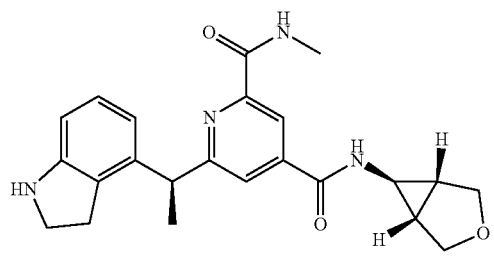

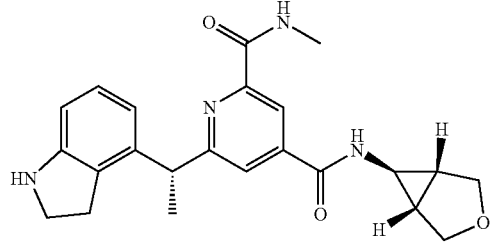

Example 128 (22.3 mg) was purified by chiral HPLC. The racemate was dissolved in EtOH (1 mL). Injection: 1 mL of the solution was injected onto the column [20% EtOH/Heptane, flow rate=30 mL/min, detection wavelength=215 nm, 4. Ref 550, 100, Column 30 mm×25 cm Chiralcel OD-H (5 µm), lot no. ODH11158-01]. Total number of injections=1. Fractions from 22-26 mins were bulked and labelled peak 1. Fractions from 31-38 mins were bulked and labelled peak 2. Each set of the bulked pure fractions were concentrated in vacuo and then transferred to tarred vials and dried in vacuo.

The fractions corresponding to peak 1 were collected to afford example 144 (9.1 mg, 0.02 mmol) as a tan solid.

LCMS (2 min Formic): $R_t$=0.52 min, m/z=407 for $[MH]^+$

The fractions corresponding to peak 2 were collected to afford example 145 (9.1 mg, 0.02 mmol) as a tan solid.

LCMS (2 min Formic): $R_t$=0.51 min, m/z=407 for $[MH]^+$

Example 146

$N^4$-((1R,5S,6r)-3-oxabicyclo[3.1.0]hexan-6-yl)-6-((S*)-(2-chlorophenyl)(hydroxy)methyl)-$N^2$-methylpyridine-2,4-dicarboxamide Example 147

$N^4$-((1R,5S,6r)-3-oxabicyclo[3.1.0]hexan-6-yl)-6-((R*)-(2-chlorophenyl)(hydroxy)methyl)-$N^2$-methylpyridine-2,4-dicarboxamide

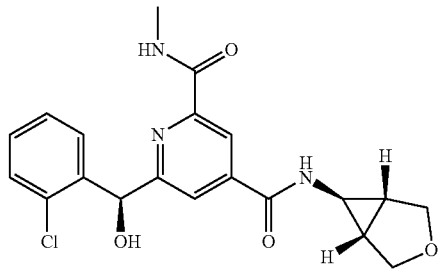

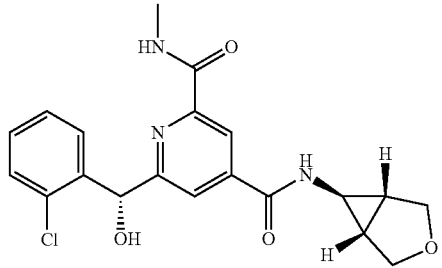

Example 138 (50 mg) was purified by chiral HPLC. The racemate was dissolved in EtOH (1.5 mL) with heat. Injection: 1.5 mL of the solution was injected onto the column (20% EtOH/heptane, flow rate=30 mL/min, detection: wavelength, 215 nm, 4. Ref. 550, 100; Column 30 mm×25 cm Chiralpak AD-H (5 µm), Lot No. ADH13231). Total number of injections=2. Fractions from 20-22.5 min were bulked and labelled peak 1. Fractions from 22.5-26 min were bulked and labelled mix. Fractions from 26-32 min were bulked and labelled peak 2. The bulked mix fractions were concentrated in vacuo and reprocessed using the same method. The bulked pure fractions were concentrated in vacuo and then transferred to weighed flasks. The final isomers were re-dissolved in DCM and Heptane in order to produce a solid, this was successful.

The fractions corresponding to peak 1 were collected to afford example 146 (23 mg)

LCMS (2 min Formic): Rt=0.80 min, [MH]+=402.3.

The fractions corresponding to peak 2 were collected to afford example 147 (22 mg)

LCMS (2 min Formic): Rt=0.80 min, [MH]+=402.3.

Example 148

6-((1H-Indol-4-yl)methyl)-$N^4$-((1R,5S,6r)-3-oxabicyclo[3.1.0]hexan-6-yl)-$N^2$-ethylpyridine-2,4-dicarboxamide

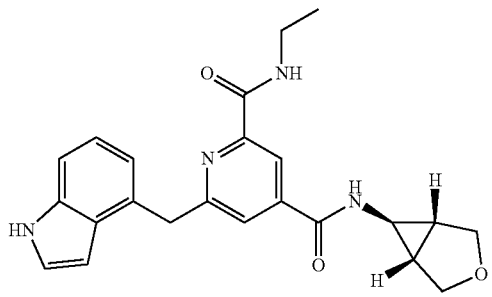 [SMILES: CCNC(=O)c1cc(C(=O)N[C@H]2[C@@H]3COC[C@@H]32)cc(Cc2cccc3[nH]ccc23)n1]

To a suspension of 2-((1H-indol-4-yl)methyl)-6-(ethylcarbamoyl)isonicotinic acid (49.3 mg, 0.15 mmol), (1R,5S,6r)-3-oxabicyclo[3.1.0]hexan-6-amine hydrochloride (31.7 mg, 0.23 mmol) and HATU (84.0 mg, 0.22 mmol) in DMF (1 mL) was added DIPEA (0.107 mL, 0.61 mmol). The resulting mixture was stirred at rt for 2 h, after which it was diluted with DMSO (approx. 2 mL) and directly purified by MDAP (high pH). The required fractions were evaporated under a stream of nitrogen, redissolved in acetonitrile (2 mL each) and combined. This solution was evaporated under a stream of nitrogen, the residue triturated with diethyl ether (approx. 1 mL) and the volatiles evaporated under a stream of nitrogen to give 6-((1H-indol-4-yl)methyl)-$N^4$-((1R,5S,6r)-3-oxabicyclo[3.1.0]hexan-6-yl)-$N^2$-ethylpyridine-2,4-dicarboxamide (51.5 mg, 0.13 mmol, 84% yield) as a white solid.

LCMS (2 min High pH): Rt=0.91 min, [MH]+=405.4.

Example 149

$N^4$-((1R,5S,6r)-3-Oxabicyclo[3.1.0]hexan-6-yl)-$N^2$-methyl-6-((R*)-1-(2-oxoindolin-4-yl)ethyl)pyridine-2,4-dicarboxamide

Example 150

$N^4$-((1R,5S,6r)-3-Oxabicyclo[3.1.0]hexan-6-yl)-$N^2$-methyl-6-((S*)-1-(2-oxoindolin-4-yl)ethyl)pyridine-2,4-dicarboxamide

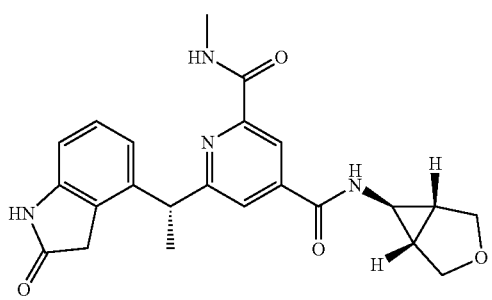

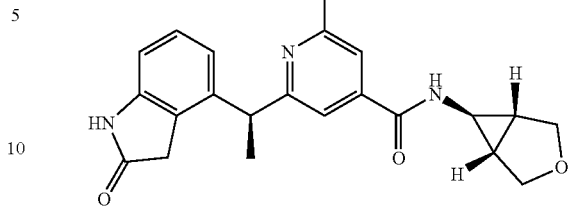

Example 115 (45 mg) was purified by chiral HPLC. The racemate was dissolved in EtOH (2 mL). Injection: 1 mL of the solution was injected onto the column (20% EtOH (+0.2% isopropylamine)/heptane (+0.2% isopropylamine), flow rate=30 mL/min, detection wavelength=215 nm, 4. Ref 550, 100, Column 30 mm×25 cm Chiralcel OD-H (5 μm), lot no. #ODH11158-01). Total number of injections=2. Fractions from 15.5-20 min were bulked and labelled peak 1. Fractions from 23-30 min were bulked and labelled peak 2. The bulked pure fractions were concentrated in vacuo and then transferred to weighed flasks.

The fractions corresponding to peak 1 were collected to afford example 149 (17 mg)

LCMS (2 min Formic): Rt=0.75 min, [MH]+=421.4.

The fractions corresponding to peak 2 were collected to afford example 150 (14 mg)

LCMS (2 min Formic): Rt=0.75 min, [MH]+=421.4.

Example 151

$N^4$-(3-((2r,5r)-5-Amino-1,3-dioxan-2-yl)propyl)-6-(3-chlorobenzyl)-$N^2$-methylpyridine-2,4-dicarboxamide

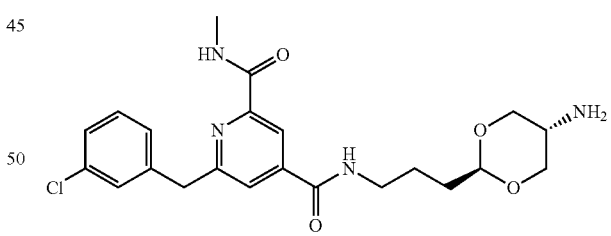

To a suspension of 6-(3-chlorobenzyl)-$N^4$-(3-((2r,5r)-5-(1,3-dioxoisoindolin-2-yl)-1,3-dioxan-2-yl)propyl)-$N^2$-methylpyridine-2,4-dicarboxamide (50 mg, 0.09 mmol) in ethanol (7 mL) was added hydrazine hydrate (90 μl, 1.84 mmol). The reaction was stirred at 40° C. overnight. The crude product was dissolved in DMSO: methanol, filtered through cotton wool and purified by MDAP (high pH). The fractions containing the desired product were concentrated in vacuo to give $N^4$-(3-((2r,5r)-5-amino-1,3-dioxan-2-yl)propyl)-6-(3-chlorobenzyl)-$N^2$-methylpyridine-2,4-dicarboxamide (25 mg, 0.05 mmol, 58% yield).

LCMS (2 min High pH): Rt=0.91 min, [MH]+=447.2.

Example 152

N$^4$-(3-((2r,5r)-5-Amino-1,3-dioxan-2-yl)propyl)-6-(2-chlorobenzyl)-N$^2$-methylpyridine-2,4-dicarboxamide

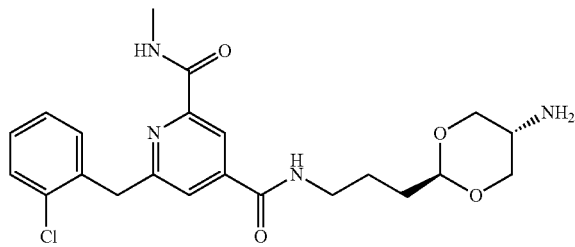 [SMILES: CNC(=O)c1cc(C(=O)NCCC[C@H]2OC[C@H](N)CO2)cc(Cc2ccccc2Cl)n1]

To a suspension of 6-(2-chlorobenzyl)-N$^4$-(3-((2r,5r)-5-(1,3-dioxoisoindolin-2-yl)-1,3-dioxan-2-yl)propyl)-N$^2$-methylpyridine-2,4-dicarboxamide (111 mg, 0.192 mmol) in ethanol (7 mL) was added hydrazine hydrate (210 μL, 4.28 mmol). The reaction was stirred at 40° C. overnight. The crude product was dissolved in DMSO: methanol, filtered through celite and purified by MDAP (high pH). Fractions containing the desired product were concentrated in vacuo to give N$^4$-(3-((2r,5r)-5-amino-1,3-dioxan-2-yl)propyl)-6-(2-chlorobenzyl)-N$^2$-methylpyridine-2,4-dicarboxamide (56 mg, 0.11 mmol, 59% yield).

LCMS (2 min Formic): Rt=0.68 min, [MH]+=447.4.

Example 153

N$^4$-(3-((2r,5r)-5-Amino-1,3-dioxan-2-yl)propyl)-N$^2$-methyl-6-(3-methylbenzyl)pyridine-2,4-dicarboxamide

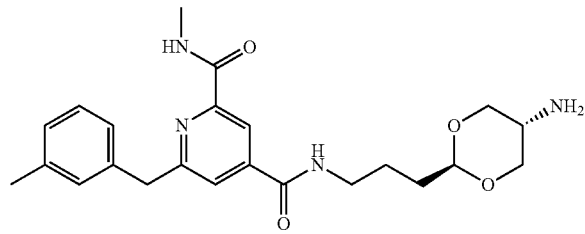 [SMILES: CNC(=O)c1cc(C(=O)NCCC[C@H]2OC[C@H](N)CO2)cc(Cc2cccc(C)c2)n1]

To a suspension of N$^4$-(3-((2r,5r)-5-(1,3-dioxoisoindolin-2-yl)-1,3-dioxan-2-yl)propyl)-N$^2$-methyl-6-(3-methylbenzyl)pyridine-2,4-dicarboxamide (64 mg, 0.12 mmol) in ethanol (5 mL) was added hydrazine hydrate (150 μL, 3.06 mmol). The reaction was stirred at 40° C. overnight. The crude product was dissolved in DMSO:methanol, filtered through cotton wool and purified by MDAP (high pH). The fractions containing desired product were concentrated in vacuo to give N$^4$-(3-((2r,5r)-5-amino-1,3-dioxan-2-yl)propyl)-N$^2$-methyl-6-(3-methylbenzyl)pyridine-2,4-dicarboxamide (33 mg, 0.07 mmol, 61% yield).

LCMS (2 min Formic): Rt=0.66 min, [MH]+=427.5.

Example 154

N$^4$-((1R,5S,6r)-3-Oxabicyclo[3.1.0]hexan-6-yl)-6-((S*)-hydroxy(m-tolyl)methyl)-N2-methylpyridine-2,4-dicarboxamide

Example 170

N$^4$-((1R,5S,6r)-3-Oxabicyclo[3.1.0]hexan-6-yl)-6-((R*)-hydroxy(m-tolyl)methyl)-N2-methylpyridine-2,4-dicarboxamide

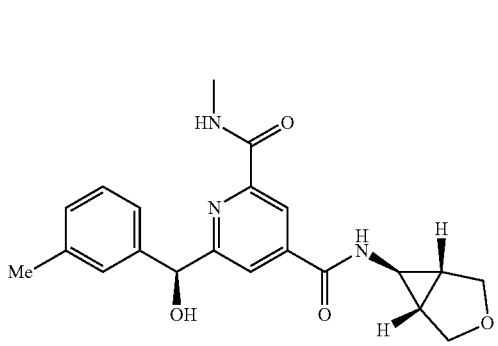

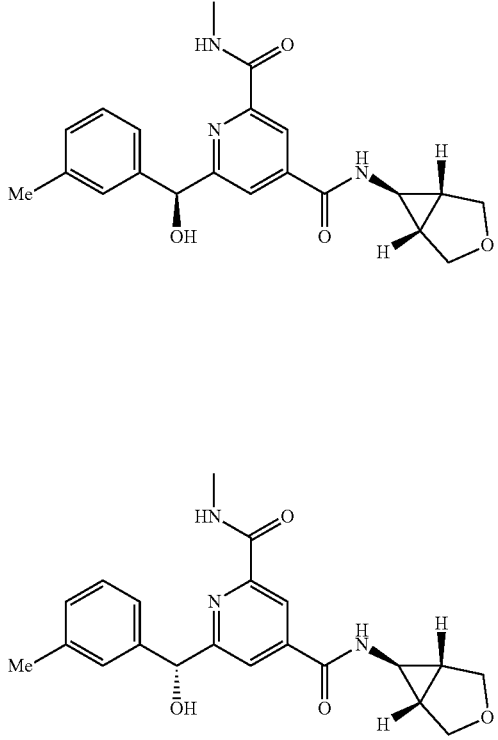

Example 129 (78 mg) was purified by chiral HPLC. The racemate was dissolved in EtOH (2 mL). Injection: 2 mL of the solution was injected onto the column (30% EtOH (+0.2% isopropylamine)/heptane (+0.2% isopropylamine), flow rate=30 mL/min, detection: wavelength, 215 nm, 4. Ref. 550, 100; Column 30 mm×25 cm Chiralpak AD-H (5 μm), Lot No. ADH13231). Total number of injections=1. Fractions from 11-14 min were bulked and labelled peak 1. Fractions from 19-23 min were bulked and labelled peak 2. The bulked pure fractions were concentrated in vacuo and then transferred to weighed flasks.

The fractions corresponding to peak 1 were collected to afford example 154 (36 mg)

LCMS (2 min Formic): Rt=0.80 min, [MH]+=382.3.

The fractions corresponding to peak 1 were collected to afford example 170 (34 mg)

LCMS (2 min Formic): Rt=0.80 min, [MH]+=382.4.

Example 155

(+/−)-$N^4$-(3-((2r,5r)-5-Amino-1,3-dioxan-2-yl)propyl)-6-(methoxy(phenyl)methyl)-$N^2$-methylpyridine-2,4-dicarboxamide

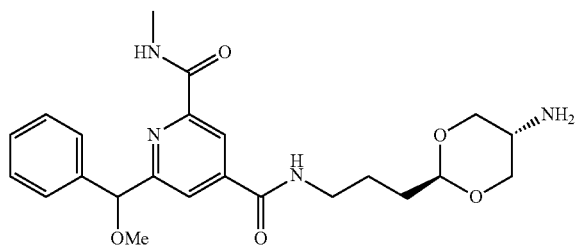 [SMILES: CNC(=O)c1cc(C(=O)NCCC[C@H]2OC[C@H](N)CO2)cc(C(OC)c2ccccc2)n1]

To a suspension of $N^4$-(3-((2r,5r)-5-(1,3-dioxoisoindolin-2-yl)-1,3-dioxan-2-yl)propyl)-6-(methoxy(phenyl)methyl)-$N^2$-methylpyridine-2,4-dicarboxamide (162 mg, 0.28 mmol) in ethanol (2 mL) was added hydrazine hydrate (0.100 mL, 2.06 mmol); the resulting suspension was stirred at 40° C. overnight. The solvent was removed under a positive pressure of nitrogen and the crude product then redissolved in DMSO (2.7 mL), filtered and purified by MDAP (3× high pH). The appropriate fractions were collected and concentrated in vacuo to afford the desired free base $N^4$-(3-((2r,5r)-5-amino-1,3-dioxan-2-yl)propyl)-6-(methoxy(phenyl)methyl)-$N^2$-methylpyridine-2,4-dicarboxamide (75 mg, 0.17 mmol, 60% yield)

LCMS (2 min Formic): Rt=0.60 min, [MH]+=443.4.

$^1$H NMR (400 MHz, DMSO-$d_6$) δ ppm 8.97 (t, J=5.5 Hz, 1H) 8.63 (q, J=4.4 Hz, 1H) 8.30 (d, J=1.7 Hz, 1H) 8.04 (d, J=1.7 Hz, 1H) 7.44-7.52 (m, 2H) 7.31-7.40 (m, 2H) 7.23-7.30 (m, 1H) 5.49 (s, 1H) 4.39 (t, J=4.8 Hz, 1H) 3.91 (dd, J=11.0, 4.9 Hz, 2H) 3.37 (s, 3H) 3.22-3.31 (obs. m, 2H) 3.13 (t, J=10.9 Hz, 2H) 2.86 (d, J=4.9 Hz, 3H) 2.74 (tt, J=10.4, 5.0 Hz, 1H) 1.48-1.65 (m, 4H). Two exchangeable protons not observed.

Example 156

$N^4$-((1R,5S,6r)-3-Oxabicyclo[3.1.0]hexan-6-yl)-6-((S*)-(3-fluorophenyl)(hydroxy)methyl)-$N^2$-methylpyridine-2,4-dicarboxamide

Example 157

$N^4$-((1R,5S,6r)-3-Oxabicyclo[3.1.0]hexan-6-yl)-6-((R*)-(3-fluorophenyl)(hydroxy)methyl)-$N^2$-methylpyridine-2,4-dicarboxamide

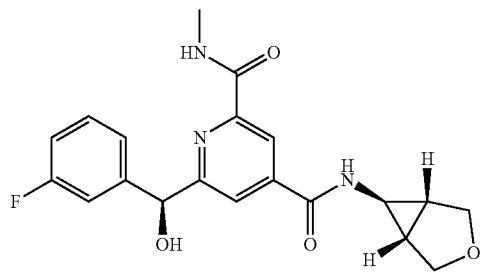

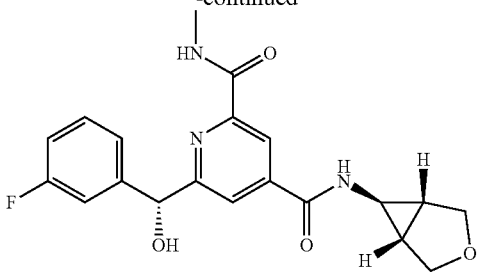

2-((3-Fluorophenyl)(hydroxy)methyl)-6-(methylcarbamoyl)isonicotinic acid (100 mg, 0.33 mmol) was suspended in DCM (5 mL) and Et$_3$N (0.137 ml, 0.99 mmol) and HATU (187 mg, 0.49 mmol) were added, then the mixture was stirred for 20 min before the addition of (1R,5S,6r)-3-oxabicyclo[3.1.0]hexan-6-amine, hydrochloride (66.8 mg, 0.49 mmol). The resulting solution was stirred for 2 h, then washed with water (10 mL), the organic layer dried and evaporated in vacuo and the residue purified by chromatography on a silica column (25 g) eluting with 0-100% (25% EtOH/EtOAc)/cyclohexane. The product-containing fractions were evaporated in vacuo to give $N^4$-((1R,5S,6r)-3-oxabicyclo[3.1.0]hexan-6-yl)-6-((3-fluorophenyl)(hydroxy)methyl)-$N^2$-methylpyridine-2,4-dicarboxamide (124 mg, 0.32 mmol, 98% yield).

The racemate (100 mg) was purified by chiral HPLC. The racemate was dissolved in EtOH (2 mL). Injection: 1 mL of the solution was injected onto the column (25% EtOH (+0.2% isopropylamine)/heptane (+0.2% isopropylamine), flow rate=30 mL/min, detection: wavelength, 215 nm, 4. Ref. 550, 100; Column 30 mm×25 cm Chiralpak AD-H (5 μm), Lot No. ADH13231). Total number of injections=2. Fractions from 14.5-17.5 min were bulked and labelled peak 1. Fractions from 21-25 min were bulked and labelled peak 2. The bulked pure fractions were concentrated in vacuo and then transferred to weighed flasks.

The fractions corresponding to peak 1 were collected to afford example 156 (50 mg)

LCMS (2 min High pH): Rt=0.80 min, [MH]+=382.3.

The fractions corresponding to peak 2 were collected to afford example 157 (50 mg)

LCMS (2 min High pH): Rt=0.80 min, [MH]+=382.4.

Example 158

$N^4$-(3-((2r,5r)-5-Amino-1,3-dioxan-2-yl)propyl)-6-(2-methoxybenzyl)-$N^2$-methylpyridine-2,4-dicarboxamide

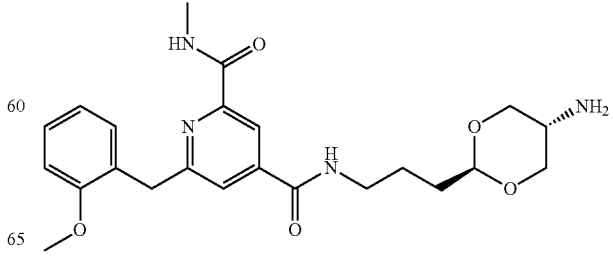

To a suspension of $N^4$-(3-((2r,5r)-5-(1,3-dioxoisoindolin-2-yl)-1,3-dioxan-2-yl)propyl)-6-(2-methoxybenzyl)-$N^2$-methylpyridine-2,4-dicarboxamide (51 mg, 0.089 mmol) in ethanol (3 mL) was added hydrazine hydrate (90 µL, 1.84 mmol). The reaction was stirred at 40° C. overnight. The crude product was dissolved in DMSO: methanol, filtered through cotton wool and purified by MDAP (high pH). The fractions containing the desired product were concentrated in vacuo to give $N^4$-(3-((2r,5r)-5-amino-1,3-dioxan-2-yl)propyl)-6-(2-methoxybenzyl)-$N^2$-methylpyridine-2,4-dicarboxamide (23 mg, 0.05 mmol, 53% yield).

LCMS (2 min High pH): Rt=0.85 min, [MH]+=443.3.

Example 159

$N^4$-((1R,5S,6r)-3-Oxabicyclo[3.1.0]hexan-6-yl)-6-(4-fluorobenzyl)-$N^2$-methylpyridine-2,4-dicarboxamide

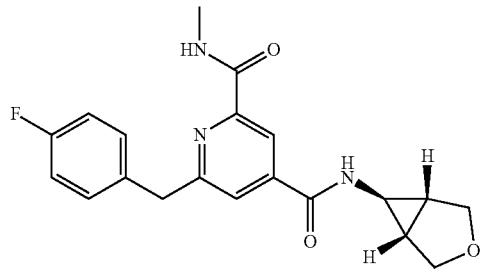 [SMILES: CNC(=O)c1cc(C(=O)N[C@H]2[C@@H]3COC[C@@H]32)cc(Cc2ccc(F)cc2)n1]

2-(4-Fluorobenzyl)-6-(methylcarbamoyl)isonicotinic acid (127 mg, 0.441 mmol) was dissolved in DMF (1 mL). HATU (251 mg, 0.661 mmol) was added followed by (1R,5S,6r)-3-oxabicyclo[3.1.0]hexan-6-amine, hydrochloride (106 mg, 0.782 mmol) and then DIPEA (0.385 mL, 2.20 mmol). The reaction mixture was stirred under nitrogen for 16 h. The reaction mixture was purified by MDAP (Formic). The fractions containing desired product were partitioned between DCM and sat. sodium bicarbonate solution. The layers were separated (by hydrophobic frit), followed by two further extractions from the aqueous with DCM (2×15 mL). The organic layers were combined and concentrated in vacuo to give $N^4$-((1R,5S,6r)-3-oxabicyclo[3.1.0]hexan-6-yl)-6-(4-fluorobenzyl)-$N^2$-methylpyridine-2,4-dicarboxamide (157 mg, 0.38 mmol, 87% yield).

LCMS (2 min Formic): Rt=0.89 min, [MH]+=370.2.

Example 160

$N^4$-(3-((2r,5S)-5-Amino-1,3-dioxan-2-yl)propyl)-6-((S*)-methoxy(phenyl)methyl)-N2-methylpyridine-2,4-dicarboxamide

Example 161

$N^4$-(3-((2r,5S)-5-Amino-1,3-dioxan-2-yl)propyl)-6-((R*)-methoxy(phenyl)methyl)-N2-methylpyridine-2,4-dicarboxamide

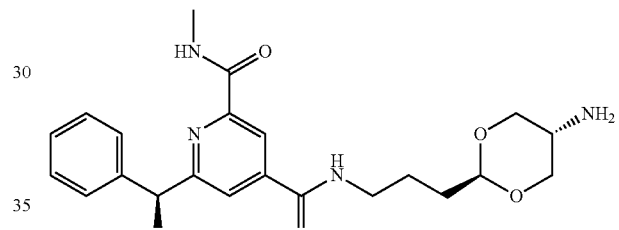

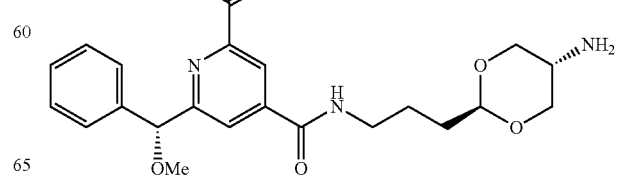

Example 155 (55 mg) was purified by chiral HPLC. The racemate was dissolved in EtOH (2 mL). Injection: 1 mL of the solution was injected onto the column (30% EtOH (+0.2% isopropylamine)/heptane (+0.2% isopropylamine), flow rate=30 mL/min, detection: wavelength, 215 nm, 4. Ref. 550, 100; Column 30 mm×25 cm Chiralpak AD-H (5 µm), Lot No. ADH13231). Total number of injections=3. Fractions from 20-23 min were bulked and labelled peak 1. Fractions from 23-26 min were bulked and labelled mix. Fractions from 26-31 min were bulked and labelled peak 2. The bulked mix fractions were concentrated in vacuo and reprocessed using the procedure above. The bulked pure fractions were concentrated in vacuo and then transferred to weighed flasks.

The fractions corresponding to peak 1 were collected to afford example 160 (26 mg)

LCMS (2 min Formic): Rt=0.57 min, [MH]+=443.2.

The fractions corresponding to peak 2 were collected to afford example 161 (26 mg)

LCMS (2 min Formic): Rt=0.57 min, [MH]+=443.2.

$^1$H NMR (400 MHz, DMSO-$d_6$) δ ppm 8.98 (t, J=5.5 Hz, 1H) 8.64 (q, J=4.6 Hz, 1H) 8.30 (d, J=1.5 Hz, 1H) 8.04 (d, J=1.5 Hz, 1H) 7.45-7.53 (m, 2H) 7.31-7.39 (m, 2H) 7.23-7.30 (m, 1H) 5.49 (s, 1H) 4.39 (t, J=4.8 Hz, 1H) 3.90 (dd, J=11.2, 4.9 Hz, 2H) 3.37 (s, 3H) 3.25 (q, J=6.5 Hz, 2H) 3.13 (t, J=11.0 Hz, 2H) 2.86 (d, J=5.0 Hz, 3H) 2.74 (tt, J=10.4, 5.1 Hz, 1H) 1.49-1.65 (m, 4H). Two exchangeable protons not observed.

Example 162

6-Benzyl-$N^4$-(3-((2r,5r)-5-(dimethylamino)-1,3-dioxan-2-yl)propyl)-$N^2$-methylpyridine-2,4-dicarboxamide

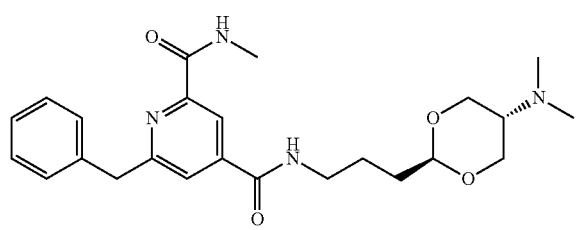 [SMILES: CNC(=O)c1cc(C(=O)NCCC[C@H]2OC[C@H](N(C)C)CO2)cc(Cc2ccccc2)n1]

To a mixture of $N^4$-(3-((2r,5r)-5-amino-1,3-dioxan-2-yl)propyl)-6-benzyl-$N^2$-methylpyridine-2,4-dicarboxamide (33.6 mg, 0.081 mmol) in formaldehyde (37% solution in water, 0.334 mL, 4.48 mmol) and water (0.5 mL) was added formic acid (0.172 mL, 4.48 mmol) in a microwave vial. The vial was sealed and the mixture heated in a microwave reactor at 110° C. for 30 min. The mixture was concentrated under a stream of nitrogen and the remaining residue was diluted with DMSO to a total volume of 1 mL and purified by MDAP (1×1 mL injection; high pH). The desired fraction was concentrated under a stream of nitrogen. The residue was dissolved in DCM (5 mL) and transferred to a tarred vial before being concentrated under a stream of nitrogen and dried in vacuo to give 6-benzyl-$N^4$-(3-((2r,5r)-5-(dimethylamino)-1,3-dioxan-2-yl)propyl)-N2-methylpyridine-2,4-dicarboxamide (3.9 mg, 8.85 µmol, 11% yield) as a colourless glass.

LCMS (2 min formic) Peak $R_t$=0.60 min, m/z=441 for [MH]+

Example 172

(+/−)-$N^4$-((1R,5S,6r)-3-Oxabicyclo[3.1.0]hexan-6-yl)-6-(2-cyano-1-phenyl)ethyl)-$N^2$-methylpyridine-2,4-dicarboxamide

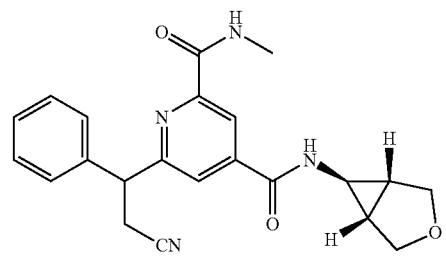 [SMILES: CNC(=O)c1cc(C(=O)N[C@H]2[C@@H]3COC[C@@H]32)cc(C(CC#N)c2ccccc2)n1]

2-(2-Cyano-1-phenylethyl)-6-(methylcarbamoyl)isonicotinic acid (180 mg, 0.291 mmol) was taken up in DMF (2 mL). DIPEA (0.152 mL, 0.873 mmol) then HATU (166 mg, 0.436 mmol) were added and the solution stirred at rt for 10 min. (1R,5S,6r)-3-Oxabicyclo[3.1.0]hexan-6-amine, hydrochloride (59.2 mg, 0.436 mmol) was added and stirring at rt continued for 1 h. Additional portions of (1R,5S,6r)-3-oxabicyclo[3.1.0]hexan-6-amine, hydrochloride (59.2 mg, 0.436 mmol), DIPEA (0.152 mL, 0.873 mmol) and HATU (166 mg, 0.436 mmol) were added and stirring continued at rt for 1 h and then overnight. The reaction was concentrated in vacuo. The residue was partitioned between EtOAc and sat. NaHCO$_3$ solution (10 mL each). The aqueous layer was re-extracted with EtOAc (10 mL) and the combined organics were washed with brine (25 mL), then dried (Na$_2$SO$_4$), filtered through a hydrophobic frit and concentrated in vacuo to yield a brown oil. The crude product was purified by MDAP (high pH). The appropriate fractions were concentrated in vacuo to give (+/−)-$N^4$-((1R,5S,6r)-3-oxabicyclo[3.1.0]hexan-6-yl)-6-(2-cyano-1-phenylethyl)-$N^2$-methylpyridine-2,4-dicarboxamide (20.5 mg, 0.050 mmol, 17% yield) as an orange solid.

LCMS (2 min High pH) $R_t$=0.87 min, m/z=391.6 for [MH]+

Examples 163-166 and 171

Examples 163-166 and 171 were prepared in an analogous manner to the previous examples:

| Ex No. | Name | Structure | [MH]+ | Rt (min)* |
|---|---|---|---|---|
| 163 | (+/−)-tert-Butyl 4-(3-(2-benzyl-6-(methylcarbamoyl)isonicotinamido)propyl)-3,3-difluoropiperidine-1-carboxylate | 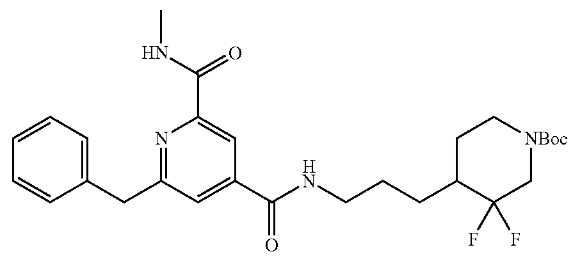 [SMILES: CNC(=O)c1cc(C(=O)NCCCC2CCN(C(=O)OC(C)(C)C)CC2(F)F)cc(Cc2ccccc2)n1] | 531.4 (formic) | 1.26 |
| 164 | (+/−)-$N^4$-((1R,5S,6r)-3-Oxabicyclo[3.1.0]hexan-6-yl)-6-(2-fluoro-1-phenylethyl)-$N^2$-methylpyridine-2,4-dicarboxamide | 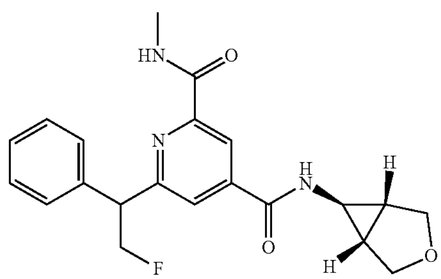 [SMILES: CNC(=O)c1cc(C(=O)N[C@H]2[C@@H]3COC[C@@H]32)cc(C(CF)c2ccccc2)n1] | 384.4 (formic) | 0.95 |
| 165 | $N^4$-((1R,5S,6r)-3-Oxabicyclo[3.1.0]hexan-6-yl)-6-((S*)-2-fluoro-1-phenylethyl)-$N^2$-methylpyridine-2,4-dicarboxamide | 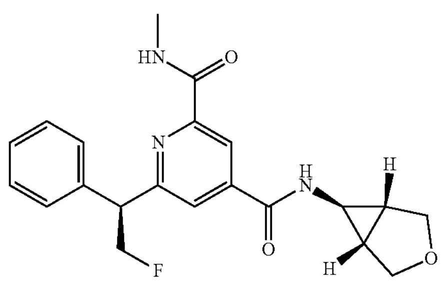 [SMILES: CNC(=O)c1cc(C(=O)N[C@H]2[C@@H]3COC[C@@H]32)cc([C@@H](CF)c2ccccc2)n1] | 384.4 (formic) | 0.94 |
| 166 | $N^4$-((1R,5S,6r)-3-Oxabicyclo[3.1.0]hexan-6-yl)-6-((R*)-2-fluoro-1-phenylethyl)-$N^2$-methylpyridine-2,4-dicarboxamide | 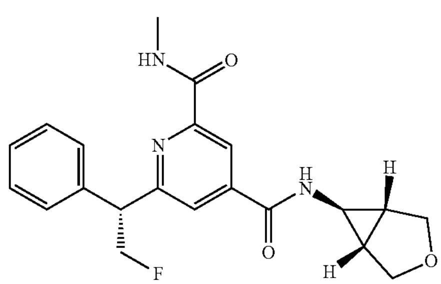 [SMILES: CNC(=O)c1cc(C(=O)N[C@H]2[C@@H]3COC[C@@H]32)cc([C@H](CF)c2ccccc2)n1] | 384.4 (formic) | 0.93 |
| 171 | $N^4$-(3-((2r,5r)-5-Amino-1,3-dioxan-2-yl)propyl)-6-(3-methoxybenzyl)-$N^2$-methylpyridine-2,4-dicarboxamide | 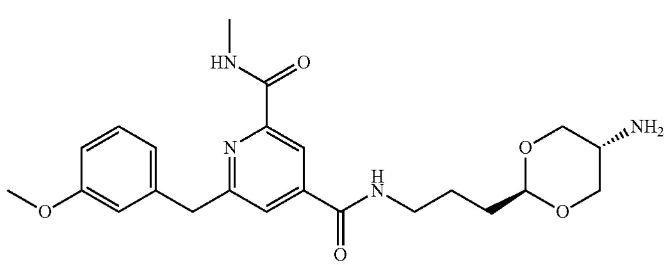 [SMILES: CNC(=O)c1cc(C(=O)NCCC[C@H]2OC[C@H](N)CO2)cc(Cc2cccc(OC)c2)n1] | 487.4 (formic) | 0.62 |

Biological Data

The compounds of formula (I) may be tested in one or more of the following assays:

Time Resolved Fluorescence Resonance Energy Transfer (TR-FRET) Assay

Bromodomain binding was assessed utilising a time resolved fluorescent resonance energy transfer (TR-FRET) competition assay. To enable this approach a known, high affinity, pan-BET interacting small molecule was labelled with Alexa Fluor® 647, which is a far-red-fluorescent dye (Reference Compound X). Reference Compound X acts as a reporter of bromodomain binding and is the acceptor fluorophore component of the TR-FRET pair. Europium chelate, conjugated to an anti-6*His antibody, was utilised as the donor fluorophore in the TR-FRET pair. The anti-6*His antibody binds selectively to a six Histidine purification epitope added to the amino-terminus of each of the BET tandem bromodomain protein constructs used in this study. A TR-FRET signal is generated when the donor and acceptor fluorophores are in close proximity, between 20-80 Å, which is enabled in this assay by binding of Reference Compound X to the bromodomain protein.

Reference Compound X: 4-((Z)-3-(6-((5-(2-((4S)-6-(4-chlorophenyl)-8-methoxy-1-methyl-4H-benzo[f][1,2,4]triazolo[4,3-a][1,4]diazepin-4-yl)acetamido)pentyl)amino)-6-oxohexyl)-2-((2E,4E)-5-(3,3-dimethyl-5-sulfo-1-(4-sulfobutyl)-3H-indol-1-ium-2-yl)penta-2,4-dien-1-ylidene)-3-methyl-5-sulfoindolin-1-yl)butane-1-sulphonate)

To a solution of N-(5-aminopentyl)-2-((4S)-6-(4-chlorophenyl)-8-methoxy-1-methyl-4H-benzo[f][1,2,4]triazolo[4,3-a][1,4]diazepin-4-yl)acetamide (for a preparation see Reference Compound J, WO2011/054848A1, 1.7 mg, 3.53 μmol) in DMF (40 μL) was added a solution of AlexaFluor647-ONSu (2.16 mg, 1.966 μmol) also in DMF (100 μL). The mixture was basified with DIPEA (1 μl, 5.73 μmol) and agitated overnight on a vortex mixer.

The reaction mixture was evaporated to dryness. The solid was dissolved in MeCN/water/AcOH (5/4/1, <1 mL) filtered and was applied to a Phenomenex Jupiter C18 preparative column and eluted with the following gradient (A=0.1% trifluoroacetic acid in water, B=0.1% TFA/90% MeCN/10% water): Flow rate=10 mL/min., AU=20/10 (214 nm):

5-35%, t=0 min: B=5%; t=10 min: B=5%; t=100 min: B=35%; t=115 min: B=100% (Sep. grad: 0.33%/min)

The major component was eluted over the range 26-28% B but appeared to be composed of two peaks. The middle fraction (F1.26) which should contain "both" components was analysed by analytical HPLC (Spherisorb ODS2, 1 to 35% over 60 min): single component eluting at 28% B.

Fractions F1.25/26&27 were combined and evaporated to dryness. Transfered with DMF, evaporated to dryness, triturated with dry ether and the blue solid dried overnight at <0.2 mbar: 1.54 mg.

Analytical HPLC (Sphersisorb ODS2, 1 to 35% B over 60 min): MSM10520-1: $[M+H]^+$ (obs): 661.8/– corresponding with M-29. This equates to $[(M+2H)/2]^+$ for a calculated

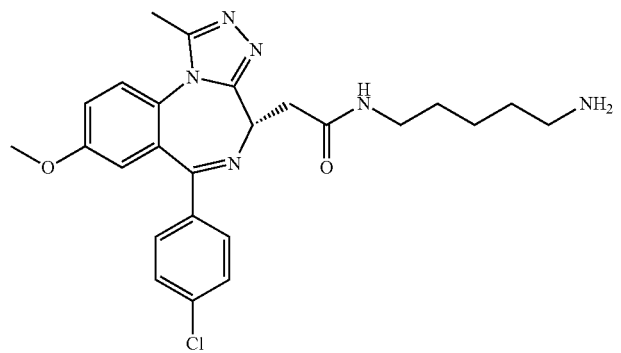

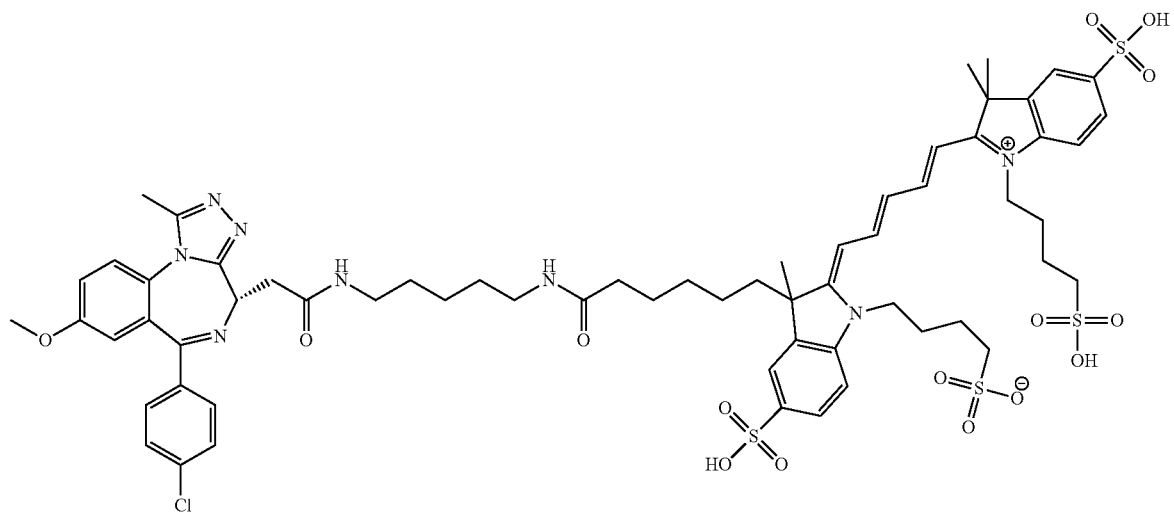

mass of 1320.984 which is M-29. This is a standard occurence with the Alexa Fluor 647 dye and represents a theoretical loss of two methylene groups under the conditions of the mass spectrometer.

Assay Principle: In order to generate a TR-FRET signal, donor fluorophore is excited by a laser at A337 nm, which subsequently leads to emission at A618 nm. If the acceptor fluorophore is in close proximity then energy transfer can occur, which leads to emission of Alexa Fluor® 647 at λ665 nm. In the presence of competitor compound, Reference Compound X can be displaced from binding to the bromodomain. If displacement occurs, the acceptor fluorophore is no longer in proximity to the donor fluorophore, which prevents fluorescent energy transfer and, subsequently, a loss of Alexa Fluor® 647 emission at λ665 nm.

The competition of the compounds of formula (I) with Reference Compound X for binding to the BET family (BRD2, BRD3, BRD4 and BRDT) was assessed using protein truncates spanning both bromodomain 1 (BD1) and bromodomain 2 (BD2). In order to monitor differential binding to either BD1 or BD2, single residue mutations of key tyrosines to alanine were made in the acetyl lysine binding pockets. To validate this approach, a double residue mutant tandem domain protein was produced for each of the BET family members. Utilising a Fluorescence Polarisation approach, binding affinities for each of the single and double mutants for Reference Compound X were determined. The affinities of the double mutant tandem proteins for Reference Compound X were greatly greatly reduced in comparison to the non mutated, wild type tandem BET proteins (>1000 fold reduction in Kd). The affinities of the single mutated bromodomain tandem proteins for Reference Compound X were equi-potent with the corresponding non-mutated BET protein. These data demonstrated that single mutations of Tyrosine to Alanine reduce the Kd of the interaction between the mutated bromodomain and Reference Compound X by >1000 fold. In the TR-FRET competition assay, Reference Compound X is used at a concentration that is equivalent to the Kd for the non-mutated bromodomain, which ensures that no binding at the mutated bromodomain is detected.

Protein production: Recombinant Human Bromodomains [(BRD2 (1-473) (Y113A) and (Y386A), BRD3 (1-435) (Y73A) and (Y348A) BRD4 (1-477) (Y97A) and (Y390A) and BRDT (1-397) (Y66A) and (Y309A)] were expressed in *E. coli* cells (in pET15b vector for BRD2/3/4 and in pET28a vector for BRDT) with a 6-His tag at the N-terminal. The His-tagged Bromodomain pellet was resuspended in 50 mM HEPES (pH7.5), 300 mM NaCl, 10 mM imidazole & 1 µL/mL protease inhibitor cocktail and extracted from the *E. coli* cells using sonication and purified using a nickel sepharose high performance column, the proteins were washed and then eluted with a linear gradient of 0-500 mM imidazole with buffer 50 mM HEPES (pH7.5), 150 mM NaCl, 500 mM imidazole, over 20 column volumes. Final purification was completed by Superdex 200 prep grade size exclusion column. Purified protein was stored at -80° C. in 20 mM HEPES pH 7.5 and 100 mM NaCl. Protein identity was confirmed by peptide mass fingerprinting and predicted molecular weight confirmed by mass spectrometry.

Protocol for Bromodomain BRD2, 3, 4 and T, BD1+BD2 mutant TR-FRET competition assays:

All assay components were dissolved in an assay buffer composing of 50 mM HEPES pH7.4, 50 mM NaCl, 5% Glycerol, 1 mM DTT and 1 mM CHAPS. Reference Compound X was diluted, in assay buffer containing 20 nM single mutant, tandem bromodomain protein, to a concentration equivalent to 2*Kd for this bromodomain. The solution containing bromodomain and Reference Compound X was added to dose response dilutions of test compound or DMSO vehicle (a maximum of 0.5% DMSO is used in this assay) in Greiner 384 well black low volume microtitre plates and subsequently incubated for 30 minutes at room temperature. An equal volume of 3 nM of anti-6*His Europium chelate was added to all wells, followed by a further 30 minute incubation at room temperature. TR-FRET was detected using a Perkin Elmer Multimode plate reader, by exciting the donor fluorophore at A337 nm and subsequently, after a delay of 50 µsecs, measuring emission of the donor and acceptor fluorophores at A615 nm and λ665 nm, respectively. In order to control these assays, 16 replicates each of uninhibited (DMSO vehicle) and inhibited ($10^*IC_{50}$ concentrations of Example 11 of WO 2011/054846A1) TR-FRET assays were included on every microtitre plate.

cA four parameter curve fit of the following form was then applied:

$$y=a+((b-a)/(1+(10^\wedge x/10^\wedge c)^\wedge d)$$

Where 'a' is the minimum, 'b' is the Hill slope, 'c' is the $pIC_{50}$ and 'd' is the maximum.

All compounds (Examples) were each tested in the BRD4 BD1 and the BRD4 BD2 TR-FRET assays essentially as described above. Those of skill in the art will recognise that in vitro binding assays and cell-based assays for functional activity are subject to experimental variability. Accordingly, it is to be understood that the $pIC_{50}$ values given below are exemplary only. $pIC_{50}$ values are expressed as $log_{10}$ units.

All tested compounds were found to have a $pIC_{50} \geq 5.0$ in at least one assay described above. Examples 84, 85, 87, 164, 165, and 166 were found to have a $pIC_{50} \geq 5.0$ and <6.0 in the BRD4 BD2 assay.

All other tested compounds were found to have a $pIC_{50}$ in the range ≥6.0 and ≤8.2 in the BRD4 BD2 assay. In particular, Example 38 was found to have a $pIC_{50}$ of 7.9 (n=3) in the BRD4 BD2 assay; Example 41 was found to have a $pIC_{50}$ of 7.4 (n=2) in the BRD4 BD2 assay; Example 51 was found to have a $pIC_{50}$ of 8.1 (n=3) in the BRD4 BD2 assay; Example 70 was found to have a $pIC_{50}$ of 7.8 (n=3) in the BRD4 BD2 assay; Example 105 was found to have a $pIC_{50}$ of 7.5 (n=8) in the BRD4 BD2 assay; Example 113 was found to have a $pIC_{50}$ of 7.5 (n=7) in the BRD4 BD2 assay; Example 130 was found to have a $pIC_{50}$ of 7.3 (n=5) in the BRD4 BD2 assay; and Example 161 was found to have a $pIC_{50}$ of 7.6 (n=3) in the BRD4 BD2 assay.

Calculation of Selectivity for BRD4 BD2 over BRD4 BD1

Selectivity for BRD4 BD2 over BRD4 BD1 was calculated as follows:

$$Selectivity = BRD4BD2pIC_{50} - BRD4BD1pIC_{50}$$

All Examples were found to have selectivity for BRD4 BD2 over BRD4 BD1 of ≥1 log unit in at least one of the TR-FRET assays described above, and hence are at least 10 fold selective for BRD4 BD2 over BRD4 BD1.

Examples 1 to 75 and 88 to 162 and 172 were found to have selectivity for BRD4 BD2 over BRD4 BD1 of ≥2 log unit in at least one of the TR-FRET assays described above, and hence are at least 100 fold selective for BRD4 BD2 over BRD4 BD1.

Example 38 was found to have selectivity for BRD4 BD2 over BRD4 BD1 of 3.1 log units in at least one of the TR-FRET assays described above, and hence is at least 1000-fold selective for BRD4 BD2 over BRD4 BD1.

Example 41 was found to have a selectivity for BRD4 BD2 over BRD4 BD1 of 3.0 log units in at least one of the TR-FRET assays described above, and hence is at least 1000-fold selective for BRD4 BD2 over BRD4 BD1.

Example 51 was found to have a selectivity for BRD4 BD2 over BRD4 BD1 of 3.5 log units in at least one of the TR-FRET assays described above, and hence is at least 1000-fold selective for BRD4 BD2 over BRD4 BD1.

Example 70 was found to have a selectivity for BRD4 BD2 over BRD4 BD1 of 3.1 log units in at least one of the TR-FRET assays described above, and hence is at least 1000-fold selective for BRD4 BD2 over BRD4 BD1.

Example 113 was found to have a selectivity for BRD4 BD2 over BRD4 BD1 of 3.1 log units in at least one of the TR-FRET assays described above, and hence is at least 1000-fold selective for BRD4 BD2 over BRD4 BD1.

Example 161 was found to have a selectivity for BRD4 BD2 over BRD4 BD1 of 3.2 log units in at least one of the TR-FRET assays described above, and hence is at least 1000-fold selective for BRD4 BD2 over BRD4 BD1.

The invention claimed is:

1. A compound of formula (I)

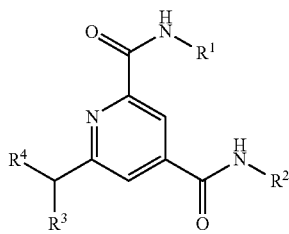

(I)

or pharmaceutically acceptable salt thereof
wherein:
$R^1$ is —$C_{1-3}$alkyl or cyclopropyl;
$R^2$ is —$C_{0-4}$alkyl-heterocyclyl, —$CH_2CH(OH)$-heterocyclyl, or —$(CH_2)_pO$-heterocyclyl, wherein heterocyclyl is selected from oxetanyl, azetidinyl, tetrahydrofuranyl, piperidinyl, piperazinyl, morpholinyl, tetrahydro-2H-pyranyl, 1,3-dioxanyl, 1,4-dioxanyl, (1r,5s)-3-oxabicyclo[3.1.0]hexanyl, and (1r,5s)-3-azabicyclo[3.1.0]hexanyl, wherein each oxetanyl, azetidinyl, tetrahydrofuranyl, piperidinyl, piperazinyl, morpholinyl, tetrahydro-2H-pyranyl, 1,3-dioxanyl, 1,4-dioxanyl, (1r,5s)-3-oxabicyclo[3.1.0]hexanyl, or (1r,5s)-3-azabicyclo[3.1.0]hexanyl is optionally substituted by one, two, or three $R^5$ groups which may be the same or different;
$R^3$ is —H, —$C_{1-4}$alkyl, cyclopropyl, fluoro, chloro, —$CH_2F$, —$C_{0-3}$alkylOR$^{10}$, or $C_{0-3}$alkylCN;
$R^4$ is phenyl, indolyl, indolinyl, pyridinyl, or pyrrolopyridinyl, wherein each phenyl, indolyl, indolinyl, pyridinyl, or pyrrolopyridinyl is optionally substituted by one, two, or three $R^6$ groups which may be the same or different;
each $R^5$ is independently halo, —$C_{1-4}$alkyl, $C_{3-4}$cycloalkyl, —$CH_2CF_3$, —$CH_2CHF_2$, —$CH_2CH_2F$, —$OCH_2CH_2OR^8$, —$C_{0-3}$alkylOR$^8$, —$C_{0-3}$alkylNR$^{11}$R$^{12}$, —$NHCH_2CH_2OR^8$, —$NHCO_2R^8$, oxo, —$CO_2R^8$, —$C(O)R^8$, or —$C(O)NR^{11}R^{12}$;

each $R^6$ is independently halo, —$C_{1-4}$alkyl, —$C_{0-3}$alkylOR$^7$, oxo, —$CO_2R^8$, —$C_{0-3}$alkylNR$^{16}$R$^{17}$, —$C_{0-3}$ alkyl-CONR$^{16}$R$^{17}$, —CN, —$SO_2$—$C_{1-3}$alkyl, or —$SO_2NR^{16}R^{17}$;
$R^7$ is —H, —$C_{2-3}$alkylNR$^{16}$R$^{17}$, or —$C_{2-3}$alkylOH;
$R^8$ is —H or —$C_{1-4}$alkyl;
$R^{10}$ is —H, —$C_{2-3}$alkylNR$^{14}$R$^{15}$, or —$C_{2-3}$alkylOH;
$R^{11}$ and $R^{12}$ are each independently selected from —H and —$C_{1-3}$alkyl;
$R^{14}$ and $R^{15}$ are each independently selected from —H and —$C_{1-3}$alkyl;
$R^{16}$ and $R^{17}$ are each independently selected from —H and —$C_{1-3}$alkyl; and
p is an integer selected from 2, 3, or 4.

2. The compound or pharmaceutically acceptable salt thereof according to claim 1, wherein $R^1$ is methyl.

3. The compound or pharmaceutically acceptable salt thereof according to claim 1, wherein $R^2$ is —$C_{0-4}$alkyl-heterocyclyl, wherein the heterocyclyl group is optionally substituted by one or two $R^5$ groups which may be the same or different.

4. The compound or pharmaceutically acceptable salt thereof according to claim 1, wherein $R^3$ is —H, methyl, ethyl, fluoro, —$OCH_3$, —OH, —$CH_2F$, —$CH_2OMe$, or —$CH_2CN$.

5. The compound or pharmaceutically acceptable salt thereof according to claim 1, wherein $R^4$ is phenyl optionally substituted by one, two, or three $R^6$ groups which may be the same or different selected from —$C_{1-4}$alkyl, —$C_{0-3}$alkylOR$^7$, and CN.

6. The compound or pharmaceutically acceptable salt thereof according to claim 1, wherein $R^5$ is selected from halo, $C_{1-4}$alkyl, —$CH_2CHF_2$, oxo, —$C_{0-3}$alkylNR$^{11}$R$^{12}$, —$CO_2C(CH_3)_3$, and —$C(O)R^8$.

7. The compound or a pharmaceutically acceptable salt thereof according to claim 6, wherein $R^5$ is selected from fluoro, —$CO_2C(CH_3)_3$, —$CH_2CHF_2$, —$CH(CH_3)_2$, —$C(O)CH_3$, oxo, and methyl.

8. The compound according to claim 1 which is:
tert-Butyl 4-(3-(2-benzyl-6-(methylcarbamoyl)isonicotinamido)propyl)piperidine-1-carboxylate;
6-Benzyl-$N^2$-methyl-$N^4$-(2-(piperidin-4-yl)ethyl)pyridine-2,4-dicarboxamide;
6-Benzyl-$N^2$-methyl-$N^4$-(3-(piperidin-4-yl)propyl)pyridine-2,4-dicarboxamide;
6-Benzyl-$N^4$-((1R,5S,6r)-3-oxabicyclo[3.1.0]hexan-6-yl)-$N^2$-methylpyridine-2,4-dicarboxamide;
6-Benzyl-$N^2$-methyl-$N^4$-(oxetan-3-yl)pyridine-2,4-dicarboxamide;
(+/−)-6-(3-Methoxybenzyl)-$N^2$-methyl-$N^4$-(2-(morpholin-2-yl)ethyl)pyridine-2,4-dicarboxamide;
(+/−)-6-(3-Methoxybenzyl)-$N^2$-methyl-$N^4$-(2-(4-methylmorpholin-2-yl)ethyl)pyridine-2,4-dicarboxamide;
(+/−)-tert-Butyl 2-(2-(2-(methylcarbamoyl)-6-(1-phenylethyl)isonicotinamido)ethyl)morpholine-4-carboxylate;
6-Benzyl-$N^2$-methyl-$N^4$-(3-morpholinopropyl)pyridine-2,4-dicarboxamide;
(+/−)-6-Benzyl-$N^2$-methyl-$N^4$-(tetrahydrofuran-3-yl)pyridine-2,4-dicarboxamide;
6-Benzyl-$N^2$-methyl-$N^4$-(3-(piperazin-1-yl)propyl)pyridine-2,4-dicarboxamide;
(+/−)-6-Benzyl-$N^2$-methyl-$N^4$-(2-(4-methylmorpholin-2-yl)ethyl)pyridine-2,4-dicarboxamide;
(+/−)-$N^2$-Methyl-$N^4$-(2-(morpholin-2-yl)ethyl)-6-(1-phenylethyl)pyridine-2,4-dicarboxamide;

N⁴-((1R,5S,6s)-3-Oxabicyclo[3.1.0]hexan-6-yl)-6-(3-methoxybenzyl)-N²-methylpyridine-2,4-dicarboxamide;

(+/−)-tert-Butyl 4-(2-(2-(methylcarbamoyl)-6-(1-phenylethyl)isonicotinamido)ethyl)piperidine-1-carboxylate;

(+/−)-N²-Methyl-6-(1-phenylethyl)-N4-(2-(piperidin-4-yl)ethyl)pyridine-2,4-dicarboxamide;

N⁴-((1R,5S,6s)-3-Azabicyclo[3.1.0]hexan-6-yl)-6-(3-methoxybenzyl)-N²-methylpyridine-2,4-dicarboxamide;

(1R,5S,6s)-tert-Butyl 6-(2-(3-methoxybenzyl)-6-(methylcarbamoyl)isonicotinamido)-3-azabicyclo[3.1.0]hexane-3-carboxylate;

6-(3-Methoxybenzyl)-N²-methyl-N⁴-((1R,5S,6s)-3-methyl-3-azabicyclo[3.1.0]hexan-6-yl)pyridine-2,4-dicarboxamide;

N⁴-((1R,5S,6s)-3-Acetyl-3-azabicyclo[3.1.0]hexan-6-yl)-6-(3-methoxybenzyl)-N²-methylpyridine-2,4-dicarboxamide;

6-Benzyl-N²-methyl-N⁴-(tetrahydro-2H-pyran-4-yl)pyridine-2,4-dicarboxamide;

6-Benzyl-N⁴-((1R,5S,6s)-3-azabicyclo[3.1.0]hexan-6-yl)-N²-methylpyridine-2,4-dicarboxamide hydrochloride;

N⁴-((1R,5S,6r)-3-Oxabicyclo[3.1.0]hexan-6-yl)-6-(3-(2-hydroxyethoxy)benzyl)-N²-methylpyridine-2,4-dicarboxamide;

(+/−)-6-Benzyl-N²-methyl-N⁴-(2-(piperidin-3-yl)ethyl)pyridine-2,4-dicarboxamide hydrochloride;

6-Benzyl-N²-methyl-N⁴-(2-(tetrahydro-2H-pyran-4-yl)ethyl)pyridine-2,4-dicarboxamide;

(+/−)-6-(3-Methoxybenzyl)-N²-methyl-N⁴-(3-(morpholin-2-yl)propyl)pyridine-2,4-dicarboxamide;

N²-Methyl-N⁴-(3-((S)-morpholin-2-yl)propyl)-6-(1-phenylethyl)pyridine-2,4-dicarboxamide;

(R)-6-(3-Methoxybenzyl)-N²-methyl-N⁴-(3-(morpholin-2-yl)propyl)pyridine-2,4-dicarboxamide;

(S)-6-(3-Methoxybenzyl)-N²-methyl-N⁴-(3-(morpholin-2-yl)propyl)pyridine-2,4-dicarboxamide;

N²-Methyl-N⁴-(2-((S)-morpholin-2-yl)ethyl)-6-(1-phenylethyl)pyridine-2,4-dicarboxamide;

N²-Methyl-N⁴-(2-((R)-morpholin-2-yl)ethyl)-6-(1-phenylethyl)pyridine-2,4-dicarboxamide;

(+/−)-N⁴-((1R,5S,6r)-3-Oxabicyclo[3.1.0]hexan-6-yl)-N²-methyl-6-(1-phenylethyl)pyridine-2,4-dicarboxamide;

(+/−)-6-Benzyl-N⁴-(3-(3-fluoropiperidin-3-yl)propyl)-N²-methylpyridine-2,4-dicarboxamide;

(+/−)-tert-Butyl 3-(3-(2-benzyl-6-(methylcarbamoyl)isonicotinamido)propyl)-3-fluoropiperidine-1-carboxylate;

(S)-6-((1H-Indol-4-yl)methyl)-N²-methyl-N⁴-(3-(morpholin-2-yl)propyl)pyridine-2,4-dicarboxamide;

(R)-6-Benzyl-N²-methyl-N⁴-(2-(morpholin-2-yl)ethyl)pyridine-2,4-dicarboxamide;

(S)-6-Benzyl-N²-methyl-N⁴-(3-(morpholin-2-yl)propyl)pyridine-2,4-dicarboxamide;

N⁴-((1R,5S,6r)-3-Oxabicyclo[3.1.0]hexan-6-yl)-N²-methyl-6-((S*)-1-phenylethyl)pyridine-2,4-dicarboxamide;

N⁴-((1R,5S,6r)-3-oxabicyclo[3.1.0]hexan-6-yl)-N²-methyl-6-((R*)-1-phenylethyl)pyridine-2,4-dicarboxamide;

N²-Methyl-N⁴-(2-((S)-morpholin-2-yl)ethyl)-6-((R*)-1-phenylethyl)pyridine-2,4-dicarboxamide;

N²-Methyl-N⁴-(2-((S)-morpholin-2-yl)ethyl)-6-((S*)-1-phenylethyl)pyridine-2,4-dicarboxamide;

N²-Methyl-N⁴-(2-((S)-morpholin-2-yl)ethyl)-6-((S*)-1-phenylethyl)pyridine-2,4-dicarboxamide hydrochloride;

(S)-6-Benzyl-N²-methyl-N⁴-(2-(morpholin-2-yl)ethyl)pyridine-2,4-dicarboxamide;

(S)-6-Benzyl-N⁴-(3-(4-isopropylmorpholin-2-yl)propyl)-N²-methylpyridine-2,4-dicarboxamide;

6-Benzyl-N⁴-((R*)-2-hydroxy-2-((S)-morpholin-2-yl)ethyl)-N²-methylpyridine-2,4-dicarboxamide;

6-Benzyl-N⁴-((S*)-2-hydroxy-2-((S)-morpholin-2-yl)ethyl)-N²-methylpyridine-2,4-dicarboxamide;

(S)-6-((1H-Indol-4-yl)methyl)-N⁴-(3-(4-isopropylmorpholin-2-yl)propyl)-N²-methylpyridine-2,4-dicarboxamide;

(R)-6-Benzyl-N⁴-(3-(3-fluoropiperidin-3-yl)propyl)-N²-methylpyridine-2,4-dicarboxamide;

(S)-6-Benzyl-N⁴-(3-(3-fluoro-1-isopropylpiperidin-3-yl)propyl)-N²-methylpyridine-2,4-dicarboxamide;

(R)-6-Benzyl-N⁴-(2-(4-isopropylmorpholin-2-yl)ethyl)-N²-methylpyridine-2,4-dicarboxamide;

(±)-6-Benzyl-N⁴-(3-(4,4-difluoropiperidin-3-yl)propyl)-N²-methylpyridine-2,4-dicarboxamide;

6-((1H-Indol-4-yl)methyl)-N⁴-((1R,5S,6r)-3-oxabicyclo[3.1.0]hexan-6-yl)-N²-methylpyridine-2,4-dicarboxamide;

(S)-6-((1H-Indol-4-yl)methyl)-N⁴-(3-(3-fluoropiperidin-3-yl)propyl)-N²-methylpyridine-2,4-dicarboxamide;

N²-Methyl-N⁴-(2-((R)-morpholin-2-yl)ethyl)-6-((S*)-1-phenylethyl)pyridine-2,4-dicarboxamide;

N²-Methyl-N⁴-(2-((R)-morpholin-2-yl)ethyl)-6-((R*)-1-phenylethyl)pyridine-2,4-dicarboxamide;

6-((1H-Indol-4-yl)methyl)-N⁴-((1R,5S,6s)-3-azabicyclo[3.1.0]hexan-6-yl)-N²-methylpyridine-2,4-dicarboxamide;

(R)-6-Benzyl-N⁴-(2-(3-fluoropiperidin-3-yl)ethyl)-N²-methylpyridine-2,4-dicarboxamide;

N2-Methyl-N⁴-(3-((S)-morpholin-2-yl)propyl)-6-((R*)-1-phenylethyl)pyridine-2,4-dicarboxamide;

N⁴-((1R,5S,6s)-3-Acetyl-3-azabicyclo[3.1.0]hexan-6-yl)-6-benzyl-N²-methylpyridine-2,4-dicarboxamide;

(R)-6-Benzyl-N⁴-(2-(4-(2,2-difluoroethyl)morpholin-2-yl)ethyl)-N²-methylpyridine-2,4-dicarboxamide;

6-Benzyl-N²-methyl-N⁴-(3-(4-methyl-3-oxopiperazin-1-yl)propyl)pyridine-2,4-dicarboxamide;

6-Benzyl-N²-methyl-N⁴-(3-(3-oxopiperazin-1-yl)propyl)pyridine-2,4-dicarboxamide;

(±)-tert-Butyl 4-(2-(2-benzyl-6-(methylcarbamoyl)isonicotinamido)ethyl)-3,3-difluoropiperidine-1-carboxylate;

N⁴-(3-((R)-3-Fluoropiperidin-3-yl)propyl)-N²-methyl-6-(1-phenylethyl)pyridine-2,4-dicarboxamide;

6-Benzyl-N²-methyl-N⁴-(3-(2-oxopiperazin-1-yl)propyl)pyridine-2,4-dicarboxamide, hydrochloride;

6-Benzyl-N⁴-((1R,5S,6s)-3-(2,2-difluoroethyl)-3-azabicyclo[3.1.0]hexan-6-yl)-N²-methylpyridine-2,4-dicarboxamide;

(±)-6-Benzyl-N⁴-(2-(4,4-difluoropiperidin-3-yl)ethyl)-N²-methylpyridine-2,4-dicarboxamide, hydrochloride;

(±)-6-Benzyl-N⁴-(2-(3,3-difluoropiperidin-4-yl)ethyl)-N²-methylpyridine-2,4-dicarboxamide, hydrochloride;

N⁴-((1R,5S,6r)-3-Oxabicyclo[3.1.0]hexan-6-yl)-6-(4-cyanobenzyl)-N²-methylpyridine-2,4-dicarboxamide;

N⁴-((1R,5S,6r)-3-Oxabicyclo[3.1.0]hexan-6-yl)-N2-methyl-6-(4-methylbenzyl)pyridine-2,4-dicarboxamide;

N⁴-((1R,5S,6r)-3-Oxabicyclo[3.1.0]hexan-6-yl)-6-((S)-hydroxy(phenyl)methyl)-N²-methylpyridine-2,4-dicarboxamide;
N⁴-((1R,5S,6r)-3-Oxabicyclo[3.1.0]hexan-6-yl)-6-((R)-hydroxy(phenyl)methyl)-N²-methylpyridine-2,4-dicarboxamide;
N⁴-((1R,5S,6r)-3-Oxabicyclo[3.1.0]hexan-6-yl)-N²-methyl-6-(3-methylbenzyl)pyridine-2,4-dicarboxamide;
N⁴-((1R,5S,6r)-3-Oxabicyclo[3.1.0]hexan-6-yl)-6-(3-cyanobenzyl)-N²-methylpyridine-2,4-dicarboxamide;
(R)—N²-Methyl-6-(3-methylbenzyl)-N⁴-(2-(morpholin-2-yl)ethyl)pyridine-2,4-dicarboxamide;
N⁴-((1R,5S,6r)-3-Oxabicyclo[3.1.0]hexan-6-yl)-6-(2-methoxybenzyl)-N²-methylpyridine-2,4-dicarboxamide;
(+/−)-N⁴-((1R,5S,6r)-3-Oxabicyclo[3.1.0]hexan-6-yl)-6-(hydroxy(phenyl)methyl)-N²-methylpyridine-2,4-dicarboxamide;
(+/−)-tert-Butyl 2-(3-(2-(3-methoxybenzyl)-6-(methylcarbamoyl)isonicotinamido)propyl)morpholine-4-carboxylate;
(±)-tert-Butyl 3-(2-(2-benzyl-6-(methylcarbamoyl)isonicotinamido)ethyl)-4,4-difluoropiperidine-1-carboxylate;
6-(3-Methoxybenzyl)-N²-methyl-N⁴-(tetrahydro-2H-pyran-4-yl)pyridine-2,4-dicarboxamide;
(+/−)-N⁴-(2-(4-Acetylmorpholin-2-yl)ethyl)-6-(3-methoxybenzyl)-N²-methylpyridine-2,4-dicarboxamide;
(+/−)-6-Benzyl-N²-methyl-N⁴-(tetrahydro-2H-pyran-3-yl)pyridine-2,4-dicarboxamide;
(+/−)-6-Benzyl-N²-methyl-N⁴-((tetrahydrofuran-3-yl)methyl)pyridine-2,4-dicarboxamide;
(+/−)-N⁴-(2-(4-Acetylmorpholin-2-yl)ethyl)-6-benzyl-N²-methylpyridine-2,4-dicarboxamide;
(+/−)-6-Benzyl-N²-methyl-N⁴-((tetrahydrofuran-2-yl)methyl)pyridine-2,4-dicarboxamide;
(+/−)-6-Benzyl-N²-methyl-N⁴-((tetrahydro-2H-pyran-2-yl)methyl)pyridine-2,4-dicarboxamide;
N⁴-(Azetidin-3-yl)-6-benzyl-N²-methylpyridine-2,4-dicarboxamide;
6-Benzyl-N²-methyl-N⁴-((tetrahydro-2H-pyran-4-yl)methyl)pyridine-2,4-dicarboxamide;
N²-Methyl-N⁴-(3-((S)-morpholin-2-yl)propyl)-6-((S*)-1-phenylethyl)pyridine-2,4-dicarboxamide;
6-((1H-Pyrrolo[2,3-c]pyridin-4-yl)methyl)-N⁴-((1R,5S,6s)-3-oxabicyclo[3.1.0]hexan-6-yl)-N²-methylpyridine-2,4-dicarboxamide;
N⁴-((1R,5S,6s)-3-Azabicyclo[3.1.0]hexan-6-yl)-N²-methyl-6-(3-methylbenzyl)pyridine-2,4-dicarboxamide;
N⁴-((1R,5S,6r)-3-Azabicyclo[3.1.0]hexan-6-yl)-N²-methyl-6-(3-methylbenzyl)pyridine-2,4-dicarboxamide;
N⁴-((1R,5S,6r)-3-Oxabicyclo[3.1.0]hexan-6-yl)-6-(1-(3-methoxyphenyl)ethyl)-N²-methylpyridine-2,4-dicarboxamide;
N⁴-((1R,5S,6r)-3-Oxabicyclo[3.1.0]hexan-6-yl)-6-((2-cyano-1H-indol-4-yl)methyl)-N²-methylpyridine-2,4-dicarboxamide;
N⁴-((1R,5S,6r)-3-Oxabicyclo[3.1.0]hexan-6-yl)-6-((3-cyano-1H-indol-4-yl)methyl)-N²-methylpyridine-2,4-dicarboxamide;
N⁴-((1R,5S,6r)-3-Oxabicyclo[3.1.0]hexan-6-yl)-N²-methyl-6-(1-phenylpropyl)pyridine-2,4-dicarboxamide;
N⁴-((1R,5S,6r)-3-Oxabicyclo[3.1.0]hexan-6-yl)-N²-methyl-6-((R*)-1-phenylpropyl)pyridine-2,4-dicarboxamide;
N⁴-((1R,5S,6r)-3-Oxabicyclo[3.1.0]hexan-6-yl)-N²-methyl-6-((S*)-1-phenylpropyl)pyridine-2,4-dicarboxamide;
N⁴-((1R,5S,6r)-3-Oxabicyclo[3.1.0]hexan-6-yl)-6-((1-(2-hydroxyethyl)-1H-indol-4-yl)methyl)-N²-methylpyridine-2,4-dicarboxamide;
N⁴-((1R,5S,6r)-3-Oxabicyclo[3.1.0]hexan-6-yl)-N²-methyl-6-((3-(2,2,2-trifluoroacetyl)-1H-indol-4-yl)methyl)pyridine-2,4-dicarboxamide;
(±)-6-Benzyl-N⁴-(3-(3,3-difluoropiperidin-4-yl)propyl)-N²-methylpyridine-2,4-dicarboxamide hydrochloride;
N⁴-((1R,5S,6r)-3-Oxabicyclo[3.1.0]hexan-6-yl)-6-(methoxy(phenyl)methyl)-N²-methylpyridine-2,4-dicarboxamide;
N⁴-((1R,5S,6r)-3-Oxabicyclo[3.1.0]hexan-6-yl)-6-((S*)-1-(3-methoxyphenyl)ethyl)-N²-methylpyridine-2,4-dicarboxamide;
N⁴-((1R,5S,6r)-3-Oxabicyclo[3.1.0]hexan-6-yl)-6-((R*)-1-(3-methoxyphenyl)ethyl)-N²-methylpyridine-2,4-dicarboxamide;
N⁴-((1R,5S,6r)-3-Oxabicyclo[3.1.0]hexan-6-yl)-6-((S*)-methoxy(phenyl)methyl)-N²-methylpyridine-2,4-dicarboxamide;
N⁴-((1R,5S,6r)-3-oxabicyclo[3.1.0]hexan-6-yl)-6-((R*)-methoxy(phenyl)methyl)-N²-methylpyridine-2,4-dicarboxamide;
(+/−)-6-(1-(1H-Indol-4-yl)ethyl)-N⁴-((1R,5S,6r)-3-oxabicyclo[3.1.0]hexan-6-yl)-N2-methylpyridine-2,4-dicarboxamide;
(+/−)-6-Benzyl-N²-methyl-N⁴-(3-(2-methylmorpholin-2-yl)propyl)pyridine-2,4-dicarboxamide;
N⁴-((1R,5S,6r)-3-Oxabicyclo[3.1.0]hexan-6-yl)-6-(chloro(pyridin-2-yl)methyl)-N²-methylpyridine-2,4-dicarboxamide;
N⁴-(2-((2r,5r)-5-Amino-1,3-dioxan-2-yl)ethyl)-6-benzyl-N2-methylpyridine-2,4-dicarboxamide;
6-((S*)-1-(1H-Indol-4-yl)ethyl)-N⁴-((1R,5S,6r)-3-oxabicyclo[3.1.0]hexan-6-yl)-N²-methylpyridine-2,4-dicarboxamide;
6-((R*)-1-(1H-Indol-4-yl)ethyl)-N⁴-((1R,5S,6r)-3-oxabicyclo[3.1.0]hexan-6-yl)-N²-methylpyridine-2,4-dicarboxamide;
(+/−)-N⁴-((1R,5S,6r)-3-Oxabicyclo[3.1.0]hexan-6-yl)-6-(1-(2-methoxyphenyl)ethyl)-N²-methylpyridine-2,4-dicarboxamide;
N⁴-(3-((2r,5r)-5-Amino-1,3-dioxan-2-yl)propyl)-6-benzyl-N²-methylpyridine-2,4-dicarboxamide;
N⁴-((1R,5S,6r)-3-Oxabicyclo[3.1.0]hexan-6-yl)-6-(2-methoxy-1-phenylethyl)-N²-methylpyridine-2,4-dicarboxamide;
(+/−)-N⁴-((1R,5S,6r)-3-Oxabicyclo[3.1.0]hexan-6-yl)-N2-methyl-6-(1-(2-oxoindolin-4-yl)ethyl)pyridine-2,4-dicarboxamide;
(+/−)-N⁴-((1R,5S,6r)-3-Oxabicyclo[3.1.0]hexan-6-yl)-6-(hydroxy(2-methoxyphenyl)methyl)-N²-methylpyridine-2,4-dicarboxamide;
tert-Butyl 3,3-difluoro-4-(3-(2-(methylcarbamoyl)-6-((S)-1-phenylethyl)isonicotinamido)propyl)piperidine-1-carboxylate;
tert-Butyl 3,3-difluoro-4-(2-(2-(methylcarbamoyl)-6-((S)-1-phenylethyl)isonicotinamido)ethyl)piperidine-1-carboxylate;

tert-Butyl 4,4-difluoro-3-(2-(2-(methylcarbamoyl)-6-((S)-1-phenylethyl)isonicotinamido)ethyl)piperidine-1-carboxylate;

$N^4$-((1R,5S,6r)-3-Oxabicyclo[3.1.0]hexan-6-yl)-6-((S*)-2-methoxy-1-phenylethyl)-$N^2$-methylpyridine-2,4-dicarboxamide;

$N^4$-((1R,5S,6r)-3-Oxabicyclo[3.1.0]hexan-6-yl)-6-((R*)-2-methoxy-1-phenylethyl)-$N^2$-methylpyridine-2,4-dicarboxamide;

$N^4$-((1R,5S,6r)-3-Oxabicyclo[3.1.0]hexan-6-yl)-6-((S*)-hydroxy(2-methoxyphenyl)methyl)-N2-methylpyridine-2,4-dicarboxamide;

$N^4$-((1R,5S,6r)-3-Oxabicyclo[3.1.0]hexan-6-yl)-6-((R*)-hydroxy(2-methoxyphenyl)methyl)-$N^2$-methylpyridine-2,4-dicarboxamide;

$N^4$-(2-((S*)-3,3-Difluoropiperidin-4-yl)ethyl)-$N^2$-methyl-6-((S)-1-phenylethyl)pyridine-2,4-dicarboxamide, hydrochloride;

$N^4$-(2-((R*)-3,3-Difluoropiperidin-4-yl)ethyl)-$N^2$-methyl-6-((S)-1-phenylethyl)pyridine-2,4-dicarboxamide, hydrochloride;

(±)-$N^4$-((1R,5S,6s)-3-Oxabicyclo[3.1.0]hexan-6-yl)-6-(1-(1-formylindolin-4-yl)ethyl)-$N^2$-methylpyridine-2,4-dicarboxamide;

$N^4$-((1R,5S,6r)-3-Oxabicyclo[3.1.0]hexan-6-yl)-6-((S*)-1-(2-methoxyphenyl)ethyl)-$N^2$-methylpyridine-2,4-dicarboxamide;

$N^4$-((1R,5S,6r)-3-Oxabicyclo[3.1.0]hexan-6-yl)-6-((R*)-1-(2-methoxyphenyl)ethyl)-$N^2$-methylpyridine-2,4-dicarboxamide;

(±)-$N^4$-((1R,5S,6r)-3-Oxabicyclo[3.1.0]hexan-6-yl)-6-(1-(indolin-4-yl)ethyl)-N2-methylpyridine-2,4-dicarboxamide;

(+/−)-$N^4$-((1R,5S,6r)-3-Oxabicyclo[3.1.0]hexan-6-yl)-6-(hydroxy(m-tolyl)methyl)-$N^2$-methylpyridine-2,4-dicarboxamide;

$N^4$-((1R,5S,6r)-3-Oxabicyclo[3.1.0]hexan-6-yl)-6-(indolin-4-ylmethyl)-$N^2$-methylpyridine-2,4-dicarboxamide;

(+/−)-N4-((1R,5S,6r)-3-Oxabicyclo[3.1.0]hexan-6-yl)-6-(hydroxy(o-tolyl)methyl)-N2-methylpyridine-2,4-dicarboxamide;

$N^4$-(3-((2r,5S)-5-Amino-1,3-dioxan-2-yl)propyl)-$N^2$-methyl-6-((S)-1-phenylethyl)pyridine-2,4-dicarboxamide;

$N^4$-(3-((S*)-3,3-Difluoropiperidin-4-yl)propyl)-$N^2$-methyl-6-((S)-1-phenylethyl)pyridine-2,4-dicarboxamide hydrochloride;

$N^4$-(3-((R*)-3,3-Difluoropiperidin-4-yl)propyl)-$N^2$-methyl-6-((S)-1-phenylethyl)pyridine-2,4-dicarboxamide hydrochloride;

$N^4$-(2-((S*)-4,4-Difluoropiperidin-3-yl)ethyl)-$N^2$-methyl-6-((S)-1-phenylethyl)pyridine-2,4-dicarboxamide hydrochloride;

$N^4$-(2-((R*)-4,4-Difluoropiperidin-3-yl)ethyl)-$N^2$-methyl-6-((S)-1-phenylethyl)pyridine-2,4-dicarboxamide hydrochloride;

(+/−)-$N^4$-((1R,5S,6r)-3-Oxabicyclo[3.1.0]hexan-6-yl)-6-(hydroxy(p-tolyl)methyl)-$N^2$-methylpyridine-2,4-dicarboxamide;

(+/−)-$N^4$-((1R,5S,6r)-3-Oxabicyclo[3.1.0]hexan-6-yl)-6-(2-chlorophenyl)(hydroxy)methyl)-N2-methylpyridine-2,4-dicarboxamide;

(R*)-6-Benzyl-$N^2$-methyl-$N^4$-(3-(2-methylmorpholin-2-yl)propyl)pyridine-2,4-dicarboxamide;

(S*)-6-Benzyl-$N^2$-methyl-$N^4$-(3-(2-methylmorpholin-2-yl)propyl)pyridine-2,4-dicarboxamide;

6-Benzyl-$N^4$-((1R,5S,6r)-3-oxabicyclo[3.1.0]hexan-6-yl)-N2-ethylpyridine-2,4-dicarboxamide;

$N^4$-((1R,5S,6r)-3-Oxabicyclo[3.1.0]hexan-6-yl)-6-((R*)-hydroxy(p-tolyl)methyl)-$N^2$-methylpyridine-2,4-dicarboxamide;

$N^4$-((1R,5S,6r)-3-Oxabicyclo[3.1.0]hexan-6-yl)-6-((S*)-hydroxy(p-tolyl)methyl)-$N^2$-methylpyridine-2,4-dicarboxamide;

$N^4$-((1R,5S,6r)-3-Oxabicyclo[3.1.0]hexan-6-yl)-6-((R*)-hydroxy(o-tolyl)methyl)-$N^2$-methylpyridine-2,4-dicarboxamide;

$N^4$-((1R,5S,6r)-3-Oxabicyclo[3.1.0]hexan-6-yl)-6-((S*)-hydroxy(o-tolyl)methyl)-$N^2$-methylpyridine-2,4-dicarboxamide;

$N^4$-((1R,5S,6r)-3-Oxabicyclo[3.1.0]hexan-6-yl)-6-((S*)-1-(indolin-4-yl)ethyl)-N2-methylpyridine-2,4-dicarboxamide;

$N^4$-((1R,5S,6r)-3-Oxabicyclo[3.1.0]hexan-6-yl)-6-((R*)-1-(indolin-4-yl)ethyl)-$N^2$-methylpyridine-2,4-dicarboxamide;

$N^4$-((1R,5S,6r)-3-oxabicyclo[3.1.0]hexan-6-yl)-6-((S*)-(2-chlorophenyl)(hydroxy)methyl)-$N^2$-methylpyridine-2,4-dicarboxamide;

$N^4$-((1R,5S,6r)-3-oxabicyclo[3.1.0]hexan-6-yl)-6-((R*)-(2-chlorophenyl)(hydroxy)methyl)-$N^2$-methylpyridine-2,4-dicarboxamide;

6-((1H-Indol-4-yl)methyl)-$N^4$-((1R,5S,6r)-3-oxabicyclo[3.1.0]hexan-6-yl)-N2-ethylpyridine-2,4-dicarboxamide;

$N^4$-((1R,5S,6r)-3-Oxabicyclo[3.1.0]hexan-6-yl)-$N^2$-methyl-6-((R*)-1-(2-oxoindolin-4-yl)ethyl)pyridine-2,4-dicarboxamide;

$N^4$-((1R,5S,6r)-3-Oxabicyclo[3.1.0]hexan-6-yl)-$N^2$-methyl-6-((S*)-1-(2-oxoindolin-4-yl)ethyl)pyridine-2,4-dicarboxamide;

$N^4$-(3-((2r,5r)-5-Amino-1,3-dioxan-2-yl)propyl)-6-(3-chlorobenzyl)-$N^2$-methylpyridine-2,4-dicarboxamide;

$N^4$-(3-((2r,5r)-5-Amino-1,3-dioxan-2-yl)propyl)-6-(2-chlorobenzyl)-$N^2$-methylpyridine-2,4-dicarboxamide;

$N^4$-(3-((2r,5r)-5-Amino-1,3-dioxan-2-yl)propyl)-$N^2$-methyl-6-(3-methylbenzyl)pyridine-2,4-dicarboxamide;

$N^4$-((1R,5S,6r)-3-Oxabicyclo[3.1.0]hexan-6-yl)-6-((S*)-hydroxy(m-tolyl)methyl)-$N^2$-methylpyridine-2,4-dicarboxamide;

$N^4$-((1R,5S,6r)-3-Oxabicyclo[3.1.0]hexan-6-yl)-6-((R*)-hydroxy(m-tolyl)methyl)-$N^2$-methylpyridine-2,4-dicarboxamide;

(+/−)-$N^4$-(3-((2r,5r)-5-Amino-1,3-dioxan-2-yl)propyl)-6-(methoxy(phenyl)methyl)-$N^2$-methylpyridine-2,4-dicarboxamide;

$N^4$-((1R,5S,6r)-3-Oxabicyclo[3.1.0]hexan-6-yl)-6-((S*)-(3-fluorophenyl)(hydroxy)methyl)-$N^2$-methylpyridine-2,4-dicarboxamide;

$N^4$-((1R,5S,6r)-3-Oxabicyclo[3.1.0]hexan-6-yl)-6-((R*)-(3-fluorophenyl)(hydroxy)methyl)-$N^2$-methylpyridine-2,4-dicarboxamide;

$N^4$-(3-((2r,5r)-5-Amino-1,3-dioxan-2-yl)propyl)-6-(2-methoxybenzyl)-$N^2$-methylpyridine-2,4-dicarboxamide;

$N^4$-((1R,5S,6r)-3-Oxabicyclo[3.1.0]hexan-6-yl)-6-(4-fluorobenzyl)-$N^2$-methylpyridine-2,4-dicarboxamide;

$N^4$-(3-((2r,5S)-5-Amino-1,3-dioxan-2-yl)propyl)-6-((S*)-methoxy(phenyl)methyl)-$N^2$-methylpyridine-2,4-dicarboxamide;

$N^4$-(3-((2r,5S)-5-Amino-1,3-dioxan-2-yl)propyl)-6-((R*)-methoxy(phenyl)methyl)-$N^2$-methylpyridine-2,4-dicarboxamide;

6-Benzyl-$N^4$-(3-((2r,5r)-5-(dimethylamino)-1,3-dioxan-2-yl)propyl)-$N^2$-methylpyridine-2,4-dicarboxamide;

(+/−)-$N^4$-((1R,5S,6r)-3-Oxabicyclo[3.1.0]hexan-6-yl)-6-(2-cyano-1-phenylethyl)-$N^2$-methylpyridine-2,4-dicarboxamide;

(+/−)-tert-Butyl 4-(3-(2-benzyl-6-(methylcarbamoyl)isonicotinamido)propyl)-3,3-difluoropiperidine-1-carboxylate;

(+/−)-$N^4$-((1R,5S,6r)-3-Oxabicyclo[3.1.0]hexan-6-yl)-6-(2-fluoro-1-phenylethyl)-$N^2$-methylpyridine-2,4-dicarboxamide;

$N^4$-((1R,5S,6r)-3-Oxabicyclo[3.1.0]hexan-6-yl)-6-((S*)-2-fluoro-1-phenylethyl)-$N^2$-methylpyridine-2,4-dicarboxamide;

$N^4$-((1R,5S,6r)-3-Oxabicyclo[3.1.0]hexan-6-yl)-6-((R*)-2-fluoro-1-phenylethyl)-$N^2$-methylpyridine-2,4-dicarboxamide; or $N^4$-(3-((2r,5r)-5-Amino-1,3-dioxan-2-yl)propyl)-6-(3-methoxybenzyl)-$N^2$-methylpyridine-2,4-dicarboxamide;

or a pharmaceutically acceptable salt thereof.

9. A pharmaceutical composition comprising the compound or pharmaceutically acceptable salt thereof as defined in claim 1 and one or more pharmaceutically acceptable excipients.

* * * * *